US008486952B2

(12) United States Patent
Boy et al.

(10) Patent No.: US 8,486,952 B2
(45) Date of Patent: Jul. 16, 2013

(54) COMPOUNDS FOR THE REDUCTION OF β-AMYLOID PRODUCTION

(75) Inventors: Kenneth M. Boy, Durham, CT (US); Jason M. Guernon, Moodus, CT (US); John E. Macor, Guilford, CT (US); Richard E. Olson, Orange, CT (US); Jianliang Shi, Madison, CT (US); Lorin A. Thompson, III, Higganum, CT (US); Yong-Jin Wu, Madison, CT (US); Li Xu, Middletown, CT (US); Yunhui Zhang, Glastonbury, CT (US); Dmitry S. Zuev, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 157 days.

(21) Appl. No.: 12/845,045

(22) Filed: Jul. 28, 2010

(65) Prior Publication Data
US 2011/0212937 A1    Sep. 1, 2011

Related U.S. Application Data

(60) Provisional application No. 61/324,201, filed on Apr. 14, 2010, provisional application No. 61/230,202, filed on Jul. 31, 2009.

(51) Int. Cl.
| | |
|---|---|
| *A01N 43/54* | (2006.01) |
| *A01N 43/90* | (2006.01) |
| *A61K 31/517* | (2006.01) |
| *A61K 31/519* | (2006.01) |
| *A61K 31/52* | (2006.01) |
| *A61K 31/497* | (2006.01) |
| *A61K 31/00* | (2006.01) |
| *A61K 31/535* | (2006.01) |
| *C07D 239/70* | (2006.01) |
| *C07D 491/00* | (2006.01) |
| *C07D 495/00* | (2006.01) |
| *C07D 471/00* | (2006.01) |
| *C07D 413/00* | (2006.01) |

(52) U.S. Cl.
USPC ............. 514/258.1; 514/264.11; 514/252.16; 514/210.21; 514/260.1; 514/234.2; 514/230.5; 544/253; 544/278; 544/279; 544/117

(58) Field of Classification Search
USPC ............. 514/258.1, 264.11, 252.16, 210.21, 514/260.1, 234.2, 230.5; 544/253, 278, 279, 544/117
See application file for complete search history.

(56) References Cited

U.S. PATENT DOCUMENTS

| | | | |
|---|---|---|---|
| 6,696,452 | B2 | 2/2004 | Davies et al. |
| 7,115,739 | B2 | 10/2006 | Bebbington et al. |
| 2010/0297128 | A1 | 11/2010 | Huang et al. |
| 2010/0298359 | A1 | 11/2010 | Huang et al. |
| 2010/0298372 | A1 | 11/2010 | Huang et al. |
| 2010/0298381 | A1 | 11/2010 | Zhu et al. |
| 2011/0009392 | A1 | 1/2011 | Zhu et al. |
| 2011/0015190 | A1 | 1/2011 | Huang et al. |

FOREIGN PATENT DOCUMENTS

| | | |
|---|---|---|
| WO | WO 02/50065 | 6/2002 |
| WO | WO 2008/136756 | 11/2008 |
| WO | WO 2009/087127 | 7/2009 |
| WO | WO 2009/103652 | 8/2009 |
| WO | WO 2010/040661 | 4/2010 |
| WO | WO 2010/088408 | 8/2010 |
| WO | WO 2010/088414 | 8/2010 |
| WO | WO 2010/132015 | 11/2010 |
| WO | WO 2011/006903 | 1/2011 |

OTHER PUBLICATIONS

Anderson, D.H. et al., "Characterization of β amyloid assemblies in drusen: the deposits associated with aging and age-related macular degeneration," Experimental Eye Research, 78, pp. 243-256, 2004.

Barten, D.M. et al., "γ-Secretase Inhibitors for Alzheimer's Disease," Drugs R D, 7, 2, pp. 87-97, 2006.

Cleary, J.P. et al., "Natural oligomers of the amyloid-βprotein specifically disrupt cognitive function," Nature Neuroscience, vol. 8, No. 1, pp. 79-84, Jan. 2005.

Deramecourt V. et al., "Biochemical staging of Synucleinopathy and Amyloid Deposition in Dementia with Lewy Bodies," Journal of Neuropathology and Experimental Neurol., vol. 65, No. 3, pp. 278-288, Mar. 2006.

Dess D.B. et al., "Readily Accessible12-1-5[1] Oxidant for the Conversion of Primary and Secondary Alcohols to Aldehydes and Ketones," Journal of Organic Chemistry, 48, pp. 4155-4156, 1983.

Dirat O. et al., "Expeditious synthesis of novel $NK_1$ antagonists based on a 1,2,4-trisubstituted cyclohexane," Tetrahedron Letters, 47, pp. 1295-1298, 2006.

Fox J.M. et al., Highly Active and Selective Catalysts for the Formation of α-Aryl Ketones, Journal of the American Chemical Society, 122, pp. 1360-1370, 2000.

(Continued)

Primary Examiner — Samira Jean-Louis
(74) Attorney, Agent, or Firm — John F. Levis

(57) ABSTRACT

The present disclosure provides a series of compounds of the formula (I)

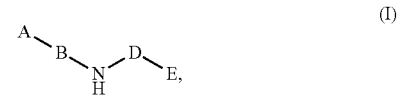

which modulate β-amyloid peptide (β-AP) production and are useful in the treatment of Alzheimer's Disease and other conditions affected by β-amyloid peptide (β-AP) production.

15 Claims, No Drawings

OTHER PUBLICATIONS

Goldstein L.E. et al., "Cytosolic β-amyloid deposition and supranuclear cataracts in lenses from people with Alzheimer's disease," The Lancet, vol. 361, pp. 1258-1265, Apr. 12, 2003.

Grundman M et al., "Mild Cognitive Impairment Can Be Distinguished from Alzheimer Disease and Normal Aging for Clinical Trials," Archives of Neurology, vol. 61, pp. 59-66, Jan. 2004.

Hamilton R.L. et al., "Alzheimer disease pathology in amyotrophic lateral sclerosis," Acta Neuropathology, 107, pp. 515-522, 2004.

Larsen J.S. et al., "Synthesis of annelated analogues of 6-benzyl-1-(ethoxymethyl)-5-isopropyluracil (MKC-442) using 1,2-oxazine-2,4(3H)-diones as key intermediates," J. Chem. Soc., Perkin Trans. 1, pp. 3035-3038, 2000.

Loane D.J. et al., "Amyloid precursor protein secretases as therapeutic targets for traumatic brain injury," Nature Medicine, vol. 15, No. 4, pp. 377-379, Apr. 2009.

"Consensus Recommendations for the Postmortem Diagnosis of Alzheimer's Disease," Neurobiology of Aging, vol. 18, No. S4, pp. S1-S2, 1997.

Murphy, M.P. et al., "Inclusion-body myositis and Alzheimer disease: Two sides of the same coin, or different currencies altogether?" Neurology, 66, Suppl 1, pp. S65-S68, 2006.

Nencka R. et al., "Discovery of 5-Substituted -6-chlorouracils as Efficient Inhibitors of Human Thymidine Phosphorylase," Journal of Medicinal Chemistry, 50, pp. 6016-6023, 2007.

Neumann M. et al., Ubiquitinated TDP-43 in Frontotemporal Lobar Degeneration and Amyotrophic Lateral Sclerosis, Science, vol. 314, pp. 130-133, Oct. 6, 2006.

Tyle, "Iontophoretic Devices for Drug Delivery," Pharmaceutical Research, vol. 3, No. 6, pp. 318-326, 1986.

Selkoe, "Alzheimer's Disease: Genes, Proteins, and Therapy," Physiological Reviews, vol. 81, No. 2, pp. 741-766, Apr. 2001.

Thaher B.A. et al., "A Convenient Synthesis of 1-(4-Fluorophenyl)-2-(4-pyridyl)cyclopentene from Cyclopentanone," Synthesis, No. 2, pp. 225-228, 2008.

Thal D.R. et al., "Two Types of Sporadic Cerebral Amyloid Angiopathy," Journal of Neuropathology and Experimental Neurology, vol. 61, No. 3, pp. 282-293, Mar. 2002.

Walsh D.M. et al., "Deciphering the Molecular Basis of Memory Failure in Alzheimer's Disease," Neuron, vol. 44, pp. 181-193, Sep. 30, 2004.

Watkins T.A. et al., "Distinct Stages of Myelination Regulated by γ-Secretase and Astrocytes in a Rapidly Myelinating CNS Coculture System," Neuron, 60, pp. 555-569, Nov. 26, 2008.

Wolfe M.S. et al., "Intramembrane Proteolysis: Theme and Variations," Science, vol. 305, pp. 1119-1123, Aug. 20, 2004.

Wolfe M.S., "Secretase Targets for Alzheimer's Disease, Identification and Therapeutic Potential," Journal of Medicinal Chemistry, vol. 44, No. 13, pp. 2039-2060, Jun. 21, 2001.

Yokota O. et al., "NACP/α-Synuclein, NAC, and β-amyloid pathology of familial Alzheimer's disease with the E184D presenilin-1 mutation: a clinicopathological study of two autopsy cases," Acta Neuropathol, 104, pp. 637-648, 2002.

Yoshida T. et al., "The potential role of amyloid β in the pathogenesis of age-related macular degeneration," The Journal of Clinical Investigation, vol. 115, No. 10, pp. 2793-2800, Oct. 2005.

COMPOUNDS FOR THE REDUCTION OF β-AMYLOID PRODUCTION

CROSS REFERENCE TO RELATED APPLICATION

The present application claims the benefit of U.S. provisional application Ser. No. 61/324,201 filed Apr. 14, 2010 and U.S. provisional application Ser. No. 61/230,202 filed Jul. 31, 2009, the contents of which are herein incorporated by reference.

FIELD OF THE INVENTION

The present disclosure relates to methods of treating Alzheimer's Disease (AD) and other conditions related to β-amyloid production using compounds which are inhibitors of β-amyloid peptide (Aβ) production. The disclosure further relates to pharmaceutical compositions comprising these compounds.

BACKGROUND OF THE INVENTION

Alzheimer's disease (AD) is a progressive neurodegenerative disease which begins with memory loss and progresses to include severe cognitive impairment, altered behavior, and decreased motor function (Grundman, M. et al., *Arch Neurol.* (2004) 61: 59-66; Walsh, D. M. et al., *Neuron* (2004) 44: 181-193). It is the most common form of dementia and represents the third leading cause of death after cardiovascular disorders and cancer. The cost of AD is enormous and includes the suffering of the patients and families and the lost productivity of patients and caregivers. No treatment that effectively prevents AD or reverses the clinical symptoms and underlying pathophysiology is currently available.

A definitive diagnosis of AD for a demented patient requires a histopathological evaluation of the number and localization of neuritic plaques and neurofibrillary tangles upon autopsy (Consensus recommendations for the postmortem diagnosis of Alzheimer's disease. *Neurobiol Aging* (1997) 18: S1-2). Similar alterations are observed in patients with Trisomy 21 (Down syndrome). Plaques primarily consist of β-amyloid (Aβ) peptides that are formed by a stepwise proteolytic cleavage of the amyloid precursor protein (APP) by β-site APP-cleaving enzyme (BACE), to generate the N-terminus, and γ-secretase, to generate the C-terminus (Selkoe, D. J., *Physiol Rev.* (2001) 81: 741-766). γ-Secretase is a transmembrane protein complex that includes Nicastrin, Aph-1, PEN-2, and either Presenilin-1 (PS-1) or Presenilin-2 (PS-2) (Wolfe, M. S. et al., *Science* (2004) 305: 1119-1123). PS-1 and PS-2 are believed to contain the catalytic sites of γ-secretase.

Aβ40 is the most abundant form of Aβ synthesized (80-90%), while Aβ42 is most closely linked with AD pathogenesis. In particular, mutations in the APP, PS-1, and PS-2 genes that lead to rare, familial forms of AD implicate Aβ42 aggregates as the primary toxic species (Selkoe, D. J., *Physiol Rev.*, (2001) 81: 741-766). Current evidence suggests that oligomeric, protofibrillar and intracellular Aβ42 play a significant role in the disease process (Cleary, J. P. et al., *Nat. Neurosci.* (2005) δ: 79-84). Inhibitors of the enzymes that form Aβ42, such as γ-secretase, represent potential disease-modifying therapeutics for the treatment of AD.

Evidence suggests that a reduction in brain Aβ levels by inhibition of γ-secretase may prevent the onset and progression of AD (Selkoe, D. *Physiol. Rev.* (2001) 81: 741-766; Wolfe, M., *J. Med. Chem.* (2001) 44: 2039-2060). There are emerging data for the role of Aβ in other diseases, including mild cognitive impairment (MCI), Down syndrome, cerebral amyloid angiopathy (CAA), dementia with Lewy bodies (DLB), amyotrophic lateral sclerosis (ALS-D), inclusion body myositis (IBM), and age-related macular degeneration. Advantageously, compounds that inhibit γ-secretase and reduce production of Aβ could be used to treat these or other Aβ-dependent diseases.

Excess production and/or reduced clearance of Aβ causes CAA (Thal, D. et al., *J. Neuropath. Exp. Neuro.* (2002) 61: 282-293). In these patients, vascular amyloid deposits cause degeneration of vessel walls and aneurysms that may be responsible for 10-15% of hemorrhagic strokes in elderly patients. As in AD, mutations in the gene encoding Aβ lead to an early onset form of CAA, referred to as cerebral hemorrhage with amyloidosis of the Dutch type, and mice expressing this mutant protein develop CAA that is similar to patients. Compounds that reduce Aβ levels could reduce or prevent CAA.

DLB manifests with visual hallucinations, delusions, and parkinsonism. Interestingly, familial AD mutations that cause Aβ deposits can also cause Lewy bodies and DLB symptoms (Yokota, O. et al., *Acta Neuropathol* (Berl) (2002) 104: 637-648). Further, sporadic DLB patients have Aβ deposits similar to those in AD (Deramecourt, V. et al., *J Neuropathol Exp Neurol* (2006) 65: 278-288). Based on this data, Aβ likely drives Lewy body pathology in DLB and, therefore, compounds that reduce Aβ levels could reduce or prevent DLB.

Approximately 25% of ALS patients have significant dementia or aphasia (Hamilton, R. L. et al., *Acta Neuropathol* (Berl) (2004) 107: 515-522). The majority (~60%) of these patients, designated ALS-D, contain ubiquitin-positive inclusions comprised primarily of the TDP-43 protein (Neumann, M. et al., *Science* (2006) 314: 130-133). About 30% of the ALS-D patients have amyloid plaques consistent with Aβ causing their dementia (Hamilton, R. L. et al., *Acta Neuropathol* (Berl) (2004) 107: 515-522). These patients should be identifiable with amyloid imaging agents and potentially could be treated by compounds that reduce Aβ levels.

IBM is a rare, age-related degenerative disease of skeletal muscle. The appearance of Aβ deposits in IBM muscle and the recapitulation of several aspects of the disease by directing APP overexpression to muscle in transgenic mice support the role of Aβ in IBM (reviewed in Murphy, M. P. et al., *Neurology* (2006) 66: S65-68). Compounds that reduce Aβ levels could reduce or prevent IBM.

In age-related macular degeneration, Aβ was identified as one of several components of drusen, extracellular deposits beneath the retinal pigment epithelium (RPE) (Anderson, D. H. et al., *Exp Eye Res* (2004) 78: 243-256). A recent study has shown potential links between Aβ and macular degeneration in mice (Yoshida, T. et al., *J Clin Invest* (2005) 115: 2793-2800). Increases in Aβ deposition and supranuclear cataracts have been found in AD patients (Goldstein, L. E. et al., *Lancet* (2003) 361: 1258-1265). Compounds that reduce Aβ levels could reduce or prevent age-related macular degeneration.

Compounds which inhibit gamma secretase may also be useful in treating conditions associated with loss of myelination, for example multiple sclerosis (Watkins, T. A., et al., *Neuron* (2008) 60: 555-569).

A recent study by Georgetown University Medical Center researchers suggests that gamma-secretase inhibitors may prevent long-term damage from traumatic brain injury (Loane, D. J., et al., *Nature Medicine* (2009): 1-3).

A logical approach to reducing Aβ levels is to block the action of the secretases. A complementary approach is to selectively reduce production of Aβ1-42 by the action of certain compounds that serve to direct the γ-secretase-mediated cleavage of APP to instead produce shorter forms of Aβ. These shorter forms appear to aggregate less easily and solutions of the shorter forms of Aβ are less neurotoxic than solutions of Aβ1-42 (See Barten, Donna M.; Meredith, Jere E., Jr.; Zaczek, Robert; Houston, John G.; Albright, Charles F. Drugs in R&D (2006), 7(2), 87-97). Thus, compounds that selectively reduce Aβ1-42 production and their pharmaceutical compositions are beneficial agents that will prevent damage from overproduction of Aβ and are useful in treating Alzheimer's disease, Down syndrome, CAA, and inclusion body myositis, DLB, and other disorders where Aβ is overproduced.

SUMMARY OF THE INVENTION

In its first aspect the present disclosure provides a compound of formula (I)

$$\underset{H}{\overset{A}{\underset{B}{\diagdown}}\underset{N}{\diagdown}\underset{E,}{\overset{D}{\diagup}}}$$
(I)

or a pharmaceutically acceptable salt thereof, wherein

A is a five- or six-membered heteroaromatic ring containing from one to three heteroatoms independently selected from nitrogen, oxygen, and sulfur; wherein said heteroaromatic ring is optionally substituted with one or two groups selected from halo, haloC$_{1-6}$alkyl, hydroxy, amino, C$_{1-6}$alkoxy, and C$_{1-6}$alkyl;

B is selected from phenyl and pyridinyl, wherein the phenyl and pyridinyl are optionally substituted with one or two substituents independently selected from C$_{1-6}$alkoxy, C$_{1-6}$alkyl, C$_{1-3}$alkylamino-C$_{1-6}$alkoxy, cyano, C$_{1-3}$dialkylamino-C$_{1-6}$alkoxy, halo, haloC$_{1-6}$alkoxy, haloC$_{1-6}$alkyl, hydroxy, methylamino, and amino;

D is selected from

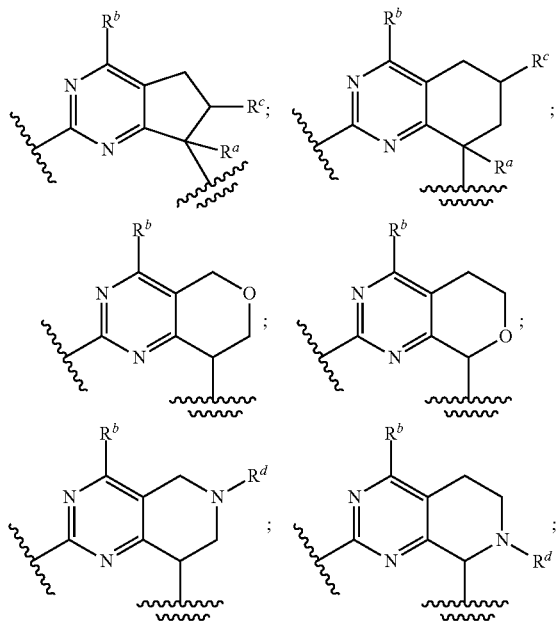

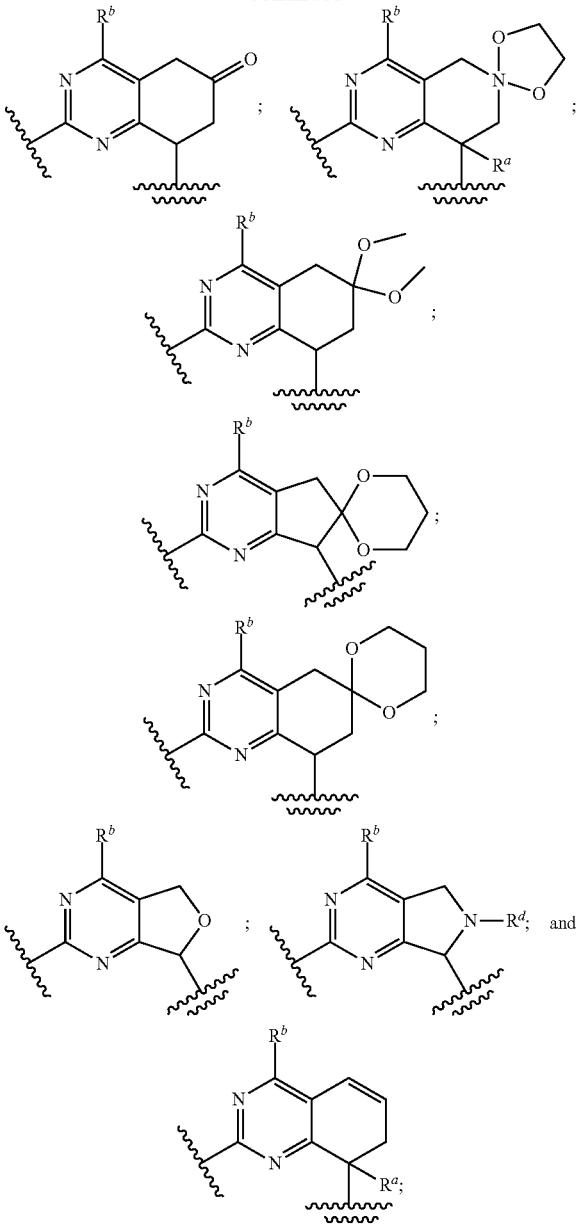

"$\xi$" denotes the point of attachment to the nitrogen atom of the parent molecule;

"$\sim\!\sim\!\sim$" denotes the point of attachment to the 'E' moiety;

R$^a$ is selected from hydrogen, C$_{1-6}$alkyl, C$_{2-6}$alkenyl, and hydroxy;

R$^b$ is —NR$^x$R$^y$, wherein R$^x$ and R$^y$ are independently selected from hydrogen, C$_{1-4}$alkoxy, C$_{1-4}$alkoxyC$_{1-4}$alkyl, C$_{1-4}$alkoxycarbonyl, C$_{1-6}$alkyl, C$_{3-7}$cycloalkyl, (C$_{3-7}$cycloalkyl)C$_{1-4}$alkyl, hydroxyC$_{1-4}$alkyl, and trideuteromethyl, wherein the alkyl part of the (C$_{3-7}$cycloalkyl)C$_{1-4}$alkyl can be optionally substituted with a C$_{1-4}$alkoxy group; or, R$^x$ and R$^y$, together with the nitrogen atom to which they are attached, form a four- to seven-membered monocyclic or bicyclic ring optionally containing one double bond and optionally containing one additional heteroatom selected from O, NR$^z$, and S; wherein R$^z$ is selected from hydrogen, C$_{1-6}$alkyl, and C$_{1-4}$alkoxycarbonyl; and wherein the ring is optionally substituted with one or two substituents independently selected from $C_{1-6}$alkoxy, $C_{1-6}$alkyl, halo, halo$C_{1-4}$alkyl, hydroxy, —NR$^f$R$^g$, oxo, spirocyclic dioxolanyl; wherein R$^f$ and R$^g$ are independently selected from hydrogen, $C_{1-4}$alkoxycarbonyl, and $C_{1-6}$alkyl;

R$^c$ is selected from hydrogen, $C_{1-4}$alkylsulfonyl, $C_{1-4}$alkylsulfonylamido, amino, $C_{1-4}$alkylamino, $C_{1-6}$dialkylamino, $C_{3-7}$cycloalkylamino, hydroxy, and $C_{1-4}$alkoxy;

R$^d$ is selected from hydrogen, $C_{1-6}$alkyl, $C_{1-4}$alkoxy$C_{1-4}$alkylcarbonyl, $C_{1-6}$alkoxycarbonyl, $C_{1-6}$alkylcarbonyl, $C_{1-6}$alkylsulfonyl, $C_{3-7}$cycloalkylsulfonyl, $C_{3-7}$cycloalkylcarbonyl, $C_{1-6}$dialkylamino$C_{1-4}$alkylcarbonyl, and halo$C_{1-4}$alkyl, wherein the alkyl part of the alkoxycarbonyl, the alkylcarbonyl, and the alkylsulfonyl are optionally substituted with one substituent selected from $C_{1-4}$dialkylamino, and $C_{1-4}$alkoxy; and E is selected from $C_{1-6}$alkyl, $C_{4-6}$cycloalkyl, $(C_{4-7}$cycloalkyl)$C_{1-4}$alkyl, benzyl, phenyl, and a five- to six-membered heteroaromatic ring containing one or two nitrogen atoms, wherein the phenyl, the phenyl part of the benzyl, and the heteroaromatic ring are each optionally substituted with one, two, or three substituents independently selected from $C_{1-6}$alkyl, $C_{1-6}$alkoxy, cyano, halo, halo $C_{1-6}$alkoxy, and halo$C_{1-6}$alkyl.

The present invention is directed to these, as well as other important ends, hereinafter described.

DETAILED DESCRIPTION OF THE EMBODIMENTS

In a first embodiment of the first aspect the present disclosure provides a compound of formula (I), or a pharmaceutically acceptable salt thereof, as set forth above wherein A is a five-membered heteroaromatic ring containing from one to three nitrogen atoms; and wherein said heteroaromatic ring is optionally substituted with one group selected from halo and $C_{1-6}$alkyl. In a second embodiment, B is selected from phenyl and pyridinyl, wherein the phenyl and pyridinyl are optionally substituted with one or two substituents independently selected from $C_{1-6}$alkoxy and halo. In a third embodiment, E is phenyl optionally substituted with one, two, or three substituents independently selected from $C_{1-6}$alkyl, $C_{1-6}$alkoxy, cyano, halo, halo$C_{1-6}$alkoxy, and halo$C_{1-6}$alkyl. In a fourth embodiment, D is selected from

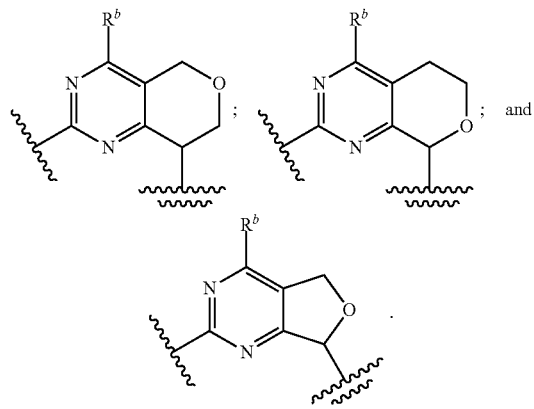

In a fifth embodiment, R$^b$ is —NR$^x$R$^y$, wherein R$^x$ and R$^y$ are independently selected from hydrogen, $C_{1-4}$alkoxy$C_{1-4}$alkyl, $C_{1-6}$alkyl, $C_{3-7}$cycloalkyl, hydroxy$C_{1-4}$alkyl, and trideuteromethyl, wherein the alkyl part of the $(C_{3-7}$cycloalkyl)$C_{1-4}$alkyl can be optionally substituted with a $C_{1-4}$alkoxy group.

In a sixth embodiment of the first aspect, the present disclosure provides a compound of formula (I), or a pharmaceutically acceptable salt thereof, wherein:

A is a five-membered heteroaromatic ring containing from one to three nitrogen atoms; wherein said heteroaromatic ring is optionally substituted with one group selected from halo and $C_{1-6}$alkyl;

B is selected from phenyl and pyridinyl, wherein the phenyl and pyridinyl are optionally substituted with one or two substituents independently selected from $C_{1-6}$alkoxy and halo;

E is phenyl optionally substituted with one, two, or three substituents independently selected from $C_{1-6}$alkyl, $C_{1-6}$alkoxy, cyano, halo, halo$C_{1-6}$alkoxy, and halo$C_{1-6}$alkyl;

D is selected from

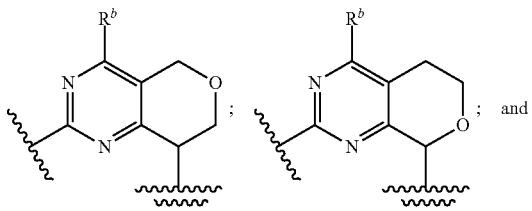

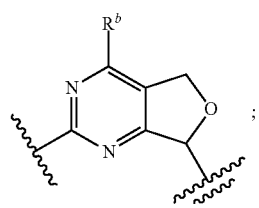

and

R$^b$ is —NR$^x$R$^y$, wherein R$^x$ and R$^y$, together with the nitrogen atom to which they are attached, form a four- to seven-membered monocyclic or bicyclic ring optionally containing one additional heteroatom selected from O and NR$^z$; wherein R$^z$ is selected from $C_{1-6}$alkyl, and $C_{1-4}$alkoxycarbonyl; and wherein the ring is optionally substituted with one or two substituents independently selected from $C_{1-6}$alkoxy, $C_{1-6}$alkyl, halo, halo$C_{1-4}$alkyl, hydroxy, —NR$^f$R$^g$, oxo, and spirocycle dioxolanyl; wherein R$^f$ and R$^g$ are independently selected from hydrogen, $C_{1-4}$alkoxycarbonyl, and $C_{1-6}$alkyl.

In a seventh embodiment of the first aspect, the present disclosure provides a compound of formula (I), or a pharmaceutically acceptable salt thereof, wherein:

A is a five-membered heteroaromatic ring containing from one to three nitrogen atoms; wherein said heteroaromatic ring is optionally substituted with one group selected from halo and $C_{1-6}$alkyl;

B is selected from phenyl and pyridinyl, wherein the phenyl and pyridinyl are optionally substituted with one or two substituents independently selected from $C_{1-6}$alkoxy and halo;

E is phenyl optionally substituted with one, two, or three substituents independently selected from $C_{1-6}$alkyl, $C_{1-6}$alkoxy, cyano, halo, halo$C_{1-6}$alkoxy, and halo$C_{1-6}$alkyl; and

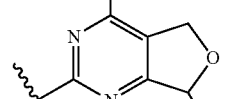

D is selected from

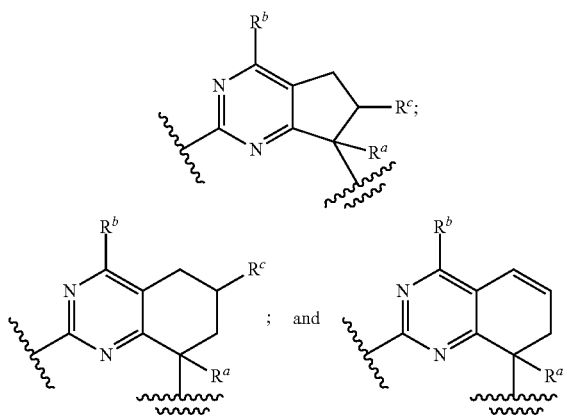

In an eighth embodiment of the first aspect, the present disclosure provides a compound of formula (I), or a pharmaceutically acceptable salt thereof, wherein:

A is a five-membered heteroaromatic ring containing from one to three nitrogen atoms; wherein said heteroaromatic ring is optionally substituted with one group selected from halo and $C_{1-6}$alkyl;

B is selected from phenyl and pyridinyl, wherein the phenyl and pyridinyl are optionally substituted with one or two substituents independently selected from $C_{1-6}$alkoxy and halo;

E is phenyl optionally substituted with one, two, or three substituents independently selected from $C_{1-6}$alkyl, $C_{1-6}$alkoxy, cyano, halo, halo$C_{1-6}$alkoxy, and halo$C_{1-6}$alkyl;

D is selected from

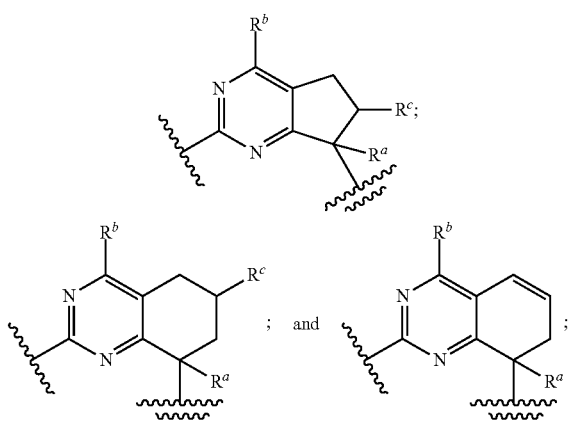

and $R^b$ is —$NR^xR^y$, wherein $R^x$ and $R^y$ are independently selected from hydrogen, $C_{1-4}$alkoxy$C_{1-4}$alkyl, $C_{1-6}$alkyl, $C_{3-7}$cycloalkyl, hydroxy$C_{1-4}$alkyl, and trideuteromethyl, wherein the alkyl part of the ($C_{3-7}$cycloalkyl)$C_{1-4}$alkyl can be optionally substituted with a $C_{1-4}$alkoxy group.

In a ninth embodiment of the first aspect, the present disclosure provides a compound of formula (I), or a pharmaceutically acceptable salt thereof, wherein:

A is a five-membered heteroaromatic ring containing from one to three nitrogen atoms; wherein said heteroaromatic ring is optionally substituted with one group selected from halo and $C_{1-6}$alkyl;

B is selected from phenyl and pyridinyl, wherein the phenyl and pyridinyl are optionally substituted with one or two substituents independently selected from $C_{1-6}$alkoxy and halo;

E is phenyl optionally substituted with one, two, or three substituents independently selected from $C_{1-6}$alkyl, $C_{1-6}$alkoxy, cyano, halo, halo$C_{1-6}$alkoxy, and halo$C_{1-6}$alkyl;

D is selected from

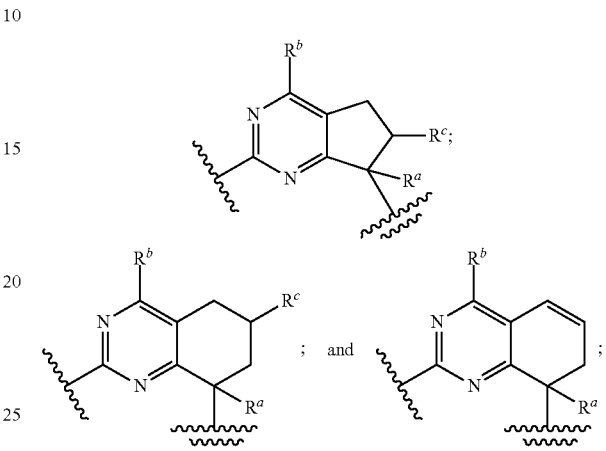

and $R^b$ is —$NR^xR^y$, wherein $R^x$ and $R^y$, together with the nitrogen atom to which they are attached, form a four- to seven-membered monocyclic or bicyclic ring optionally containing one additional heteroatom selected from O and $NR^z$; wherein $R^z$ is selected from $C_{1-6}$alkyl, and $C_{1-4}$alkoxycarbonyl; and wherein the ring is optionally substituted with one or two substituents independently selected from $C_{1-6}$alkoxy, $C_{1-6}$alkyl, halo, halo$C_{1-4}$alkyl, hydroxy, —$NR^fR^g$, oxo, and spirocycle dioxolanyl; wherein $R^f$ and $R^g$ are independently selected from hydrogen, $C_{1-4}$alkoxycarbonyl, and $C_{1-6}$alkyl.

In a tenth embodiment of the first aspect, the present disclosure provides a compound of formula (I), or a pharmaceutically acceptable salt thereof, wherein:

A is a five-membered heteroaromatic ring containing from one to three nitrogen atoms; wherein said heteroaromatic ring is optionally substituted with one group selected from halo and $C_{1-6}$alkyl;

B is selected from phenyl and pyridinyl, wherein the phenyl and pyridinyl are optionally substituted with one or two substituents independently selected from $C_{1-6}$alkoxy and halo;

E is phenyl optionally substituted with one, two, or three substituents independently selected from $C_{1-6}$alkyl, $C_{1-6}$alkoxy, cyano, halo, halo$C_{1-6}$alkoxy, and halo$C_{1-6}$alkyl; and D is selected from

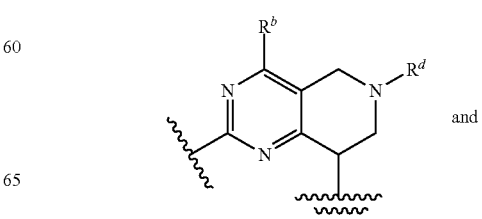

and

-continued

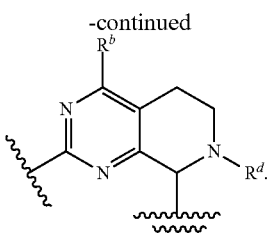

In an eleventh embodiment of the first aspect, the present disclosure provides a compound of formula (I), or a pharmaceutically acceptable salt thereof, wherein:

A is a five-membered heteroaromatic ring containing from one to three nitrogen atoms; wherein said heteroaromatic ring is optionally substituted with one group selected from halo and $C_{1-6}$alkyl;

B is selected from phenyl and pyridinyl, wherein the phenyl and pyridinyl are optionally substituted with one or two substituents independently selected from $C_{1-6}$alkoxy and halo;

E is phenyl optionally substituted with one, two, or three substituents independently selected from $C_{1-6}$alkyl, $C_{1-6}$alkoxy, cyano, halo, halo$C_{1-6}$alkoxy, and halo$C_{1-6}$alkyl;

D is selected from

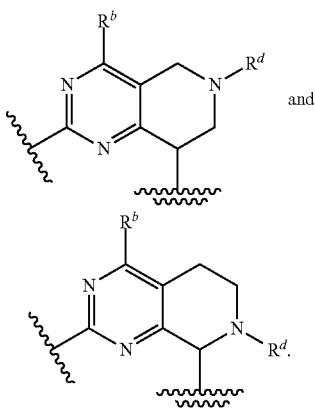

and $R^b$ is —$NR^xR^y$, wherein $R^x$ and $R^y$ are independently selected from hydrogen, $C_{1-4}$alkoxy$C_{1-4}$alkyl, $C_{1-6}$alkyl, $C_{3-7}$cycloalkyl, hydroxy$C_{1-4}$alkyl, and trideuteromethyl, wherein the alkyl part of the ($C_{3-7}$cycloalkyl)$C_{1-4}$alkyl can be optionally substituted with a $C_{1-4}$alkoxy group.

In a twelfth embodiment of the first aspect, the present disclosure provides a compound of formula (I), or a pharmaceutically acceptable salt thereof, wherein:

A is a five-membered heteroaromatic ring containing from one to three nitrogen atoms; wherein said heteroaromatic ring is optionally substituted with one group selected from halo and $C_{1-6}$alkyl;

B is selected from phenyl and pyridinyl, wherein the phenyl and pyridinyl are optionally substituted with one or two substituents independently selected from $C_{1-6}$alkoxy and halo;

E is phenyl optionally substituted with one, two, or three substituents independently selected from $C_{1-6}$alkyl, $C_{1-6}$alkoxy, cyano, halo, halo$C_{1-6}$alkoxy, and halo$C_{1-6}$alkyl;

D is selected from

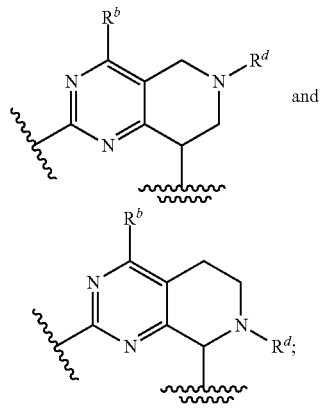

and $R^b$ is —$NR^xR^y$, wherein $R^x$ and $R^y$, together with the nitrogen atom to which they are attached, form a four- to seven-membered monocyclic or bicyclic ring optionally containing one additional heteroatom selected from O and $NR^z$; wherein $R^z$ is selected from $C_{1-6}$alkyl, and $C_{1-4}$alkoxycarbonyl; and wherein the ring is optionally substituted with one or two substituents independently selected from $C_{1-6}$alkoxy, $C_{1-6}$alkyl, halo, halo$C_{1-4}$alkyl, hydroxy, —$NR^f R^g$, oxo, and spirocycle dioxolanyl; wherein $R^f$ and $R^g$ are independently selected from hydrogen, $C_{1-4}$alkoxycarbonyl, and $C_{1-6}$alkyl.

In a thirteenth embodiment of the first aspect, the definition of A is expanded to also include acyl, acetyl, nitrile, $CF_3$, bromo, and $CH_2CN$; and the heteroaromatic ring may be additionally substituted with $CHCF_2$ and/or CN.

In a fourteenth embodiment of the first aspect, B may also include pyrimidinyl.

In a fifteenth embodiment of the first aspect, $R^b$ as part of D may also include $SO_2C_{1-6}$alkyl, acetyl, and phenyl optionally substituted with 1-3$C_{1-6}$alkyl; and further wherein the ring as part of $R^z$ can also include spirocyclic tetrahydrofuranyl. In addition, D may also include

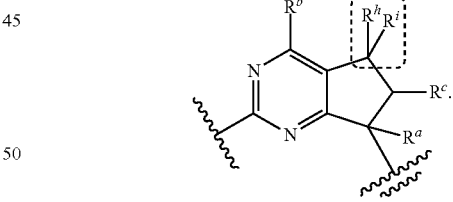

wherein $R^h$, Ri=H, OH, or taken together to form C=O, C=N—OH, or C=N—O$C_{1-6}$alkyl.

In a second aspect, the present disclosure provides a pharmaceutical composition for the treatment of disorders responsive to the reduction of β-amyloid peptide production comprising a therapeutically effective amount of a compound of formula (I), or a pharmaceutically acceptable salt thereof, in association with a pharmaceutically acceptable carrier or diluent.

In a third aspect, the present disclosure provides a method for the treatment of disorders responsive to the reduction of β-amyloid peptide production in a mammal in need thereof, which comprises administering to said mammal a therapeutically effective amount of a compound of formula (I), or a pharmaceutically acceptable salt thereof. In a first embodiment of the first aspect said disorder is selected from Alzheimer's Disease (AD), Down Syndrome, mild cognitive impairment (MCI), cerebral amyloid angiopathy (CAA), dementia with Lewy bodies (DLB), amyotrophic lateral sclerosis (ALS-D), inclusion body myositis (IBM), age-related macular degeneration, and cancer. In a second embodiment of the third aspect, said disorder is selected from Alzheimer's Disease and Down Syndrome. In a third embodiment of the third aspect, said disorder is Alzheimer's Disease.

Other aspects of the present disclosure may include suitable combinations of embodiments disclosed herein.

Yet other aspects and embodiments may be found in the description provided herein.

The description of the present disclosure herein should be construed in congruity with the laws and principals of chemical bonding. In some instances it may be necessary to remove a hydrogen atom in order accommodate a substituent at any given location.

It should be understood that the compounds encompassed by the present disclosure are those that are suitably stable for use as pharmaceutical agent.

It is intended that the definition of any substituent or variable at a particular location in a molecule be independent of its definitions elsewhere in that molecule.

All patents, patent applications, and literature references cited in the specification are herein incorporated by reference in their entirety. In the case of inconsistencies, the present disclosure, including definitions, will prevail.

In some instances, the number of carbon atoms in any particular group is denoted before the recitation of the group. For example, the term "halo$C_{1-6}$alkoxy" denotes a haloalkoxy group containing one to six carbon atoms and the term "$C_{1-4}$alkoxy$C_{1-2}$alkyl" denotes an alkoxy group containing one to four alkoxy groups attached to the parent molecular moiety through an alkyl group of one or two carbon atoms. Where these designations exist they supersede all other definitions contained herein.

As used herein, the singular forms "a", "an", and "the" include plural reference unless the context clearly dictates otherwise.

The term "alkoxy," as used herein, refers to an alkyl group attached to the parent molecular moiety through an oxygen atom.

The term "alkoxyalkyl," as used herein, refers to an alkyl group substituted with one, two, or three alkoxy groups.

The term "alkoxyalkylcarbonyl," as used herein, refers to an alkoxyalkyl group attached to the parent molecular moiety through a carbonyl group.

The term "alkoxycarbonyl," as used herein, refers to an alkoxy group attached to the parent molecular moiety through a carbonyl group.

The term "alkyl," as used herein, refers to a group derived from a straight or branched chain saturated hydrocarbon containing from one to ten carbon atoms.

The term "alkylamino," as used herein, refers to —NHR$^x$, wherein R$^x$ is an alkyl group.

The term "alkylaminoalkoxy," as used herein, refers to an alkylamino group attached to the parent molecular moiety through an alkoxy group.

The term "alkylcarbonyl," as used herein, refers to an alkyl group attached to the parent molecular moiety through a carbonyl group.

The term "alkylsulfonyl," as used herein, refers to an alkyl group attached to the parent molecular moiety through a sulfonyl group.

The term "alkylsulfonylamido," as used herein refers to —C(O)NHS(O)$_2$R$^x$ wherein R$^x$ is an alkyl group.

The term "amino," as used herein, refers to —NH$_2$.

The term "carbonyl," as used herein, refers to —C(O)—.

The term "cyano," as used herein, refers to —CN.

The term "cycloalkyl," as used herein, refers to a saturated monocyclic hydrocarbon ring system having three to fourteen carbon atoms and zero heteroatoms.

The term "(cycloalkyl)alkyl," as used herein, refers to an alkyl group substituted with one, two, or three cycloalkyl groups.

The term "cycloalkylamino," as used herein, refers to —NHR$^x$ wherein R$^x$ is a cycloalkyl group.

The term "cycloalkylcarbonyl," as used herein, refers to a cycloalkyl group attached to the parent molecular moiety through a carbonyl group.

The term "cycloalkylsulfonyl," as used herein, refers to a cycloalkyl group attached to the parent molecular moiety through a sulfonyl group.

The term "dialkylamino," as used herein, refers to —NR$^x$R$^y$, wherein R$^x$ and R$^y$ are each alkyl groups.

The term "dialkylaminoalkoxy," as used herein, refers to a dialkylamino group attached to the parent molecular moiety through an alkoxy group.

The term "dialkylaminoalkyl," as used herein, refers to an alkyl group substituted with one, two, or three dialkylamino groups.

The term "dialkylaminoalkylcarbonyl," as used herein, refers to a dialkylaminoalkyl group attached to the parent molecular moiety through a carbonyl group.

The terms "halo" and "halogen," as used herein, refer to F, Cl, Br, and I.

The term "haloalkoxy," as used herein, refers to a haloalkyl group attached to the parent molecular moiety through an oxygen atom.

The term "haloalkyl," as used herein, refers to an alkyl group substituted with one, two, three, or four halogen atoms.

The term "hydroxy," as used herein, refers to —OH.

The term "hydroxyalkyl," as used herein, refers to an alkyl group substituted with one, two, or three hydroxy groups.

The term "methylamino," as used herein, refers to —NHCH$_3$.

The term "oxo," as used herein, refers to =O.

The term "sulfonyl," as used herein, refers to —SO$_2$—.

It should be understood that the disclosure encompasses all stereochemical forms, or mixtures thereof, which possess the ability to reduce β-amyloid peptide production.

Certain compounds of the present disclosure may also exist in different stable conformational forms which may be separable. Torsional asymmetry due to restricted rotation about an asymmetric single bond, for example because of steric hindrance or ring strain, may permit separation of different conformers. The present disclosure includes each conformational isomer of these compounds and mixtures thereof.

The present disclosure is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}$C and $^{14}$C. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Certain compounds of the present disclosure may exist in zwitterionic form and the present disclosure includes each zwitterionic form of these compounds and mixtures thereof.

The compounds of the present disclosure can exist as pharmaceutically acceptable salts. The term "pharmaceutically acceptable salt," as used herein, represents salts or zwitterionic forms of the compounds of the present disclosure which are water or oil-soluble or dispersible, which are, within the scope of sound medical judgment, suitable for use in contact with the tissues of patients without excessive toxicity, irritation, allergic response, or other problem or complication commensurate with a reasonable benefit/risk ratio, and are effective for their intended use. The salts can be prepared during the final isolation and purification of the compounds or separately by reacting a suitable nitrogen atom with a suitable acid. Representative acid addition salts include acetate, adipate, alginate, citrate, aspartate, benzoate, benzenesulfonate, bisulfate, butyrate, camphorate, camphorsulfonate; digluconate, glycerophosphate, hemisulfate, heptanoate, hexanoate, formate, fumarate, hydrochloride, hydrobromide, hydroiodide, 2-hydroxyethanesulfonate, lactate, maleate, mesitylenesulfonate, methanesulfonate, naphthylenesulfonate, nicotinate, 2-naphthalenesulfonate, oxalate, palmoate, pectinate, persulfate, 3-phenylproprionate, picrate, pivalate, propionate, succinate, tartrate, trichloroacetate, trifluoroacetate, phosphate, glutamate, bicarbonate, para-toluenesulfonate, and undecanoate. Examples of acids which can be employed to form pharmaceutically acceptable addition salts include inorganic acids such as hydrochloric, hydrobromic, sulfuric, and phosphoric, and organic acids such as oxalic, maleic, succinic, and citric.

Basic addition salts can be prepared during the final isolation and purification of the compounds by reacting a carboxy group with a suitable base such as the hydroxide, carbonate, or bicarbonate of a metal cation or with ammonia or an organic primary, secondary, or tertiary amine The cations of pharmaceutically acceptable salts include lithium, sodium, potassium, calcium, magnesium, and aluminum, as well as nontoxic quaternary amine cations such as ammonium, tetramethylammonium, tetraethylammonium, methylamine, dimethylamine, trimethylamine, triethylamine, diethylamine, ethylamine, tributylamine, pyridine, N,N-dimethylaniline, N-methylpiperidine, N-methylmorpholine, dicyclohexylamine, procaine, dibenzylamine, N,N-dibenzylphenethylamine, and N,N'-dibenzylethylenediamine Other representative organic amines useful for the formation of base addition salts include ethylenediamine, ethanolamine, diethanolamine, piperidine, and piperazine.

When it is possible that, for use in therapy, therapeutically effective amounts of a compound of formula (I), as well as pharmaceutically acceptable salts thereof, may be administered as the raw chemical, it is possible to present the active ingredient as a pharmaceutical composition. Accordingly, the disclosure further provides pharmaceutical compositions, which include therapeutically effective amounts of compounds of formula (I) or pharmaceutically acceptable salts thereof, and one or more pharmaceutically acceptable carriers, diluents, or excipients. The compounds of formula (I) and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of formula (I), or a pharmaceutically acceptable salt thereof, with one or more pharmaceutically acceptable carriers, diluents, or excipients.

The dosage of the compounds of Formula I to achieve a therapeutic effect will depend not only on such factors as the age, weight and sex of the patient and mode of administration, but also on the degree of $\beta$-AP reduction desired and the potency of the particular compound being utilized for the particular disorder of disease concerned. It is also contemplated that the treatment and dosage of the particular compound may be administered in unit dosage form and that the unit dosage form would be adjusted accordingly by one skilled in the art to reflect the relative level of activity. The decision as to the particular dosage to be employed (and the number of times to be administered per day) is within the discretion of the physician, and may be varied by titration of the dosage to the particular circumstances of this invention to produce the desired therapeutic effect.

A suitable dose of a compound of Formula I or pharmaceutical composition thereof for a mammal, including man, suffering from, or likely to suffer from any condition related to $\beta$-AP production as described herein, generally the daily dose will be from about 0.05 mg/kg to about 10 mg/kg and preferably, about 0.1 to 2 mg/kg when administered parenterally. For oral administration, the dose may be in the range from about 0.1 to about 75 mg/kg and preferably from 0.1 to 10 mg/kg body weight. The active ingredient will preferably be administered in equal doses from one to four times a day. However, usually a small dosage is administered, and the dosage is gradually increased until the optimal dosage for the host under treatment is determined In accordance with good clinical practice, it is preferred to administer the instant compounds at a concentration level that will produce an effective anti-amyloid effect without causing any harmful or untoward side effects. However, it will be understood that the amount of the compound actually administered will be determined by a physician, in the light of the relevant circumstances including the condition to be treated, the choice of compound of be administered, the chosen route of administration, the age, weight, and response of the individual patient, and the severity of the patient's symptoms.

Pharmaceutical formulations may be adapted for administration by any appropriate route, for example by the oral (including buccal or sublingual), rectal, nasal, topical (including buccal, sublingual, or transdermal), vaginal, or parenteral (including subcutaneous, intracutaneous, intramuscular, intra-articular, intrasynovial, intrasternal, intrathecal, intralesional, intravenous, or intradermal injections or infusions) route. Such formulations may be prepared by any method known in the art of pharmacy, for example by bringing into association the active ingredient with the carrier(s) or excipient(s).

Pharmaceutical formulations adapted for oral administration may be presented as discrete units such as capsules or tablets; powders or granules; solutions or suspensions in aqueous or non-aqueous liquids; edible foams or whips; or oil-in-water liquid emulsions or water-in-oil emulsions.

For instance, for oral administration in the form of a tablet or capsule, the active drug component can be combined with an oral, non-toxic pharmaceutically acceptable inert carrier such as ethanol, glycerol, water, and the like. Powders are prepared by comminuting the compound to a suitable fine size and mixing with a similarly comminuted pharmaceutical carrier such as an edible carbohydrate, as, for example, starch or mannitol. Flavoring, preservative, dispersing, and coloring agent can also be present.

Capsules are made by preparing a powder mixture, as described above, and filling formed gelatin sheaths. Glidants and lubricants such as colloidal silica, talc, magnesium stearate, calcium stearate, or solid polyethylene glycol can be added to the powder mixture before the filling operation. A disintegrating or solubilizing agent such as agar-agar, calcium carbonate, or sodium carbonate can also be added to improve the availability of the medicament when the capsule is ingested.

Moreover, when desired or necessary, suitable binders, lubricants, disintegrating agents, and coloring agents can also be incorporated into the mixture. Suitable binders include starch, gelatin, natural sugars such as glucose or beta-lactose, corn sweeteners, natural and synthetic gums such as acacia, tragacanth or sodium alginate, carboxymethylcellulose, polyethylene glycol, and the like. Lubricants used in these dosage forms include sodium oleate, sodium chloride, and the like. Disintegrators include, without limitation, starch, methyl cellulose, agar, betonite, xanthan gum, and the like. Tablets are formulated, for example, by preparing a powder mixture, granulating or slugging, adding a lubricant and disintegrant, and pressing into tablets. A powder mixture is prepared by mixing the compound, suitable comminuted, with a diluent or base as described above, and optionally, with a binder such as carboxymethylcellulose, an aliginate, gelating, or polyvinyl pyrrolidone, a solution retardant such as paraffin, a resorption accelerator such as a quaternary salt and/or and absorption agent such as betonite, kaolin, or dicalcium phosphate. The powder mixture can be granulated by wetting with a binder such as syrup, starch paste, acadia mucilage, or solutions of cellulosic or polymeric materials and forcing through a screen. As an alternative to granulating, the powder mixture can be run through the tablet machine and the result is imperfectly formed slugs broken into granules. The granules can be lubricated to prevent sticking to the tablet forming dies by means of the addition of stearic acid, a stearate salt, talc, or mineral oil. The lubricated mixture is then compressed into tablets. The compounds of the present disclosure can also be combined with a free flowing inert carrier and compressed into tablets directly without going through the granulating or slugging steps. A clear or opaque protective coating consisting of a sealing coat of shellac, a coating of sugar or polymeric material, and a polish coating of wax can be provided. Dyestuffs can be added to these coatings to distinguish different unit dosages.

Oral fluids such as solution, syrups, and elixirs can be prepared in dosage unit form so that a given quantity contains a predetermined amount of the compound. Syrups can be prepared by dissolving the compound in a suitably flavored aqueous solution, while elixirs are prepared through the use of a non-toxic vehicle. Solubilizers and emulsifiers such as ethoxylated isostearyl alcohols and polyoxyethylene sorbitol ethers, preservatives, flavor additive such as peppermint oil or natural sweeteners, or saccharin or other artificial sweeteners, and the like can also be added.

Where appropriate, dosage unit formulations for oral administration can be microencapsulated. The formulation can also be prepared to prolong or sustain the release as for example by coating or embedding particulate material in polymers, wax, or the like.

The compounds of formula (I), and pharmaceutically acceptable salts thereof, can also be administered in the form of liposome delivery systems, such as small unilamellar vesicles, large unilamellar vesicles, and multilamellar vesicles. Liposomes can be formed from a variety of phopholipids, such as cholesterol, stearylamine, or phophatidylcholines.

The compounds of formula (I) and pharmaceutically acceptable salts thereof may also be delivered by the use of monoclonal antibodies as individual carriers to which the compound molecules are coupled. The compounds may also be coupled with soluble polymers as targetable drug carriers. Such polymers can include polyvinylpyrrolidone, pyran copolymer, polyhydroxypropylmethacrylamidephenol, polyhydroxyethylaspartamidephenol, or polyethyleneoxide-polylysine substituted with palitoyl residues. Furthermore, the compounds may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates, and cross-linked or amphipathic block copolymers of hydrogels.

Pharmaceutical formulations adapted for transdermal administration may be presented as discrete patches intended to remain in intimate contact with the epidermis of the recipient for a prolonged period of time. For example, the active ingredient may be delivered from the patch by iontophoresis as generally described in Pharmaceutical Research, 3(6), 318 (1986).

Pharmaceutical formulations adapted for topical administration may be formulated as ointments, creams, suspensions, lotions, powders, solutions, pastes, gels, sprays, aerosols, or oils.

For treatments of the eye or other external tissues, for example mouth and skin, the formulations are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in oil base.

Pharmaceutical formulations adapted for topical administrations to the eye include eye drops wherein the active ingredient is dissolved or suspended in a suitable carrier, especially an aqueous solvent.

Pharmaceutical formulations adapted for topical administration in the mouth include lozenges, pastilles, and mouth washes.

Pharmaceutical formulations adapted for rectal administration may be presented as suppositories or as enemas.

Pharmaceutical formulations adapted for nasal administration wherein the carrier is a solid include a course powder which is administered in the manner in which snuff is taken, i.e., by rapid inhalation through the nasal passage from a container of the powder held close up to the nose. Suitable formulations wherein the carrier is a liquid, for administration as a nasal spray or nasal drops, include aqueous or oil solutions of the active ingredient.

Pharmaceutical formulations adapted for administration by inhalation include fine particle dusts or mists, which may be generated by means of various types of metered, dose pressurized aerosols, nebulizers, or insufflators.

Pharmaceutical formulations adapted for vaginal administration may be presented as pessaries, tampons, creams, gels, pastes, foams, or spray formulations.

Pharmaceutical formulations adapted for parenteral administration include aqueous and non-aqueous sterile injection solutions which may contain anti-oxidants, buffers, bacteriostats, and soutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

It should be understood that in addition to the ingredients particularly mentioned above, the formulations may include other agents conventional in the art having regard to the type of formulation in question, for example those suitable for oral administration may include flavoring agents.

The present disclosure will now be described in connection with certain embodiments which are not intended to limit its scope. On the contrary, the present disclosure covers all alternatives, modifications, and equivalents as can be included within the scope of the claims. Thus, the following examples, which include specific embodiments, will illustrate one practice of the present disclosure, it being understood that the examples are for the purposes of illustration of certain embodiments and are presented to provide what is believed to be the most useful and readily understood description of its procedures and conceptual aspects.

The compounds of the present application can be synthesized using the methods described below, together with synthetic methods known in the art of synthetic organic chemistry, or variations thereon as appreciated by those skilled in the art. Preferred methods include, but are not limited to, those described below. All references cited herein are hereby incorporated in their entirety herein by reference.

The compounds may be prepared using the reactions and techniques described in this section. The reactions are performed in solvents appropriate to the reagents and materials employed and are suitable for the transformations being effected. Also, in the description of the synthetic methods described below, it is to be understood that all proposed reaction conditions, including choice of solvent, reaction atmosphere, reaction temperature, duration of the experiment and workup procedures, are chosen to be the conditions standard for that reaction, which should be readily recognized by one skilled in the art. It is understood by one skilled in the art of organic synthesis that the functionality present on various portions of the molecule must be compatible with the reagents and reactions proposed. Such restrictions to the substituents which are compatible with the reaction conditions will be readily apparent to one skilled in the art and alternate methods must then be used.

The starting materials useful to synthesize the compounds of the present disclosure are known to those skilled in the art and can be readily manufactured or are commercially available.

The following methods set forth below are provided for illustrative purposes and are not intended to limit the scope of the claims. It will be recognized that it may be necessary to prepare such a compound in which a functional group is protected using a conventional protecting group then to remove the protecting group to provide a compound of the present disclosure. The details concerning the use of protecting groups in accordance with the present disclosure are known to those skilled in the art.

The abbreviations used in the present application, including particularly in the illustrative schemes and examples which follow, are well-known to those skilled in the art. Some of the abbreviations used are as follows:

Chemical abbreviations used in the specification and Examples are defined as follows: "dba" for dibenzylideneacetone; "t-Bu" for tert-butyl; "DCM" for dichloromethane; "LDA" for lithium diisopropylamide; "Ph" for phenyl; "TFA" for trifluoracetic acid; "Et" for ethyl; "DMF" for N,N-dimethylformamide; "OAc" for acetate; "h" for hours, "min" for minutes; and "THF" for tetrahydrofuran.

Examples of methods useful for the production of compounds of this disclosure are illustrated in Schemes 1-24. Schemes 1-3 outline different routes for the synthesis of substituted aniline fragments used in the preparation of the title compounds. As illustrated in Scheme 1, a variety of substituted heterocycles 1, including but not limited to 1H-imidazole, 4-methyl-1H-imidazole, 4-chloro-1H-imidazole, 4-(difluoromethyl)-1H-imidazole can be added to substituted chloro- or fluoronitroarenes 2, including but not limited to 2-chloro-4-nitroanisole, under basic conditions to provide heteroaryl substituted nitroarenes 3. Reduction of the compounds 3 using reagents including iron in acidic medium or catalytic hydrogenation, employing catalysts such as palladium on carbon or other catalysts known to one skilled in the art, affords substituted anilines 4. While Scheme 1 illustrates the preparation of 4-(1H-imidazol-1-yl)anilines 4, it should be recognized to one skilled in the art that this method is widely applicable to the synthesis of other 4-heteroarylanilines, including but not limited to variously substituted 4-(1H-1,2,4-triazol-1-yl)anilines and 4-(1H-1,2,3-triazol-1-yl)anilines. In addition, substituted nitropyridines can be used in place of the nitroarenes of formula 2 to ultimately provide amino-substituted pyridines.

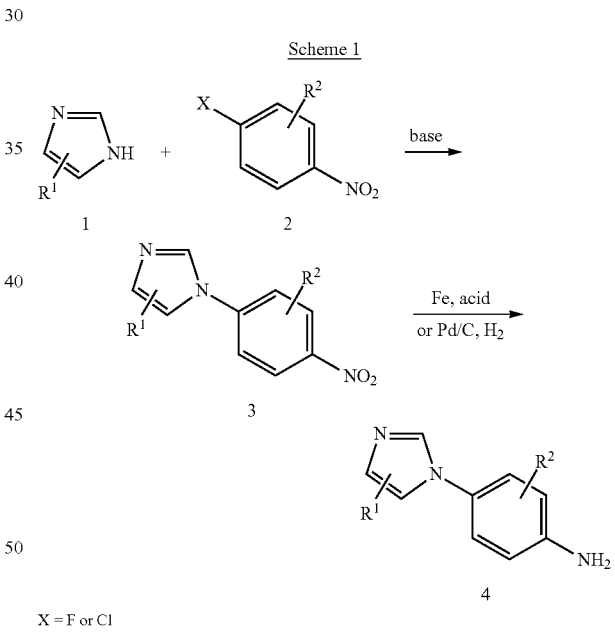

Scheme 1

X = F or Cl

Additional procedures for creating substituted anilines rely on the palladium-catalyzed coupling of aryl halides or heteroaryl halides to boronic acids (the Suzuki coupling reaction). As shown in Scheme 2, biaryl anilines 10 and 11, and their nitro precursors 8 and 9, can be created by the coupling of an aryl or heteroaryl boronic esters 5 and 7, respectively, to substituted aryl halides 6, including 1-bromo-2-methoxy-4-nitrobenzene. Alternatively, the coupling partners can be reversed as is shown in Scheme 3, where coupling of an aryl halide 12 or heteroaryl halide 14 to the boronic ester of the nitro arene 13 creates the substituted nitro arenes 8 and 9, respectively.

Scheme 2

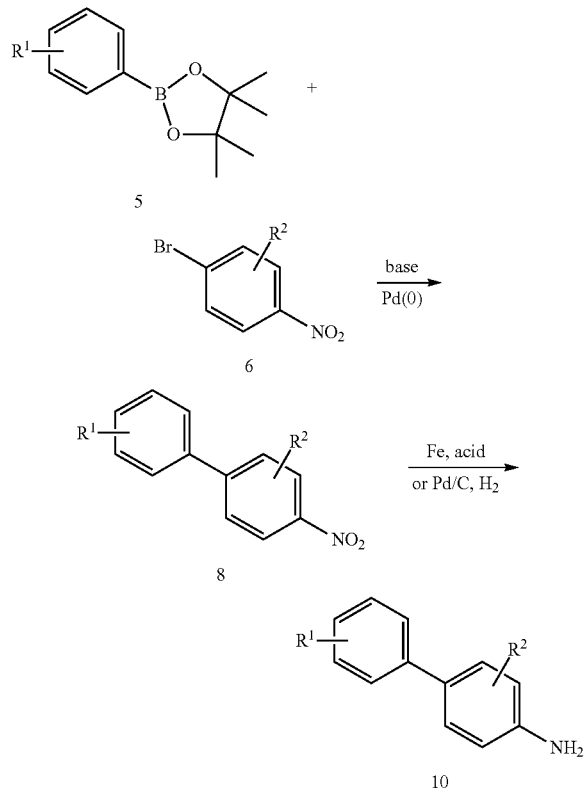

Z = CH, N, O, S
n = 1, 2

Scheme 3

Z = CH, N, O, S
n = 1, 2

These general reaction schemes are intended as illustrations of a general reaction process that is highly tolerant of a variety of functional groups, and these processes are not limited by the specific structures shown in Schemes 2 and 3. Those skilled in the art will also recognize that similar processes including the Stille coupling of aryl or heteroaryl halides and aryl or heteroaryl stannanes are also excellent processes to prepare the necessary anilines or their nitro precursors.

The following schemes outline different routes for the synthesis of 2,4-dichloro-7-aryl-6,7-dihydro-5H-cyclopenta[d]pyrimidines used in the preparation of the title compounds. As illustrated on Scheme 4, cyclopentanone 15 can react with a variety of arylmagnesium halides to produce tertiary alcohols 16. In the presence of dehydrating agents, such as mineral acids or thionyl chloride, these tertiary alcohols can undergo elimination of water to yield olefins 17. Upon treatment with peroxidizing agents, such as performic acid, olefins 17 can be transformed to 2-arylcyclopentanones 18. Abu Thaher, B.; Koch, P.; Del Amo, V.; Knochel, P.; Laufer, S. *Synthesis* 2008, 2, 225-228.

Scheme 4

-continued

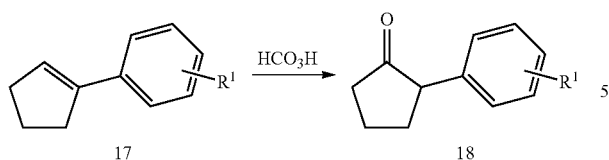

Alternatively, as indicated in Scheme 5, 2-arylcyclopentanones 18 can be prepared by treatment of cyclopenteneoxide 19 with various arylmagnesium halides, in the presence of copper salts, such as copper iodide, followed by oxidation of resulting alcohols 20. The said oxidation can be carried out by a number of oxidation agents known to those skilled in the arts, with superior results achieved by the use of Dess-Martin periodinane. Dess, D. B.; Martin, J. C. *J. Org. Chem.* 1983, 48, 4155-4156.

Scheme 5

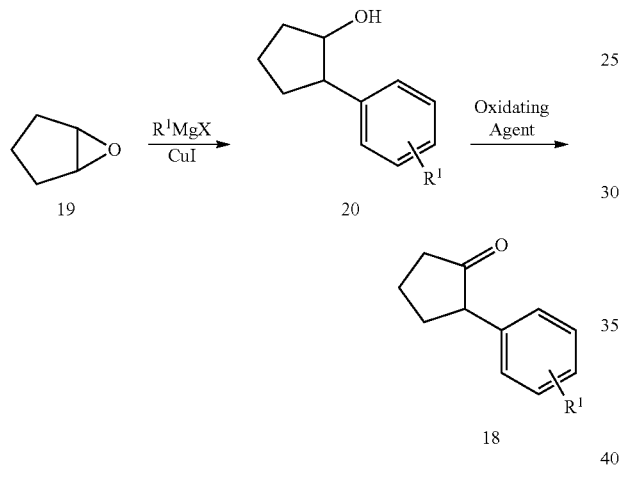

Additional ketones useful in the preparation of compounds of claim 1 can be prepared using the method described in 0. Dirat et al, *Tetrahedron Letters,* 2006, 47, 1295. This method, described in Scheme 6, relies on alpha-arylation (Fox et al, *Journal of the American Chemical Society,* 2000, 122, 1360) of available ketones 21 that incorporate acetals or ketals at the 4-position. The corresponding ketone starting materials 21 are available commercially or can easily be prepared by those skilled in the art, and a variety of acetals can be used, including the shown ethylene glycol ketal or ketals of other alcohols including 1,3-propanediol, methanol, ethanol, and others. This chemistry works equally well to produce unsubstituted alpha-aryl ketones 24.

Scheme 6

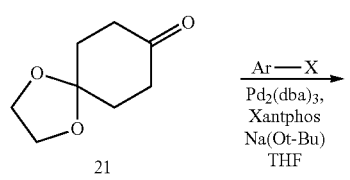

-continued

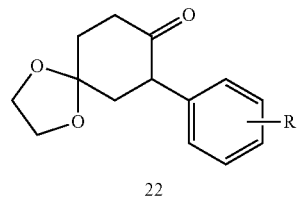

where X = Br, I

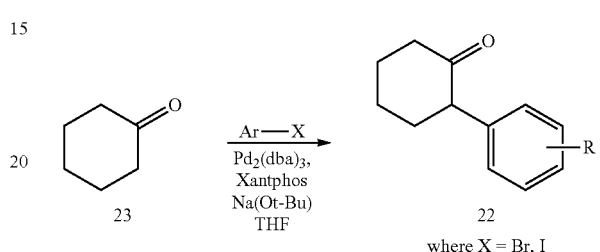

where X = Br, I

Additional alpha-aryl ketones can be prepared using the chemistry shown in Scheme 7, where tetrahydro-4H-pyran-4-one is brominated, typically using bromine in dichloromethane or pyrrolidine hydrotribromide as a brominating agent. The resulting alpha-bromo ketone can then be reacted with a Grignard reagent, and after migration of the aryl group the desired alpha-aryl ketone 27 is obtained.

Scheme 7

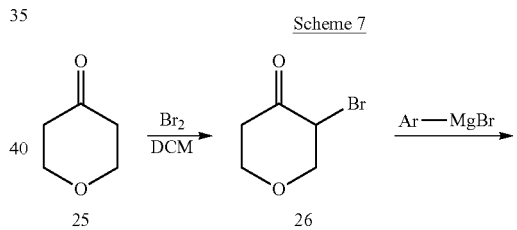

As indicated in Scheme 8, 2-arylcyclopentanones 18 can be deprotonated with a strong base, such as LDA and treated with alkylcyanoformate to give ketoesters 28, which upon reaction with 2-methyl-2-thiopseudourea provide 2-amino-7-aryl-6,7-dihydrocyclopenta[e][1,3]oxazin-4(5H)-ones 29. The latter compounds undergo acid-catalyzed hydrolysis to form 7-aryl-6,7-dihydrocyclopenta[e][1,3]oxazine-2,4(3H, 5H)-diones 30. Larsen, J. S.; Christensen, L.; Ludvig, G.; Jørgensen, P. T.; Pedersen, E. B.; Nielsen, C. *J. Chem. Soc., Perkin Trans.* 1 2000, 3035-3038.

Scheme 8

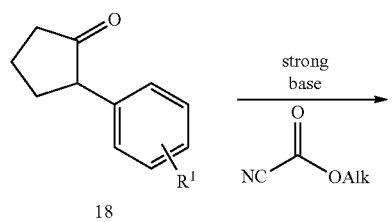

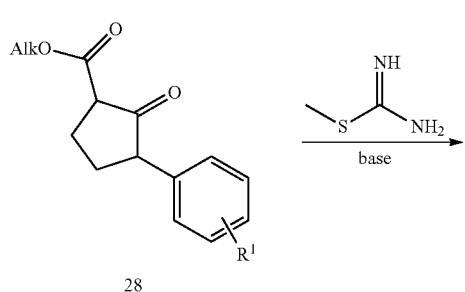

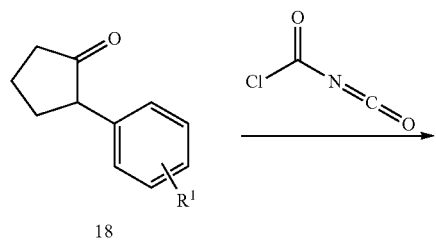

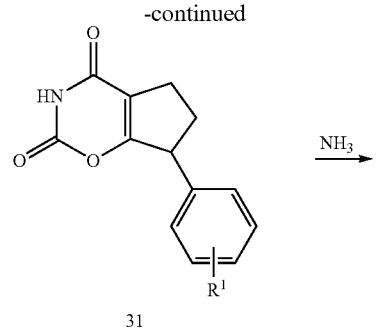

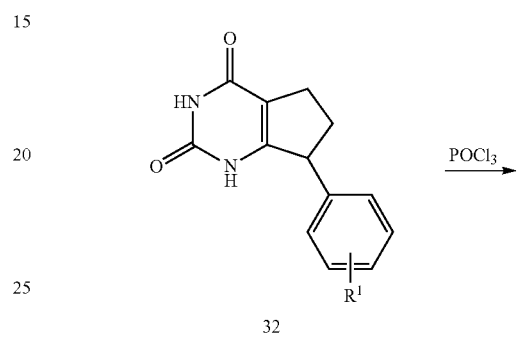

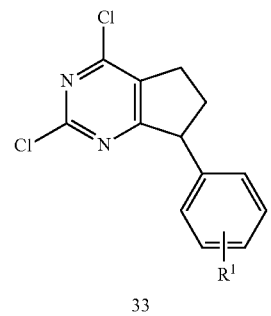

Alternatively, 7-aryl-6,7-dihydrocyclopenta[e][1,3]oxazine-2,4(3H,5H)-diones 31 are available by reaction of 2-arylcyclopentanones 18 with N-(chlorocarbonyl)isocyanate (Scheme 9). Subsequent treatment of 7-aryl-6,7-dihydrocyclopenta[e][1,3]oxazine-2,4(3H,5H)-diones 31 with ammonia in water, followed by chlorination with phosphorus oxychloride affords 2,4-dichloro-7-aryl-6,7-dihydro-5H-cyclopenta[d]pyrimidines 33.

In a similar manner to the synthesis described in Scheme 9, additional ketones can be reacted with N-(chlorocarbonyl)isocyanate to provide additional oxazine diones 35 that can be reacted with ammonia to provide the pyrimidine diones 36 (Scheme 10). Chlorination then provides the intermediate dichlorides 37. In a similar way, this chemistry can be performed using the ketal-protected ketones produced in Scheme 6 to prepare the corresponding fused dichloropyrimidines (Scheme 11).

Scheme 9

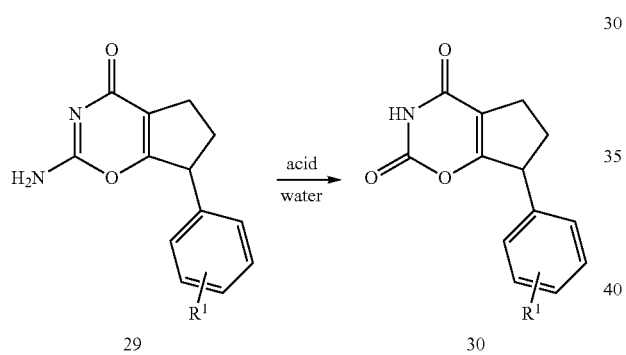

Scheme 10

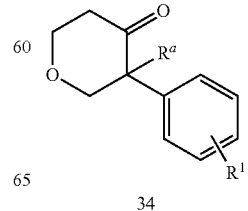

-continued

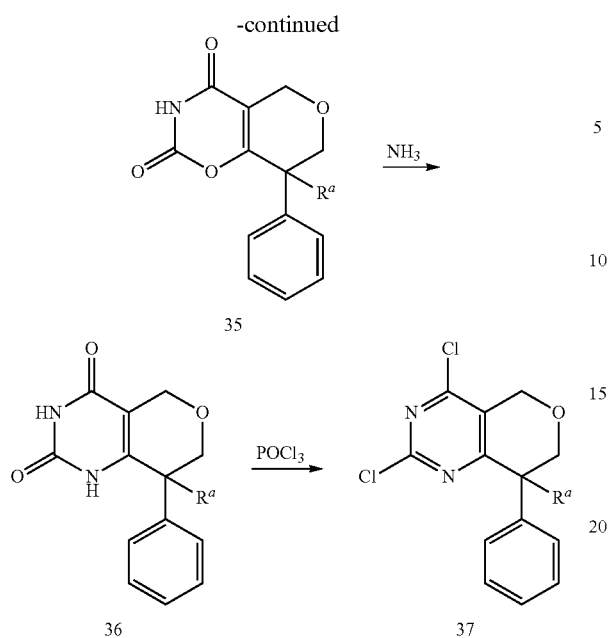

Scheme 11

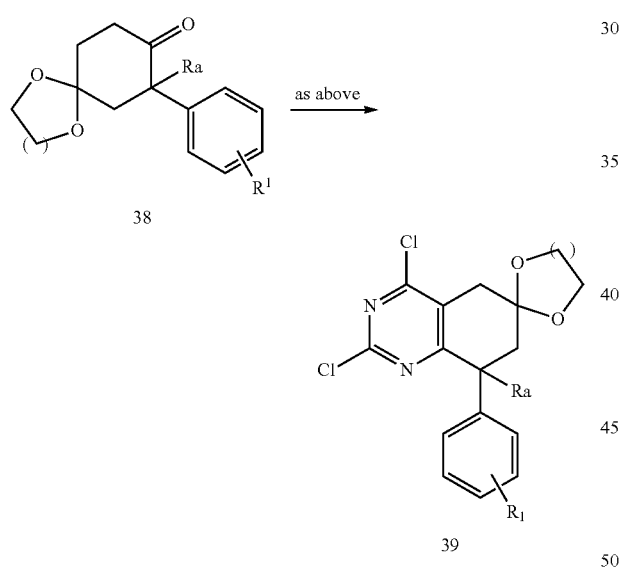

Synthesis of 2,4-dichloro-7-aryl-6,7-dihydro-5H-cyclopenta[d]pyrimidines 33 could also be performed according to the pathway described on Scheme 12. 4-Chloro-2,6-dimethoxypyrimidine 40 could be deprotonated with a strong base, such as n-butyllithium or 2,2,6,6-tetramethylpiperidine, and quenched with allyl bromide to give 5-allyl-4-chloro-2,6-dimethoxypyrimidine 41. Nencka, R.; Votruba, I.; Hřebabecký, H.; Jansa, P.; Tloušt'ová, E.; Horská, K.; Masojídková, M.; Holý, A. *J. Med. Chem.* 2007, 50, 6016-6023. The latter compound can react with α-styrylborinic acids in the presence of a palladium catalyst, such as tetrakis(triphenylphosphine)palladium, to provide compounds of formula 42 which can undergo ring closure olefin metathesis under Grubbs conditions to form 2,4-dimethoxy-7-aryl-5H-cyclopenta[d]pyrimidines 43. Grubbs, R. H. *Handbook of Metathesis*, 2003, First Edition, Wiley-VCH. The double bond in compounds 43 can be reduced to give 2,4-dimethoxy-7-aryl-6,7-dihydro-5H-cyclopenta[d]pyrimidines 44, which upon acid-catalyzed hydrolysis, followed by chlorination with phosphorus oxychloride afford intermediates 33.

Scheme 12

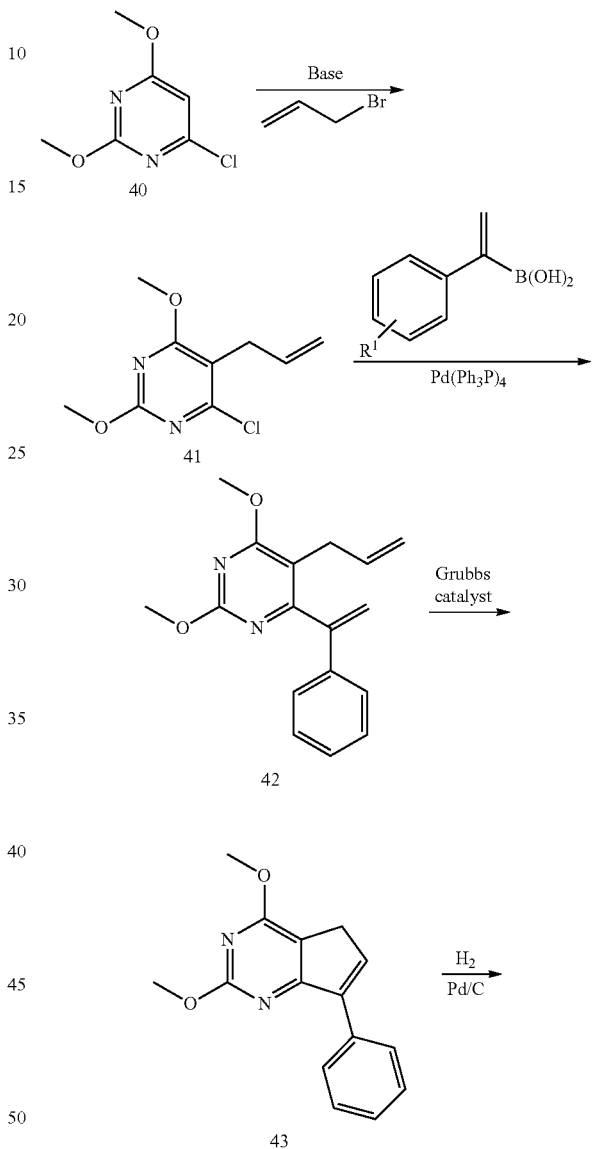

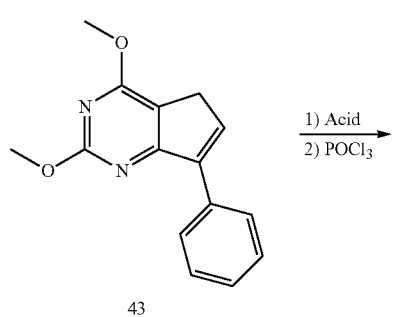

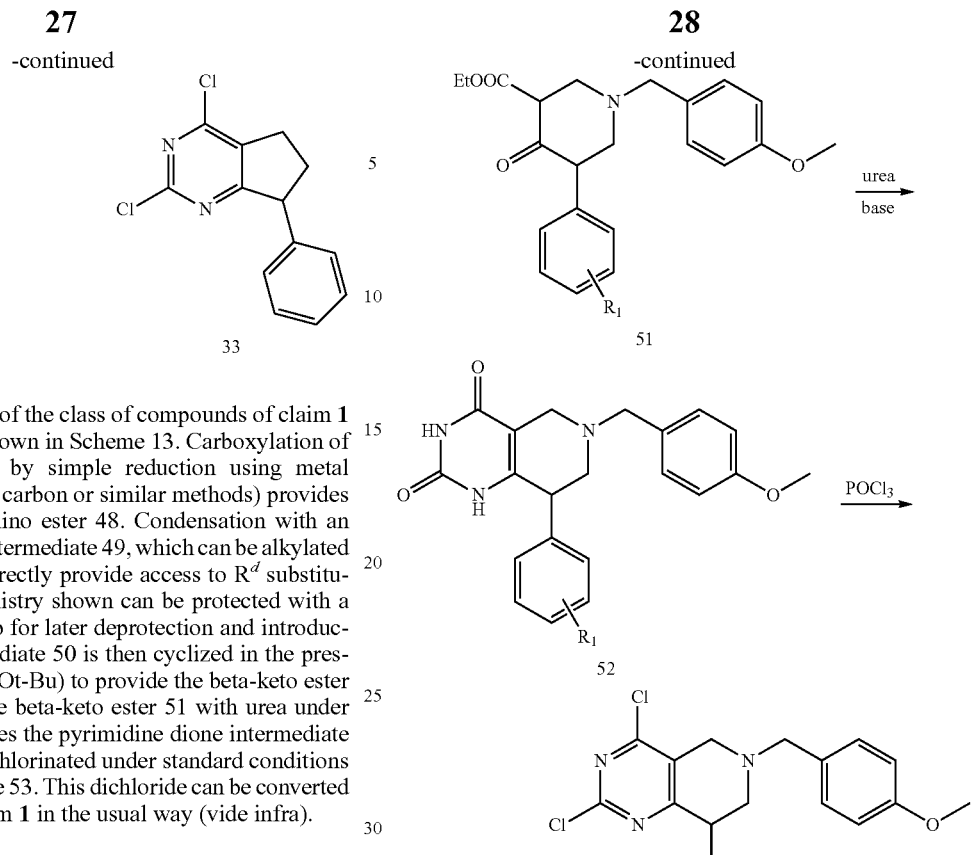

Additional members of the class of compounds of claim 1 can be prepared as is shown in Scheme 13. Carboxylation of benzonitriles followed by simple reduction using metal catalysis (Palladium on carbon or similar methods) provides the substituted beta-amino ester 48. Condensation with an acrylic ester provides intermediate 49, which can be alkylated on nitrogen to either directly provide access to $R^d$ substituents, or using the chemistry shown can be protected with a p-methoxybenzyl group for later deprotection and introduction of $R^d$. The intermediate 50 is then cyclized in the presence of base (usually KOt-Bu) to provide the beta-keto ester 51. Condensation of the beta-keto ester 51 with urea under basic conditions provides the pyrimidine dione intermediate 52, which can then be chlorinated under standard conditions to provide the dichloride 53. This dichloride can be converted into compounds of claim 1 in the usual way (vide infra).

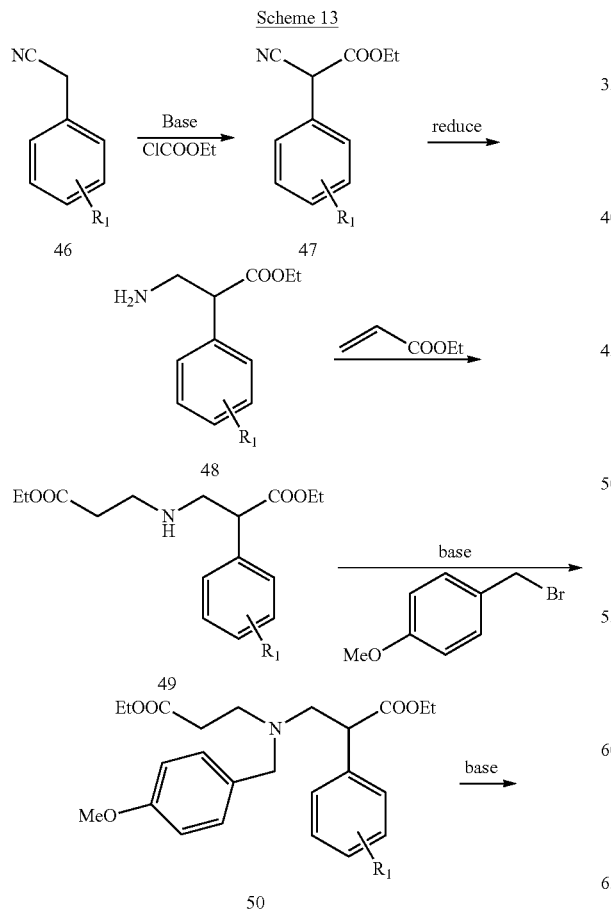

Additional members of the class of compounds of claim 1 can be prepared as is shown in Scheme 14. Esterification of an amino acid followed by alkylation with ethyl 4-bromobutyrate provides intermediate 56, which can be alkylated on nitrogen to either directly provide access to $R^d$ substituents, or using the chemistry shown can be protected with a p-methoxybenzyl group for later deprotection and introduction of $R^d$. The intermediate 57 is then cyclized in the presence of base (usually KOt-Bu) to provide the beta-keto ester 58. Condensation of the beta-keto ester 58 with urea under basic conditions provides the pyrimidine dione intermediate 59, which can then be chlorinated under standard conditions to provide the dichloride 60. This dichloride can be converted into compounds of claim 1 in the usual way (vide infra).

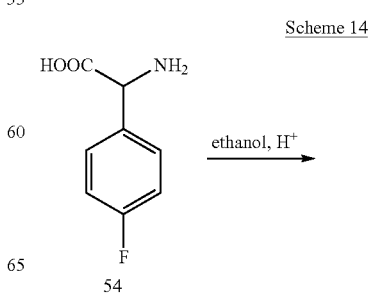

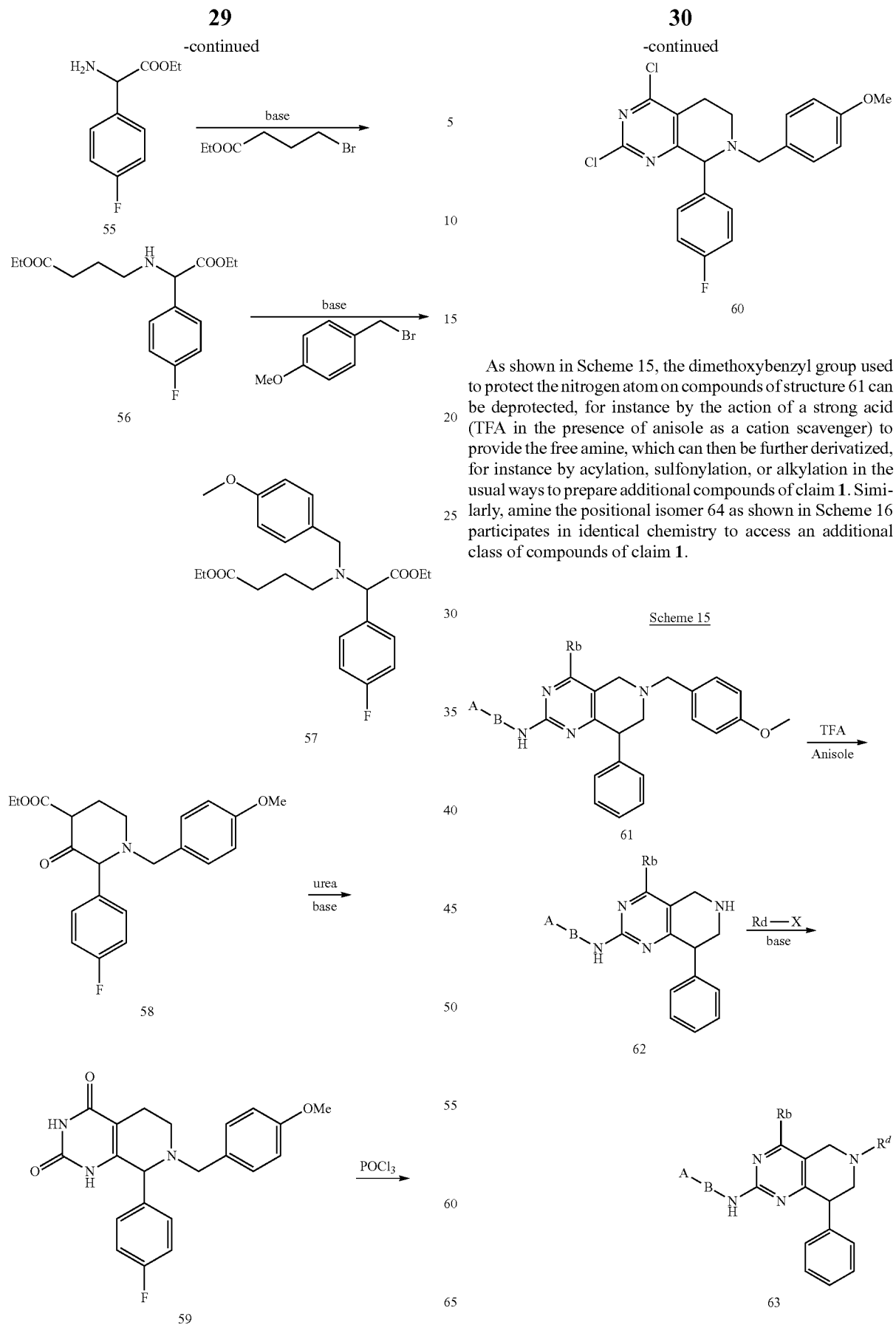

As shown in Scheme 15, the dimethoxybenzyl group used to protect the nitrogen atom on compounds of structure 61 can be deprotected, for instance by the action of a strong acid (TFA in the presence of anisole as a cation scavenger) to provide the free amine, which can then be further derivatized, for instance by acylation, sulfonylation, or alkylation in the usual ways to prepare additional compounds of claim 1. Similarly, amine the positional isomer 64 as shown in Scheme 16 participates in identical chemistry to access an additional class of compounds of claim 1.

Scheme 16

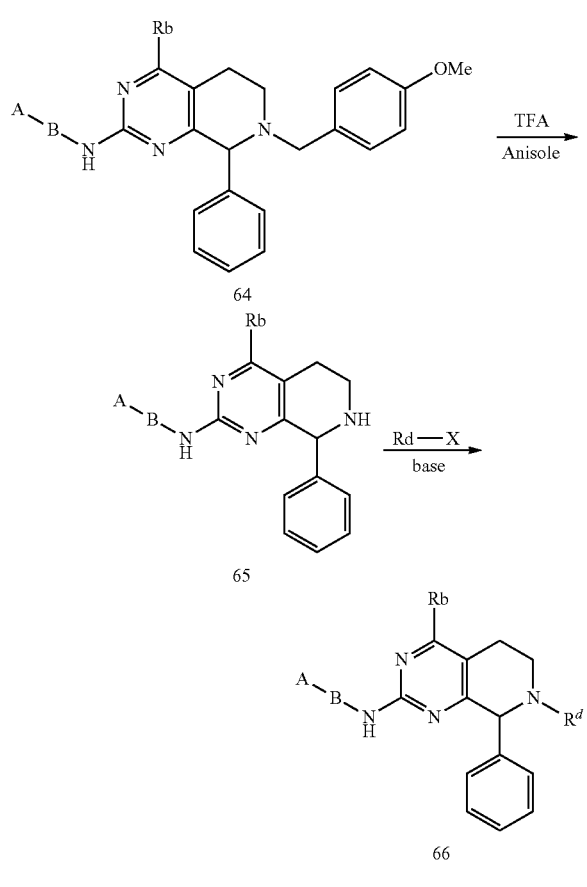

Further analogs can be prepared by the chemistry detailed in Scheme 17. Formation of the ester from commercial hydroxyacids 67 under Fisher conditions is followed by alkylation of the alcohol under silver(I) oxide catalysis. Reduction of the olefin and cyclization gives the beta-keto ester 71. Formation of the pyrimidine dione with KOt-Bu and urea followed by chlorination with POCl$_3$ gives the dichloride 73, which is carried forward to compounds of claim 1 as described in Scheme 22.

Scheme 17

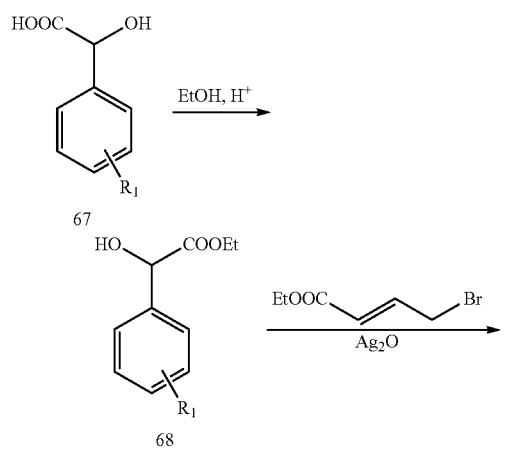

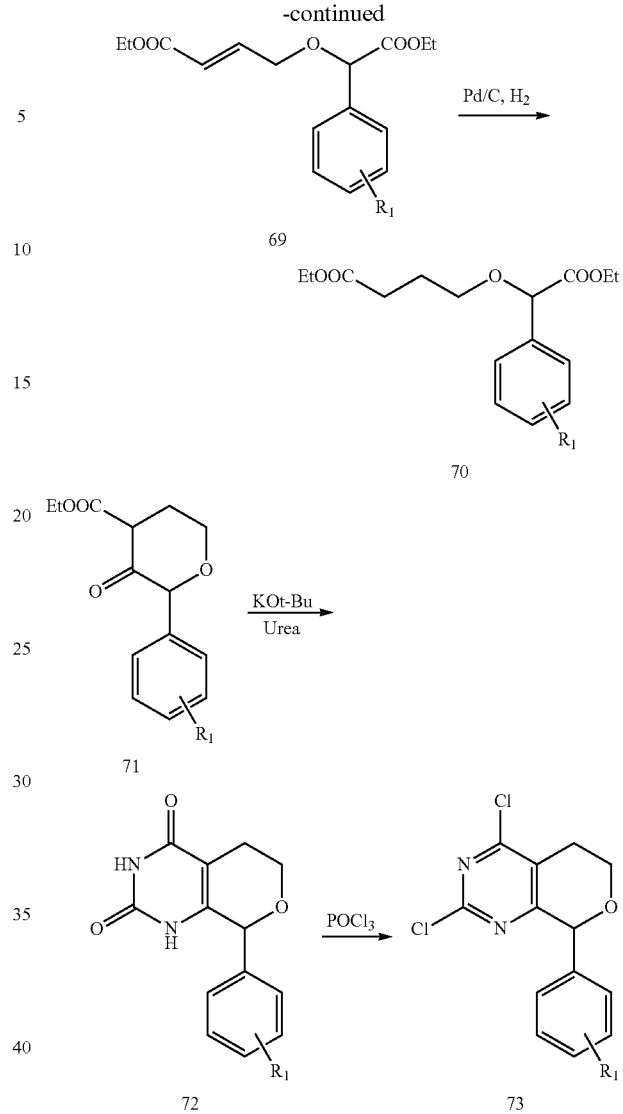

Additional analogs can be prepared using the chemistry shown in Scheme 18. Reaction of pyrimidine-2,4,6-triol with POCl$_3$ in DMF provides the chlorinated aldehyde 75. Protection of the aldehyde is followed by reaction with a Grignard reagent to produce the dichloride reagent 77. After hydrolytic deprotection and reduction of the aldehyde to the alcohol, the tetrahydrofuran ring can be closed by the action of lead tetraacetate to provide the substituted dichloride 80 which can then be used according to the methods described below to prepare further compounds of claim 1.

Scheme 18

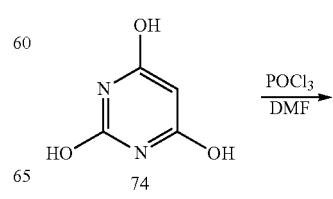

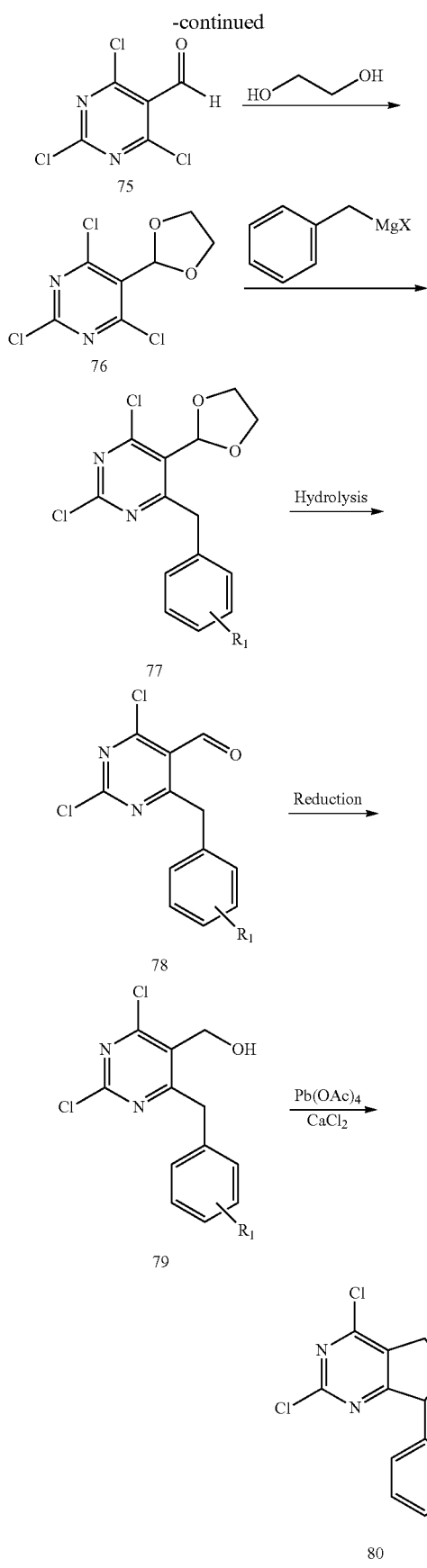

2,4-Dichloro-7-aryl-6,7-dihydro-5H-cyclopenta[d]pyrimidines 81 selectively react with primary and secondary amines to give 2-amino derivatives 82, which under heating can be coupled with anilines 4 to form title compounds 83. (Scheme 19). The said coupling can be performed either under acidic conditions (for example, using acetic acid), or under basic conditions, (for example, using sodium hydride). Alternatively, the coupling can be completed under metal catalysis, with conditions known in the literature, for instance the use of palladium Xantphos catalyst in the presence of a strong base (NaOt-Bu) or $Na_2CO_3$ in an aqueous cosolvent mixture (typically THF/water or dioxane/water).

Scheme 19

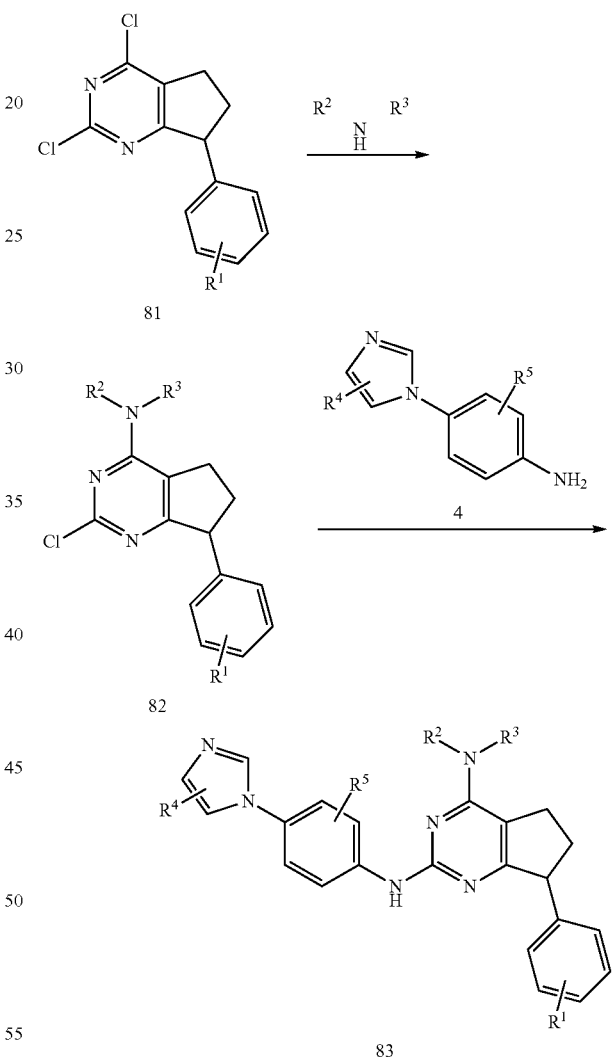

Additional compounds of claim 1 can be prepared by condensation of the appropriate ketal-containing dichlorides with amines and anilines in the manner already described to prepare intermediates 86 (Scheme 20). Deprotection of the ketal, for instance with aqueous acid produces the ketone 88 which is a very useful intermediate for the production of further compounds. The ketone can be directly condensed with amines under reductive conditions (reductive alkylation) to prepare substituted amine compounds 89. Alternatively, the ketone can be reduced with hydride reagents such as NaBH$_4$ or LiAlH$_4$ to provide the alcohol. The alcohol 90 can be activated, for instance as the methanesulfonate, and then displaced with nucleophiles including thiols, azide or other nucleophiles. Oxidation of the thiol prepares the sulfoxide and the sulfone. Reduction of the azide produces a facile entry into the amine, which can also be further alkylated to produce additional compounds of claim 1.

Scheme 20

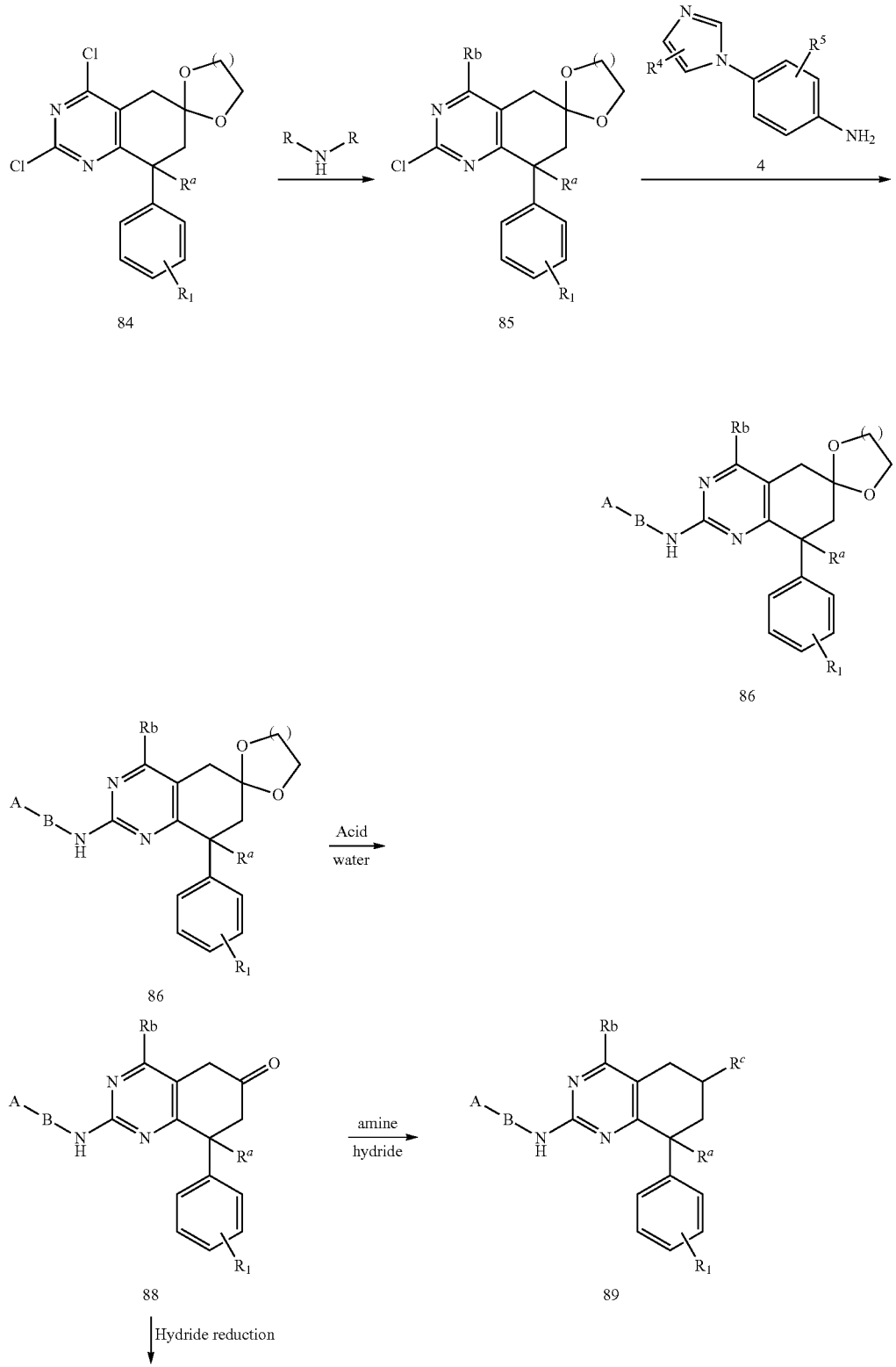

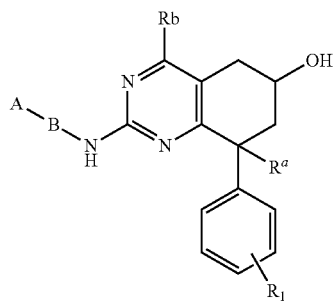

90

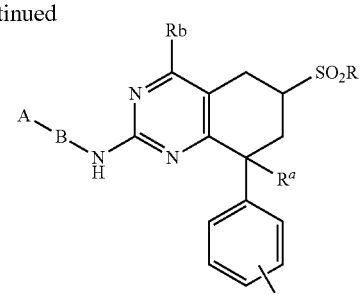

91 activate
thiol
displacement
oxidize

An additional method for the preparation of analogs of claim 1 is described in Scheme 21. Again starting with the aldehyde 76, addition of lithiated phenyldithiane provides intermediate 92. Deprotection of the protecting groups provides the keto aldehyde 93, which can be closed to the substituted pyrrolidine 94 by sequential reductive alkylation. The amine can either directly introduce a desired $R^d$ substituent, or as is described in the scheme an amine that introduces a protecting group (including 4-methoxybenzyl) can be used. According to the methods herein, the dichloride thus obtained can be transformed into compounds of claim 1. Additional analogs can then be prepared by deprotection of the 4-methoxybenzyl group using methods known to those in the art, such as TFA with Anisole as a cation scavenger, followed by additional alkylation, acylation, or sulfonylation using known methods.

Scheme 21

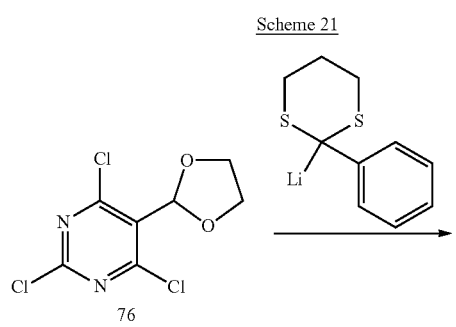

76

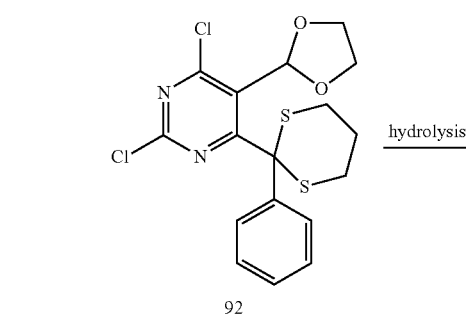

92

-continued

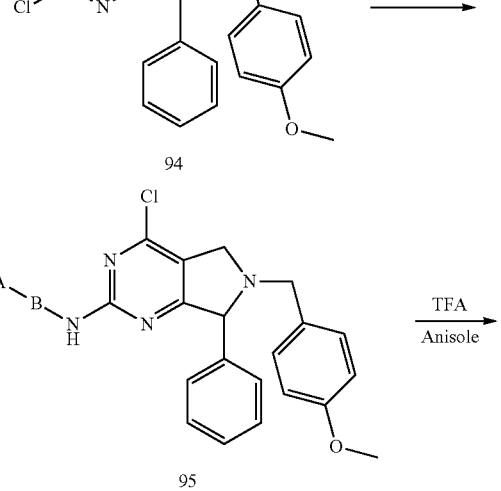

93

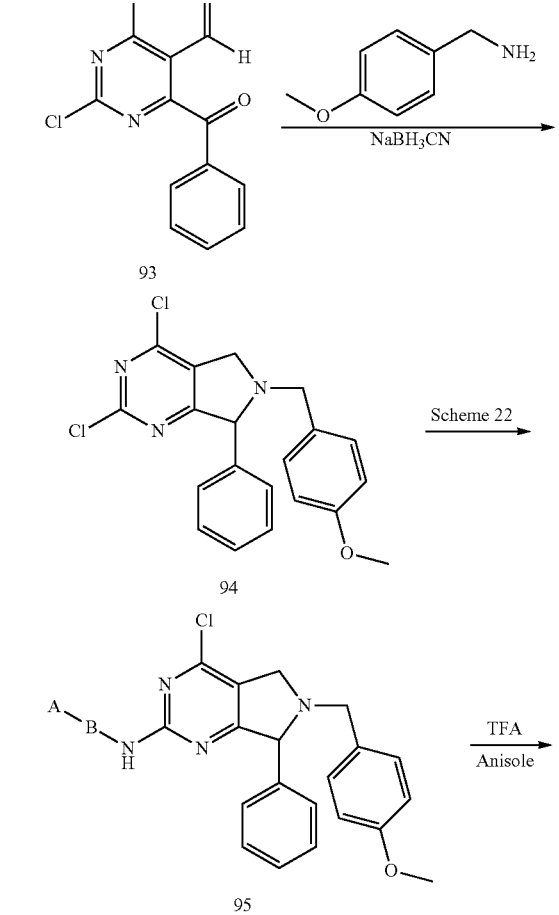

94

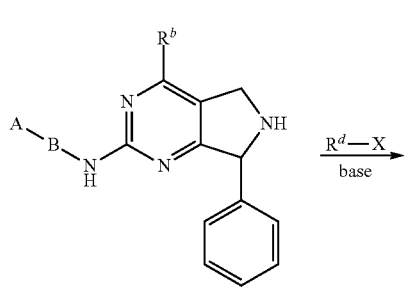

95

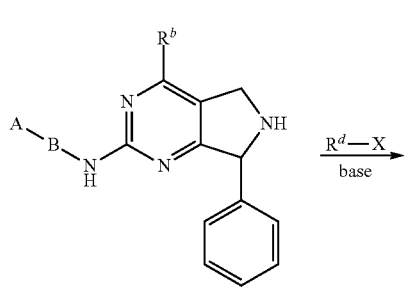

96

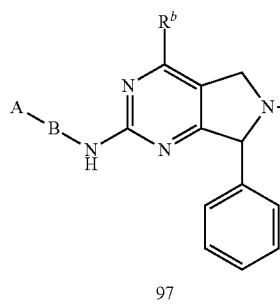

97

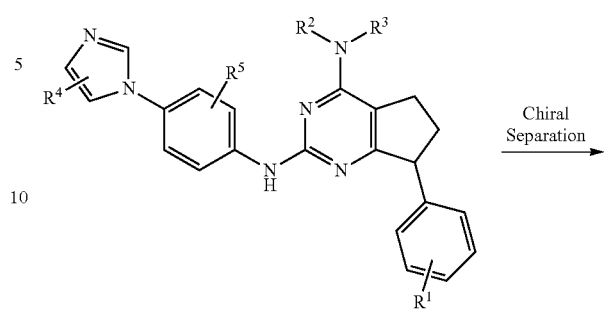

101

In a general way, the additional pyrimidine dichlorides prepared using the methods described above, or other methods known in the art can be transformed into additional analogs of claim 1 as demonstrated in Scheme 22. Pyrimidine dichlorides are reacted with amines to provide the chlorides 99 which correspond to the structures D-E as described in claim 1, where the bond that attaches the structure D-E to the ABNH fragment is activated as a displaceable chloride group. The title compounds of claim 1 are then prepared by condensing the chlorides 99 with the anilines ABNH$_2$ according to the methods previously described (Scheme 19).

Scheme 22

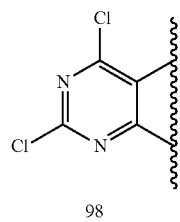 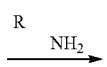

98

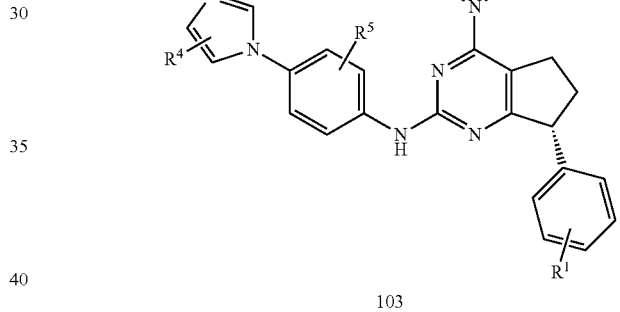

102

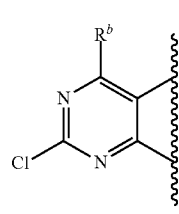 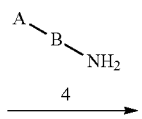

99        100

103

An additional method for producing compounds of claim 1 is demonstrated in Scheme 23. Commercial 4-chloro-2,6-dimethoxypyrimidine 101 can be deprotonated using either butyllithium or lithium tetramethylpiperidide followed by allylation to produce the protected pyrimidine 102. Suzuki coupling of phenyl vinyl boronic acid under palladium catalysis provides the diene 103 which can be efficiently cyclized by ring-closing metathesis using standard conditions with Grubbs' II catalyst. The olefin can then be reduced to provide intermediate 105. Deprotection and chlorination under standard conditions provides an additional route to make dichlorides 106 which can be converted to compounds of claim 1 using the chemistry shown in Scheme 22.

The racemic title compounds can be separated by chiral methods known to a reasonable person skilled in the arts, to provide individual enantiomers (Scheme 23). This is demonstrated below in the cyclopenta[d]pyrimidine series, but equally applies to the other racemic compounds described herein.

Scheme 23

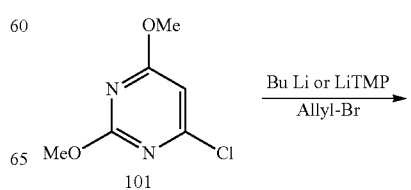

101

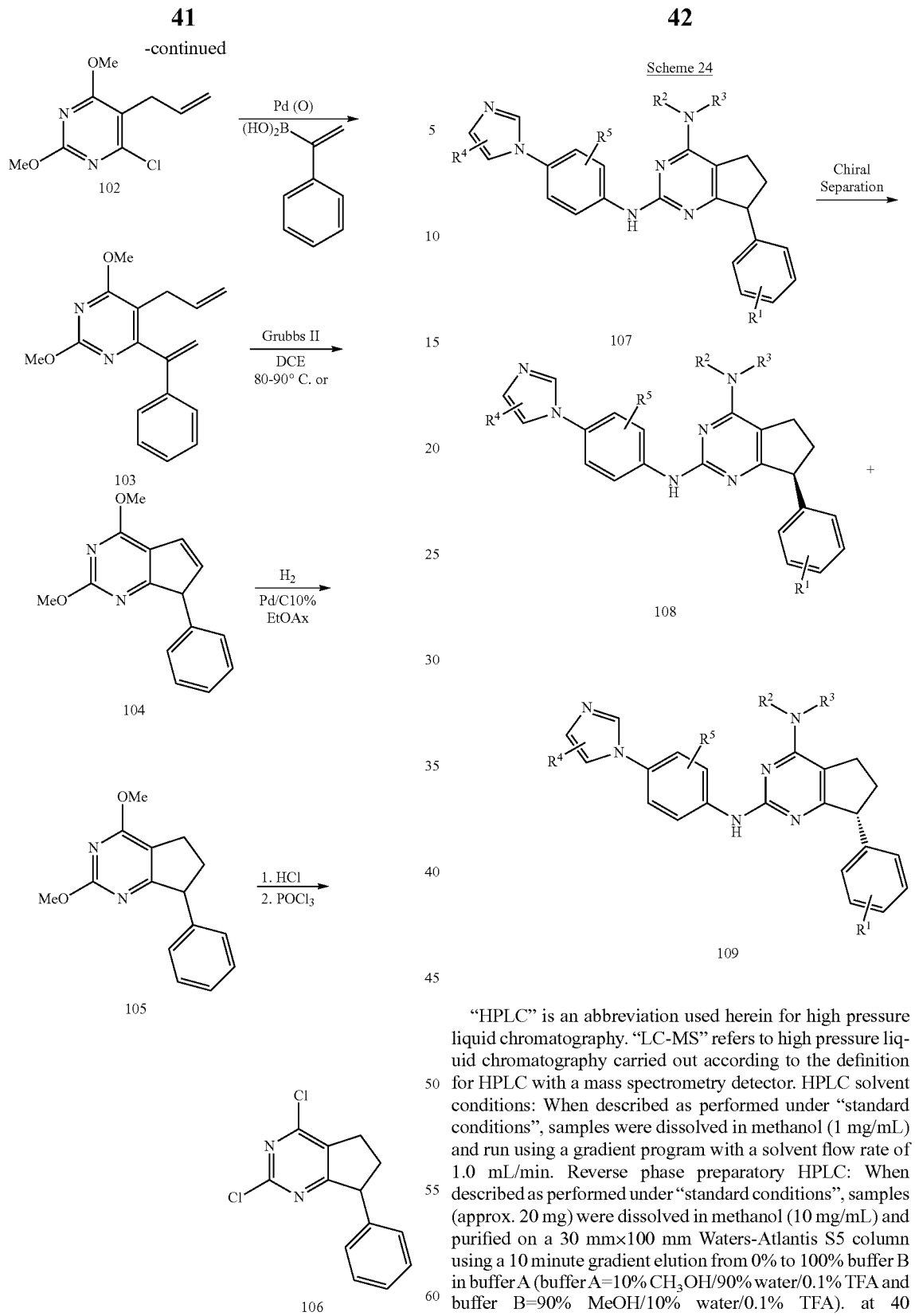

The racemic title compounds can be separated by chiral methods known to a reasonable person skilled in the arts, to provide individual enantiomers (Scheme 24). This is demonstrated below in the cyclopenta[d]pyrimidine series, but equally applies to the other racemic compounds described herein.

"HPLC" is an abbreviation used herein for high pressure liquid chromatography. "LC-MS" refers to high pressure liquid chromatography carried out according to the definition for HPLC with a mass spectrometry detector. HPLC solvent conditions: When described as performed under "standard conditions", samples were dissolved in methanol (1 mg/mL) and run using a gradient program with a solvent flow rate of 1.0 mL/min. Reverse phase preparatory HPLC: When described as performed under "standard conditions", samples (approx. 20 mg) were dissolved in methanol (10 mg/mL) and purified on a 30 mm×100 mm Waters-Atlantis S5 column using a 10 minute gradient elution from 0% to 100% buffer B in buffer A (buffer A=10% $CH_3OH$/90% water/0.1% TFA and buffer B=90% MeOH/10% water/0.1% TFA). at 40 mL/minute.

Proton NMR spectra were obtained on a Bruker 400 or 500 spectrometer. Data were referred to the lock solvent.

The examples provided are intended to assist in a further understanding of the present disclosure. Particular materials employed, species and conditions are intended to further illustrate the specific embodiments of the invention and not limit the reasonable scope thereof.

Synthesis of Intermediates Preparation A 4-(4-chloro-1H-imidazol-1-yl)-3-methoxyaniline

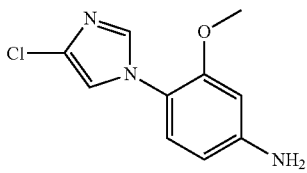

Intermediate A(1)

4-chloro-1-(2-methoxy-4-nitrophenyl)-1H-imidazole

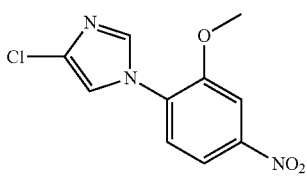

A mixture of 4-chloro-1H-imidazole (5.0 g, 48.8 mmol), 1-chloro-2-methoxy-4-nitrobenzene (9.15 g, 48.8 mmol), and potassium hydroxide flakes (2.74 g, 48.8 mmol) in anhydrous DMSO (50 mL) was heated at 80° C. for 20 h. The reaction mixture was allowed to cool to rt and was poured into 800 mL of water with vigorous stirring. The resulting yellow-orange precipitate was collected by vacuum filtration using a coarse sintered glass funnel The crude wet solid was transferred to a 1 L Erlenmeyer flask. Absolute ethanol (250 mL) was added to the flask and the resulting suspension was heated until all of the solids dissolved. The clear solution was cooled to rt and the desired product slowly crystallized. After 2 h, the crystalline solid was collected by vacuum filtration and rinsed with 100 mL of fresh ethanol. The solid was dried under high vacuum to afford 4-chloro-1-(2-methoxy-4-nitrophenyl)-1H-imidazole (5.2 g, 42% yield) as an off-white crystalline solid. LC-MS (M+H)$^+$=254.0. $^1$H NMR (500 MHz, CDCl$_3$) δ ppm 7.94-8.01 (m, 2H) 7.76 (d, J=1.53 Hz, 1H) 7.45 (d, J=8.55 Hz, 1H) 7.21 (d, J=1.53 Hz, 1H) 4.02 (s, 3H).

Preparation A 4-(4-chloro-1H-imidazol-1-yl)-3-methoxyaniline

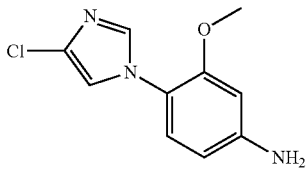 [SMILES: COc1cc([N+](=O)[O-])ccc1-n1cnc(Cl)c1]

Iron powder-325 mesh (4.6 g, 82 mmol) was added to a 500 mL round bottom flask charged with a mixture of 4-chloro-1-(2-methoxy-4-nitrophenyl)-1H-imidazole (5.2 g, 20.5 mmol), absolute ethanol (100 mL), and glacial acetic acid (50 mL). A water-cooled reflux condenser was attached to the flask and the heterogeneous mixture was heated to 100° C. with vigorous stirring for 30 min. The reaction mixture allowed to cool to rt and was added to a chilled and stirred solution of 3 M NaOH (291 mL). The resulting mixture was poured into a separatory funnel and extracted with EtOAc (3×250 mL). The combined organic layers were dried over sodium sulfate, filtered, and concentrated in vacuo to afford 4-(4-chloro-1H-imidazol-1-yl)-3-methoxyaniline (4.57 g, 97% yield) as a solid. LC-MS (M+H)$^+$224.0. $^1$H NMR (500 MHz, CDCl$_3$) δ ppm 7.47 (d, J=1.22 Hz, 1H) 7.00 (d, J=8.24 Hz, 1H) 6.99 (d, J=1.53 Hz, 1H) 6.32 (d, J=2.44 Hz, 1H) 6.29 (dd, J=8.24, 2.44 Hz, 1H) 3.88 (br. s., 2H) 3.78 (s, 3H).

Preparation AA 4-(4-cyano-1H-imidazol-1-yl)-3-methoxyaniline

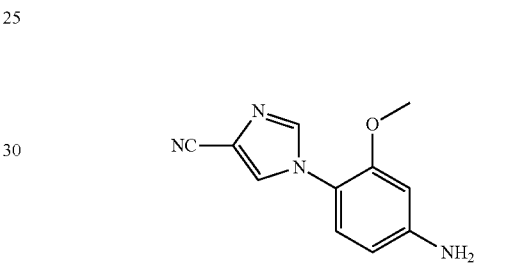

Intermediate AA(1)

4-cyano-1-(2-methoxy-4-nitrophenyl)-1H-imidazole

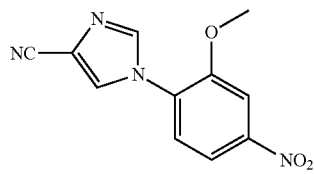

To a solution of 1H-Imidazole-4-carbonitrile (300 mg, 3.22 mmol) and 4-Fluoro-3-methoxynitrobenzene (552 mg, 3.22 mmol) in DMF (Volume: 6446 µl) was added K2CO3 (891 mg, 6.45 mmol). The resulting mixture was brought to 120° C. and stirred overnight. The reaction mixture was diluted with EtOAc (20 mL), washed with water (2×10 mL), brine (10 mL), dried over MgSO$_4$, filtered and concentrated in vacuo to give 1-(2-methoxy-4-nitrophenyl)-1H-imidazole-4-carbonitrile (698 mg, 2.86 mmol, 89% yield). LC-MS (M+H)$^+$=245.0. $^1$H NMR (500 MHz, MeOD) δ ppm 8.30-8.34 (1H), 8.19-8.23 (1H), 8.09-8.12 (1H), 8.00-8.05 (1H), 7.71-7.79 (1H), 4.02-4.10 (3H).

Preparation AA 4-(4-cyano-1H-imidazol-1-yl)-3-methoxyaniline

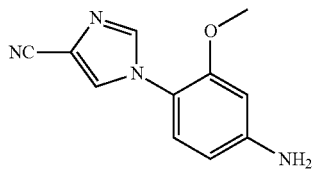 [SMILES: COc1cc(N)ccc1-n1cnc(C#N)c1]

To a solution of 1-(2-methoxy-4-nitrophenyl)-1H-imidazole-4-carbonitrile (689 mg, 2.82 mmol) in EtOH (Ratio: 2, Volume: 15 mL) was added Acetic Acid (Ratio: 1.000, Volume: 7.50 mL) and Iron (630 mg, 11.29 mmol). The resulting mixture was brought to 100° C. and stirred for 2 h. The reaction was then diluted with water and brought to pH 8 by the addition of 1 N aqueous sodium hydroxide. This mixture was extracted with EtOAc (3×5 mL). The combined extracts were washed with water (5 mL), brine (5 mL), dried over $MgSO_4$, filtered and concentrated in vacuo. LC-MS $(M+H)^+$ =215.0.

Preparation B 3-fluoro-4-(3-methyl-1H-1,2,4-triazol-1-yl)aniline

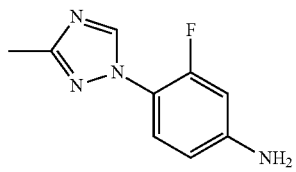

Intermediate B(1)

1-(2-fluoro-4-nitrophenyl)-3-methyl-1H-1,2,4-triazole

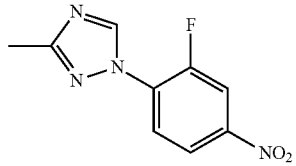 [SMILES: Cc1ncn(-c2ccc([N+](=O)[O-])cc2F)n1]

A mixture of 3-methyl-1H-1,2,4-triazole (15.0 g, 181 mmol), 1,2-difluoro-4-nitrobenzene (28.7 g, 181 mmol), and sodium bicarbonate (15.2 g, 181 mmol) in DMSO (100 mL) was heated at 80° C. for 48 h. The reaction mixture was allowed to cool to rt and was poured into water (800 mL). The aqueous mixture was extracted with EtOAc (3×200 mL). The combined organic extracts were sequentially washed with water (500 mL) and brine solution (100 mL). The organic layer was dried over sodium sulfate, filtered, and concentrated in vacuo. The crude reaction mixture was purified using silica gel chromatography (30-80% EtOAc/hexane, linear gradient) to afford two regioisomeric products. Pure fractions of the less polar regioisomer were combined and concentrated to afford 1-(2-fluoro-4-nitrophenyl)-3-methyl-1H-1,2,4-triazole (7.2 g, 30.8 mmol, 17% yield) as an off-white solid. Pure fractions of the more polar regioisomer were combined and concentrated to afford 1-(2-fluoro-4-nitrophenyl)-5-methyl-1H-1,2,4-triazole (6.23 g, 28.0 mmol, 15% yield) as an off-white solid. Data for 1-(2-fluoro-4-nitrophenyl)-3-methyl-1H-1,2,4-triazole: LC-MS $(M+H)^+$=223.1. $^1$H NMR (500 MHz, $CDCl_3$) δ ppm 8.73 (d, J=2.7 Hz, 1H), 8.15-8.26 (m, 3H), 2.53 (s, 3H).

Preparation B 3-fluoro-4-(3-methyl-1H-1,2,4-triazol-1-yl)aniline

10% Palladium on carbon (2.50 g, 23.5 mmol) was added under an atmosphere of nitrogen to a chilled (ice-water bath) solution of 1-(2-fluoro-4-nitrophenyl)-5-methyl-1H-1,2,4-triazole (15.0 g, 67.5 mmol, from preparation A, step 1) dissolved in methanol (400 mL). The flask was repeatedly evacuated and flushed with hydrogen gas (double balloon). The resulting mixture was allowed to warm to rt and left to stir for 72 h under the hydrogen atmosphere. The vessel was subsequently purged with nitrogen gas. The reaction vessel and it contents were chilled (ice-water bath) and an additional portion of 10% Palladium on carbon (2.50 g, 23.5 mmol) was added. The flask was repeatedly evacuated and flushed with hydrogen gas (double balloon). The resulting mixture was allowed to warm to rt and left to stir for 6 h under the hydrogen atmosphere. The vessel was subsequently purged with nitrogen gas. The crude reaction mixture was filtered through a short plug of diatomaceous earth (Celite®). The reaction vessel and the Celite® were rinsed with fresh methanol. The combined filtrates were concentrated in vacuo. The residue was dried under high vacuum overnight to afford 3-fluoro-4-(3-methyl-1H-1,2,4-triazol-1-yl)aniline (12.1 g, 63.0 mmol, 93% yield) as a blackish/grey solid. LC-MS $(M+H)^+$193.2. $^1$H NMR (500 MHz, $CDCl_3$) δ ppm 8.31 (d, J=2.4 Hz, 1H), 7.47 (t, J=8.7 Hz, 1H), 6.47-6.58 (m, 2H), 3.97 (br. s., 2H), 2.48 (s, 3H).

Preparation C

3-Fluoro-4-(5-methyl-1H-1,2,4-triazol-1-yl)aniline

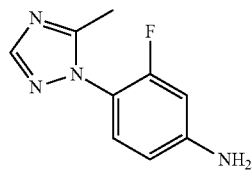

Intermediate C(1)

1-(2-fluoro-4-nitrophenyl)-5-methyl-1H-1,2,4-triazole

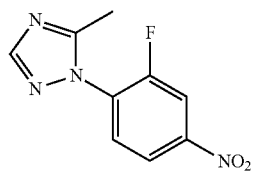 [SMILES: Cc1ncnn1-c1ccc([N+](=O)[O-])cc1F]

A mixture of 3-methyl-1H-1,2,4-triazole (15.0 g, 181 mmol), 1,2-difluoro-4-nitrobenzene (28.7 g, 181 mmol), and sodium bicarbonate (15.2 g, 181 mmol) in DMSO (100 mL) was heated at 80° C. for 48 h. The reaction mixture was allowed to cool to rt and was poured into water (800 mL). The aqueous mixture was extracted with EtOAc (3×200 mL). The combined organic extracts were sequentially washed with water (500 mL) and brine solution (100 mL). The organic layer was dried over sodium sulfate, filtered, and concentrated in vacuo. The crude reaction mixture was purified using silica gel chromatography (30-80% EtOAc/hexane, linear gradient) to afford two regioisomeric products. Pure fractions of the less polar regioisomer were combined and concentrated to afford 1-(2-fluoro-4-nitrophenyl)-3-methyl-1H-1,2,4-triazole (7.2 g, 30.8 mmol, 17% yield) as an off-white solid. Pure fractions of the more polar regioisomer were combined and concentrated to afford 1-(2-fluoro-4-nitrophenyl)-5-methyl-1H-1,2,4-triazole (6.23 g, 28.0 mmol, 15% yield) as an off-white solid. Data for 1-(2-fluoro-4-nitrophenyl)-5-methyl-1H-1,2,4-triazole: LC-MS $(M+H)^+=223.1$. $^1$H NMR (500 MHz, CDCl$_3$) δ ppm 8.18-8.24 (m, 2H) 8.04 (s, 1H) 7.69-7.78 (m, 1H) 2.47-2.53 (m, 3H).

Preparation C

3-Fluoro-4-(5-methyl-1H-1,2,4-triazol-1-yl)aniline

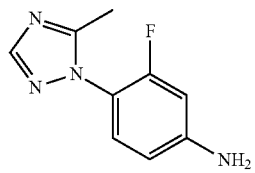

10% Palladium on carbon (1.5 g, 14.1 mmol) was added under an atmosphere of nitrogen to a chilled (ice-water bath) solution of 1-(2-fluoro-4-nitrophenyl)-5-methyl-1H-1,2,4-triazole (3.7 g, 17 mmol) dissolved in methanol (200 mL). The flask was repeatedly evacuated and flushed with hydrogen gas (double balloon). The resulting mixture was allowed to warm to rt and left to stir for 18 h under the hydrogen atmosphere. The vessel was subsequently purged with nitrogen gas. The crude reaction mixture was filtered through a short plug of diatomaceous earth (Celite®). The reaction vessel and Celite® were rinsed with fresh methanol. The combined filtrates were concentrated in vacuo. The residue was dried under high vacuum to afford 3-fluoro-4-(5-methyl-1H-1,2,4-triazol-1-yl)aniline (3.14 g, 91% yield) as a blackish/grey solid. LC-MS $(M+H)^+$193.1. $^1$H NMR (500 MHz, CDCl$_3$) δ ppm 7.91 (s, 1H) 7.14 (t, J=8.55 Hz, 1H) 6.43-6.53 (m, 2H) 4.04 (br. s., 2H) 2.36 (s, 3H).

Preparation D 3-methoxy-4-(3-methyl-1H-1,2,4-triazol-1-yl)aniline

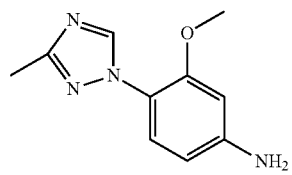 [SMILES: COc1cc([N+](=O)[O-])ccc1-n1cnc(C)n1]

Intermediate D(1)

1-(2-methoxy-4-nitrophenyl)-3-methyl-1H-1,2,4-triazole

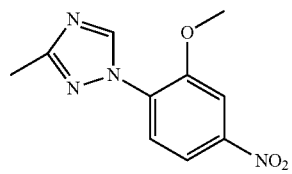

A mixture of 3-methyl-1H-1,2,4-triazole (5.0 g, 60.2 mmol), 1-chloro-2-methoxy-4-nitrobenzene (11.3 g, 60.2 mmol), and KOH flakes (3.4 g, 48.1 mmol) in anhydrous DMSO (50 mL) was heated at 80° C. for 6 h. The reaction mixture was allowed to cool to rt and was poured into 800 mL of water with vigorous stirring. The aqueous mixture was extracted with EtOAc (3×200 mL). The combined organics were washed with brine, dried over Na$_2$SO$_4$, filtered and concentrated in vacuo. The crude residue was purified using silica gel chromatography (0-2% MeOH/chloroform, linear gradient) to afford 1-(2-methoxy-4-nitrophenyl)-3-methyl-1H-1,2,4-triazole (3.7 g, 26% yield). LC-MS $(M+H)^+$+235.2.

Preparation D 3-methoxy-4-(3-methyl-1H-1,2,4-triazol-1-yl)aniline

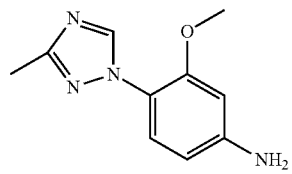

10% Palladium on carbon (1.2 g) was added under an atmosphere of nitrogen to a chilled (ice-water bath) solution of 1-(2-methoxy-4-nitrophenyl)-3-methyl-1H-1,2,4-triazole (3.7 g, 12.7 mmol) dissolved in methanol (250 mL). The flask was repeated evacuated and flushed with hydrogen gas (double balloon). The resulting mixture was allowed to warm to rt and left to stir for 18 h under the hydrogen atmosphere. Purged with nitrogen gas. Filtered the crude reaction mixture through a short diatomaceous earth (Celite®) plug. Rinsed reaction vessel and plug with methanol. Concentrated filtrate in vacuo. Dried residue on high vacuum overnight to afford 3-methoxy-4-(3-methyl-1H-1,2,4-triazol-1-yl)aniline (2.44 g, 94% yield) as a reddish solid. LC-MS (M+H)⁺205.2. ¹H NMR (500 MHz, CDCl₃) δ ppm 8.35 (s, 1H) 7.36 (d, J=8.55 Hz, 1H) 6.29-6.34 (m, 2H) 3.80 (s, 3H) 2.46 (s, 3H).

Preparation DD 3-methoxy-4-(5-methyl-1H-1,2,4-triazol-1-yl)aniline

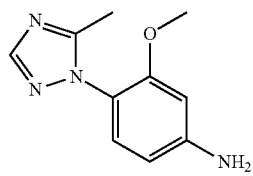

Intermediate C(1) was reacted with NaOMe in DMF to afford 1-(2-methoxy-4-nitrophenyl)-5-methyl-1H-1,2,4-triazole, which was reduced with Fe and ammonium chloride to afford the title compound. LC-MS (M+H)⁺205.1. ¹H NMR (500 MHz, CHLOROFORM-d) δ ppm 7.90 (1H, s), 7.05 (1H, d, J=7.93 Hz), 6.27-6.34 (2H, m), 3.91 (2H, br. s.), 3.73 (3H, s), 2.29 (3H, s).

Preparation E 3-methoxy-4-(4-methyl-1H-imidazol-1-yl)aniline

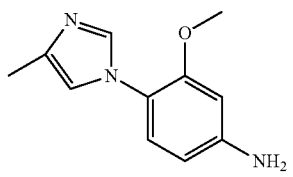

Intermediate E(1)

1-(2-methoxy-4-nitrophenyl)-4-methyl-1H-imidazole

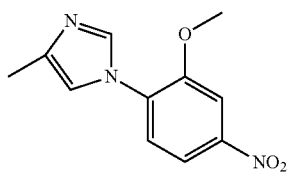

A mixture of 4-methyl-1H-imidazole (18.0 g, 53.5 mmol), 1-chloro-2-methoxy-4-nitrobenzene (10.0 g, 53.5 mmol), and potassium hydroxide (4.5 g, 80.3 mmol) in DMSO (50 mL) was heated at 110° C. for 24 h. The reaction mixture was allowed to cool to rt and was poured into 1000 mL of water. The aqueous mixture was extracted with dichloromethane (3×250 mL). The combined organic extracts were washed with brine, dried over sodium sulfate, filtered, and concentrated in vacuo. The crude reaction mixture was purified using silica gel chromatography (330 g silica cartridge, 0-2% MeOH/chloroform, linear gradient over 72 min, flow 25 mL/min) to afford 1-(2-methoxy-4-nitrophenyl)-4-methyl-1H-imidazole (2.56 g, 20% yield) as a yellow/orange solid. LC-MS (M+H)⁺=234.1. ¹H NMR (500 MHz, CDCl₃) δ ppm 7.97-8.00 (m, 1H) 7.93-7.97 (m, 2H) 7.45 (d, J=8.85 Hz, 1H) 7.02 (s, 1H) 4.02 (s, 3H) 2.35 (s, 3H).

Preparation E 3-methoxy-4-(4-methyl-1H-imidazol-1-yl)aniline

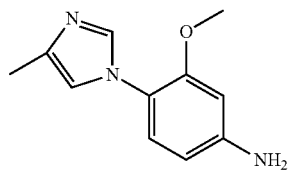 [SMILES: COc1cc([N+](=O)[O-])ccc1-n1cnc(C)c1]

10% Palladium on carbon (250 mg) was added under an atmosphere of nitrogen to a chilled (ice-water bath) solution of 1-(2-methoxy-4-nitrophenyl)-4-methyl-1H-imidazole (2.56 g, 11.0 mmol) dissolved in methanol (150 mL). The flask was repeated evacuated and flushed with hydrogen gas (double balloon). The resulting mixture was allowed to warm to rt and left to stir for 18 h under the hydrogen atmosphere. Purged with nitrogen gas. Filtered the crude reaction mixture through a short diatomaceous earth (Celite®) plug. Rinsed reaction vessel and plug with methanol. Concentrated filtrate in vacuo. Dried residue on high vacuum overnight to afford 3-methoxy-4-(4-methyl-1H-imidazol-1-yl)aniline (2.25 g, 100% yield) as a blackish/grey waxy solid. LC-MS (M+H)⁺ 204.1. ¹H NMR (500 MHz, CDCl₃) δ ppm 7.69 (s, 1H) 7.01 (d, J=8.55 Hz, 1H) 6.82 (s, 1H) 6.33 (d, J=2.14 Hz, 1H) 6.30 (d, J=8.55 Hz, 1H) 3.78 (s, 3H) 2.33 (s, 3H).

Preparation EE 3-methoxy-4-(4-difluoromethyl-1H-imidazol-1-yl)aniline

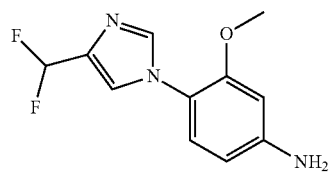

Intermediate EE(1)

4-(difluoromethyl)-1H-imidazole

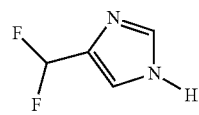

A solution of 1-trityl-1H-imidazole-4-carbaldehyde in dichloromethane at 0° C. was added deoxyfluor and stirred for 3 days. The product was then treated with 1:5 AcOH/HCl at ambient temperature overnight to afford 4-(difluoromethyl)-1H-imidazole.

Preparation EE 3-methoxy-4-(4-difluoromethyl-1H-imidazol-1-yl)aniline

Intermediate EE(1) was reacted as described for Preparation E to afford the desired Preparation EE. LC-MS (M+H)+ 240.2. $^1$H NMR (400 MHz, DMSO-d6) δ ppm 8.42 (s, 1H) 7.93 (s, 1H), 7.48 (d, J=8.4 Hz, 1H) 7.19-6.88 (m, 3H) 3.81 (s, 3H).

Preparation F 4-(3-chloro-1H-1,2,4-triazol-1-yl)-3-methoxyaniline

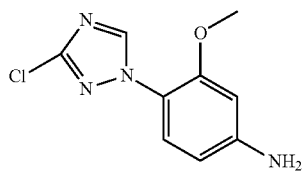

Intermediate F(1)

2-(3-chloro-1H-1,2,4-triazol-1-yl)-5-nitrophenol

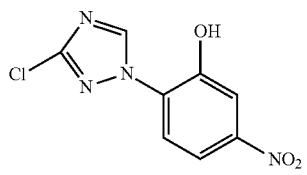 [SMILES: O=[N+]([O-])c1ccc(-n2cnc(Cl)n2)c(O)c1]

A mixture of 3-chloro-1H-1,2,4-triazole (2.76 g, 26.7 mmol), 1-chloro-2-methoxy-4-nitrobenzene (5.0 g, 26.7 mmol), potassium hydroxide flakes (1.496 g, 26.7 mmol), and DMSO (25 mL) was heated in a sealed reaction vessel 100° C. for 24 h. The reaction was allowed to cool to rt and additional portions of 3-chloro-1H-1,2,4-triazole (1.38 g, 0.5 equiv) and potassium hydroxide (0.75 g, 0.5 equiv) were added. The reaction vessel was resealed and heated to 110° C. for an additional 24 h. The resulting mixture was allowed to cool to rt and was poured into 500 mL of water. The aqueous mixture was extracted with EtOAc (3×100 mL). The combined organics were washed with brine, dried over Na$_2$SO$_4$, filtered and concentrated in vacuo. The crude residue was purified using silica gel chromatography (0-5% MeOH/chloroform, linear gradient over 144 min, flow 25 mL/min) to afford 2-(3-chloro-1H-1,2,4-triazol-1-yl)-5-nitrophenol (0.924 g, 3.84 mmol, 14.4% yield). LC-MS (M+H)+=241.0. $^1$H NMR (500 MHz, CDCl$_3$) δ ppm 11.97 (br. s., 1H) 9.24 (s, 1H) 7.90-7.95 (m, 1H) 7.89 (d, J=2.44 Hz, 1H) 7.84 (dd, J=8.85, 2.44 Hz, 1H).

Intermediate F(2)

3-chloro-1-(2-methoxy-4-nitrophenyl)-1H-1,2,4-triazole

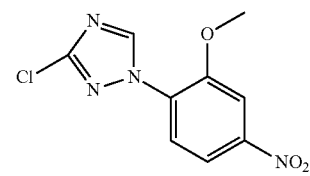

Iodomethane (0.860 mL, 13.82 mmol) was added to a mixture of 2-(3-chloro-1H-1,2,4-triazol-1-yl)-5-nitrophenol (1.33 g, 5.53 mmol), potassium hydroxide (0.388 g, 6.91 mmol), and DMSO (25 mL). The mixture was left to stir at rt for 24 h. The reaction mixture was poured into water (250 mL) and extracted with EtOAc (3×100 mL). The combined extracts were washed with water, washed with brine, dried over sodium sulfate, filtered and concentrated in vacuo. The crude residue was purified using silica gel column chromatography (0-1% MeOH/chloroform, linear gradient over 72 min, flow 25 mL/min). The pure fractions were combined and concentrated to afford 3-chloro-1-(2-methoxy-4-nitrophenyl)-1H-1,2,4-triazole (0.924 g, 3.63 mmol, 65.6% yield) as a light yellow solid. LC-MS (M+H)+=255.0. $^1$H NMR (500 MHz, CDCl$_3$) δ ppm 8.35 (s, 1H) 7.36 (d, J=8.55 Hz, 1H) 6.29-6.34 (m, 2H) 3.80 (s, 3H) 2.46 (s, 3H).

Preparation F 4-(3-chloro-1H-1,2,4-triazol-1-yl)-3-methoxyaniline

Water (8 mL) and dioxane (8 mL) were added to a mixture of 3-chloro-1-(2-methoxy-4-nitrophenyl)-1H-1,2,4-triazole (0.900 g, 3.53 mmol) and sodium sulfide (1.379 g, 17.67 mmol) in a 20 mL vial. The vial was capped and heated at 70-80° C. for 24 hours. The mixture was cooled to rt, poured into water (300 mL) and extracted with EtOAc (2×150 mL). The combined organic layers were washed with brine, dried over sodium sulfate, filtered, and concentrated in vacuo to afford 4-(3-chloro-1H-1,2,4-triazol-1-yl)-3-methoxyaniline (577 mg, 73%) as a brown solid. LC-MS (M+H)+225.1.

Preparation FF 6-(4-chloro-1H-imidazol-1-yl)-5-methoxypyridin-3-amine

Intermediate FF(1)

2-(4-chloro-1H-imidazol-1-yl)-3-methoxy-5-nitropyridine

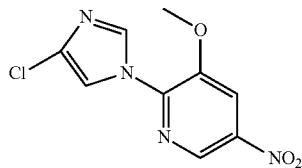

A mixture of 4-chloro-1H-imidazole (2.72 g, 26.5 mmol), 2-chloro-3-methoxy-5-nitropyridine (5.0 g, 26.5 mmol), and KOH flakes 1.488 g, 26.5 mmol) in anhydrous DMSO (25 mL) was heated at 80° C. for 5 h. The reaction mixture was allowed to cool to rt and was poured into 1.0 L of water with vigorous stirring. The mixture was stirred at rt for 16 h. The precipitate was collected by vacuum filtration using a coarse sintered glass funnel The solid was dried under high vacuum for 24 h to provide 2-(4-chloro-1H-imidazol-1-yl)-3-methoxy-5-nitropyridine (5.22 g, 20.50 mmol, 77% yield) as a light brown solid. LC-MS (M+H)$^+$=255.0. $^1$H NMR (500 MHz, DMSO-d$_6$) δ ppm 8.94 (d, J=2.44 Hz, 1H) 8.51 (d, J=1.83 Hz, 1H) 8.42 (d, J=2.44 Hz, 1H) 8.02 (d, J=1.83 Hz, 1H) 4.12 (s, 3H).

Preparation FF 6-(4-chloro-1H-imidazol-1-yl)-5-methoxypyridin-3-amine

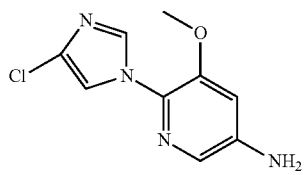

Iron powder-325 mesh (2.19 g, 39.3 mmol) was added to a flask charged with a mixture of 2-(4-chloro-1H-imidazol-1-yl)-3-methoxy-5-nitropyridine (5.0 g, 19.64 mmol), absolute ethanol (50 mL), and glacial acetic acid (20 mL). A water-cooled reflux condenser was attached to the flask and the heterogeneous mixture was heated to 100° C. with vigorous stirring for 30 min. The reaction mixture was allowed to cool to rt and was neutralized upon addition to a chilled and vigorously stirred solution of 5 M NaOH. The resulting mixture was poured into a separatory funnel and extracted with EtOAc. The combined organic layers were dried over sodium sulfate, filtered, and concentrated in vacuo to afford 6-(4-chloro-1H-imidazol-1-yl)-5-methoxypyridin-3-amine (3.12 g, 71% yield). LC-MS (M+H)$^+$225.1. $^1$H NMR (500 MHz, CDCl$_3$) δ ppm 8.06 (d, J=1.83 Hz, 1H) 7.53 (dd, J=13.28, 1.98 Hz, 2H) 6.70 (d, J=2.44 Hz, 1H) 3.90 (s, 3H) 3.86 (br. s., 2H).

Preparation FFF 2-fluoro-5-methoxy-4-(3-methyl-1H-1,2,4-triazol-1-yl)aniline

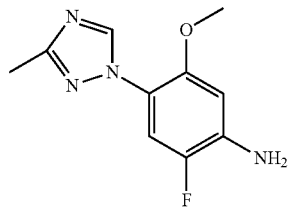 [SMILES: COc1cc(N)c(F)cc1-n1cnc(C)n1]

Intermediate FFF(1)

1-(5-fluoro-2-methoxy-4-nitrophenyl)-3-methyl-1H-1,2,4-triazole

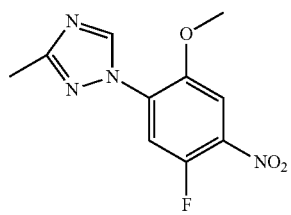 [SMILES: COc1cc([N+](=O)[O-])c(F)cc1-n1cnc(C)n1]

A mixture of 3-methyl-1H-1,2,4-triazole (2.20 g, 26.4 mmol), 1,5-difluoro-2-methoxy-4-nitrobenzene (5.00 g, 26.4 mmol), and potassium carbonate (3.65 g, 26.4 mmol) in anhydrous DMSO (50 mL) was heated at 80° C. for 24 h. The reaction mixture was allowed to cool to rt and was poured into 500 mL of water/10 mL brine solution. The aqueous mixture was extracted with EtOAc (2×250 mL). The combined organic extracts were washed with water (500 mL), dried over sodium sulfate, filtered, and concentrated in vacuo. The crude reaction mixture was purified using silica gel column chromatography (50% EtOAc/hexane) to afford 1-(5-fluoro-2-methoxy-4-nitrophenyl)-3-methyl-1H-1,2,4-triazole (1.24 g, 18% yield). LC-MS (M+H)$^+$=253.2. $^1$H NMR (500 MHz, CDCl$_3$) δ ppm 8.95 (s, 1H) 8.00 (d, J=11.60 Hz, 1H) 7.80 (d, J=6.10 Hz, 1H) 4.09 (s, 3H) 2.50 (s, 3H).

Preparation FFF 2-fluoro-5-methoxy-4-(3-methyl-1H-1,2,4-triazol-1-yl)aniline

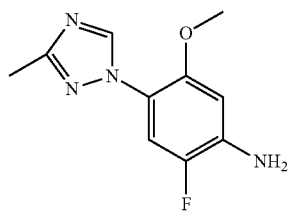 [SMILES: COc1cc(N)c(F)cc1-n1cnc(C)n1]

10% Palladium on carbon (0.523 g, 4.92 mmol) was added under an atmosphere of nitrogen to a chilled (ice-water bath) solution of 1-(5-fluoro-2-methoxy-4-nitrophenyl)-3-methyl-1H-1,2,4-triazole (1.24 g, 4.92 mmol) dissolved in methanol (100 mL). The flask was repeatedly evacuated and flushed with hydrogen gas (double balloon). The resulting mixture was allowed to warm to rt and left to stir for 18 h under the hydrogen atmosphere. The vessel was subsequently purged with nitrogen gas. The crude reaction mixture was filtered through a short diatomaceous earth (Celite®) plug. The reaction vessel and plug were rinsed with fresh methanol. The combined filtrates were concentrated in vacuo. The residue was dried on high vacuum overnight to afford 2-fluoro-5-methoxy-4-(3-methyl-1H-1,2,4-triazol-1-yl)aniline (1.05 g, 96% yield) as a gray solid. LC-MS (M+H)$^+$223.1. $^1$H NMR (500 MHz, CDCl$_3$) δ ppm 8.46 (s, 1H) 7.39 (d, J=11.29 Hz, 1H) 6.44 (d, J=7.63 Hz, 1H) 3.89 (br. s., 2H) 3.83 (s, 3H) 2.47 (s, 3H).

Preparation G 2,4-Dichloro-7-phenyl-6,7-dihydro-5H-cyclopenta[d]pyrimidine

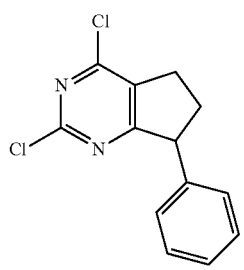 [SMILES: Clc1nc(Cl)c2c(n1)C(c1ccccc1)CC2]

Intermediate G(1)

Cyclopentenylbenzene

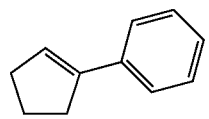 [SMILES: C1=C(c2ccccc2)CCC1]

To a solution of 3.0 M solution of phenylmagnesium bromide in ether (49.7 mL, 149 mmol) was added THF (300 mL). To this solution cooled to 0° C. cyclopentanone (13.23 mL, 149 mmol) was added. The reaction mixture was stirred at room temperature for 30 min, then—at reflux for 2 h. Ice (20 g) was added, followed by 6N HCl, until the precipitate dissolved. The product was extracted with ether. The combined etherial layers were washed with saturated sodium bicarbonate solution, dried over anhydrous magnesium sulfate and filtered. The solvent was removed in vacuum and the residue was purified by column chromatography on silica gel to give cyclopentenylbenzene (21.49 g, 149 mmol, 100% yield) as colorless oil. LC-MS (M+H)$^+$=145.1. $^1$H NMR (500 MHz, CDCl$_3$) δ ppm 7.48 (2H, d, J=7.3 Hz), 7.35 (2H, t, J=7.8 Hz), 7.22-7.27 (1H, m), 6.22 (1H, t, J=2.1 Hz), 2.70-2.80 (2H, m), 2.52-2.64 (2H, m), 2.01-2.12 (2H, m).

Intermediate G(2)

2-Phenylcyclopentanone

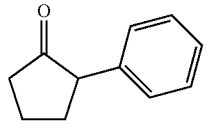 [SMILES: O=C1CCCC1c1ccccc1]

A mixture of 30% hydrogen peroxide (23 mL, 149 mmol) and 85% formic acid (100 mL, 2619 mmol) was heated at 40° C. for 15 minutes. The mixture was carefully added to cyclopentenylbenzene (21.49 g, 149 mmol) and the resulting two-phase system was vigorously stirred at room temperature for 4 h. An exothermic reaction was observed in the beginning. In the end of the stirring the solution became homogeneous. The reaction mixture was carefully quenched with saturated aqueous solution of sodium bicarbonate. The product was extracted with ether. The combined etherial layers were dried over anhydrous magnesium sulfate and filtered. The solvent was removed in vacuum and the product was purified by column chromatography on silica gel to give 2-phenylcyclopentanone (19.995 g, 125 mmol, 84% yield) as brown oil. LC-MS (M+H)$^+$=161.0. $^1$H NMR (500 MHz, CDCl$_3$) δ ppm 7.38 (1H, t, J=7.3 Hz), 7.30-7.35 (2H, m), 7.19 (2H, d, J=7.3 Hz), 3.28-3.37 (1H, m), 2.71 (1H, td, J=4.6, 2.7 Hz), 2.58-2.63 (1H, m), 2.43-2.55 (1H, m), 2.29 (1H, ddd, J=19.0, 10.5, 9.0 Hz), 2.07-2.21 (1H, m), 1.88-1.99 (1H, m).

Intermediate G(3)

Ethyl 2-oxo-3-phenylcyclopentanecarboxylate

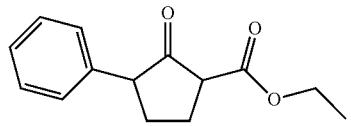 [SMILES: CCOC(=O)C1CCC(c2ccccc2)C1=O]

To a solution of diisopropylamine (6.62 mL, 46.8 mmol) in THF (200 mL) at −78° C. was added a 1.6 M solution of n-butyllithium in hexanes (29.3 mL, 46.8 mmol). The solution was stirred for 30 min at −78° C. and treated with a solution of 2-phenylcyclopentanone (5 g, 31.2 mmol) in 50 mL of dry THF. After stirring for 30 min at −78° C., ethyl carbonocyanidate (3.36 mL, 34.3 mmol) was added to the reaction mixture. The resulting solution was warmed to 25° C. with stirring over 3 h. The reaction mixture was quenched with 10 mL of water, washed with brine, dried over anhydrous sodium sulfate, concentrated in vacuum, and purified by column chromatography on silica gel to afford ethyl 2-oxo-3-phenylcyclopentanecarboxylate (5.3 g, 22.82 mmol, 73% yield) as colorless oil. LC-MS (M+K)⁺=273.2. ¹H NMR (500 MHz, CDCl₃) δ ppm 7.32-7.39 (2H, m), 7.25-7.31 (1H, m), 7.19-7.25 (2H, m), 4.18-4.32 (2H, m), 3.29-3.55 (2H, m), 1.87-2.62 (4H, m), 1.28-1.39 (3H, m).

Intermediate G(4)

2-Amino-7-phenyl-6,7-dihydrocyclopenta[e][1,3]oxazin-4(5H)-one

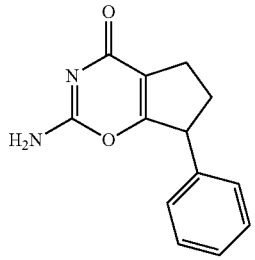 [SMILES: Nc1nc(=O)c2c(o1)C(c1ccccc1)CC2]

2-Methyl-2-thiopseudourea sulfate (1.336 g, 9.61 mmol) was dissolved in water (10 mL) and KOH (1.128 g, 20.10 mmol) was added. Under stirring, ethyl 2-oxo-3-phenylcyclopentanecarboxylate (2.03 g, 8.74 mmol) was added and the reaction mixture was stirred at room temperature overnight. The reaction mixture was filtered, washed with water and ether, and dried over anhydrous sodium sulfate to afford 2-amino-7-phenyl-6,7-dihydrocyclopenta[e][1,3]oxazin-4(5H)-one (1.22 g, 5.35 mmol, 61.2% yield) as white solid. LC-MS (M+H)⁺=229.1. ¹H NMR (500 MHz, dimethylsulfoxide-d6) δ ppm 7.57-7.85 (2H, m), 7.08-7.47 (5H, m), 4.25-4.38 (1H, m), 1.72-2.73 (3H, m), 1.09-1.31 (1H, m).

Intermediate G(5)

7-Phenyl-6,7-dihydrocyclopenta[e][1,3]oxazine-2,4(3H,5H)-dione

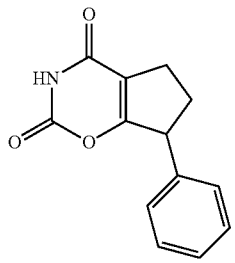 [SMILES: O=c1[nH]c(=O)c2c(o1)C(c1ccccc1)CC2]

2-Amino-7-phenyl-6,7-dihydrocyclopenta[e][1,3]oxazin-4(5H)-one (900 mg, 3.94 mmol) was dissolved in a 3M aqueous hydrogen chloride solution (32 mL, 96 mmol) under stirring. The mixture was heated at reflux for 1 h. The reaction mixture was cooled and extracted with ethyl acetate. The organic layer was washed with saturated aqueous sodium bicarbonate solution and brine, dried over anhydrous sodium sulfate, concentrated in vacuum and purified by column chromatography on silica gel to afford 7-phenyl-6,7-dihydrocyclopenta[e][1,3]oxazine-2,4(3H,5H)-dione (350 mg, 1.527 mmol, 38.7% yield). LC-MS (M+H)⁺=230.0. ¹H NMR (500 MHz, CDCl₃) δ ppm 8.34 (1H, br s), 7.35 (2H, t, J=7.3 Hz), 7.27-7.32 (1H, m), 7.18 (2H, d, J=7.3 Hz), 4.20 (1H, t, J=7.6 Hz), 2.82-2.91 (1H, m), 2.61-2.79 (2H, m), 2.11-2.21 (1H, m).

or

A solution of 2-phenylcyclopentanone (19.995 g, 125 mmol) and N-(chlorocarbonyl)isocyanate (23.70 g, 225 mmol) was stirred at 58° C. for 1 h and at 130° C. for 45 min. The resulting tarrified reaction mixture was dissolved in ethyl acetate and neutralized with saturated aqueous sodium bicarbonate solution. The organic layer was dried over anhydrous magnesium sulfate and filtered. The product was purified by column chromatography on silica gel to give 7-phenyl-6,7-dihydrocyclopenta[e][1,3]oxazine-2,4(3H,5H)-dione (3.751 g, 16.36 mmol, 13% yield) as brownish solid. LC-MS (M+H)⁺=230.0. ¹H NMR (500 MHz, CDCl₃) δ ppm 8.34 (1H, br s), 7.35 (2H, t, J=7.3 Hz), 7.27-7.32 (1H, m), 7.18 (2H, d, J=7.3 Hz), 4.20 (1H, t, J=7.6 Hz), 2.82-2.91 (1H, m), 2.61-2.79 (2H, m), 2.11-2.21 (1H, m).

Intermediate G(6)

7-Phenyl-6,7-dihydro-1H-cyclopenta[d]pyrimidine-2,4(3H,5H)-dione

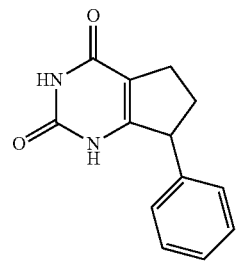 [SMILES: O=c1[nH]c2c(c(=O)[nH]1)CCC2c1ccccc1]

A solution of 7-phenyl-6,7-dihydrocyclopenta[e][1,3]oxazine-2,4(3H,5H)-dione (3.751 g, 16.36 mmol) in concentrated ammonia in water (80 mL, 16.36 mmol) was heated in a 350 mL high-pressure flask for 5 h. The solvent was removed in vacuum to give 7-phenyl-6,7-dihydro-1H-cyclopenta[d]pyrimidine-2,4(3H,5H)-dione (3.73 g, 16.34 mmol, 100% yield) as brown solid. LC-MS (M+H)⁺=229.1. ¹H NMR (500 MHz, dimethylsulfoxide-d6) δ ppm 7.34 (2H, t, J=7.5 Hz), 7.26 (1H, t, J=7.3 Hz), 7.18 (2H, d, J=7.3 Hz), 5.39 (1H, br s), 4.14 (1H, d, J=7.3 Hz), 2.43-2.68 (2H, m), 1.80-1.88 (2H, m).

Preparation G 2,4-Dichloro-7-phenyl-6,7-dihydro-5H-cyclopenta[d]pyrimidine

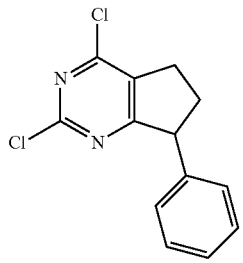 [SMILES: Clc1nc(Cl)c2c(n1)C(c1ccccc1)CC2]

A solution of 7-phenyl-6,7-dihydro-1H-cyclopenta[d]pyrimidine-2,4(3H,5H)-dione (1.241 g, 5.44 mmol) in phosphoryl trichloride (14.93 mL, 163 mmol) was heated in microwave at 110° C. for 1 h. Once ice melted, the product was extracted with dichloromethane. The combined organic extracts were dried over anhydrous magnesium sulfate and filtered. The solvent was removed in vacuum and the residue was purified by column chromatography on silica gel to give 2,4-dichloro-7-phenyl-6,7-dihydro-5H-cyclopenta[d]pyrimidine (3.132 g, 72%) as light brown solid. LC-MS (M+H)$^+$ =265.0. $^1$H NMR (500 MHz, CDCl$_3$) δ ppm 7.31-7.37 (2H, m), 7.27 (1H, d, J=7.0 Hz), 7.15 (2H, d, J=7.9 Hz), 4.44 (1H, t, J=8.2 Hz), 3.09-3.18 (1H, m), 2.97-3.06 (1H, m), 2.73 (1H, ddd, J=9.0, 4.7, 4.6 Hz), 2.26 (1H, ddd, J=8.5, 7.0, 6.7 Hz).

Preparation Ga 2-chloro-N-methyl-7-phenyl-6,7-dihydro-5H-cyclopenta[d]pyrimidin-4-amine

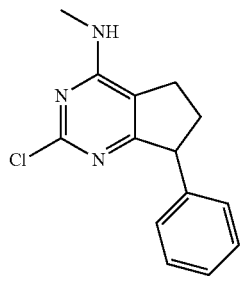 [SMILES: CNc1nc(Cl)nc2c1CCC2c1ccccc1]

To a solution of 2,4-dichloro-7-phenyl-6,7-dihydro-5H-cyclopenta[d]pyrimidine (Preparation G) (395 mg, 1.49 mmol) in THF (3700 μL), 2 M MeNH$_2$ in THF (3700 μL, 7.45 mmol) was added. The reaction was allowed to stir at rt. When the reaction was complete, removed solvent and applied residue to silica gel. Eluted with EtOAc/Hex to afford the desired 2-chloro-N-methyl-7-phenyl-6,7-dihydro-5H-cyclopenta[d]pyrimidin-4-amine (80.8 mg, 0.220 mmol, 69.1% yield). LC-MS (M+H)$^+$=260.1. $^1$H NMR (500 MHz, CDCl$_3$) δ ppm 7.07 (3H, dd, J=8.5, 5.5 Hz), 6.96 (2H, t, J=8.7 Hz), 4.72 (1H, br s), 4.23 (1H, t, J=7.2 Hz), 3.09 (3H, d, J=4.9 Hz), 2.67-2.77 (1H, m), 2.58-2.67 (2H, m), 2.01-2.11 (1H, m).

Preparation Gb

2-Chloro-N,N-dimethyl-7-phenyl-6,7-dihydro-5H-cyclopenta[d]pyrimidin-4-amine

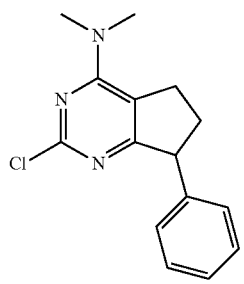 [SMILES: CN(C)c1nc(Cl)nc2c1CCC2c1ccccc1]

A solution of 2,4-dichloro-7-phenyl-6,7-dihydro-5H-cyclopenta[d]pyrimidine (200 mg, 0.754 mmol) and excess dimethylamine (3.77 mL, 7.54 mmol) in MeOH (2 mL) was stirred at rt for 1 h. The solvent was removed in vacuum to afford 2-chloro-N,N-dimethyl-7-phenyl-6,7-dihydro-5H-cyclopenta[d]pyrimidin-4-amine (207 mg, 0.756 mmol, 100% yield). LC-MS (M+H)$^+$=274.2.

Preparation Gc

2-Chloro-N-ethyl-N-methyl-7-phenyl-6,7-dihydro-5H-cyclopenta[d]pyrimidin-4-amine

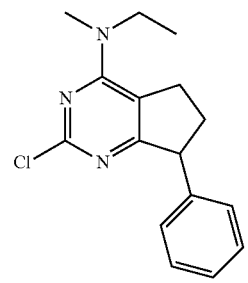 [SMILES: CCN(C)c1nc(Cl)nc2c1CCC2c1ccccc1]

A solution of 2,4-dichloro-7-phenyl-6,7-dihydro-5H-cyclopenta[d]pyrimidine (150 mg, 0.566 mmol) and excess N-methylethanamine (0.486 mL, 5.66 mmol) in MeOH (2 mL) was stirred at rt for 1 h. The solvent was removed in vacuum to afford 2-chloro-N-ethyl-N-methyl-7-phenyl-6,7-dihydro-5H-cyclopenta[d]pyrimidin-4-amine (163 mg, 0.566 mmol, 100% yield). LC-MS (M+H)$^+$=288.2.

Preparation Gd 4-(Azetidin-1-yl)-2-chloro-7-phenyl-6,7-dihydro-5H-cyclopenta[d]pyrimidine

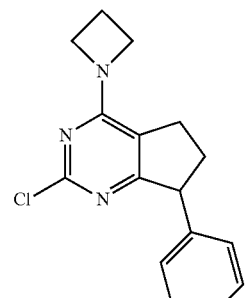

A solution of 2,4-dichloro-7-phenyl-6,7-dihydro-5H-cyclopenta[d]pyrimidine (150 mg, 0.566 mmol) and excess azetidine (162 mg, 2.83 mmol) in methanol (1 mL) was stirred at rt for 30 min. The solvent was removed in vacuum to afford 4-(azetidin-1-yl)-2-chloro-7-phenyl-6,7-dihydro-5H-cyclopenta[d]pyrimidine (162 mg, 0.567 mmol, 100% yield). LC-MS (M+H)$^+$=286.3.

Preparation Ge

2-Chloro-N-trideuteromethyl-7-phenyl-6,7-dihydro-5H-cyclopenta[d]pyrimidin-4-amine

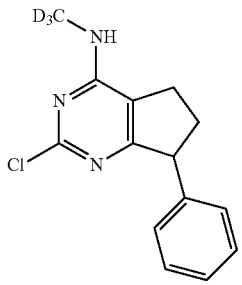 [SMILES: [2H]C([2H])([2H])Nc1nc(Cl)nc2c1CCC2c1ccccc1]

To a solution of 2,4-dichloro-7-(4-fluorophenyl)-6,7-dihydro-5H-cyclopenta[d]pyrimidine (350 mg, 1.236 mmol) and trideuteromethylamine hydrochloride (174 mg, 2.472 mmol) in methanol (3 mL) was added DIPEA (0.432 mL, 2.472 mmol). The reaction mixture was stirred at room temperature overnight. The solvent was removed in vacuum and the residue was purified by column chromatography on silica gel to give 2-chloro-N-trideuteromethyl-7-phenyl-6,7-dihydro-5H-cyclopenta[d]pyrimidin-4-amine as brown oil. LC-MS (M+H)$^+$=281.2.

Preparation Gf 2-chloro-N-cyclopropyl-7-phenyl-6,7-dihydro-5H-cyclopenta[d]pyrimidin-4-amine

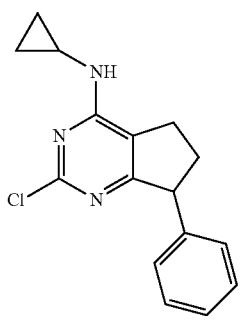 [SMILES: Clc1nc(NC2CC2)c2c(n1)C(c1ccccc1)CC2]

To a solution of 2,4-dichloro-7-phenyl-6,7-dihydro-5H-cyclopenta[d]pyrimidine (170 mg, 0.641 mmol) in NMP (2 mL) was added cyclopropanamine (110 mg, 1.924 mmol) dropwise. The mixture was stirred at RT for 3 hours. 8 mL of water was added to precipitate out the product. The solid was filtered out and air-dried to give a crude 2-chloro-N-cyclopropyl-7-phenyl-6,7-dihydro-5H-cyclopenta[d]pyrimidin-4-amine (175 mg, 0.612 mmol, 96% yield), which was used for the next step without any purification. LC-MS (M+H)$^+$=286.1

Preparation Gg 2-chloro-N-cyclobutyl-7-phenyl-6,7-dihydro-5H-cyclopenta[d]pyrimidin-4-amine

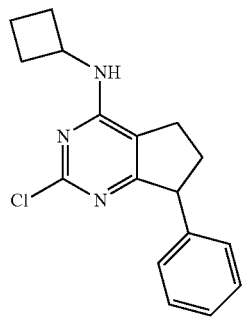 [SMILES: Clc1nc(NC2CCC2)c2c(n1)C(c1ccccc1)CC2]

To a solution of 2,4-dichloro-7-phenyl-6,7-dihydro-5H-cyclopenta[d]pyrimidine (160 mg, 0.60 mmol) in NMP (2 mL) was added cyclobutanamine (129 mg, 1.81 mmol) dropwise. The mixture was stirred at RT for 3 hrs. 8 mL of water was added to precipitate out the product. The solid was filtered out and air-dried to give a crude 2-chloro-N-cyclobutyl-7-phenyl-6,7-dihydro-5H-cyclopenta[d]pyrimidin-4-amine (177 mg, 0.57 mmol, 94% yield), which was used for the next step without any purification. LC-MS (M+H)$^+$=300.1

Preparation Gh 2-chloro-7-phenyl-N-isopropyl-6,7-dihydro-5H-cyclopenta[d]pyrimidin-4-amine

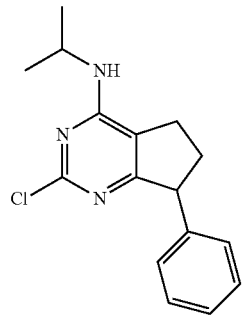 [SMILES: CC(C)Nc1nc(Cl)nc2c1CCC2c1ccccc1]

To a solution of 2,4-dichloro-7-phenyl-6,7-dihydro-5H-cyclopenta[d]pyrimidine (172 mg, 0.65 mmol) in NMP (2 mL) was added propan-2-amine (115 mg, 1.95 mmol) dropwise. The mixture was stirred at RT for 3 hrs. 8 mL of water was added to precipitate out the product. The solid was filtered out, air-dried, and purified via Biotage (12 g, hexanes-70% EtOAc) to give 2-chloro-N-isopropyl-7-phenyl-6,7-dihydro-5H-cyclopenta[d]pyrimidin-4-amine (154 mg, 0.535 mmol, 82% yield). $^1$H NMR (500 MHz, CDCl$_3$) δ ppm 7.30 (2H, t, J=7.5 Hz), 7.20-7.25 (1H, m), 7.15 (1H, d, J=1.5 Hz), 7.13 (1H, s), 4.53 (1H, d, J=7.3 Hz), 4.37-4.45 (1H, m), 4.23-4.28 (1H, m), 2.58-2.78 (3H, m), 2.10-2.17 (1H, m), 1.27-1.29 (6H, m).

Preparation Gi 2-chloro-4-(3-chloroazetidin-1-yl)-7-phenyl-6,7-dihydro-5H-cyclopenta[d]pyrimidine

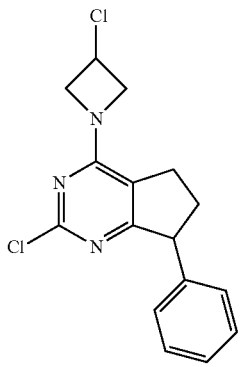 [SMILES: Clc1nc2c(c(N3CC(Cl)C3)n1)CCC2c1ccccc1]

The mixture of 3-chloroazetidine, HCl (217 mg, 1.697 mmol), 2,4-dichloro-7-phenyl-6,7-dihydro-5H-cyclopenta[d]pyrimidine (150 mg, 0.566 mmol) and DIEA (0.395 mL, 2.263 mmol) in N-Methyl-2-pyrrolidinone (2.0 mL) was stirred at RT for 3 h. Water (8 ml) was added to the reaction mixture. The product precipitated out which was filtered, rinsed with water and air dried. LC-MS (M+H)$^+$=320.0. $^1$H NMR (500 MHz, CHLOROFORM-d) δ ppm 7.21-7.39 (m, 3H) 7.14 (d, J=7.02 Hz, 2H) 4.65-4.84 (m, 3H) 4.34-4.48 (m, 2H) 4.23 (dd, J=9.16, 6.41 Hz, 1H) 3.00 (dd, J=8.85, 5.80 Hz, 1H) 2.83-2.93 (m, 1H) 2.54-2.72 (m, 1H) 2.02-2.20 (m, 1H).

Preparation Gj 2-chloro-4-(3-fluoroazetidin-1-yl)-7-phenyl-6,7-dihydro-5H-cyclopenta[d]pyrimidine

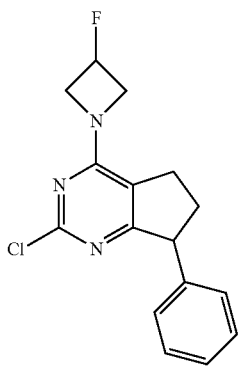 [SMILES: FC1CN(c2nc(Cl)nc3c2CCC3c2ccccc2)C1]

3-fluoroazetidine was reacted with Preparation G in the manner of Preparation Gi to afford the title compound. LC-MS (M+H)$^+$=304.1. $^1$H NMR (500 MHz, CHLOROFORM-d) δ ppm 7.19-7.37 (m, 3H) 7.15 (d, J=7.32 Hz, 2H) 5.39-5.52 (m, 1H) 4.59 (dddd, J=14.88, 10.15, 5.19, 4.88 Hz, 2H) 4.30-4.50 (m, 2H) 4.23 (dd, J=9.00, 6.26 Hz, 1H) 2.96-3.07 (m, 1H) 2.84-2.96 (m, 1H) 2.56-2.70 (m, 1H) 2.05-2.21 (m, 1H).

Preparation Gk 2-chloro-4-(3-methoxyazetidin-1-yl)-7-phenyl-6,7-dihydro-5H-cyclopenta[d]pyrimidine

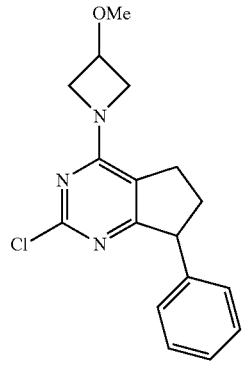 [SMILES: COC1CN(c2nc(Cl)nc3c2CCC3c2ccccc2)C1]

3-methoxyazetidine was reacted with Preparation G in the manner of Preparation Gi to afford the title compound. LC-MS (M+H)$^+$=316.1.

Preparation Gl 2-(2-chloro-7-phenyl-6,7-dihydro-5H-cyclopenta[d]pyrimidin-4-yl)-5,8-dioxa-2-azaspiro[3.4]octane

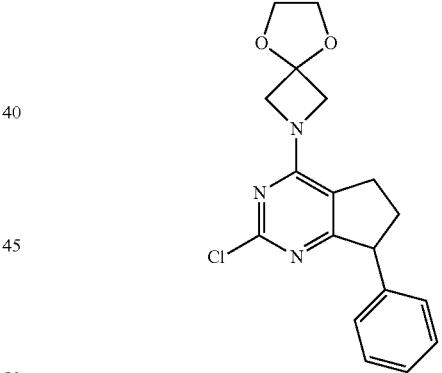

Azetidin-3-one was reacted with Preparation G in the manner of Preparation Gi to afford 1-(2-chloro-7-phenyl-6,7-dihydro-5H-cyclopenta[d]pyrimidin-4-yl)azetidin-3-one. LC-MS (M+H)$^+$=300.0 A mixture of ethylene glycol (119 μL, 2.135 mmol), 1-(2-chloro-7-phenyl-6,7-dihydro-5H-cyclopenta[d]pyrimidin-4-yl)azetidin-3-one (320 mg, 1.068 mmol) and 4-methylbenzenesulfonic acid, H2O (20.31 mg, 0.107 mmol) in Benzene (2965 μL) was heated at reflux for 24 h in a Dean-stark apparatus. The resulting mixture was concentrated and purified by Prep-HPLC to afford the title compound. LC-MS (M+H)$^+$=344.0. $^1$H NMR (500 MHz, CHLOROFORM-d) δ ppm 7.21-7.40 (m, 3H) 7.15 (d, J=7.63 Hz, 2H) 4.35-4.53 (m, 4H) 4.23 (dd, J=9.00, 6.26 Hz, 1H) 4.03 (s, 4H) 2.96-3.09 (m, 1H) 2.80-2.96 (m, 1H) 2.51-2.70 (m, 1H) 2.03-2.16 (m, 1H).

Preparation Gm 2-(2-chloro-7-phenyl-6,7-dihydro-5H-cyclopenta[d]pyrimidin-4-yl)-5-oxa-2-azaspiro[3.4]octane

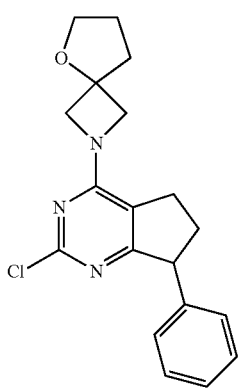 [SMILES: Clc1nc2c(c(N3CC4(CCCO4)C3)n1)CCC2c1ccccc1]

5-oxa-2-azaspiro[3.4]octane was reacted with Preparation G in the manner of Preparation Gi to afford the title compound. LC-MS (M+H)⁺=342.1.

Preparation Gn 1-(2-chloro-7-phenyl-6,7-dihydro-5H-cyclopenta[d]pyrimidin-4-yl)pyrrolidin-3-one

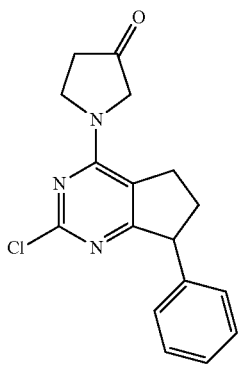 [SMILES: O=C1CCN(c2nc(Cl)nc3c2CCC3c2ccccc2)C1]

Pyrrolidin-3-one was reacted with Preparation G in the manner of Preparation Gi to afford the title compound. LC-MS (M+H)⁺=314.1.

Preparation Go 7-(2-chloro-7-phenyl-6,7-dihydro-5H-cyclopenta[d]pyrimidin-4-yl)-1,4-dioxa-7-azaspiro[4.4]nonane

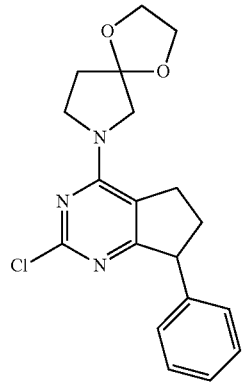 [SMILES: Clc1nc2c(c(N3CCC4(C3)OCCO4)n1)CCC2c1ccccc1]

The mixture of ethylene glycol (46.9 μL, 0.841 mmol), 1-(2-chloro-7-phenyl-6,7-dihydro-5H-cyclopenta[d]pyrimidin-4-yl)pyrrolidin-3-one (Intermediate Gn) (132 mg, 0.421 mmol) and 4-methylbenzenesulfonic acid, H2O (8.00 mg, 0.042 mmol) in Benzene (1169 μL) was heated at reflux for 24 h in a Dean-stark apparatus. The resulting mixture was concentrated and purified by Prep-HPLC (Column: PHENOMENEX LUNA C18 30×100 mm, Solvent A=10 mM Ammonium Acetate in 95:5 H2O/ACN, Solvent B=10 mM Ammonium Acetate in 5:95 H2O/ACN. Flow rate: 40 ml/min, 30-100, 20 min) to get 7-(2-chloro-7-phenyl-6,7-dihydro-5H-cyclopenta[d]pyrimidin-4-yl)-1,4-dioxa-7-azaspiro[4.4]nonane (24 mg, 0.067 mmol, 15.94% yield). LC-MS (M+H)⁺=358.1. ¹H NMR (500 MHz, CHLOROFORM-d) δ ppm 7.31 (2H, t, J=7.63 Hz), 7.20-7.25 (1H, m), 7.15 (2H, d, J=7.63 Hz), 4.21 (1H, dd, J=9.16, 6.10 Hz), 4.01-4.06 (4H, m), 3.89-3.97 (2H, m), 3.77-3.84 (2H, m), 3.26 (1H, ddd, J=15.03, 8.62, 5.95 Hz), 3.13 (1H, ddd, J=14.95, 8.85, 5.80 Hz), 2.53-2.63 (1H, m), 2.17 (2H, t, J=7.17 Hz), 2.03-2.12 (1H, m).

Preparation Gp 2-chloro-N-(5-isopropyl-2-methylphenyl)-7-phenyl-6,7-dihydro-5H-cyclopenta[d]pyrimidin-4-amine

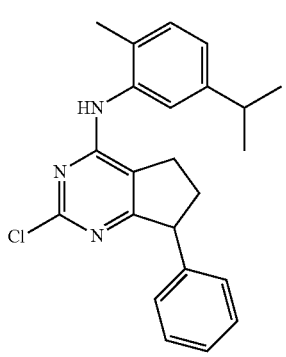 [SMILES: Cc1ccc(C(C)C)cc1Nc1nc(Cl)nc2c1CCC2c1ccccc1]

To a solution of 2,4-dichloro-7-phenyl-6,7-dihydro-5H-cyclopenta[d]pyrimidine (500 mg, 1.886 mmol) in NMP (Volume: 7543 nl) was added 5-isopropyl-2-methylaniline (281 mg, 1.886 mmol) and DIPEA (329 μl, 1.886 mmol). The resulting mixture was brought to 120° C. and stirred for 2 h. The mixture was then diluted with EtOAc (25 mL), washed with water (2×10 mL), brine (10 mL), dried over MgSO$_4$, filtered, and concentrated in vacuo. Purification by flash chromatography (Silica, Thomson 40 g, 0-35% EtOAc/Hexanes) gave 2-chloro-N-(5-isopropyl-2-methylphenyl)-7-phenyl-6,7-dihydro-5H-cyclopenta[d]pyrimidin-4-amine (81421-078-01) (220 mg, 0.582 mmol, 30.9% yield). LC-MS (M+H)$^+$=378.1. $^1$H NMR (500 MHz, MeOD) δ ppm 7.30-7.41 (3H, m), 7.19-7.26 (3H, m), 7.16 (2H, d, J=7.93 Hz), 7.11 (1H, d, J=7.63 Hz), 4.27 (1H, t, J=7.63 Hz), 2.91 (1H, ddd, J=13.89, 6.87, 6.71 Hz), 2.77-2.86 (1H, m), 2.61-2.76 (2H, m), 2.24 (3H, s), 2.03-2.13 (1H, m), 1.27 (5H, dd, J=7.02, 1.53 Hz).

Preparation H 2,4-Dichloro-7-(4-fluorophenyl)-6,7-dihydro-5H-cyclopenta[d]pyrimidine

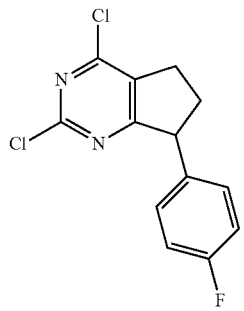 [SMILES: Fc1ccc(C2CCc3c(Cl)nc(Cl)nc32)cc1]

Intermediate H(1)

1-Cyclopentenyl-4-fluorobenzene

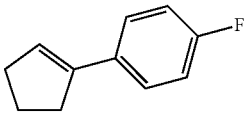 [SMILES: Fc1ccc(C2=CCCC2)cc1]

To a 0.5M solution of 4-fluorophenylmagnesium bromide (298 mL, 149 mmol) in THF at 0° C. was carefully added cyclopentanone (13.23 mL, 149 mmol). Upon the end of the addition, the reaction mixture was heated at reflux for 2 h. Ice (10 g) and 6N aqueous hydrochloric acid were added. The reaction mixture was extracted with ether. The combined organic extracts were washed with a saturated aqueous solution of sodium hydrogen sulfite, a saturated aqueous solution of sodium bicarbonate and water. The organic layer was dried over anhydrous magnesium sulfate and filtered. The solvent was removed in vacuum and the residue was purified by column chromatography on silica gel to give 1-cyclopentenyl-4-fluorobenzene (24.155 g, 149 mmol, 100% yield) as colorless oil. LC-MS (M+H)$^+$=163.0. $^1$H NMR (500 MHz, CDCl$_3$) δ ppm 7.35-7.42 (2H, m), 6.95-7.02 (2H, m), 6.06-6.13 (1H, m), 2.63-2.71 (2H, m), 2.47-2.56 (2H, m), 1.96-2.06 (2H, m).

Intermediate H(2)

2-(4-Fluorophenyl)cyclopentanone

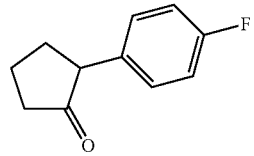 [SMILES: O=C1CCCC1c1ccc(F)cc1]

A mixture of 80% formic acid (100 mL, 2618 mmol) and 30% hydrogen peroxide (23 mL, 149 mmol) was warmed at 40° C. for 10 min. The resulting solution was carefully added to 1-cyclopentenyl-4-fluorobenzene (24.155 g, 149 mmol) under stirring. The two-phase system was initially stirred at room temperature. After a certain period of time, a spontaneous exothermic reaction took place, and the temperature rose to about 50° C. The reaction mixture was stirred at room temperature for 1 h. The reaction mixture was quenched by careful addition of a saturated sodium bicarbonate solution. Ether was added and the content of the separatory funnel was vigorously shaken. The organic layer was separated and the aqueous layer was extracted with ether. The combined organic extracts were dried over anhydrous magnesium sulfate and filtered. The solvent was removed in vacuum and the residue was purified by column chromatography on silica gel to give 2-(4-fluorophenyl)cyclopentanone (18.557 g, 104 mmol, 69.9% yield) as colorless oil. LC-MS (M+H)$^+$=177.2. $^1$H NMR (500 MHz, CDCl$_3$) δ ppm 7.12-7.18 (2H, m), 6.98-7.04 (2H, m), 3.29 (1H, dd, J=11.6, 8.5 Hz), 2.42-2.54 (2H, m), 2.27 (1H, ddd, J=19.1, 10.5, 8.9 Hz), 2.12-2.20 (1H, m), 2.01-2.12 (1H, m), 1.87-1.99 (1H, m, J=11.7, 11.7, 8.2, 6.3 Hz).

Intermediate H(3)

7-(4-Fluorophenyl)-6,7-dihydrocyclopenta[e][1,3]oxazine-2,4(3H,5H)-dione

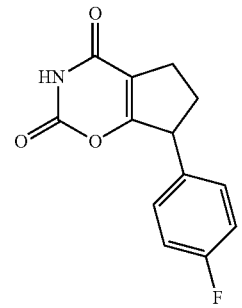

A mixture of 2-(4-fluorophenyl)cyclopentanone (18.557 g, 104 mmol) and carbonisocyanatidic chloride (19.77 g, 187 mmol) was heated at 58° C. for 1 h and at 130° C. for 2 h. Upon cooling to room temperature, the tarrified reaction mixture was dissolved in ethyl acetate and washed with saturated aqueous solution of sodium bicarbonate. The organic layer was separated and the aqueous layer was extracted with ethyl acetate. The combined organic extracts were dried over anhydrous magnesium sulfate and filtered. The solvent was removed in vacuum and the residue was purified by column chromatography on silica gel to give 7-(4-fluorophenyl)-6,7- dihydrocyclopenta[e][1,3]oxazine-2,4(3H,5H)-dione (13.527 g, 54.7 mmol, 52.5% yield) as brown solid. LC-MS (M+H)+=248.1. ¹H NMR (500 MHz, CDCl₃) δ ppm 11.80 (1H, br s), 7.31-7.39 (2H, m), 7.16-7.22 (2H, m), 4.30-4.38 (1H, m), 2.63-2.73 (1H, m), 2.53-2.63 (2H, m), 1.84-1.95 (1H, m).

Intermediate H(4)

7-(4-Fluorophenyl)-6,7-dihydro-1H-cyclopenta[d]pyrimidine-2,4(3H,5H)-dione

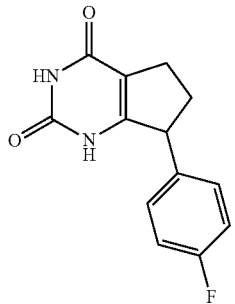 [SMILES: O=c1[nH]c2c(c(=O)[nH]1)CCC2c1ccc(F)cc1]

A solution of 7-(4-fluorophenyl)-6,7-dihydrocyclopenta[e][1,3]oxazine-2,4(3H,5H)-dione (13.527 g, 54.7 mmol) in concentrated ammonium hydroxide (150 mL, 3852 mmol) was heated at 100° C. in a high-pressure (350 mL) vessel overnight. The reaction mixture was cooled to 0° C. and filtered. The precipitate was consecutively washed with water and dried, first—by passing air through the filter, and then—in pump vacuum to give 7-(4-fluorophenyl)-6,7-dihydro-1H-cyclopenta[d]pyrimidine-2,4(3H,5H)-dione (4.670 g, 18.97 mmol, 34.7% yield). LC-MS (M+H)+=247.3. ¹H NMR (500 MHz, CDCl₃) δ ppm 11.70-11.81 (2H, br s), 7.31-7.39 (2H, m), 7.16-7.22 (2H, m), 4.30-4.38 (1H, m), 2.63-2.73 (1H, m), 2.53-2.63 (2H, m), 1.84-1.95 (1H, m).

Preparation H 2,4-Dichloro-7-(4-fluorophenyl)-6,7-dihydro-5H-cyclopenta[d]pyrimidine

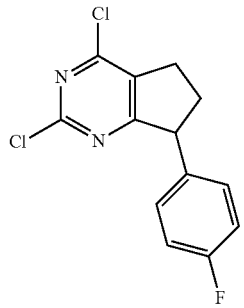 [SMILES: Fc1ccc(C2CCc3c(Cl)nc(Cl)nc32)cc1]

A solution of 7-(4-fluorophenyl)-6,7-dihydro-1H-cyclopenta[d]pyrimidine-2,4(3H,5H)-dione (1 g, 4.06 mmol) in phosphorus oxychloride (11.81 mL, 127 mmol) and N,N-dimethylaniline (3.94 mL, 31.1 mmol) was stirred at 110° C. overnight. The reaction mixture was carefully poured into ice. Once the ice melted, the aqueous layer was extracted with dichloromethane. The combined organic extracts were dried over anhydrous magnesium sulfate and filtered. The solvent was removed in vacuum and the residue was purified by column chromatography on silica gel to give 2,4-dichloro-7-(4-fluorophenyl)-6,7-dihydro-5H-cyclopenta[d]pyrimidine (700.0 mg, 2.472 mmol, 60.9% yield) as dark burgundy solid. LC-MS (M+H)+=283.1. ¹H NMR (500 MHz, CDCl₃) δ ppm 7.09-7.15 (2H, m), 7.03 (2H, t, J=8.5 Hz), 4.42 (1H, t, J=8.4 Hz), 3.10 (1H, dd, J=9.2, 4.6 Hz), 3.01 (1H, d, J=8.2 Hz), 2.73 (1H, d, J=8.9 Hz), 2.15-2.27 (1H, m).

Preparation Ha 2-chloro-4-(3,3-difluoroazetidin-1-yl)-7-(4-fluorophenyl)-6,7-dihydro-5H-cyclopenta[d]pyrimidine

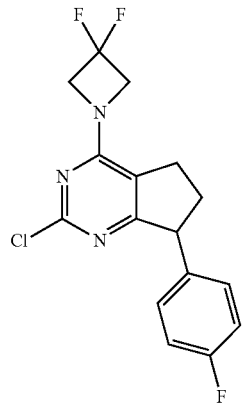 [SMILES: Fc1ccc(C2CCc3c2nc(Cl)nc3N2CC(F)(F)C2)cc1]

To a solution of 2,4-dichloro-7-(4-fluorophenyl)-6,7-dihydro-5H-cyclopenta[d]pyrimidine (Preparation H) (521 mg, 1.840 mmol) in MeOH (18.400 mL) was added DIPEA (0.803 mL, 4.60 mmol), then 3,3-difluoroazetidine, HCl (358 mg, 2.76 mmol). The reaction was allowed to stir at RT for 2 h and was then concentrated in vacuo. Purification by flash chromatography (silica, ethyl acetate/hexanes) gave 2-chloro-4-(3,3-difluoroazetidin-1-yl)-7-(4-fluorophenyl)-6,7-dihydro-5H-cyclopenta[d]pyrimidine (528 mg, 1.554 mmol, 84% yield) as a clear, colorless oil which crystallized on standing. LC-MS (M+H)+=340.0. ¹H NMR (500 MHz, CDCl₃) δ ppm 7.05-7.13 (2H, m), 6.94-7.02 (2H, m), 4.60 (4H, td, J=11.75, 4.27 Hz), 4.18-4.30 (1H, m), 2.93-3.06 (1H, m), 2.80-2.95 (1H, m), 2.56-2.70 (1H, m), 1.96-2.18 (1H, m).

Preparation Hb (1S,4S)-5-(2-chloro-7-(4-fluorophenyl)-6,7-dihydro-5H-cyclopenta[d]pyrimidin-4-yl)-2-oxa-5-azabicyclo[2.2.1]heptane

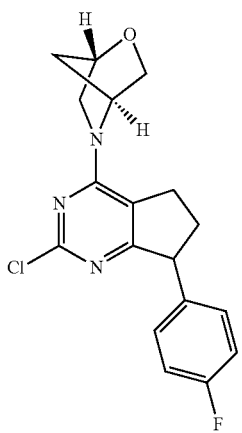 [SMILES: Fc1ccc(C2CCc3c2nc(Cl)nc3N2C[C@@H]3C[C@H]2CO3)cc1]

To a solution of 2,4-dichloro-7-(4-fluorophenyl)-6,7-dihydro-5H-cyclopenta[d]pyrimidine (Preparation H) (200 mg, 0.706 mmol) in MeOH (7064 µL) was added (1S,4S)-2-Oxa-5-azabicyclo[2.2.1]heptane monohydrochloride (115 mg, 0.848 mmol) and DIPEA (271 µL, 1.554 mmol). The resulting mixture was stirred at RT overnight. The reaction mixture was then concentrated in vacuo. The resulting oil was purified by flash chromatography (Silica, EtOAc/Hexanes) to give (1S,4S)-5-(2-chloro-7-(4-fluorophenyl)-6,7-dihydro-5H-cyclopenta[d]pyrimidin-4-yl)-2-oxa-5-azabicyclo[2.2.1]heptane (148 mg, 0.428 mmol, 60.6% yield). LC-MS (M+H)$^+$=346.1. $^1$H NMR (500 MHz, MeOD) δ ppm 7.12-7.21 (2H, m), 7.00-7.08 (2H, m), 5.11-5.21 (1H, m), 4.69-4.74 (1H, m), 4.15-4.26 (1H, m), 3.88-3.94 (2H, m), 3.68-3.86 (2H, m), 3.11-3.21 (1H, m), 2.56-2.69 (1H, m), 1.92-2.11 (2H, m), 1.24-1.42 (2H, m).

Preparations Hc1 and Hc2

2-chloro-7-(4-fluorophenyl)-4-(2-methylpyrrolidin-1-yl)-6,7-dihydro-5H-cyclopenta[d]pyrimidine

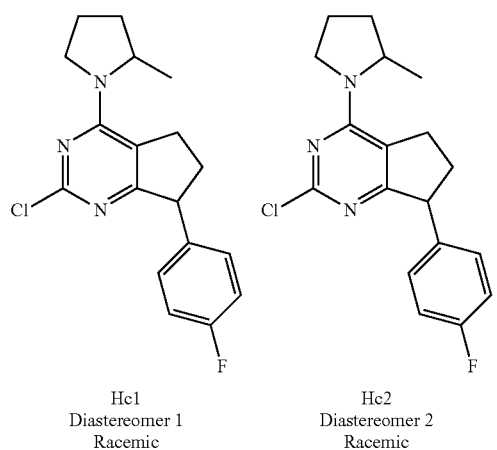 [SMILES: CC1CCCN1c1nc(Cl)nc2c1CCC2c1ccc(F)cc1 ; CC1CCCN1c1nc(Cl)nc2c1CCC2c1ccc(F)cc1]

Hc1
Diastereomer 1
Racemic

Hc2
Diastereomer 2
Racemic

To a solution of 2,4-dichloro-7-(4-fluorophenyl)-6,7-dihydro-5H-cyclopenta[d]pyrimidine (Preparation H) (200 mg, 0.706 mmol) in MeOH (7064 µL) was added 2-Methylpyrrolidine (82 µL, 0.848 mmol). The resulting mixture was stirred at RT for 2 days. The reaction mixture was then concentrated in vacuo. The resulting oil was purified by flash chromatography (Silica, EtOAc/Hexanes) to give two racemic pairs of diasteriomers 2-chloro-7-(4-fluorophenyl)-4-(2-methylpyrrolidin-1-yl)-6,7-dihydro-5H-cyclopenta[d]pyrimidine. (Hc1, Diastereomer 1, racemic, first to elute) (79.5 mg, 0.240 mmol, 33.9% yield). LC-MS (M+H)$^+$=332.1; $^1$H NMR (500 MHz, MeOD) δ ppm 7.16 (2H, d, J=5.49 Hz), 7.04 (2H, s), 4.42-4.54 (1H, m), 4.09-4.22 (1H, m), 3.86-4.00 (1H, m), 3.71-3.82 (1H, m), 3.24-3.31 (1H, m), 3.10-3.22 (1H, m), 2.54-2.65 (1H, m), 2.05-2.16 (2H, m), 1.94-2.05 (2H, m), 1.69-1.80 (1H, m), 1.27 (3H, d, J=6.10 Hz). (Hc2, Diastereomer 2, racemic, second to elute) (89.5 mg, 0.270 mmol, 38% yield). LC-MS (M+H)$^+$=332.1; $^1$H NMR (500 MHz, MeOD) δ ppm 7.14 (2H, d, J=5.49 Hz), 6.99-7.08 (2H, m), 4.42-4.54 (1H, m), 4.13-4.22 (1H, m), 3.86-4.00 (1H, m), 3.71-3.83 (1H, m), 3.25-3.32 (1H, m), 3.14-3.25 (1H, m), 2.52-2.67 (1H, m), 2.05-2.19 (2H, m), 1.94-2.05 (2H, m), 1.68-1.78 (1H, m), 1.19-1.32 (3H, m). The relative stereochemistry for Hc1 and Hc2 was not determined Preparation Hd (2S,6R)-4-(2-chloro-7-(4-fluorophenyl)-6,7-dihydro-5H-cyclopenta[d]pyrimidin-4-yl)-2,6-dimethylmorpholine

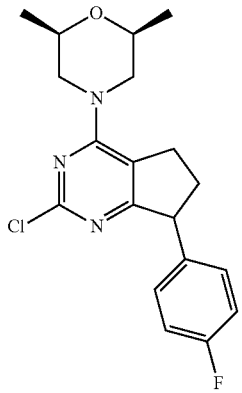 [SMILES: C[C@@H]1CN(c2nc(Cl)nc3c2CCC3c2ccc(F)cc2)C[C@H](C)O1]

To a solution of 2,4-dichloro-7-(4-fluorophenyl)-6,7-dihydro-5H-cyclopenta[d]pyrimidine (Preparation H) (200 mg, 0.706 mmol) in MeOH (7064 µL) was added cis-2,6-Dimethylmorpholine (105 µL, 0.848 mmol). The resulting mixture was stirred at RT overnight. An additional 2 equ. of cis-2,6-Dimethylmorpholine was then added and the mixture was again stirred overnight at RT. The reaction mixture was then concentrated in vacuo. The resulting oil was purified by flash chromatography (Silica, EtOAc/Hexanes) to give (2S,6R)-4-(2-chloro-7-(4-fluorophenyl)-6,7-dihydro-5H-cyclopenta[d]pyrimidin-4-yl)-2,6-dimethylmorpholine (223 mg, 0.616 mmol, 87% yield). LC-MS (M+H)$^+$=332.1. $^1$H NMR (500 MHz, MeOD) δ ppm 7.11-7.24 (2H, m), 6.99-7.09 (2H, m), 4.39-4.51 (2H, m), 4.20 (1H, s), 3.70 (2H, td, J=4.12, 2.44 Hz), 3.14-3.25 (1H, m), 3.03-3.13 (1H, m), 2.69-2.80 (2H, m), 2.54-2.68 (1H, m), 1.95-2.13 (1H, m), 1.23 (6H, d, J=6.10 Hz).

Preparation He 1-(2-chloro-7-(4-fluorophenyl)-6,7-dihydro-5H-cyclopenta[d]pyrimidin-4-yl)-4-methylpiperidin-4-ol

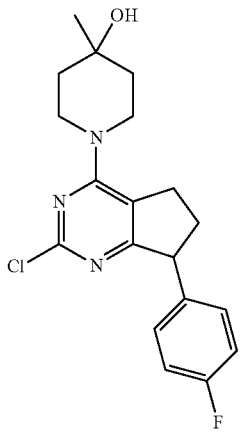 [SMILES: CC1(O)CCN(c2nc(Cl)nc3c2CCC3c2ccc(F)cc2)CC1]

To a solution of 2,4-dichloro-7-(4-fluorophenyl)-6,7-dihydro-5H-cyclopenta[d]pyrimidine (Preparation 11) (400 mg, 1.413 mmol) in MeOH (14.100 mL) was added 4-methylpiperidin-4-ol (163 mg, 1.413 mmol). The resulting mixture was stirred at RT overnight. The reaction mixture was then concentrated in vacuo. Purification by flash chromatography (Silica, EtOAc/Hexanes) gave 1-(2-chloro-7-(4-fluorophenyl)-6,7-dihydro-5H-cyclopenta[d]pyrimidin-4-yl)-4-methylpiperidin-4-ol (374 mg, 1.034 mmol, 73.2% yield). LC-MS (M+H)$^+$=362.0. $^1$H NMR (500 MHz, MeOD) δ ppm 7.12-7.21 (2H, m), 7.04 (2H, t, J=8.85 Hz), 4.11-4.30 (3H, m), 3.48-3.63 (2H, m), 3.14-3.23 (1H, m), 3.00-3.12 (1H, m), 2.54-2.66 (1H, m), 1.94-2.09 (1H, m), 1.68 (4H, t, J=4.12 Hz), 1.28 (3H, s).

Preparations Hf1 and Hf2

2-chloro-4-(2-ethylpyrrolidin-1-yl)-7-(4-fluorophenyl)-6,7-dihydro-5H-cyclopenta[d]pyrimidine

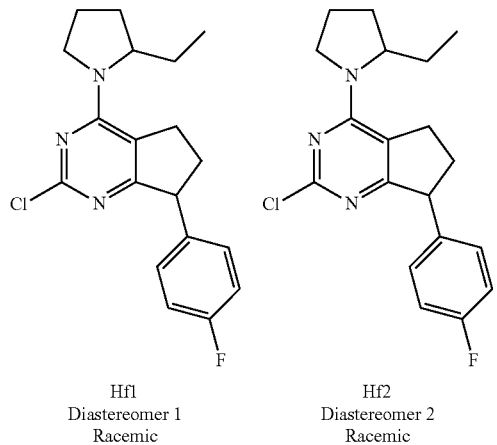 [SMILES: CCC1CCCN1c1nc(Cl)nc2c1CCC2c1ccc(F)cc1 ; CCC1CCCN1c1nc(Cl)nc2c1CCC2c1ccc(F)cc1]

Hf1
Diastereomer 1
Racemic

Hf2
Diastereomer 2
Racemic 2,4-dichloro-7-(4-fluorophenyl)-6,7-dihydro-5H-cyclopenta[d]pyrimidine (Preparation H) (200 mg, 0.706 mmol) and 2-ethylpyrrolidine (84 mg, 0.848 mmol) were combined and purified as per Preparation Hd to give two pairs of racemic diasteriomers 2-chloro-4-(2-ethylpyrrolidin-1-yl)-7-(4-fluorophenyl)-6,7-dihydro-5H-cyclopenta[d]pyrimidine. (Hf1, Diastereomer 1, racemic, first to elute) (77 mg, 0.223 mmol, 32% yield) LC-MS (M+H)$^+$=346. (Hf2, Diastereomer 2, racemic, second to elute) (80 mg, 0.232 mmol, 33% yield); LC-MS (M+H)$^+$=346.2. The relative stereochemistry for Hf1 and Hf2 was not determined Preparation Hg tert-butyl 1-(2-chloro-7-(4-fluorophenyl)-6,7-dihydro-5H-cyclopenta[d]pyrimidin-4-yl)-4-methylpiperidin-4-ylcarbamate To a solution of 2,4-dichloro-7-(4-fluorophenyl)-6,7-dihydro-5H-cyclopenta[d]pyrimidine (Preparation H) (400 mg, 1.413 mmol) in MeOH (14.100 mL) was added tert-butyl 4-methylpiperidin-4-ylcarbamate (303 mg, 1.413 mmol). The resulting mixture was stirred at RT for 7 days. At that time, the reaction mixture was concentrated in vacuo. Purification by flash chromatography (Silica, EtOAc/Hexanes) gave tert-butyl 1-(2-chloro-7-(4-fluorophenyl)-6,7-dihydro-5H-cyclopenta[d]pyrimidin-4-yl)-4-methylpiperidin-4-ylcarbamate (159 mg, 0.345 mmol, 24.41% yield) as a yellow foam. LC-MS (M+H)$^+$=461.2. $^1$H NMR (500 MHz, MeOD) δ ppm 7.12-7.22 (2H, m), 6.98-7.09 (2H, m), 4.19 (3H, d, J=2.14 Hz), 3.38-3.56 (2H, m), 3.13-3.25 (1H, m), 3.02-3.13 (1H, m), 2.53-2.67 (1H, m), 2.11-2.24 (2H, m), 1.96-2.08 (1H, m), 1.53-1.65 (2H, m), 1.47 (9H, s), 1.37 (3H, s).

Preparation Hh 2-chloro-7-(4-fluorophenyl)-N-methyl-6,7-dihydro-5H-cyclopenta[d]pyrimidin-4-amine

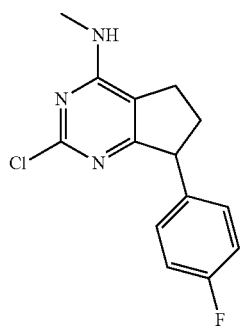 [SMILES: CNc1nc(Cl)nc2c1CCC2c1ccc(F)cc1]

2,4-dichloro-7-(4-fluorophenyl)-6,7-dihydro-5H-cyclopenta[d]pyrimidine (Preparation H) (500 mg, 1.766 mmol) and methanamine hydrochloride (179 mg, 2.65 mmol) were combined and purified as per Preparation Ha to give 2-chloro-7-(4-fluorophenyl)-N-methyl-6,7-dihydro-5H-cyclopenta[d]pyrimidin-4-amine (344 mg, 1.239 mmol, 70.1% yield). LC-MS (M+H)$^+$=278.0. $^1$H NMR (500 MHz, CDCl$_3$) δ ppm 7.03-7.12 (2H, m), 6.91-7.03 (2H, m), 4.53-4.79 (1H, m), 4.19-4.29 (1H, m), 3.09 (3H, d, J=4.88 Hz), 2.56-2.80 (3H, m), 2.00-2.15 (1H, m).

Preparation Hi 1-(2-chloro-7-(4-fluorophenyl)-6,7-dihydro-5H-cyclopenta[d]pyrimidin-4-yl)-3-(trifluoromethyl)pyrrolidin-3-ol

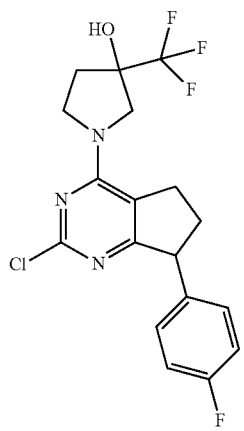 [SMILES: OC1(C(F)(F)F)CCN(c2nc(Cl)nc3c2CCC3c2ccc(F)cc2)C1]

2,4-dichloro-7-(4-fluorophenyl)-6,7-dihydro-5H-cyclopenta[d]pyrimidine (Preparation H) (286 mg, 1.010 mmol) and 3-(trifluoromethyl)pyrrolidin-3-ol (157 mg, 1.010 mmol) were combined and purified as per Preparation Hb to give 1-(2-chloro-7-(4-fluorophenyl)-6,7-dihydro-5H-cyclopenta[d]pyrimidin-4-yl)-3-(trifluoromethyl)pyrrolidin-3-ol (62% yield). LC-MS (M+H)$^+$=402.0.

Preparation Hj 1-(2-chloro-7-(4-fluorophenyl)-6,7-dihydro-5H-cyclopenta[d]pyrimidin-4-yl)-N,N-dimethylpyrrolidin-3-amine

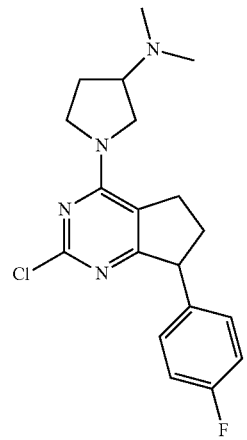 [SMILES: CN(C)C1CCN(c2nc(Cl)nc3c2CCC3c2ccc(F)cc2)C1]

2,4-dichloro-7-(4-fluorophenyl)-6,7-dihydro-5H-cyclopenta[d]pyrimidine (Preparation H) (100 mg, 0.353 mmol) and N,N-dimethylpyrrolidin-3-amine (44.3 µL, 0.353 mmol) were combined and purified as per Preparation Hb to give 1-(2-chloro-7-(4-fluorophenyl)-6,7-dihydro-5H-cyclopenta[d]pyrimidin-4-yl)-N,N-dimethylpyrrolidin-3-amine (109 mg, 86% yield). LC-MS (M+H)$^+$=361.2.

Preparation Hk 2-chloro-7-(4-fluorophenyl)-4-(4-methylpiperazin-1-yl)-6,7-dihydro-5H-cyclopenta[d]pyrimidine

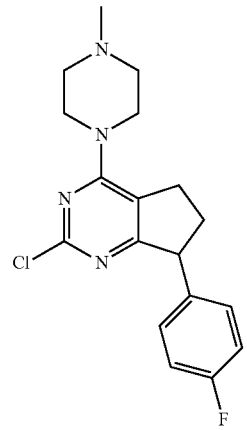 [SMILES: CN1CCN(c2nc(Cl)nc3c2CCC3c2ccc(F)cc2)CC1]

2,4-dichloro-7-(4-fluorophenyl)-6,7-dihydro-5H-cyclopenta[d]pyrimidine (Preparation H) (100 mg, 0.353 mmol) and 1-methylpiperazine (39.2 µL, 0.353 mmol) were combined and purified as per Preparation Hb to give 2-chloro-7-(4-fluorophenyl)-4-(4-methylpiperazin-1-yl)-6,7-dihydro-5H-cyclopenta[d]pyrimidine (109 mg, 0.314 mmol, 89% yield). LC-MS (M+H)$^+$=347.2.

Preparation Hl tert-butyl 4-(2-chloro-7-(4-fluorophenyl)-6,7-dihydro-5H-cyclopenta[d]pyrimidin-4-yl)piperazine-1-carboxylate

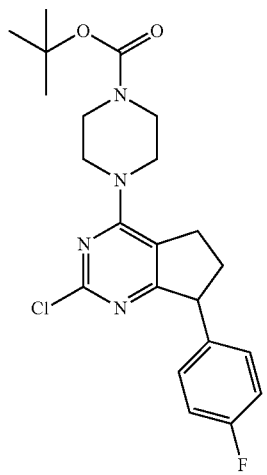 [SMILES: CC(C)(C)OC(=O)N1CCN(c2nc(Cl)nc3c2CCC3c2ccc(F)cc2)CC1]

2,4-dichloro-7-(4-fluorophenyl)-6,7-dihydro-5H-cyclopenta[d]pyrimidine (Preparation H) (100 mg, 0.353 mmol) and tert-Butyl 1-piperazinecarboxylate (65.8 mg, 0.353 mmol) were combined and purified as per Preparation Hb to give tert-butyl 4-(2-chloro-7-(4-fluorophenyl)-6,7-dihydro-5H-cyclopenta[d]pyrimidin-4-yl)piperazine-1-carboxylate (116.9 mg, 76% yield). LC-MS (M+H)$^+$=433.3.

Preparation Hm tert-butyl 1-(2-chloro-7-(4-fluorophenyl)-6,7-dihydro-5H-cyclopenta[d]pyrimidin-4-yl)pyrrolidin-3-ylmethyl)carbamate

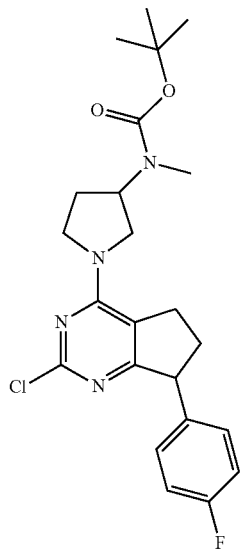 [SMILES: CN(C(=O)OC(C)(C)C)C1CCN(c2nc(Cl)nc3c2CCC3c2ccc(F)cc2)C1]

2,4-dichloro-7-(4-fluorophenyl)-6,7-dihydro-5H-cyclopenta[d]pyrimidine (Preparation H) (100 mg, 0.353 mmol) and 3-(N-tert-Butoxycarbonyl-N-methylamino)pyrrolidine (69.4 µL, 0.353 mmol) were combined and purified as per Preparation Hb to give tert-butyl 1-(2-chloro-7-(4-fluorophenyl)-6,7-dihydro-5H-cyclopenta[d]pyrimidin-4-yl)pyrrolidin-3-ylmethyl)carbamate (148 mg, 94% yield). LC-MS (M+H)$^+$=447.2.

Preparation Hn tert-butyl 1-(2-chloro-7-(4-fluorophenyl)-6,7-dihydro-5H-cyclopenta[d]pyrimidin-4-yl)azetidin-3-yl(methyl)carbamate

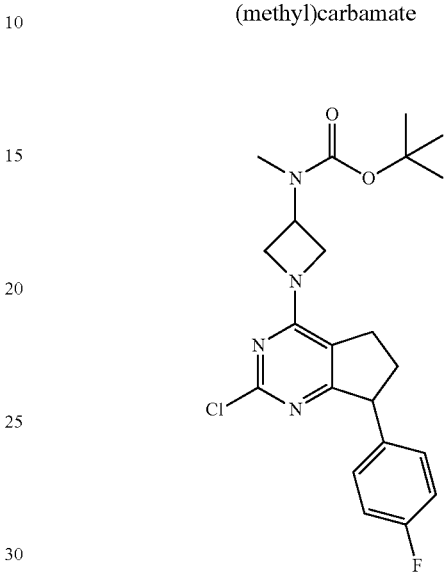

2,4-Dichloro-7-(4-fluorophenyl)-6,7-dihydro-5H-cyclopenta[d]pyrimidine (Preparation H) (100 mg, 0.353 mmol) and carbamic acid, 3-azetidinylmethyl-, 1,1-dimethylethyl ester (82 mg, 0.441 mmol) were combined and purified as per Preparation Hb to give tert-butyl 1-(2-chloro-7-(4-fluorophenyl)-6,7-dihydro-5H-cyclopenta[d]pyrimidin-4-yl)azetidin-3-yl(methyl)carbamate (147 mg, 96% yield). LC-MS (M+H)$^+$=377.1.

Preparation Ho 1-(2-chloro-7-(4-fluorophenyl)-6,7-dihydro-5H-cyclopenta[d]pyrimidin-4-yl)-N,N-dimethylazetidin-3-amine

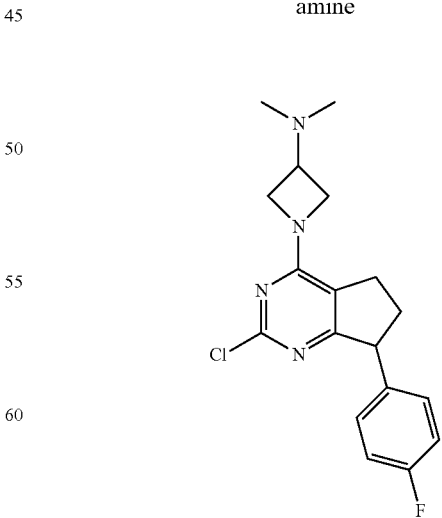

2,4-Dichloro-7-(4-fluorophenyl)-6,7-dihydro-5H-cyclopenta[d]pyrimidine (Preparation H) (100 mg, 0.353 mmol)

and N,N-dimethylazetidin-3-amine, 2HCl (122 mg, 0.706 mmol) were combined and purified as per Preparation Hb to give 1-(2-chloro-7-(4-fluorophenyl)-6,7-dihydro-5H-cyclopenta[d]pyrimidin-4-yl)-N,N-dimethylazetidin-3-amine (quantitative). LC-MS (M+H)+=347.2.

Preparation Hp1 and Hp2

2-chloro-7-(4-fluorophenyl)-4-((S)-3-fluoropyrrolidin-1-yl)-6,7-dihydro-5H cyclopenta[d]pyrimidine

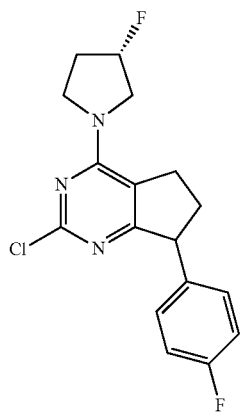 [SMILES: Fc1ccc(C2CCc3c2nc(Cl)nc3N2CC[C@H](F)C2)cc1]

To a solution of 2,4-dichloro-7-(4-fluorophenyl)-6,7-dihydro-5H-cyclopenta[d]pyrimidine (Preparation H) (135 mg, 0.477 mmol) in MeOH (4768 μL) was added DIPEA (208 μL, 1.192 mmol), then (S)-3-fluoropyrrolidine (46.7 mg, 0.524 mmol). The reaction was allowed to stir at ambient temperature for 2 h. The solvent was removed and the residue applied to Silica gel and eluted with an EtOAc/Hex gradient to afford two diasteriomers (Hp1 and Hp2). Hp1: LC-MS (M+H)+=336.2. $^1$H NMR (500 MHz, CDCl$_3$) δ ppm 7.06-7.13 (2H, m), 6.93-7.00 (2H, m), 5.32 (1H, td, J=52.57, 3.17 Hz), 4.17 (1H, dd, J=9.16, 5.49 Hz), 4.06-4.14 (1H, m), 3.98-4.06 (1H, m), 3.76-3.90 (2H, m), 3.25 (1H, ddd, J=15.11, 8.55, 6.26 Hz), 3.08-3.16 (1H, m), 2.51-2.60 (1H, m, J=13.20, 9.12, 9.12, 6.41 Hz), 2.32-2.42 (1H, m), 2.00-2.17 (2H, m). Hp2: LC-MS (M+H)+=336.2. $^1$H NMR (500 MHz, CDCl$_3$) δ ppm 7.06-7.14 (2H, m), 6.94-7.02 (2H, m), 5.25-5.40 (1H, m), 3.99-4.24 (3H, m), 3.75-3.92 (2H, m), 3.19-3.28 (1H, m), 3.10-3.19 (1H, m), 2.57 (1H, dddd, J=13.24, 8.74, 8.55, 4.58 Hz), 2.31-2.43 (1H, m), 1.94-2.17 (2H, m)

Preparation Hq 2-chloro-7-(4-fluorophenyl)-4-((R)-3-fluoropyrrolidin-1-yl)-6,7-dihydro-5H cyclopenta[d]pyrimidine

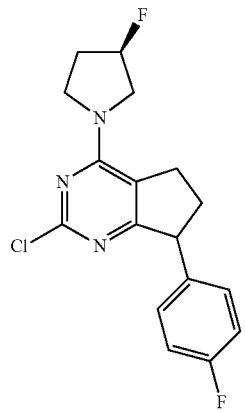 [SMILES: Fc1ccc(C2CCc3c2nc(Cl)nc3N2CC[C@@H](F)C2)cc1]

2,4-dichloro-7-(4-fluorophenyl)-6,7-dihydro-5H-cyclopenta[d]pyrimidine (Preparation H) was reacted as described in Preparation Hp1 and Hp2 with (R)-3-fluoropyrrolidine. The solvent was removed and the residue applied to Silica gel and eluted with an EtOAc/Hex gradient to afford the combined two diasteriomers (Hq). Ha1: LC-MS (M+H)+=336.0.

Preparation Hr 2-chloro-4-(4,4-difluoropiperidin-1-yl)-7-(4-fluorophenyl)-6,7-dihydro-5H-cyclopenta[d]pyrimidine

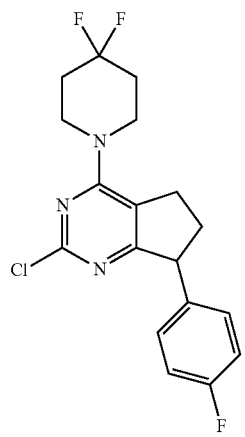 [SMILES: Fc1ccc(C2CCc3c2nc(Cl)nc3N2CCC(F)(F)CC2)cc1]

To a solution of 2,4-dichloro-7-(4-fluorophenyl)-6,7-dihydro-5H-cyclopenta[d]pyrimidine (Preparation H) (90 mg, 0.318 mmol) in MeOH (3179 μL), 4,4-difluoropiperidine (115 mg, 0.95 mmol) was added. The reaction was allowed to stir at rt. When the reaction was complete, removed solvent and applied residue to Silica gel. Eluted with EtOAc/Hex to afford the desired 2-chloro-4-(4,4-difluoropiperidin-1-yl)-7-(4-fluorophenyl)-6,7-dihydro-5H-cyclopenta[d]pyrimidine (80.8 mg, 0.220 mmol, 69.1% yield). LC-MS (M+H)+= 368.0.

Preparation Hs 2-chloro-4-(4-fluoro-5,6-dihydropyridin-1(2H)-yl)-7-(4-fluorophenyl)-6,7-dihydro-5H-cyclopenta[d]pyrimidine

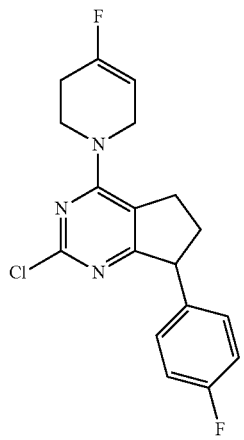 [SMILES: FC1=CCN(c2nc(Cl)nc3c2CCC3c2ccc(F)cc2)CC1]

2,4-dichloro-7-(4-fluorophenyl)-6,7-dihydro-5H-cyclopenta[d]pyrimidine (Preparation H) was reacted as described in Preparation Hc with 4-fluoro-1,2,3,6-tetrahydropyridine to afford 2-chloro-4-(4-fluoro-5,6-dihydropyridin-1(2H)-yl)-7-(4-fluorophenyl)-6,7-dihydro-5H-cyclopenta[d]pyrimidine (Preparation Hs).

Preparation Ht 2-chloro-7-(4-fluorophenyl)-4-(3-(trifluoromethyl)pyrrolidin-1-yl)-6,7-dihydro-5H-cyclopenta[d]pyrimidine-4-fluorophenyl)-6,7-dihydro-5H-cyclopenta[d]pyrimidine

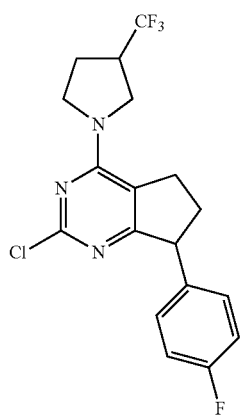 [SMILES: Fc1ccc(C2CCc3c2nc(Cl)nc3N2CCC(C(F)(F)F)C2)cc1]

2,4-dichloro-7-(4-fluorophenyl)-6,7-dihydro-5H-cyclopenta[d]pyrimidine (Preparation H) was reacted as described in Preparation Hr with 3-trifluoromethylpyrrolidine to afford 2-chloro-7-(4-fluorophenyl)-4-(3-(trifluoromethyl)pyrrolidin-1-yl)-6,7-dihydro-5H-cyclopenta[d]pyrimidine-4-fluorophenyl)-6,7-dihydro-5H-cyclopenta[d]pyrimidine (Preparation Ht) as a mixture of 4 diasteriomers. LC-MS (M+H)$^+$= 386.1. $^1$H NMR (500 MHz, CDCl$_3$) δ ppm 7.05-7.11 (2H, m), 6.96 (2H, t, J=8.70 Hz), 4.14-4.20 (1H, m), 3.89-4.02 (2H, m), 3.75-3.86 (2H, m), 3.17-3.28 (1H, m), 3.06-3.16 (1H, m), 2.99 (1H, dq, J=15.95, 8.01 Hz), 2.50-2.61 (1H, m), 2.13-2.30 (2H, m), 1.95-2.06 (1H, m)

Preparation Hu 2-chloro-N-(3-ethoxypropyl)-7-(4-fluorophenyl)-6,7-dihydro-5H-cyclopenta[d]pyrimidin-4-amine

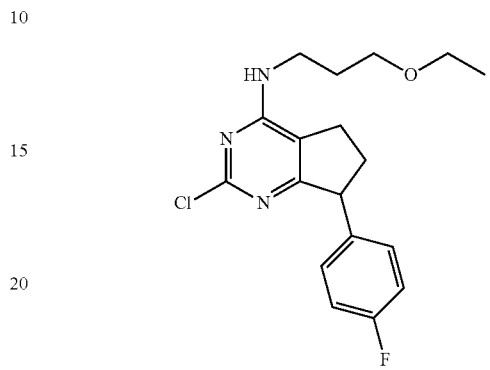

2,4-dichloro-7-(4-fluorophenyl)-6,7-dihydro-5H-cyclopenta[d]pyrimidine (Preparation H) was reacted as described in Preparation Hr with 3-ethoxypropan-1-amine to afford 2-chloro-N-(3-ethoxypropyl)-7-(4-fluorophenyl)-6,7-dihydro-5H-cyclopenta[d]pyrimidin-4-amine (Preparation Hu). LC-MS (M+H)$^+$=350.1.

Preparation Hv 3-(2-chloro-7-(4-fluorophenyl)-6,7-dihydro-5H-cyclopenta[d]pyrimidin-4-ylamino)propan-1-ol

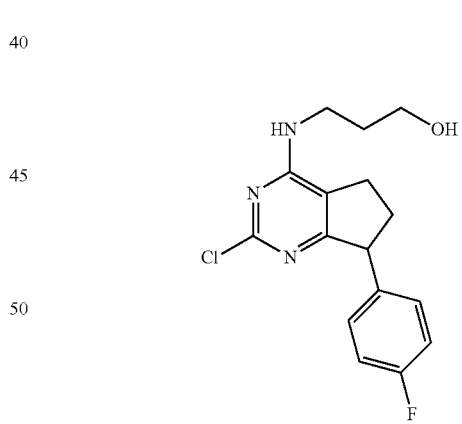

2,4-dichloro-7-(4-fluorophenyl)-6,7-dihydro-5H-cyclopenta[d]pyrimidine (Preparation H) was reacted as described in Preparation Hr with 3-hydroxypropan-1-amine to afford 3-(2-chloro-7-(4-fluorophenyl)-6,7-dihydro-5H-cyclopenta[d]pyrimidin-4-ylamino)propan-1-ol (Preparation Hv). LC-MS (M+H)$^+$=322.1. $^1$H NMR (500 MHz, CDCl$_3$) δ ppm 7.08 (2H, dd, J=8.55, 5.49 Hz), 6.97 (2H, t, J=8.70 Hz), 5.18 (1H, br. s.), 4.22-4.27 (1H, m), 3.66-3.75 (4H, m), 3.18 (1H, br. s.), 2.60-2.77 (3H, m), 2.02-2.12 (1H, m), 1.78-1.86 (2H, m)

Preparation Hw 2-chloro-N-(1-cyclopropyl-2-methoxyethyl)-7-(4-fluorophenyl)-6,7-dihydro-5H-cyclopenta[d]pyrimidin-4-amine

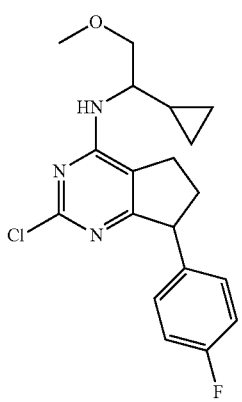 [SMILES: COCC(Nc1nc(Cl)nc2c1CCC2c1ccc(F)cc1)C1CC1]

2,4-dichloro-7-(4-fluorophenyl)-6,7-dihydro-5H-cyclopenta[d]pyrimidine (Preparation H) was reacted as described in Preparation Hr with 1-cyclopropyl-2-methoxyethanamine to afford 2-chloro-N-(1-cyclopropyl-2-methoxyethyl)-7-(4-fluorophenyl)-6,7-dihydro-5H-cyclopenta[d]pyrimidin-4-amine (Preparation Hw) as a mixture of 4 diasteriomers. LC-MS (M+H)$^+$=362.1.

Preparation Hx

2-Chloro-7-(4-fluorophenyl)-N,N-dimethyl-6,7-dihydro-5H-cyclopenta[d]pyrimidin-4-amine

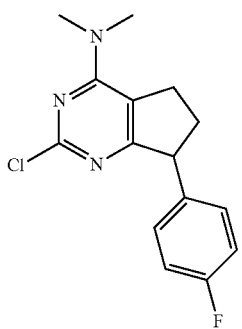 [SMILES: CN(C)c1nc(Cl)nc2c1CCC2c1ccc(F)cc1]

A solution of 2,4-dichloro-7-(4-fluorophenyl)-6,7-dihydro-5H-cyclopenta[d]pyrimidine (260 mg, 0.918 mmol) and excess dimethylamine (4.59 mL, 9.18 mmol) in methanol (2 mL) was stirred at rt for 30 min. The solvent was removed in vacuum to afford crude 2-chloro-7-(4-fluorophenyl)-N,N-dimethyl-6,7-dihydro-5H-cyclopenta[d]pyrimidin-4-amine (268 mg, 0.919 mmol, 100% yield). LC-MS (M+H)$^+$=292.3.

Preparation Hy

2-Chloro-7-(4-fluorophenyl)-N-trideuteromethyl-6,7-dihydro-5H-cyclopenta[d]pyrimidin-4-amine

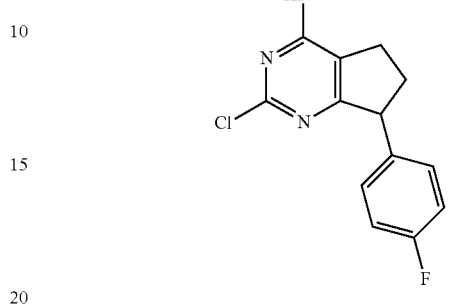

To a solution of 2,4-dichloro-7-(4-fluorophenyl)-6,7-dihydro-5H-cyclopenta[d]pyrimidine (350 mg, 1.236 mmol) and trideuteromethylamine hydrochloride (174 mg, 2.472 mmol) in methanol (3 mL) was added DIPEA (0.432 mL, 2.472 mmol). The reaction mixture was stirred at room temperature overnight. The solvent was removed in vacuum and the residue was purified by column chromatography on silica gel to give 2,4-dichloro-7-(4-fluorophenyl)-6,7-dihydro-5H-cyclopenta[d]pyrimidine (350 mg, 1.236 mmol) as brown oil. LC-MS (M+H)$^+$=281.2.

Preparation Hz 2-chloro-7-(4-fluorophenyl)-N-((R)-1-methoxybutan-2-yl)-6,7-dihydro-5H-cyclopenta[d]pyrimidin-4-amine

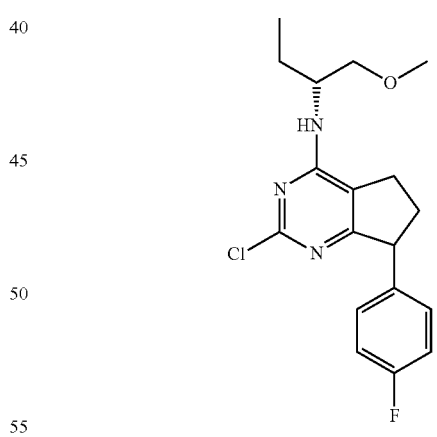

To a mixture of 2,4-dichloro-7-(4-fluorophenyl)-6,7-dihydro-5H-cyclopenta[d]pyrimidine (Preparation H) (100 mg, 0.353 mmol) in THF (1766 μL) was added (R)-1-methoxybutan-2-amine, HCl (197 mg, 1.413 mmol) and DIEA (493 μL, 2.83 mmol). The mixture was heated at 60° C. for 3 days. The crude product was purified by Prep-HPLC to get 2-chloro-7-(4-fluorophenyl)-N—((R)-1-methoxybutan-2-yl)-6,7-dihydro-5H-cyclopenta[d]pyrimidin-4-amine (Preparation Hz) (78 mg, 0.223 mmol, 63.1% yield). LC-MS (M+H)$^+$=350.4. $^1$H NMR (500 MHz, CDCl$_3$) δ ppm 7.12 (dd, J=8.24, 5.49 Hz, 2H) 6.87-7.05 (m, 2H) 4.86 (d, J=7.63 Hz, 1H) 4.35 (d, J=3.05

Hz, 1H) 4.18-4.30 (m, 1H) 3.47-3.60 (m, 2H) 3.40 (d, J=6.71 Hz, 3H) 2.62-2.82 (m, 3H) 2.03-2.15 (m, 1H) 1.58-1.78 (m, 2H) 0.89-1.07 (m, 3H).

Preparation Haa 2-chloro-N—((R)-1-cyclopropylethyl)-7-(4-fluorophenyl)-6,7-dihydro-5H-cyclopenta[d]pyrimidin-4-amine

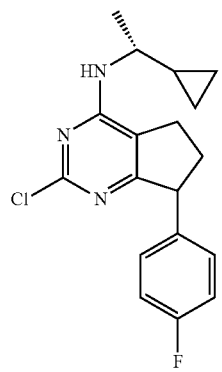 [SMILES: C[C@@H](Nc1nc(Cl)nc2c1CCC2c1ccc(F)cc1)C1CC1]

To a solution of 2,4-dichloro-7-(4-fluorophenyl)-6,7-dihydro-5H-cyclopenta[d]pyrimidine (Preparation H) (100 mg, 0.353 mmol) in THF (1766 μL) was added (R)-1-cyclopropylethanamine, HCl (172 mg, 1.413 mmol) and DIEA (493 μL, 2.83 mmol). The mixture was stirred at 60° C. for 5 days. The crude product was purified by Prep-HPLC get 2-chloro-N—((R)-1-cyclopropylethyl)-7-(4-fluorophenyl)-6,7-dihydro-5H-cyclopenta[d]pyrimidin-4-amine (Preparation Haa) (74 mg, 0.223 mmol, 63.1% yield). LC-MS (M+H)+=332.3. 1H NMR (500 MHz, CDCl3) δ ppm 7.06-7.18 (m, 2H) 7.00 (td, J=8.70, 1.53 Hz, 2H) 4.65 (d, J=5.80 Hz, 1H) 4.26 (t, J=7.17 Hz, 1H) 3.63-3.79 (m, 1H) 2.62-2.82 (m, 3H) 2.04-2.16 (m, 1H) 1.26-1.40 (m, 3H) 0.94 (qd, J=8.24, 3.36 Hz, 1H) 0.42-0.62 (m, 3H) 0.24-0.40 (m, 1H).

Preparation Hab 2-chloro-N—((S)-1-cyclopropylethyl)-7-(4-fluorophenyl)-6,7-dihydro-5H-cyclopenta[d]pyrimidin-4-amine

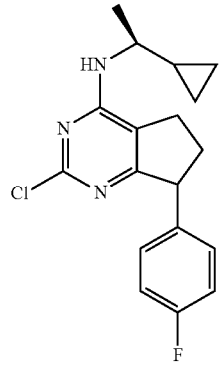 [SMILES: C[C@H](Nc1nc(Cl)nc2c1CCC2c1ccc(F)cc1)C1CC1]

2,4-dichloro-7-(4-fluorophenyl)-6,7-dihydro-5H-cyclopenta[d]pyrimidine (Preparation H) was reacted as described in Preparation Haa with (S)-1-cyclopropylethanamine, HCl to give 2-chloro-N—((S)-1-cyclopropylethyl)-7-(4-fluorophenyl)-6,7-dihydro-5H-cyclopenta[d]pyrimidin-4-amine (Preparation Hab). LC-MS (M+H)+=332.3. 1H NMR (500 MHz, CDCl3) δ ppm 7.07-7.21 (m, 2H) 6.93-7.07 (m, 2H) 4.65 (d, J=5.80 Hz, 1H) 4.26 (t, J=7.32 Hz, 1H) 3.61-3.79 (m, 1H) 2.62-2.82 (m, 3H) 2.05-2.16 (m, 1H) 1.25-1.39 (m, 3H) 0.84-1.00 (m, 1H) 0.42-0.62 (m, 3H) 0.29-0.40 (m, 1H).

Preparation Hac 1-(2-chloro-7-(4-fluorophenyl)-6,7-dihydro-5H-cyclopenta[d]pyrimidin-4-yl)-3-methylazetidine-3-carbonitrile

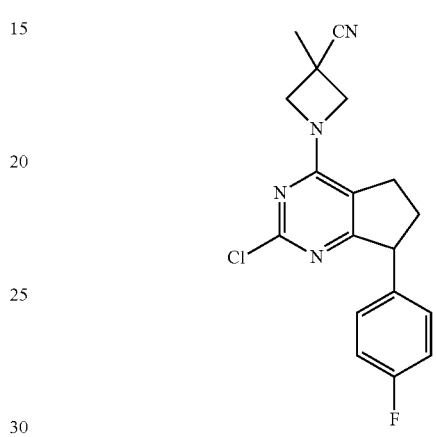

3-cyano-3-methylazetidine was reacted with Preparation H in the manner of Preparation Gi to afford the title compound. LC-MS (M+H)+=343.0 1H NMR (500 MHz, CHLOROFORM-d) δ ppm 6.96-7.13 (m, 5H) 4.73 (d, J=6.71 Hz, 1H) 4.35 (d, J=7.32 Hz, 2H) 4.33 (br. s., 1H) 4.27 (dd, J=9.00, 2.90 Hz, 1H) 2.99-3.09 (m, 1H) 2.85-2.99 (m, 1H) 2.64-2.78 (m, 1H) 2.11 (dd, J=13.89, 7.48 Hz, 1H) 1.76-1.91 (m, 3H).

Preparation Had 2-chloro-4-(3-ethoxyazetidin-1-yl)-7-(4-fluorophenyl)-6,7-dihydro-5H-cyclopenta[d]pyrimidine

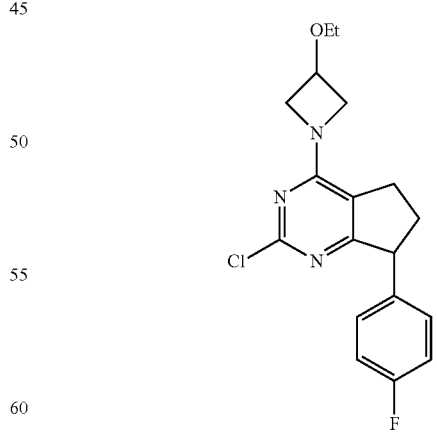

3-ethoxyazetidine was reacted with Preparation H in the manner of Preparation Gi to afford the title compound. LC-MS (M+H)+=348.0 1H NMR (500 MHz, CHLOROFORM-d) δ ppm 7.03-7.12 (m, 2H) 6.91-7.01 (m, 2H) 4.51 (br. s., 2H) 4.36-4.48 (m, 1H) 4.13-4.32 (m, 3H) 3.50 (qd, J=6.97, 3.20

Hz, 2H) 2.97-3.10 (m, 1H) 2.82-2.96 (m, 1H) 2.51-2.70 (m, 1H) 1.93-2.11 (m, 1H) 1.16-1.35 (m, 3H).

Preparation Hae 1-(2-chloro-7-(4-fluorophenyl)-6,7-dihydro-5H-cyclopenta[d]pyrimidin-4-yl)-3-methylazetidin-3-ol

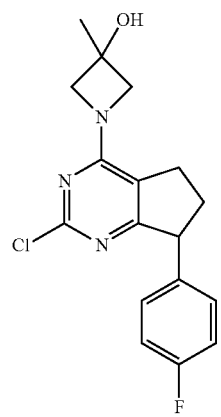 [SMILES: CC1(O)CN(c2nc(Cl)nc3c2CCC3c2ccc(F)cc2)C1]

3-methylazetidin-3-ol was reacted with Preparation H in the manner of Preparation Gi to afford the title compound. LC-MS (M+H)⁺=334.0 ¹H NMR (500 MHz, CHLOROFORM-d) δ ppm 7.04-7.13 (m, 2H) 7.00 (t, J=8.55 Hz, 2H) 4.41 (d, J=6.71 Hz, 2H) 4.39 (br. s., 3H) 3.05-3.17 (m, 1H) 2.90-3.04 (m, 1H) 2.73 (ddd, J=9.08, 4.88, 4.65 Hz, 1H) 2.03-2.19 (m, 1H) 1.65 (s, 3H).

Preparation Haf 2-chloro-7-(4-fluorophenyl)-4-(3-methoxy-3-methylazetidin-1-yl)-6,7-dihydro-5H-cyclopenta[d]pyrimidine

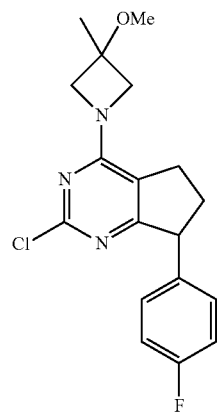 [SMILES: COC1(C)CN(c2nc(Cl)nc3c2CCC3c2ccc(F)cc2)C1]

3-methoxy-3-methylazetidine was reacted with Preparation H in the manner of Preparation Gi to afford the title compound. LC-MS (M+H)⁺=348.

Preparation I 2,4-dichloro-8-phenyl-7,8-dihydro-5H-pyrano[4,3-d]pyrimidine

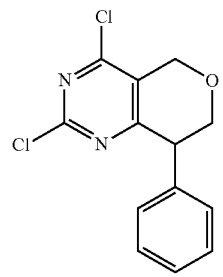 [SMILES: Clc1nc(Cl)c2c(n1)C(c1ccccc1)COC2]

Intermediate I(1)

3-iodo-4,4-dimethoxytetrahydro-2H-pyran

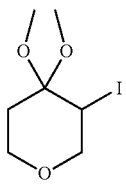

To a mixture of tetrahydro-4H-pyran-4-one (18.52 mL, 200 mmol) and trimethyl orthoformate (100 mL, 914 mmol) at 0° C. was added Iodine (49.2 mL, 200 mmol) slowly over 10 min. When the addition was complete, the reaction mixture was allowed to stir at 0° C. for 30 min. and was then allowed to come to RT and stir until TLC indicated all starting material had been consumed (approx. 1 h). The reaction was then cooled to 0° C. and quenched by the slow addition of sat. aqu. sodium thiosulfate (300 mL). The resulting mixture was extracted with EtOAc (3×75 mL). The combined organic layers were washed with brine (100 mL), dried over MgSO₄, filtered and concentrated in vacuo. Purification by flash chromatography (Silica, EtOAc/Hexanes) gave 3-iodo-4,4-dimethoxytetrahydro-2H-pyran (43.95 g, 162 mmol, 81% yield) as a yellow oil. ¹H NMR (500 MHz, CDCl₃) δ ppm 4.25 (1H, q, J=2.44 Hz), 3.93-4.01 (1H, m), 3.84-3.93 (2H, m), 3.57 (1H, td, J=11.75, 2.44 Hz), 3.19-3.30 (6H, m), 2.34 (1H, ddd, J=14.34, 12.21, 4.88 Hz), 1.80 (1H, dq, J=14.34, 2.44 Hz).

Intermediate I(2)

3-phenyldihydro-2H-pyran-4(3H)-one

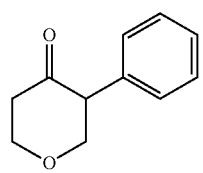 [SMILES: O=C1CCOCC1c1ccccc1]

To a stirred mixture of phenylboronic acid (16.81 g, 138 mmol), trans-2-Aminocyclohexanol hydrochloride (1.393 g, 9.19 mmol), and Nickel(II) chloride hexahydrate (1.092 g, 4.59 mmol) in THF (92 mL) at 0° C. was added Sodium bis(trimethylsilyl)amide (1.0 M in THF) (184 mL, 184 mmol) dropwise over 10 min. When the addition was complete, the reaction mixture was sparged with $N_2$ for 15 min. To the reaction mixture at 0° C. was then added 2-Propanol (375 mL)(previously sparged with $N_2$). The resulting mixture was allowed to come to RT at which time 3-iodo-4,4-dimethoxytetrahydro-2H-pyran (Intermediate I(1)) (25 g, 92 mmol) was added dropwise over 5 min. The reaction mixture was then brought to 60° C. and stirred overnight. The reaction mixture was then cooled to 0° C. and quenched by the careful addition of aqu. 1 N HCl until acidic. The resulting mixture was extracted with EtOAc (3×150 mL). The combined organic extracts were washed with Brine (100 mL), dried over $MgSO_4$, filtered and concentrated in vacuo. Purification by flash chromatography (Silica, EtOAc/Hexanes) gave 3-phenyldihydro-2H-pyran-4(3H)-one (8.37 g, 47.5 mmol, 51.7% yield) as a slightly orange oil. $^1H$ NMR (500 MHz, $CDCl_3$) δ ppm 7.32-7.39 (2H, m), 7.26-7.31 (1H, m), 7.21-7.26 (2H, m), 4.17-4.31 (2H, m), 3.91-4.05 (2H, m), 3.78 (1H, dd, J=8.55, 6.10 Hz), 2.61-2.74 (1H, m), 2.51-2.61 (1H, m).

Intermediate I(3)

8-phenyl-7,8-dihydropyrano[3,4-e][1,3]oxazine-2,4(3H,5H)-dione

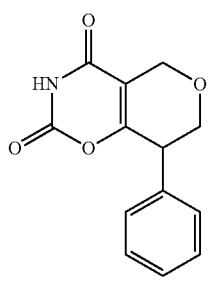 [SMILES: O=c1[nH]c(=O)c2c(o1)C(c1ccccc1)COC2]

A mixture of 3-phenyldihydro-2H-pyran-4(3H)-one (Intermediate I(2)) (3 g, 17.02 mmol) and carbonisocyanatidic chloride (10.48 g, 29.8 mmol) in a sealed tube was heated to 58° C. and stirred for 1 h. The mixture was then brought to 130° C. and stirred for an additional 2 h. The reaction turned black during this time. After cooling to RT, the tar was taken up in EtOAc (100 mL). The resulting solution was washed with saturated aqueous sodium bicarbonate (2×50 mL), brine (50 mL), dried over $MgSO_4$, filtered and concentrated in vacuo. Purification by flash chromatography (Silica, EtOAc/Hexanes) gave 8-phenyl-7,8-dihydropyrano[3,4-e][1,3]oxazine-2,4(3H,5H)-dione (2.58 g, 10.52 mmol, 61.8% yield) as a brown solid. LC-MS (M+H)$^+$=246.0. $^1H$ NMR (500 MHz, MeOD) δ ppm 7.34-7.41 (4H, m), 7.29-7.34 (1H, m), 4.42-4.63 (2H, m), 4.08-4.15 (1H, m), 3.94 (1H, dd, J=11.44, 4.12 Hz), 3.85 (1H, ddd, J=4.20, 2.44, 2.21 Hz).

Intermediate I(4)

8-phenyl-7,8-dihydro-1H-pyrano[4,3-d]pyrimidine-2,4(3H,5H)-dione

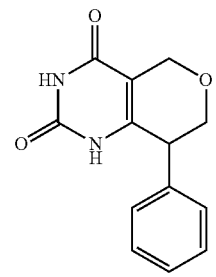 [SMILES: O=c1[nH]c2c(c(=O)[nH]1)COCC2c1ccccc1]

A solution of 8-phenyl-7,8-dihydropyrano[3,4-e][1,3]oxazine-2,4(3H,5H)-dione (Intermediate 43)) (2.58 g, 10.52 mmol) in ammonium hydroxide (28.7 mL, 736 mmol) was heated to 80° C. in a sealed tube and stirred overnight. The reaction mixture was then concentrated to dryness giving 8-phenyl-7,8-dihydro-1H-pyrano[4,3-d]pyrimidine-2,4(3H,5H)-dione. The crude material was carried on as-is. LC-MS (M+H)$^+$=245.2.

Preparation I 2,4-dichloro-8-phenyl-7,8-dihydro-5H-pyrano[4,3-d]pyrimidine

A mixture of 8-phenyl-7,8-dihydro-1H-pyrano[4,3-d]pyrimidine-2,4(3H,5H)-dione (Intermediate 44)) (2569 mg, 10.52 mmol) and $POCl_3$ (29.400 mL, 315 mmol) was heated to 100° C. under microwave irradiation in a sealed tube for 1 h. The resulting mixture was poured over ice. When all the ice was melted, the mixture was extracted with EtOAc (3×15 mL). The combined organic extracts were washed with brine (20 mL), dried over $MgSO_4$, filtered and concentrated in vacuo. Purification by flash chromatography (Silica, EtOAc/Hexanes) gave 2,4-dichloro-8-phenyl-7,8-dihydro-5H-pyrano[4,3-d]pyrimidine (194 mg, 0.690 mmol, 6.56% yield). LC-MS (M+H)$^+$=281.1. $^1H$ NMR (500 MHz, MeOD) δ ppm 7.30-7.37 (2H, m), 7.25-7.30 (1H, m), 7.18-7.25 (2H, m), 4.90-5.00 (1H, m), 4.75-4.84 (1H, m), 4.16-4.26 (2H, m), 4.02-4.15 (1H, m).

Preparation Ia 2-chloro-N-methyl-8-phenyl-7,8-dihydro-5H-pyrano[4,3-d]pyrimidin-4-amine

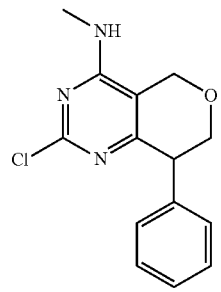 [SMILES: CNc1nc(Cl)nc2c1COCC2c1ccccc1]

To a solution of 2,4-dichloro-8-phenyl-7,8-dihydro-5H-pyrano[4,3-d]pyrimidine (Preparation I) (194 mg, 0.690 mmol) in MeOH (6901 μL) was added methanamine hydrochloride (69.9 mg, 1.035 mmol) and N,N-Diisopropylethylamine (301 μL, 1.725 mmol). The resulting mixture was stirred at RT for 2 h. The reaction mixture was then concentrated in vacuo. Purification by flash chromatography (Silica, EtOAc/Hexanes) gave 2-chloro-N-methyl-8-phenyl-7,8-dihydro-5H-pyrano[4,3-d]pyrimidin-4-amine (126 mg, 0.457 mmol, 66.2% yield). LC-MS (M+H)$^+$=276.0. $^1$H NMR (500 MHz, CDCl$_3$) δ ppm 7.28 (2H, t, J=7.32 Hz), 7.20-7.25 (1H, m), 7.14-7.20 (2H, m), 4.47-4.62 (2H, m), 4.47 (1H, s), 4.00-4.11 (2H, m), 3.95 (1H, d, J=3.36 Hz), 3.08 (3H, d, J=4.88 Hz).

Preparation Ib

2-Chloro-N,N-dimethyl-8-phenyl-7,8-dihydro-5H-pyrano[4,3-d]pyrimidin-4-amine

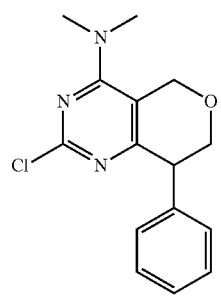 [SMILES: CN(C)c1nc(Cl)nc2c1COCC2c1ccccc1]

A solution of 2,4-dichloro-8-phenyl-7,8-dihydro-5H-pyrano[4,3-d]pyrimidine (135 mg, 0.480 mmol) and excess dimethylamine (216 mg, 4.80 mmol) in MeOH (2 mL) was stirred at rt for 1.5 h. The solvent was removed in vacuum to afford 2-chloro-N,N-dimethyl-8-phenyl-7,8-dihydro-5H-pyrano[4,3-d]pyrimidin-4-amine (139 mg, 0.480 mmol, 100% yield). LC-MS (M+H)$^+$=290.3.

Preparation Ic

2-Chloro-N-ethyl-N-methyl-8-phenyl-7,8-dihydro-5H-pyrano[4,3-d]pyrimidin-4-amine

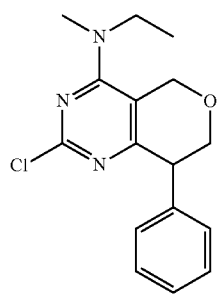 [SMILES: CCN(C)c1nc(Cl)nc2c1COCC2c1ccccc1]

A solution of 2,4-dichloro-8-phenyl-7,8-dihydro-5H-pyrano[4,3-d]pyrimidine (135 mg, 0.480 mmol) and excess N-methylethanamine (284 mg, 4.80 mmol) in MeOH (2 mL) was stirred at rt for 1 h. The solvent was removed in vacuum to afford 2-chloro-N-ethyl-N-methyl-8-phenyl-7,8-dihydro-5H-pyrano[4,3-d]pyrimidin-4-amine (146 mg, 0.481 mmol, 100% yield). LC-MS (M+H)$^+$=304.2.

Preparation J:

2,4-dichloro-8-(4-fluorophenyl)-7,8-dihydro-5H-pyrano[4,3-d]pyrimidine

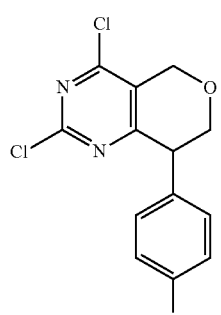

Intermediate J(1):

3-bromodihydro-2H-pyran-4(3H)-one

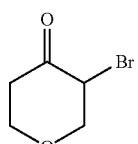

To a cooled solution of dihydro-2H-pyran-4(3H)-one (10.0 g, 99.8 mmol) in THF was added a solution of pyrrolidone hydrotribromide (49.54 g, 99.8 mmol) in THF over a period of 10 min. at 0° C. The reaction mixture was allowed to come to room temperature and stirred for 2 h. The solvent was removed under reduced pressure and the residue was diluted with ethyl acetate (300 mL). The organic solution was washed with aqueous saturated NaHCO$_3$ (100 mL), water (100 mL×2), brine solution (50 mL), dried over anhydrous Na$_2$SO$_4$ and evaporated under reduced pressure to give 3-bromodihydro-2H-pyran-4(3H)-one (12.0 g, 67%) as oily liquid. The crude compound was taken to the next step without further purification. $^1$H NMR (400 MHz, DMSO-d6): δ ppm 4.89-4.87 (1H, m) 4.28-4.27 (1H, m) 4.25-4.4.24 (1H, m) 3.85-3.74 (2H, m) 2.71-2.66 (2H, m).

Intermediate J(2):

3-(4-fluorophenyl)dihydro-2H-pyran-4(3H)-one

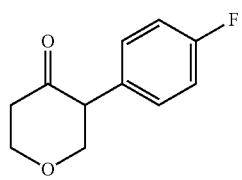 [SMILES: O=C1CCOCC1c1ccc(F)cc1]

To a solution of Intermediate J(1) (12.0 g, 66.9 mmol) in benzene was added 2 M solution of 4-fluorophenyl magnesium bromide in ether (13.34 g, 33.48 mL, 66.9 mmol) at 0° C. The reaction mixture was stirred at room temperature for 40 min. The reaction mixture was quenched with aqueous 1.5 N HCl (80 mL). The organic layer was separated and the aqueous layer was extracted with ethyl acetate (100×2). The combined organic layer was washed with water (100 mL×2), brine solution (50 mL), dried over anhydrous Na$_2$SO$_4$ and evaporated under reduced pressure to give crude compound as oily liquid. The crude compound was dissolved in benzene and was added a solution of 4-fluorophenyl magnesium bromide in ether (9.7 g, 24.5 mL, 49.0 mmol) at 0° C. The reaction mixture was heated at reflux for 30 min. The reaction mixture was quenched with aqueous 1.5 N HCl (50 mL). The organic layer was separated and the aqueous layer was extracted with ethyl acetate (100×2). The combined organic layer was washed with water (100 mL×2), brine solution (50 mL), dried over anhydrous Na$_2$SO$_4$ and evaporated under reduced pressure to give crude compound. The crude compound was purified by column chromatography (Silica gel, 230-400 mesh) using 5% ethyl acetate in pet-ether as mobile phase to give 3-(4-fluorophenyl)dihydro-2H-pyran-4(3H)-one (3.0 g, 36%) as oily liquid. LC-MS (M+H)$^+$=195.2. $^1$H NMR (400 MHz, chloroform-d): δ ppm 7.7.21-7.18 (2H, m), 7.06-7.01 (2H, m), 4.28-4.21 (2H, m), 3.99-3.91 (2H, m), 3.79-3.76 (1H, m) 2.72-2.67 (1H, m) 2.64-2.55 (1H, m).

Intermediate J(3)

8-(4-fluorophenyl)-7,8-dihydropyrano[3,4-e][1,3]oxazine-2,4(3H,5H)-dione

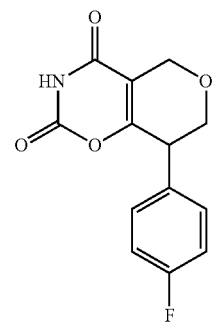 [SMILES: O=c1[nH]c(=O)c2c(o1)C(c1ccc(F)cc1)COC2]

A solution of Intermediate J(2) (1.5 g, 7.72 mmol) and N-chlorocarbonyl isocyanate (0.97 g, 9.2 mmol) was heated at 58° C. under nitrogen atmosphere for 1 h. Then, the reaction temperature was increased to 130° C. and maintained for 2 h. The reaction mass was diluted with ethyl acetate (50 mL). The resulting organic solution was washed with saturated NaHCO$_3$ (25 mL), brine solution (25 mL), dried over anhydrous Na$_2$SO$_4$ and evaporated under reduced pressure to get crude compound. The crude compound was purified by column chromatography (Silica gel, 60-120 mesh) using 50% ethyl acetate in pet-ether as mobile phase to give 8-(4-fluorophenyl)-7,8-dihydropyrano[3,4-e][1,3]oxazine-2,4(3H, 5H)-dione (0.8 g, 38%) as brown solid. LC-MS (M−H)$^+$=262.0. $^1$H NMR (400 MHz, DMSO-d6): δ ppm 11.97 (1H, s), 7.43-7.39 (2H, m), 7.21-7.16 (2H, m), 4.48-4.32 (2H, m), 4.05 (2H, m), 3.77 (1H, m).

Intermediate J(4)

8-(4-fluorophenyl)-7,8-dihydro-1H-pyrano[4,3-d]pyrimidine-2,4 (3H,5H)-dione

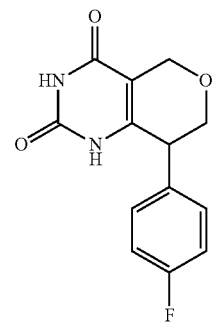 [SMILES: O=c1[nH]c2c(c(=O)[nH]1)COCC2c1ccc(F)cc1]

A solution of Intermediate J(3) (0.8 g, 3.0 mmol) in aqueous ammonia (50 mL) was heated at reflux for 18 h. The excess ammonia was removed under reduced pressure and the aqueous solution was extracted with ethyl acetate (25 mL×4). The combined organic layer was washed with brine solution (25 mL), dried over anhydrous Na$_2$SO$_4$ and evaporated under reduced pressure to give 8-(4-fluorophenyl)-7,8-dihydro-1H-pyrano[4,3-d]pyrimidine-2,4(3H,5H)-dione (0.4 g, 50%). The crude compound was taken to the next step without further purification. LC-MS (M+H)$^+$=263.4. $^1$H NMR (400

MHz, DMSO-d6): δ ppm 11.16 (1H, s), 10.79 (1H, s), 7.33-7.29 (2H, m), 7.19-7.15 (2H, m), 4.43 (1H, m), 4.25 (1H, m), 3.90 (1H, m), 3.75-3.68 (2H, m).

Preparation J 2,4-dichloro-8-(4-fluorophenyl)-7,8-dihydro-5H-pyrano[4,3-d]pyrimidine

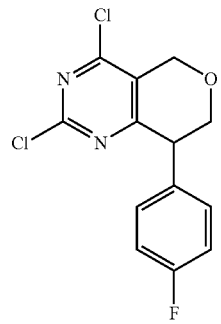 [SMILES: Fc1ccc(C2COCc3c(Cl)nc(Cl)nc32)cc1]

A solution of Intermediate J(4) (0.7 g, 2.6 mmol) and catalytic amount of DMF in POCl₃ (20 vol.) was heated at reflux for 18 h. The excess of POCl₃ was evaporated under reduced pressure. The residue was poured in to crushed ice and stirred for 15 min. The aqueous solution was extracted with ethyl acetate (20 mL×2). The combined organic layer was washed with aqueous saturated NaHCO₃ (50 mL×2), brine solution (25 mL), dried over Na₂SO₄ and evaporated under reduced pressure to give 2,4-dichloro-8-(4-fluorophenyl)-7,8-dihydro-5H-pyrano[4,3-d]pyrimidine (0.79 g) as crude compound. The crude compound was taken to the next step without further purification. LC-MS (M+H)⁺=299.0.

Preparation Ja 2-chloro-8-(4-fluorophenyl)-N-methyl-7,8-dihydro-5H-pyrano[4,3-d]pyrimidin-4-amine

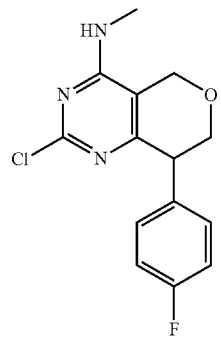 [SMILES: CNc1nc(Cl)nc2c1COCC2c1ccc(F)cc1]

To a solution of Preparation J (0.7 g, 2.3 mmol) in methanol was added Cs₂CO₃ (1.49 g, 4.6 mmol) followed by addition of methylamine hydrochloride (0.78 g, 11.7 mmol) at room temperature. The reaction mixture was stirred at room temperature for 18 h. The solvent was removed under reduced pressure and the residue diluted with ethyl acetate (25 mL), washed with water (25 mL), brine solution (25 mL), dried over anhydrous Na₂SO₄ and evaporated under reduced pressure to get crude compound. The crude compound was purified by column chromatography (60-120 mesh) using 50% ethyl acetate in pet-ether as mobile phase to give 2-chloro-8-(4-fluorophenyl)-N-methyl-7,8-dihydro-5H-pyrano[4,3-d]pyrimidin-4-amine (0.34 g, 49%) as off-white solid. LC-MS (M+H)⁺=294.2. ¹H NMR (400 MHz, DMSO-d6): δ ppm 7.22-7.19 (2H, m), 7.13-7.07 (2H, m), 4.91 (1H, m), 4.75 (1H, m), 4.12-4.08 (2H, m), 3.74 (1H, m), 3.05 (6H, s).

Preparation Jb 2-chloro-N-ethyl-8-(4-fluorophenyl)-7,8-dihydro-5H-pyrano[4,3-d]pyrimidin-4-amine

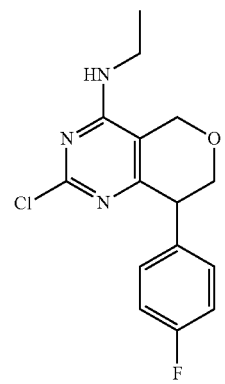 [SMILES: CCNc1nc(Cl)nc2c1COCC2c1ccc(F)cc1]

To a solution of Preparation J (0.350 g, 1.17 mmol) in methanol was added diisopropylethylamine (0.30 g, 2.2 mmol) followed by ethylamine hydrochloride (0.113 g, 1.17 mmol) at room temperature. The reaction mixture was stirred at room temperature for 18 h. The solvent was removed under reduced pressure and the residue diluted with ethyl acetate (25 mL), washed with water (25 mL), brine solution (25 mL), dried over anhydrous Na₂SO₄ and evaporated under reduced pressure to get crude compound. The crude compound was purified by column chromatography (60-120 mesh) using 50-55% ethyl acetate in pet-ether as mobile phase to give 2-chloro-N-ethyl-8-(4-fluorophenyl)-7,8-dihydro-5H-pyrano[4,3-d]pyrimidin-4-amine (0.16 g, 60%) as off-white solid. LC-MS (M+H)⁺=308.2.

Preparation Jc1 and Jc2

2-chloro-8-(4-fluorophenyl)-4-((S)-3-fluoropyrrolidin-1-yl)-7,8-dihydro-5H-pyrano[4,3-d]pyrimidine

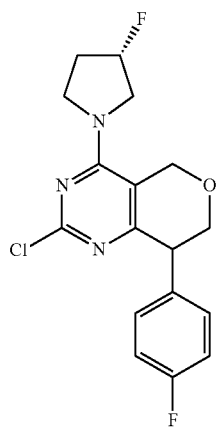

1

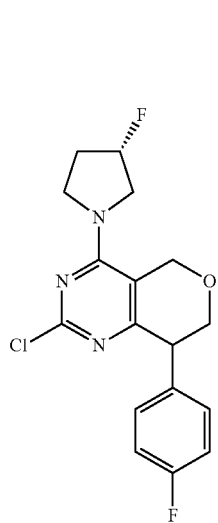

2

To a solution of Preparation J (0.70 g, 2.34 mmol) in methanol was added diisopropylethylamine (0.60 g, 4.6 mmol) followed by (R)-3-fluoropyrrolidine (0.58 g, 4.6 mmol) at room temperature. The reaction mixture was stirred at room temperature for 18 h. The solvent was removed under reduced pressure and the residue was purified by prep-HPLC (40% ethanol in hexane) to give 2-chloro-8-(4-fluorophenyl)-4-((S)-3-fluoropyrrolidin-1-yl)-7,8-dihydro-5H-pyrano[4,3-d]pyrimidine (0.90 g, 11% Isomer 1, 0.110 g, 13% Isomer 2) as off-white solid. LC-MS (M+H)$^+$=352.2. $^1$H NMR (400 MHz, DMSO-d6): δ ppm 7.24 (2H, m), 7.13 (2H, m), 5.40 (1H, m), 4.12 (1H, d, J=14.8 Hz), 4.88 (1H, d, J=14.8 Hz), 4.14-4.09 (2H, m), 3.91-3.81 (3H, m), 3.75-3.66 (2H, m), 2.51-2.18 (2H, m).

Preparation Jd1 and Jd2

2-chloro-8-(4-fluorophenyl)-4-((R)-3-fluoropyrrolidin-1-yl)-7,8-dihydro-5H-pyrano[4,3-d]pyrimidine

1

2

To a solution of Preparation J (0.70 g, 2.34 mmol) in methanol was added diisopropylethylamine (0.60 g, 4.6 mmol) followed by (S)-3-fluoropyrrolidine (0.58 g, 4.6 mmol) at room temperature. The reaction mixture was stirred at room temperature for 18 h. The solvent was removed under reduced pressure and the residue was purified by prep-HPLC (40% ethanol in hexane) to give 2-chloro-8-(4-fluorophenyl)-4-((R)-3-fluoropyrrolidin-1-yl)-7,8-dihydro-5H-pyrano[4,3-d]pyrimidine (0.100 g, 12% Isomer 1, 0.110 g, 13% Isomer 2) as off-white solid. LC-MS (M+H)$^+$=352.2.

Jd1: $^1$H NMR (400 MHz, DMSO-d6): δ ppm 7.24 (2H, m), 7.13 (2H, m), 5.40 (1H, m), 4.12 (1H, d, J=14.4 Hz), 4.88 (1H, d, J=14.4 Hz), 4.11 (2H, m), 3.94-3.89 (3H, m), 3.72-3.58 (2H, m), 2.20-2.01 (2H, m).

Jd2: $^1$H NMR (400 MHz, DMSO-d6): δ ppm 7.21 (2H, m), 7.13 (2H, m), 5.39 (1H, m), 5.02 (2H, m), 4.02-3.97 (2H, m), 3.91-3.84 (4H, m), 3.73 (1H, m), 2.23-2.01 (2H, m).

Preparation Je 2-chloro-8-(4-fluorophenyl)-N,N-dimethyl-7,8-dihydro-5H-pyrano[4,3-d]pyrimidin-4-amine

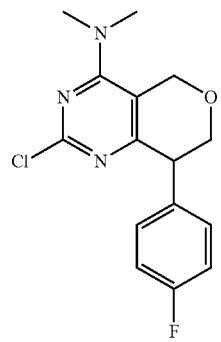 [SMILES: CN(C)c1nc(Cl)nc2c1COCC2c1ccc(F)cc1]

To a solution of Preparation J (0.7 g, 2.3 mmol) in methanol was added $Cs_2CO_3$ (1.49 g, 4.6 mmol) followed by addition of dimethylamine hydrochloride (0.95 g, 11.7 mmol) at room temperature. The reaction mixture was stirred at room temperature for 18 h. The solvent was removed under reduced pressure and the residue diluted with ethyl acetate (50 mL), washed with water (25 mL), brine solution (25 mL), dried over anhydrous $Na_2SO_4$ and evaporated under reduced pressure to get crude compound. The crude compound was purified by column chromatography (60-120 mesh) using 40% ethyl acetate in pet-ether as mobile phase to give 2-chloro-8-(4-fluorophenyl)-N,N-dimethyl-7,8-dihydro-5H-pyrano[4,3-d]pyrimidin-4-amine (0.35 g, 49%) as off-white solid. LC-MS $(M+H)^+=308.2$. This compound was taken to the next step without further purification.

Preparation Jf 2-chloro-N-ethyl-8-(4-fluorophenyl)-N-methyl-7,8-dihydro-5H-pyrano[4,3-d]pyrimidin-4-amine

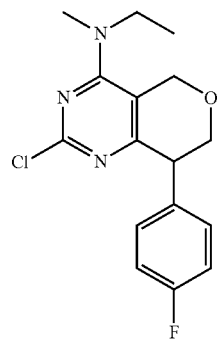 [SMILES: CCN(C)c1nc(Cl)nc2c1COCC2c1ccc(F)cc1]

To a solution of Preparation J (0.7 g, 2.3 mmol) in methanol was added $Cs_2CO_3$ (1.49 g, 4.6 mmol) followed by addition of ethylmethylamine hydrochloride (1.1 g, 11.7 mmol) at room temperature. The reaction mixture was stirred at room temperature for 18 h. The solvent was removed under reduced pressure and the residue diluted with ethyl acetate (25 mL), washed with water (25 mL), brine solution (25 mL), dried over anhydrous $Na_2SO_4$ and evaporated under reduced pressure to get crude compound. The crude compound was purified by column chromatography (60-120 mesh) using 50% ethyl acetate in pet-ether as mobile phase to give 2-chloro-N-ethyl-8-(4-fluorophenyl)-N-methyl-7,8-dihydro-5H-pyrano[4,3-d]pyrimidin-4-amine (0.39 g, 52%) as off-white solid. LC-MS $(M+H)^+=322.2$. This compound was taken to the next step without further purification.

Preparation Jg 2-chloro-4-(3,3-difluoroazetidin-1-yl)-8-(4-fluorophenyl)-7,8-dihydro-5H-pyrano[4,3-d]pyrimidine

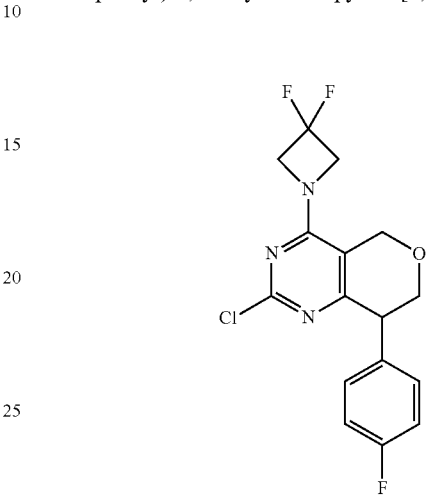

To a solution of Preparation J (0.7 g, 2.3 mmol) in methanol was added $Cs_2CO_3$ (1.49 g, 4.6 mmol) followed by addition of 3,3-difluoroazetidine hydrochloride (0.60 g, 4.6 mmol) at room temperature. The reaction mixture was stirred at room temperature for 18 h. The solvent was removed under reduced pressure and the residue diluted with ethyl acetate (25 mL), washed with water (25 mL), brine solution (25 mL), dried over anhydrous $Na_2SO_4$ and evaporated under reduced pressure to get crude compound. The crude compound was purified by column chromatography (60-120 mesh) using 50% ethyl acetate in pet-ether as mobile phase to give 2-chloro-4-(3,3-difluoroazetidin-1-yl)-8-(4-fluorophenyl)-7,8-dihydro-5H-pyrano[4,3-d]pyrimidine (0.42 g, 50%) as off-white solid. LC-MS $(M+H)^+=355.2$. This compound was taken to the next step without further purification.

Preparation K 2,4-dichloro-8-(4-chlorophenyl)-7,8-dihydro-5H-pyrano[4,3-d]pyrimidine

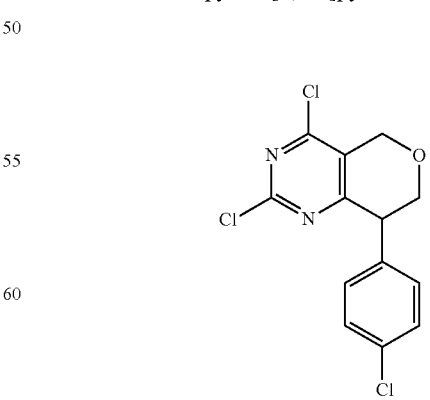

The title compound was prepared in the analogous fashion to Preparation J, as a pale yellow solid. LC-MS $(M+H)^+$ =315.0. ¹H NMR (400 MHz, CDCl₃) δ ppm 7.30 (2H, dd, J=2.0, 6.4 Hz), 7.17 (2H, dd, J=2.0, 6.4 Hz), 4.91 (1H, d, J=16.4 Hz), 4.76 (1H, d, J=16.0 Hz), 4.18-4.09 (3H, m).

Preparation Ka 2-chloro-8-(4-chlorophenyl)-4-(3,3-di fluoro azetidin-1-yl)-7,8-dihydro-5H-pyrano[4,3-d]pyrimidine

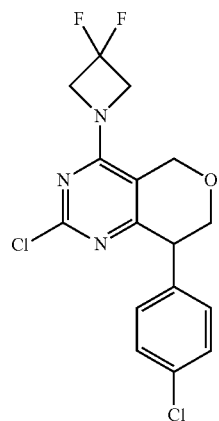 [SMILES: FC1(F)CN(c2nc(Cl)nc3c2COCC3c2ccc(Cl)cc2)C1]

2,4-dichloro-8-(4-chlorophenyl)-7,8-dihydro-5H-pyrano[4,3-d]pyrimidine (Preparation K) (500 mg, 1.584 mmol) and 3,3-Difluoroazetidine hydrochloride (308 mg, 2.377 mmol) were combined and purified as per Preparation Ha to give 2-chloro-8-(4-chlorophenyl)-4-(3,3-difluoro azetidin-1-yl)-7,8-dihydro-5H-pyrano[4,3-d]pyrimidine (400 mg, 1.075 mmol, 67.8% yield) as a white solid. LC-MS (M+H)⁺=372.0. ¹H NMR (500 MHz, CDCl₃) δ ppm 7.22-7.34 (2H, m), 7.12 (2H, d, J=8.24 Hz), 4.63-4.85 (2H, m), 4.46-4.64 (3H, m), 4.04-4.17 (1H, m), 3.91-4.04 (2H, m).

Preparation Kb 2-chloro-8-(4-chlorophenyl)-N-methyl-7,8-dihydro-5H-pyrano[4,3-d]pyrimidin-4-amine

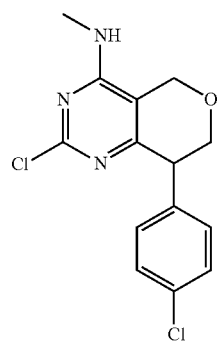 [SMILES: CNc1nc(Cl)nc2c1COCC2c1ccc(Cl)cc1]

2,4-dichloro-8-(4-chlorophenyl)-7,8-dihydro-5H-pyrano[4,3-d]pyrimidine (Preparation K) (500 mg, 1.584 mmol) and methanamine hydrochloride (160 mg, 2.377 mmol) were combined and purified as per Preparation Ha to give 2-chloro-8-(4-chlorophenyl)-N-methyl-7,8-dihydro-5H-pyrano[4,3-d]pyrimidin-4-amine (150 mg, 0.484 mmol, 30.5% yield). LC-MS (M+H)⁺=310.0. ¹H NMR (500 MHz, CDCl₃) δ ppm 7.22-7.31 (2H, m), 7.13 (2H, d, J=8.55 Hz), 4.46-4.64 (1H, m), 4.43 (1H, br. s.), 3.97-4.14 (1H, m), 3.91 (1H, d, J=3.36 Hz), 3.09 (3H, d, J=4.88 Hz).

Preparation Kc 2-chloro-8-(4-chlorophenyl)-N,N-dimethyl-7,8-dihydro-5H-pyrano[4,3-d]pyrimidin-4-amine

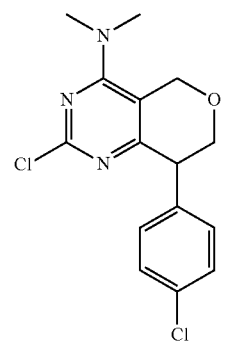 [SMILES: CN(C)c1nc(Cl)nc2c1COCC2c1ccc(Cl)cc1]

2,4-dichloro-8-(4-chlorophenyl)-7,8-dihydro-5H-pyrano[4,3-d]pyrimidine (Preparation K) (500 mg, 1.584 mmol) and Dimethylamine (2.0 M in THF) (1.188 mL, 2.377 mmol) were combined an purified as per Preparation Ha to give 2-chloro-8-(4-chlorophenyl)-N,N-dimethyl-7,8-dihydro-5H-pyrano[4,3-d]pyrimidin-4-amine (400 mg, 1.234 mmol, 78% yield) as a white solid. LC-MS (M+H)⁺=324.0. ¹H NMR (500 MHz, CDCl₃) δ ppm 7.20-7.31 (2H, m), 7.04-7.15 (2H, m), 4.70-4.89 (2H, m), 4.17 (1H, dd, J=11.60, 5.49 Hz), 4.05 (1H, t, J=5.49 Hz), 3.87 (1H, dd, J=11.60, 5.49 Hz), 3.05-3.19 (6H, m).

Preparation L 2,4-dichloro-8-(4-bromophenyl)-7,8-dihydro-5H-pyrano[4,3-d]pyrimidine

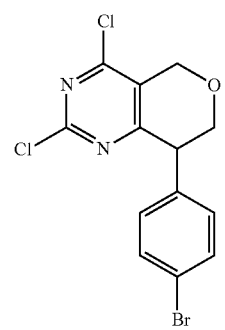

The title compound was prepared in the analogous fashion to Preparation J, as a pale yellow solid. LC-MS (M+H)⁺=359.0. ¹H NMR (400 MHz, CD₃OD) δ ppm 7.52 (2H, d, J=8.4 Hz), 7.22 (2H, d, J=8.4 Hz), 4.87 (1H, d, J=16.0 Hz), 4.30 (1H, t, J=4.6 Hz), 4.14 (1H, dd, J=4.6, 11.4 Hz), 3.95 (1H, dd, J=4.8, 11.6 Hz).

Preparation La 8-(4-bromophenyl)-2-chloro-N-methyl-7,8-dihydro-5H-pyrano[4,3-d]pyrimidin-4-amine

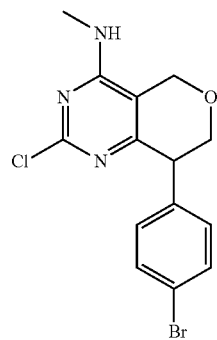 [SMILES: CNc1nc(Cl)nc2c1COCC2c1ccc(Br)cc1]

8-(4-bromophenyl)-2,4-dichloro-7,8-dihydro-5H-pyrano[4,3-d]pyrimidine (Preparation L) (500 mg, 1.389 mmol) and methanamine hydrochloride (141 mg, 2.083 mmol) were combined and purified as per Preparation Ha to give 8-(4-bromophenyl)-2-chloro-N-methyl-7,8-dihydro-5H-pyrano[4,3-d]pyrimidin-4-amine (210 mg, 0.592 mmol, 42.6% yield). LC-MS (M+H)$^+$=356.0. $^1$H NMR (500 MHz, MeOD) δ ppm 7.46 (2H, d, J=8.24 Hz), 7.13 (2H, d, J=8.55 Hz), 4.43-4.71 (2H, m), 4.09 (1H, dd, J=11.44, 4.12 Hz), 3.92-4.03 (1H, m), 3.86 (1H, d, J=3.05 Hz), 3.00 (3H, s).

Preparation M 2,4-dichloro-7-(4-fluorophenyl)-5,7-dihydrofuro[3,4-d]pyrimidine

Intermediate M(1)

ethyl 2-hydroxy-2-phenylacetate

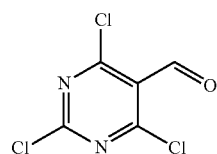 [SMILES: O=Cc1c(Cl)nc(Cl)nc1Cl]

A solution of pyrimidine-2,4,6-triol (10.0 g, 78.2 mmol), DMF (12 mL) in POCl$_3$ (10 vol.) was heated at reflux for 15 h. The excess of POCl$_3$ was evaporated under reduced pressure. The residue was poured in to crushed ice. The precipitated solid was filtered and washed with water to give 2,4,6-trichloropyrimidine-5-carbaldehyde (8.0 g, 47%) as yellow solid. This compound was taken to the next step without further purification.

Intermediate M(2)

2,4,6-trichloro-5-(1,3-dioxolan-2-yl)pyrimidine

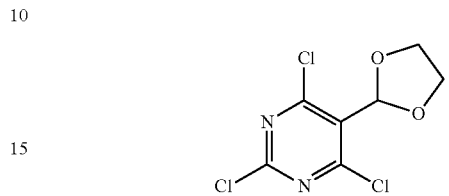

To a solution of Intermediate M(1) (5.0 g, 23.6 mmol) in dry benzene was added ethylene glycol (4.0 mL, 64.5 mmol) followed by p-toluenesulfonic acid (0.15 g, 0.87 mmol) at room temperature. The reaction mixture was heated at reflux for 20 h. The reaction mixture was filtered and washed with warm benzene. The filtrate was evaporated under reduced pressure and the residue was purified by column chromatography (Silica gel, 60-120 mesh) using 10% ethyl acetate in pet-ether as mobile phase to give (4.5 g, 75%) as off-white solid. LC-MS (M+H)$^+$=256.0. $^1$H NMR (400 MHz, DMSO-d6): δ ppm 9.6 (1H, s), 7.99 (1H, s), 7.98 (1H, s), 7.76-7.41 (3H, m), 7.23-7.13 (4H, m), 5.87 (1H, s), 5.33 (1H, dd, J=27, 8 Hz), 5.17 (1H, dd, J=27, 8), 4.67 (4H, m), 3.72 (3H, s).

Intermediate M(3)

2,4-dichloro-5-(1,3-dioxolan-2-yl)-6-(4-fluorobenzyl)pyrimidine

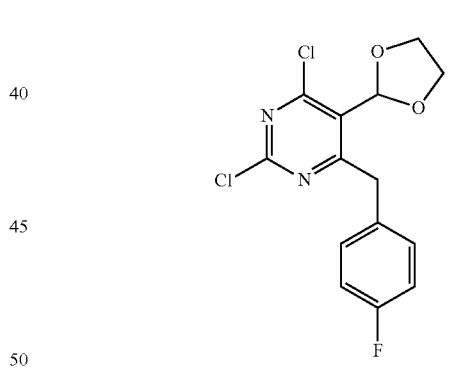

To a solution of Intermediate M(2) (4.0 g, 15.6 mmol) in dry diethyl ether was added 4-fluorobenzyl magnesium bromide (75.2 mL, 18.8 mmol, 0.25 M solution in THF) at 0° C. The reaction mixture was allowed to come to room temperature and stirred for 4 h. The reaction mixture was quenched with aqueous saturated ammonium chloride. The organic layer was separated and the aqueous layer was extracted with diethyl ether (50 mL×2). The combined organic layer was washed with water, dried over anhydrous Na$_2$SO$_4$ and evaporated to get crude compound. The crude compound was purified by combiflash using 1.4% ethyl acetate in pet ether as mobile phase to give 2,4-dichloro-5-(1,3-dioxolan-2-yl)-6-(4-fluorobenzyl)pyrimidine (2.2 g, 43.1%) as off-white solid. LC-MS (M−H)$^+$=327.0. $^1$H NMR (400 MHz, DMSO-d6): δ ppm 7.26 (2H, m), 7.10 (2H, m), 6.19 (1H, s), 4.25 (2H, s), 4.19 (2H, m), 4.02 (2H, m).

Intermediate M(4)

(2,4-dichloro-6-(4-fluorobenzyl)pyrimidin-5-yl)methanol

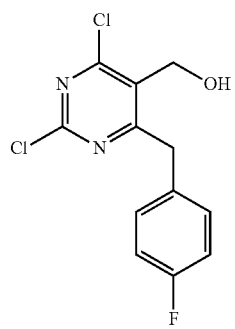 [SMILES: OCc1c(Cl)nc(Cl)nc1Cc1ccc(F)cc1]

To a solution of Intermediate M(3) (2.0 g, 6.07 mmol) in THF was added aqueous 6 N HCl over a period of 5 min. at room temperature. The reaction mixture was heated at reflux for 1 h. The reaction volume was reduced to half and the solution was extracted with diethyl ether (50 mL×2). The combined organic layer was washed with water (50 mL), brine solution (50 mL), dried over anhydrous $Na_2SO_4$ and evaporated under reduced pressure to get crude compound (1.2 g). The crude compound was dissolved in methanol and cooled to 0° C. Sodium borohydride (0.234 g) was added to the reaction mixture. The resulting solution was allowed to come to room temperature and stirred for 1 h. The reaction mixture was quenched with aqueous saturated ammonium chloride, and then solvent was evaporated under reduced pressure. The residue was diluted with ethyl acetate (50 mL). The organic solution was washed with water (25 mL), brine solution (25 mL), dried over anhydrous $Na_2SO_4$ and evaporated under reduced pressure to get crude compound. The crude compound was purified by column chromatography (Silica gel, 60-120 mesh) using 20% ethyl acetate in pet ether as mobile phase to give (2,4-dichloro-6-(4-fluorobenzyl)pyrimidin-5-yl)methanol (1.0 g, 58%) as oily liquid. LC-MS $(M+H)^+=488.1$. $^1H$ NMR (300 MHz, $CDCl_3$): δ ppm 7.25 (2H, m), 7.01 (2H, m), 4.82 (2H, m), 4.27 (2H, s).

Preparation M 2,4-dichloro-7-(4-fluorophenyl)-5,7-dihydrofuro[3,4-d]pyrimidine

To a solution of Intermediate M(4) (1.0 g, 3.48 mmol) in dry benzene (100 mL) was added $Cs_2CO_3$ (0.4 g, 3.48 mmol) followed by lead tetra acetate (0.3 g, 3.48 mmol) at room temperature (the color of the reaction mixture was changed from colorless to brown). The reaction mass was heated at reflux for 18 h using Dean Stark apparatus. The reaction mixture was filtered through celite bed and washed with diethyl ether. The filtrate was evaporated under reduced pressure and the residue was diluted with diethyl ether. The organic solution was washed with water (25 mL×2), aqueous saturated $NaHCO_3$, brine solution (10 mL), dried over anhydrous $Na_2SO_4$ and evaporated under reduced pressure to get crude compound. The crude compound was purified by Combiflash using 0.9% ethyl acetate in pet-ether as mobile phase to give 2,4-dichloro-7-(4-fluorophenyl)-5,7-dihydrofuro[3,4-d]pyrimidine (0.250 mg, 30%) as oily liquid. LC-MS $(M+H)^+=485.0$. $^1H$ NMR (400 MHz, methanol-d4): δ ppm 7.48-7.44 (2H, m), 7.16-7.12 (2H, m), 6.15 (1H, s), 5.40 (1H, dd, J=13.6 Hz), 5.27 (1H, dd, J=13.6).

Preparation Ma 2-chloro-7-(4-fluorophenyl)-N-methyl-5,7-dihydrofuro[3,4-d]pyrimidin-4-amine

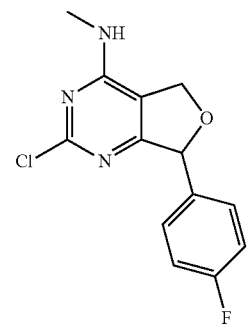 [SMILES: CNc1nc(Cl)nc2c1COC2c1ccc(F)cc1]

2,4-dichloro-7-(4-fluorophenyl)-5,7-dihydrofuro[3,4-d]pyrimidine (Preparation M) (250 mg, 0.877 mmol) and methanamine hydrochloride (89 mg, 1.315 mmol) were combined and purified as per Preparation Ia to give 2-chloro-7-(4-fluorophenyl)-N-methyl-5,7-dihydrofuro[3,4-d]pyrimidin-4-amine (149 mg, 0.533 mmol, 60.8% yield). LC-MS $(M+H)^+=280.0$. $^1H$ NMR (500 MHz, MeOD) δ ppm 7.31-7.44 (2H, m), 7.05-7.17 (2H, m), 5.80-5.95 (1H, m), 4.94-5.21 (2H, m), 2.93-3.07 (3H, m).

Preparation Mb 2-chloro-N-ethyl-7-(4-fluorophenyl)-5,7-dihydrofuro[3,4-d]pyrimidin-4-amine

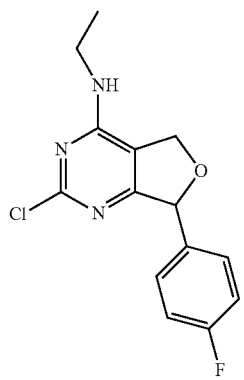 [SMILES: CCNc1nc(Cl)nc2c1COC2c1ccc(F)cc1]

2,4-dichloro-7-(4-fluorophenyl)-5,7-dihydrofuro[3,4-d]pyrimidine (Preparation M) (125 mg, 0.438 mmol) and ethylamine hydrochloride (53.6 mg, 0.658 mmol) were combined and purified as per Preparation Ha to give 2-chloro-N-ethyl-7-(4-fluorophenyl)-5,7-dihydrofuro[3,4-d]pyrimidin-4-amine (38.17 mg, 0.130 mmol, 29.6% yield). LC-MS (M+H)$^+$=294.0. $^1$H NMR (500 MHz, CDCl$_3$) δ ppm 7.24-7.38 (2H, m), 6.92-7.08 (2H, m), 5.73-5.98 (1H, m), 4.83-5.21 (2H, m), 3.36-3.63 (2H, m), 1.13-1.28 (3H, m).

Preparations Mc1 and Mc2

2-chloro-7-(4-fluorophenyl)-4-((S)-3-fluoropyrrolidin-1-yl)-5,7-dihydrofuro[3,4-d]pyrimidine Mc1

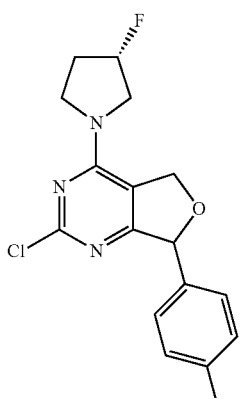

Diastereomer 1
Racemic

Mc2

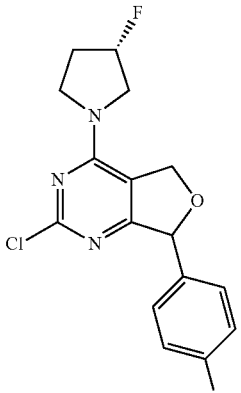

Diastereomer 2
Racemic 2,4-dichloro-7-(4-fluorophenyl)-5,7-dihydrofuro[3,4-d]pyrimidine (Preparation M) (125 mg, 0.438 mmol) and (S)-3-fluoropyrrolidine, HCl (83 mg, 0.658 mmol) were combined and purified as per Preparation Ha to give 2-chloro-7-(4-fluorophenyl)-4-((S)-3-fluoropyrrolidin-1-yl)-5,7-dihydrofuro[3,4-d]pyrimidine (Mc1, Diastereomer 1, first to elute) (49 mg, 0.145 mmol, 33.1% yield). LC-MS (M+H)$^+$=338.0.

(Mc2, Diastereomer 2, second to elute) (40 mg, 0.118 mmol, 27.0% yield).

LC-MS (M+H)$^+$=338.0. The relative stereochemistry of Mc1 and Mc2 was not determined Preparation Md 2-chloro-4-(3,3-difluoroazetidin-1-yl)-7-(4-fluorophenyl)-5,7-dihydrofuro[3,4-d]pyrimidine

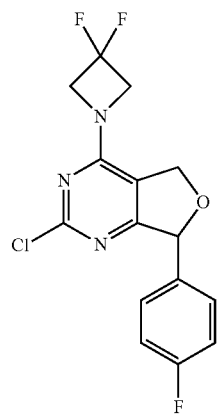 [SMILES: Fc1ccc(C2OCc3c2nc(Cl)nc3N2CC(F)(F)C2)cc1]

To a solution of Preparation M (0.05 g, 0.176 mmol) in methanol was added diisopropylethylamine (0.045 g, 0.30 mmol) followed by addition of 3,3-difluoroazitidine hydrochloride (0.03 g, 0.193 mmol) at room temperature. The reaction mixture was stirred at room temperature for 18 h. The solvent was removed under reduced pressure and the residue was purified by column chromatography (60-120 mesh) using 6% ethyl acetate in pet-ether as mobile phase to give 2-chloro-4-(3,3-difluoroazetidin-1-yl)-7-(4-fluorophenyl)-5,7-dihydrofuro[3,4-d]pyrimidine (0.035 g, 46%) as white solid. LC-MS (M+H)$^+$=342.2.

Preparation Me 2-chloro-7-(4-fluorophenyl)-4-((S)-2-methylpyrrolidin-1-yl)-5,7-dihydrofuro[3,4-d]pyrimidine

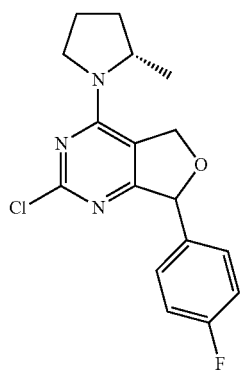 [SMILES: C[C@H]1CCCN1c1nc(Cl)nc2c1COC2c1ccc(F)cc1]

2,4-dichloro-7-(4-fluorophenyl)-5,7-dihydrofuro[3,4-d]pyrimidine (Preparation M) was reacted as described in Preparation Hp1 and Hp2 with (S)-2-methylpyrrolidine p-toluenesulfonate salt to afford 2-chloro-7-(4-fluorophenyl)-4-((S)-2-methylpyrrolidin-1-yl)-5,7-dihydrofuro[3,4-d]pyrimidine (Preparation Me) as a mixture of 2 diasteriomers. LC-MS (M+H)$^+$=334.1.

Preparation Mf 2-chloro-N—((R)-1-cyclopropylethyl)-7-(4-fluorophenyl)-5,7-dihydrofuro[3,4-d]pyrimidin-4-amine

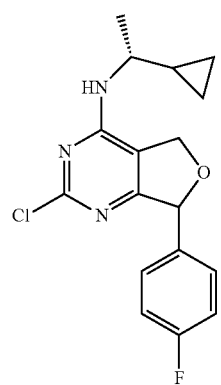 [SMILES: C[C@@H](Nc1nc(Cl)nc2c1COC2c1ccc(F)cc1)C1CC1]

To a solution of 2,4-dichloro-7-(4-fluorophenyl)-5,7-dihydrofuro[3,4-d]pyrimidine (Preparation M) (150 mg, 0.526 mmol) in THF (2631 µL) was added (R)-1-cyclopropylethanamine, HCl (128 mg, 1.052 mmol) and DIEA (368 µL, 2.105 mmol). The mixture was heated at 40° C. for 2 h and stirred at RT overnight. The mixture was concentrated and purified by column chromatography on silica gel to give 2-chloro-N—((R)-1-cyclopropylethyl)-7-(4-fluorophenyl)-5,7-dihydrofuro[3,4-d]pyrimidin-4-amine (Preparation Mf) (25 mg, 0.075 mmol, 14.24% yield) as a mixture of 2 diasteriomers. LC-MS (M+H)$^+$=334.1.

Preparation Mg 2-chloro-7-(4-fluorophenyl)-4-((R)-3-fluoropyrrolidin-1-yl)-5,7-dihydrofuro[3,4-d]pyrimidine

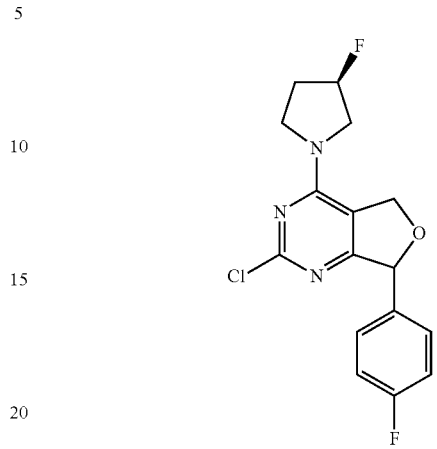

2,4-dichloro-7-(4-fluorophenyl)-5,7-dihydrofuro[3,4-d]pyrimidine (Preparation M) was reacted as described in Preparation Xa with (R)-3-fluoropyrrolidine, HCl to give 2-chloro-7-(4-fluorophenyl)-4-((R)-3-fluoropyrrolidin-1-yl)-5,7-dihydrofuro[3,4-d]pyrimidine (Preparation Mg). LC-MS (M+H)$^+$=338.1. $^1$H NMR (400 MHz, CDCl$_3$) δ ppm 7.33-7.47 (m, 2H) 7.00-7.14 (m, 2H) 5.83-5.97 (m, 1H) 5.54 (dd, J=11.33, 3.53 Hz, 1H) 5.36-5.49 (m, 2H) 3.88-4.00 (m, 1H) 3.65-3.88 (m, 3H) 2.30-2.52 (m, 1H) 2.02-2.20 (m, 1H).

Preparation Mh 2-chloro-4-((2S,6R)-2,6-dimethylmorpholino)-7-(4-fluorophenyl)-5,7-dihydrofuro[3,4-d]pyrimidine

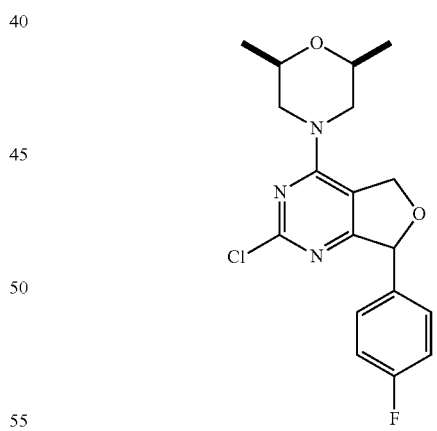

2,4-dichloro-7-(4-fluorophenyl)-5,7-dihydrofuro[3,4-d]pyrimidine (Preparation M) was reacted as described in Preparation Xa with (2R,6S)-2,6-dimethylmorpholine to give 2-chloro-4-((2S,6R)-2,6-dimethylmorpholino)-7-(4-fluorophenyl)-5,7-dihydrofuro[3,4-d]pyrimidine (Preparation Mh). LC-MS (M+H)$^+$=364.2. $^1$H NMR (500 MHz, CDCl$_3$) δ ppm 7.39 (dd, J=8.70, 5.34 Hz, 2H) 7.07 (t, J=8.70 Hz, 2H) 5.90 (br. s., 1H) 5.34-5.42 (m, 1H) 5.24-5.34 (m, 1H) 4.14 (q, J=7.02 Hz, 2H) 3.67 (ddd, J=10.38, 6.41, 2.44 Hz, 4H), 1.20 (m, 6H).

Preparation N 2,4-dichloro-8-phenyl-6,8-dihydro-5H-pyrano[3,4-d]pyrimidine

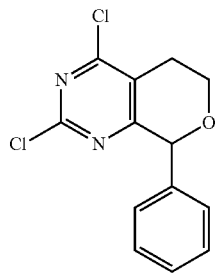 [SMILES: Clc1nc(Cl)c2c(n1)C(c1ccccc1)OCC2]

Intermediate N(1)

ethyl 2-hydroxy-2-phenylacetate

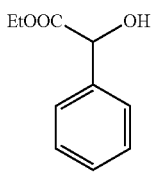

To a cooled solution of ethyl 2-hydroxy-2-phenylacetate (25.0 g, 164.3 mmol) in ethanol was added con. $H_2SO_4$ (15 mL) over a period of 10 min. The reaction mixture was heated at reflux for 5 h. The solvent was evaporated under reduced pressure and the residue was diluted with ethyl acetate (250 mL). The organic solution was washed with aqueous saturated $NaHCO_3$ (200 mL×2), water (100 mL×2), brine solution (100 mL), dried over anhydrous $Na_2SO_4$ and evaporated under reduced pressure to give ethyl 2-hydroxy-2-phenylacetate (24.5 g, 83%) as crude compound (oily liquid). The crude compound was taken to the next step without further purification. LC-MS $(M+H_2O)^+$=198.2. $^1$H NMR (400 MHz, DMSO-d6): δ ppm 7.41-7.28 (5H, m), 6.04 (1H, d, J=4.0 Hz), 5.11 (1H, d, J=4.0 Hz), 4.13 (2H, m), 1.13 (3H, t, J=7.2 Hz).

Intermediate N(2)

ethyl 4-(2-ethoxy-2-oxo-1-phenylethoxy)but-2-enoate

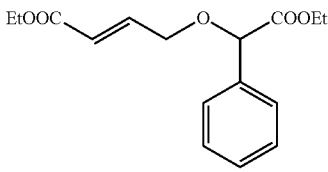 [SMILES: CCOC(=O)/C=C/COC(C(=O)OCC)c1ccccc1]

To a solution of Intermediate N(1) (20.0 g, 110.9 mmol) in hexane was added silver oxide (66.75 g, 288.5 mmol) followed by magnesium sulphate (2.66 g, 220 mmol) at room temperature. The reaction mixture was heated at reflux for 1 h. The reaction mixture was cooled to 0° C. and was added silver oxide (71.8 g, 310.9 mmol) followed by ethyl-4-bromochrotonate (32.0 g, 166 mmol). The resulting solution was stirred at room temperature for 3 days. The reaction mass was filtered through a bed of diatomaceous earth (Celite®) and washed with ethyl acetate. The filtrate was evaporated under reduced pressure to give ethyl 4-(2-ethoxy-2-oxo-1-phenylethoxy)but-2-enoate (20.0 g, 62.5%) as oily liquid. LC-MS $(M+H_2O)^+$=310.2. $^1$H NMR (400 MHz, DMSO-d6): δ ppm 7.42-7.35 (5H, m), 6.90 (1H, m), 6.05 (1H, m), 5.09 (1H, s), 4.26 (2H, m), 4.16 (4H, m), 1.21 (3H, t, J=7.2 Hz), 1.13 (3H, t, J=7.2 Hz).

Intermediate N(3)

ethyl 4-(2-ethoxy-2-oxo-1-phenylethoxy)butanoate

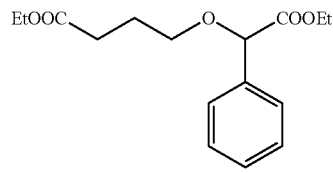 [SMILES: CCOC(=O)CCCOC(C(=O)OCC)c1ccccc1]

To a solution of Intermediate N(2) (20.0 g, 68.41 mmol) in ethanol was added palladium on carbon (10%, w/w) at room temperature. The reaction mixture was hydrogenated under balloon pressure of hydrogen for 30 h. The reaction mass was filtered through a bed of diatomaceous earth (Celite®) and washed with ethanol. The solvent was removed under reduced pressure and the residue was purified by column chromatography (Silica gel, 60-120 mesh) using 5% ethyl acetate in petroleum-ether as mobile phase to give ethyl 4-(2-ethoxy-2-oxo-1-phenylethoxy)butanoate (12.0 g, 59.5%) as oily liquid. LC-MS $(M+H)^+$=295.2. $^1$H NMR (400 MHz, DMSO-d6): δ ppm 7.41-7.27 (5H, m), 4.96 (1H, s), 4.07 (4H, m), 3.62 (1H, m), 3.49 (1H, m), 2.36 (2H, m), 1.79 (2H, m), 1.15 (6H, m).

Intermediate N(4)

ethyl 3-oxo-2-phenyltetrahydro-2H-pyran-4-carboxylate

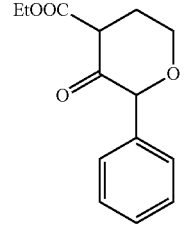

To a cooled solution of Intermediate N(3) (12.0 g, 40.76 mmol) in THF was added t-BuOK (9.13 g, 81.3 mmol) at 0° C. The reaction mixture was allowed to come to room temperature and stirred for 1 h. The reaction mixture was quenched with water and evaporated the solvent under reduced pressure. The residue was diluted with ethyl acetate (200 mL). The organic layer was washed with water (100 mL×2), brine solution (100 mL), dried over anhydrous $Na_2SO_4$ and evaporated under reduced pressure to get crude compound. The crude compound was purified by column chromatography (Silica gel, 60-120 mesh) using 50% ethyl acetate in pet-ether as mobile phase to give ethyl 3-oxo-2- phenyltetrahydro-2H-pyran-4-carboxylate (6.0 g, 59.4%) as oily liquid. LC-MS (M+H)+=249.2. ¹H NMR (400 MHz, DMSO-d6): δ ppm 11.81 (1H, s), 7.36 (5H, m), 5.20 (1H, s), 4.23 (2H, q, J=7.2.0 Hz), 3.71 (1H, m), 3.67 (1H, m), 2.36 (1H, m), 2.32 (1H, m), 1.29 (3H, t, J=7.2 Hz).

Intermediate N(5)

8-phenyl-5,6-dihydro-1H-pyrano[3,4-d]pyrimidine-2,4(3H,8H)-dione

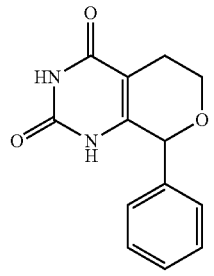 [SMILES: O=c1[nH]c2c(c(=O)[nH]1)CCOC2c1ccccc1]

To a solution of Intermediate N(4) (6.0 g, 24.16 mmol) in ethanol was added t-BuOK (6.76 g, 60.41 mmol) followed by urea (3.62 g, 60.41 mmol) at room temperature. The reaction mass was heated at reflux for 18 h. The reaction mixture was quenched with water and evaporated the solvent under reduced pressure. The residue was diluted with ethyl acetate (100 mL). The organic layer was washed with water (100 mL×2), brine solution (100 mL), dried over anhydrous Na₂SO₄ and evaporated under reduced pressure to get crude compound. The crude compound was purified by column chromatography (Silica gel, 60-120 mesh) using ethyl acetate as mobile phase to give 8-phenyl-5,6-dihydro-1H-pyrano[3,4-d]pyrimidine-2,4(3H,8H)-dione (3.0 g, 50.8%) as pale yellow solid. LC-MS (M-H)+=243.2. ¹H NMR (400 MHz, DMSO-d6): δ ppm 11.10 (1H, s), 10.57 (1H, s), 7.42-7.39 (3H, m), 7.32 (2H, m), 5.32 (1H, s), 3.71-3.56 (2H, m), 2.38-2.27 (2H, m).

Preparation N 2,4-dichloro-8-phenyl-6,8-dihydro-5H-pyrano[3,4-d]pyrimidine

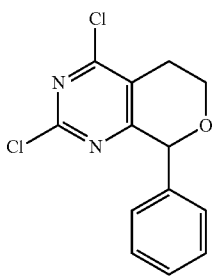 [SMILES: Clc1nc(Cl)c2c(n1)C(c1ccccc1)OCC2]

A solution of Intermediate N(5) (2.0 g, 8.18 mmol) and catalytic amount of DMF in POCl₃ (10 vol.) was heated at reflux for 18 h. The excess of POCl₃ was evaporated under reduced pressure. The residue was poured in to crushed ice and stirred for 15 min. The aqueous solution was extracted with ethyl acetate (50 mL×3). The combined organic layer was washed with aqueous saturated NaHCO₃ (50 mL×2), brine solution (50 mL), dried over Na₂SO₄ and evaporated under reduced pressure to give 2,4-dichloro-8-phenyl-6,8-dihydro-5H-pyrano[3,4-d]pyrimidine (2.0 g, crude) as brown solid. LC-MS (M+H)+=281.0.

Preparation Na 2-chloro-N-methyl-8-phenyl-6,8-dihydro-5H-pyrano[3,4-d]pyrimidin-4-amine

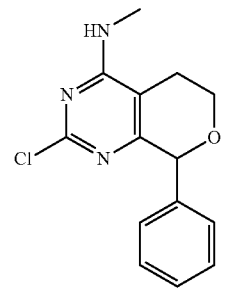 [SMILES: CNc1nc(Cl)nc2c1CCOC2c1ccccc1]

To a solution of Preparation N (2.1 g, crude) in acetonitrile was added diisopropylethylamine (1.83 g, 14.2 mmol) followed by addition of methylamine hydrochloride (0.96 g, 14.2 mmol) at room temperature. The reaction mixture was stirred at room temperature for 18 h. The solvent was removed under reduced pressure and the residue was purified by column chromatography (60-120 mesh) using 40% ethyl acetate in pet-ether as mobile phase to give 2-chloro-N-methyl-8-phenyl-6,8-dihydro-5H-pyrano[3,4-d]pyrimidin-4-amine (0.7 g, 35.7%) as off-white solid. LC-MS (M+H)+=276.0. ¹H NMR (400 MHz, DMSO-d6): δ ppm 7.49 (1H, m), 7.36-7.31 (3H, m), 7.25-7.23 (2H, m), 5.45 (1H, s), 4.0 (1H, m), 3.79 (1H, m), 2.87 (3H, d, J=4.4 Hz), 2.55 (1H, m), 2.44 (1H, m).

Preparation O 2,4-dichloro-8-(4-fluorophenyl)-6,8-dihydro-5H-pyrano[3,4-d]pyrimidine

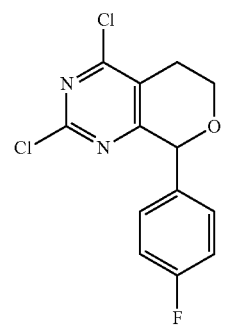 [SMILES: Fc1ccc(C2OCCc3c(Cl)nc(Cl)nc32)cc1]

Intermediate O(1)

ethyl 2-(4-fluorophenyl)-2-hydroxyacetate

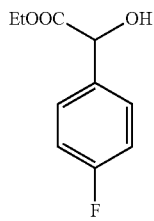

To a cooled solution of 2-(4-fluorophenyl)-2-hydroxyacetic acid (5.0 g, 29.4 mmol) in ethanol was added con. $H_2SO_4$ (10 mL) over a period of 10 min. The reaction mixture was heated at reflux for 5 h. The solvent was evaporated under reduced pressure and the residue was diluted with ethyl acetate (25 mL). The organic solution was washed with aqueous saturated $NaHCO_3$ (25 mL×2), water (20 mL), brine solution (10 mL), dried over anhydrous $Na_2SO_4$ and evaporated under reduced pressure to give ethyl 2-(4-fluorophenyl)-2-hydroxyacetate (5.0 g, 90%) as crude compound (oily liquid). The crude compound was taken to the next step without further purification. LC-MS $(M+H_2O)^+=216$. $^1$H NMR (400 MHz, DMSO-d6): δ 7.43-7.46 (2H, m), 7.17-7.20 (2H, m), 6.11-6.13 (1H, m), 5.14 (1H, d, J=5.20 Hz), 3.35-4.13 (2H, m), 1.12-1.15 (3H, m).

Intermediate O(2)

ethyl 4-(2-ethoxy-1-(4-fluorophenyl)-2-oxoethoxy)but-2-enoate

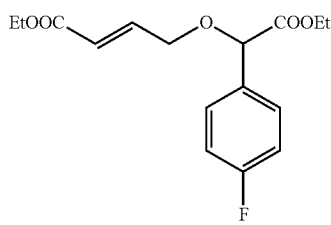 [SMILES: CCOC(=O)/C=C/COC(C(=O)OCC)c1ccc(F)cc1]

To a solution of Intermediate O(1) (3.0 g, 15.1 mmol) in hexane was added silver oxide (9.1 g, 39.3 mmol) followed by magnesium sulphate (1.8 g, 3.0 mmol) at room temperature. The reaction mixture was heated at reflux for 1 h. The reaction mixture was cooled to 0° C. and was added silver oxide (9.7 g, 39.9 mmol) followed by ethyl-4-bromochrotonate (4.3 g, 22.7 mmol). The resulting solution was stirred at room temperature for 3 days. The reaction mass was filtered through a bed of diatomaceous earth (Celite®) and washed with ethyl acetate. The filtrate was evaporated under reduced pressure to give ethyl 4-(2-ethoxy-1-(4-fluorophenyl)-2-oxoethoxy)but-2-enoate (3.0 g, 90%) as oily liquid. LC-MS $(M+H_2O)^+$=328.2. $^1$H NMR (400 MHz, CDCl$_3$): δ ppm 7.42-7.45 (2H, m), 7.04-7.26 (2H, m), 6.95 (1H, m), 6.12 (1H, m), 4.89 (1H, s), 4.13-4.28 (6H, m), 1.30 (3H, t, J=7.20 Hz), 1.26 (3H, J=6.8 Hz).

Intermediate O(3)

ethyl 4-(2-ethoxy-1-(4-fluorophenyl)-2-oxoethoxy)butanoate

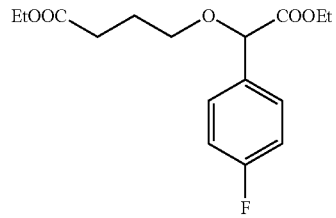 [SMILES: CCOC(=O)CCCOC(C(=O)OCC)c1ccc(F)cc1]

To a solution of Intermediate O(2) (3.0 g, 9.6 mmol) in ethanol was added palladium on carbon (10%, w/w) at room temperature. The reaction mixture was hydrogenated under balloon pressure of hydrogen for 30 h. The reaction mass was filtered through a bed of diatomaceous earth (Celite®) and washed with ethanol. The solvent was removed under reduced pressure and the residue was purified by column chromatography (Silica gel, 60-120 mesh) using 5% ethyl acetate in pet-ether as mobile phase to give ethyl 4-(2-ethoxy-1-(4-fluorophenyl)-2-oxoethoxy)butanoate (3.0 g, 63%) as oily liquid. LC-MS $(M+H)^+$=313.2 $^1$H NMR (400 MHz, CDCl$_3$): δ ppm 7.29-7.46 (2H, m), 7.05-7.09 (2H, m), 4.84 (1H, s), 4.10-4.23 (4H, m), 3.59-3.63 (1H, m), 3.42-3.53 (1H, m), 2.47 (2H, t, J=7.6 Hz), 1.99 (2H, t, J=7.6 Hz), 1.22-1.32 (6H, m).

Intermediate O(4)

ethyl 2-(4-fluorophenyl)-3-oxotetrahydro-2H-pyran-4-carboxylate

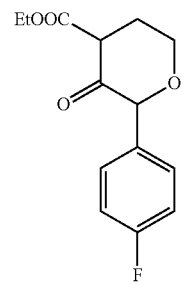

To a cooled solution of Intermediate O(3) (3.0 g, 9.6 mmol) in THF was added t-BuOK (2.1 g, 19.0 mmol) at 0° C. The reaction mixture was allowed to come to room temperature and stirred for 1 h. The reaction mixture was quenched with water and evaporated the solvent under reduced pressure. The residue was diluted with ethyl acetate (200 mL). The organic layer was washed with water (100 mL×2), brine solution (100 mL), dried over anhydrous $Na_2SO_4$ and evaporated under reduced pressure to get crude compound. The crude compound was purified by column chromatography (Silica gel, 60-120 mesh) using 50% ethyl acetate in petroleum-ether as mobile phase to give ethyl 2-(4-fluorophenyl)-3-oxotetrahydro-2H-pyran-4-carboxylate (1.0 g, 55%) as oily liquid. LC-MS $(M+H)^+$=267.1. $^1$H NMR (400 MHz, DMSO-d6): δ ppm 11.81 (1H, s), 7.22-7.42 (2H, m), 7.12-7.20 (2H, m), 5.23 (1H, s), 4.22 (2H, q, J=7.2 Hz), 3.87-3.88 (1H, m), 3.69-3.84 (1H, m), 2.34-2.35 (1H, m), 2.30-2.33 (1H, m), 1.27 (3H, t, J=7.2 Hz).

Intermediate O(5)

8-(4-fluorophenyl)-5,6-dihydro-1H-pyrano[3,4-d]pyrimidine-2,4(3H,8H)-dione

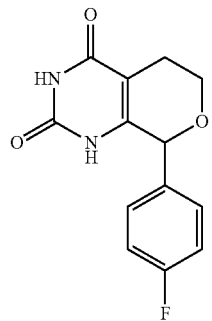 [SMILES: O=c1[nH]c2c(c(=O)[nH]1)CCOC2c1ccc(F)cc1]

To a solution of Intermediate O(4) (0.30 g, 1.12 mmol) in ethanol was added t-BuOK (0.253 g, 2.2 mmol) followed by urea (0.135 g, 2.2 mmol) at room temperature. The reaction mass was heated at reflux for 18 h. The reaction mixture was quenched with water and evaporated the solvent under reduced pressure. The residue was diluted with ethyl acetate (100 mL). The organic layer was washed with water (100 mL×2), brine solution (100 mL), dried over anhydrous $Na_2SO_4$ and evaporated under reduced pressure to get crude compound. The crude compound was purified by column chromatography (Silica gel, 60-120 mesh) using ethyl acetate as mobile phase to give 8-(4-fluorophenyl)-5,6-dihydro-1H-pyrano[3,4-d]pyrimidine-2,4(3H,8H)-dione (0.150 g, 40%) as pale yellow solid. LC-MS $(M–H)^+$=263.1. $^1$H NMR (400 MHz, DMSO-d6): δ ppm 11.14 (1H, s), 10.57 (1H, s), 7.35-7.36 (2H, m), 7.22 (2H, m), 5.34 (1H, s), 3.66-3.71 (1H, m), 3.58-3.64 (1H, m), 2.33 (2H, m).

Preparation O 2,4-dichloro-8-(4-fluorophenyl)-6,8-dihydro-5H-pyrano[3,4-d]pyrimidine

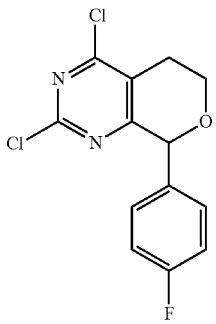 [SMILES: Fc1ccc(C2OCCc3c(Cl)nc(Cl)nc32)cc1]

A solution of Intermediate O(5) (0.30 g, 1.1 mmol) and catalytic amount of DMF in $POCl_3$ (10 vol.) was heated at reflux for 18 h. The excess of $POCl_3$ was evaporated under reduced pressure. The residue was poured in to crushed ice and stirred for 15 min. The aqueous solution was extracted with ethyl acetate (50 mL×3). The combined organic layer was washed with aqueous saturated $NaHCO_3$ (50 mL×2), brine solution (50 mL), dried over $Na_2SO_4$ and evaporated under reduced pressure to give 2,4-dichloro-8-(4-fluorophenyl)-6,8-dihydro-5H-pyrano[3,4-d]pyrimidine (0.20 g, crude) as brown liquid. LC-MS $(M+H)^+$=299.0.

Preparation Oa 2-chloro-N-ethyl-8-(4-fluorophenyl)-6,8-dihydro-5H-pyrano[3,4-d]pyrimidin-4-amine

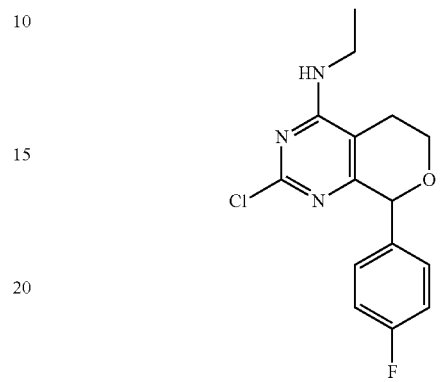

To a solution of Preparation O (0.35 g, 1.1 mmol) in methanol was added diisopropylethylamine (0.30 g, 2.2 mmol) followed by addition of ethylamine hydrochloride (0.113 g, 1.1 mmol) at room temperature. The reaction mixture was stirred at room temperature for 18 h. The solvent was removed under reduced pressure and the residue was purified by column chromatography (60-120 mesh) using 35% ethyl acetate in pet-ether as mobile phase to give 2-chloro-N-ethyl-8-(4-fluorophenyl)-6,8-dihydro-5H-pyrano[3,4-d]pyrimidin-4-amine (0.15 g, crude) as off-white solid. LC-MS $(M+H)^+$=308.2.0.

Preparation Ob 2-chloro-N-ethyl-8-(4-fluorophenyl)-N-methyl-6,8-dihydro-5H-pyrano[3,4-d]pyrimidin-4-amine

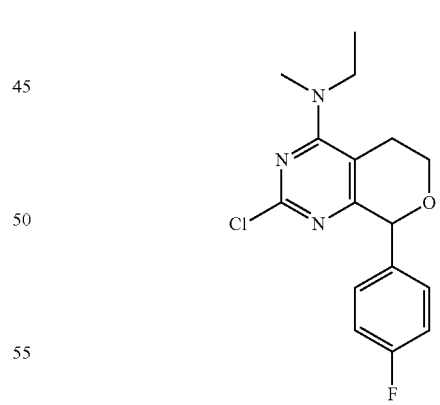

To a solution of Preparation O (0.20 g, 0.61 mmol) in methanol was added diisopropylethylamine (0.172 g, 1.3 mmol) followed by addition of ethylmethylamine hydrochloride (0.47 g, 0.81 mmol) at room temperature. The reaction mixture was stirred at room temperature for 18 h. The solvent was removed under reduced pressure and the residue was purified by column chromatography (60-120 mesh) using 40% ethyl acetate in pet-ether as mobile phase to give 2-chloro-N-ethyl-8-(4-fluorophenyl)-N-methyl-6,8-dihydro-5H-pyrano[3,4-d]pyrimidin-4-amine (0.020 g crude) as off-white solid. LC-MS (M+H)+=322.2.

Preparation Oc1 and Oc2

2-chloro-8-(4-fluorophenyl)-4-((R)-3-fluoropyrrolidin-1-yl)-6,8-dihydro-5H-pyrano[3,4-d]pyrimidine

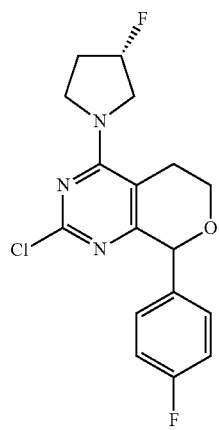

1

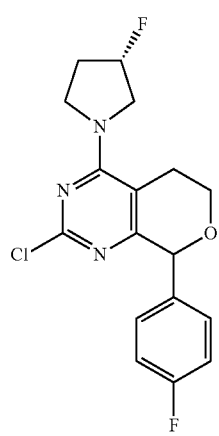

2

Preparation Od1 and Od2

2-chloro-8-(4-fluorophenyl)-4-((S)-3-fluoropyrrolidin-1-yl)-6,8-dihydro-5H-pyrano[3,4-d]pyrimidine

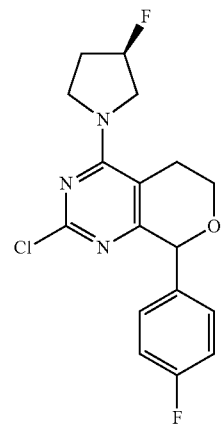

1

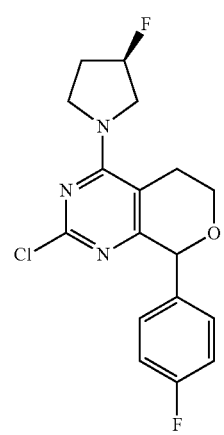

2

To a solution of Preparation O (0.60 g, 2.1 mmol) in methanol was added diisopropylethylamine (0.516 g, 4.6 mmol) followed by addition of (R)-3-fluoropyrrolidine (0.301 g, 2.2 mmol) at room temperature. The reaction mixture was stirred at room temperature for 18 h. The solvent was removed under reduced pressure and the residue was purified by pep-HPLC to give 2-chloro-8-(4-fluorophenyl)-4-((R)-3-fluoropyrrolidin-1-yl)-6,8-dihydro-5H-pyrano[3,4-d]pyrimidine (0.110 g, 40% Isomer 1, 0.109 g, 40% Isomer 2) as off-white solid. LC-MS (M+H)+=352.0.

Oc1: $^1$H NMR (400 MHz, DMSO-d6): δ ppm 7.36-7.36 (2H, m), 7.16 (2H, m), 5.50 (2H, d, J=8.40 Hz), 5.35 (1H, s), 3.58-3.98 (7H, m), 3.24-3.34 (1H, m), 2.78 (1H, m), 2.04-2.28 (2H, m).

Oc2: $^1$H NMR (400 MHz, DMSO-d6): δ ppm 7.19-7.33 (2H, m), 7.15-7.20 (2H, m), 5.34 (1H, m), 5.40 (1H, m), 3.91-4.10 (2H, m), 3.75-3.90 (2H, m), 3.69-3.75 (2H, m), 3.05 (2H, t, J=5.20 Hz), 2.01 (2H, d, J=8.0 Hz).

To a solution of Preparation O (0.60 g, 2.1 mmol) in methanol was added diisopropylethylamine (0.516 g, 4.6 mmol) followed by addition of (S)-3-fluoropyrrolidine (0.301 g, 2.2 mmol) at room temperature. The reaction mixture was stirred at room temperature for 18 h. The solvent was removed under reduced pressure and the residue was purified by pep-HPLC to give 2-chloro-8-(4-fluorophenyl)-4-((S)-3-fluoropyrrolidin-1-yl)-6,8-dihydro-5H-pyrano[3,4-d]pyrimidine (0.102 g, 39% Isomer 1, 0.111 g, 40% Isomer 2) as off-white solid. LC-MS (M+H)+=352.0.

Od1: $^1$H NMR (400 MHz, DMSO-d6): δ ppm 7.36-7.36 (2H, m), 7.16 (2H, m), 5.50 (2H, d, J=8.4 Hz), 5.35 (1H, s), 3.58-3.98 (7H, m), 3.24-3.34 (1H, m), 2.78 (1H, d, J=8.4 Hz), 2.04-2.28 (2H, m).

Od2: $^1$H NMR (400 MHz, DMSO-d6): δ ppm 7.19-7.33 (2H, m), 7.15-7.20 (2H, m), 5.34 (1H, m), 5.40 ((1H, m), 3.91-4.10 (2H, m), 3.75-3.90 (2H, m), 3.69-3.75 (m, 2H), 3.05 (2H, t, J=5.20 Hz), 2.01 (2H, d, J=8.0 Hz).

Preparation P 2,4-Dichloro-7-(4-chlorophenyl)-6,7-dihydro-5H-cyclopenta[d]pyrimidine

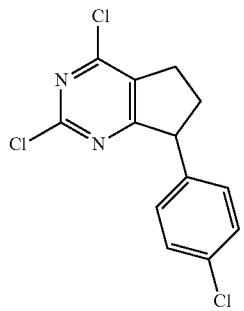 [SMILES: Clc1ccc(C2CCc3c(Cl)nc(Cl)nc32)cc1]

Intermediate P(1)

1-Chloro-4-cyclopentenylbenzene

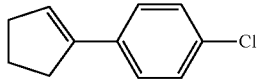 [SMILES: Clc1ccc(C2=CCCC2)cc1]

To a 1 M solution of 4-chlorophenyl)magnesium bromide (149 mL, 149 mmol) was added cyclopentanone (13.23 mL, 149 mmol). The solution turned warm upon the addition. The reaction mixture was stirred at reflux for 2 h. The reaction mixture was cooled to room temperature and quenched with 10 g of ice. 6N hydrochloric acid solution was added until the precipitate dissolved completely. Ether was added. The organic layer was separated and the aqueous phase was extracted with ether. The combined organic extracts were washed with saturated aqueous solution of sodium hydrogen sulfite, saturated aqueous solution of sodium bicarbonate and water. The organic layer was dried over anhydrous magnesium sulfate and filtered. The solvent was removed in vacuum and the residue was purified by column chromatography on silica gel to give 1-chloro-4-cyclopentenylbenzene (20.0 g, 112 mmol, 75% yield) as a colorless oil. LC-MS (M+H)$^+$=179.2. $^1$H NMR (500 MHz, CDCl$_3$) δ ppm 7.27-7.39 (4H, m), 6.19 (1H, s), 2.66-2.74 (2H, m), 2.52-2.61 (2H, m), 2.01-2.12 (2H, m).

Intermediate P(2)

2-(4-Chlorophenyl)cyclopentanone

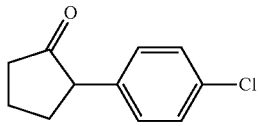 [SMILES: O=C1CCCC1c1ccc(Cl)cc1]

A mixture of formic acid (60 mL, 84 mmol) and hydrogen peroxide (15 mL, 84 mmol) was warmed at 40° C. for 10 min. The resulting solution was carefully added to 1-chloro-4-cyclopentenylbenzene (15 g, 84 mmol) under stirring. The two-phase system was initially stirred at room temperature. After a certain period of time, a spontaneous exothermic reaction took place, and the temperature rose to about 50° C. The reaction mixture was stirred at room temperature for 1 h. The LC/MS analysis of the reaction mixture shows the disappearance of the starting material and the formation of the product. The reaction mixture was quenched by careful addition of a saturated sodium bicarbonate solution. Ether was added and the reaction mixture was vigorously shaken. The organic layer was separated and the aqueous layer was extracted with ether. The combined organic extracts were dried over anhydrous magnesium sulfate and filtered. The solvent was removed in vacuum and the residue was purified by column chromatography on silica gel to give 2-(4-chlorophenyl)cyclopentanone (5.7 g, 29.3 mmol, 34.9% yield) as a colorless oil. LC-MS (M+H)$^+$=195.2. $^1$H NMR (500 MHz, CDCl$_3$) δ ppm 7.21-7.37 (2H, m), 7.11 (2H, d, J=8.5 Hz), 3.25 (1H, dd, J=11.6, 8.5 Hz), 2.44 (2H, d, J=6.1 Hz), 2.15-2.31 (1H, m), 1.96-2.15 (3H, m), 1.78-1.95 (1H, m).

Intermediate P(3)

7-(4-Chlorophenyl)-6,7-dihydrocyclopenta[e][1,3]oxazine-2,4(3H,5H)-dione

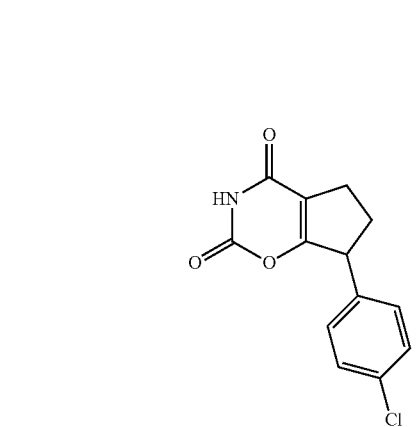 [SMILES: O=c1[nH]c(=O)c2c(o1)C(c1ccc(Cl)cc1)CC2]

A solution of 2-(4-chlorophenyl)cyclopentanone (7.80 g, 40.1 mmol) and carbonisocyanatidic chloride (7.61 g, 72.1 mmol) was stirred at 58° C. in a high-pressure vessel for 1 h. The temperature was raised to 130° C. and the reaction mixture was stirred for an additional 2 h. After cooling to rt, the reaction mixture solidified. The solid residue was dissolved in ethyl acetate and washed with saturated aqueous solution of sodium bicarbonate. The organic layer was separated and the aqueous layer was extracted twice with ethyl acetate. The combined organic extracts were dried over anhydrous sodium sulfate and filtered. The solvent was removed in vacuum and the oily residue was purified by column chromatography on silica gel to provide 7-(4-chlorophenyl)-6,7-dihydrocyclopenta[e][1,3]oxazine-2,4(3H,5H)-dione (5.4 g, 20.48 mmol, 51.1% yield). LC-MS (M+H)$^+$=264.2. $^1$H NMR (500 MHz, CDCl$_3$) δ ppm 7.32 (2H, d, J=8.5 Hz), 7.12 (2H, d, J=8.5 Hz), 4.15-4.25 (1H, m), 2.56-2.93 (4H, m).

Intermediate P(4)

7-(4-Chlorophenyl)-6,7-dihydro-1H-cyclopenta[d]pyrimidine-2,4(3H,5H)-dione

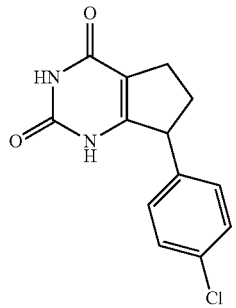 [SMILES: O=c1[nH]c2c(c(=O)[nH]1)CCC2c1ccc(Cl)cc1]

A solution of 7-(4-chlorophenyl)-6,7-dihydrocyclopenta[e][1,3]oxazine-2,4(3H,5H)-dione (5.4 g, 20.48 mmol) in concentrated ammonium hydroxide (59.8 mL, 1536 mmol) was stirred at 100° C. in a high-pressure vessel for 6 h. The formation of white precipitate was observed during the heating. The solvent was removed in vacuum to provide 7-(4-chlorophenyl)-6,7-dihydro-1H-cyclopenta[d]pyrimidine-2,4(3H,5H)-dione (4.9 g, 18.65 mmol, 91% yield) as a off-white solid. LC-MS (M+H)$^+$=263.2. $^1$H NMR (500 MHz, DMSO-d6) δ ppm 7.37 (2H, d, J=8.2 Hz), 7.19 (1H, d, J=8.5 Hz), 4.16 (1H, d, J=5.2 Hz), 3.79 (1H, br s), 3.17 (1H, s), 2.51 (2H, d, J=1.8 Hz), 1.75-1.85 (1H, m).

Preparation P 2,4-Dichloro-7-(4-chlorophenyl)-6,7-dihydro-5H-cyclopenta[d]pyrimidine

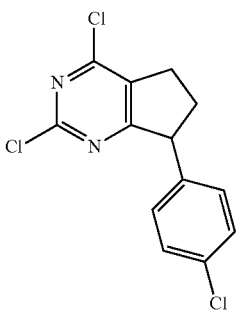 [SMILES: Clc1ccc(C2CCc3c(Cl)nc(Cl)nc32)cc1]

A mixture of 7-(4-chlorophenyl)-6,7-dihydro-1H-cyclopenta[d]pyrimidine-2,4(3H,5H)-dione (4.7 g, 17.89 mmol), POCl$_3$ (53.4 mL, 573 mmol) and N,N-dimethylaniline (18.26 mL, 143 mmol) was heated at 110° C. overnight. The reaction mixture was poured into a beaker with ice. The inside walls of the reaction vessel was washed with DCM. As soon as the ice completely melted, the organic layer was separated and the aqueous layer was extracted with DCM. The combined organic extracts were dried over anhydrous sodium sulfate and filtered. The solvent was removed in vacuum and the residue was purified by column chromatography on silica gel to provide 2,4-dichloro-7-(4-chlorophenyl)-6,7-dihydro-5H-cyclopenta[d]pyrimidine (1.2 g, 4.01 mmol, 22.39% yield). LC-MS (M+H)$^+$=299.0. $^1$H NMR (500 MHz, CDCl$_3$) δ ppm 7.41-7.99 (2H, m), 7.09 (2H, d, J=8.5 Hz), 4.41 (1H, t, J=8.4 Hz), 2.94-3.18 (2H, m), 2.73 (1H, dt, J=8.9, 4.5 Hz), 2.15-2.33 (1H, m).

Preparation Pa

2-Chloro-7-(4-chlorophenyl)-N,N-dimethyl-6,7-dihydro-5H-cyclopenta[d]pyrimidin-4-amine

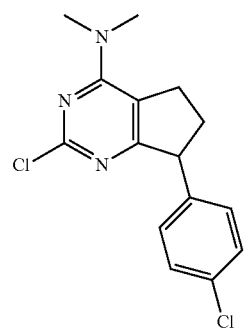 [SMILES: CN(C)c1nc(Cl)nc2c1CCC2c1ccc(Cl)cc1]

A solution of 2,4-dichloro-7-(4-chlorophenyl)-6,7-dihydro-5H-cyclopenta[d]pyrimidine (200 mg, 0.668 mmol) and excess dimethylamine (3.34 mL, 6.68 mmol) in MeOH (4 mL) was stirred at rt for 30 min. The solvent was removed in vacuum and the crude product was purified by column chromatography on silica gel to afford 2-chloro-7-(4-chlorophenyl)-N,N-dimethyl-6,7-dihydro-5H-cyclopenta[d]pyrimidin-4-amine (98 mg, 0.318 mmol, 47.6% yield). LC-MS (M+H)$^+$=308.1.

Preparation Pb

2-Chloro-7-(4-chlorophenyl)-4-(3,3-difluoroazetidin-1-yl)-6,7-dihydro-5H-cyclopenta[d]pyrimidine

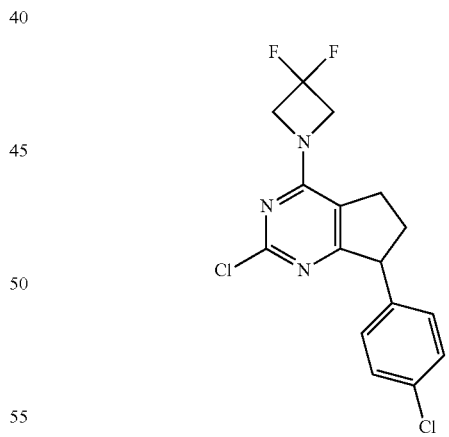

A solution of 2,4-dichloro-7-(4-chlorophenyl)-6,7-dihydro-5H-cyclopenta[d]pyrimidine (325 mg, 1.085 mmol), N-ethyl-N-isopropylpropan-2-amine (0.945 mL, 5.42 mmol) and 3,3-difluoroazetidine, HCl salt (281 mg, 2.170 mmol) in MeOH (5 mL) was stirred at rt for 1 h. The solvent was removed in vacuum and the crude product was purified by column chromatography on silica gel to afford 2-chloro-7-(4-chlorophenyl)-4-(3,3-difluoroazetidin-1-yl)-6,7-dihydro-5H-cyclopenta[d]pyrimidine (70 mg, 0.197 mmol, 18.12% yield). LC-MS (M+H)$^+$=356.1.

Preparation Pc

2-Chloro-7-(4-chlorophenyl)-N-methyl-6,7-dihydro-5H-cyclopenta[d]pyrimidin-4-amine

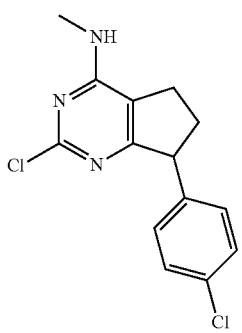 [SMILES: CNc1nc(Cl)nc2c1CCC2c1ccc(Cl)cc1]

A solution of 2,4-dichloro-7-(4-chlorophenyl)-6,7-dihydro-5H-cyclopenta[d]pyrimidine (300 mg, 1.001 mmol), methanamine, HCl salt (135 mg, 2.003 mmol) and DIPEA (0.700 mL, 4.01 mmol) in MeOH (6 mL) was stirred at rt for 30 min. The solvent was removed in vacuum and the crude product was purified by column chromatography on silica gel to afford 2-chloro-7-(4-chlorophenyl)-N-methyl-6,7-dihydro-5H-cyclopenta[d]pyrimidin-4-amine (101 mg, 0.343 mmol, 34.3% yield). LC-MS (M+H)+=294.2.

Preparation Q 2,4-Dichloro-7-(3,4-difluorophenyl)-6,7-dihydro-5H-cyclopenta[d]pyrimidine

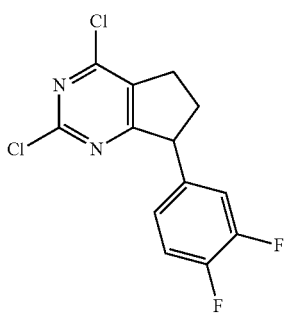 [SMILES: Fc1ccc(C2CCc3c(Cl)nc(Cl)nc32)cc1F]

Intermediate Q(1)

7-(3,4-Difluorophenyl)-6,7-dihydrocyclopenta[e][1,3]oxazine-2,4(3H,5H)-dione

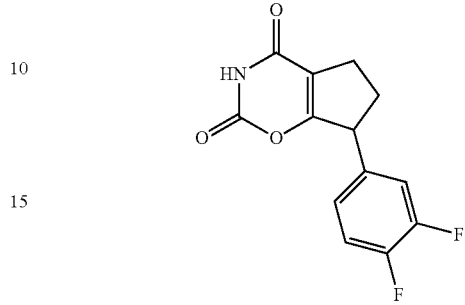

A solution of 2-(3,4-difluorophenyl)cyclopentanone, (prepared in the manner of Intermediate P(1) and P(2)) (1.5 g, 7.65 mmol) and carbonisocyanatidic chloride (1.129 g, 10.70 mmol) was stirred at 58° C. in a high-pressure vessel for 1 h. The temperature was raised to 130° C. and the reaction mixture was stirred for an additional 2 h. After cooling to rt, the reaction mixture solidified. The solid residue was dissolved in ethyl acetate and washed with saturated aqueous solution of sodium bicarbonate. The organic layer was separated and the aqueous layer was extracted twice with ethyl acetate. The combined organic extracts were dried over anhydrous sodium sulfate and filtered. The solvent was removed in vacuum and the oily residue was purified by column chromatography on silica gel to provide 7-(3,4-difluorophenyl)-6,7-dihydrocyclopenta[e][1,3]oxazine-2,4(3H,5H)-dione (1.05 g, 3.96 mmol, 51.8% yield) as a white solid.

$^1$H NMR (500 MHz, CDCl$_3$) δ ppm 8.16 (1H, br s), 7.15 (1H, dt, J=10.0, 8.3 Hz), 6.97-7.05 (1H, m), 6.88-6.95 (1H, m), 2.80-2.90 (1H, m), 2.61-2.78 (2H, m), 0.78-0.86 (2H, m).

Intermediate Q(2)

7-(3,4-Difluorophenyl)-6,7-dihydro-1H-cyclopenta[d]pyrimidine-2,4(3H,5H)-dione

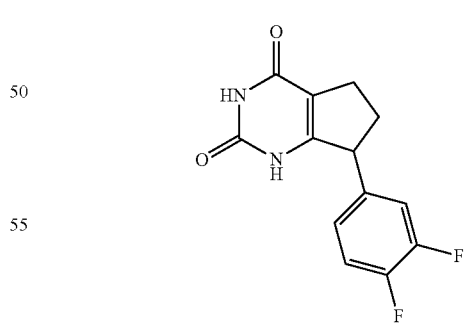

A solution of 7-(3,4-difluorophenyl)-6,7-dihydrocyclopenta[e][1,3]oxazine-2,4(3H,5H)-dione (1.05 g, 3.96 mmol) in concentrated ammonium hydroxide (0.154 mL, 3.96 mmol) was stirred at 100° C. in a high-pressure vessel (75 mL) for 6 h. The formation of white precipitate was observed during the heating. The solvent was removed in vacuum to provide 7-(3,4-difluorophenyl)-6,7-dihydro-1H-cyclopenta

[d]pyrimidine-2,4(3H,5H)-dione (1.046 g, 3.96 mmol, 100% yield) as a off-white solid. LC-MS (M+H)⁺=265.2.

Preparation Q 2,4-Dichloro-7-(3,4-difluorophenyl)-6,7-dihydro-5H-cyclopenta[d]pyrimidine

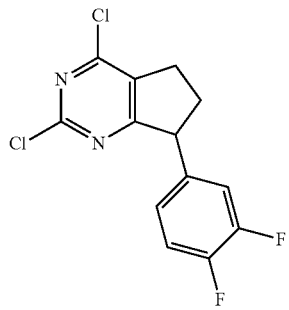 [SMILES: Fc1ccc(C2CCc3c(Cl)nc(Cl)nc32)cc1F]

A mixture of 7-(3,4-difluorophenyl)-6,7-dihydro-1H-cyclopenta[d]pyrimidine-2,4(3H,5H)-dione (500 mg, 1.892 mmol), POCl₃ (5644 μL, 60.6 mmol) and N,N-dimethylaniline (1931 μL, 15.14 mmol) was heated at 120° C. overnight. The reaction mixture was poured into a beaker with ice. The inside walls of the reaction vessel was washed with DCM. As soon as the ice completely melted, the content of the beaker was placed into a separatory funnel. The organic layer was separated and the aqueous layer was extracted with DCM. The combined organic extracts were dried over anhydrous sodium sulfate and filtered. The solvent was removed in vacuum and the residue was purified by column chromatography on silica gel to provide 2,4-dichloro-7-(3,4-difluorophenyl)-6,7-dihydro-5H-cyclopenta[d]pyrimidine (446 mg, 1.481 mmol, 78% yield). LC-MS (M+H)⁺=301.1.

Preparation Qa

2-Chloro-7-(3,4-difluorophenyl)-N,N-dimethyl-6,7-dihydro-5H-cyclopenta[d]pyrimidin-4-amine

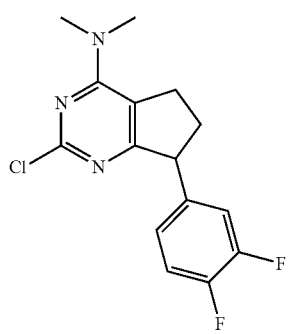 [SMILES: CN(C)c1nc(Cl)nc2c1CCC2c1ccc(F)c(F)c1]

A solution of 2,4-dichloro-7-(3,4-difluorophenyl)-6,7-dihydro-5H-cyclopenta[d]pyrimidine (446 mg, 1.481 mmol) and excess dimethylamine (2.222 mL, 4.44 mmol) in MeOH (6 mL) was stirred at rt for 30 min. The solvent was removed in vacuum and the crude product was purified by column chromatography on silica gel to afford 2-chloro-7-(3,4-difluorophenyl)-N,N-dimethyl-6,7-dihydro-5H-cyclopenta[d]pyrimidin-4-amine (146 mg, 0.471 mmol, 31.8% yield). LC-MS (M+H)⁺=310.2.

Preparation Qb

2-Chloro-7-(3,4-difluorophenyl)-N-methyl-6,7-dihydro-5H-cyclopenta[d]pyrimidin-4-amine

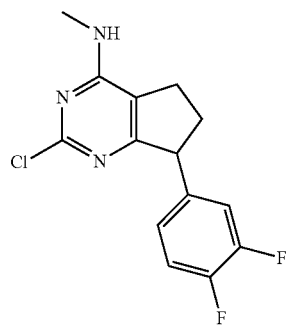 [SMILES: CNc1nc(Cl)nc2c1CCC2c1ccc(F)c(F)c1]

A solution of 2,4-dichloro-7-(3,4-difluorophenyl)-6,7-dihydro-5H-cyclopenta[d]pyrimidine (421 mg, 1.398 mmol), methanamine, HCl (283 mg, 4.19 mmol) and DIPEA (1.465 mL, 8.39 mmol) in methanol (10 mL) was stirred at rt for 1 h. The solvent was removed in vacuum and the crude product was purified by column chromatography on silica gel to afford 2-chloro-7-(3,4-difluorophenyl)-N-methyl-6,7-dihydro-5H-cyclopenta[d]pyrimidin-4-amine (154 mg, 0.521 mmol, 37.2% yield). LC-MS (M+H)⁺=296.2.

Preparation R 2,4-dichloro-7-(4-(trifluoromethoxy)phenyl)-6,7-dihydro-5H-cyclopenta[d]pyrimidine

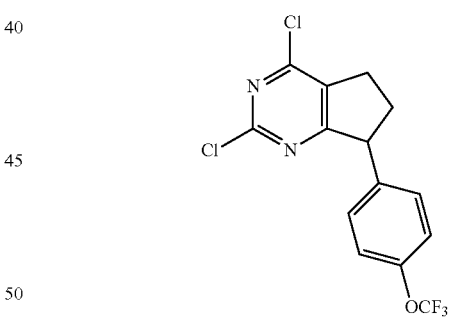

Intermediate R(1)

1-cyclopentenyl-4-(trifluoromethoxy)benzene

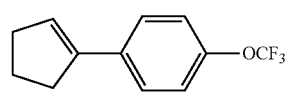

(4-(trifluoromethoxy)phenyl)magnesium bromide was reacted in the manner of Intermediate P(1) to give 1-cyclopentenyl-4-(trifluoromethoxy)benzene.

Intermediate R(2)

2-(4-(trifluoromethoxy)phenyl)cyclopentanone

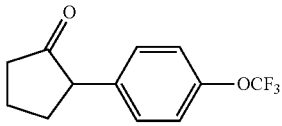 [SMILES: O=C1CCCC1c1ccc(OC(F)(F)F)cc1]

1-cyclopentenyl-4-(trifluoromethoxy)benzene was reacted in the manner of Intermediate P(2) to give 2-(4-(trifluoromethoxy)phenyl)cyclopentanone.

Intermediate R(3)

7-(4-(trifluoromethoxy)phenyl)-6,7-dihydrocyclopenta[e][1,3]oxazine-2,4(3H,5H)-dione

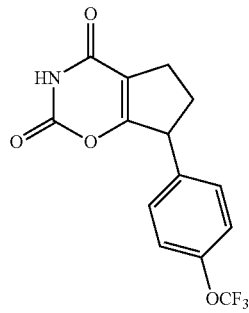 [SMILES: O=c1[nH]c(=O)c2c(o1)C(c1ccc(OC(F)(F)F)cc1)CC2]

2-(4-(trifluoromethoxy)phenyl)cyclopentanone was reacted in the manner of Intermediate P(3) to provide 7-(4-(trifluoromethoxy)phenyl)-6,7-dihydrocyclopenta[e][1,3]oxazine-2,4(3H,5H)-dione.

Intermediate R(4)

7-(4-(trifluoromethoxy)phenyl)-6,7-dihydro-1H-cyclopenta[d]pyrimidine-2,4(3H,5H)-dione

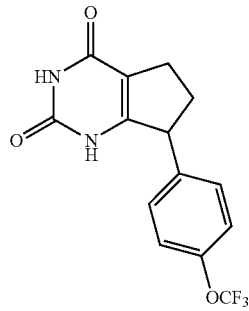 [SMILES: O=c1[nH]c2c(c(=O)[nH]1)CCC2c1ccc(OC(F)(F)F)cc1]

7-(4-(trifluoromethoxy)phenyl)-6,7-dihydrocyclopenta[e][1,3]oxazine-2,4(3H,5H)-dione was reacted in the manner of Intermediate P(4) to provide 7-(4-(trifluoromethoxy)phenyl)-6,7-dihydro-1H-cyclopenta[d]pyrimidine-2,4(3H,5H)-dione.

Preparation R 2,4-dichloro-7-(4-(trifluoromethoxy)phenyl)-6,7-dihydro-5H-cyclopenta[d]pyrimidine

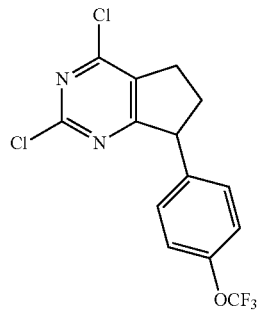 [SMILES: FC(F)(F)Oc1ccc(C2CCc3c(Cl)nc(Cl)nc32)cc1]

7-(4-(trifluoromethoxy)phenyl)-6,7-dihydro-1H-cyclopenta[d]pyrimidine-2,4(3H,5H)-dione was reacted in the manner of Preparation P to provide 2,4-dichloro-7-(4-(trifluoromethoxy)phenyl)-6,7-dihydro-5H-cyclopenta[d]pyrimidine as a pink solid. LC-MS (M+H)$^+$=349.2. $^1$H NMR (500 MHz, CD3OD) δ ppm 7.31 (2H, dd, J=2.0, 7.7 Hz), 7.25 (2H, d, J=7.4 Hz), 4.56 (1H, t, J=8.8 Hz), 3.15 (1H, ddd, J=3.8, 9.1, 16.9 Hz), 3.09-3.00 (1H, m), 2.81-2.72 (1H, m), 2.27-2.22 (1H, m).

Preparation Ra

2-Chloro-N-methyl-7-(4-(trifluoromethoxy)phenyl)-6,7-dihydro-5H-cyclopenta[d]pyrimidin-4-amine

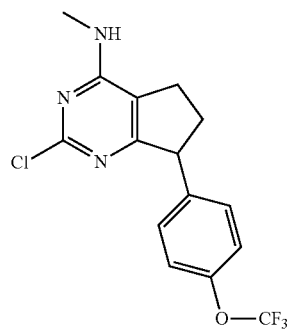 [SMILES: CNc1nc(Cl)nc2c1CCC2c1ccc(OC(F)(F)F)cc1]

A solution of 2,4-dichloro-7-(4-(trifluoromethoxy)phenyl)-6,7-dihydro-5H-cyclopenta[d]pyrimidine (200 mg, 0.573 mmol), and methanamine (0.286 mL, 0.573 mmol) in MeOH (5 mL) was stirred at rt for 1 h. The solvent was removed in vacuum to afford crude 2-chloro-N-methyl-7-(4-(trifluoromethoxy)phenyl)-6,7-dihydro-5H-cyclopenta[d]pyrimidin-4-amine (220 mg, 0.640 mmol, 112% yield). LC-MS (M+H)$^+$=343.9.

Preparation Rb

2-Chloro-N-ethyl-7-(4-(trifluoromethoxy)phenyl)-6,7-dihydro-5H-cyclopenta[d]pyrimidin-4-amine

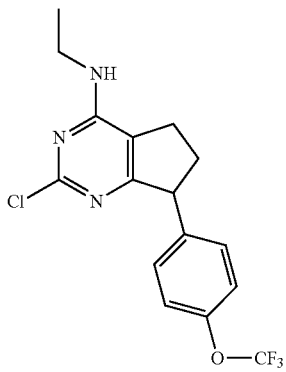 [SMILES: CCNc1nc(Cl)nc2c1CCC2c1ccc(OC(F)(F)F)cc1]

A solution of 2,4-dichloro-7-(4-(trifluoromethoxy)phenyl)-6,7-dihydro-5H-cyclopenta[d]pyrimidine (200 mg, 0.573 mmol), and ethanamine (0.286 mL, 0.573 mmol) in MeOH (2 mL) was stirred at rt for 1 h. The solvent was removed in vacuum and the crude product was purified by column chromatography on silica gel to afford 2-chloro-N-ethyl-7-(4-(trifluoromethoxy)phenyl)-6,7-dihydro-5H-cyclopenta[d]pyrimidin-4-amine (190 mg, 0.531 mmol, 93% yield). LC-MS $(M+H)^+=358.2$.

Preparation Rc

2-Chloro-4-(3,3-difluoroazetidin-1-yl)-7-(4-(trifluoromethoxy)phenyl)-6,7-dihydro-5H-cyclopenta[d]pyrimidine

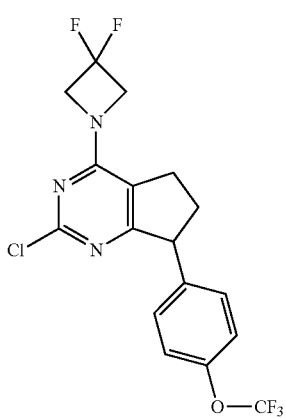 [SMILES: FC1(F)CN(c2nc(Cl)nc3c2CCC3c2ccc(OC(F)(F)F)cc2)C1]

A solution of 2,4-dichloro-7-(4-(trifluoromethoxy)phenyl)-6,7-dihydro-5H-cyclopenta[d]pyrimidine (250 mg, 0.716 mmol), 3,3-difluoroazetidine, HCl salt (186 mg, 1.432 mmol) and DIPEA (0.500 mL, 2.86 mmol) in MeOH (3 mL) was stirred at rt for 1.5 h. The solvent was removed in vacuum and the crude product was purified by column chromatography on silica gel to afford 2-chloro-4-(3,3-difluoroazetidin-1-yl)-7-(4-(trifluoromethoxy)phenyl)-6,7-dihydro-5H-cyclopenta[d]pyrimidine (244 mg, 0.601 mmol, 84% yield). LC-MS $(M+H)^+=406.0$.

Preparation Rd

2-Chloro-N,N-dimethyl-7-(4-(trifluoromethoxy)phenyl)-6,7-dihydro-5H-cyclopenta[d]pyrimidin-4-amine

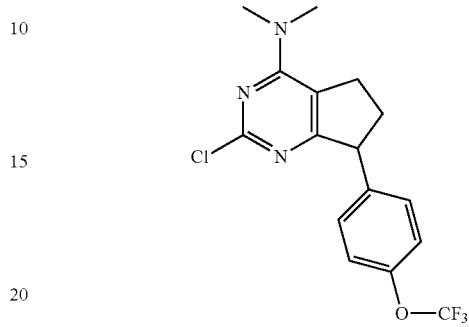

A solution of 2,4-dichloro-7-(4-(trifluoromethoxy)phenyl)-6,7-dihydro-5H-cyclopenta[d]pyrimidine (250 mg, 0.716 mmol) and dimethylamine (0.716 mL, 1.432 mmol) in MeOH (2 mL) was stirred at rt for 1 h. The solvent was removed in vacuum and the crude product was purified by column chromatography on silica gel to afford 2-chloro-N,N-dimethyl-7-(4-(trifluoromethoxy)phenyl)-6,7-dihydro-5H-cyclopenta[d]pyrimidin-4-amine (250 mg, 0.699 mmol, 98% yield). LC-MS $(M+H)^+=358.0$.

Preparation Re 4-(Azetidin-1-yl)-2-chloro-7-(4-(trifluoromethoxy)phenyl)-6,7-dihydro-5H-cyclopenta[d]pyrimidine

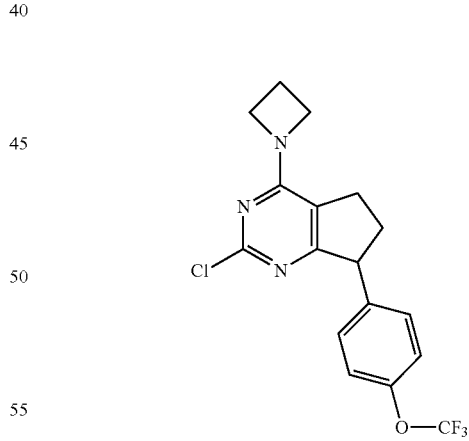

A solution of 2,4-dichloro-7-(4-(trifluoromethoxy)phenyl)-6,7-dihydro-5H-cyclopenta[d]pyrimidine (250 mg, 0.716 mmol) and azetidine (82 mg, 1.432 mmol) in MeOH (3 mL) was stirred at rt for 1 h. The solvent was removed in vacuum and the crude product was purified by column chromatography on silica gel to afford 4-(azetidin-1-yl)-2-chloro-7-(4-(trifluoromethoxy)phenyl)-6,7-dihydro-5H-cyclopenta[d]pyrimidine (238 mg, 0.644 mmol, 90% yield). LC-MS $(M+H)^+=371.2$.

Preparation S 2,4-Dichloro-7-(3,5-difluorophenyl)-6,7-dihydro-5H-cyclopenta[d]pyrimidine

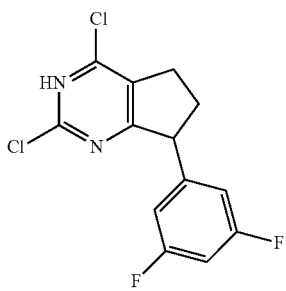 [SMILES: Fc1cc(F)cc(C2CCc3c(Cl)nc(Cl)nc32)c1]

Intermediate S(1)

(1S,2R)-2-(3,5-Difluorophenyl)cyclopentanol

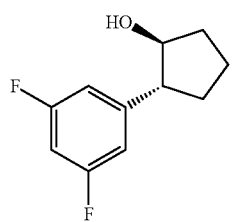

A flask was charged with (3,5-difluorophenyl)magnesium bromide (149 mL, 149 mmol) and copper (I) iodide (1.901 g, 9.98 mmol). To this reaction mixture, 6-oxabicyclo[3.1.0]hexane (12.53 g, 149 mmol) dissolved in THF (25 mL) was added dropwise. The reaction mixture warmed upon the addition of the epoxide. The reaction was stirred at rt for 2 h at rt. The reaction mixture was quenched by the addition of a solution of ammonium chloride. Ether was added and the organic layer was collected, dried ($Na_2SO_4$) and concentrated. The crude product was purified by column chromatography on silica gel to afford (1S,2R)-2-(3,5-difluorophenyl)cyclopentanol (26.5 g, 134 mmol, 90% yield).

$^1$H NMR (500 MHz, $CDCl_3$) δ ppm 6.72 (2H, dd, J=8.7, 2.0 Hz), 6.50-6.63 (1H, m), 2.97 (1H, br s), 2.78 (1H, d, J=10.1 Hz), 1.96-2.15 (2H, m), 1.66-1.85 (2H, m), 1.53-1.65 (2H, m).

Intermediate S(2)

2-(3,5-Difluorophenyl)cyclopentanone

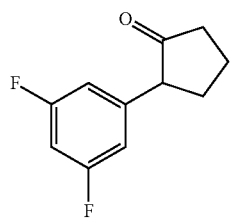 [SMILES: O=C1CCCC1c1cc(F)cc(F)c1]

To a solution of (1S,2R)-2-(3,5-difluorophenyl)cyclopentanol (6 g, 30.3 mmol) in $CH_2Cl_2$ (150 mL) was added Dess-Martin periodinane (15.41 g, 36.3 mmol). The reaction mixture was stirred at rt for 3 h. The reaction mixture was diluted with dichloromethane and quenched with the addition of 1 N NaOH. The organic layer was collected, dried ($Na_2SO_4$) and concentrated. The crude product was purified by column chromatography on silica gel to afford 2-(3,5-difluorophenyl)cyclopentanone (4.765 g, 24.29 mmol, 80% yield). LC-MS $(M+H)^+$=197.0. $^1$H NMR (500 MHz, $CDCl_3$) δ ppm 6.70 (2H, d, J=6.7 Hz), 6.52-6.67 (1H, m), 3.17-3.33 (1H, m), 2.33-2.56 (2H, m), 2.06-2.26 (2H, m), 2.01 (1H, dd, J=11.7, 6.3 Hz), 1.89 (1H, br s).

Intermediate S(3)

7-(3,5-difluorophenyl)-6,7-dihydrocyclopenta[e][1,3]oxazine-2,4(3H,5H)-dione

A mixture of 2-(3,5-difluorophenyl)cyclopentanone (4.765 g, 24.29 mmol) and carbonisocyanatidic chloride (4.61 g, 43.7 mmol) was heated at 58° C. for 1 h and at 130° C. for 2 h. Upon cooling to room temperature, the reaction mixture was dissolved in ethyl acetate and washed with saturated aqueous solution of sodium bicarbonate. The organic layer was separated and the aqueous layer was extracted with ethyl acetate. The combined organic extracts were dried over anhydrous magnesium sulfate and filtered. The solvent was removed in vacuum and the residue was purified by column chromatography on silica gel to give 7-(3,5-difluorophenyl)-6,7-dihydrocyclopenta[e][1,3]oxazine-2,4(3H,5H)-dione (700 mg, 2.64 mmol, 10.87% yield). LC-MS $(M+H)^+$=266.1. $^1$H NMR (500 MHz, $CDCl_3$) δ ppm 8.79 (1H, br s), 6.68-6.86 (3H, m), 4.22 (1H, br s), 2.87 (1H, dt, J=7.0, 4.4 Hz), 2.63-2.82 (2H, m), 2.15 (1H, br s).

Intermediate S(4)

7-(3,5-Difluorophenyl)-6,7-dihydro-1H-cyclopenta[d]pyrimidine-2,4(3H,5H)-dione

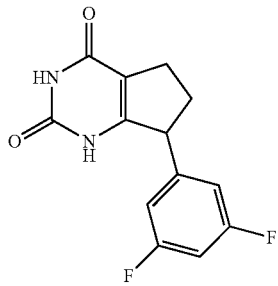 [SMILES: O=c1[nH]c2c(c(=O)[nH]1)CCC2c1cc(F)cc(F)c1]

A solution of 7-(3,5-difluorophenyl)-6,7-dihydrocyclopenta[e][1,3]oxazine-2,4(3H,5H)-dione (700 mg, 2.64 mmol) in concentrated ammonium hydroxide (50 mL, 1284 mmol) was heated at 100° C. in a high-pressure (350 mL) vessel overnight. The reaction mixture was cooled and concentrated in vacuum to give crude 7-(3,5-difluorophenyl)-6,7-dihydro-1H-cyclopenta[d]pyrimidine-2,4(3H,5H)-dione (740 mg, 2.80 mmol, 106% yield). LC-MS $(M+H)^+=265.0$.

Preparation S 2,4-Dichloro-7-(3,5-difluorophenyl)-6,7-dihydro-5H-cyclopenta[d]pyrimidine

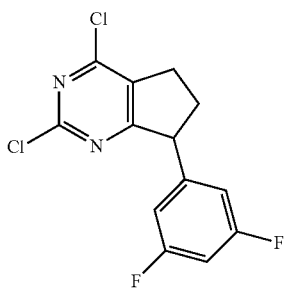 [SMILES: Fc1cc(F)cc(C2CCc3c(Cl)nc(Cl)nc32)c1]

A solution of 7-(3,5-difluorophenyl)-6,7-dihydro-1H-cyclopenta[d]pyrimidine-2,4(3H,5H)-dione (740 mg, 2.80 mmol) in phosphoryl trichloride (7.691 mL, 84 mmol) was heated in microwave at 110° C. for 1 h. The reaction mixture was poured into ice. Once ice melted, the product was extracted with dichloromethane. The combined organic extracts were dried over anhydrous magnesium sulfate and filtered. The solvent was removed in vacuum and the residue was purified by column chromatography on silica gel to give 2,4-dichloro-7-(3,5-difluorophenyl)-6,7-dihydro-5H-cyclopenta[d]pyrimidine (200 mg, 0.664 mmol, 23.72% yield). LC-MS $(M+H)^+=301.0$.

Preparation Sa

2-Chloro-7-(3,5-difluorophenyl)-N-methyl-6,7-dihydro-5H-cyclopenta[d]pyrimidin-4-amine

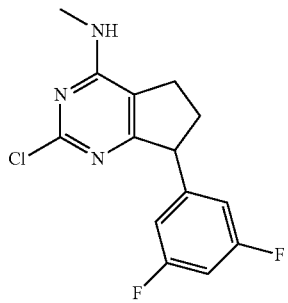 [SMILES: CNc1nc(Cl)nc2c1CCC2c1cc(F)cc(F)c1]

A solution of 2,4-dichloro-7-(3,5-difluorophenyl)-6,7-dihydro-5H-cyclopenta[d]pyrimidine (200 mg, 0.664 mmol) and methanamine (0.664 mL, 1.328 mmol) in MeOH (3 mL) was stirred at rt for 1 h. The solvent was removed in vacuum and the crude product was purified by column chromatography on silica gel to give 2-chloro-7-(3,5-difluorophenyl)-N-methyl-6,7-dihydro-5H-cyclopenta[d]pyrimidin-4-amine (60 mg, 0.203 mmol, 30.5% yield). LC-MS $(M+H)^+=296.1$.

Preparation T 2,4-Dichloro-7-(3,4,5-trifluorophenyl)-6,7-dihydro-5H-cyclopenta[d]pyrimidine

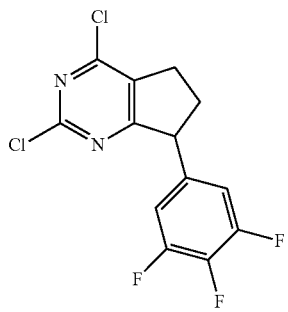 [SMILES: Fc1cc(C2CCc3c(Cl)nc(Cl)nc32)cc(F)c1F]

Intermediate T(1)

(1S,2R)-2-(3,4,5-Trifluorophenyl)cyclopentanol

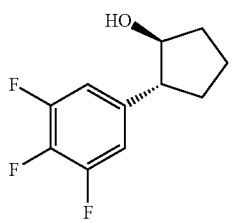 [SMILES: O[C@H]1CCC[C@@H]1c1cc(F)c(F)c(F)c1]

To a suspension of magnesium (2.88 g, 118 mmol) in THF (110 mL) was slowly added 5-bromo-1,2,3-trifluorobenzene (25 g, 118 mmol). After the addition, the reaction mixture was heated at reflux for 2 h. To this reaction mixture, copper (I)

iodide (1.506 g, 7.91 mmol) and 6-oxabicyclo[3.1.0]hexane (9.93 g, 118 mmol) dissolved in THF (20 mL) were added dropwise. The reaction mixture warmed upon the addition of the epoxide. The reaction was stirred at rt for 2 h at rt. The reaction mixture was quenched by the addition of a solution of ammonium chloride. Ether was added and the organic layer was collected, dried (Na$_2$SO$_4$) and concentrated. The crude product was purified by column chromatography on silica gel to give (1S,2R)-2-(3,4,5-trifluorophenyl)cyclopentanol (20.2 g, 93 mmol, 79% yield).

$^1$H NMR (500 MHz, CDCl$_3$) δ ppm 6.79-7.02 (2H, m), 4.10-4.21 (1H, m), 2.75-2.91 (1H, m), 2.08-2.24 (2H, m), 1.75-1.93 (2H, m), 1.50-1.75 (2H, m).

Intermediate T(2)

2-(3,4,5-Trifluorophenyl)cyclopentanone

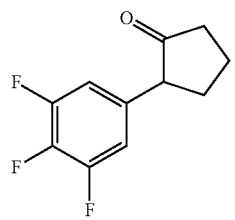

To a solution of (1S,2R)-2-(3,4,5-trifluorophenyl)cyclopentanol (1 g, 4.63 mmol) in CH$_2$Cl$_2$ (20 mL) was added Dess-Martin periodinane (2.354 g, 5.55 mmol). The reaction mixture was stirred at rt for 1 h. The reaction was diluted with dichloromethane and quenched with the addition of 1 N NaOH. The organic layer was collected, dried (Na$_2$SO$_4$) and concentrated. The crude product was purified by column chromatography on silica gel to afford 2-(3,4,5-trifluorophenyl)cyclopentanone (310 mg, 1.447 mmol, 31.3% yield). LC-MS (M+H)$^+$=215.1.

Intermediate T(3)

7-(3,4,5-Trifluorophenyl)-6,7-dihydrocyclopenta[e][1,3]oxazine-2,4(3H,5H)-dione

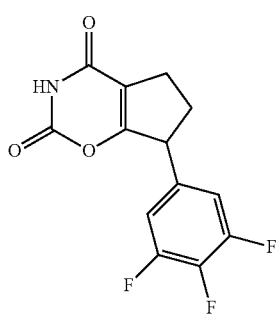

A mixture of 2-(3,4,5-trifluorophenyl)cyclopentanone (2 g, 9.34 mmol) and carbonisocyanatidic chloride (1.773 g, 16.81 mmol) was heated at 58° C. for 1 h and at 130° C. for 2 h. Upon cooling to room temperature, the reaction mixture was dissolved in ethyl acetate and washed with saturated aqueous solution of sodium bicarbonate. The organic layer was separated and the aqueous layer was extracted with ethyl acetate. The combined organic extracts were dried over anhydrous magnesium sulfate and filtered. The solvent was removed in vacuum and the residue was purified by column chromatography on silica gel to give 7-(3,4,5-trifluorophenyl)-6,7-dihydrocyclopenta[e][1,3]oxazine-2,4(3H,5H)-dione (1.227 g, 4.33 mmol, 46.4% yield). LC-MS (M+H)$^+$=284.0.

Intermediate T(4)

7-(3,4,5-Trifluorophenyl)-6,7-dihydro-1H-cyclopenta[d]pyrimidine-2,4(3H,5H)-dione

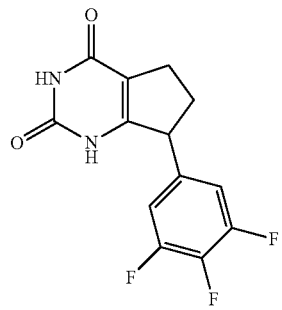 [SMILES: O=c1[nH]c2c(c(=O)[nH]1)CCC2c1cc(F)c(F)c(F)c1]

A solution of 7-(3,4,5-trifluorophenyl)-6,7-dihydrocyclopenta[e][1,3]oxazine-2,4(3H,5H)-dione (1.23 g, 4.34 mmol) in concentrated ammonium hydroxide (75 mL, 1926 mmol) was heated at 100° C. in a high-pressure (350 mL) vessel overnight. The reaction mixture was cooled and concentrated in vacuum to give crude 7-(3,4,5-trifluorophenyl)-6,7-dihydro-1H-cyclopenta[d]pyrimidine-2,4(3H,5H)-dione (1.3 g, 4.61 mmol, 106% yield). LC-MS (M+H)$^+$=283.0.

Preparation T 2,4-Dichloro-7-(3,4,5-trifluorophenyl)-6,7-dihydro-5H-cyclopenta[d]pyrimidine

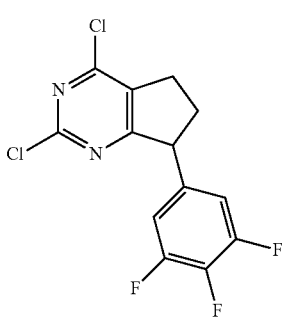 [SMILES: Fc1cc(C2CCc3c(Cl)nc(Cl)nc32)cc(F)c1F]

A solution of 7-(3,4,5-trifluorophenyl)-6,7-dihydro-1H-cyclopenta[d]pyrimidine-2,4(3H,5H)-dione (1.3 g, 4.61 mmol) in phosphoryl trichloride (5 mL, 54.6 mmol) was heated in microwave at 110° C. for 1 h. The reaction was repeated with an additional 800 mg of the starting material. The reaction mixtures was poured into ice and combined. Once ice melted, the product was extracted with dichloromethane. The combined organic extracts were dried over anhydrous magnesium sulfate and filtered. The solvent was removed in vacuum and the residue was purified by column chromatography on silica gel to give 2,4-dichloro-7-(3,4,5-trifluorophenyl)-6,7-dihydro-5H-cyclopenta[d]pyrimidine (498 mg, 1.561 mmol, 33.9% yield). LC-MS (M+H)$^+$=318.9.

Preparation Ta

2-Chloro-N-methyl-7-(3,4,5-trifluorophenyl)-6,7-dihydro-5H-cyclopenta[d]pyrimidin-4-amine

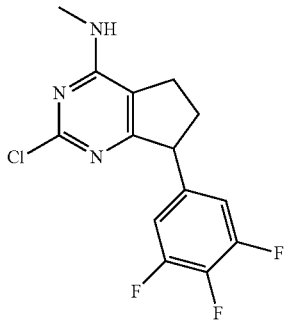 [SMILES: CNc1nc(Cl)nc2c1CCC2c1cc(F)c(F)c(F)c1]

A solution of 2,4-dichloro-7-(3,4,5-trifluorophenyl)-6,7-dihydro-5H-cyclopenta[d]pyrimidine (498 mg, 1.561 mmol) and methanamine (1.561 mL, 3.12 mmol) in MeOH (10 mL) was stirred at rt for 1 h. Incomplete reaction was observed. Additional portions of methanamine (1.561 mL, 3.12 mmol) were added to the reaction mixture until the reaction was complete. The solvent was removed in vacuum and the residue was purified by column chromatography on silica gel to give 2-chloro-7-(3,5-difluorophenyl)-N-methyl-6,7-dihydro-5H-cyclopenta[d]pyrimidin-4-amine (60 mg, 0.203 mmol, 30.5% yield). LC-MS $(M+H)^+=314.0$.

Preparation Tb

2-Chloro-4-(3,3-difluoropyrrolidin-1-yl)-7-(3,4,5-trifluorophenyl)-6,7-dihydro-5H-cyclopenta[d]pyrimidine

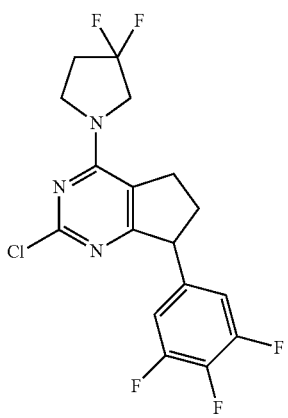 [SMILES: Fc1cc(C2CCc3c2nc(Cl)nc3N2CCC(F)(F)C2)cc(F)c1F]

A solution of 2,4-dichloro-7-(3,4,5-trifluorophenyl)-6,7-dihydro-5H-cyclopenta[d]pyrimidine (100 mg, 0.313 mmol), DIPEA (0.066 mL, 0.376 mmol) and 3,3-difluoropyrrolidine, HCl salt (45.0 mg, 0.313 mmol) were stirred at rt for 1 h. The solvent was removed in vacuum and the residue was purified by column chromatography on silica gel to give 2-chloro-4-(3,3-difluoropyrrolidin-1-yl)-7-(3,4,5-trifluorophenyl)-6,7-dihydro-5H-cyclopenta[d]pyrimidine (105 mg, 0.269 mmol, 86% yield). LC-MS $(M+H)^+=390.0$.

Preparation Tc

2-Chloro-4-(3,3-difluoroazetidin-1-yl)-7-(3,4,5-trifluorophenyl)-6,7-dihydro-5H-cyclopenta[d]pyrimidine

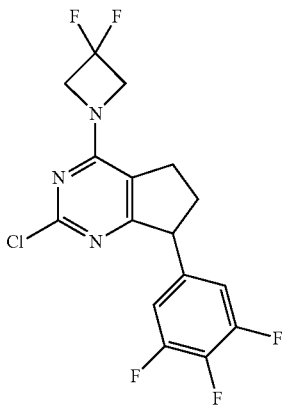 [SMILES: Fc1cc(C2CCc3c2nc(Cl)nc3N2CC(F)(F)C2)cc(F)c1F]

A solution of 2,4-dichloro-7-(3,4,5-trifluorophenyl)-6,7-dihydro-5H-cyclopenta[d]pyrimidine (100 mg, 0.313 mmol), DIPEA (0.109 mL, 0.627 mmol) and 3,3-difluoroazetidine, HCl salt (44.7 mg, 0.345 mmol) were stirred at rt for 1 h. The solvent was removed in vacuum and the residue was purified by column chromatography on silica gel to give 2-chloro-4-(3,3-difluoroazetidin-1-yl)-7-(3,4,5-trifluorophenyl)-6,7-dihydro-5H-cyclopenta[d]pyrimidine (105 mg, 0.279 mmol, 89% yield). LC-MS $(M+H)^+=376.0$.

Preparation U 2,4-Dichloro-7-(2,4-difluorophenyl)-6,7-dihydro-5H-cyclopenta[d]pyrimidine

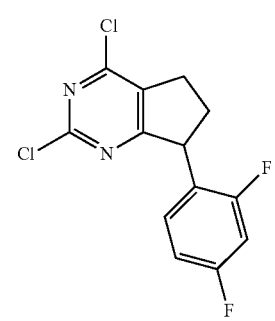 [SMILES: Fc1ccc(C2CCc3c(Cl)nc(Cl)nc32)c(F)c1]

Intermediate U(1)

1-Cyclopentenyl-2,4-difluorobenzene

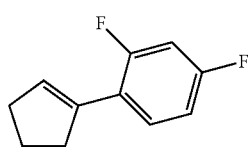 [SMILES: Fc1ccc(C2=CCCC2)c(F)c1]

To a 0.497M solution of (2,4-difluorophenyl)magnesium bromide (32.4 g, 149 mmol) in THF at 0° C. was carefully added cyclopentanone (13.23 mL, 149 mmol). Upon the end of the addition, the reaction mixture was heated at reflux for 2 h. Ice (10 g) and 6N aqueous hydrochloric acid were added. The reaction mixture was extracted with ether. The combined organic extracts were washed with a saturated aqueous solution of sodium hydrogen sulfite, a saturated aqueous solution of sodium bicarbonate and water. The organic layer was dried over anhydrous magnesium sulfate and filtered. The solvent was removed in vacuum and the residue was purified by column chromatography on silica gel to give 1-cyclopentenyl-2,4-difluorobenzene (7.064 g, 39.2 mmol, 26.3% yield) as colorless oil. LC-MS (M+H)$^+$=181.0. $^1$H NMR (500 MHz, CDCl$_3$) δ ppm 7.22-7.31 (1H, m), 6.75-6.85 (2H, m), 6.26-6.31 (1H, m), 2.68-2.74 (2H, m), 2.51-2.58 (2H, m), 1.93-2.02 (2H, m).

Intermediate U(2)

2-(2,4-Difluorophenyl)cyclopentanone

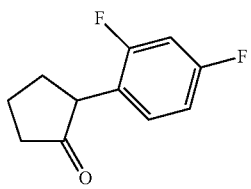 [SMILES: O=C1CCCC1c1ccc(F)cc1F]

A mixture of 90% formic acid (26.4 mL, 689 mmol) and 30% hydrogen peroxide (6.0 mL, 39.2 mmol) was warmed at 40° C. for 10 min. The resulting solution was carefully added to 1-cyclopentenyl-2,4-difluorobenzene (7.064 g, 39.2 mmol) under stirring. The two-phase system was initially stirred at room temperature. After a certain period of time, a spontaneous exothermic reaction took place, and the temperature rose to about 50° C. The reaction mixture was stirred at room temperature for 2 h. The reaction mixture was quenched by careful addition of a saturated sodium bicarbonate solution. Ether was added and the content of the separatory funnel was vigorously shaken. The organic layer was separated and the aqueous layer was extracted with ether. The combined organic extracts were dried over anhydrous magnesium sulfate and filtered. The solvent was removed in vacuum and the residue was purified by column chromatography on silica gel to give 2-(2,4-difluorophenyl)cyclopentanone (3.503 g, 17.85 mmol, 45.5% yield) as colorless oil. LC-MS (M+H)$^+$=195.2. $^1$H NMR (500 MHz, CDCl$_3$) δ ppm 7.08 (1H, td, J=8.4, 6.4 Hz), 6.76-6.86 (2H, m), 3.42 (1H, dd, J=12.2, 8.9 Hz), 2.42-2.53 (2H, m), 2.28-2.39 (1H, m), 2.13-2.23 (1H, m), 1.86-2.10 (2H, m).

Intermediate U(3)

7-(2,4-Difluorophenyl)-6,7-dihydrocyclopenta[e][1,3]oxazine-2,4(3H,5H)-dione

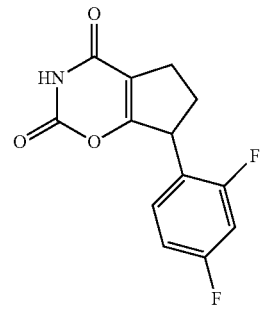 [SMILES: O=c1[nH]c(=O)c2c(o1)C(c1ccc(F)cc1F)CC2]

A mixture of 2-(2,4-difluorophenyl)cyclopentanone (1.014 g, 5.17 mmol) and 50% wt. carbonisocyanatidic chloride solution in toluene (1.963 g, 9.30 mmol) was heated at 58° C. for 1 h and at 120° C. for 3 h. The reaction mixture was dissolved in ethyl acetate and washed with an aqueous solution of sodium bicarbonate. The organic layer was separated and the aqueous layer was extracted with ethyl acetate. The combined organic extracts were dried over anhydrous magnesium sulfate and filtered. The solvent was removed in vacuum and the residue was purified by column chromatography on silica gel to give 7-(2,4-difluorophenyl)-6,7-dihydrocyclopenta[e][1,3]oxazine-2,4(3H,5H)-dione (499.3 mg, 1.883 mmol, 36.4% yield) as brown solid. LC-MS (M+H)$^+$=266.2. $^1$H NMR (500 MHz, CDCl$_3$) δ ppm 8.19-8.64 (1H, m), 7.10 (1H, td, J=8.5, 6.3 Hz), 6.78-6.92 (2H, m), 4.36-4.49 (1H, m), 2.79-2.92 (1H, m), 2.59-2.78 (2H, m), 2.08 (1H, ddd, J=9.3, 6.9, 6.7 Hz).

Intermediate U(4)

7-(2,4-Difluorophenyl)-6,7-dihydro-1H-cyclopenta[d]pyrimidine-2,4(3H,5H)-dione

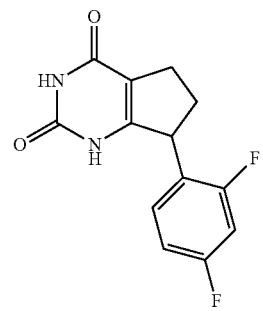 [SMILES: O=c1[nH]c2c(c(=O)[nH]1)CCC2c1ccc(F)cc1F]

A mixture of 2-(2,4-difluorophenyl)cyclopentanone (1.014 g, 5.17 mmol) and 50% wt. carbonisocyanatidic chloride solution in toluene (1.963 g, 9.30 mmol) was heated at 58° C. for 1 h and at 120° C. for 3 h. The reaction mixture was dissolved in ethyl acetate and washed with an aqueous solution of sodium bicarbonate. The organic layer was separated and the aqueous layer was extracted with ethyl acetate. The combined organic extracts were dried over anhydrous magnesium sulfate and filtered. The solvent was removed in vacuum and the residue was purified by column chromatography on silica gel to give 7-(2,4-difluorophenyl)-6,7-dihydrocyclopenta[e][1,3]oxazine-2,4(3H,5H)-dione (499.3 mg, 1.883 mmol, 36.4% yield) as brown solid. LC-MS (M+H)+= 265.1.

Preparation U 2,4-Dichloro-7-(2,4-difluorophenyl)-6,7-dihydro-5H-cyclopenta[d]pyrimidine

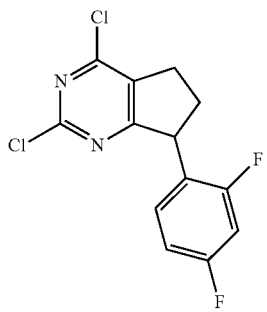 [SMILES: Fc1ccc(C2CCc3c(Cl)nc(Cl)nc32)c(F)c1]

A solution of 7-phenyl-6,7-dihydro-1H-cyclopenta[d]pyrimidine-2,4(3H,5H)-dione (248.5 mg, 0.940 mmol) in phosphoryl trichloride (10 mL) was heated in microwave at 130° C. for 2 h. The reaction mixture was poured in a beaker with ice. Once ice melted, the product was extracted with dichloromethane. The combined organic extracts were dried over anhydrous magnesium sulfate and filtered. The solvent was removed in vacuum and the residue was purified by column chromatography on silica gel to give 2,4-dichloro-7-phenyl-6,7-dihydro-5H-cyclopenta[d]pyrimidine (267.9 mg, 95%) as light brown solid. LC-MS (M+H)+=301.1.

Preparation Ua

2-Chloro-7-(2,4-difluorophenyl)-N-methyl-6,7-dihydro-5H-cyclopenta[d]pyrimidin-4-amine

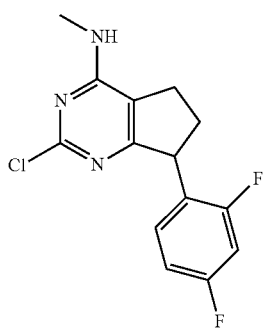 [SMILES: CNc1nc(Cl)nc2c1CCC2c1ccc(F)cc1F]

To a solution of 2,4-dichloro-7-(2,4-difluorophenyl)-6,7-dihydro-5H-cyclopenta[d]pyrimidine (267.9 mg, 0.890 mmol) in methanol (5 mL) was added a 2M solution of methylamine in methanol (0.890 mL, 1.779 mmol). The reaction mixture was stirred at room temperature overnight. The solvent was removed in vacuum and the residue was partitioned between ethyl acetate and water. The organic layer was separated and the aqueous layer was extracted with ethyl acetate. The combined organic extracts were dried over anhydrous magnesium sulfate and filtered. The solvent was removed in vacuum and the residue was purified by column chromatography on silica gel to give 2-chloro-7-(2,4-difluorophenyl)-N-methyl-6,7-dihydro-5H-cyclopenta[d]pyrimidin-4-amine (184.6 mg, 0.624 mmol, 70.2% yield) as brown solid. LC-MS (M+H)+=296.1.

Preparation V 2,4-dichloro-7-methyl-7-phenyl-6,7-dihydro-5H-cyclopenta[d]pyrimidine

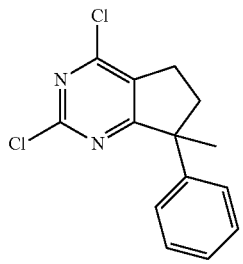 [SMILES: CC1(c2ccccc2)CCc2c(Cl)nc(Cl)nc21]

Intermediate V(1)

2-methyl-2-phenylcyclopentanone

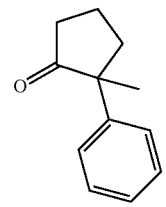

To a slurry of 60% NaH (125 mg, 3.12 mmol) in DME (3571 µL) at 0° C. was added 2-phenylcyclopentanone (500 mg, 3.12 mmol). After stirring for 1 h, Met (898 µL, 14.36 mmol) was added, and the solution heated to reflux for 2 h. The reaction was poured onto ice and extracted 3 times into Et$_2$O. The organic extracts were washed with brine, dried over MgSO$_4$, filtered and concentrated in vacuo. Applied to Silica gel and eluted with an EtOAc/Hex gradient to afford 2-methyl-2-phenylcyclopentanone (401.7 mg, 2.305 mmol, 73.9% yield). LC-MS (M+H)+=175.1. $^1$H NMR (500 MHz, CDCl$_3$) δ ppm 7.29-7.37 (4H, m), 7.20-7.24 (1H, m), 2.54 (1H, dt, J=12.51, 6.26 Hz), 2.34 (2H, t, J=7.63 Hz), 1.82-2.05 (3H, m), 1.38 (3H, s).

Intermediate V(2)

7-methyl-7-phenyl-6,7-dihydrocyclopenta[e][1,3]oxazine-2,4(3H,5H)-dione

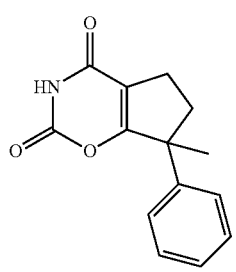 [SMILES: CC1(c2ccccc2)CCc2c1oc(=O)[nH]c2=O]

Combined 2-methyl-2-phenylcyclopentanone (Intermediate V(1)) (705.5 mg, 4.05 mmol) and carbonisocyanatidic chloride (1700 mg, 8.06 mmol), flushed with N2, and sealed in a sealed tube. Heated at 58° C. for 1 h, then 130° C. for 1.75 h. Let cool to rt. Carefully opened the tube (HCl), and dissolved the residue in EtOAc. Partitioned with NaHCO₃ (aq), and extracted 3 times into EtOAc. Washed combined organic layers with brine, dried over MgSO₄, filtered, and concentrated in vacuo. Loaded the residue onto Silica gel and eluted with an EtOAc/Hexane gradient to afford 7-methyl-7-phenyl-6,7-dihydrocyclopenta[e][1,3]oxazine-2,4(3H,5H)-dione (43% yield)LC-MS (M+H)$^+$=244.1. $^1$H NMR (500 MHz, CDCl₃) δ ppm 8.12 (1H, br. s.), 7.32-7.38 (2H, m), 7.26-7.30 (3H, m), 2.69-2.75 (2H, m), 2.43-2.52 (1H, m), 2.21-2.29 (1H, m), 1.68 (3H, s).

Intermediate V(3)

7-methyl-7-phenyl-6,7-dihydro-1H-cyclopenta[d]pyrimidine-2,4(3H,5H)-dione

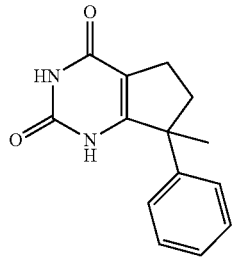 [SMILES: CC1(c2ccccc2)CCc2c1[nH]c(=O)[nH]c2=O]

To solid 7-methyl-7-phenyl-6,7-dihydrocyclopenta[e][1,3]oxazine-2,4(3H,5H)-dione (420 mg, 1.727 mmol) was added concentrated Ammonium Hydroxide (4706 μL, 121 mmol) in a sealed tube. The tube was heated for 4 h at 80° C. Cooled to rt. Removed the solvent under a stream of N2. Loaded the residue onto Silica gel and eluted with an EtOAc/Hexane gradient to afford 7-methyl-7-phenyl-6,7-dihydro-1H-cyclopenta[d]pyrimidine-2,4(3H,5H)-dione (293 mg, 1.209 mmol, 70.0% yield). LC-MS (M+H)$^+$=243.1.

Preparation V 2,4-dichloro-7-methyl-7-phenyl-6,7-dihydro-5H-cyclopenta[d]pyrimidine

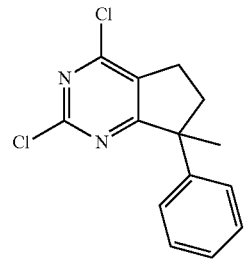 [SMILES: CC1(c2ccccc2)CCc2c(Cl)nc(Cl)nc21]

Dissolved 7-methyl-7-phenyl-6,7-dihydro-1H-cyclopenta[d]pyrimidine-2,4(3H,5H)-dione (48.2 mg, 0.199 mmol) in POCl₃ (742 μL, 7.96 mmol) and placed in a microwave vial. Heated the reaction for 1 h at 120° C. in the microwave. Cooled to rt, and poured into ice. As soon as the ice melted, extracted 3 times into EtOAc. Dried over MgSO₄, filtered, and concentrated in vacuo. A quick EtOAc/Hex SG column provided 2,4-dichloro-7-methyl-7-phenyl-6,7-dihydro-5H-cyclopenta[d]pyrimidine (43.1 mg, 0.154 mmol, 78% yield). LC-MS (M+H)$^+$=279.1.

Preparation Va 2-chloro-N-ethyl-7-methyl-7-phenyl-6,7-dihydro-5H-cyclopenta[d]pyrimidin-4-amine

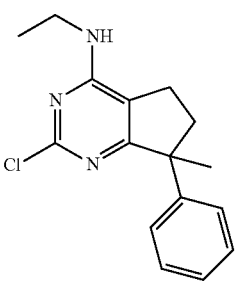 [SMILES: CCNc1nc(Cl)nc2c1CCC2(C)c1ccccc1]

To a solution of 2,4-dichloro-7-methyl-7-phenyl-6,7-dihydro-5H-cyclopenta[d]pyrimidine (Preparation V) (43.1 mg, 0.154 mmol) in THF (772 μL) at rt was added a solution of 2M Ethylamine (386 μL, 0.772 mmol) diluted with 390 uL MeOH (overall reaction is 0.1M in 1:1 THF/MeOH). Let stir at rt. Removed the solvent and subjected the residue to a Silica gel column with an EtOAc/Hex gradient to afford 2-chloro-N-ethyl-7-methyl-7-phenyl-6,7-dihydro-5H-cyclopenta[d]pyrimidin-4-amine (38.0 mg, 0.132 mmol, 86% yield).

Preparation W 2,4-dichloro-7-allyl-7-phenyl-6,7-dihydro-5H-cyclopenta[d]pyrimidine

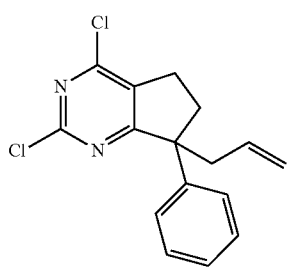 [SMILES: C=CCC1(c2ccccc2)CCc2c(Cl)nc(Cl)nc21]

Intermediate W(1)

2-allyl-2-phenylcyclopentanone

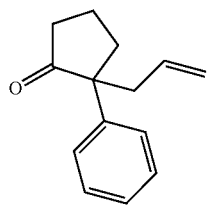

The procedure of Intermediate V(1) was utilized with allyl bromide to obtain 2-allyl-2-phenylcyclopentanone.

Intermediate W(2)

7-allyl-7-phenyl-6,7-dihydrocyclopenta[e][1,3]oxazine-2,4(3H,5H)-dione

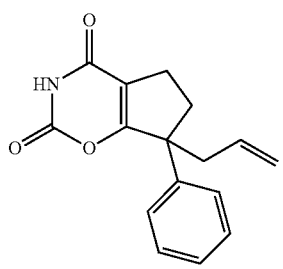 [SMILES: C=CCC1(c2ccccc2)CCc2c1oc(=O)[nH]c2=O]

The method of Intermediate V(2) was utilized to obtain 7-allyl-7-phenyl-6,7-dihydrocyclopenta[e][1,3]oxazine-2,4(3H,5H)-dione.

$^1$H NMR (500 MHz, CDCl$_3$) δ ppm 8.06 (1H, br. s.), 7.23-7.43 (5H, m), 5.59-5.72 (1H, m, J=17.09, 9.99, 7.21, 7.21 Hz), 5.08-5.23 (2H, m), 2.73-2.87 (2H, m), 2.63-2.71 (2H, m), 2.38-2.49 (2H, m)

Intermediate W(3)

7-allyl-7-phenyl-6,7-dihydro-1H-cyclopenta[d]pyrimidine-2,4(3H,5H)-dione

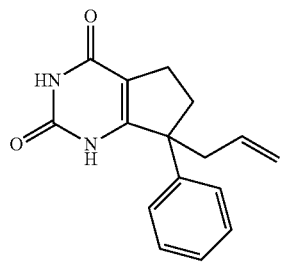 [SMILES: C=CCC1(c2ccccc2)CCc2c1[nH]c(=O)[nH]c2=O]

The method of Intermediate V(3) was utilized to obtain 7-allyl-7-phenyl-6,7-dihydro-1H-cyclopenta[d]pyrimidine-2,4(3H,5H)-dione. LC-MS (M+H)$^+$=269.1.

Preparation W 2,4-dichloro-7-allyl-7-phenyl-6,7-dihydro-5H-cyclopenta[d]pyrimidine

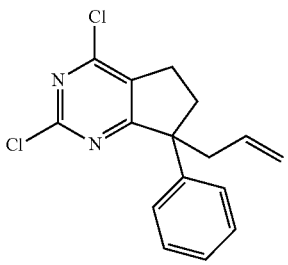 [SMILES: C=CCC1(c2ccccc2)CCc2c(Cl)nc(Cl)nc21]

The method of Preparation V was used to obtain 2,4-dichloro-7-allyl-7-phenyl-6,7-dihydro-5H-cyclopenta[d]pyrimidine. LC-MS (M+H)$^+$=305.0.

Preparation Wa 2-chloro-N-ethyl-7-allyl-7-phenyl-6,7-dihydro-5H-cyclopenta[d]pyrimidin-4-amine

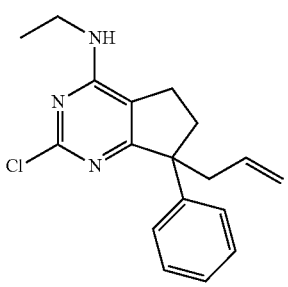 [SMILES: C=CCC1(c2ccccc2)CCc2c(NCC)nc(Cl)nc21]

Utilizing the procedure for Preparation Va, 2-chloro-N-ethyl-7-allyl-7-phenyl-6,7-dihydro-5H-cyclopenta[d]pyrimidin-4-amine was obtained. LC-MS (M+H)$^+$=314.1.

Preparation X 2,4-dichloro-8-(3,5-difluorophenyl)-7,8-dihydro-5H-pyrano[4,3-d]pyrimidine

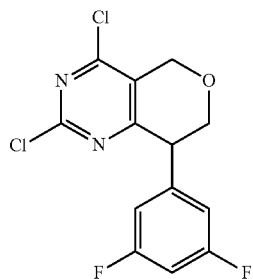 [SMILES: Fc1cc(F)cc(C2COCc3c(Cl)nc(Cl)nc32)c1]

Intermediate X(1)

3-iodo-4,4-dimethoxytetrahydro-2H-pyran

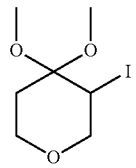

The mixture of trimethoxymethane (82 mL, 745 mmol) and dihydro-2H-pyran-4(3H)-one (14.92 g, 149 mmol) was cooled to 4° C. Added diiodine (37.8 g, 149 mmol) in lots and keep the temperature between 4° C. and 5° C. The reaction mixture was stirred at 4° C. for 10 min. Cooling bath was removed, stirred at 28° C. for 10 min. The mixture was cooled to 10° C. and stirred for 10 min, and then stirred at RT for 1 h.

The reaction mixture was diluted with $CH_2Cl_2$ and cooled in ice water. Slowly quenched with saturated $Na_2S_2O_3$ solution. The mixed layers were separated. The aqueous layer was extracted with CH2Cl2. The combined organic layer was washed with brine, dried over $Na_2SO_4$ and concentrated. The crude product was purified by column chromatography on silica gel to give 3-iodo-4,4-dimethoxytetrahydro-2H-pyran (33.05 g, 121 mmol, 82% yield). $^1$H NMR (500 MHz, CDCl$_3$) δ ppm 4.24 (1H, t, J=2.29 Hz), 3.93-4.02 (1H, m), 3.83-3.92 (2H, m), 3.55 (1H, d, J=2.44 Hz), 3.24 (3H, s), 3.20 (3H, s), 2.33 (1H, dd, J=4.88, 2.14 Hz), 1.79 (1H, dd, J=14.34, 2.44 Hz)

Intermediate X(2)

3-(3,5-difluorophenyl)dihydro-2H-pyran-4(3H)-one

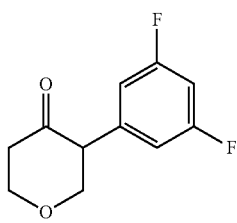 [SMILES: O=C1CCOCC1c1cc(F)cc(F)c1]

To a mixture of (1R,2R)-2-aminocyclohexanol hydrochloride (0.418 g, 2.76 mmol), nickel(II) chloride hexahydrate (0.328 g, 1.378 mmol) and 3,5-difluorophenylboronic acid (6.53 g, 41.3 mmol) was added NaHMDS in THF (55.1 mL, 55.1 mmol) at 10° C. dropwise under $N_2$. After addition, the mixture was stirred at 10° C. for 20 min. 2-Propanol (113 mL) (previously bubbled by N2) was added at 0° C. and then the mixture was stirred at RT for 10 min. 3-iodo-4,4-dimethoxytetrahydro-2H-pyran (Preparation X1) (7.5 g, 27.6 mmol). in THF was added dropwise and the mixture was heated at 60° C. overnight. The reaction mixture was cooled in ice bath, added 1.0 HCl until acidic and stirred for 10 min. Concentrated in vacuum. Extracted with EtOAc and the organic layer was washed with brine and concentrated. The residue was purified by column chromatography on silica gel to give 3-(3,5-difluorophenyl)dihydro-2H-pyran-4(3H)-one (1.6 g, 7.54 mmol, 27.4% yield). $^1$H NMR (500 MHz, CDCl$_3$) δ ppm 6.78 (dd, J=8.24, 2.14 Hz, 2H) 6.62-6.75 (m, 1H) 4.21 (dd, J=11.44, 5.65 Hz, 2H) 3.85-4.01 (m, 2H) 3.76 (dd, J=8.55, 6.10 Hz, 1H) 2.60-2.75 (m, 1H) 2.48-2.60 (m, 1H)

Intermediate X(3)

8-(3,5-difluorophenyl)-7,8-dihydropyrano[3,4-e][1,3]oxazine-2,4(3H,5H)-dione

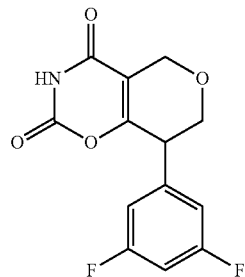 [SMILES: O=c1[nH]c(=O)c2c(o1)C(c1cc(F)cc(F)c1)COC2]

The mixture of 3-(3,5-difluorophenyl)dihydro-2H-pyran-4(3H)-one (Preparation X2) (800 mg, 3.77 mmol) and carbonisocyanatidic chloride (557 mg, 5.28 mmol) was heated in a sealed bottle at 55° C. for 1 h and then at 130° C. for 2 h. The mixture was cooled to RT. Partition between EtOAc and saturated NaHCO$_3$ solution. Extracted with EtOAc(×3 times). The combined organic layers was washed with brine, dried over $Na_2SO_4$ and concentrated. The crude product was purified by column chromatography on silica gel to give 8-(3,5-difluorophenyl)-7,8-dihydropyrano[3,4-e][1,3]oxazine-2,4(3H,5H)-dione (230 mg, 0.818 mmol, 21.69% yield). LC-MS (M+H)$^+$=282.0. $^1$H NMR (500 MHz, CDCl$_3$) δ ppm 8.94 (br, s., 1H) 6.85-7.01 (m, 2H) 6.81 (tt, J=8.81, 2.17 Hz, 1H) 4.70 (d, J=15.56 Hz, 1H) 4.49 (dd, J=15.56, 2.14 Hz, 1H) 4.03-4.12 (m, 2H) 3.68 (br. s., 1H)

Intermediate X(4)

8-(3,5-difluorophenyl)-7,8-dihydro-1H-pyrano[4,3-d]pyrimidine-2,4(3H,5H)-dione

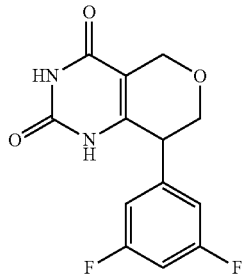 [SMILES: O=c1[nH]c2c(c(=O)[nH]1)COCC2c1cc(F)cc(F)c1]

The mixture of 8-(3,5-difluorophenyl)-7,8-dihydropyrano[3,4-e][1,3]oxazine-2,4(3H,5H)-dione (Preparation X3)(230 mg, 0.818 mmol) and ammonium hydroxide (2229 mL, 57.3 mmol) in a sealed bottle was heated at 80° C. for 4 h. Blowed by N2 overnight to get 8-(3,5-difluorophenyl)-7,8-dihydro-1H-pyrano[4,3-d]pyrimidine-2,4(3H,5H)-dione (191 mg, 0.682 mmol, 83% yield) which was used as is. LC-MS (M+H)$^+$=281.1.

Preparation X 2,4-dichloro-8-(3,5-difluorophenyl)-7,8-dihydro-5H-pyrano[4,3-d]pyrimidine

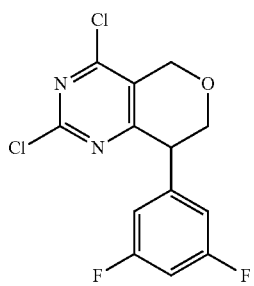 [SMILES: Fc1cc(F)cc(C2COCc3c(Cl)nc(Cl)nc32)c1]

The mixture of 8-(3,5-difluorophenyl)-7,8-dihydro-1H-pyrano[4,3-d]pyrimidine-2,4(3H,5H)-dione (Intermediate X(4)) (191 mg, 0.682 mmol) and POCl$_3$ (1906 mL, 20.45 mmol) in a microwave vial was heated by microwave at 100° C. for 2.5 h. The mixture was poured on ice, as long as ice was melted, extracted with EtOAc (×3 times), washed with brine, dried over Na$_2$SO$_4$ and concentrated. The crude product was purified by column chromatography on silica gel to give 2,4-dichloro-8-(3,5-difluorophenyl)-7,8-dihydro-5H-pyrano[4,3-d]pyrimidine (117 mg, 0.369 mmol, 54.1% yield). LC-MS (M+H)$^+$=317.1. $^1$H NMR (400 MHz, CDCl$_3$) δ ppm 6.66-6.91 (m, 3H) 4.87-5.01 (m, 1H) 4.70-4.83 (m, 1H) 4.13-4.27 (m, 2H) 4.10 (t, J=4.03 Hz, 1H)

Preparation Xa 2-chloro-8-(3,5-difluorophenyl)-N-ethyl-7,8-dihydro-5H-pyrano[4,3-d]pyrimidin-4-amine

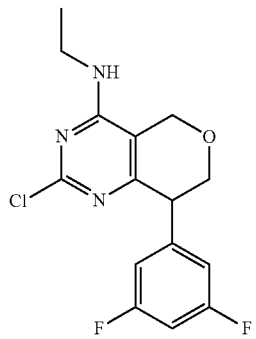 [SMILES: CCNc1nc(Cl)nc2c1COCC2c1cc(F)cc(F)c1]

The mixture of ethanamine (406 μL, 0.812 mmol), 2,4-dichloro-8-(3,5-difluorophenyl)-7,8-dihydro-5H-pyrano[4,3-d]pyrimidine (Preparation X)(117 mg, 0.369 mmol) and DIEA (161 μL, 0.922 mmol) in THF (1845 μL) was stirred at RT for 2 h. The mixture was concentrated and purified by column chromatography on silica gel to give 2-chloro-8-(3,5-difluorophenyl)-N-ethyl-7,8-dihydro-5H-pyrano[4,3-d]pyrimidin-4-amine (104 mg, 0.319 mmol, 87% yield). LC-MS (M+H)$^+$=326.1.

Preparation Y 2,4-dichloro-8-(3,4-difluorophenyl)-7,8-dihydro-5H-pyrano[4,3-d]pyrimidine

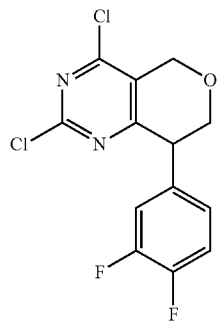 [SMILES: Fc1ccc(C2COCc3c(Cl)nc(Cl)nc32)cc1F]

Intermediate Y(2)

3-(3,4-difluorophenyl)dihydro-2H-pyran-4(3H)-one

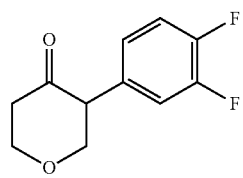 [SMILES: O=C1CCOCC1c1ccc(F)c(F)c1]

3,4-difluorophenylboronic acid was reacted as described in Intermediate X(2) with 3-iodo-4,4-dimethoxytetrahydro-2H-pyran (Intermediate X(1)) to give 3-(3,4-difluorophenyl)dihydro-2H-pyran-4(3H)-one (Intermediate Y(2)).

¹H NMR (500 MHz, CDCl₃) δ ppm 7.03-7.22 (m, 2H) 6.95 (ddd, J=6.33, 4.20, 1.98 Hz, 1H) 4.17-4.32 (m, 2H) 3.96 (ddd, J=11.52, 9.84, 3.97 Hz, 1H) 3.91 (dd, J=11.44, 9.00 Hz, 1H) 3.77 (dd, J=8.85, 5.80 Hz, 1H) 2.63-2.76 (m, 1H) 2.49-2.62 (m, 1H).

Intermediate Y(3)

8-(3,4-difluorophenyl)-7,8-dihydropyrano[3,4-e][1,3]oxazine-2,4(3H,5H)-dione

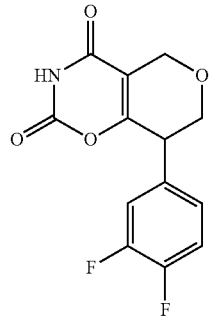 [SMILES: O=c1[nH]c(=O)c2c(o1)C(c1ccc(F)c(F)c1)COC2]

3-(3,4-difluorophenyl)dihydro-2H-pyran-4(3H)-one (Intermediate Y(2)) was reacted as described in Intermediate X(3) with carbonisocyanatidic chloride to give 8-(3,4-difluorophenyl)-7,8-dihydropyrano[3,4-e][1,3]oxazine-2,4(3H,5H)-dione (Intermediate Y(3)). LC-MS (M+H)⁺=282.1. ¹H NMR (500 MHz, CDCl₃) δ ppm 7.08-7.20 (m, 3H) 4.67 (d, J=15.26 Hz, 1H) 4.46 (dd, J=15.56, 2.14 Hz, 1H) 3.98-4.10 (m, 2H) 3.67 (br. s., 1H).

Intermediate Y(4)

8-(3,4-difluorophenyl)-7,8-dihydro-1H-pyrano[4,3-d]pyrimidine-2,4(3H,5H)-dione

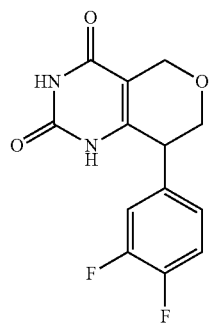 [SMILES: O=c1[nH]c2c(c(=O)[nH]1)COCC2c1ccc(F)c(F)c1]

8-(3,4-difluorophenyl)-7,8-dihydropyrano[3,4-e][1,3]oxazine-2,4(3H,5H)-dione (Intermediate Y(3)) was reacted as described in Intermediate X(4) with ammonium hydroxide to give 8-(3,4-difluorophenyl)-7,8-dihydro-1H-pyrano[4,3-d]pyrimidine-2,4(3H,5H)-dione (Intermediate Y(4)). LC-MS (M−H)⁺=279.1.

Preparation Y 2,4-dichloro-8-(3,4-difluorophenyl)-7,8-dihydro-5H-pyrano[4,3-d]pyrimidine

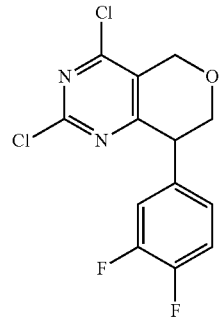 [SMILES: Fc1ccc(C2COCc3c(Cl)nc(Cl)nc32)cc1F]

2,4-dichloro-8-(3,4-difluorophenyl)-7,8-dihydro-5H-pyrano[4,3-d]pyrimidine (Intermediate Y(4)) was reacted as described in Preparation X with POCl₃ to give 2,4-dichloro-8-(3,4-difluorophenyl)-7,8-dihydro-5H-pyrano[4,3-d]pyrimidine (Preparation Y). LC-MS (M+H)⁺=317.1.

Preparation Ya 2-chloro-8-(3,4-difluorophenyl)-N-ethyl-7,8-dihydro-5H-pyrano[4,3-d]pyrimidin-4-amine

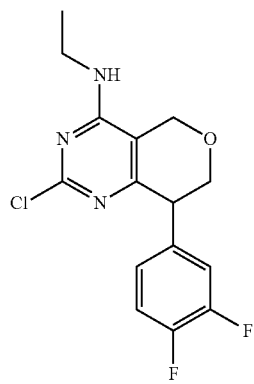 [SMILES: CCNc1nc(Cl)nc2c1COCC2c1ccc(F)c(F)c1]

2,4-dichloro-8-(3,4-difluorophenyl)-7,8-dihydro-5H-pyrano[4,3-d]pyrimidine (Preparation Y) was reacted as described in Preparation Xa with ethanamine to give 2-chloro-8-(3,4-difluorophenyl)-N-ethyl-7,8-dihydro-5H-pyrano[4,3-d]pyrimidin-4-amine (Preparation Ya). LC-MS (M+H)⁺=326.1.

Preparation Yb 2-chloro-4-(3,3-difluoroazetidin-1-yl)-8-(3,4-difluorophenyl)-7,8-dihydro-5H-pyrano[4,3-d]pyrimidine

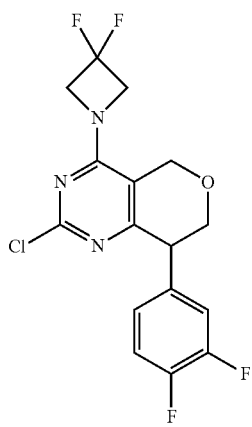 [SMILES: Fc1ccc(C2COCc3c2nc(Cl)nc3N2CC(F)(F)C2)cc1F]

2,4-dichloro-8-(3,4-difluorophenyl)-7,8-dihydro-5H-pyrano[4,3-d]pyrimidine (Preparation Y) was reacted as described in Preparation Xa with 3,3-difluoroazetidine, HCl to give 2-chloro-4-(3,3-difluoroazetidin-1-yl)-8-(3,4-difluorophenyl)-7,8-dihydro-5H-pyrano[4,3-d]pyrimidine (Preparation Yb). LC-MS (M+H)$^+$=374.1.

Preparation Yc 2-chloro-8-(3,4-difluorophenyl)-N-methyl-7,8-dihydro-5H-pyrano[4,3-d]pyrimidin-4-amine

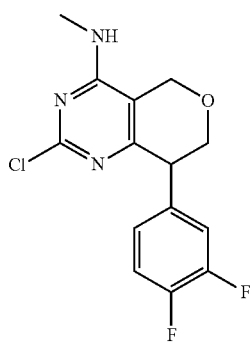 [SMILES: CNc1nc(Cl)nc2c1COCC2c1ccc(F)c(F)c1]

2,4-dichloro-8-(3,4-difluorophenyl)-7,8-dihydro-5H-pyrano[4,3-d]pyrimidine (Preparation Y) was reacted as described in Preparation Xa with methanamine to give 2-chloro-8-(3,4-difluorophenyl)-N-methyl-7,8-dihydro-5H-pyrano[4,3-d]pyrimidin-4-amine (Preparation Yc). LC-MS (M+H)$^+$=312.3.

Preparation Z 2,4-dichloro-8-(4-(trifluoromethyl)phenyl)-7,8-dihydro-5H-pyrano[4,3-d]pyrimidine

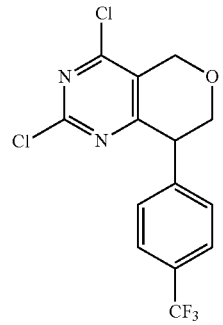 [SMILES: FC(F)(F)c1ccc(C2COCc3c(Cl)nc(Cl)nc32)cc1]

Intermediate Z(2)

3-(4-(trifluoromethyl)phenyl)dihydro-2H-pyran-4(3H)-one

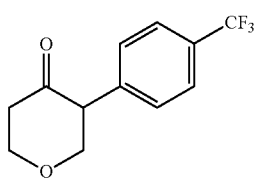 [SMILES: O=C1CCOCC1c1ccc(C(F)(F)F)cc1]

4-(trifluoromethyl)phenylboronic acid was reacted as described in Intermediate X(2) with 3-iodo-4,4-dimethoxytetrahydro-2H-pyran (Intermediate X(1)) to give 3-(4-(trifluoromethyl)phenyl)dihydro-2H-pyran-4(3H)-one (Intermediate Z(2)).

$^1$H NMR (500 MHz, CDCl$_3$) δ ppm 7.61 (m, J=8.24 Hz, 2H) 7.37 (m, J=7.93 Hz, 2H) 4.26 (dd, J=11.44, 5.95 Hz, 2H) 3.93-4.05 (m, 2H) 3.82-3.93 (m, 1H) 2.64-2.81 (m, 1H) 2.49-2.64 (m, 1H)

Intermediate Z(3)

8-(4-(trifluoromethyl)phenyl)-7,8-dihydropyrano[3,4-e][1,3]oxazine-2,4(3H,5H)-dione

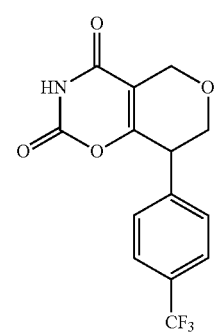 [SMILES: O=c1[nH]c(=O)c2c(o1)C(c1ccc(C(F)(F)F)cc1)COC2]

3-(4-(trifluoromethyl)phenyl)dihydro-2H-pyran-4(3H)-one (Intermediate Z(2)) was reacted as described in Intermediate X(3) with carbonisocyanatidic chloride to give 8-(4-(trifluoromethyl)phenyl)-7,8-dihydropyrano[3,4-e][1,3]oxazine-2,4(3H,5H)-dione (Intermediate Z(3)).

$^1$H NMR (500 MHz, CDCl$_3$) δ ppm 9.47 (br. s., 1H) 7.58-7.75 (m, 2H) 7.42-7.55 (m, 2H) 4.68 (d, J=15.56 Hz, 1H) 4.42-4.57 (m, 1H) 4.03-4.22 (m, 2H) 3.79 (br. s., 1H)

Intermediate Z(4)

8-(4-(trifluoromethyl)phenyl)-7,8-dihydro-1H-pyrano[4,3-d]pyrimidine-2,4 (3H,5H)-dione

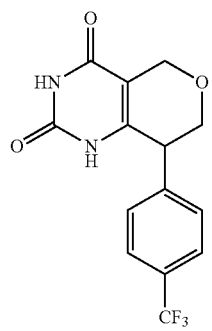 [SMILES: O=c1[nH]c2c(c(=O)[nH]1)COCC2c1ccc(C(F)(F)F)cc1]

8-(4-(trifluoromethyl)phenyl)-7,8-dihydropyrano[3,4-e][1,3]oxazine-2,4(3H,5H)-dione (Intermediate Z(3)) was reacted as described in Intermediate X(4) with ammonium hydroxide to give 8-(4-(trifluoromethyl)phenyl)-7,8-dihydro-1H-pyrano[4,3-d]pyrimidine-2,4(3H,5H)-dione (Intermediate Z(4)). LC-MS (M−H)$^+$=313.1.

Preparation Z 2,4-dichloro-8-(4-(trifluoromethyl)phenyl)-7,8-dihydro-5H-pyrano[4,3-d]pyrimidine

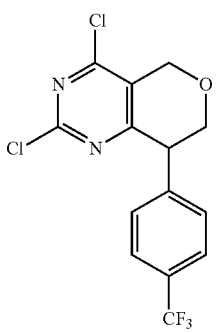 [SMILES: FC(F)(F)c1ccc(C2COCc3c(Cl)nc(Cl)nc32)cc1]

8-(4-(trifluoromethyl)phenyl)-7,8-dihydro-1H-pyrano[4,3-d]pyrimidine-2,4(3H,5H)-dione (Intermediate Z(4)) was reacted as described in Preparation X with POCl$_3$ to give 2,4-dichloro-8-(4-(trifluoromethyl)phenyl)-7,8-dihydro-5H-pyrano[4,3-d]pyrimidine (Preparation Z). LC-MS (M+H)$^+$=349.1.

Preparation Za 2-chloro-N-ethyl-8-(4-(trifluoromethyl)phenyl)-7,8-dihydro-5H-pyrano[4,3-d]pyrimidin-4-amine

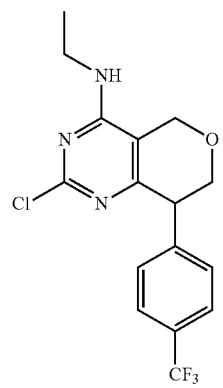 [SMILES: CCNc1nc(Cl)nc2c1COCC2c1ccc(C(F)(F)F)cc1]

2,4-dichloro-8-(4-(trifluoromethyl)phenyl)-7,8-dihydro-5H-pyrano[4,3-d]pyrimidine (Preparation Z) was reacted as described in Preparation Xa with ethanamine to give 2-chloro-N-ethyl-8-(4-(trifluoromethyl)phenyl)-7,8-dihydro-5H-pyrano[4,3-d]pyrimidin-4-amine (Preparation Za). LC-MS (M+H)$^+$=358.1.

Preparation Zb 2-chloro-N-methyl-8-(4-(trifluoromethyl)phenyl)-7,8-dihydro-5H-pyrano[4,3-d]pyrimidin-4-amine

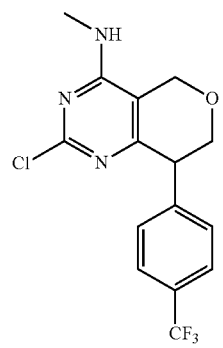 [SMILES: CNc1nc(Cl)nc2c1COCC2c1ccc(C(F)(F)F)cc1]

2,4-dichloro-8-(4-(trifluoromethyl)phenyl)-7,8-dihydro-5H-pyrano[4,3-d]pyrimidine (Preparation Z) was reacted as described in Preparation Xa with methanamine to give 2-chloro-N-methyl-8-(4-(trifluoromethyl)phenyl)-7,8-dihydro-5H-pyrano[4,3-d]pyrimidin-4-amine (Preparation Zb). LC-MS (M+H)$^+$=344.1.

Preparation Zc 2-chloro-N—((R)-1-cyclopropylethyl)-8-(4-(trifluoromethyl)phenyl)-7,8-dihydro-5H-pyrano[4,3-d]pyrimidin-4-amine

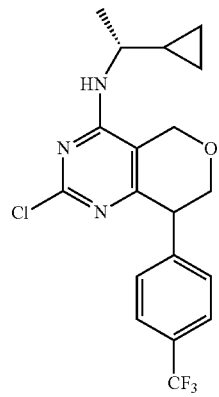 [SMILES: C[C@@H](Nc1nc(Cl)nc2c1COCC2c1ccc(C(F)(F)F)cc1)C1CC1]

2,4-dichloro-8-(4-(trifluoromethyl)phenyl)-7,8-dihydro-5H-pyrano[4,3-d]pyrimidine (Preparation Z) was reacted as described in Preparation Xa with (R)-1-cyclopropylethanamine, HCl to give 2-chloro-N—((R)-1-cyclopropylethyl)-8-(4-(trifluoromethyl)phenyl)-7,8-dihydro-5H-pyrano[4,3-d]pyrimidin-4-amine (Preparation Zc). LC-MS (M+H)$^+$= 398.2.

Preparation AAa 4-(2-chloro-4-(ethylamino)-7,8-dihydro-5H-pyrano[4,3-d]pyrimidin-8-yl)benzonitrile

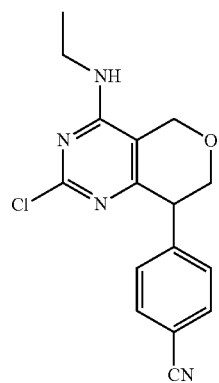 [SMILES: CCNc1nc(Cl)nc2c1COCC2c1ccc(C#N)cc1]

Intermediate AA(2)

4-(4-oxotetrahydro-2H-pyran-3-yl)benzonitrile

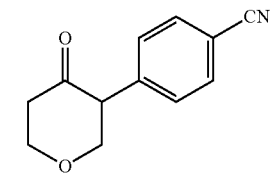 [SMILES: N#Cc1ccc(C2COCCC2=O)cc1]

4-cyanophenylboronic acid was reacted as described in Intermediate X(2) with 3-iodo-4,4-dimethoxytetrahydro-2H-pyran (Intermediate X(1)) to give 4-(4-oxotetrahydro-2H-pyran-3-yl)benzonitrile (Intermediate AA(2)). LC-MS (M+H)$^+$=202.1. $^1$H NMR (500 MHz, CDCl$_3$) δ ppm 7.66 (d, J=8.24 Hz, 2H) 7.38 (d, J=8.55 Hz, 2H) 4.23-4.31 (m, 2H) 3.94-4.02 (m, 2H) 3.85-3.92 (m, 1H) 2.55-2.65 (m, 1H) 2.52 (t, J=5.80 Hz, 1H).

Intermediate AA(3)

4-(2,4-dioxo-2,3,4,5,7,8-hexahydropyrano[3,4-e][1,3]oxazin-8-yl)benzonitrile

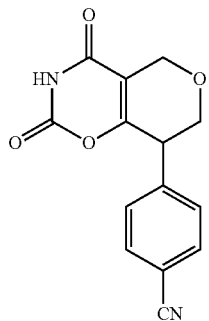 [SMILES: N#Cc1ccc(C2COCc3c2oc(=O)[nH]c3=O)cc1]

4-(4-oxotetrahydro-2H-pyran-3-yl)benzonitrile (Intermediate AA(2)) was reacted as described in Intermediate X(3) with carbonisocyanatidic chloride to give 4-(2,4-dioxo-2,3,4,5,7,8-hexahydropyrano[3,4-e][1,3]oxazin-8-yl)benzonitrile (Intermediate AA(3)). LC-MS (M+H)$^+$=271.1. $^1$H NMR (400 MHz, CDCl$_3$) δ ppm 7.57-7.78 (m, 2H) 7.41-7.51 (m, 2H) 4.61-4.75 (m, 1H) 4.50 (dd, J=15.49, 2.14 Hz, 1H) 4.04-4.20 (m, 2H) 3.78 (br. s., 1H).

Intermediate AA(4)

4-(2,4-dioxo-2,3,4,5,7,8-hexahydro-1H-pyrano[4,3-d]pyrimidin-8-yl)benzonitrile

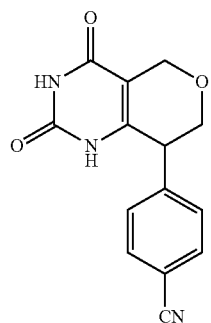 [SMILES: N#Cc1ccc(C2COCc3c2[nH]c(=O)[nH]c3=O)cc1]

4-(2,4-dioxo-2,3,4,5,7,8-hexahydropyrano[3,4-e][1,3]oxazin-8-yl)benzonitrile (Intermediate AA(3)) was reacted as described in Intermediate X(4) with ammonium hydroxide to give 4-(2,4-dioxo-2,3,4,5,7,8-hexahydro-1H-pyrano[4,3-d]pyrimidin-8-yl)benzonitrile (Intermediate AA(4)). LC-MS (M−H)⁺=270.2.

Preparation AA 4-(2,4-dichloro-7,8-dihydro-5H-pyrano[4,3-d]pyrimidin-8-yl)benzonitrile

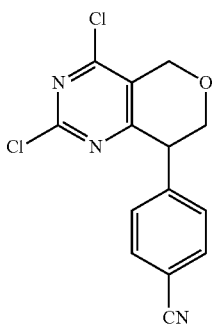 [SMILES: N#Cc1ccc(C2COCc3c(Cl)nc(Cl)nc32)cc1]

4-(2,4-dioxo-2,3,4,5,7,8-hexahydro-1H-pyrano[4,3-d]pyrimidin-8-yl)benzonitrile (Intermediate AA(4)) was reacted as described in Preparation X with POCl₃ to give 4-(2,4-dichloro-7,8-dihydro-5H-pyrano[4,3-d]pyrimidin-8-yl)benzonitrile (Preparation AA). LC-MS (M+H)⁺=306.1.

Preparation AAa 4-(2-chloro-4-(ethylamino)-7,8-dihydro-5H-pyrano[4,3-d]pyrimidin-8-yl)benzonitrile

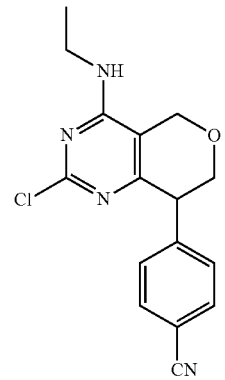 [SMILES: CCNc1nc(Cl)nc2c1COCC2c1ccc(C#N)cc1]

4-(2,4-dichloro-7,8-dihydro-5H-pyrano[4,3-d]pyrimidin-8-yl)benzonitrile (Preparation AA) was reacted as described in Preparation Xa with ethanamine to give 4-(2-chloro-4-(ethylamino)-7,8-dihydro-5H-pyrano[4,3-d]pyrimidin-8-yl)benzonitrile (Preparation AAa). LC-MS (M+H)⁺=315.1.

Preparation AB 2,4-dichloro-8-(4-(trifluoromethoxy)phenyl)-7,8-dihydro-5H-pyrano[4,3-d]pyrimidine

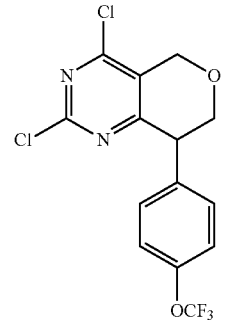 [SMILES: FC(F)(F)Oc1ccc(C2COCc3c(Cl)nc(Cl)nc32)cc1]

Intermediate AB(2)

3-(4-(trifluoromethoxy)phenyl)dihydro-2H-pyran-4(3H)-one

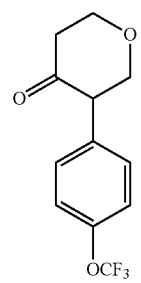

The procedure of Intermediate X(2) was utilized with 4-(trifluoromethoxy)phenylboronic acid to obtain 3-(4-(trifluoromethoxy)phenyl)dihydro-2H-pyran-4(3H)-one. $^1$H NMR (400 MHz, CDCl$_3$) δ ppm 7.29 (2H, d, J=7.05 Hz), 7.19-7.25 (2H, m), 4.23-4.32 (2H, m), 3.91-4.04 (2H, m), 3.84 (1H, dd, J=8.81, 6.30 Hz), 2.66-2.77 (1H, m), 2.56-2.63 (1H, m)

Intermediate AB(3)

8-(4-(trifluoromethoxy)phenyl)-7,8-dihydropyrano[3,4-e][1,3]oxazine-2,4(3H,5H)-dione

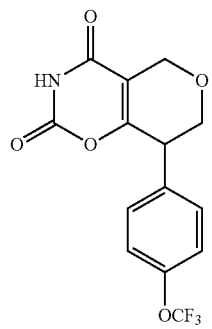 [SMILES: O=c1[nH]c(=O)c2c(o1)C(c1ccc(OC(F)(F)F)cc1)COC2]

The procedure of Intermediate X(3) was utilized to obtain 8-(4-(trifluoromethoxy)phenyl)-7,8-dihydropyrano[3,4-e][1,3]oxazine-2,4(3H,5H)-dione. $^1$H NMR (500 MHz, DMSO-d$_6$) δ ppm 11.98 (1H, s), 7.52 (2H, d, J=8.55 Hz), 7.37 (2H, d, J=7.93 Hz), 4.45-4.51 (1H, m), 4.36 (1H, dd, J=14.95, 2.14 Hz), 4.00-4.08 (2H, m), 3.82 (1H, dd, J=10.68, 3.36 Hz).

Intermediate AB(4)

8-(4-(trifluoromethoxy)phenyl)-7,8-dihydro-1H-pyrano[4,3-d]pyrimidine-2,4(3H,5H)-dione

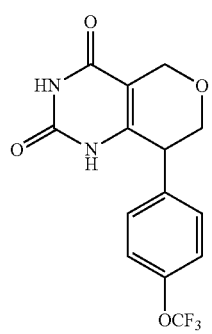 [SMILES: O=c1[nH]c2c(c(=O)[nH]1)COCC2c1ccc(OC(F)(F)F)cc1]

The procedure of Intermediate X(4) was utilized to obtain 8-(4-(trifluoromethoxy)phenyl)-7,8-dihydro-1H-pyrano[4,3-d]pyrimidine-2,4(3H,5H)-dione. LC-MS (M+H)$^+$=329.0.

Preparation AB 2,4-dichloro-8-(4-(trifluoromethoxy)phenyl)-7,8-dihydro-5H-pyrano[4,3-d]pyrimidine

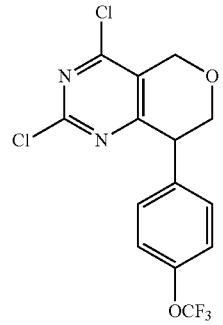 [SMILES: FC(F)(F)Oc1ccc(C2COCc3c(Cl)nc(Cl)nc32)cc1]

The procedure of Preparation X was utilized to obtain 2,4-dichloro-8-(4-(trifluoromethoxy)phenyl)-7,8-dihydro-5H-pyrano[4,3-d]pyrimidine. LC-MS (M+H)$^+$=365.0.

Preparation ABa 2-chloro-N-methyl-8-(4-(trifluoromethoxy)phenyl)-7,8-dihydro-5H-pyrano[4,3-d]pyrimidin-4-amine

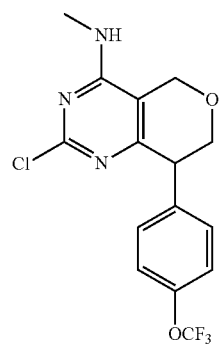 [SMILES: CNc1nc(Cl)nc2c1COCC2c1ccc(OC(F)(F)F)cc1]

To a solution of 2,4-dichloro-8-(4-(trifluoromethoxy)phenyl)-7,8-dihydro-5H-pyrano[4,3-d]pyrimidine (Preparation AB) (80.7 mg, 0.221 mmol) in MeOH (2210 μL) was added methylamine (1000 μL, 2.0 mmol) (2M in THF). The reaction was allowed to stir overnight. Removed the solvent and applied to silica gel, eluting with an EtOAc/Hex gradient to afford 2-chloro-N-methyl-8-(4-(trifluoromethoxy)phenyl)-7,8-dihydro-5H-pyrano[4,3-d]pyrimidin-4-amine (69.8 mg, 0.194 mmol, 88% yield). LC-MS (M+H)$^+$=360.0.

Preparation ABb 2-chloro-4-((R)-3-fluoropyrrolidin-1-yl)-8-(4-(trifluoromethoxy)phenyl)-7,8-dihydro-5H-pyrano[4,3-d]pyrimidine

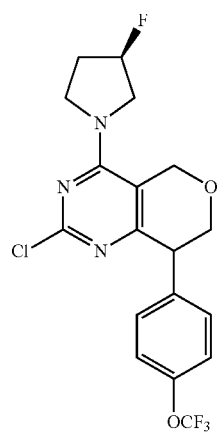 [SMILES: F[C@@H]1CCN(c2nc(Cl)nc3c2COCC3c2ccc(OC(F)(F)F)cc2)C1]

To a solution of 2,4-dichloro-8-(4-(trifluoromethoxy)phenyl)-7,8-dihydro-5H-pyrano[4,3-d]pyrimidine (Preparation AB) (56.4 mg, 0.154 mmol) in MeOH (1545 µL) was added DIPEA (67.4 µL, 0.386 mmol), then solid (R)-3-fluoropyrrolidine, HCl (21.34 mg, 0.170 mmol). The reaction was allowed to stir at rt. Removed the solvent and applied to silica gel. Eluted with a EtOAc/Hex gradient to afford the diasteriomeric mixture 2-chloro-4-((R)-3-fluoropyrrolidin-1-yl)-8-(4-(trifluoromethoxy)phenyl)-7,8-dihydro-5H-pyrano[4,3-d]pyrimidine (57.6 mg, 0.138 mmol, 89% yield). LC-MS (M+H)$^+$=418.1.

Preparation AC 2,4-Dichloro-8-phenyl-5,6,7,8-tetrahydroquinazoline

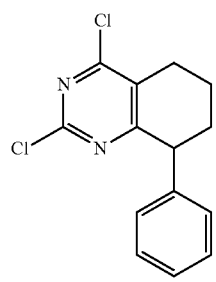 [SMILES: Clc1nc(Cl)c2c(n1)C(c1ccccc1)CCC2]

Intermediate AC(1)

8-Phenyl-5,6,7,8-tetrahydro-2H-benzo[e][1,3]oxazine-2,4(3H)-dione

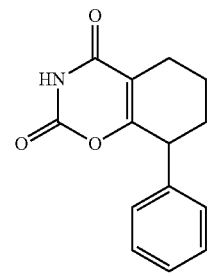 [SMILES: O=c1[nH]c(=O)c2c(o1)C(c1ccccc1)CCC2]

A solution of 2-phenylcyclohexanone (1.500 g, 8.61 mmol) and carbonisocyanatidic chloride (0.966 mL, 12 mmol) was stirred at 58° C. in a high-pressure vessel (75 mL) for 1 h. The temperature was raised to 130° C. and the reaction mixture was stirred for 2 h. After cooling to room temperature, the reaction mixture solidified. The solid residue was dissolved in ethyl acetate and washed with saturated aqueous solution of sodium bicarbonate. The organic layer was separated and the aqueous layer was extracted twice with ethyl acetate. The combined organic extracts were dried over anhydrous sodium sulfate and filtered. The solvent was removed in vacuum and the oily residue was purified by column chromatography on silica gel to provide 8-phenyl-5,6,7,8-tetrahydro-2H-benzo[e][1,3]oxazine-2,4(3H)-dione (415.0 mg, 1.689 mmol, 19.62% yield) as white solid and 4a-phenyl-4a,5,6,7-tetrahydro-2H-benzo[e][1,3]oxazine-2,4(3H)-dione (746.4 mg, 3.04 mmol, 35.3% yield) as white solid.

8-phenyl-5,6,7,8-tetrahydro-2H-benzo[e][1,3]oxazine-2,4(31-1)-dione. LC-MS (M+H)$^+$=244.1. $^1$H NMR (500 MHz, CDCl$_3$) δ ppm 8.61 (1H, br s), 7.22-7.38 (3H, m), 7.09-7.19 (2H, m), 3.81 (1H, t, J=4.9 Hz), 2.39-2.63 (2H, m), 2.15 (1H, dddd, J=13.2, 9.8, 6.3, 3.1 Hz), 1.84-1.96 (1H, m), 1.52-1.84 (2H, m).

4a-phenyl-4a,5,6,7-tetrahydro-2H-benzo[e][1,3]oxazine-2,4(3H)-dione. LC-MS (M+H)$^+$=244.1. $^1$H NMR (500 MHz, CDCl$_3$) δ ppm 7.66 (1H, br s), 7.40-7.46 (2H, m), 7.29-7.39 (3H, m), 5.99-6.06 (1H, m), 2.37 (1H, ddd, J=14.0, 3.4, 3.1 Hz), 2.10-2.29 (3H, m), 1.54-1.64 (1H, m), 1.21-1.36 (1H, m).

Intermediate AC(2)

8-Phenyl-5,6,7,8-tetrahydroquinazoline-2,4(1H,3H)-dione

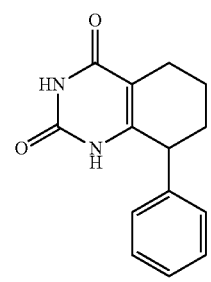 [SMILES: O=c1[nH]c2c(c(=O)[nH]1)CCCC2c1ccccc1]

A solution of 8-phenyl-5,6,7,8-tetrahydro-2H-benzo[e][1,3]oxazine-2,4(3H)-dione (415.0 mg, 1.706 mmol) in concentrated ammonium hydroxide (35 mL, 899 mmol) was stirred at 100° C. in a high-pressure vessel (75 mL) for 6 h. The formation of white precipitate was observed during the heating. The LC/MS analysis of the filtrate shows the presence of the product with the desired mass (M+H)=243.20. The solvent was removed in vacuum to provide 8-phenyl-5,6,7,8-tetrahydroquinazoline-2,4(1H,3H)-dione (435 mg, 1.706 mmol, 100% yield) as off-white solid. LC-MS (M+H)⁺ =243.2. ¹H NMR (500 MHz, DMSO-d₆) δ ppm 10.2 (2H, br. s.), 7.34 (2H, t, J=7.5 Hz), 7.26 (1H, t, J=7.3 Hz), 7.14 (2H, d, J=7.3 Hz), 3.80 (1H, br. s.), 2.32-2.43 (1H, m), 2.15 (1H, ddd, J=16.9, 10.5, 6.1 Hz), 1.93-2.04 (1H, m), 1.67-1.75 (1H, m), 1.56 (1H, ddd, J=7.8, 5.2, 2.6 Hz), 1.36 (1H, dt, J=13.1, 2.7 Hz).

Preparation AC 2,4-Dichloro-8-phenyl-5,6,7,8-tetrahydroquinazoline

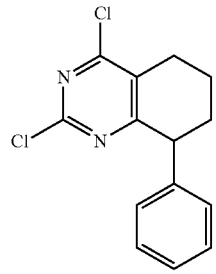 [SMILES: Clc1nc(Cl)c2c(n1)C(c1ccccc1)CCC2]

A mixture of 8-phenyl-5,6,7,8-tetrahydroquinazoline-2,4 (1H,3H)-dione (233.1 mg, 0.962 mmol), phosphorus oxychloride (2798 µL, 30.0 mmol) and N,N-dimethylaniline (933 µL, 7.36 mmol) was heated at 110° C. in a capped vial overnight. The reaction mixture was poured into a beaker with ice and the inside of the reaction vessel was washed with dichloromethane. As soon as the ice completely melted, the content of the beaker was placed into a separatory funnel The organic layer was separated and the aqueous layer was extracted with dichloromethane. The combined organic extracts were dried over anhydrous sodium sulfate and filtered. The solvent was removed in vacuum and the residue was purified by column chromatography on silica gel to provide 2,4-dichloro-8-phenyl-5,6,7,8-tetrahydroquinazoline (320.3 mg, 83%) as yellow oil. LC-MS (M+H)⁺=279.1. ¹H NMR (500 MHz, CDCl₃) δ ppm 7.28 (2H, t, J=7.5 Hz), 7.19-7.24 (1H, m), 6.95 (2H, d, J=7.3 Hz), 4.23 (1H, t, J=5.6 Hz), 2.82-2.92 (1H, m), 2.72-2.82 (1H, m), 2.10-2.22 (1H, m), 1.97-2.06 (1H, m), 1.76-1.93 (2H, m).

Preparation ACa

2-Chloro-N-ethyl-N-methyl-8-phenyl-5,6,7,8-tetrahydroquinazolin-4-amine

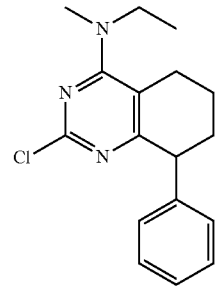 [SMILES: CCN(C)c1nc(Cl)nc2c1CCCC2c1ccccc1]

To a solution of 2,4-dichloro-8-phenyl-5,6,7,8-tetrahydroquinazoline (53.9 mg, 0.193 mmol) in methanol (1 mL) was added N-methylethanamine (0.033 mL, 0.386 mmol). The reaction mixture was stirred at room temperature for 2 h. The solvent was removed in vacuum and the residue was purified by column chromatography on silica gel to give 2-chloro-N-ethyl-N-methyl-8-phenyl-5,6,7,8-tetrahydroquinazolin-4-amine (42.9 mg, 0.141 mmol, 72.9% yield) as colorless oil. LC-MS (M+H)⁺=302.2. ¹H NMR (500 MHz, CDCl₃) δ ppm 7.25 (2H, t, J=7.5 Hz), 7.13-7.20 (1H, m), 7.01 (2H, d, J=7.3 Hz), 4.06-4.14 (1H, m), 3.42-3.53 (2H, m), 3.05 (3H, s), 2.56-2.74 (2H, m), 2.17-2.27 (1H, m), 1.76-1.89 (2H, m), 1.52-1.64 (1H, m), 1.24 (3H, t, J=7.2 Hz).

Preparation ACb

2-Chloro-8-phenyl-5,6,7,8-tetrahydroquinazoline

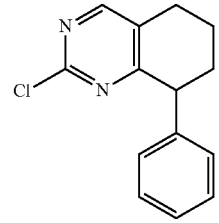 [SMILES: Clc1ncc2c(n1)C(c1ccccc1)CCC2]

A mixture of 2,4-dichloro-8-phenyl-5,6,7,8-tetrahydroquinazoline (51.9 mg, 0.186 mmol), ammonium chloride (13.0 mg, 0.243 mmol) and zinc (130 mg, 1.988 mmol) in acetone (0.75 mL) and water (0.75 mL) was heated at 90° C. with stirring for 2 h. The reaction mixture was filtered through a short plug of diatomaceous earth (Celite®). The solvent was removed in vacuum, and the residue was partitioned between dichloromethane and water. The organic layer was separated and the aqueous layer was extracted with dichloromethane. The combined organic extracts were dried over anhydrous magnesium sulfate and filtered. The solvent was removed in vacuum and the residue was purified by column chromatography on silica gel to give 2-chloro-8-phenyl-5,6,7,8-tetrahydroquinazoline (24.1 mg, 0.097 mmol, 52.4% yield) as white solid. LC-MS (M+H)⁺=245.1. ¹H NMR (500 MHz, CDCl₃) δ ppm 8.39 (1H, s), 7.27 (2H, t, J=7.6 Hz), 7.16-7.23 (1H, m), 6.95 (2H, d, J=7.3 Hz), 4.21 (1H, t, J=6.0 Hz), 2.72-2.91 (2H, m), 2.14-2.26 (1H, m), 1.95-2.06 (1H, m), 1.81-1.93 (1H, m), 1.71-1.81 (1H, m).

Preparation AD

2,4-dichloro-8-(4-fluorophenyl)-5,6,7,8-tetrahydroquinazoline

Intermediate AD(1)

8-Phenyl-5,6,7,8-tetrahydro-2H-benzo[e][1,3]oxazine-2,4(3H)-dione

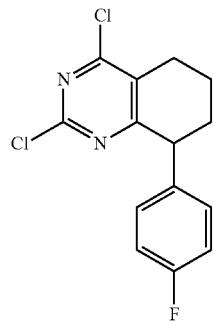 [SMILES: Fc1ccc(C2CCCc3c(Cl)nc(Cl)nc32)cc1]

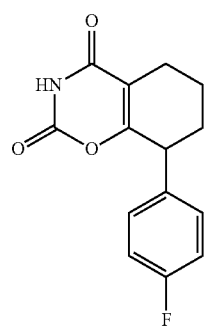 [SMILES: O=c1[nH]c(=O)c2c(o1)C(c1ccc(F)cc1)CCC2]

2-(4-fluorophenyl)cyclohexanone and carbonisocyanatidic chloride (0.966 mL, 12 mmol) was reacted as in Intermediate AC(1) to provide 8-(4-fluorophenyl)-5,6,7,8-tetrahydro-2H-benzo[e][1,3]oxazine-2,4(3H)-dione (415.0 mg, 1.689 mmol, 19.62% yield) as white solid and 4a-(4-fluorophenyl)-4a,5,6,7-tetrahydro-2H-benzo[e][1,3]oxazine-2,4(3H)-dione (746.4 mg, 3.04 mmol, 35.3% yield) as white solid. 8-(4-fluorophenyl)-5,6,7,8-tetrahydro-2H-benzo[e][1,3]oxazine-2,4(3H)-dione. LC-MS (M+H)$^+$=262.1. $^1$H NMR (500 MHz, CDCl$_3$) δ ppm 9.61 (1H, br s), 7.10 (2H, dd, J=5.0, 8.5 Hz), 6.98 (2H, app t, J=8.5 Hz), 3.77 (1H, t, J=4.9 Hz), 2.38-2.53 (2H, m), 2.16-2.07 (1H, m), 1.87-1.62 (3H, m).

Intermediate AD(2)

8-(4-fluorophenyl)-5,6,7,8-tetrahydroquinazoline-2,4(1H,3H)-dione

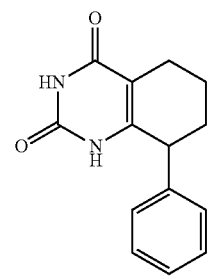 [SMILES: O=c1[nH]c2c(c(=O)[nH]1)CCCC2c1ccccc1]

A solution of 8-(4-fluorophenyl)-5,6,7,8-tetrahydro-2H-benzo[e][1,3]oxazine-2,4(3H)-dione was reacted in the manner of Intermediate AC(2) to provide 8-(4-fluorophenyl)-5,6,7,8-tetrahydroquinazoline-2,4(1H,3H)-dione. LC-MS (M+H)$^+$=261.2.

Preparation AD

2,4-dichloro-8-(4-fluorophenyl)-5,6,7,8-tetrahydroquinazoline

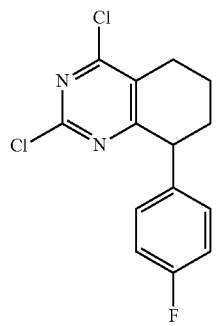 [SMILES: Fc1ccc(C2CCCc3c(Cl)nc(Cl)nc32)cc1]

A mixture of 8-(4-fluorophenyl)-5,6,7,8-tetrahydroquinazoline-2,4(1H,3H)-dione was reacted in the manner of Preparation AC to provide 2,4-dichloro-8-(4-fluorophenyl)-5,6,7,8-tetrahydroquinazoline, which was not characterized at this step.

Preparation ADa

2-Chloro-N-ethyl-8-(4-fluorophenyl)-N-methyl-5,6,7,8-tetrahydroquinazolin-4-amine

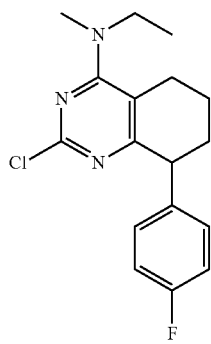 [SMILES: CCN(C)c1nc(Cl)nc2c1CCCC2c1ccc(F)cc1]

A solution of 2,4-dichloro-8-(4-fluorophenyl)-5,6,7,8-tetrahydroquinazoline (115 mg, 0.387 mmol) and excess N-methylethanamine (0.332 mL, 3.87 mmol) in MeOH (2 mL) was stirred at room temperature for 30 min. The solvent was removed in vacuum to afford 2-chloro-N-ethyl-8-(4-fluorophenyl)-N-methyl-5,6,7,8-tetrahydroquinazolin-4-amine (124 mg, 0.388 mmol, 100% yield). LC-MS $(M+H)^+=320.2$.

Preparation ADb

2-Chloro-8-(4-fluorophenyl)-N,N-dimethyl-5,6,7,8-tetrahydroquinazolin-4-amine

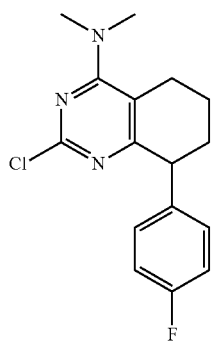 [SMILES: CN(C)c1nc(Cl)nc2c1CCCC2c1ccc(F)cc1]

A solution of 2,4-dichloro-8-(4-fluorophenyl)-5,6,7,8-tetrahydroquinazoline (115 mg, 0.387 mmol) and excess dimethylamine (1.935 mL, 3.87 mmol) in MeOH (1 mL) was stirred at room temperature for 1 h. The solvent was removed in vacuum to afford 2-chloro-8-(4-fluorophenyl)-N,N-dimethyl-5,6,7,8-tetrahydroquinazolin-4-amine (118 mg, 0.386 mmol, 100% yield). LC-MS $(M+H)^+=306.2$.

Preparation ADc

2-Chloro-8-(4-fluorophenyl)-5,6,7,8-tetrahydroquinazoline

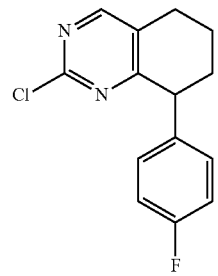 [SMILES: Fc1ccc(C2CCCc3cnc(Cl)nc32)cc1]

A mixture of 2,4-dichloro-8-(4-fluorophenyl)-5,6,7,8-tetrahydroquinazoline (115 mg, 0.387 mmol), Ammonium chloride (26.9 mg, 0.503 mmol) and zinc (266 mg, 4.06 mmol) in acetone (1 mL) and water (1.000 mL) was heated at 90° C. with stirring for 2 h. The reaction mixture was filtered through a short plug of celite. The solvent was removed in vacuum, and the residue was partitioned between dichloromethane and water. The organic layer was separated and the aqueous layer was extracted with dichloromethane. The combined organic extracts were dried over anhydrous magnesium sulfate and filtered. The solvent was removed in vacuum and the residue was purified by column chromatography on silica gel to give 2-chloro-8-(4-fluorophenyl)-5,6,7,8-tetrahydroquinazoline (20 mg, 0.076 mmol, 19.67% yield) as a white solid. LC-MS $(M+H)^+=263.2$.

Preparation AE 2,4-dichloro-6-(4-methoxybenzyl)-8-phenyl-5,6,7,8-tetrahydropyrido[4,3-d]pyrimidine

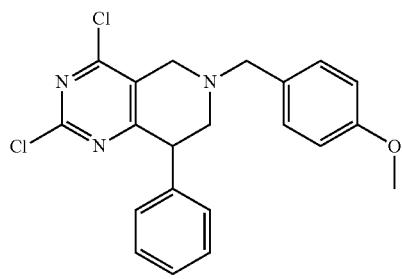 [SMILES: COc1ccc(CN2Cc3c(Cl)nc(Cl)nc3C(c3ccccc3)C2)cc1]

Intermediate AE(1)

Ethyl 2-cyano-2-phenylacetate

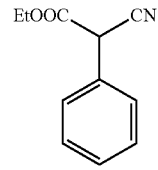

To a solution of sodium hydride (24.5 g, 1.02 mol) in THF was added benzyl cyanide (50.0 g, 0.426 mol) at −10° C. The reaction mixture was stirred for 15 min at the same temperature. Diethyl carbonate (60.5 g, 0.512 mol) was added to the reaction mixture and the reaction mixture was allowed to come to room temperature and heated to 40° C. (Caution: Reaction will start suddenly and exothermic). The heating path was removed immediately once the reaction was started and the reaction mixture was cooled under ice/acetone. The solution was allowed to come to room temperature and stirred for 1 h. The reaction mass was cooled to 0° C. and quenched with aqueous saturated ammonium chloride and extracted with ethyl acetate (250 mL×3). The combined organic layer was washed with water (200 mL), brine solution (200 mL), dried over anhydrous Na$_2$SO$_4$ and evaporated under reduced pressure to give ethyl 2-cyano-2-phenylacetate as crude compound as crude compound (71.0 g). The crude compound was taken to the next step without further purification. LC-MS (M+H)$^+$=190.1. $^1$H NMR (400 MHz, DMSO-d6) δ ppm 7.45 (5H, m), 5.65 (1H, s), 4.18 (2H, m), 1.18 (3H, t, J=7.2 Hz).

Intermediate AE(2)

ethyl 3-amino-2-phenylpropanoate

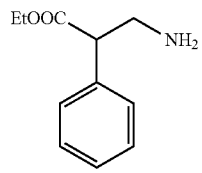

To a solution of Intermediate AE(1) (25.0 g, 0.132 mol) in methanol was added palladium on carbon (10%, w/w) followed by trifluoroacetic acid (2.0 vol., 50 mL) at room temperature. The reaction mixture was hydrogenated under 5 kg of hydrogen pressure for 3 h. The reaction mixture was filtered through celite bed and washed with methanol. The filtrate was evaporated under reduced pressure and the residue was neutralized with aqueous saturated bicarbonate solution. The aqueous solution was extracted with ethyl acetate (200 mL×4). The combined organic layer was washed with brine solution (200 mL), dried over anhydrous Na$_2$SO$_4$ and evaporated under reduced pressure to get crude compound. The crude compound was purified by column chromatography (Silica gel, 60-120 mesh) using 10% methanol in dichloromethane as mobile phase to give ethyl 3-amino-2-phenylpropanoate (17.0 g, 67%) as oily liquid. LC-MS (M+H)$^+$=194.0. $^1$H NMR (400 MHz, DMSO-d6): δ ppm 7.42-7.2 (7H, m), 4.11 (2H, m), 4.09 (1H, m), 3.44 (1H, m), 3.09 (1H, m), 1.15 (3H, t, J=5.6 Hz).

Intermediate AE(3)

ethyl 3-(3-ethoxy-3-oxopropylamino)-2-phenylpropanoate

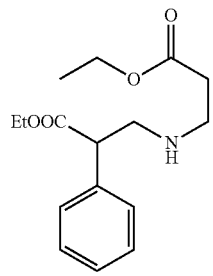 [SMILES: CCOC(=O)CCNCC(C(=O)OCC)c1ccccc1]

To a solution of Intermediate AE(2) (10.0 g, 51.7 mmol) in ethanol was added ethyl acrylate (4.1 g, 40.9 mmol) at room temperature. The reaction mixture was stirred at the same temperature for 18 h. The solvent was evaporated under reduced pressure and the crude compound was purified by column chromatography (Silica gel, 60-120 mesh) using 50% ethyl acetate in pet-ether as mobile phase to give ethyl 3-(3-ethoxy-3-oxopropylamino)-2-phenylpropanoate (12.1 g, 80%) as yellowish oily liquid. LC-MS (M+H)$^+$=294.1. $^1$H NMR (400 MHz, CDCl$_3$): δ ppm 7.29 (5H, m), 4.11 (4H, m), 3.76 (1H, m), 3.26 (1H, m), 2.90 (3H, m), 2.44 (2H, m), 1.20 (6H, m).

Intermediate AE(4)

ethyl 3-((3-ethoxy-3-oxopropyl)(4-methoxybenzyl)amino)-2-phenylpropanoate

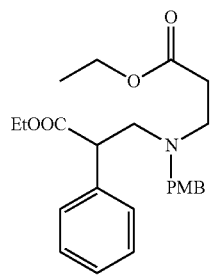

To a solution Intermediate AE(3) (15.0 g, 51.1 mmol) in acetone was added K$_2$CO$_3$ (8.4 g, 61.4 mmol) followed by p-methoxybenzyl bromide (15.4 g, 76.7 mmol) at room temperature. The reaction mixture was heated at reflux for 3 h. The solvent was removed under reduced pressure and the residue was diluted with water. The aqueous layer was extracted with ethyl acetate (100×3). The combined organic layer was washed with brine solution (100 mL), dried over anhydrous Na$_2$SO$_4$ and evaporated under reduced pressure to get crude compound. The crude compound was purified by column chromatography (Silica gel, 60-120 mesh) using 30% ethyl acetate in pet-ether as mobile phase to give ethyl 3-((3-ethoxy-3-oxopropyl)(4-methoxybenzyl)amino)-2-phenylpropanoate (12.1 g, 60%) as oily liquid. LC-MS (M+H)$^+$=414.2. $^1$H NMR (400 MHz, CDCl$_3$): δ ppm 7.27 (5H, m), 7.13, (2H, m), 6.82 (2H, m), 4.11 (4H, m), 4.08 (3H, s), 4.06 (1H, m), 3.81 (1H, d, J=4.0 Hz), 3.79 (1H, d, J=4.0 Hz), 3.25 (1H, m), 2.73 (3H, m), 2.43 (2H, m), 1.24 (6H, m).

Intermediate AE(5)

ethyl 1-(4-methoxybenzyl)-4-oxo-5-phenylpiperidine-3-carboxylate

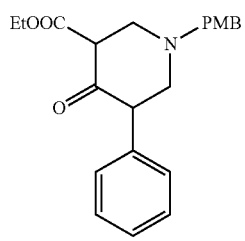

To a cooled solution of Intermediate AE(4) (12.0 g, 29.0 mmol) in THF was added t-BuOK (6.5 g, 58.0 mmol). The reaction mixture was stirred at room temperature for 2 h. The reaction mass was quenched with water then evaporated the solvent under reduced pressure. The residue was diluted with water and extracted with ethyl acetate (100 mL×2). The combined organic layer was washed with brine solution (100 mL), dried over anhydrous $Na_2SO_4$ and evaporated under reduced pressure to get crude compound. The crude compound was purified by column chromatography (Silica gel, 60-120 mesh) using 25% ethyl acetate in pet-ether as mobile phase to give ethyl 1-(4-methoxybenzyl)-4-oxo-5-phenylpiperidine-3-carboxylate (7.1 g, 67%) as oily liquid. LC-MS $(M+H)^+$ =368.2. $^1H$ NMR (400 MHz, $CDCl_3$): δ ppm 7.26 (4H, m), 7.15 (2H, m), 6.88 (2H, m), 4.15 (2H, m), 4.09 (3H, s), 3.82 (2H, m), 3.66 (2H, m), 2.80 (3H, m), 2.40 (1H, m), 1.24 (3H, m).

Intermediate AE(6)

6-(4-methoxybenzyl)-8-phenyl-5,6,7,8-tetrahydropyrido[4,3-d]pyrimidine-2,4(1H,3H)-dione

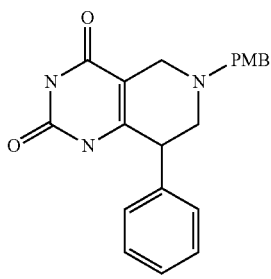

To a cooled solution of Intermediate AE(5) (7.0 g, 19.0 mmol) in ethanol was added t-BuOK (5.3 g, 47.6 mmol) followed by urea (2.8 g, 47.6 mmol). The reaction mixture was heated at reflux for 24 h. The reaction mass was quenched with water and evaporated the solvent under reduced pressure. The residue was diluted with water and extracted with ethyl acetate (100 mL×3). The combined organic layer was washed with brine solution (100 mL), dried over $Na_2SO_4$ and evaporated under reduced pressure to get crude compound. The crude compound was purified by column chromatography (Silica gel, 60-120 mesh) using 10% pet-ether in ethyl acetate as mobile phase to give 6-(4-methoxybenzyl)-8-phenyl-5,6,7,8-tetrahydropyrido[4,3-d]pyrimidine-2,4(1H,3H)-dione (4.0 g, 57%) as pale yellow solid. LC-MS $(M+H)^+$ =364.2. $^1H$ NMR (400 MHz, DMSO-d6): δ ppm 11.05 (1H, s), 10.60 (1H, s), 7.30 (5H, m), 6.99 (2H, m), 6.77 (2H, m), 3.72 (2H, m), 3.57 (3H, s), 3.44 (1H, m), 3.34 (1H, m), 2.90 (1H, m), 2.51 (2H, m).

Preparation AE 2,4-dichloro-6-(4-methoxybenzyl)-8-phenyl-5,6,7,8-tetrahydropyrido[4,3-d]pyrimidine

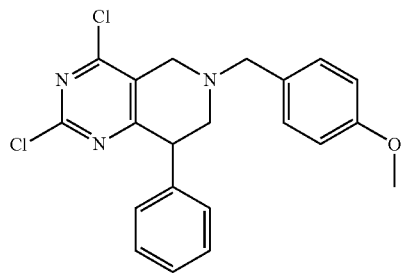 [SMILES: COc1ccc(CN2Cc3c(Cl)nc(Cl)nc3C(c3ccccc3)C2)cc1]

A solution of Intermediate AE(6) (2.0 g, 5.5 mmol) and catalytic amount of DMF in $POCl_3$ (20 vol.) was heated at reflux for 10 h. The excess of $POCl_3$ was evaporated under reduced pressure. The residue was poured in to crushed ice and stirred for 15 min. The aqueous solution was extracted with ethyl acetate (75 mL×3). The combined organic layer was washed with aqueous saturated $NaHCO_3$ (50 mL×2), brine solution (100 mL), dried over $Na_2SO_4$ and evaporated under reduced pressure to give 2,4-dichloro-6-(4-methoxybenzyl)-8-phenyl-5,6,7,8-tetrahydropyrido[4,3-d]pyrimidine (1.5 g, 69%) as brown solid. LC-MS $(M+H)^+$=400.0. $^1H$ NMR (400 MHz, $CDCl_3$): δ ppm 7.30 (3H, m), 7.26 (4H, m), 6.81 (2H, m), 4.20 (1H, m), 3.79 (2H, m), 3.72 (3H, s), 3.68 (2H, m), 3.57 (1H, m), 3.02 (1H, m), 2.98 (1H, m).

Preparation AEa 2-chloro-6-(4-methoxybenzyl)-N-methyl-8-phenyl-5,6,7,8-tetrahydropyrido[4,3-d]pyrimidin-4-amine

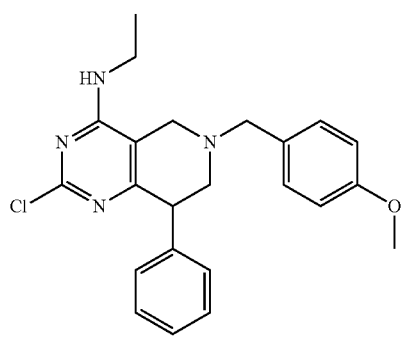 [SMILES: CCNc1nc(Cl)nc2c1CN(Cc1ccc(OC)cc1)CC2c1ccccc1]

To a solution of Preparation AE (1.1 g, 2.7 mmol) in acetonitrile was added diisopropylethylamine (1.0 g, 8.3 mmol) followed by addition of methylamine hydrochloride (0.28 g, 4.1 mmol) at room temperature. The reaction mixture was stirred at room temperature for 18 h. The solvent was removed under reduced pressure and the residue was purified by column chromatography (60-120 mesh) using 30% ethyl acetate in pet-ether as mobile phase to give 2-chloro-6-(4-methoxybenzyl)-N-methyl-8-phenyl-5,6,7,8-tetrahydropyrido[4,3-d]

pyrimidin-4-amine (0.8 g, 74%) as off-white solid. LC-MS (M+H)$^+$=395.2. $^1$H NMR (400 MHz, DMSO-d6): δ ppm 7.29 (4H, m), 7.16 (4H, m), 6.80 (2H, m), 3.93 (1H, m), 3.73 (3H, s), 3.66 (2H, m), 3.57 (1H, m), 3.46 (1H, m), 3.23 (1H, m), 2.67 (3H, d, J=4.0 Hz), 2.51 (1H, m).

Preparation AEb 2-chloro-N-ethyl-6-(4-methoxybenzyl)-8-phenyl-5,6,7,8-tetrahydropyrido[4,3-d]pyrimidin-4-amine

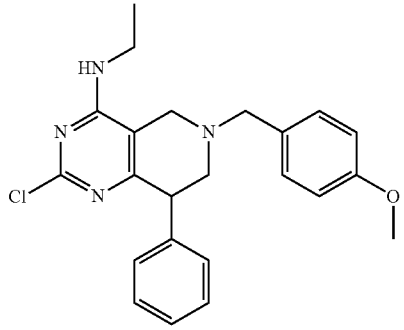 [SMILES: CCNc1nc(Cl)nc2c1CN(Cc1ccc(OC)cc1)CC2c1ccccc1]

To a solution of Preparation AE (1.6 g, 4.0 mmol) in acetonitrile was added diisopropylethylamine (1.5 g, 12.0 mmol) followed by addition of ethylamine hydrochloride (0.52 g, 6.0 mmol) at room temperature. The reaction mixture was stirred at the same temperature for 18 h. The solvent was removed under reduced pressure and the residue was purified by column chromatography (60-120 mesh) using 30% ethyl acetate in pet-ether as mobile phase to give 2-chloro-N-ethyl-6-(4-methoxybenzyl)-8-phenyl-5,6,7,8-tetrahydropyrido[4,3-d]pyrimidin-4-amine (0.9 g, 56%) as off-white solid. LC-MS (M−H)$^+$=407.0. $^1$H NMR (400 MHz, DMSO-d6): δ ppm 7.31-7.12 (7H, m), 6.83-6.79 (2H, m), 4.47 (1H, bs), 4.06 (1H, m), 3.83 (3H, s), 3.66 (2H, m), 3.58 (2H, m), 3.44 (1H, m), 3.20 (1H, m), 3.08 (1H, m), 2.88 (1H, m), 1.25 (3H, d, J=7.2 Hz).

Preparation AEc 2-chloro-N,N-dimethyl-6-(4-methoxybenzyl)-8-phenyl-5,6,7,8-tetrahydropyrido[4,3-d]pyrimidin-4-amine

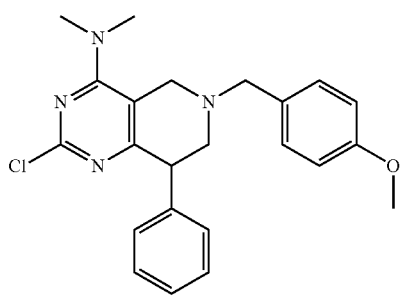 [SMILES: COc1ccc(CN2Cc3c(nc(Cl)nc3N(C)C)C(c3ccccc3)C2)cc1]

Using the procedure of Preparation AEb, utilized dimethylamine to produce 2-chloro-N,N-dimethyl-6-(4-methoxybenzyl)-8-phenyl-5,6,7,8-tetrahydropyrido[4,3-d]pyrimidin-4-amine Preparation AEd N2-(4-(4-chloro-1H-imidazol-1-yl)-3-methoxyphenyl)-N4-methyl-8-phenyl-5,6,7,8-tetrahydropyrido[4,3-d]pyrimidine-2,4-diamine

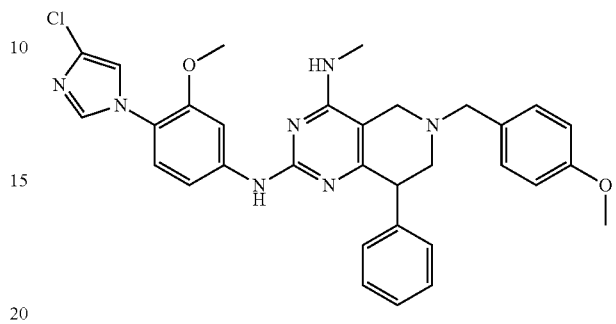

A solution of Preparation A (0.229 g, 1.02 mmol), Preparation AEa (0.45 g, 1.14 mmol), Na$_2$CO$_3$ (0.24 g, 2.28 mmol) and xantphos (0.659 g, 1.14 mmol) in dioxane/water (9:1) was purged with argon for 1 h at room temperature. Pd(dba)$_3$ (0.59 g, 0.57 mmol) was added to the reaction mixture and the resulting solution was purged for another 1 h. The reaction mass was heated at 110° C. for 24 h. The reaction mass was filtered through celite bed and washed with ethyl acetate. The filtrate was evaporated under reduced pressure and the residue was diluted with water. The aqueous solution was extracted with ethyl acetate (100 mL×2). The combined organic layer was washed with brine solution (100 mL), dried over anhydrous Na$_2$SO$_4$ and evaporated under reduced pressure to get crude compound. The crude compound was purified by column chromatography (Silica gel, 60-120 mesh) using 5% ethyl acetate in dichloromethane as mobile phase to give N2-(4-(4-chloro-1H-imidazol-1-yl)-3-methoxyphenyl)-N4-methyl-8-phenyl-5,6,7,8-tetrahydropyrido[4,3-d]pyrimidine-2,4-diamine (0.28 g, 43%) as off-white solid. LC-MS (M+H)$^+$=582.2. $^1$H NMR (400 MHz, DMSO-d6): δ ppm 9.06 (1H, s), 8.05 (1H, s), 7.71 (1H, s), 7.4 (1H, s), 7.39-7.06 (11H, m), 6.79 (2H, m), 6.73 (1H, m), 3.93 (1H, m), 3.71 (3H, s), 3.62 (2H, m), 3.55 (3H, s), 3.46 (1H, m), 3.26 (1H, m), 2.92 (3H, d, J=4.4 Hz).

Preparation AEe

N2-(4-(4-chloro-1H-imidazol-1-yl)-3-methoxyphenyl)-N4-ethyl-6-(4-methoxybenzyl)-8-phenyl-5,6,7,8-tetrahydropyrido[4,3-d]pyrimidine-2,4-diamine

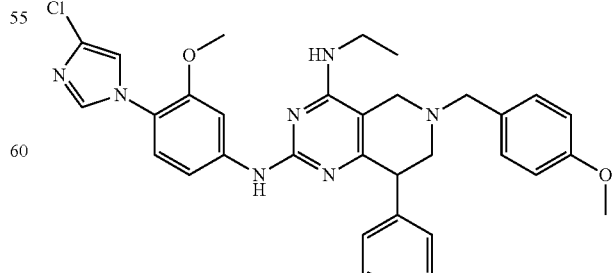

A solution of Preparation A (0.442 g, 1.98 mmol), Preparation AEb (0.9 g, 2.2 mmol), Na₂CO₃ (0.467 g, 4.4 mmol) and xantphos (1.27 g, 2.2 mmol) in dioxane/water (9:1) was purged with argon for 1 h at room temperature. Pd(dba)₃ (1.1 g, 1.1 mmol) was added to the reaction mixture and the resulting solution was purged for another 1 h. The reaction mass was heated at 110° C. for 24 h. The reaction mass was filtered through celite bed and washed with ethyl acetate. The filtrate was evaporated under reduced pressure and the residue was diluted with water. The aqueous solution was extracted with ethyl acetate (100 mL×3). The combined organic layer was washed with brine solution (100 mL), dried over anhydrous Na₂SO₄ and evaporated under reduced pressure to get crude compound. The crude compound was purified by column chromatography (Silica gel, 60-120 mesh) using 5% ethyl acetate in dichloromethane as mobile phase to give N2-(4-(4-chloro-1H-imidazol-1-yl)-3-methoxyphenyl)-N4-ethyl-6-(4-methoxybenzyl)-8-phenyl-5,6,7,8-tetrahydropyrido[4,3-d]pyrimidine-2,4-diamine (0.71 g, 54%) as off-white solid. LC-MS (M+H)⁺=596.2. ¹H NMR (400 MHz, DMSO-d6): δ ppm 9.03 (1H, s), 7.98 (1H, s), 7.71 (1H, s), 7.40 (1H, s), 7.27-7.10 (9H, m), 6.81-6.78 (2H, m), 6.72 (1H, m), 3.91 (1H, m), 3.71 (3H, s), 3.65 (2H, m), 3.56 (3H, s), 3.51-3.49 (3H, m), 3.28 (1H, m), 2.87 (1H, m), 2.65 (1H, m), 1.18 (3H, t, J=7.2 Hz).

Preparation AEf

N2-(3-fluoro-4-(3-methyl-1H-1,2,4-triazol-1-yl)phenyl)-6-(4-methoxybenzyl)-N4-methyl-8-phenyl-5,6,7,8-tetrahydropyrido[4,3-d]pyrimidine-2,4-diamine

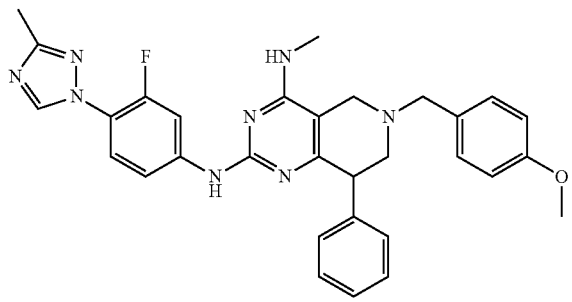 [SMILES: CNc1nc(Nc2ccc(-n3cnc(C)n3)c(F)c2)nc2c1CN(Cc1ccc(OC)cc1)CC2c1ccccc1]

A solution of Preparation B (0.175 g, 0.913 mmol), Preparation AEa (0.40 g, 1.01 mmol), Na₂CO₃ (0.20 g, 2.02 mmol) and xantphos (0.585 g, 1.01 mmol) in dioxane/water (9:1) was purged with argon for 1 h at room temperature. Pd(dba)₃ (0.525 g, 0.50 mmol) was added to the reaction mixture and the resulting solution was purged for another 1 h. The reaction mass was heated at 110° C. for 24 h. The reaction mass was filtered through celite bed and washed with ethyl acetate. The filtrate was evaporated under reduced pressure and the residue was diluted with water. The aqueous solution was extracted with ethyl acetate (100 mL×2). The combined organic layer was washed with brine solution (100 mL), dried over anhydrous Na₂SO₄ and evaporated under reduced pressure to get crude compound. The crude compound was purified by column chromatography (Silica gel, 60-120 mesh) using 5% ethyl acetate in dichloromethane as mobile phase to give N2-(3-fluoro-4-(3-methyl-1H-1,2,4-triazol-1-yl)phenyl)-6-(4-methoxybenzyl)-N4-methyl-8-phenyl-5,6,7,8-tetrahydropyrido[4,3-d]pyrimidine-2,4-diamine (0.24 g, 42%) as off-white solid. LC-MS (M+H)⁺=551.1.

Preparation AEg

N4-ethyl-N2-(3-fluoro-4-(3-methyl-1H-1,2,4-triazol-1-yl)phenyl)-6-(4-methoxybenzyl)-8-phenyl-5,6,7,8-tetrahydropyrido[4,3-d]pyrimidine-2,4-diamine

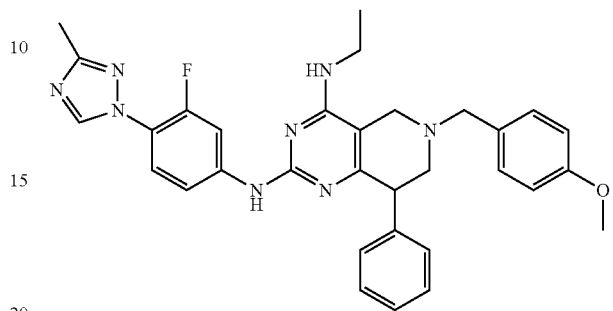

A solution of Preparation B (0.423 g, 2.20 mmol), Preparation AEb (1.0 g, 2.44 mmol), Na₂CO₃ (0.520 g, 4.89 mmol) and xantphos (1.41 g, 2.44 mmol) in dioxane/water (9:1) was purged with argon for 1 h at room temperature. Pd(dba)₃ (1.26 g, 1.22 mmol) was added to the reaction mixture and the resulting solution was purged for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (100 mL×3). The combined organic layer was washed with brine solution (100 mL), dried over anhydrous Na₂SO₄ and evaporated under reduced pressure to get crude compound. The crude compound was purified by column chromatography (Silica gel, 60-120 mesh) using 5% ethyl acetate in dichloromethane as mobile phase to give N4-ethyl-N2-(3-fluoro-4-(3-methyl-1H-1,2,4-triazol-1-yl)phenyl)-6-(4-methoxybenzyl)-8-phenyl-5,6,7,8-tetrahydropyrido[4,3-d]pyrimidine-2,4-diamine (0.70 g, 53%) as off-white solid. LC-MS (M+H)⁺=565.2.

Preparation AEh

N2-(3-fluoro-4-(5-methyl-1H-1,2,4-triazol-1-yl)phenyl)-6-(4-methoxybenzyl)-N4-methyl-8-phenyl-5,6,7,8-tetrahydropyrido[4,3-d]pyrimidine-2,4-diamine

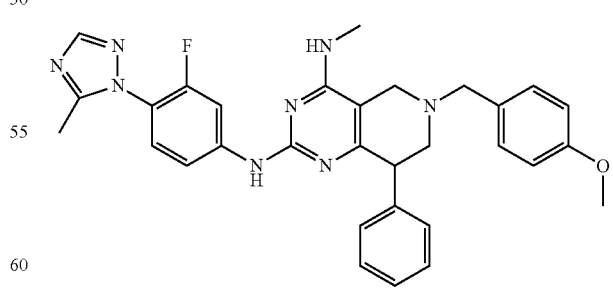

A solution of Preparation C (0.175 g, 0.913 mmol), Preparation AEa (0.40 g, 1.01 mmol), Na₂CO₃ (0.20 g, 2.02 mmol) and xantphos (0.586 g, 1.01 mmol) in dioxane/water (9:1) was purged with argon for 1 h at room temperature. Pd(dba)₃ (0.525 g, 0.50 mmol) was added to the reaction mixture and the resulting solution was purged for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (100 mL×2). The combined organic layer was washed with brine solution (100 mL), dried over anhydrous $Na_2SO_4$ and evaporated under reduced pressure to get crude compound. The crude compound was purified by column chromatography (Silica gel, 60-120 mesh) using 5% ethyl acetate in dichloromethane as mobile phase to give N2-(3-fluoro-4-(5-methyl-1H-1,2,4-triazol-1-yl)phenyl)-6-(4-methoxybenzyl)-N4-methyl-8-phenyl-5,6,7,8-tetrahydropyrido[4,3-d]pyrimidine-2,4-diamine (0.27 g, 51%) as off-white solid. LC-MS (M+H)⁺=565.2.

Preparation AEi

N4-ethyl-N2-(3-fluoro-4-(5-methyl-1H-1,2,4-triazol-1-yl)phenyl)-6-(4-methoxybenzyl)-8-phenyl-5,6,7,8-tetrahydropyrido[4,3-d]pyrimidine-2,4-diamine

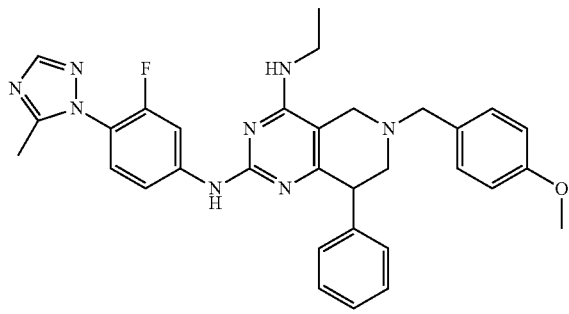 [SMILES: CCNc1nc(Nc2ccc(-n3ncnc3C)c(F)c2)nc2c1CN(Cc1ccc(OC)cc1)CC2c1ccccc1]

A solution of Preparation C (0.423 g, 2.20 mmol), Preparation AEb (1.0 g, 2.44 mmol), $Na_2CO_3$ (0.520 g, 4.89 mmol) and xantphos (1.41 g, 2.44 mmol) in dioxane/water (9:1) was purged with argon for 1 h at room temperature. Pd(dba)₃ (1.26 g, 1.22 mmol) was added to the reaction mixture and the resulting solution was purged for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (100 mL×3). The combined organic layer was washed with brine solution (100 mL), dried over anhydrous $Na_2SO_4$ and evaporated under reduced pressure to get crude compound. The crude compound was purified by column chromatography (Silica gel, 60-120 mesh) using 5% ethyl acetate in dichloromethane as mobile phase to give N4-ethyl-N2-(3-fluoro-4-(5-methyl-1H-1,2,4-triazol-1-yl)phenyl)-6-(4-methoxybenzyl)-8-phenyl-5,6,7,8-tetrahydropyrido[4,3-d]pyrimidine-2,4-diamine (0.72 g, 54%) as off-white solid. LC-MS (M+H)⁺=565.4.

Preparation AEj

N2-(4-(4-chloro-1H-imidazol-1-yl)-3-methoxyphenyl)-N4-methyl-8-phenyl-5,6,7,8-tetrahydropyrido[4,3-d]pyrimidine-2,4-diamine

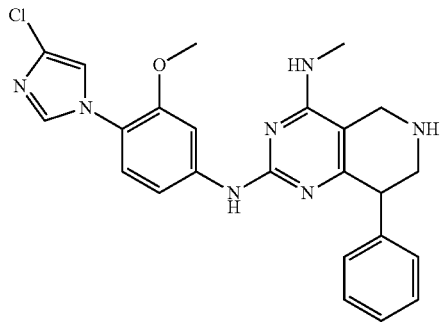 [SMILES: CNc1nc(Nc2ccc(-n3cnc(Cl)c3)c(OC)c2)nc2c1CNCC2c1ccccc1]

To a solution of Preparation AEd (0.28 g, 0.48 mmol) in toluene was added trifluoromethanesulfonic acid (3.0 vol.) at room temperature. The reaction mixture was heated at reflux for 1 h. The solvent was removed under reduced pressure and the residue was diluted with water. The aqueous solution was washed with dichloromethane (25 mL×2), basified by using aqueous saturated $NaHCO_3$ and extracted with ethyl acetate (50 mL×2). The combined organic layer was washed with brine solution (50 mL), dried over anhydrous $Na_2SO_4$ and evaporated under reduced pressure to give N2-(4-(4-chloro-1H-imidazol-1-yl)-3-methoxyphenyl)-N4-methyl-8-phenyl-5,6,7,8-tetrahydropyrido[4,3-d]pyrimidine-2,4-diamine as crude compound (0.195 g). The crude compound was taken to the next step without further purification. LC-MS (M+H)⁺=462.2. ¹H NMR (400 MHz, DMSO-d6): δ ppm 9.03 (1H, s), 8.06 (1H, s), 7.71 (1H, s), 7.39 (1H, s), 7.27-7.24 (2H, m), 7.18-7.05 (5H, m), 6.68 (1H, m), 5.76 (1H, s), 3.81 (1H, m), 3.69-3.63 (2H, m), 3.57 (3H, s), 3.22 (1H, m), 2.95 (3H, d, J=4.0 Hz), 2.84 (1H, m).

Preparation AEk

N2-(4-(4-chloro-1H-imidazol-1-yl)-3-methoxyphenyl)-N4-ethyl-8-phenyl-5,6,7,8-tetrahydropyrido[4,3-d]pyrimidine-2,4-diamine

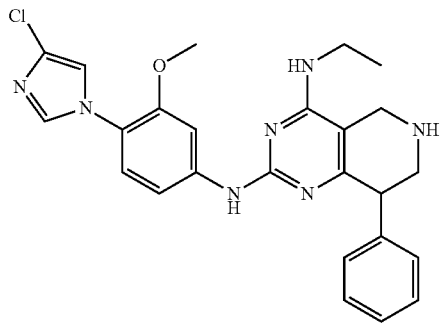 [SMILES: CCNc1nc(Nc2ccc(-n3cnc(Cl)c3)c(OC)c2)nc2c1CNCC2c1ccccc1]

To a solution of Preparation AEe (0.25 g, 0.42 mmol) in toluene was added trifluoromethanesulfonic acid (3.0 vol.) at room temperature. The reaction mixture was heated at reflux for 1 h. The solvent was removed under reduced pressure and the residue was diluted with water. The aqueous solution was washed with dichloromethane (50 mL×2), basified by using aqueous saturated NaHCO₃ and extracted with ethyl acetate (50 mL×3). The combined organic layer was washed with brine solution (50 mL), dried over anhydrous Na₂SO₄ and evaporated under reduced pressure to give N2-(4-(4-chloro-1H-imidazol-1-yl)-3-methoxyphenyl)-N4-ethyl-8-phenyl-5,6,7,8-tetrahydropyrido[4,3-d]pyrimidine-2,4-diamine as crude compound (0.19 g). The crude compound was taken to the next step without further purification. LC-MS (M+H)$^+$= 476.2. $^1$H NMR (400 MHz, DMSO-d6): δ ppm 9.00 (1H, s), 7.99 (1H, s), 7.71 (1H, s), 7.40 (1H, s), 7.28-7.24 (2H, m), 7.19-7.09 (6H, m), 5.76 (1H, m), 3.70 (1H, m), 3.58 (2H, m), 3.51 (3H, s), 3.48 (2H, m), 3.25 (1H, m), 2.80 (1H, m), 1.20 (3H, t, J=7.2 Hz).

Preparation AEl

N2-(3-fluoro-4-(3-methyl-1H-1,2,4-triazol-1-yl)phenyl)-N4-methyl-8-phenyl-5,6,7,8-tetrahydropyrido[4,3-d]pyrimidine-2,4-diamine

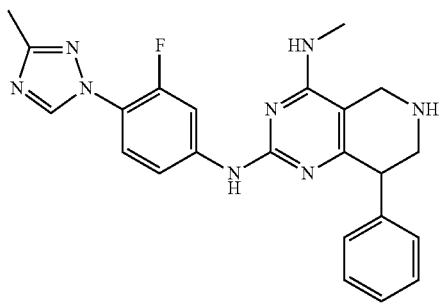 [SMILES: CNc1nc(Nc2ccc(-n3cnc(C)n3)c(F)c2)nc2c1CNCC2c1ccccc1]

To a solution of Preparation AEf (0.24 g, 0.436 mmol) in toluene was added trifluoromethanesulfonic acid (3.0 vol.) at room temperature. The reaction mixture was heated at reflux for 1 h. The solvent was removed under reduced pressure and the residue was diluted with water. The aqueous solution was washed with dichloromethane (25 mL×2), basified by using aqueous saturated NaHCO₃ and extracted with ethyl acetate (50 mL×2). The combined organic layer was washed with brine solution (50 mL), dried over anhydrous Na₂SO₄ and evaporated under reduced pressure to give N2-(3-fluoro-4-(3-methyl-1H-1,2,4-triazol-1-yl)phenyl)-N4-methyl-8-phenyl-5,6,7,8-tetrahydropyrido[4,3-d]pyrimidine-2,4-diamine as crude compound (0.190 g). The crude compound was taken to the next step without further purification. LC-MS (M+H)$^+$= 431.2. $^1$H NMR (400 MHz, DMSO-d6): δ ppm 9.13 (1H, s), 8.66 (1H, s), 8.00 (1H, m), 7.43-7.36 (2H, m), 7.29-7.26 (3H, m), 7.25-7.17 (3H, m), 6.75 (1H, m), 5.78 (1H, m), 3.83 (1H, m), 3.65 (2H, m), 3.33 (1H, m), 2.94 (3H, d, J=4.4 Hz), 2.33 (3H, s).

Preparation AEm

N4-ethyl-N2-(3-fluoro-4-(3-methyl-1H-1,2,4-triazol-1-yl)phenyl)-8-phenyl-5,6,7,8-tetrahydropyrido[4,3-d]pyrimidine-2,4-diamine

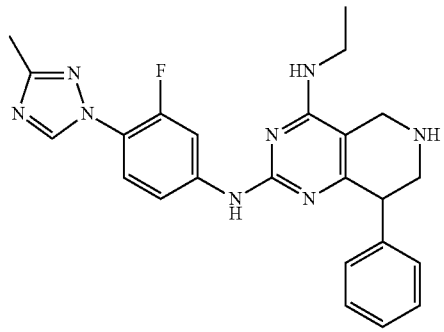 [SMILES: CCNc1nc(Nc2ccc(-n3cnc(C)n3)c(F)c2)nc2c1CNCC2c1ccccc1]

To a solution of Preparation AEg (0.490 g, 0.868 mmol) in toluene was added trifluoromethanesulfonic acid (3.0 vol.) at room temperature. The reaction mixture was heated at reflux for 1 h. The solvent was removed under reduced pressure and the residue was diluted with water. The aqueous solution was washed with dichloromethane (50 mL×2), basified by using aqueous saturated NaHCO₃ and extracted with ethyl acetate (50 mL×3). The combined organic layer was washed with brine solution (50 mL), dried over anhydrous Na₂SO₄ and evaporated under reduced pressure to give N4-ethyl-N2-(3-fluoro-4-(3-methyl-1H-1,2,4-triazol-1-yl)phenyl)-8-phenyl-5,6,7,8-tetrahydropyrido[4,3-d]pyrimidine-2,4-diamine as crude compound (0.220 g). The crude compound was taken to the next step without further purification. LC-MS (M+H)$^+$= 445.2.

Preparation AEn

N2-(3-fluoro-4-(5-methyl-1H-1,2,4-triazol-1-yl)phenyl)-N4-methyl-8-phenyl-5,6,7,8-tetrahydropyrido[4,3-d]pyrimidine-2,4-diamine

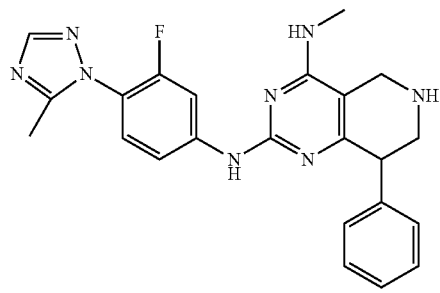 [SMILES: CNc1nc(Nc2ccc(-n3ncnc3C)c(F)c2)nc2c1CNCC2c1ccccc1]

To a solution of Preparation AEh (0.27 g, 0.490 mmol) in toluene was added trifluoromethanesulfonic acid (3.0 vol.) at room temperature. The reaction mixture was heated at reflux for 1 h. The solvent was removed under reduced pressure and the residue was diluted with water. The aqueous solution was washed with dichloromethane (25 mL×2), basified by using aqueous saturated NaHCO₃ and extracted with ethyl acetate (50 mL×2). The combined organic layer was washed with brine solution (50 mL), dried over anhydrous Na₂SO₄ and evaporated under reduced pressure to give N2-(3-fluoro-4-(5- methyl-1H-1,2,4-triazol-1-yl)phenyl)-N4-methyl-8-phenyl-5,6,7,8-tetrahydropyrido[4,3-d]pyrimidine-2,4-diamine as crude compound (0.210 g). The crude compound was taken to the next step without further purification. LC-MS (M+H)$^+$=551.2.

Preparation AEo

N4-ethyl-N2-(3-fluoro-4-(5-methyl-1H-1,2,4-triazol-1-yl)phenyl)-8-phenyl-5,6,7,8-tetrahydropyrido[4,3-d]pyrimidine-2,4-diamine

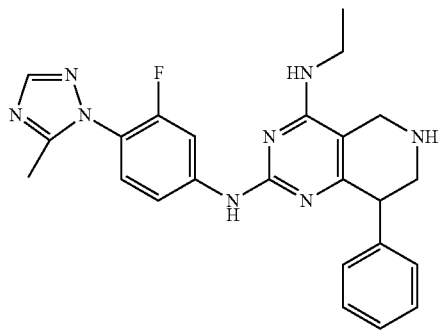 [SMILES: CCNc1nc(Nc2ccc(-n3ncnc3C)c(F)c2)nc2c1CNCC2c1ccccc1]

To a solution of Preparation AEi (0.75 g, 1.32 mmol) in toluene was added trifluoromethanesulfonic acid (3.0 vol.) at room temperature. The reaction mixture was heated at reflux for 1 h. The solvent was removed under reduced pressure and the residue was diluted with water. The aqueous solution was washed with dichloromethane (50 mL×2), basified by using aqueous saturated NaHCO$_3$ and extracted with ethyl acetate (50 mL×3). The combined organic layer was washed with brine solution (50 mL), dried over anhydrous Na$_2$SO$_4$ and evaporated under reduced pressure to give N4-ethyl-N2-(3-fluoro-4-(3-methyl-1H-1,2,4-triazol-1-yl)phenyl)-8-phenyl-5,6,7,8-tetrahydropyrido[4,3-d]pyrimidine-2,4-diamine as crude compound (0.60 g). The crude compound was taken to the next step without further purification. LC-MS (M+H)$^+$=445.2.

Preparation AEp 1-(4-(ethylamino)-2-(3-fluoro-4-(3-methyl-1H-1,2,4-triazol-1-yl)phenylamino)-8-phenyl-7,8-dihydropyrido[4,3-d]pyrimidin-6(5H)-yl)-2,2,2-trifluoroethanone

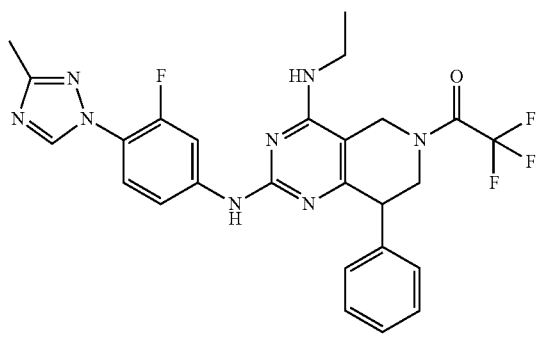 [SMILES: CCNc1nc(Nc2ccc(-n3cnc(C)n3)c(F)c2)nc2c1CN(C(=O)C(F)(F)F)CC2c1ccccc1]

To a solution of Preparation AEm (0.20 g, 0.449 mmol) in dichloromethane was added triethylamine (0.068 g, 0.67 mmol) followed by trifluoroacetic anhydride (0.14 g, 0.67 mmol) and catalytic amount of DMAP at 0° C. The reaction mixture was allowed to come to room temperature and stirred for 18 h. The reaction mixture was diluted with dichloromethane, washed with aqueous saturated NaHCO$_3$ (25 mL), brine solution (20 mL), dried over anhydrous Na$_2$SO$_4$ and evaporated under reduced pressure to give 1-(4-(ethylamino)-2-(3-fluoro-4-(3-methyl-1H-1,2,4-triazol-1-yl)phenylamino)-8-phenyl-7,8-dihydropyrido[4,3-d]pyrimidin-6(5H)-yl)-2,2,2-trifluoroethanone as crude compound (0.18 g, 74%). The crude compound was taken to the next step without further purification. LC-MS (M+H)$^+$=541.2.

Preparation AEq 1-(4-(ethylamino)-2-(3-fluoro-4-(5-methyl-1H-1,2,4-triazol-1-yl)phenylamino)-8-phenyl-7,8-dihydropyrido[4,3-d]pyrimidin-6(5H)-yl)-2,2,2-trifluoroethanone

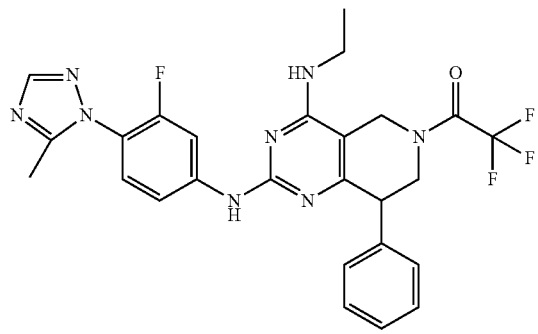 [SMILES: CCNc1nc(Nc2ccc(-n3ncnc3C)c(F)c2)nc2c1CN(C(=O)C(F)(F)F)CC2c1ccccc1]

To a solution of Preparation AEo (0.21 g, 0.47 mmol) in dichloromethane was added triethylamine (0.071 g, 0.70 mmol) followed by trifluoroacetic anhydride (0.15 g, 0.70 mmol) and catalytic amount of DMAP at 0° C. The reaction mixture was allowed to come to room temperature and stirred for 18 h. The reaction mixture was diluted with dichloromethane, washed with aqueous saturated NaHCO$_3$ (25 mL), brine solution (20 mL), dried over anhydrous Na$_2$SO$_4$ and evaporated under reduced pressure to give 1-(4-(ethylamino)-2-(3-fluoro-4-(5-methyl-1H-1,2,4-triazol-1-yl)phenylamino)-8-phenyl-7,8-dihydropyrido[4,3-d]pyrimidin-6 (5H)-yl)-2,2,2-trifluoroethanone as crude compound (0.185 g, 73%). The crude compound was taken to the next step without further purification. LC-MS (M+H)$^+$=541.2.

Preparation AF

2,4-dichloro-6-methyl-8-phenyl-5,6,7,8-tetrahydro-pyrido[4,3-d]pyrimidine

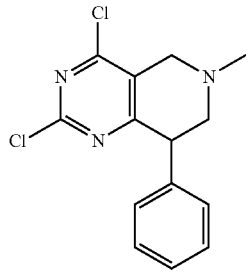 [SMILES: CN1Cc2c(Cl)nc(Cl)nc2C(c2ccccc2)C1]

Intermediate AF(1)

ethyl 3-((3-ethoxy-3-oxopropyl)(methyl)amino)-2-(4-fluorophenyl)propanoate

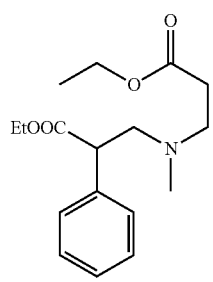 [SMILES: CCOC(=O)CCN(C)CC(C(=O)OCC)c1ccccc1]

To a solution of Intermediate AE(3) (4.0 g, 13.65 mmol) in acetone was added K$_2$CO$_3$ (3.7 g, 27.3 mmol) followed by methyl iodide (2.3 g, 16.3 mmol) at 0° C. The reaction mixture was stirred at room temperature for 2 h. The solvent was removed under reduced pressure and the residue was diluted with water. The aqueous layer was extracted with ethyl acetate (25×3). The combined organic layer was washed with brine solution (50 mL), dried over anhydrous Na$_2$SO$_4$ and evaporated under reduced pressure to get crude compound. The crude compound was purified by column chromatography (Silica gel, 60-120 mesh) using 40% ethyl acetate in pet-ether as mobile phase to give ethyl 3-((3-ethoxy-3-oxopropyl)(methyl)amino)-2-phenylpropanoate (0.9 g, 22%) as oily liquid. LC-MS (M+H)$^+$=308.0. $^1$H NMR (400 MHz, DMSO-d): δ ppm 7.33-7.26 (5H, m), 4.07-4.01 (4H, m), 3.83 (1H, m), 3.07 (1H, m), 2.69-2.52 (2H, m), 2.47-2.41 (3H, m), 2.21 (3H, s), 1.19-0.10 (6H, m).

Intermediate AF(2)

ethyl 1-methyl-4-oxo-5-phenylpiperidine-3-carboxylate

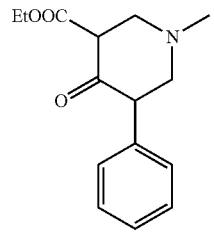 [SMILES: CCOC(=O)C1CN(C)CC(c2ccccc2)C1=O]

To a cooled solution of Intermediate AF(1) (0.9 g, 2.93 mmol) in THF was added t-BuOK (0.65 g, 5.86 mmol). The reaction mixture was stirred at room temperature for 2 h. The reaction mass was quenched with water then evaporated the solvent under reduced pressure. The residue was diluted with water and extracted with ethyl acetate (25 mL×2). The combined organic layer was washed with brine solution (25 mL), dried over anhydrous Na$_2$SO$_4$ and evaporated under reduced pressure to get crude compound. The crude compound was purified by column chromatography (Silica gel, 60-120 mesh) using 10% ethyl acetate in pet-ether as mobile phase to give ethyl 1-methyl-4-oxo-5-phenylpiperidine-3-carboxylate (7.1 g, 67%) as oily liquid. LC-MS (M+H)$^+$=262.2.

Intermediate AF(3)

6-methyl-8-phenyl-5,6,7,8-tetrahydropyrido[4,3-d]pyrimidine-2,4(1H,3H)-dione

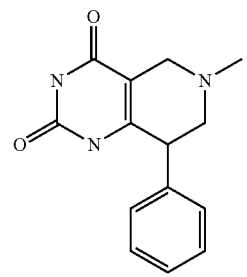 [SMILES: CN1Cc2c([nH]c(=O)[nH]c2=O)C(c2ccccc2)C1]

To a cooled solution of Intermediate AF(2) (4.5 g, 17.2 mmol) in ethanol was added t-BuOK (4.8 g, 43.1 mmol) followed by urea (2.58 g, 43.1 mmol). The reaction mixture was heated at reflux for 24 h. The reaction mass was quenched with water and evaporated the solvent under reduced pressure. The residue was diluted with water and extracted with ethyl acetate (50 mL×3). The combined organic layer was washed with brine solution (50 mL), dried over Na$_2$SO$_4$ and evaporated under reduced pressure to get crude compound. The crude compound was purified by column chromatography (Silica gel, 60-120 mesh) using 10% methanol in dichloromethane as mobile phase to give 6-methyl-8-phenyl-5,6,7,8-tetrahydropyrido[4,3-d]pyrimidine-2,4(1H,3H)-dione (2.5 g, 56%) as pale yellow solid. LC-MS (M+H)$^+$=258.2 $^1$H NMR (400 MHz, DMSO-d6): δ ppm 11.04 (1H, s), 10.56 (1H, s), 7.33-7.23 (5H, m), 3.73 (1H, m), 4.75 (1H, m), 2.83 (1H, m), 2.78 (1H, m), 2.68 (1H, m), 2.22 (3H, s).

Preparation AF 2,4-dichloro-6-methyl-8-phenyl-5,6,7,8-tetrahydropyrido[4,3-d]pyrimidine

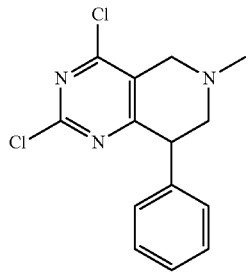 [SMILES: CN1Cc2c(Cl)nc(Cl)nc2C(c2ccccc2)C1]

A solution of Intermediate AF(3) (4.0 g, 15.56 mmol) and catalytic amount of DMF in POCl$_3$ (20 vol.) was heated at reflux for 10 h. The excess of POCl$_3$ was evaporated under reduced pressure. The residue was poured in to crushed ice and stirred for 15 min. The aqueous solution was extracted with ethyl acetate (75 mL×3). The combined organic layer was washed with aqueous saturated NaHCO$_3$ (50 mL×2), brine solution (75 mL), dried over Na$_2$SO$_4$ and evaporated under reduced pressure to give 2,4-dichloro-6-methyl-8-phenyl-5,6,7,8-tetrahydropyrido[4,3-d]pyrimidine (1.2 g, 27%) as brown solid. LC-MS (M+H)$^+$=294.0.

Preparation AFa 2-chloro-N,6-dimethyl-8-phenyl-5,6,7,8-tetrahydropyrido[4,3-d]pyrimidin-4-amine

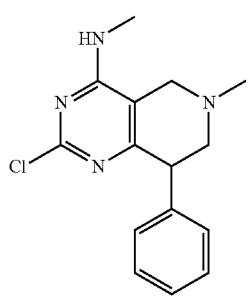 [SMILES: CNc1nc(Cl)nc2c1CN(C)CC2c1ccccc1]

To a solution of Preparation AF (1.0 g, 3.4 mmol) in acetonitrile was added diisopropylethylamine (1.3 g, 10.2 mmol) followed by addition of methylamine hydrochloride (0.34 g, 5.1 mmol) at room temperature. The reaction mixture was stirred at room temperature for 18 h. The solvent was removed under reduced pressure and the residue was purified by column chromatography (60-120 mesh) using 10% methanol in dichloromethane as mobile phase to give 2-chloro-N,6-dimethyl-8-phenyl-5,6,7,8-tetrahydropyrido[4,3-d]pyrimidin-4-amine (0.9 g, 91%) as off-white solid. LC-MS (M+H)$^+$= 289.2.

Preparation AFb 2-chloro-N-ethyl-6-methyl-8-phenyl-5,6,7,8-tetrahydropyrido[4,3-d]pyrimidin-4-amine

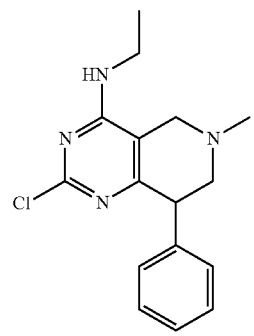 [SMILES: CCNc1nc(Cl)nc2c1CN(C)CC2c1ccccc1]

To a solution of Preparation AF (0.4 g, 1.36 mmol) in acetonitrile was added diisopropylethylamine (0.52 g, 4.0 mmol) followed by addition of ethylamine hydrochloride (0.16 g, 2.0 mmol) at room temperature. The reaction mixture was stirred at the same temperature for 18 h. The solvent was removed under reduced pressure and the residue was purified by column chromatography (60-120 mesh) using 50% ethyl acetate in pet-ether as mobile phase to give 2-chloro-N-ethyl-6-methyl-8-phenyl-5,6,7,8-tetrahydropyrido[4,3-d]pyrimidin-4-amine (0.4 g, 97%) as off-white solid. LC-MS (M−H)$^+$= 303.2.

Preparation AG 2,4-dichloro-8-(4-fluorophenyl)-6-(4-methoxybenzyl)-5,6,7,8-tetrahydropyrido[4,3-d]pyrimidine

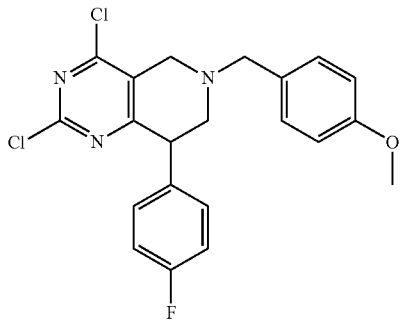 [SMILES: COc1ccc(CN2Cc3c(Cl)nc(Cl)nc3C(c3ccc(F)cc3)C2)cc1]

Intermediate AG(1)

ethyl 2-cyano-2-(4-fluorophenyl)acetate

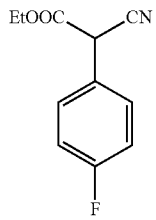

To a solution of sodium hydride (4.2 g, 177.7 mmol) in THF was added 4-fluoro phenyl acetonitrile (10 g, 74.0 mmol) at −10° C. The reaction mixture was stirred for 15 min at the same temperature. Diethyl carbonate (10.5 g, 88.0 mmol) was added to the reaction mixture and the reaction mixture was allowed to come to room temperature and heated to 40° C. (Caution: Reaction will start suddenly and exothermic). The heating path was removed immediately once the reaction was started and the reaction mixture was cooled under ice/acetone. The solution was allowed to come to room temperature and stirred for 1 h. The reaction mass was cooled to 0° C. and quenched with aqueous saturated ammonium chloride and extracted with ethyl acetate (50 mL×3). The combined organic layer was washed with water (50 mL), brine solution (50 mL), dried over anhydrous $Na_2SO_4$ and evaporated under reduced pressure to give ethyl 2-cyano-2-(4-fluorophenyl)acetate as crude compound as crude compound (10 g). The crude compound was taken to the next step without further purification. LC-MS (M−H)$^+$=206.2. $^1$H NMR (400 MHz, CDCl$_3$) δ ppm 7.44 (2H, m), 7.11 (2H, m), 4.69 (1H, s), 4.27-4.22 (2H, q, J=7.2 Hz). 1.26 (3H, m)

Intermediate AG(2)

ethyl 3-amino-2-(4-fluorophenyl)propanoate

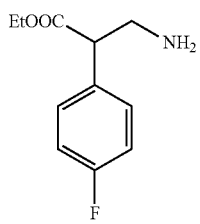 [SMILES: CCOC(=O)C(CN)c1ccc(F)cc1]

To a solution of Intermediate AG(1) (10.0 g, 40.0 mmol) in acetic acid was added palladium on carbon (10%, w/w) followed by $H_2SO_4$ (0.5 vol., 5 mL) at room temperature. The reaction mixture was hydrogenated under 5 kg of hydrogen pressure for 18 h. The reaction mixture was filtered through celite bed and washed with methanol. The filtrate was evaporated under reduced pressure and the residue was neutralized with aqueous saturated bicarbonate solution. The aqueous solution was extracted with ethyl acetate (100 mL×4). The combined organic layer was washed with brine solution (100 mL), dried over anhydrous $Na_2SO_4$ and evaporated under reduced pressure to get crude compound. The crude compound was purified by column chromatography (Silica gel, 60-120 mesh) using 10% methanol in dichloromethane as mobile phase to give ethyl 3-amino-2-(4-fluorophenyl)propanoate (6.0 g, 59%) as oily liquid. LC-MS (M+H)$^+$=212.2. $^1$H NMR (400 MHz, CDCl$_3$): δ ppm 7.26-7.22 (2H, m), 7.04-6.98 (2H, m), 4.15 (2H, m), 3.66 (1H, m), 3.28 (1H, m), 2.99 (1H, m). 1.20 (3H, m).

Intermediate AG(3)

ethyl 3-(3-ethoxy-3-oxopropylamino)-2-(4-fluorophenyl)propanoate

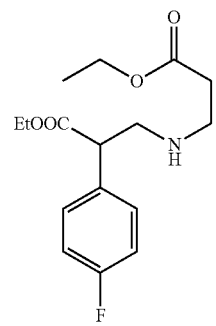 [SMILES: CCOC(=O)CCNCC(C(=O)OCC)c1ccc(F)cc1]

To a solution of Intermediate AG(2) (3.0 g, 14.0 mmol) in ethanol was added ethyl acrylate (1.7 g, 17.0 mmol) at room temperature. The reaction mixture was stirred at the same temperature for 18 h. The solvent was evaporated under reduced pressure and the crude compound was purified by column chromatography (Silica gel, 60-120 mesh) using 50% ethyl acetate in pet-ether as mobile phase to give ethyl 3-(3-ethoxy-3-oxopropylamino)-2-(4-fluorophenyl)propanoate (2.5 g, 60%) as yellowish oily liquid. LC-MS (M+H)$^+$=313.2. $^1$H NMR (400 MHz, CDCl$_3$): δ ppm 7.27-7.21 (2H, m), 7.03-6.97 (2H, m), 4.13 (4H, m), 3.77 (1H, m), 3.23 (1H, m), 2.89 (3H, m), 2.48 (2H, m). 1.22 (6H, m).

Intermediate AG(4)

ethyl 3-((3-ethoxy-3-oxopropyl)(4-methoxybenzyl)amino)-2-(4-fluorophenyl)propanoate

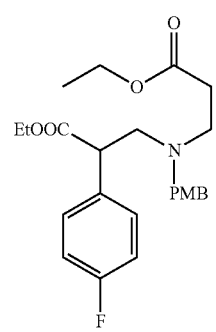

To a solution of Intermediate AG(3) (2.0 g, 6.42 mmol) in acetone was added $K_2CO_3$ (1.39 g, 9.6 mmol) followed by p-methoxybenzyl bromide (1.68 g, 8.35 mmol) at room temperature. The reaction mixture was heated at reflux for 3 h. The solvent was removed under reduced pressure and the residue was diluted with water. The aqueous layer was extracted with ethyl acetate (25×2). The combined organic layer was washed with brine solution (25 mL), dried over anhydrous $Na_2SO_4$ and evaporated under reduced pressure to get crude compound. The crude compound was purified by column chromatography (Silica gel, 60-120 mesh) using 30% ethyl acetate in pet-ether as mobile phase to give ethyl 3-((3-ethoxy-3-oxopropyl)(4-methoxybenzyl)amino)-2-(4-fluorophenyl)propanoate (1.6 g, 60%) as oily liquid. LC-MS (M+H)$^+$=432.2. $^1$H NMR (400 MHz, CDCl$_3$): δ ppm 7.22 (2H, m), 7.09, (2H, m), 6.95 (2H, m), 6.78 (2H, m) 4.14 (4H, m), 3.80 (3H, s), 3.77 (2H, m), 3.53 (2H, m), 3.16 (1H, m), 2.79 (2H, m), 2.43 (2H, m), 1.24 (6H, m).

Intermediate AG(5)

ethyl 5-(4-fluorophenyl)-1-(4-methoxybenzyl)-4-oxopiperidine-3-carboxylate

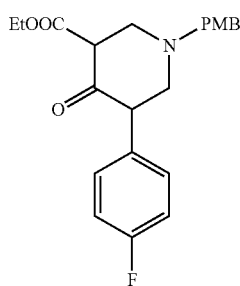

To a cooled solution of Intermediate AG(4) (1.6 g, 3.71 mmol) in THF was added t-BuOK (0.62 g, 5.56 mmol). The reaction mixture was stirred at room temperature for 2 h. The reaction mass was quenched with water then evaporated the solvent under reduced pressure. The residue was diluted with water and extracted with ethyl acetate (25 mL×2). The combined organic layer was washed with brine solution (30 mL), dried over anhydrous Na$_2$SO$_4$ and evaporated under reduced pressure to get crude compound. The crude compound was purified by column chromatography (Silica gel, 60-120 mesh) using 25% ethyl acetate in pet-ether as mobile phase to give ethyl 5-(4-fluorophenyl)-1-(4-methoxybenzyl)-4-oxopiperidine-3-carboxylate (1.0 g, 70%) as oily liquid. LC-MS (M+H)$^+$=386.2. $^1$H NMR (400 MHz, CDCl$_3$): δ ppm 12.0 (1H, s) 7.26 (4H, m), 7.15 (2H, m), 6.88 (2H, m), 4.15 (2H, m), 3.80 (3H, s), 3.77 (2H, m), 3.57 (2H, m), 2.80 (1H, m), 2.40 (1H, m), 1.24 (3H, m).

Intermediate AG(6)

8-(4-fluorophenyl)-6-(4-methoxybenzyl)-5,6,7,8-tetrahydropyrido[4,3-d]pyrimidine-2,4(1H,3H)-dione

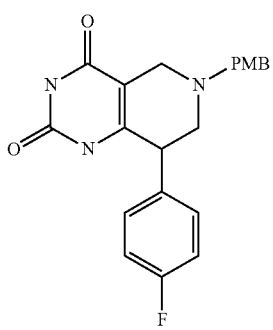

To a cooled solution of Intermediate AG(5) (1.0 g, 2.59 mmol) in ethanol was added t-BuOK (0.436 g 3.89 mmol) followed by urea (0.233 g, 3.89 mmol). The reaction mixture was heated at reflux for 24 h. The reaction mass was quenched with water and evaporated the solvent under reduced pressure. The residue was diluted with water and extracted with ethyl acetate (25 mL×2). The combined organic layer was washed with brine solution (30 mL), dried over Na$_2$SO$_4$ and evaporated under reduced pressure to get crude compound. The crude compound was purified by column chromatography (Silica gel, 60-120 mesh) using 10% pet-ether in ethyl acetate as mobile phase to give 8-(4-fluorophenyl)-6-(4-methoxybenzyl)-5,6,7,8-tetrahydropyrido[4,3-d]pyrimidine-2,4(1H,3H)-dione (0.6 g, 63%) as pale yellow solid. LC-MS (M+H)$^+$=382.2. $^1$H NMR (400 MHz, DMSO-d6): δ ppm 11.06 (1H, s), 10.60 (1H, s), 7.35 (2H, m), 7.29 (2H, m), 7.05 (2H, m), 6.77 (2H, m), 4.05 (1H m), 3.75 (3H, s), 3.53 (1H, m), 3.44 (2H, m), 2.88 (1H, m), 2.65 (2H, m).

Preparation AG 2,4-dichloro-8-(4-fluorophenyl)-6-(4-methoxybenzyl)-5,6,7,8-tetrahydropyrido[4,3-d]pyrimidine

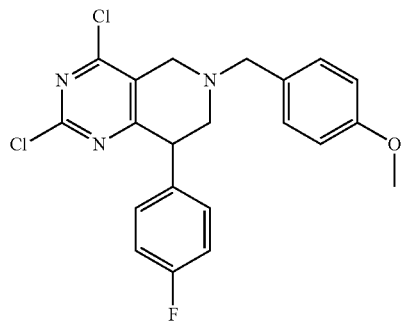 [SMILES: COc1ccc(CN2Cc3c(Cl)nc(Cl)nc3C(c3ccc(F)cc3)C2)cc1]

A solution of Intermediate AG(6) (0.6 g, 1.57 mmol) and catalytic amount of DMF in POCl$_3$ (20 vol.) was heated at reflux for 10 h. The excess of POCl$_3$ was evaporated under reduced pressure. The residue was poured in to crushed ice and stirred for 15 min. The aqueous solution was extracted with ethyl acetate (20 mL×3). The combined organic layer was washed with aqueous saturated NaHCO$_3$ (10 mL×2), brine solution (10 mL), dried over anhydrous Na$_2$SO$_4$ and evaporated under reduced pressure to give 2,4-dichloro-8-(4-fluorophenyl)-6-(4-methoxybenzyl)-5,6,7,8-tetrahydropyrido[4,3-d]pyrimidine (0.35 g,) as brown solid. LC-MS (M+H)$^+$=418.3.

Preparation AGa 2-chloro-8-(4-fluorophenyl)-6-(4-methoxybenzyl)-N-methyl-5,6,7,8-tetrahydropyrido[4,3-d]pyrimidin-4-amine

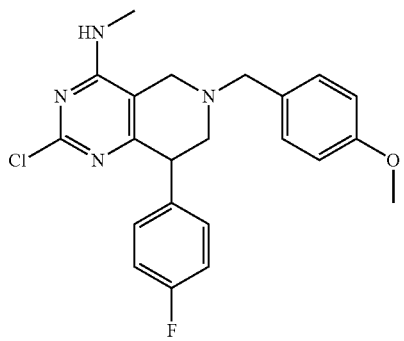 [SMILES: CNc1nc(Cl)nc2c1CN(Cc1ccc(OC)cc1)CC2c1ccc(F)cc1]

To a solution of Preparation AG (1.0 g, 2.39 mmol) in methanol was added diisopropylethylamine (0.62 g, 4.79 mmol) followed by methylamine hydrochloride (0.192 g, 2.87 mmol) at room temperature. The reaction mixture was stirred at room temperature for 18 h. The solvent was removed under reduced pressure and the residue was purified by column chromatography (60-120 mesh) using 35% ethyl acetate in pet-ether as mobile phase to give 2-chloro-8-(4-fluorophenyl)-6-(4-methoxybenzyl)-N-methyl-5,6,7,8-tetrahydropyrido[4,3-d]pyrimidin-4-amine (0.408 g, 41%) as off-white solid. LC-MS (M+H)$^+$=413.0. $^1$H NMR (400 MHz, DMSO-d6): δ ppm 7.32 (1H, m), 7.24-7.20 (2H, m), 7.14-7.06 (4H, m), 6.82 (2H, m), 3.96 (1H, m), 3.72 (3H, s), 3.67 (1H, m), 3.59 (1H, m), 3.50 (1H, m), 3.20 (1H, m), 2.82 (3H, d, J=4.0 Hz), 2.80 (1H, m), 2.51 (1H, m).

Preparation AGb 2-chloro-N-ethyl-8-(4-fluorophenyl)-6-(4-methoxybenzyl)-5,6,7,8-tetrahydropyrido[4,3-d]pyrimidin-4-amine

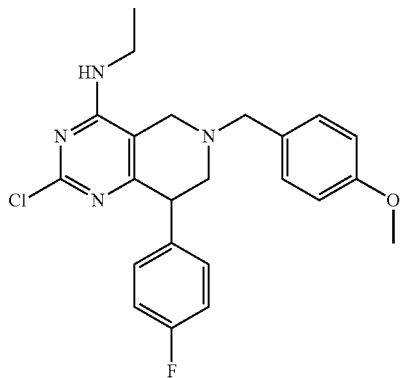 [SMILES: CCNc1nc(Cl)nc2c1CN(Cc1ccc(OC)cc1)CC2c1ccc(F)cc1]

To a solution of Preparation AG (1.0 g, 2.39 mmol) in methanol was added diisopropylethylamine (0.61 g, 4.79 mmol) followed by ethylamine hydrochloride (0.23 g, 2.86 mmol) at room temperature. The reaction mixture was stirred at room temperature for 18 h. The solvent was removed under reduced pressure and the residue was purified by column chromatography (60-120 mesh) using 30-35% ethyl acetate in pet-ether as mobile phase to give 2-chloro-N-ethyl-8-(4-fluorophenyl)-6-(4-methoxybenzyl)-5,6,7,8-tetrahydropyrido[4,3-d]pyrimidin-4-amine (0.54 g, 54%) as off-white solid. LC-MS (M+H)$^+$=427.2. $^1$H NMR (400 MHz, DMSO-d6): δ ppm 7.32 (1H, m), 7.30-7.19 (2H, m), 7.13-7.05 (4H, m), 6.80 (2H, m), 3.93 (1H, m), 3.71 (3H, s), 3.68-3.48 (5H, m), 3.22 (1H, m), 2.80 (1H, m), 2.68 (1H, m), 1.15 (3H, m).

Preparation AGc 2-chloro-N-ethyl-8-(4-fluorophenyl)-6-(4-methoxybenzyl)-N-methyl-5,6,7,8-tetrahydropyrido[4,3-d]pyrimidin-4-amine

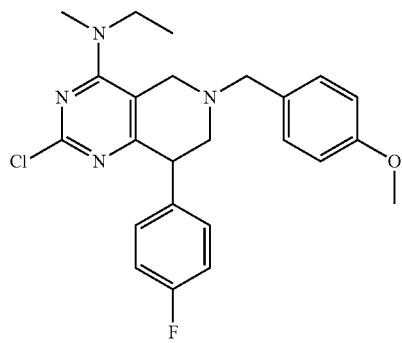 [SMILES: CCN(C)c1nc(Cl)nc2c1CN(Cc1ccc(OC)cc1)CC2c1ccc(F)cc1]

To a solution of Preparation AG (1.2 g, 2.87 mmol) in methanol was added diisopropylethylamine (0.74 g, 5.75 mmol) followed by ethylmethylamine (0.20 g, 3.44 mmol) at room temperature. The reaction mixture was stirred at room temperature for 18 h. The solvent was removed under reduced pressure and the residue was purified by column chromatography (60-120 mesh) using 30-35% ethyl acetate in petroleum-ether as mobile phase to give 2-chloro-N-ethyl-8-(4-fluorophenyl)-6-(4-methoxybenzyl)-N-methyl-5,6,7,8-tetrahydropyrido[4,3-d]pyrimidin-4-amine (0.50 g, 41%) as off-white solid. LC-MS (M+H)$^+$=441.2. $^1$H NMR (400 MHz, DMSO-d6): δ ppm 7.23-7.16 (4H, m), 7.11-7.07 (2H, m), 6.84 (2H, m), 4.10 (1H, m), 3.73 (3H, s), 3.65-3.56 (3H, m), 3.51-3.40 (3H, m), 3.04 (1H, m), 2.99 (3H, s), 2.58 (1H, m), 1.11 (3H, t, J=7.0 Hz).

Preparation AGd 2-chloro-4-(3,3-difluoroazetidin-1-yl)-8-(4-fluorophenyl)-6-(4-methoxybenzyl)-5,6,7,8-tetrahydropyrido[4,3-d]pyrimidine

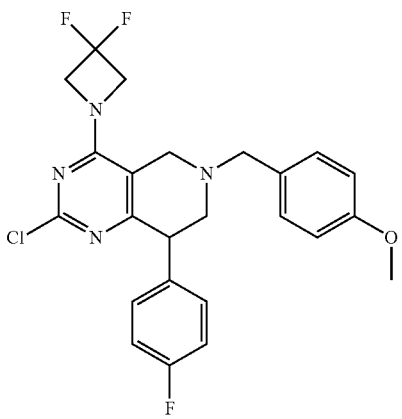 [SMILES: COc1ccc(CN2Cc3c(nc(Cl)nc3N3CC(F)(F)C3)C(c3ccc(F)cc3)C2)cc1]

To a solution of Preparation AG (0.75 g, 1.79 mmol) in methanol was added diisopropylethylamine (0.58 g, 4.49 mmol) followed by 3,3-difluoroazetidine (0.25 g, 1.97 mmol) at room temperature. The reaction mixture was stirred at room temperature for 18 h. The solvent was removed under reduced pressure and the residue was purified by column chromatography (60-120 mesh) using 30% ethyl acetate in pet-ether as mobile phase to give 2-chloro-4-(3,3-difluoroazetidin-1-yl)-8-(4-fluorophenyl)-6-(4-methoxybenzyl)-5,6,7,8-tetrahydropyrido[4,3-d]pyrimidine (0.4 g, 48%) as off-white solid. LC-MS (M+H)$^+$=475.2. $^1$H NMR (400 MHz, CDCl$_3$): δ ppm 7.25-7.10 (4H, m), 6.97-6.82 (2H, m), 6.80 (2H, m), 4.52 (4H, m), 4.07 (1H, m), 3.80 (3H, s), 3.59 (3H, m), 3.36 (1H, m), 2.93 (1H, m), 2.80 (1H, m).

Preparation AGe

N2-(4-(4-chloro-1H-imidazol-1-yl)-3-methoxyphenyl)-8-(4-fluorophenyl)-6-(4-methoxybenzyl)-N4-methyl-5,6,7,8-tetrahydropyrido[4,3-d]pyrimidine-2,4-diamine

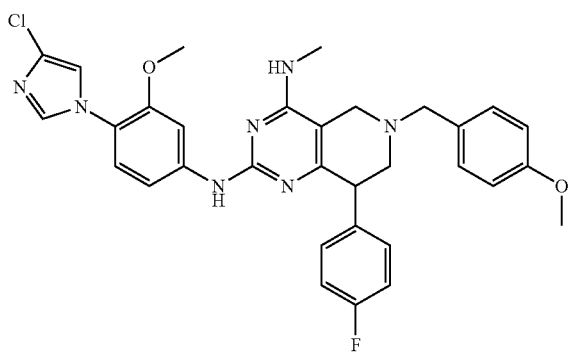 [SMILES: CNc1nc(Nc2ccc(-n3cnc(Cl)c3)c(OC)c2)nc2c1CN(Cc1ccc(OC)cc1)CC2c1ccc(F)cc1]

A solution of Preparation A (0.215 g, 0.966 mmol), Preparation AGa (0.40 g, 0.966 mmol), Na$_2$CO$_3$ (0.205 g, 1.93 mmol) and xantphos (0.558 g, 0.966 mmol) in dioxane/water (9:1) was purged with argon for 1 h at room temperature. Pd(dba)$_3$ (0.50 g, 0.48 mmol) was added to the reaction mixture and the resulting solution was purged with argon for another 1 h. The reaction mass was heated at 110° C. for 24 h. The reaction mass was filtered through celite bed and washed with ethyl acetate. The filtrate was evaporated under reduced pressure and the residue was diluted with water. The aqueous solution was extracted with ethyl acetate (25 mL×3). The combined organic layer was washed with brine solution (25 mL), dried over anhydrous Na$_2$SO$_4$ and evaporated under reduced pressure to get crude compound. The crude compound was purified by column chromatography (Silica gel, 60-120 mesh) using 5% ethyl acetate in dichloromethane as mobile phase to give N2-(4-(4-chloro-1H-imidazol-1-yl)-3-methoxyphenyl)-8-(4-fluorophenyl)-6-(4-methoxybenzyl)-N4-methyl-5,6,7,8-tetrahydropyrido[4,3-d]pyrimidine-2,4-diamine (0.20 g, 35%) as off-white solid. LC-MS (M+H)$^+$= 600.2. $^1$H NMR (400 MHz, DMSO-d6): δ ppm 9.09 (1H, s), 8.05 (1H, s), 7.72 (1H, s), 7.41 (1H, s), 7.26-7.22 (2H, m), 7.14-7.05 (7H, m), 6.82-6.75 (2H, m), 3.93 (1H, m), 3.76 (4H, m), 3.74 (2H, m), 3.72 (1H, m), 3.70 (3H, s), 2.92 (3H, d, J=4.0 Hz), 2.90 (1H, m), 2.70 (1H, m).

Preparation AGf

N2-(4-(4-chloro-1H-imidazol-1-yl)-3-methoxyphenyl)-N4-ethyl-8-(4-fluorophenyl)-6-(4-methoxybenzyl)-5,6,7,8-tetrahydropyrido[4,3-d]pyrimidine-2,4-diamine

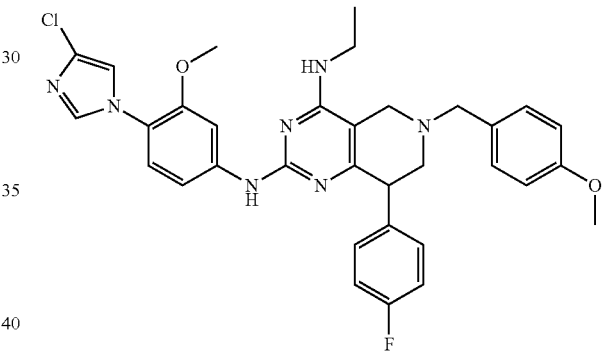

A solution of Preparation A (0.283 g, 1.26 mmol), Preparation AGb (0.54 g, 1.26 mmol), Na$_2$CO$_3$ (0.26 g, 2.53 mmol) and xantphos (0.73 g, 1.26 mmol) in dioxane/water (9:1) was purged with argon for 1 h at room temperature. Pd(dba)$_3$ (0.65 g, 0.63 mmol) was added to the reaction mixture and the resulting solution was purged with argon for another 1 h. The reaction mass was heated at 110° C. for 24 h. The reaction mass was filtered through celite bed and washed with ethyl acetate. The filtrate was evaporated under reduced pressure and the residue was diluted with water. The aqueous solution was extracted with ethyl acetate (50 mL×2). The combined organic layer was washed with brine solution (50 mL), dried over anhydrous Na$_2$SO$_4$ and evaporated under reduced pressure to get crude compound. The crude compound was purified by column chromatography (Silica gel, 60-120 mesh) using 7% ethyl acetate in dichloromethane as mobile phase to give N2-(4-(4-chloro-1H-imidazol-1-yl)-3-methoxyphenyl)-N4-ethyl-8-(4-fluorophenyl)-6-(4-methoxybenzyl)-5,6,7,8-tetrahydropyrido[4,3-d]pyrimidine-2,4-diamine (0.22 g, 29%) as off-white solid. LC-MS (M+H)$^+$=614.2. $^1$H NMR (400 MHz, DMSO-d6): δ ppm 9.05 (1H, s), 7.97 (1H, s), 7.72 (1H, s), 7.41 (1H, s), 7.39-7.29 (3H, m), 7.25-7.09 (6H, m), 6.81-6.75 (2H, m), 6.72 (1H, m), 3.93 (1H, m), 3.71 (3H, s), 3.67 (1H, m), 3.57 (3H, s), 3.52 (1H, m), 3.49 (2H, m), 3.24 (1H, m) 2.83 (1H, m), 2.65 (1H, m), 1.16 (3H, t, J=7.2 Hz).

Preparation AGg

N4-ethyl-N2-(3-fluoro-4-(3-methyl-1H-1,2,4-triazol-1-yl)phenyl)-8-(4-fluorophenyl)-6-(4-methoxybenzyl)-5,6,7,8-tetrahydropyrido[4,3-d]pyrimidine-2,4-diamine

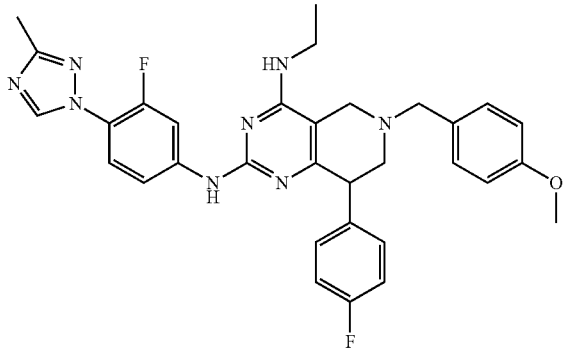 [SMILES: CCNc1nc(Nc2ccc(-n3cnc(C)n3)c(F)c2)nc2c1CN(Cc1ccc(OC)cc1)CC2c1ccc(F)cc1]

A solution of Preparation B (0.275 g, 1.43 mmol), Preparation AGb (0.68 g, 1.59 mmol), Na$_2$CO$_3$ (0.33 g, 3.19 mmol) and xantphos (0.92 g, 1.59 mmol) in dioxane/water (9:1) was purged with argon for 1 h at room temperature. Pd(dba)$_3$ (0.82 g, 0.79 mmol) was added to the reaction mixture and the resulting solution was purged with argon for another 1 h. The reaction mass was heated at 110° C. for 24 h. The reaction mass was filtered through celite bed and washed with ethyl acetate. The filtrate was evaporated under reduced pressure and the residue was diluted with water. The aqueous solution was extracted with ethyl acetate (50 mL×2). The combined organic layer was washed with brine solution (50 mL), dried over anhydrous Na$_2$SO$_4$ and evaporated under reduced pressure to get crude compound. The crude compound was purified by column chromatography (Silica gel, 60-120 mesh) using 10% ethyl acetate in dichloromethane as mobile phase to give N4-ethyl-N2-(3-fluoro-4-(3-methyl-1H-1,2,4-triazol-1-yl)phenyl)-8-(4-fluorophenyl)-6-(4-methoxybenzyl)-5,6,7,8-tetrahydropyrido[4,3-d]pyrimidine-2,4-diamine (0.6 g, 65%) as off-white solid. LC-MS (M+H)$^+$=583.2.

Preparation AGh

N4-ethyl-N2-(3-fluoro-4-(5-methyl-1H-1,2,4-triazol-1-yl)phenyl)-8-(4-fluorophenyl)-6-(4-methoxybenzyl)-5,6,7,8-tetrahydropyrido[4,3-d]pyrimidine-2,4-diamine

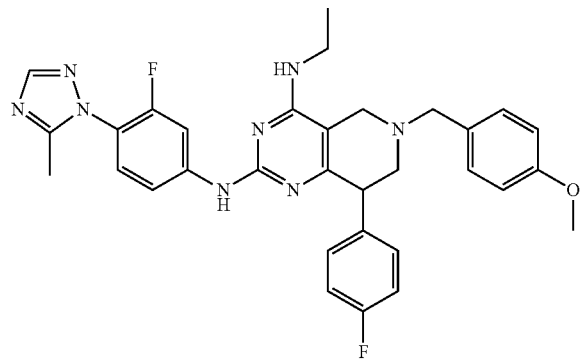 [SMILES: CCNc1nc(Nc2ccc(-n3ncnc3C)c(F)c2)nc2c1CN(Cc1ccc(OC)cc1)CC2c1ccc(F)cc1]

A solution of Preparation C (0.20 g, 1.05 mmol), Preparation AGb (0.50 g, 1.17 mmol), Na$_2$CO$_3$ (0.24 g, 2.34 mmol) and xantphos (0.67 g, 1.17 mmol) in dioxane/water (9:1) was purged with argon for 1 h at room temperature. Pd(dba)$_3$ (0.60 g, 0.58 mmol) was added to the reaction mixture and the resulting solution was purged with argon for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (25 mL×2). The combined organic layer was washed with brine solution (20 mL), dried over anhydrous Na$_2$SO$_4$ and evaporated under reduced pressure to get crude compound. The crude compound was purified by column chromatography (Silica gel, 60-120 mesh) using 10% ethyl acetate in dichloromethane as mobile phase to give N4-ethyl-N2-(3-fluoro-4-(5-methyl-1H-1,2,4-triazol-1-yl)phenyl)-8-(4-fluorophenyl)-6-(4-methoxybenzyl)-5,6,7,8-tetrahydropyrido[4,3-d]pyrimidine-2,4-diamine (0.51 g, 73%) as off-white solid. LC-MS (M+H)$^+$=583.2.

Preparation AGi

N2-(4-(4-chloro-1H-imidazol-1-yl)-3-methoxyphenyl)-N4-ethyl-8-(4-fluorophenyl)-6-(4-methoxybenzyl)-N4-methyl-5,6,7,8-tetrahydropyrido[4,3-d]pyrimidine-2,4-diamine

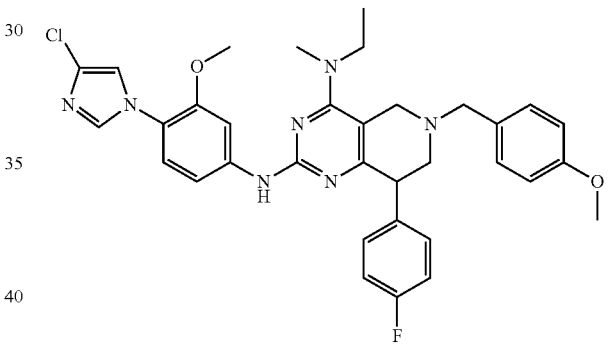

A solution of Preparation A (0.25 g, 1.13 mmol), Preparation AGc (0.50 g, 1.13 mmol), Na$_2$CO$_3$ (0.24 g, 2.28 mmol) and xantphos (0.65 g, 1.14 mmol) in dioxane/water (9:1) was purged with argon for 1 h at room temperature. Pd(dba)$_3$ (0.60 g, 0.560 mmol) was added to the reaction mixture and the resulting solution was purged with argon for another 1 h. The reaction mass was heated at 110° C. for 24 h. The reaction mass was filtered through celite bed and washed with ethyl acetate. The filtrate was evaporated under reduced pressure and the residue was diluted with water. The aqueous solution was extracted with ethyl acetate (20 mL×3). The combined organic layer was washed with brine solution (25 mL), dried over anhydrous Na$_2$SO$_4$ and evaporated under reduced pressure to get crude compound. The crude compound was purified by column chromatography (Silica gel, 60-120 mesh) using 5-10% ethyl acetate in dichloromethane as mobile phase to give N2-(4-(4-chloro-1H-imidazol-1-yl)-3-methoxyphenyl)-N4-ethyl-8-(4-fluorophenyl)-6-(4-methoxybenzyl)-N4-methyl-5,6,7,8-tetrahydropyrido[4,3-d]pyrimidine-2,4-diamine (0.45 g, 63%) as off-white solid. LC-MS (M+H)$^+$=628.2. $^1$H NMR (400 MHz, DMSO-d6): δ ppm 9.15 (1H, s), 7.86 (1H, s), 7.73 (1H, s), 7.42 (1H, s), 7.24-7.21 (4H, m), 7.18-7.07 (4H, m), 6.86 (2H, m), 4.11 (1H, m), 3.70 (3H, s), 3.65 (2H, m), 3.56 (3H, s), 3.47 (2H, m), 3.40 (2H, m), 3.07 (1H, m), 2.98 (3H, s), 2.51 (1H, m), 1.24 (3H, t, J=7.2 Hz).

Preparation AGj

N-(4-(4-chloro-1H-imidazol-1-yl)-3-methoxyphenyl)-4-(3,3-difluoroazetidin-1-yl)-8-(4-fluorophenyl)-6-(4-methoxybenzyl)-5,6,7,8-tetrahydropyrido[4,3-d]pyrimidin-2-amine

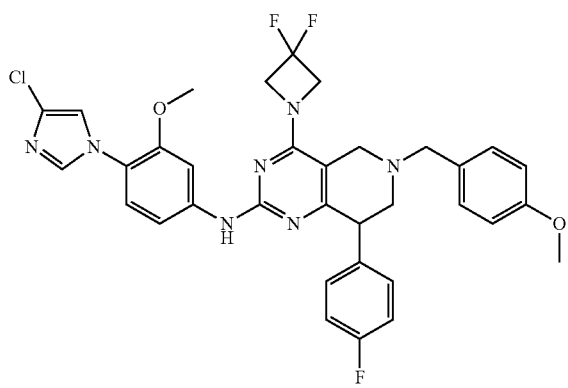 [SMILES: COc1ccc(CN2Cc3c(nc(Nc4ccc(-n5cnc(Cl)c5)c(OC)c4)nc3N3CC(F)(F)C3)C(c3ccc(F)cc3)C2)cc1]

A solution of Preparation A (0.20 g, 0.92 mmol), Preparation AGd (0.40 g, 0.84 mmol), Na$_2$CO$_3$ (0.18 g, 1.77 mmol) and xantphos (0.48 g, 0.84 mmol) in dioxane/water (9:1) was purged with argon for 1 h at room temperature. Pd(dba)$_3$ (0.43 g, 0.420 mmol) was added to the reaction mixture and the resulting solution was purged for another 1 h. The reaction mass was heated at 110° C. for 24 h. The reaction mass was filtered through celite bed and washed with ethyl acetate. The filtrate was evaporated under reduced pressure and the residue was diluted with water. The aqueous solution was extracted with ethyl acetate (25 mL×3). The combined organic layer was washed with brine solution (25 mL), dried over anhydrous Na$_2$SO$_4$ and evaporated under reduced pressure to get crude compound. The crude compound was purified by column chromatography (Silica gel, 60-120 mesh) using 5% ethyl acetate in dichloromethane as mobile phase to give N-(4-(4-chloro-1H-imidazol-1-yl)-3-methoxyphenyl)-4-(3,3-difluoroazetidin-1-yl)-8-(4-fluorophenyl)-6-(4-methoxybenzyl)-5,6,7,8-tetrahydropyrido[4,3-d]pyrimidin-2-amine (0.25 g, 49%) as off-white solid. LC-MS (M+H)$^+$= 663.0.

Preparation AGk

N2-(4-(4-chloro-1H-imidazol-1-yl)-3-methoxyphenyl)-8-(4-fluorophenyl)-N4-methyl-5,6,7,8-tetrahydropyrido[4,3-d]pyrimidine-2,4-diamine

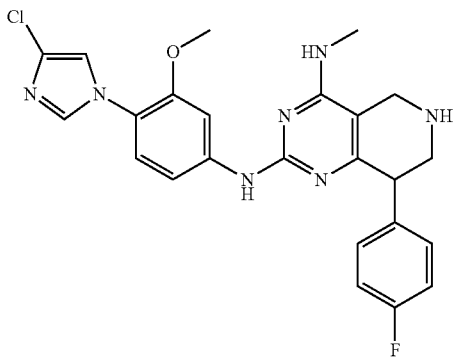 [SMILES: CNc1nc(Nc2ccc(-n3cnc(Cl)c3)c(OC)c2)nc2c1CNCC2c1ccc(F)cc1]

To a solution of Preparation AGe (0.20 g, 0.330 mmol) in toluene was added trifluoromethanesulfonic acid (3.0 vol.) at room temperature. The reaction mixture was heated at reflux for 1 h. The solvent was removed under reduced pressure and the residue was diluted with water. The aqueous solution was washed with dichloromethane (25 mL×2), basified by using aqueous saturated NaHCO$_3$ and extracted with ethyl acetate (25 mL×3). The combined organic layer was washed with brine solution (25 mL), dried over anhydrous Na$_2$SO$_4$ and evaporated under reduced pressure to give N2-(4-(4-chloro-1H-imidazol-1-yl)-3-methoxyphenyl)-8-(4-fluorophenyl)-N4-methyl-5,6,7,8-tetrahydropyrido[4,3-d]pyrimidine-2,4-diamine (0.08 g, 51%) as crude compound. The crude compound was taken to the next step without further purification. LC-MS (M+H)$^+$=480.2. $^1$H NMR (400 MHz, DMSO-d6): δ ppm 9.36 (1H, s), 7.86 (1H, s), 7.75 (1H, s), 7.43 (1H, s), 7.32-7.28 (3H, m), 7.23-7.11 (4H, m), 4.30 (1H, m), 4.02 (1H, m), 3.98 (1H, m), 3.71 (1H, m), 3.56 (3H, s), 3.38 (1H, m), 2.98 (3H, d, J=4.0 Hz).

Preparation AGl (BBRC-7610)

N2-(4-(4-chloro-1H-imidazol-1-yl)-3-methoxyphenyl)-N4-ethyl-8-(4-fluorophenyl)-5,6,7,8-tetrahydropyrido[4,3-d]pyrimidine-2,4-diamine

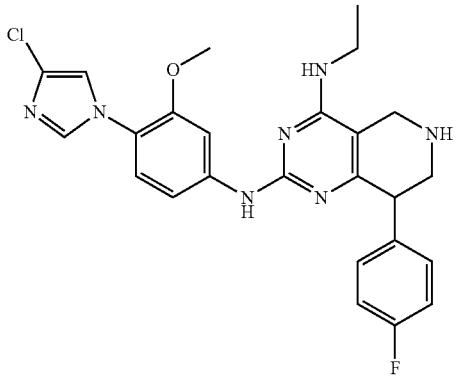 [SMILES: CCNc1nc(Nc2ccc(-n3cnc(Cl)c3)c(OC)c2)nc2c1CNCC2c1ccc(F)cc1]

To a solution of Preparation AGf (0.22 g, 0.35 mmol) in toluene was added trifluoromethanesulfonic acid (3.0 vol.) at room temperature. The reaction mixture was heated at reflux for 1 h. The solvent was removed under reduced pressure and the residue was diluted with water. The aqueous solution was washed with dichloromethane (25 mL×2), basified by using aqueous saturated NaHCO$_3$ and extracted with ethyl acetate (50 mL×3). The combined organic layer was washed with brine solution (25 mL), dried over anhydrous Na$_2$SO$_4$ and evaporated under reduced pressure to give N2-(4-(4-chloro-1H-imidazol-1-yl)-3-methoxyphenyl)-N4-ethyl-8-(4-fluorophenyl)-5,6,7,8-tetrahydropyrido[4,3-d]pyrimidine-2,4-diamine as crude compound (0.16 g, 93%). The crude compound was taken to the next step without further purification. LC-MS (M+H)$^+$=494.2. $^1$H NMR (400 MHz, DMSO-d6): δ ppm 9.01 (1H, s), 7.98 (1H, s), 7.72 (1H, s), 7.41 (1H, s), 7.21-7.17 (2H, m), 7.13-7.05 (4H, m), 6.67 (1H, m), 3.82 (1H, m), 3.66 (2H, m), 3.56 (3H, s), 3.50 (2H, m), 3.20 (1H, m), 2.85 (1H, m), 1.20 (3H, t, J=7.2 Hz).

Preparation AGm

N4-ethyl-N2-(3-fluoro-4-(3-methyl-1H-1,2,4-triazol-1-yl)phenyl)-8-(4-fluorophenyl)-5,6,7,8-tetrahydropyrido[4,3-d]pyrimidine-2,4-diamine

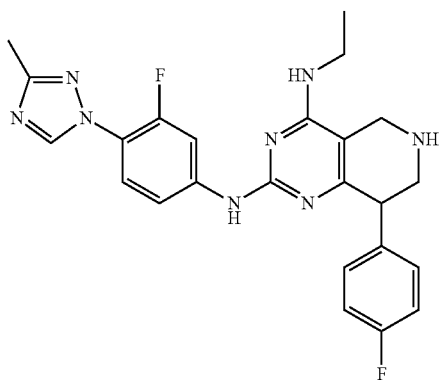 [SMILES: CCNc1nc(Nc2ccc(-n3cnc(C)n3)c(F)c2)nc2c1CNCC2c1ccc(F)cc1]

To a solution of Preparation AGg (0.40 g, 0.68 mmol) in toluene was added trifluoromethanesulfonic acid (3.0 vol.) at room temperature. The reaction mixture was heated at reflux for 1 h. The solvent was removed under reduced pressure and the residue was diluted with water. The aqueous solution was washed with dichloromethane (20 mL×2), basified by using aqueous saturated NaHCO$_3$ and extracted with ethyl acetate (25 mL×3). The combined organic layer was washed with brine solution (25 mL), dried over anhydrous Na$_2$SO$_4$ and evaporated under reduced pressure to give N4-ethyl-N2-(3-fluoro-4-(3-methyl-1H-1,2,4-triazol-1-yl)phenyl)-8-(4-fluorophenyl)-5,6,7,8-tetrahydropyrido[4,3-d]pyrimidine-2,4-diamine (0.30 g, 94%) as crude compound. The crude compound was taken to the next step without further purification. LC-MS (M+H)$^+$=463.2. $^1$H NMR (400 MHz, DMSO-d6): δ ppm 9.29 (1H, s), 8.68 (1H, s), 8.03 (1H, m), 7.44-7.37 (2H, m), 7.25-7.21 (2H, m), 7.12-7.07 (2H, m), 6.76 (1H, m), 3.83 (1H, m), 3.68-3.60 (2H, m), 3.55-3.46 (2H, m), 3.22 (1H, m), 2.91 (1H, m), 2.34 (3H, s), 1.20 (3H, t, J=7.2 Hz).

Preparation AGn

N4-ethyl-N2-(3-fluoro-4-(5-methyl-1H-1,2,4-triazol-1-yl)phenyl)-8-(4-fluorophenyl)-5,6,7,8-tetrahydropyrido[4,3-d]pyrimidine-2,4-diamine

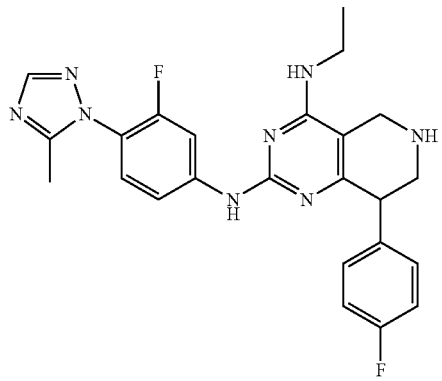 [SMILES: CCNc1nc(Nc2ccc(-n3ncnc3C)c(F)c2)nc2c1CNCC2c1ccc(F)cc1]

To a solution of Preparation AGh (0.51 g, 0.87 mmol) in toluene was added trifluoromethanesulfonic acid (3.0 vol.) at room temperature. The reaction mixture was heated at reflux for 1 h. The solvent was removed under reduced pressure and the residue was diluted with water. The aqueous solution was washed with dichloromethane (25 mL×2), basified by using aqueous saturated NaHCO$_3$ and extracted with ethyl acetate (25 mL×3). The combined organic layer was washed with brine solution (25 mL), dried over anhydrous Na$_2$SO$_4$ and evaporated under reduced pressure to give N4-ethyl-N2-(3-fluoro-4-(5-methyl-1H-1,2,4-triazol-1-yl)phenyl)-8-(4-fluorophenyl)-5,6,7,8-tetrahydropyrido[4,3-d]pyrimidine-2,4-diamine (0.31 g, 78%) as crude compound. The crude compound was taken to the next step without further purification. LC-MS (M+H)$^+$=463.2. $^1$H NMR (400 MHz, DMSO-d6): δ ppm 9.29 (1H, s), 8.68 (1H, s), 8.02 (1H, m), 7.42 (2H, m), 7.23 (2H, m), 7.28-7.10 (2H, m), 6.75 (1H, m), 3.80 (1H, m), 3.67-3.60 (2H, m), 3.55-3.48 (2H, m), 3.22 (1H, m), 2.89 (1H, m), 2.34 (3H, s), 1.24 (3H, t, J=7.0 Hz).

Preparation AGo(BBRC-4363)

N2-(4-(4-chloro-1H-imidazol-1-yl)-3-methoxyphenyl)-N4-ethyl-8-(4-fluorophenyl)-N4-methyl-5,6,7,8-tetrahydropyrido[4,3-d]pyrimidine-2,4-diamine

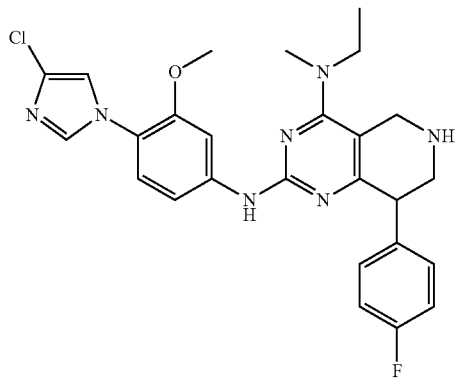 [SMILES: CCN(C)c1nc(Nc2ccc(-n3cnc(Cl)c3)c(OC)c2)nc2c1CNCC2c1ccc(F)cc1]

To a solution of Preparation AGi (0.10 g, 0.15 mmol) in toluene was added trifluoromethanesulfonic acid (3.0 vol.) at room temperature. The reaction mixture was heated at reflux for 1 h. The solvent was removed under reduced pressure and the residue was diluted with water. The aqueous solution was washed with dichloromethane (10 mL×2), basified by using aqueous saturated NaHCO₃ and extracted with ethyl acetate (20 mL×3). The combined organic layer was washed with brine solution (25 mL), dried over anhydrous Na₂SO₄ and evaporated under reduced pressure to give N2-(4-(4-chloro-1H-imidazol-1-yl)-3-methoxyphenyl)-N4-ethyl-8-(4-fluorophenyl)-N4-methyl-5,6,7,8-tetrahydropyrido[4,3-d]pyrimidine-2,4-diamine (0.03 g) as crude compound. The crude compound was taken to the next step without further purification. LC-MS (M+H)⁺=508.2. ¹H NMR (400 MHz, DMSO-d6): δ ppm 7.78 (1H, s), 7.77 (1H, s), 7.37 (1H, s), 7.20-7.16 (3H, m), 7.12-7.06 (4H, m), 4.04 (2H, m), 3.80 (1H, m), 3.50 (3H, s), 3.42-3.32 (3H, m), 3.15 (3H, s), 2.81 (1H, m), 1.17 (3H, t, J=7.2 Hz).

Preparation AGp (BBRC-4364)

N-(4-(4-chloro-1H-imidazol-1-yl)-3-methoxyphenyl)-4-(3,3-difluoroazetidin-1-yl)-8-(4-fluorophenyl)-5,6,7,8-tetrahydropyrido[4,3-d]pyrimidin-2-amine

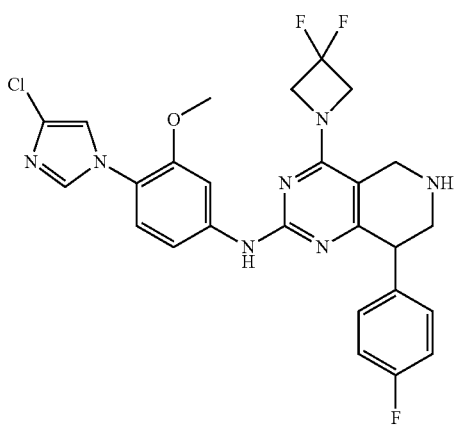 [SMILES: COc1cc(Nc2nc3c(c(N4CC(F)(F)C4)n2)CNCC3c2ccc(F)cc2)ccc1-n1cnc(Cl)c1]

To a solution of Preparation AGj (0.20 g, 0.30 mmol) in toluene was added trifluoromethanesulfonic acid (3.0 vol.) at room temperature. The reaction mixture was heated at reflux for 1 h. The solvent was removed under reduced pressure and the residue was diluted with water. The aqueous solution was washed with dichloromethane (10 mL×2), basified by using aqueous saturated NaHCO₃ and extracted with ethyl acetate (25 mL×3). The combined organic layer was washed with brine solution (50 mL), dried over anhydrous Na₂SO₄ and evaporated under reduced pressure to give N-(4-(4-chloro-1H-imidazol-1-yl)-3-methoxyphenyl)-4-(3,3-difluoroazetidin-1-yl)-8-(4-fluorophenyl)-5,6,7,8-tetrahydropyrido[4,3-d]pyrimidin-2-amine (0.12 g, 70%) as crude compound. The crude compound was taken to the next step without further purification. LC-MS (M+H)⁺=542.0. ¹H NMR (400 MHz, DMSO-d6): δ ppm 9.31 (1H, s), 7.87 (1H, s), 7.73 (1H, s), 7.41 (1H, s), 7.22 (2H, m), 7.15-7.07 (4H, m), 4.74-4.59 (4H, m), 3.97 (1H, m), 3.87 (1H, m), 3.76 (1H, m), 3.51 (3H, s), 3.27 (1H, m), 2.83 (1H, m).

Preparation AH 2,4-dichloro-8-(4-fluorophenyl)-6-methy-1-5,6,7,8-tetrahydropyrido[4,3-d]pyrimidine

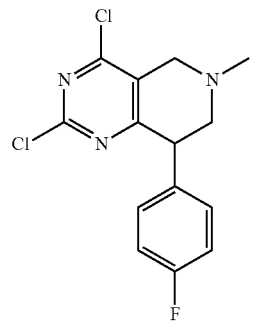 [SMILES: CN1Cc2c(Cl)nc(Cl)nc2C(c2ccc(F)cc2)C1]

Intermediate AH(1)

ethyl 3-((3-ethoxy-3-oxopropyl)(4-methoxybenzyl)amino)-2-(4-fluorophenyl)propanoate

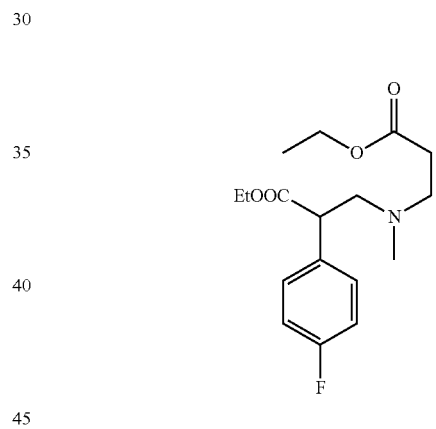

To a solution of Intermediate AG(3) (12.0 g, 38.5 mmol) in acetone was added K₂CO₃ (6.38 g, 46.3 mmol) followed by methyl iodide (6.5 g, 46.3 mmol) at 0° C. The reaction mixture was stirred at room temperature for 2 h. The solvent was removed under reduced pressure and the residue was diluted with water. The aqueous layer was extracted with ethyl acetate (50×3). The combined organic layer was washed with brine solution (75 mL), dried over anhydrous Na₂SO₄ and evaporated under reduced pressure to get crude compound. The crude compound was purified by column chromatography (Silica gel, 60-120 mesh) using 20% ethyl acetate in pet-ether as mobile phase to give ethyl 3-((3-ethoxy-3-oxopropyl)(methyl)amino)-2-phenylpropanoate (6.0 g, 50%) as oily liquid. LC-MS (M+H)⁺=326.2. ¹H NMR (400 MHz, CDCl₃): δ ppm 7.01 (2H, m), 6.98, (2H, m), 4.16-4.07 (4H, m), 3.77 (1H, m), 3.13 (1H, t, J=2.4 Hz), 2.75-2.51 (5H, m), 2.17 (3H, s), 1.26-1.19 (6H, m).

Intermediate AH(2)

ethyl 5-(4-fluorophenyl)-1-methyl-4-oxopiperidine-3-carboxylate

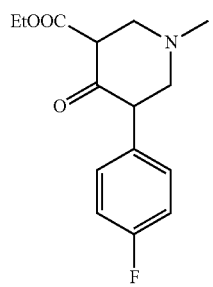 [SMILES: CCOC(=O)C1CN(C)CC(c2ccc(F)cc2)C1=O]

To a cooled solution of Intermediate AH(1) (6.0 g, 18.4 mmol) in THF was added t-BuOK (4.1 g, 36.9 mmol). The reaction mixture was stirred at room temperature for 2 h. The reaction mass was quenched with water then evaporated the solvent under reduced pressure. The residue was diluted with water and extracted with ethyl acetate (25 mL×4). The combined organic layer was washed with brine solution (30 mL), dried over anhydrous $Na_2SO_4$ and evaporated under reduced pressure to get crude compound. The crude compound was purified by column chromatography (Silica gel, 60-120 mesh) using 20% ethyl acetate in pet-ether as mobile phase to give ethyl 5-(4-fluorophenyl)-1-methyl-4-oxopiperidine-3-carboxylate (3.0 g, 51%) as oily liquid. LC-MS $(M+H)^+=$ 278.2. $^1H$ NMR (400 MHz, DMSO-d6): δ ppm 7.35 (1H, m), 7.15 (1H, m), 7.12 (1H, m), 6.98 (1H, m), 4.01 (2H, m), 3.88 (1H, m), 2.60 (1H, m), 2.38 (2H, m), 2.19 (3H, s), 1.19-1.08 (3H, m).

Intermediate AH(3)

8-(4-fluorophenyl)-6-methyl-5,6,7,8-tetrahydropyrido[4,3-d]pyrimidine-2,4(1H,3H)-dione

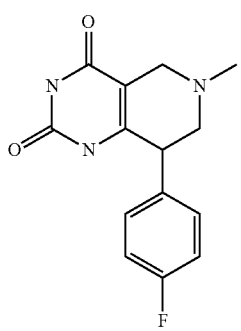 [SMILES: CN1Cc2c([nH]c(=O)[nH]c2=O)C(c2ccc(F)cc2)C1]

To a cooled solution of Intermediate AH(2) (3.0 g, 10.75 mmol) in ethanol was added t-BuOK (3.0 g 26.8 mmol) followed by urea (1.6 g, 26.8 mmol). The reaction mixture was heated at reflux for 36 h. The reaction mass was quenched with water and evaporated the solvent under reduced pressure. The residue was diluted with water and extracted with ethyl acetate (25 mL×3). The combined organic layer was washed with brine solution (30 mL), dried over $Na_2SO_4$ and evaporated under reduced pressure to get crude compound. The crude compound was purified by column chromatography (Silica gel, 60-120 mesh) using 100% ethyl acetate as mobile phase to give 8-(4-fluorophenyl)-6-methyl-5,6,7,8-tetrahydropyrido[4,3-d]pyrimidine-2,4(1H,3H)-dione (1.5 g, 51%) as pale yellow solid. LC-MS $(M+H)^+=276.0$. $^1H$ NMR (400 MHz, DMSO-d6): δ ppm 11.08 (1H, s), 10.59 (1H, s), 7.31 (2H, m), 7.13 (2H, m), 3.74 (1H, m), 3.17 (1H, m), 2.80-2.59 (2H, m), 2.23 (3H, s).

Preparation AH 2,4-dichloro-8-(4-fluorophenyl)-6-methyl-5,6,7,8-tetrahydropyrido[4,3-d]pyrimidine

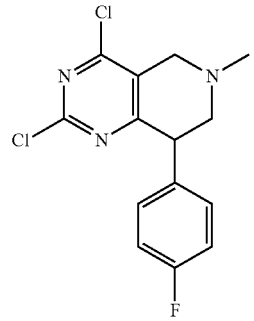 [SMILES: CN1Cc2c(Cl)nc(Cl)nc2C(c2ccc(F)cc2)C1]

A solution of Intermediate AH(3) (1.5 g, 5.45 mmol) and catalytic amount of DMF in $POCl_3$ (20 vol.) was heated at reflux for 10 h. The excess of $POCl_3$ was evaporated under reduced pressure. The residue was poured in to crushed ice and stirred for 15 min. The aqueous solution was extracted with ethyl acetate (20 mL×2). The combined organic layer was washed with aqueous saturated $NaHCO_3$ (10 mL×2), brine solution (10 mL), dried over anhydrous $Na_2SO_4$ and evaporated under reduced pressure to give 2,4-dichloro-8-(4-fluorophenyl)-6-methyl-5,6,7,8-tetrahydropyrido[4,3-d]pyrimidine (0.7 g, 56%) as brown solid. LC-MS $(M+H)^+=$ 312.2.

Preparation AHa 2-chloro-8-(4-fluorophenyl)-N,6-dimethyl-5,6,7,8-tetrahydropyrido[4,3-d]pyrimidin-4-amine

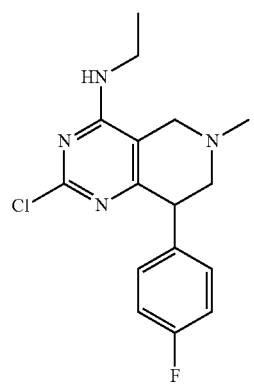 [SMILES: CCNc1nc(Cl)nc2c1CN(C)CC2c1ccc(F)cc1]

To a solution of Preparation AH (0.4 g, 1.28 mmol) in methanol was added diisopropylethylamine (0.33 g, 2.57 mmol) followed by methylamine hydrochloride (0.16 g, 2.57 mmol) at room temperature. The reaction mixture was stirred at room temperature for 18 h. The solvent was removed under reduced pressure and the residue was purified by column chromatography (60-120 mesh) using 50% ethyl acetate in pet-ether as mobile phase to give 2-chloro-8-(4-fluorophenyl)-N,6-dimethyl-5,6,7,8-tetrahydropyrido[4,3-d]pyrimidin-4-amine (0.20 g, 51.2%) as off-white solid. LC-MS (M+H)⁺=307.2.

Preparation AHb 2-chloro-N-ethyl-8-(4-fluorophenyl)-6-methyl-5,6,7,8-tetrahydropyrido[4,3-d]pyrimidin-4-amine

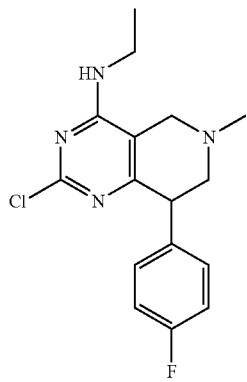 [SMILES: CCNc1nc(Cl)nc2c1CN(C)CC2c1ccc(F)cc1]

To a solution of Preparation AH (0.7 g, 2.25 mmol) in methanol was added diisopropylethylamine (0.58 g, 4.50 mmol) followed by ethylamine hydrochloride (0.4 g, 4.50 mmol) at room temperature. The reaction mixture was stirred at room temperature for 18 h. The solvent was removed under reduced pressure and the residue was purified by column chromatography (60-120 mesh) using 30-35% ethyl acetate in pet-ether as mobile phase to give 2-chloro-N-ethyl-8-(4-fluorophenyl)-6-methyl-5,6,7,8-tetrahydropyrido[4,3-d]pyrimidin-4-amine (0.21 g, 29%) as off-white solid. LC-MS (M+H)⁺=321.2.

Preparation AHc 2-chloro-N-ethyl-8-(4-fluorophenyl)-N,6-dimethyl-5,6,7,8-tetrahydropyrido[4,3-d]pyrimidin-4-amine

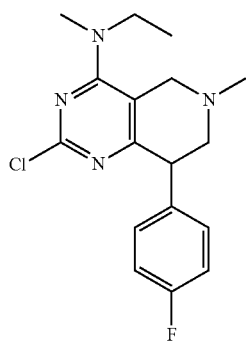 [SMILES: CCN(C)c1nc(Cl)nc2c1CN(C)CC2c1ccc(F)cc1]

To a solution of Preparation AH (0.35 g, 1.1 mmol) in methanol was added diisopropylethylamine (0.29 g, 2.2 mmol) followed by ethylmethylamine (0.67 g, 1.35 mmol) at room temperature. The reaction mixture was stirred at room temperature for 18 h. The solvent was removed under reduced pressure and the residue was purified by column chromatography (60-120 mesh) using 35% ethyl acetate in pet-ether as mobile phase to give 2-chloro-N-ethyl-8-(4-fluorophenyl)-N,6-dimethyl-5,6,7,8-tetrahydropyrido[4,3-d]pyrimidin-4-amine (0.22 g, 58%) as off-white solid. LC-MS (M+H)⁺=333.9.

Preparation AI 2,4-dichloro-8-(4-fluorophenyl)-7-(4-methoxybenzyl)-5,6,7,8-tetrahydropyrido[3,4-d]pyrimidine

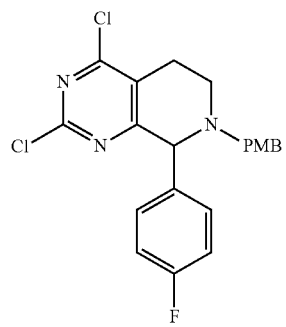

Intermediate AI(1)

ethyl 2-amino-2-(4-fluorophenyl)acetate

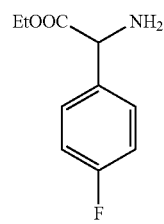 [SMILES: CCOC(=O)C(N)c1ccc(F)cc1]

To a cooled solution of 2-amino-2-(4-fluorophenyl)acetic acid (1.0 g, 6.17 mmol) in ethanol was added con. $H_2SO_4$ (1 mL) over a period of 1 min. The reaction mixture was heated at reflux for 5 h. The solvent was evaporated under reduced pressure and the residue was diluted with ethyl acetate (20 mL). The organic solution was washed with aqueous saturated $NaHCO_3$ (15 mL×2), water (20 mL), brine solution (10 mL), dried over anhydrous $Na_2SO_4$ and evaporated under reduced pressure to give ethyl 2-amino-2-(4-fluorophenyl)acetate (0.75 g, 65%) as crude compound (oily liquid). The crude compound was taken to the next step without further purification. LC-MS (M+H₂O)⁺=198.0. ¹H NMR (400 MHz, DMSO-d6): δ 7.44-7.40 (2H, m), 7.18-7.13 (2H, m), 4.51 (1H, s), 4.12-4.01 (2H, m), 2.26 (2H, s), 1.12 (3H, t, J=8.0 Hz).

Intermediate AI(2)

ethyl 4-(2-ethoxy-1-(4-fluorophenyl)-2-oxoethylamino)butanoate

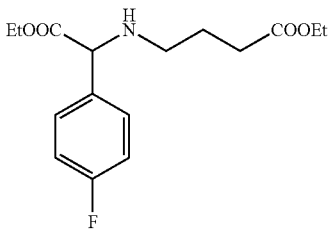 [SMILES: CCOC(=O)CCCNC(C(=O)OCC)c1ccc(F)cc1]

To a solution of Intermediate AI(1) (4.2 g, 21.3 mmol) in DMF was added cesium carbonate (8.3 g, 2.25 mmol) followed ethyl 4-bromobutyroate (4.98 g, 2.55 mmol) at room temperature. The reaction mixture was stirred at 70° C. for 18 h. The solvent was evaporated under reduced pressure and the crude compound was purified by column chromatography (Silica gel, 60-120 mesh) using 25% ethyl acetate in pet-ether as mobile phase to give ethyl 4-(2-ethoxy-1-(4-fluorophenyl)-2-oxoethylamino)butanoate (2.0 g, 30%) as yellowish oily liquid. LC-MS (M+H)$^+$=312.2. $^1$H NMR (400 MHz, CDCl$_3$): δ ppm 7.33 (2H, m), 7.06 (2H, m), 4.31 (1H, m), 4.18 (4H, m), 2.63 (1H, m), 2.49 (1H, m), 2.35 (2H, m), 1.81 (1H, m), 1.24 (6H, m).

Intermediate AI(3)

ethyl 4-((2-ethoxy-1-(4-fluorophenyl)-2-oxoethyl)(4-methoxybenzyl)amino)butanoate

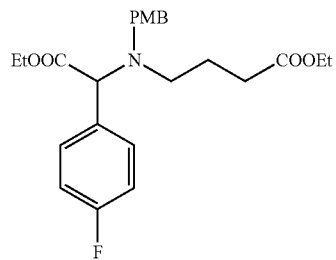

To a solution Intermediate AI(2) (15.0 g, 48.23 mmol) in acetone was added K$_2$CO$_3$ (7.9 g, 57.8 mmol) followed by 4-methoxybenzyl bromide (14.5 g, 72.3 mmol) at 0° C. The reaction mixture was heated at 70° C. for 18 h. The solvent was removed under reduced pressure and the residue was diluted with water. The aqueous layer was extracted with ethyl acetate (100×2). The combined organic layer was washed with brine solution (75 mL), dried over anhydrous Na$_2$SO$_4$ and evaporated under reduced pressure to get crude compound. The crude compound was purified by column chromatography (Silica gel, 60-120 mesh) using 30% ethyl acetate in pet-ether as mobile phase to give ethyl 4-((2-ethoxy-1-(4-fluorophenyl)-2-oxoethyl)(4-methoxybenzyl) amino)butanoate (12.0 g, 60%) as oily liquid. LC-MS (M+H)$^+$432.2. $^1$H NMR (400 MHz, CDCl$_3$): δ ppm 7.30 (2H, m), 7.22 (2H, m), 7.01 (2H, m), 6.99 (2H, m), 4.52 (1H, s), 4.22 (2H, m), 4.04 (2H, m), 3.79 (5H, m), 3.61 (1H, m), 2.71 (1H, m), 2.57 (1H, m), 2.20 (1H, m), 2.07 (1H, m), 1.70 (2H, m), 1.28 (3H, m, J=7.2 Hz), 1.20 (3H, m, J=7.2 Hz).

Intermediate AI(4)

ethyl 2-(4-fluorophenyl)-1-(4-methoxybenzyl)-3-oxopiperidine-4-carboxylate

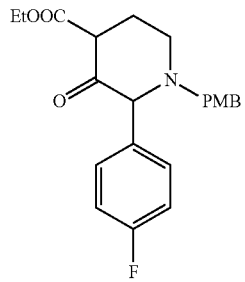

To a cooled solution of Intermediate AI(3) (12.0 g, 27.7 mmol) in THF was added t-BuOK (6.2 g, 55.5 mmol). The reaction mixture was stirred at room temperature for 3 h. The reaction mass was quenched with water then evaporated the solvent under reduced pressure. The residue was diluted with water and extracted with ethyl acetate (50 mL×4). The combined organic layer was washed with brine solution (50 mL), dried over anhydrous Na$_2$SO$_4$ and evaporated under reduced pressure to get crude compound. The crude compound was purified by column chromatography (Silica gel, 60-120 mesh) using 20% ethyl acetate in pet-ether as mobile phase to give ethyl 2-(4-fluorophenyl)-1-(4-methoxybenzyl)-3-oxopiperidine-4-carboxylate (7.0 g, 67%) as oily liquid. LC-MS (M+H)$^+$=386.2. $^1$H NMR (400 MHz, CDCl$_3$): δ ppm 12.02 (1H, s), 7.43 (2H, m), 7.15 (2H, m), 7.04 (2H, m), 6.84 (2H, m), 4.23 (2H, q, J=7.2 Hz), 4.05 (1H, s), 3.79 (3H, s), 3.65 (1H, d, J=13.6 Hz), 3.22 (1H, d, J=13.6 Hz), 2.92 (1H, m), 2.35 (3H, m), 1.32 (3H, t, J=7.2 Hz).

Intermediate AI(5)

8-(4-fluorophenyl)-7-(4-methoxybenzyl)-5,6,7,8-tetrahydropyrido[3,4-d]pyrimidine-2,4(1H,3H)-dione

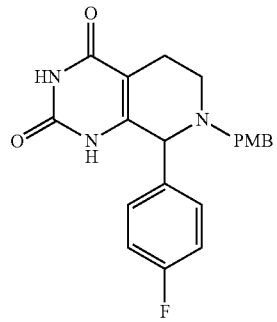

To a cooled solution of Intermediate AI(4) (7.0 g, 18.1 mmol) in ethanol was added t-BuOK (5.0 g 45.4 mmol) followed by urea (2.7 g, 45.4 mmol). The reaction mixture was heated at reflux for 18 h. The reaction mass was quenched with water and evaporated the solvent under reduced pressure. The residue was diluted with water and extracted with ethyl acetate (50 mL×3). The combined organic layer was washed with brine solution (75 mL), dried over Na$_2$SO$_4$ and evaporated under reduced pressure to get crude compound. The crude compound was purified by column chromatography (Silica gel, 60-120 mesh) using 50% pet-ether in ethyl acetate as mobile phase to give 8-(4-fluorophenyl)-7-(4-methoxybenzyl)-5,6,7,8-tetrahydropyrido[3,4-d]pyrimidine-2,4(1H,3H)-dione (3.0 g, 45%) as pale yellow solid. LC-MS (M+H)⁺=382.0. ¹H NMR (400 MHz, DMSO-d6): δ ppm 11.08 (1H, s), 10.44 (1H, s), 7.26-7.17 (6H, m), 6.92 (2H, m), 4.36 (1H, s), 3.75 (3H, s), 3.73 (1H, d, J=13.2 Hz) 3.58 (1H, d, J=13.2 Hz), 2.63 (2H, m), 2.51 (1H, m), 2.35 (1H, m).

Preparation AI 2,4-dichloro-8-(4-fluorophenyl)-7-(4-methoxybenzyl)-5,6,7,8-tetrahydropyrido[3,4-d]pyrimidine

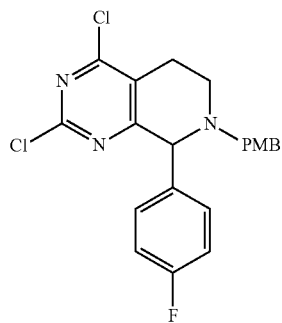

A solution of Intermediate AI(5) (2.0 g, 5.24 mmol) and catalytic amount of DMF in POCl₃ (30 vol.) was heated at 85° C. for 18 h. The excess of POCl₃ was evaporated under reduced pressure. The residue was poured in to crushed ice and stirred for 15 min. The aqueous solution was extracted with ethyl acetate (20 mL×3). The combined organic layer was washed with aqueous saturated NaHCO₃ (10 mL×4), brine solution (25 mL), dried over anhydrous Na₂SO₄ and evaporated under reduced pressure to give 2,4-dichloro-8-(4-fluorophenyl)-7-(4-methoxybenzyl)-5,6,7,8-tetrahydropyrido[3,4-d]pyrimidine (1.4 g, crude) as brown solid. LC-MS (M+H)⁺=418.0.

Preparation AIa 2-chloro-N-ethyl-8-(4-fluorophenyl)-7-(4-methoxybenzyl)-5,6,7,8-tetrahydropyrido[3,4-d]pyrimidin-4-amine

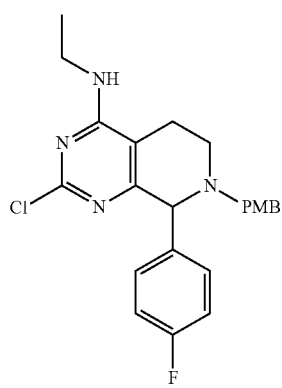

To a solution of Preparation AI (0.7 g, 1.67 mmol) in methanol was added diisopropylethylamine (0.43 g, 3.35 mmol) followed by ethylamine hydrochloride (0.27 g, 3.35 mmol) at room temperature. The reaction mixture was stirred at room temperature for 18 h. The solvent was removed under reduced pressure and the residue was purified by column chromatography (60-120 mesh) using 35% ethyl acetate in pet-ether as mobile phase to give chloro-N-ethyl-8-(4-fluorophenyl)-7-(4-methoxybenzyl)-5,6,7,8-tetrahydropyrido[3,4-d]pyrimidin-4-amine (0.36 g, 50%) as off-white solid. LC-MS (M+H)⁺=427.2. ¹H NMR: (400 MHz, DMSO-d6): δ ppm 7.38 (2H, m), 7.30 (2H, m), 7.20-7.13 (4H, m), 6.88 (2H, m), 4.45 (1H, s), 3.73 (3H, s), 3.45 (1H, m), 3.40-3.34 (3H, m), 2.88 (1H, m), 2.42 (2H, m), 1.16 (3H, t, J=7.2 Hz).

Preparation AIb 2-chloro-N-ethyl-8-(4-fluorophenyl)-7-(4-methoxybenzyl)-N-methyl-5,6,7,8-tetrahydropyrido[3,4-d]pyrimidin-4-amine

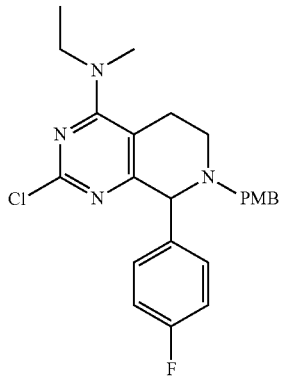

To a solution of Preparation AI (0.7 g, 1.67 mmol) in methanol was added diisopropylethylamine (0.43 g, 3.3 mmol) followed by ethylmethylamine HCl (0.19 g, 3.35 mmol) at room temperature. The reaction mixture was stirred at room temperature for 18 h. The solvent was removed under reduced pressure and the residue was purified by column chromatography (60-120 mesh) using 20% ethyl acetate in pet-ether as mobile phase to give 2-chloro-N-ethyl-8-(4-fluorophenyl)-7-(4-methoxybenzyl)-N-methyl-5,6,7,8-tetrahydropyrido[3,4-d]pyrimidin-4-amine (0.40 g, 54%) as off-white solid. LC-MS (M+H)⁺=441.2. ¹H NMR: (400 MHz, DMSO-d6) δ ppm 7.49 (2H, m), 7.19-7.14 (4H, m), 6.87 (2H, m), 4.42 (1H, s), 3.73 (3H, s), 3.55 (2H, m), 3.42 (1H, m), 3.21 (1H, m), 3.04 (3H, s), 2.95 (2H, m), 2.56 (1H, m), 2.25 (1H, m), 1.16 (3H, t, J=7.2 Hz).

Preparation AIc1 and AIc2

2-chloro-8-(4-fluorophenyl)-4-((R)-3-fluoropyrrolidin-1-yl)-7-(4-methoxybenzyl)-5,6,7,8-tetrahydropyrido[3,4-d]pyrimidine Preparation AId 2-chloro-8-(4-fluorophenyl)-4-((S)-3-fluoropyrrolidin-1-yl)-7-(4-methoxybenzyl)-5,6,7,8-tetrahydropyrido[3,4-d]pyrimidine

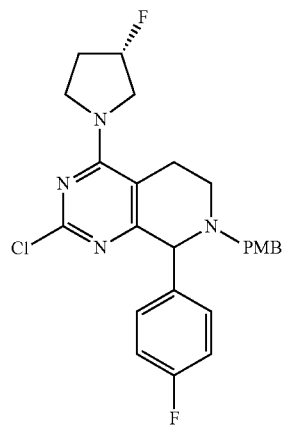

To a solution of Preparation AI (0.70 g, 1.6 mmol) in methanol was added diisopropylethylamine (0.43 g, 3.35 mmol) followed by (R)-3-fluoropyrrolidine (0.25 g, 2.2 mmol) at room temperature. The reaction mixture was stirred at room temperature for 18 h. The solvent was removed under reduced pressure and the residue was purified by pep-HPLC to give 2-chloro-8-(4-fluorophenyl)-4-((S)-3-fluoropyrrolidin-1-yl)-7-(4-methoxybenzyl)-5,6,7,8-tetrahydropyrido[3,4-d]pyrimidine (0.150 g, 37% & 190 mg, 43%). LC-MS $(M+H)^+=471.2$.

Preparation AIe

N2-(4-(4-chloro-1H-imidazol-1-yl)-3-methoxyphenyl)-N4-ethyl-8-(4-fluorophenyl)-7-(4-methoxybenzyl)-5,6,7,8-tetrahydropyrido[3,4-d]pyrimidine-2,4-diamine

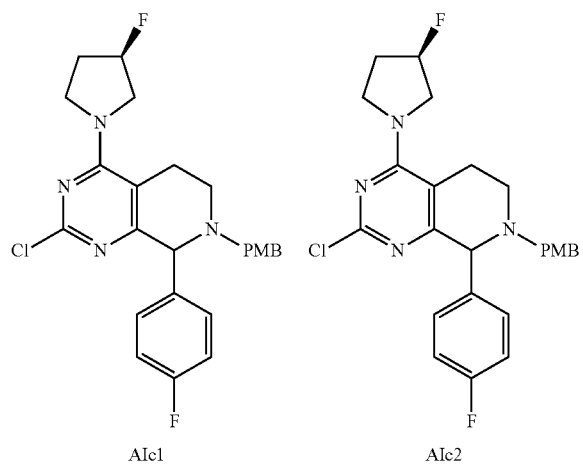

AIc1                         AIc2

To a solution of Preparation AI (0.70 g, 1.6 mmol) in methanol was added diisopropylethylamine (0.40 g, 3.35 mmol) followed by (S)-3-fluoropyrrolidine (0.25 g, 2.14 mmol) at room temperature. The reaction mixture was stirred at room temperature for 18 h. The solvent was removed under reduced pressure and the residue was purified by pep-HPLC to give 2-chloro-8-(4-fluorophenyl)-4-((R)-3-fluoropyrrolidin-1-yl)-7-(4-methoxybenzyl)-5,6,7,8-tetrahydropyrido[3,4-d]pyrimidine (0.150 g, 37% & 190 mg, 43%).

AIc1: LC-MS $(M+H)^+=471.1$. $^1$H NMR (400 MHz, chloroform-d): δ ppm 7.48 (2H, m), 7.15 (2H, m), 7.01 (2H, m), 6.83 (2H, m), 5.30 (1H, m), 4.43 (1H, s), 3.97-3.90 (4H, m), 3.88-3.72 (4H, m), 3.65 (1H, m), 3.17 (1H, m), 3.02 (2H, m), 2.33 (2H, m), 1.95 (1H, m).

AIc2: LC-MS $(M+H)^+=471.1$. $^1$H NMR (400 MHz, chloroform-d): δ ppm 7.28 (2H, m), 7.18 (2H, m), 6.99 (2H, m), 6.84 (2H, m), 5.30 (1H, m), 4.58 (1H, s), 4.20-4.11 (2H, m), 3.97-3.80 (6H, m), 3.69 (1H, m), 3.35 (1H, m), 2.88 (2H, m), 2.35 (1H, m), 2.17 (1H, m), 2.05 (1H, m).

A solution of Preparation A (0.36 g, 0.845 mmol), Preparation Ma (0.189 g, 0.845 mmol), Na$_2$CO$_3$ (0.179 g, 1.69 mmol) and xantphos (0.488 g, 0.845 mmol) in dioxane/water (9:1) was purged with argon for 1 h at room temperature. Pd(dba)$_3$ (0.870 g, 0.845 mmol) was added to the reaction mixture and the resulting solution was purged with argon for another 1 h. The reaction mass was heated at 110° C. for 24 h.

The reaction mass was filtered through celite bed and washed with ethyl acetate. The filtrate was evaporated under reduced pressure and the residue was diluted with water. The aqueous solution was extracted with ethyl acetate (50 mL×3). The combined organic layer was washed with brine solution (50 mL), dried over anhydrous Na$_2$SO$_4$ and evaporated under reduced pressure to get crude compound. The crude compound was purified by column chromatography (60-120 mesh) using 20% ethyl acetate in pet-ether as mobile phase to give N2-(4-(4-chloro-1H-imidazol-1-yl)-3-methoxyphenyl)-N4-ethyl-8-(4-fluorophenyl)-7-(4-methoxybenzyl)-5,6,7,8-tetrahydropyrido[3,4-d]pyrimidine-2,4-diamine (0.30 g, 58%) as off-white solid. LC-MS (M+H)$^+$=614.2. $^1$H NMR (400 MHz, DMSO-d6): δ ppm 8.96 (1H, s), 7.79 (1H, s), 7.74 (1H, s), 7.43 (1H, s), 7.33 (2H, m), 7.20 (6H, m), 6.89 (2H, m), 6.80 (1H, m), 4.44 (1H, s), 3.74 (3H, s), 3.66 (3H, s), 3.50 (4, m), 2.90 (1H, m), 2.33 (3H, m), 1.24 (3H, t, J=7.2 Hz).

Preparation AIf

N2-(4-(4-chloro-1H-imidazol-1-yl)-3-methoxyphenyl)-N4-ethyl-8-(4-fluorophenyl)-7-(4-methoxybenzyl)-N4-methyl-5,6,7,8-tetrahydropyrido[3,4-d]pyrimidine-2,4-diamine

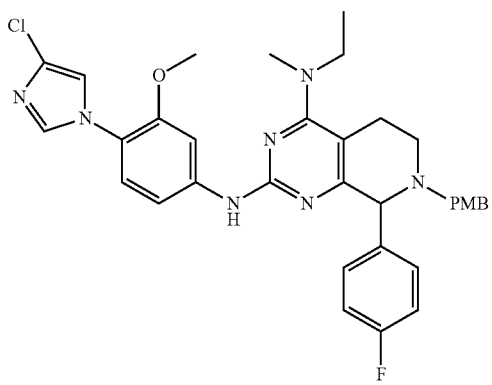

A solution of Preparation A (0.20 g, 0.90 mmol), Preparation AIb (0.41 g, 0.90 mmol), Na$_2$CO$_3$ (0.192 g, 1.80 mmol) and xantphos (0.525 g, 0.90 mmol) in dioxane/water (9:1) was purged with argon for 1 h at room temperature. Pd(dba)$_3$ (0.470 g, 0.45 mmol) was added to the reaction mixture and the resulting solution was purged with argon for another 1 h. The reaction mass was heated at 110° C. for 24 h. The reaction mass was filtered through celite bed and washed with ethyl acetate. The filtrate was evaporated under reduced pressure and the residue was diluted with water. The aqueous solution was extracted with ethyl acetate (50 mL×3). The combined organic layer was washed with brine solution (50 mL), dried over anhydrous Na$_2$SO$_4$ and evaporated under reduced pressure to get crude compound. The crude compound was purified by column chromatography (60-120 mesh) using 30% ethyl acetate in pet-ether as mobile phase to give N2-(4-(4-chloro-1H-imidazol-1-yl)-3-methoxyphenyl)-N4-ethyl-8-(4-fluorophenyl)-7-(4-methoxybenzyl)-N4-methyl-5,6,7,8-tetrahydropyrido[3,4-d]pyrimidine-2,4-diamine (0.34 g, 59%) as off-white solid. This compound was taken to the next step without further analysis. LC-MS (M+H)$^+$=628.2.

Preparation AIg

N-(4-(4-chloro-1H-imidazol-1-yl)-3-methoxyphenyl)-8-(4-fluorophenyl)-4-((R)-3-fluoropyrrolidin-1-yl)-7-(4-methoxybenzyl)-5,6,7,8-tetrahydropyrido[3,4-d]pyrimidin-2-amine

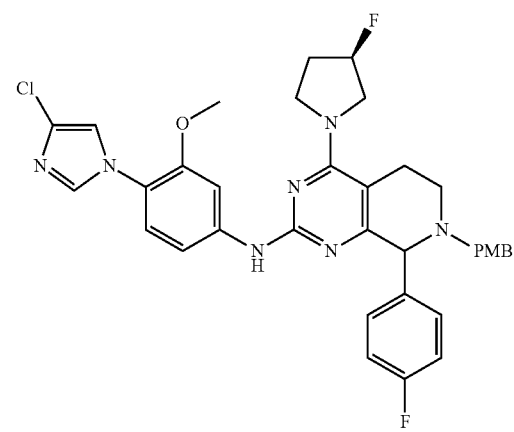

A solution of Preparation A (0.070 g, 0.319 mmol), Preparation AIc1 (0.150 g, 0.319 mmol), Na$_2$CO$_3$ (0.067 g, 0.63 mmol) and xantphos (0.184 g, 0.319 mmol) in dioxane/water (9:1) was purged with argon for 1 h at room temperature. Pd(dba)$_3$ (0.165 g, 0.159 mmol) was added to the reaction mixture and the resulting solution was purged with argon for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (20 mL×3). The combined organic layer was washed with brine solution (20 mL), dried over anhydrous Na$_2$SO$_4$ and evaporated under reduced pressure to get crude compound. The crude compound was purified by column chromatography (60-120 mesh) using 50% ethyl acetate in pet-ether as mobile phase to give N-(4-(4-chloro-1H-imidazol-1-yl)-3-methoxyphenyl)-8-(4-fluorophenyl)-4-((R)-3-fluoropyrrolidin-1-yl)-7-(4-methoxybenzyl)-5,6,7,8-tetrahydropyrido[3,4-d]pyrimidin-2-amine (0.1 g, 48%) as off-white solid. LC-MS (M+H)$^+$=658.2.

Preparation AIh

N-(4-(4-chloro-1H-imidazol-1-yl)-3-methoxyphenyl)-8-(4-fluorophenyl)-4-((R)-3-fluoropyrrolidin-1-yl)-7-(4-methoxybenzyl)-5,6,7,8-tetrahydropyrido[3,4-d]pyrimidin-2-amine

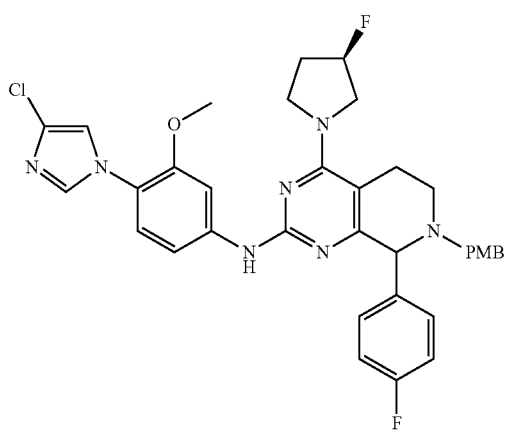

A solution of Preparation A (0.09 g, 0.404 mmol), Preparation AIc2 (0.190 g, 0.404 mmol), Na$_2$CO$_3$ (0.085 g, 0.80 mmol) and xantphos (0.230 g, 0.404 mmol) in dioxane/water (9:1) was purged with argon for 1 h at room temperature. Pd(dba)$_3$ (0.209 g, 0.202 mmol) was added to the reaction mixture and the resulting solution was purged with argon for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (20 mL×3). The combined organic layer was washed with brine solution (20 mL), dried over anhydrous Na$_2$SO$_4$ and evaporated under reduced pressure to get crude compound. The crude compound was purified by column chromatography (60-120 mesh) using 50% ethyl acetate in pet-ether as mobile phase to give N-(4-(4-chloro-1H-imidazol-1-yl)-3-methoxyphenyl)-8-(4-fluorophenyl)-4-((R)-3-fluoropyrrolidin-1-yl)-7-(4-methoxybenzyl)-5,6,7,8-tetrahydropyrido[3,4-d]pyrimidin-2-amine (0.120 g, 48%) as off-white solid. LC-MS (M+H)$^+$=538.2.

Preparation AIk

N2-(4-(4-chloro-1H-imidazol-1-yl)-3-methoxyphenyl)-N4-ethyl-8-(4-fluorophenyl)-5,6,7,8-tetrahydropyrido[3,4-d]pyrimidine-2,4-diamine

To a solution of Preparation AIe (0.30 g, 0.489 mmol) in toluene was added trifluoromethanesulfonic acid (3.0 vol.) at room temperature. The reaction mixture was heated at reflux for 1 h. The solvent was removed under reduced pressure and the residue was diluted with water. The aqueous solution was washed with dichloromethane (25 mL×2), basified by using aqueous saturated NaHCO$_3$ and extracted with ethyl acetate (50 mL×2). The combined organic layer was washed with brine solution (50 mL), dried over anhydrous Na$_2$SO$_4$ and evaporated under reduced pressure to give N2-(4-(4-chloro-1H-imidazol-1-yl)-3-methoxyphenyl)-N4-ethyl-8-(4-fluorophenyl)-5,6,7,8-tetrahydropyrido[3,4-d]pyrimidine-2,4-diamine as crude compound (0.20 g). The crude compound was taken to the next step without further purification. LC-MS (M+H)$^+$=494.2.

Preparation AIl (Example 1)

N2-(4-(4-chloro-1H-imidazol-1-yl)-3-methoxyphenyl)-N4-ethyl-8-(4-fluorophenyl)-N4-methyl-5,6,7,8-tetrahydropyrido[3,4-d]pyrimidine-2,4-diamine

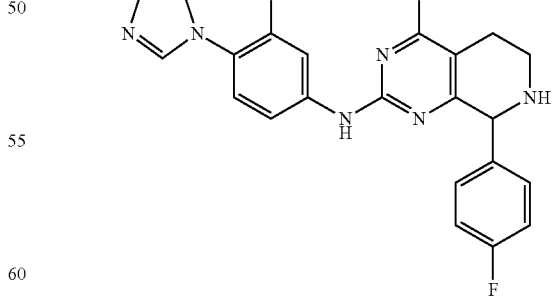

To a solution of Preparation AIf (0.340 g, 0.541 mmol) in toluene was added trifluoromethanesulfonic acid (3.0 vol.) at room temperature. The reaction mixture was heated at reflux for 1 h. The solvent was removed under reduced pressure and the residue was diluted with water. The aqueous solution was washed with dichloromethane (10 mL×2), basified by using aqueous saturated NaHCO₃ and extracted with ethyl acetate (20 mL×3). The combined organic layer was washed with brine solution (25 mL), dried over anhydrous Na₂SO₄ and evaporated under reduced pressure to give N2-(4-(4-chloro-1H-imidazol-1-yl)-3-methoxyphenyl)-N4-ethyl-8-(4-fluorophenyl)-N4-methyl-5,6,7,8-tetrahydropyrido[3,4-d]pyrimidine-2,4-diamine as crude compound (0.20 g). The crude compound was taken to the next step without further purification. LC-MS (M+H)⁺=508.2. ¹H NMR (400 MHz, DMSO-d6): δ ppm 9.05 (1H, s), 7.78 (1H, s), 7.74 (1H, s), 7.43 (1H, s), 7.32 (2H, m), 7.21-7.0 (5H, m), 4.85 (1H, s), 3.59 (3H, s), 3.49 (2H, m), 3.05 (3H, s), 2.68 (2H, m), 2.51 (2H, m), 1.22 (3H, t, J=7.2 Hz).

Preparation AIm

N-(4-(4-chloro-1H-imidazol-1-yl)-3-methoxyphenyl)-8-(4-fluorophenyl)-4-((R)-3-fluoropyrrolidin-1-yl)-5,6,7,8-tetrahydropyrido[3,4-d]pyrimidin-2-amine

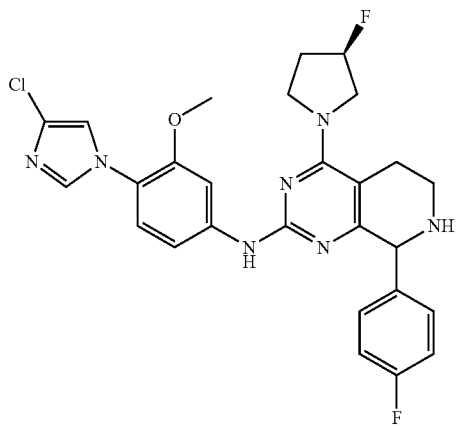 [SMILES: COc1cc(Nc2nc3c(c(N4CC[C@@H](F)C4)n2)CCNC3c2ccc(F)cc2)ccc1-n1cnc(Cl)c1]

To a solution of Intermediate AIg (0.120 g, 0.182 mmol) in toluene was added trifluoromethanesulfonic acid (3.0 vol.) at room temperature. The reaction mixture was heated at reflux for 1 h. The solvent was removed under reduced pressure and the residue was diluted with water. The aqueous solution was washed with dichloromethane (10 mL×2), basified by using aqueous saturated NaHCO₃ and extracted with ethyl acetate (20 mL×2). The combined organic layer was washed with brine solution (25 mL), dried over anhydrous Na₂SO₄ and evaporated under reduced pressure to give N-(4-(4-chloro-1H-imidazol-1-yl)-3-methoxyphenyl)-8-(4-fluorophenyl)-4-((R)-3-fluoropyrrolidin-1-yl)-5,6,7,8-tetrahydropyrido[3,4-d]pyrimidin-2-amine (0.040 g, 50%). LC-MS (M+H)⁺=538.2.

Preparation AIn

N-(4-(4-chloro-1H-imidazol-1-yl)-3-methoxyphenyl)-8-(4-fluorophenyl)-4-((R)-3-fluoropyrrolidin-1-yl)-5.6.7.8-tetrahydropyrido[3,4-d]pyrimidin-2-amine

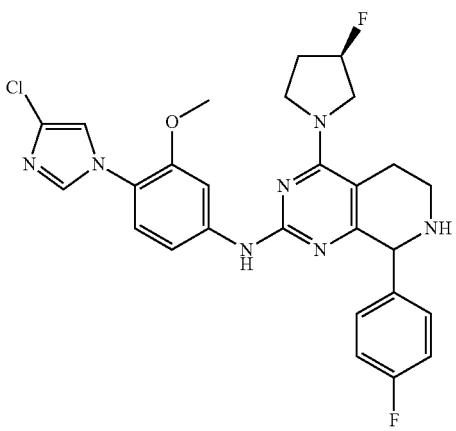 [SMILES: COc1cc(Nc2nc3c(c(N4CC[C@@H](F)C4)n2)CCNC3c2ccc(F)cc2)ccc1-n1cnc(Cl)c1]

To a solution of Preparation AIh (0.120 g, 0.182 mmol) in toluene was added trifluoromethanesulfonic acid (3.0 vol.) at room temperature. The reaction mixture was heated at reflux for 1 h. The solvent was removed under reduced pressure and the residue was diluted with water. The aqueous solution was washed with dichloromethane (10 mL×2), basified by using aqueous saturated NaHCO₃ and extracted with ethyl acetate (20 mL×2). The combined organic layer was washed with brine solution (20 mL), dried over anhydrous Na₂SO₄ and evaporated under reduced pressure to give N-(4-(4-chloro-1H-imidazol-1-yl)-3-methoxyphenyl)-8-(4-fluorophenyl)-4-((R)-3-fluoropyrrolidin-1-yl)-5,6,7,8-tetrahydropyrido[3,4-d]pyrimidin-2-amine (0.045 g, 51%). LC-MS (M+H)⁺=538.2.

Preparation AJ 2-chloro-4-(methylamino)-8-phenyl-7,8-dihydroquinazolin-8-ol

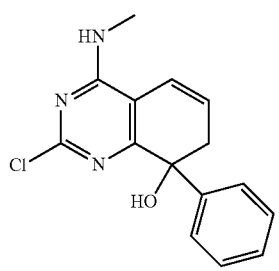 [SMILES: CNc1nc(Cl)nc2c1C=CCC2(O)c1ccccc1]

Intermediate AJ(1)

methyl 2-chloro-6-(methylamino)pyrimidine-4-carboxylate

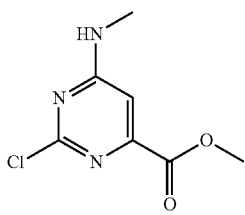

To a mixture of methyl 2,6-dichloropyrimidine-4-carboxylate (2 g), methylamine hydrochloride (0.72 g) in CH$_2$Cl$_2$ (48 mL) at 0° C. was added Hunig's base (3.7 mL) dropwise, and the reaction mixture was stirred at ice bath for 1 h and then rt for 1 h. The solvent was removed in vacuo, and the white residue was purified directly by Biotage eluting with 40-600% EtOAc/Hexanes (1000 mL) followed by 90% CH2Cl2/10% MeOH (4 L) to give the title compound as a white solid (1.8 g). These fractions were combined and evaporated in vacuo. During the solvent removal, some white solid was formed. Several filtrations gave the title compound as a white solid (1.8 g, very white solid). LC-MS (M+H)$^+$=202.00

Intermediate AJ(2)

2-chloro-N-methoxy-N-methyl-6-(methylamino)pyrimidine-4-carboxamide

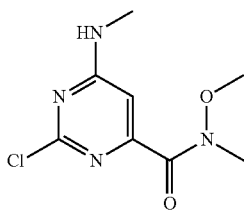

To a suspension of methyl 2-chloro-6-(methylamino)pyrimidine-4-carboxylate (1.95 g) and N,O-dimethylhydroxylamine hydrochloride (1.887 g, 19.34 mmol) in THF at −20° C. was added isopropylmagnesium chloride (23.60 mL, 47.2 mmol) dropwise through a dropping funnel over a period of 30 min, and the reaction mixture was stirred at −10° C. for 40 min. The reaction was worked up with sat. NH$_4$Cl and EtOAc, and the crude product was purified by Biotage eluting with 40-90% EtOAc/Hexanes to give the title compound as a colorless oil (786 mg). LC-MS (M+H)$^+$=231.01.

Intermediate AJ(3)

5-bromo-2-chloro-N-methoxy-N-methyl-6-(methylamino)pyrimidine-4-carboxamide

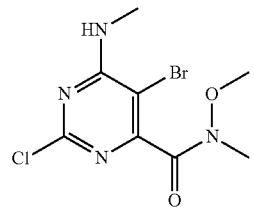 [SMILES: CNc1nc(Cl)nc(C(=O)N(C)OC)c1Br]

To a solution of 2-chloro-N-methoxy-N-methyl-6-(methylamino)pyrimidine-4-carboxamide (959 mg) in MeCN (21 mL) was added NBS (814 mg), and the reaction mixture was heated at 60° C. for 8 h. The solvent was removed, and the residue was purified by Biotage eluting with 50%-70 EtOAc/Hexanes (1.2 L) to give the title compound as a white solid (1.1 g). LC-MS (M+H)$^+$=310.95.

Intermediate AJ(4)

2-chloro-N-methoxy-N-methyl-6-(methylamino)-5-vinylpyrimidine-4-carboxamide

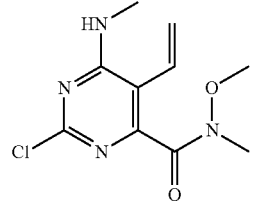 [SMILES: C=Cc1c(NC)nc(Cl)nc1C(=O)N(C)OC]

A solution of 5-bromo-2-chloro-N-methoxy-N-methyl-6-(methylamino)pyrimidine-4-carboxamide (100 mg), tributyl(vinyl)stannane (113 mg), tetrakis (23 mg) in toluene (1.6 mL) was heated at 95° C. for 12 h, and the solvent was removed. The residue was purified by preparative TLC eluting with 50% EtOAc/Hexanes to give the title compound as a colorless oil (23 mg). LC-MS (M+H)$^+$=257.06.

Intermediate AJ(5)

(2-chloro-6-(methylamino)-5-vinylpyrimidin-4-yl)(phenyl)methanone

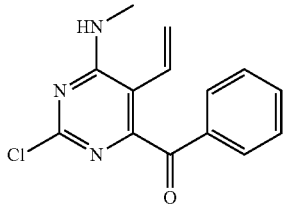 [SMILES: C=Cc1c(NC)nc(Cl)nc1C(=O)c1ccccc1]

To a solution of 2-chloro-N-methoxy-N-methyl-6-(methylamino)-5-vinylpyrimidine-4-carboxamide (136 mg) in THF (1.8 mL) at 0° C. was added phenylmagnesium bromide (1 M solution in THF, 1.3 mL)) dropwise, and the reaction mixture was stirred at 0° C. for 30 min. The reaction was worked up with EtOAc/sat. NH$_4$Cl, and the crude product was purified by preparative TLC eluting with 40% EtOAc/Hexanes to give the title compound as a colorless oil (87 mg). LC-MS (M+H)$^+$= 274.03.

Intermediate AJ(6)

1-(2-chloro-6-(methylamino)-5-vinylpyrimidin-4-yl)-1-phenylbut-3-en-1-ol

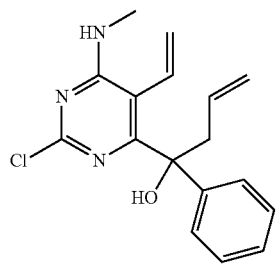 [SMILES: C=CCC(O)(c1ccccc1)c1nc(Cl)nc(NC)c1C=C]

To a solution of (2-chloro-6-(methylamino)-5-vinylpyrimidin-4-yl)(phenyl)methanone (142 mg) in THF (2.6 mL) at rt was added allylmagnesium bromide (1.0 M solution in THF, 1.1 mL) dropwise, and the reaction mixture was stirred at rt for 30 min. The reaction was worked up with EtOAc/sat. NH$_4$Cl, and the crude product was purified by prep. TLC eluting with 30% EtOAc/Hexanes to give the title compound as a colorless oil (133 mg). LC-MS (M–H$_2$O+H)$^+$=298.18.

Preparation AJ 2-chloro-4-(methylamino)-8-phenyl-7,8-dihydroquinazolin-8-ol

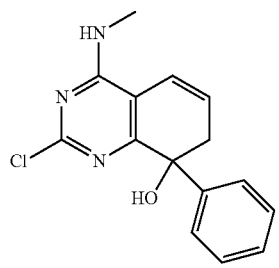 [SMILES: CNc1nc(Cl)nc2c1C=CCC2(O)c1ccccc1]

To a solution of 1-(2-chloro-6-(methylamino)-5-vinylpyrimidin-4-yl)-1-phenylbut-3-en-1-ol (60 mg) in benzene (5 mL) was added Grubbs I (16 mg), and the reaction mixture was heated at 85° C. for 1 h. The solvent was removed, and the residue was purified by preparative TLC eluting with 40% EtOAc/Hexanes to give the title compound as a colorless oil (50 mg). $^1$H NMR (500 MHz, CDCl$_3$) δ ppm 7.4 (5H, m), 6.25 (1H, m), 6.07 (1H, m), 5.14 (1H, br. S), 4.52 (1H, s), 3.10 (3H, d<J=5.0 Hz), 2.99 (2H, m). $^{13}$C NMR (125 MHz, CDCl$_3$) 164.32, 159.38, 158.85, 144.15, 128.24, 128.02, 127.83, 125.51, 117.54, 108.14, 60.51, 38.50, and 28.57. HRMS calcd. for C$_{15}$FH$_{15}$ClN$_3$O (M+H) 288.0904. found: 288.0899.

Preparation AK 2-chloro-4-(methylamino)-8-phenyl-5,6,7,8-tetrahydroquinazolin-8-ol

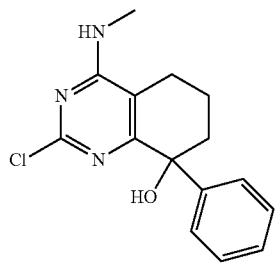 [SMILES: CNc1nc(Cl)nc2c1CCCC2(O)c1ccccc1]

To a solution of 2-chloro-4-(methylamino)-8-phenyl-7,8-dihydroquinazolin-8-ol (20 mg) in EtOAc (5 mL) was added 5% Pd/C (6 mg), and the resulting suspension was stirred under a hydrogen balloon for 1 h. The reaction mixture was filtered through a pad of Celite to give the title compound as a colorless oil (20 mg).

$^1$H NMR (500 MHz, CDCl$_3$) δ ppm 7.3 (5H, m), 4.9 (1H, br. S), 4.02 (1H, s), 3.14 (3H, br. S), 1.5-2.5 (6H, m) $^{13}$C NMR (125 MHz, CDCl$_3$) 164.82, 162.72, 158.56, 146.54, 128.02, 127.37, 126.72, 110.92, 74.81, 37.58, 28.61, 21.89, 17.47. HRMS calcd. for C$_{15}$FH$_{17}$ClN$_3$O (M+H) 290.1060. found: 290.1052.

Preparation AL 2-chloro-4-(dimethylamino)-7-phenyl-6,7-dihydro-5H-cyclopenta[d]pyrimidin-7-ol

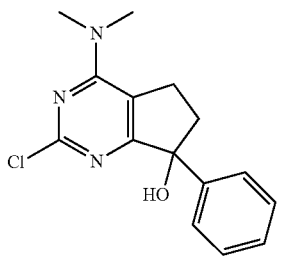 [SMILES: CN(C)c1nc(Cl)nc2c1CCC2(O)c1ccccc1]

2-chloro-4-(dimethylamino)-7-phenyl-7H-cyclopenta[d]pyrimidin-7-ol was prepared from methyl 2,6-dichloropyrimidine-4-carboxylate using the same transformations as shown in Preparation AJ/AK with the following differences: Intermediate AL(1): dimethylamine was used instead of methylamine hydrochloride, and 1.1 equiv of Hünig's base was used; Intermediate AL(6): vinylmagnesium bromide was used instead of allylmagnesium bromide. $^1$H NMR (500 MHz, CDCl$_3$) δ ppm 7.3 (5H, m), 3.28 (6H, s), 1.5-3.4 (5H, m). $^{13}$C NMR (125 MHz, CDCl$_3$) 174.66, 161.76, 159.58, 144.61, 128.49, 127.58, 125.35, 113.92, 82.86, 41.07, 39.00, 28.59. HRMS calcd. for C$_{15}$H$_{17}$ClN$_3$O (M+H) 290.1060. found: 290.1050.

Preparation AM (6S,7S)-2-chloro-4-(dimethyl amino)-7-phenyl-6,7-dihydro-5H-cyclopenta[d]pyrimidin-6-ol

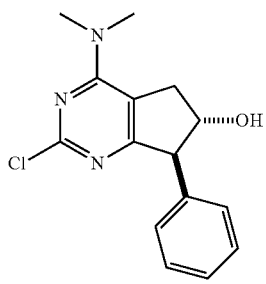 [SMILES: CN(C)c1nc(Cl)nc2c1C[C@H](O)[C@H]2c1ccccc1]

Intermediate AM(1)

2-chloro-N,N-dimethyl-7-phenyl-5H-cyclopenta[d]pyrimidin-4-amine

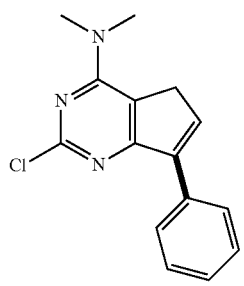

To a solution of 2-chloro-4-(dimethylamino)-7-phenyl-6,7-dihydro-5H-cyclopenta[d]pyrimidin-7-ol (85 mg) in i-PrOH (5 mL) was added HCl in ether (1M solution), and the reaction mixture was heated at 80° C. from 3 h. The solution was cloudy and turned to clear yellow solution by the end of the reaction. The solvents were removed, and the reaction mixture was worked up with EtOAc and saturated NaHCO₃ to give the title compound as a brownish solid (50 mg). LC-MS $(M-H_2O+H)^+=272.07$.

Preparation AM (6S,7S)-2-chloro-4-(dimethylamino)-7-phenyl-6,7-dihydro-5H-cyclopenta[d]pyrimidin-6-ol

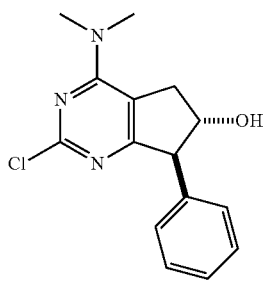 [SMILES: CN(C)c1nc(Cl)nc2c1C[C@H](O)[C@H]2c1ccccc1]

To a solution of 2-chloro-N,N-dimethyl-7-phenyl-5H-cyclopenta[d]pyrimidin-4-amine (113 mg) in THF (2 mL) at rt was added borane dimethyl sulfide complex in THF (2.0 M solution, 0.41 mL), and the reaction mixture was stirred at rt for 5 h. Water (0.50 mL) was added carefully, followed by 30% H₂O₂ (0.50 mL) and 1 N NaOH (1 mL). 5 mL EtOAc was added, and the rxn mixture was stirred at rt for 12 h. The crude product was purified by prep. TLC eluting with 50% EtOAc/Hexanes to give the title compound as a yellowish solid (44 mg). LC-MS $(M-H_2O+H)^+=290.05$.

Preparation AN 2-chloro-4-(methylamino)-7-phenyl-6,7-dihydro-5H-cyclopenta[d]pyrimidin-5-one

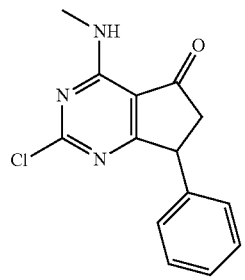 [SMILES: CNc1nc(Cl)nc2c1C(=O)CC2c1ccccc1]

Intermediate AN(1)

2,4-dichloro-6-(1-phenylvinyl)pyrimidin-5-yl)methanol

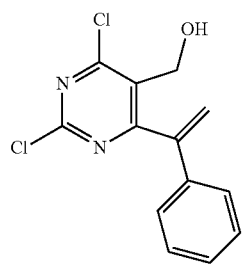 [SMILES: C=C(c1ccccc1)c1nc(Cl)nc(Cl)c1CO]

A mixture of 2,4,6-trichloropyrimidin-5-yl)methanol (1.1 g), 1-phenylvinylboronic acid (0.8 g), Tetrakis (0.3 g), sodium carbonate (1.64 g) in toluene (14 mL) and water (3 mL) was heated at 100° C. for 12 h. Water was added followed by ethyl acetate, the aqueous layer was extracted with ethyl acetate (×3), and the combined organic layers were dried over anhydrous sodium sulfate and then filtered. The filtrate was concentrated, and the residue was purified Biotage eluting with 10-40% EtOAc/Hexanes to give the title compound as a white solid (325 mg). LC-MS $(M+H)^+=281.02$. ¹H NMR (500 MHz, chloroform-d) δ ppm 7.5 (5H, m), 6.01 (1H, s), 5.67 (1H, s), 4.62 (2H, s).

Intermediate AN(2)

2,4-dichloro-6-(1-phenylvinyl)pyrimidine-5-carbaldehyde

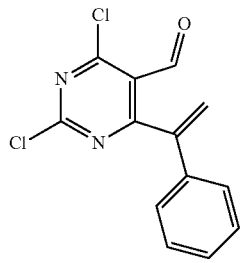 [SMILES: C=C(c1ccccc1)c1nc(Cl)nc(Cl)c1C=O]

To a solution of 2,4-dichloro-6-(1-phenylvinyl)pyrimidin-5-yl)methanol (327 mg) in CH$_2$Cl$_2$ was added PCC (600 mg) and 4A MS (600 mg), and the rxn mixture was stirred at rt for 30 min. The solution turned to dark brown from orange a few min after addition of PCC. The reaction mixture was filtered through a pad of silica gel eluting with CH$_2$Cl$_2$ to give the title compound as a s a brownish solid (209 mg) and used directly for the next step.

Intermediate AN(3)

1-(2,4-dichloro-6-(1-phenylvinyl)pyrimidin-5-yl)prop-2-en-1-ol

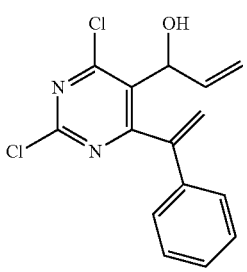 [SMILES: C=CC(O)c1c(Cl)nc(Cl)nc1C(=C)c1ccccc1]

To a solution of 2,4-dichloro-6-(1-phenylvinyl)pyrimidine-5-carbaldehyde (200 mg) in THF (3.6 mL) at −78 C. was added vinylmagnesium bromide (0.79 mL, 1M solution in THF) dropwise, and the reaction mixture was stirred at −78° C. for 20 min. Saturated NH$_4$Cl was added followed by ethyl acetate, the aqueous layer was extracted with ethyl acetate (×3), and the combined organic layers were dried over anhydrous sodium sulfate and then filtered. The filtrate was concentrated in vacuo to give the title compound (156 mg) as a colorless oil. The crude product was used directly for the next step.

Preparation AN 2-chloro-4-(methylamino)-7-phenyl-6,7-dihydro-5H-cyclopenta[d]pyrimidin-5-one

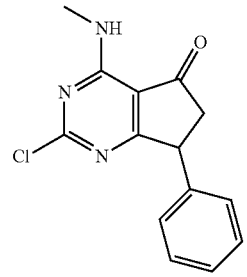 [SMILES: CNc1nc(Cl)nc2c1C(=O)CC2c1ccccc1]

To a solution of 1-(2,4-dichloro-6-(1-phenylvinyl)pyrimidin-5-yl)prop-2-en-1-ol (20 mg) in CH$_2$Cl$_2$ (6.5 mL) was added Grubbs II catalyst (6 mg), and the reaction mixture was heated under reflux for 30 min The solvent was removed, and the residue was dissolved in EtOAc (4 mL), and 10% Pd/C (5 mg) was added. The reaction mixture was stirred under a hydrogen balloon for 35 min. Hydrogen balloon was removed, and then Hunig's base (23 μL) was added followed by methylamine (36 μL, 2 M solution in methanol). The reaction mixture was stirred at room temperature for 10 min, and the solvents were removed. The residue was purified by preparative TLC eluting with 35% EtOAc/Hexanes to give the title compound as a yellow solid (6.6 mg, 37% yield). $^1$H NMR (500 MHz, chloroform-d) δ ppm 7.1-7.4 (5H, m), 4.45 (1H, dd, J=3.0, 8.0 Hz), 3.24 (1H, dd, J=8.0, 19.5 Hz), 3.20 (3H, s), 3.19 (3H, s), 2.71 (1H, dd, J=3.0, 19.5 Hz). $^{13}$C NMR (125 MHz, chloroform-d) δ 203.12, 186.69, 166.52, 159.93, 139.88 129.16 (2C), 127.73 (2C), 127.59, 110.98, 46.50, 45.48, and 27.53. HRMS calcd. for C$_{14}$H$_{13}$ClN$_3$O (M+H) 274.0742. found: 274.0741.

Preparation AO 3-methoxy-4-(1-methyl-1H-pyrazol-4-yl)aniline

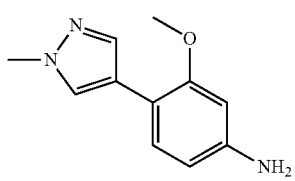

A DMF solution of diethyl 1-methyl-1H-pyrazol-4-ylboronate, 4-bromo-3-methoxy nitrobenzene together with Pd(dppf) and K2CO3 were heated at reflux overnight. The product obtained was reduced with Fe in MeOH/ammonium chloride to provide the title compound. LC-MS (M+H)$^+$= 204.2. $^1$H NMR (400 MHz, DMSO-d6): δ ppm 7.84 (1H, s), 7.66 (1H, s), 7.19 (1H, J=8.2 Hz, d), 6.29 (1H, s), 6.18 (1H, J=2.0, 8.2 Hz, dd), 5.31 (2H, br s), 3.80 (3H, s), 3.75 (3H, s).

EXAMPLES

Example 1

N2-(3-methoxy-4-(3-methyl-1H-1,2,4-triazol-1-yl)phenyl)-N4-methyl-7-phenyl-6,7-dihydro-5H-cyclopenta[d]pyrimidine-2,4-diamine

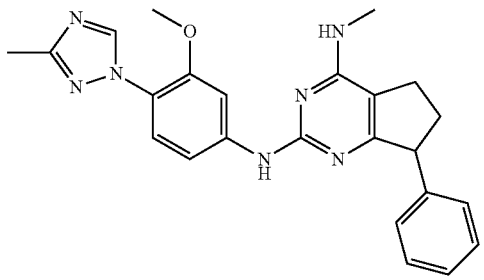 [SMILES: CNc1nc(Nc2ccc(-n3cnc(C)n3)c(OC)c2)nc2c1CCC2c1ccccc1]

The method of Example 74 was used to combine Preparation Ga and 3-methoxy-4-(3-methyl-1H-1,2,4-triazol-1-yl)aniline (Preparation D) to afford N2-(3-methoxy-4-(3-methyl-1H-1,2,4-triazol-1-yl)phenyl)-N4-methyl-7-phenyl-6,7-dihydro-5H-cyclopenta[d]pyrimidine-2,4-diamine (Example 1). LC-MS (M+H)$^+$=428.2. $^1$H NMR (500 MHz, MeOD) δ ppm 8.95 (1H, br. s.), 7.72 (1H, d, J=2.14 Hz), 7.65 (1H, d, J=8.55 Hz), 7.37-7.42 (2H, m), 7.30-7.34 (1H, m), 7.26 (2H, d, J=7.02 Hz), 7.22 (1H, dd, J=8.85, 2.14 Hz), 4.42-4.48 (1H, m), 3.93 (3H, s), 3.16 (3H, s), 2.88-2.96 (1H, m), 2.72-2.83 (2H, m), 2.46 (3H, s), 2.12-2.21 (1H, m).

Example 2

N2-(3-fluoro-4-(3-methyl-1H-1,2,4-triazol-1-yl)phenyl)-N4-methyl-7-phenyl-6,7-dihydro-5H-cyclopenta[d]pyrimidine-2,4-diamine

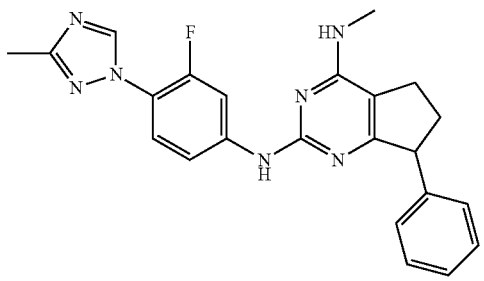 [SMILES: CNc1nc(Nc2ccc(-n3cnc(C)n3)c(F)c2)nc2c1CCC2c1ccccc1]

The method of Example 74 was used to combine Preparation Ga and 3-fluoro-4-(3-methyl-1H-1,2,4-triazol-1-yl)aniline (Preparation B) to afford N2-(3-fluoro-4-(3-methyl-1H-1,2,4-triazol-1-yl)phenyl)-N4-methyl-7-phenyl-6,7-dihydro-5H-cyclopenta[d]pyrimidine-2,4-diamine (Example 2). LC-MS (M+H)$^+$=416.2. $^1$H NMR (500 MHz, MeOD) δ ppm 8.77 (1H, br. s.), 7.95 (1H, dd, J=13.43, 2.14 Hz), 7.77 (1H, t, J=8.70 Hz), 7.48 (1H, dd, J=8.85, 1.53 Hz), 7.40 (2H, t, J=7.48 Hz), 7.33 (1H, t, J=7.48 Hz), 7.28 (2H, d, J=7.02 Hz), 4.49 (1H, dd, J=7.63, 4.58 Hz), 3.18 (3H, s), 2.88-2.98 (1H, m), 2.77-2.86 (2H, m), 2.46 (3H, s), 2.14-2.24 (1H, m).

Example 3

N2-(3-fluoro-4-(5-methyl-1H-1,2,4-triazol-1-yl)phenyl)-N4-methyl-7-phenyl-6,7-dihydro-5H-cyclopenta[d]pyrimidine-2,4-diamine

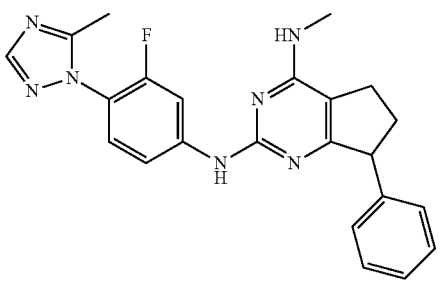 [SMILES: CNc1nc(Nc2ccc(-n3ncnc3C)c(F)c2)nc2c1CCC2c1ccccc1]

The method of Example 74 was used to combine Preparation Ga and 3-fluoro-4-(5-methyl-1H-1,2,4-triazol-1-yl)aniline (Preparation C) to afford N2-(3-fluoro-4-(5-methyl-1H-1,2,4-triazol-1-yl)phenyl)-N4-methyl-7-phenyl-6,7-dihydro-5H-cyclopenta[d]pyrimidine-2,4-diamine (Example 3). LC-MS (M+H)$^+$=416.2. $^1$H NMR (500 MHz, MeOD) δ ppm 8.11 (1H, s), 7.99 (1H, dd, J=12.51, 1.83 Hz), 7.51-7.60 (2H, m), 7.41 (2H, t, J=7.48 Hz), 7.31-7.36 (1H, m), 7.28 (2H, d, J=7.02 Hz), 4.47-4.54 (1H, m), 2.90-3.00 (1H, m), 2.76-2.87 (2H, m), 2.42 (3H, s), 2.15-2.26 (1H, m).

Example 3A $N^2$-(3-fluoro-4-(5-methyl-1H-1,2,4-triazol-1-yl)phenyl)-$N^4$-methyl-7-phenyl-6,7-dihydro-5H-cyclopenta[d]pyrimidine-2,4-diamine

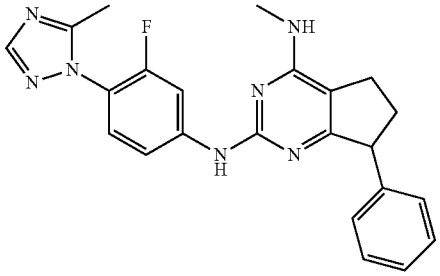

Enantiomer A

Example 3 was separated by multiple chiral prep HPLC injections (OJ-H 30×250 mm, 10 μM, 30% EtOH/Heptane/0.1% DEA) to give $N^2$-(3-fluoro-4-(5-methyl-1H-1,2,4-triazol-1-yl)phenyl)-$N^4$-methyl-7-phenyl-6,7-dihydro-5H-cyclopenta[d]pyrimidine-2,4-diamine (first to elute, enantiomer A) as a slightly yellow, opaque glass. LC-MS (M+H)$^+$=416.2. $^1$H NMR (500 MHz, MeOD) δ ppm 8.15 (1H, dd, J=13.73, 2.14 Hz), 8.03 (1H, s), 7.36-7.42 (1H, m), 7.28-7.36 (3H, m), 7.16-7.26 (3H, m), 4.21 (1H, t, J=7.78

Hz), 3.07-3.13 (3H, m), 2.78-2.88 (1H, m), 2.59-2.76 (2H, m), 2.35-2.41 (3H, m), 1.99-2.13 (1H, m).

Example 3B

N$^2$-(3-fluoro-4-(5-methyl-1H-1,2,4-triazol-1-yl)phenyl)-N$^4$-methyl-7-phenyl-6,7-dihydro-5H-cyclopenta[d]pyrimidine-2,4-diamine

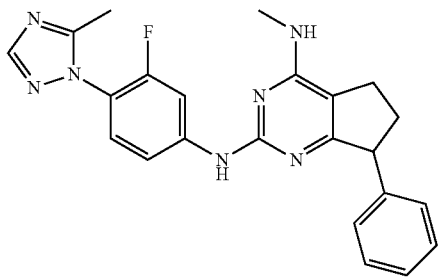

Enantiomer B

Enantiomer B of N2-(3-fluoro-4-(5-methyl-1H-1,2,4-triazol-1-yl)phenyl)-N$^4$-methyl-7-phenyl-6,7-dihydro-5H-cyclopenta[d]pyrimidine-2,4-diamine was prepared as per Example 3A except that it was the second to elute off of the chiral HPLC column as a slightly yellow, opaque glass. LC-MS (M+H)$^+$=416.2. $^1$H NMR (500 MHz, MeOD) δ ppm 8.17 (1H, dd, J=13.89, 2.29 Hz), 8.02 (1H, s), 7.28-7.46 (4H, m), 7.16-7.27 (3H, m), 4.19 (1H, t, J=7.78 Hz), 3.05-3.16 (3H, m), 2.78-2.89 (1H, m), 2.57-2.78 (2H, m), 2.33-2.48 (3H, m), 1.99-2.17 (1H, m).

Example 4

N$^2$-(4-(4-Chloro-1H-imidazol-1-yl)-3-methoxyphenyl)-N$^4$,N$^4$-dimethyl-7-phenyl-6,7-dihydro-5H-cyclopenta[d]pyrimidine-2,4-diamine

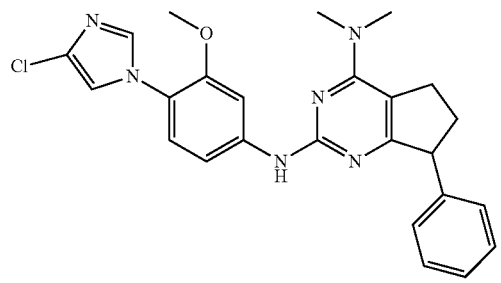 [SMILES: COc1cc(Nc2nc3c(c(N(C)C)n2)CCC3c2ccccc2)ccc1-n1cnc(Cl)c1]

2-Chloro-N,N-dimethyl-7-phenyl-6,7-dihydro-5H-cyclopenta[d]pyrimidin-4-amine (200 mg, 0.731 mmol) was added to a solution of 4-(4-chloro-1H-imidazol-1-yl)-3-methoxyaniline (163 mg, 0.731 mmol) in THF (1 mL) and acetic acid (1.000 mL). The reaction mixture was stirred overnight at 75° C. The crude reaction mixture was purified by preparative HPLC. The appropriate fractions were evaporated to afford N2-(4-(4-chloro-1H-imidazol-1-yl)-3-methoxyphenyl)-N$^4$,N$^4$-dimethyl-7-phenyl-6,7-dihydro-5H-cyclopenta[d]pyrimidine-2,4-diamine, TFA salt (180.7 mg, 0.308 mmol, 42.2% yield). LC-MS (M+H)$^+$=461.2. $^1$H NMR (500 MHz, CDCl$_3$) δ ppm 11.12 (1H, s), 7.98-8.17 (2H, m), 7.09-7.56 (6H, m), 7.01-7.09 (1H, m), 4.31-4.52 (2H, m), 3.97 (1H, s), 3.81-3.89 (2H, m), 3.45-3.55 (2H, m), 3.32-3.43 (3H, m), 3.16-3.29 (2H, m), 2.81-3.03 (1H, m), 2.56-2.75 (2H, m), 2.07-2.32 (2H, m).

Examples 4A & 4B (S)—N$^2$-(4-(4-Chloro-1H-imidazol-1-yl)-3-methoxyphenyl)-N$^4$,N$^4$-dimethyl-7-phenyl-6,7-dihydro-5H-cyclopenta[d]pyrimidine-2,4-diamine and (R)—N$^2$-(4-(4-Chloro-1H-imidazol-1-yl)-3-methoxyphenyl)-N$^4$,N$^4$-dimethyl-7-phenyl-6,7-dihydro-5H-cyclopenta[d]pyrimidine-2,4-diamine

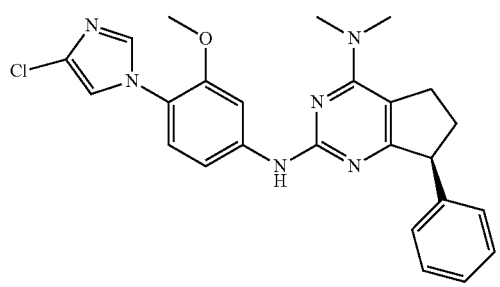

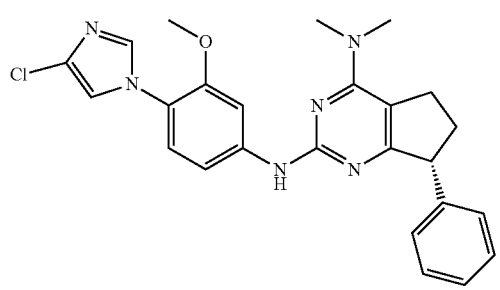

A racemic mixture of N$^2$-(4-(4-chloro-1H-imidazol-1-yl)-3-methoxyphenyl)-N$^4$,N$^4$-dimethyl-7-phenyl-6,7-dihydro-5H-cyclopenta[d]pyrimidine-2,4-diamine (Example 4) was purified using chiral SFC to afford peak A (Example 4A) and peak B (Example 4B). SFC Method: Chiralpak OJ-H (4.6× 250 mm, 5 µM), 35% methanol (0.1% diethylamine) in CO$_2$, 35° C., flow rate 2.0 mL/min for 22 min, absorbance 268 nm, injection 5 µL of 2 mg/mL solution in methanol (multiple stacked injections), t$_R$ (peak A)=5.1 min, t$_R$ (peak B) 18.1 min. The absolute stereochemistry of individual enantiomers (Examples 4A and 4B) was not determined LC-MS and $^1$H NMR analytical data for the separated enantiomers was identical to the racemate (Example 4).

Example 5

N²-(4-(4-Chloro-1H-imidazol-1-yl)-3-methoxyphenyl)-N⁴-ethyl-N⁴-methyl-7-phenyl-6,7-dihydro-5H-cyclopenta[d]pyrimidine-2,4-diamine

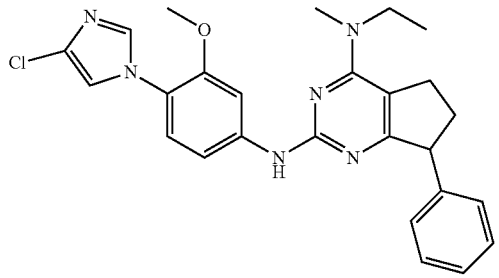 [SMILES: CCN(C)c1nc(Nc2ccc(-n3cnc(Cl)c3)c(OC)c2)nc2c1CCC2c1ccccc1]

2-Chloro-N-ethyl-N-methyl-7-phenyl-6,7-dihydro-5H-cyclopenta[d]pyrimidin-4-amine (160 mg, 0.556 mmol) was added to a solution of 4-(4-chloro-1H-imidazol-1-yl)-3-methoxyaniline (124 mg, 0.556 mmol) in THF (1.5 mL) and acetic acid (1.5 mL). The reaction mixture was stirred overnight at 80° C. The crude reaction mixture was purified by preparative HPLC. The appropriate fractions were evaporated to afford N2-(4-(4-chloro-1H-imidazol-1-yl)-3-methoxyphenyl)-N⁴-ethyl-N⁴-methyl-7-phenyl-6,7-dihydro-5H-cyclopenta[d]pyrimidine-2,4-diamine (85.3 mg, 0.171 mmol, 30.7% yield). LC-MS (M+H)⁺=475.2. ¹H NMR (500 MHz, CDCl₃) δ ppm 7.49-7.61 (1H, m), 7.38 (1H, br. s.), 7.23-7.34 (6H, m), 7.13 (1H, d, J=8.5 Hz), 7.05 (1H, s), 4.35 (1H, dd, J=9.3, 4.1 Hz), 3.69-3.82 (4H, m), 3.47 (2H, br. s.), 3.27-3.38 (4H, m), 3.11-3.23 (1H, m), 2.56-2.72 (1H, m), 2.24 (1H, ddd, J=9.0, 4.4, 4.3 Hz), 1.31 (3H, t, J=7.2 Hz).

Examples 5A & 5B (S)—N²-(4-(4-Chloro-1H-imidazol-1-yl)-3-methoxyphenyl)-N⁴-ethyl-N⁴-methyl-7-phenyl-6,7-dihydro-5H-cyclopenta[d]pyrimidine-2,4-diamine and (R)—N²-(4-(4-Chloro-1H-imidazol-1-yl)-3-methoxyphenyl)-N⁴-ethyl-N⁴-methyl-7-phenyl-6,7-dihydro-5H-cyclopenta[d]pyrimidine-2,4-diamine

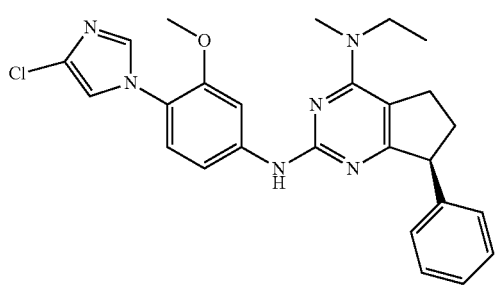

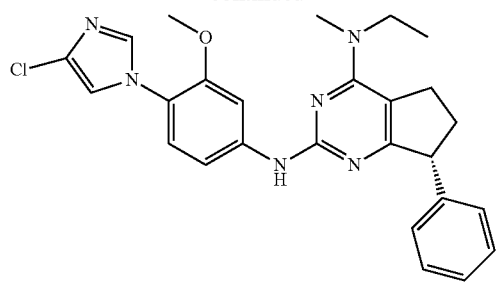

A racemic mixture of N²-(4-(4-chloro-1H-imidazol-1-yl)-3-methoxyphenyl)-N⁴-ethyl-N⁴-methyl-7-phenyl-6,7-dihydro-5H-cyclopenta[d]pyrimidine-2,4-diamine (Example 5) was purified using chiral SFC to afford peak A (Example 5A) and peak B (Example 5B). SFC Method: Chiralpak OJ-H (4.6×250 mm, 5 µM), 35% methanol (0.1% diethylamine) in CO₂, 35° C., flow rate 2.0 mL/min for 22 min, absorbance 268 nm, injection 5 µL of 2 mg/mL solution in methanol (multiple stacked injections), $t_R$ (peak A)=4.5 min, $t_R$ (peak B) 16.7 min. The absolute stereochemistry of individual enantiomers (Examples 5A and 5B) was not determined LC-MS and ¹H NMR analytical data for the separated enantiomers was identical to the racemate (Example 5).

Example 6

4-(Azetidin-1-yl)-N-(4-(4-chloro-1H-imidazol-1-yl)-3-methoxyphenyl)-7-phenyl-6,7-dihydro-5H-cyclopenta[d]pyrimidin-2-amine

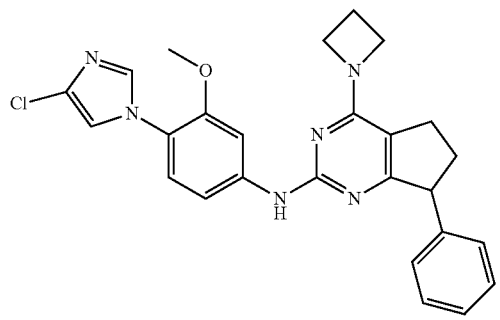

4-(Azetidin-1-yl)-2-chloro-7-phenyl-6,7-dihydro-5H-cyclopenta[d]pyrimidine (162 mg, 0.567 mmol) was added to a solution of 4-(4-chloro-1H-imidazol-1-yl)-3-methoxyaniline (127 mg, 0.567 mmol) in acetic acid (1.000 mL) and THF (1 mL). The reaction mixture was heated at 80° C. overnight. The crude reaction mixture was purified by preparative HPLC. The appropriate fractions were evaporated to afford 4-(azetidin-1-yl)-N-(4-(4-chloro-1H-imidazol-1-yl)-3-methoxyphenyl)-7-phenyl-6,7-dihydro-5H-cyclopenta[d]pyrimidin-2-amine, TFA salt (39.2 mg, 0.066 mmol, 11.66% yield). LC-MS (M+H)⁺=473.2. ¹H NMR (500 MHz, CDCl₃) δ ppm 11.44 (1H, s), 7.94 (1H, d, J=1.5 Hz), 7.52 (1H, d, J=2.1 Hz), 7.27-7.44 (4H, m), 6.96-7.23 (3H, m), 4.64 (3H, br s), 4.38 (2H, d, J=7.6 Hz), 3.83 (2H, s), 3.29-3.52 (1H, m), 3.11 (1H, d, J=7.9 Hz), 2.98 (1H, s), 2.62-2.76 (1H, m), 2.57 (2H, s), 2.14-2.38 (2H, m).

Examples 6A & 6B (S)-4-(Azetidin-1-yl)-N-(4-(4-chloro-1H-imidazol-1-yl)-3-methoxyphenyl)-7-phenyl-6,7-dihydro-5H-cyclopenta[d]pyrimidin-2-amine and (R)-4-(Azetidin-1-yl)-N-(4-(4-chloro-1H-imidazol-1-yl)-3-methoxyphenyl)-7-phenyl-6,7-dihydro-5H-cyclopenta[d]pyrimidin-2-amine

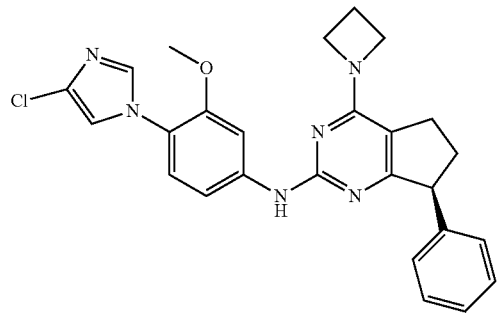

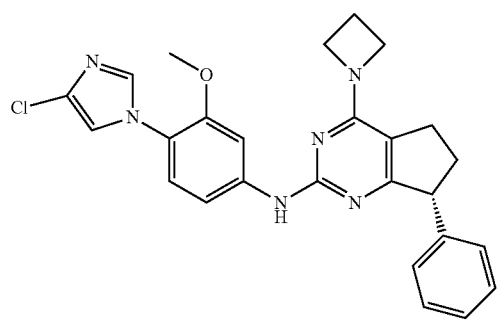 [SMILES: COc1cc(Nc2nc3c(c(N4CCC4)n2)CCC3c2ccccc2)ccc1-n1cnc(Cl)c1]

A racemic mixture of 4-(azetidin-1-yl)-N-(4-(4-chloro-1H-imidazol-1-yl)-3-methoxyphenyl)-7-phenyl-6,7-dihydro-5H-cyclopenta[d]pyrimidin-2-amine (Example 6) was purified using chiral SFC to afford peak A (Example 6A) and peak B (Example 6B). SFC Method: Chiralpak OJ-H (4.6× 250 mm, 5 μM), 35% methanol (0.1% diethylamine) in $CO_2$, 35° C., flow rate 2.0 mL/min for 30 min, absorbance 268 nm, injection 5 μL of 2 mg/mL solution in 50:50 methanol/chloroform (multiple stacked injections), $t_R$ (peak A)=5.9 min, $t_R$ (peak B) 24.6 min. The absolute stereochemistry of individual enantiomers (Examples 6A and 6B) was not determined LC-MS and $^1$H NMR analytical data for the separated enantiomers was identical to the racemate (Example 6).

Example 7

$N^2$-(4-(4-chloro-1H-imidazol-1-yl)-3-methoxyphenyl)-$N^4$-methyl-7-phenyl-6,7-dihydro-5H-cyclopenta[d]pyrimidine-2,4-diamine

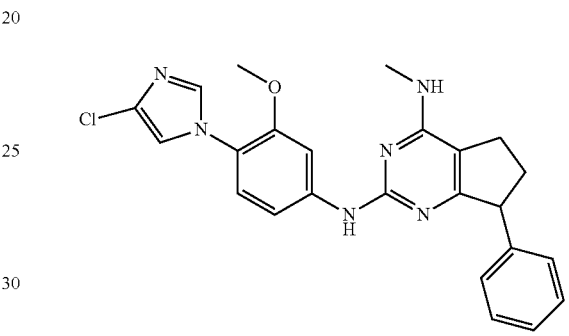

A solution of 2-chloro-N-methyl-7-phenyl-6,7-dihydro-5H-cyclopenta[d]pyrimidin-4-amine (833 mg, 3.21 mmol) and 4-(4-chloro-1H-imidazol-1-yl)-3-methoxyaniline (717.9 mg, 3.21 μmol) in THF (5.6 mL) and acetic acid (5.6 mL) was heated at 85° C. in a 350 mL high-pressure vessel overnight. The solvent was removed in vacuum and the residue was dissolved in dichloromethane and washed with saturated aqueous sodium bicarbonate solution. The organic phase was separated and the aqueous phase was extracted with dichloromethane. The combined organic extracts were dried over anhydrous magnesium sulfate and filtered. The solvent was removed in vacuum and the residue was purified by column chromatography on silica gel to give $N^2$-(4-(4-chloro-1H-imidazol-1-yl)-3-methoxyphenyl)-$N^4$-methyl-7-phenyl-6,7-dihydro-5H-cyclopenta[d]pyrimidine-2,4-diamine, which was contaminated with 4-(4-chloro-1H-imidazol-1-yl)-3-methoxyaniline. The material was triturated with methanol, cooled in the freezer and filtered. The residue was washed with freezing cold methanol and dried to give pure $N^2$-(4-(4-chloro-1H-imidazol-1-yl)-3-methoxyphenyl)-$N^4$-methyl-7-phenyl-6,7-dihydro-5H-cyclopenta[d]pyrimidine-2,4-diamine (673.5 mg, 47%) as light brown solid. LC-MS (M+H)$^+$ =446.9. $^1$H NMR (500 MHz, CDCl$_3$) δ ppm 7.99 (1H, d, J=1.8 Hz), 7.48 (1H, s), 7.27-7.33 (2H, m), 7.16-7.24 (3H, m), 6.96-7.07 (3H, m), 6.71 (1H, dd, J=8.4, 1.7 Hz), 4.50 (1H, br s), 4.20 (1H, s), 3.48 (3H, s), 3.11 (3H, d, J=4.9 Hz), 2.59-2.79 (3H, m), 2.01-2.13 (1H, m).

Examples 7A and 7B (S)—N²-(4-(4-chloro-1H-imidazol-1-yl)-3-methoxyphenyl)-N4-methyl-7-phenyl-6,7-dihydro-5H-cyclopenta[d]pyrimidine-2,4-diamine and (R)—N²-(4-(4-chloro-1H-imidazol-1-yl)-3-methoxyphenyl)-N4-methyl-7-phenyl-6,7-dihydro-5H-cyclopenta[d]pyrimidine-2,4-diamine

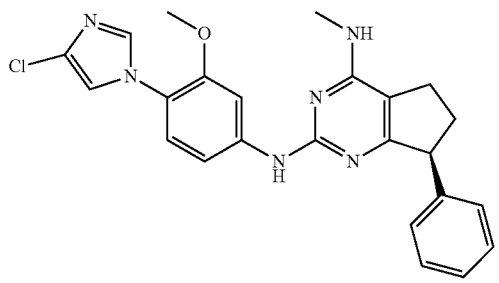

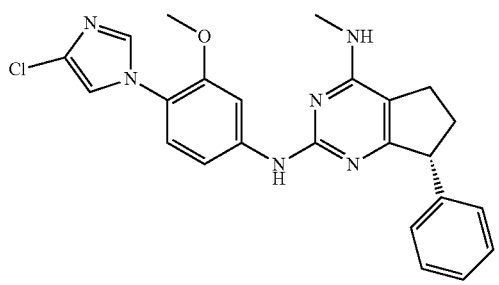 [SMILES: CNc1nc(Nc2ccc(-n3cnc(Cl)c3)c(OC)c2)nc2c1CCC2c1ccccc1]

A racemic mixture of N²-(4-(4-chloro-1H-imidazol-1-yl)-3-methoxyphenyl)-N⁴-methyl-7-phenyl-6,7-dihydro-5H-cyclopenta[d]pyrimidine-2,4-diamine (92 mg, 0.206 mmol from Example 7) was purified using chiral supercritical fluid chromatography (SFC) to afford 28.4 mg of peak A (Example 7A) and 27.4 mg of peak B (Example 7B). SFC Method: Chiralpak OJ-H (30×250 mm, 5 μM), 40% methanol (0.1% diethylamine) in CO₂, 35° C., flow rate 70 mL/min for 16 min, absorbance 268 nm, injection 1 mL of 15 mg/mL solution in methanol (multiple stacked injections), $t_R$ (peak A)=5.0 min, $t_R$ (peak B) 12.3 min. The absolute stereochemistry of individual enantiomers (Examples 7A and 7B) was not determined. LC-MS and ¹H NMR analytical data for the separated enantiomers was identical to the racemate (Example 7).

Example 8

N2-(4-(4-chloro-1H-imidazol-1-yl)-3-methoxyphenyl)-N4-cyclopropyl-7-phenyl-6,7-dihydro-5H-cyclopenta[d]pyrimidine-2,4-diamine

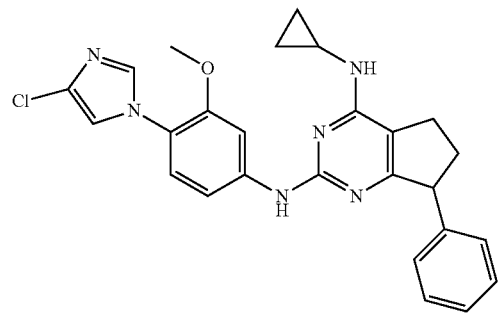 [SMILES: COc1cc(Nc2nc(NC3CC3)c3c(n2)C(c2ccccc2)CC3)ccc1-n1cnc(Cl)c1]

To a mixture of 2-chloro-N-cyclopropyl-7-phenyl-6,7-dihydro-5H-cyclopenta[d]pyrimidin-4-amine (175 mg, 0.612 mmol) and 4-(4-chloro-1H-imidazol-1-yl)-3-methoxyaniline (151 mg, 0.674 mmol) in NMP (2 mL) was added Conc. H2SO4 (0.046 mL, 0.857 mmol). The mixture was stirred at 97° C. for 20 hours. After cooled down to room temperature, 100 mL of EtOAc was added, washed with saturated NaHCO3/water and water, dried over Na2SO4, and finally removed. The residue was purified via Biotage (12 g, hexanes-80% EtOAc) to give N2-(4-(4-chloro-1H-imidazol-1-yl)-3-methoxyphenyl)-N⁴-cyclopropyl-7-phenyl-6,7-dihydro-5H-cyclopenta[d]pyrimidine-2,4-diamine (200 mg, 0.423 mmol, 69.1% yield). LC-MS (M+H)⁺=473.10. ¹H NMR (500 MHz, CDCl₃) δ ppm 7.81 (1H, d, J=1.8 Hz), 7.51 (1H, d, J=1.5 Hz), 7.44 (1H, s), 7.27-7.35 (2H, m), 7.19-7.25 (3H, m), 6.99-7.06 (2H, m), 6.95 (1H, d, J=8.2 Hz), 4.89 (1H, br. s.), 4.20 (1H, t, J=8.2 Hz), 3.45 (3H, s), 2.92 (1H, td, J=6.7, 3.1 Hz), 2.76-2.86 (1H, m), 2.59-2.75 (2H, m), 2.07-2.14 (1H, m), 0.85-0.91 (2H, m), 0.63-0.70 (2H, m).

Example 9

N2-(4-(4-chloro-1H-imidazol-1-yl)-3-methoxyphenyl)-N4-cyclobutyl-7-phenyl-6,7-dihydro-5H-cyclopenta[d]pyrimidine-2,4-diamine

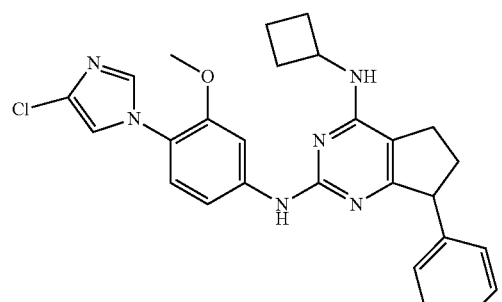

To a mixture of 2-chloro-N-cyclobutyl-7-phenyl-6,7-dihydro-5H-cyclopenta[d]pyrimidin-4-amine (165 mg, 0.55 mmol) and 4-(4-chloro-1H-imidazol-1-yl)-3-methoxyaniline (135 mg, 0.605 mmol) in NMP (2 mL) was added Conc. H2SO4 (0.041 mL, 0.771 mmol). The mixture was stirred at 97° C. for 20 hours. After cooled down to room temperature, 100 mL of EtOAc was added, washed with saturated NaHCO3/water and water, dried over Na2SO4, and finally removed. The residue was purified via Biotage (12 g, hexanes-80% EtOAc) to give N2-(4-(4-chloro-1H-imidazol-1-yl)-3-methoxyphenyl)-N4-cyclobutyl-7-phenyl-6,7-dihydro-5H-cyclopenta[d]pyrimidine-2,4-diamine (202 mg, 0.394 mmol, 71.6% yield). LC-MS (M+H)$^+$=487.14. $^1$H NMR (500 MHz, CDCl$_3$) δ ppm 7.92 (1H, d, J=1.8 Hz), 7.51 (1H, d, J=1.2 Hz), 7.28-7.33 (2H, m), 7.18-7.24 (3H, m), 7.13 (1H, s), 7.03 (1H, d, J=8.5 Hz), 7.01 (1H, d, J=1.2 Hz), 6.74 (1H, dd, J=8.5, 2.1 Hz), 4.64-4.80 (2H, m), 4.17-4.23 (1H, m), 3.49 (3H, s), 2.72-2.81 (1H, m), 2.61-2.71 (2H, m), 2.43-2.53 (2H, m), 2.09 (1H, td, J=8.0, 2.3 Hz), 1.92-2.04 (2H, m), 1.70-1.88 (2H, m).

Example 10

N2-(4-(4-chloro-1H-imidazol-1-yl)-3-methoxyphenyl)-N4-isopropyl-7-phenyl-6,7-dihydro-5H-cyclopenta[d]pyrimidine-2,4-diamine

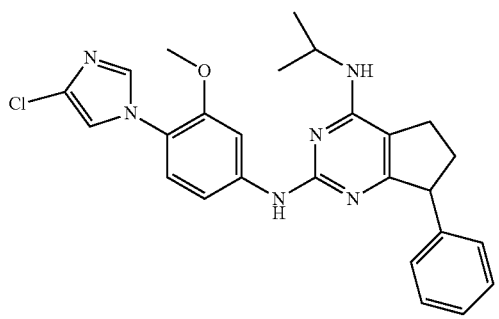 [SMILES: COc1cc(Nc2nc(NC(C)C)c3c(n2)C(c2ccccc2)CC3)ccc1-n1cnc(Cl)c1]

To a solution of 2-chloro-N-isopropyl-7-phenyl-6,7-dihydro-5H-cyclopenta[d]pyrimidin-4-amine (154 mg, 0.535 mmol) and 4-(4-chloro-1H-imidazol-1-yl)-3-methoxyaniline (114 mg, 0.508 mmol) in DMF (2.5 mL) was added Conc. H2SO4 (0.040 mL, 0.749 mmol). The mixture was stirred at 94° C. for 20 hrs. After cooled down to room temperature, 100 mL of EtOAc was added, washed with saturated NaHCO3/H2O, dried over Na2SO4, and removed. The residue was purified via Biotage (12 g, hexanes-100% EtOAC) to give N2-(4-(4-chloro-1H-imidazol-1-yl)-3-methoxyphenyl)-N4-isopropyl-7-phenyl-6,7-dihydro-5H-cyclopenta[d]pyrimidine-2,4-diamine (120 mg, 0.253 mmol, 47.2% yield). LC-MS (M+H)$^+$=475.2. $^1$H NMR (500 MHz, CDCl$_3$) δ ppm 7.92 (1H, d, J=2.1 Hz), 7.51 (1H, d, J=1.5 Hz), 7.31 (2H, d, J=7.3 Hz), 7.22-7.25 (2H, m), 7.22 (1H, s), 7.08 (1H, s), 7.04 (1H, d, J=8.5 Hz), 7.01 (1H, d, J=1.5 Hz), 6.74 (1H, dd, J=8.4, 2.3 Hz), 4.38-4.46 (1H, m), 4.33 (1H, d, J=7.9 Hz), 4.18-4.24 (1H, m), 3.49 (3H, s), 2.72-2.80 (1H, m), 2.61-2.71 (2H, m), 2.07-2.14 (1H, m), 1.33 (6H, t, J=6.6 Hz).

Example 11

N$^2$-(4-(4-Chloro-1H-imidazol-1-yl)-3-methoxyphenyl)-7-(4-fluorophenyl)-N$^4$-methyl-6,7-dihydro-5H-cyclopenta[d]pyrimidine-2,4-diamine

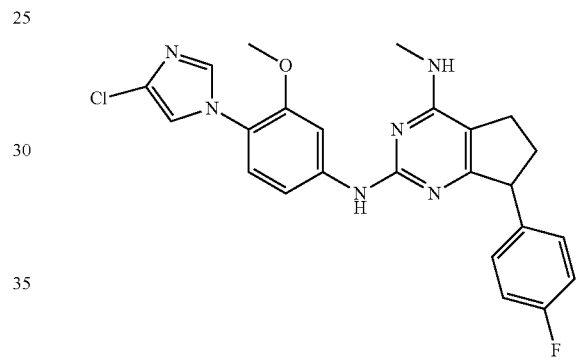

A solution of 2-chloro-7-(4-fluorophenyl)-N-methyl-6,7-dihydro-5H-cyclopenta[d]pyrimidin-4-amine (307.5 mg, 1.107 mmol) and 4-(4-chloro-1H-imidazol-1-yl)-3-methoxyaniline (248 mg, 1.107 mmol) in THF (3 mL) and acetic acid (3.00 mL) was heated at 80° C. overnight. The solvent was removed in vacuum and the residue was triturated with methanol, cooled in the freezer and filtered. The precipitate was thoroughly washed with methanol and dried to give N$^2$-(4-(4-chloro-1H-imidazol-1-yl)-3-methoxyphenyl)-7-(4-fluorophenyl)-N$^4$-methyl-6,7-dihydro-5H-cyclopenta[d]pyrimidine-2,4-diamine (207.9 mg, 0.447 mmol, 40.4% yield) as off-white solid. LC-MS (M+H)$^+$=465.0. $^1$H NMR (500 MHz, CDCl$_3$) δ ppm 9.18 (1H, s), 8.15 (1H, d, J=1.8 Hz), 7.73 (1H, d, J=1.5 Hz), 7.41 (1H, d, J=1.5 Hz), 7.18-7.26 (2H, m), 7.07-7.18 (2H, m), 6.88-7.00 (1H, m), 4.12-4.20 (1H, m), 4.04-4.12 (1H, br s), 3.60 (3H, s), 3.17 (1H, s), 2.96 (3H, d, J=4.6 Hz), 2.71-2.81 (1H, m), 2.52-2.66 (2H, m), 1.83-1.96 (1H, m).

Examples 11A and 11B (S)—$N^2$-(4-(4-Chloro-1H-imidazol-1-yl)-3-methoxyphenyl)-7-(4-fluorophenyl)-$N^4$-methyl-6,7-dihydro-5H-cyclopenta[d]pyrimidine-2,4-diamine and (R)—$N^2$-(4-(4-Chloro-1H-imidazol-1-yl)-3-methoxyphenyl)-7-(4-fluorophenyl)-N4-methyl-6,7-dihydro-5H-cyclopenta[d]pyrimidine-2,4-diamine

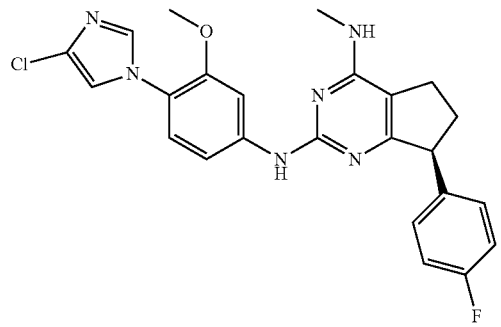 [SMILES: CNc1nc(Nc2ccc(-n3cnc(Cl)c3)c(OC)c2)nc2c1CCC2c1ccc(F)cc1]

A racemic mixture of $N^2$-(4-(4-chloro-1H-imidazol-1-yl)-3-methoxyphenyl)-$N^4$-trideuteromethyl-7-phenyl-6,7-dihydro-5H-cyclopenta[d]pyrimidine-2,4-diamine (150 mg, 0.206 mmol from Example 11) was purified using chiral supercritical fluid chromatography (SFC) to afford 74.6 mg of peak A (Example 11A) and 71.7 mg of peak B (Example 11B). SFC Method: Chiralpak OJ-H (30×250 mm, 5 μM), 35% methanol (0.1% diethylamine) in $CO_2$, 35° C., flow rate 70 mL/min for 12 min, absorbance 268 nm, injection 0.75 mL of 15 mg/mL solution in methanol (multiple stacked injections), $t_R$ (peak A)=4.0 min, $t_R$ (peak B) 8.6 min. The absolute stereochemistry of individual enantiomers (Examples 11A and 11B) was not determined LC-MS and $^1$H NMR analytical data for the separated enantiomers was identical to the racemate (Example 11).

Example 12

$N^2$-(3-Fluoro-4-(5-methyl-1H-1,2,4-triazol-1-yl)phenyl)-7-(4-fluorophenyl)-$N^4$-methyl-6,7-dihydro-5H-cyclopenta[d]pyrimidine-2,4-diamine

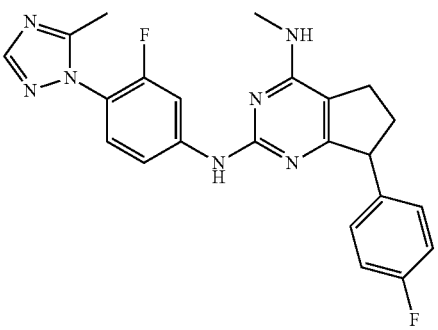 [SMILES: CNc1nc(Nc2ccc(-n3ncnc3C)c(F)c2)nc2c1CCC2c1ccc(F)cc1]

To a solution of 2-chloro-7-(4-fluorophenyl)-N-methyl-6,7-dihydro-5H-cyclopenta[d]pyrimidin-4-amine (105.0 mg, 0.378 mmol) and 3-fluoro-4-(3-methyl-1H-1,2,4-triazol-1-yl)aniline (72.7 mg, 0.378 mmol) in THF (2 mL) was added 60% suspension of sodium hydride in mineral oil (30.2 mg, 0.756 mmol). The reaction mixture was stirred at 80° C. for 40 minutes. The reaction mixture was further stirred at 80° C. for 4 h. The reaction mixture was quenched with an aqueous solution of ammonium chloride and extracted with dichloromethane. The combined organic extracts were dried over anhydrous magnesium sulfate and filtered. The solvent was removed in vacuum and the residue was purified by a reversed phase preparative HPLC system to give $N^2$-(3-fluoro-4-(3-methyl-1H-1,2,4-triazol-1-yl)phenyl)-7-(4-fluorophenyl)-$N^4$-methyl-6,7-dihydro-5H-cyclopenta[d]pyrimidine-2,4-diamine, 2 TFA (45.6 mg, 0.069 mmol, 18.25% yield) as brown oil. LC-MS (M+H)$^+$=434.0. $^1$H NMR (500 MHz, methanol-d4) δ ppm 8.86 (1H, s), 7.88 (1H, t, J=8.4 Hz), 7.21-7.31 (3H, m), 7.19 (1H, d, J=8.9 Hz), 7.07 (2H, t, J=8.7 Hz), 4.27 (1H, t, J=8.5 Hz), 3.73 (3H, s), 3.33 (3H, s), 2.52

(1H, dd, J=8.2, 4.0 Hz), 2.49 (3H, s), 2.38 (1H, d, J=7.6 Hz), 2.30 (1H, d, J=3.7 Hz), 1.95-2.07 (1H, m).

Example 13

$N^2$-(2-Fluoro-5-methoxy-4-(3-methyl-1H-1,2,4-triazol-1-yl)phenyl)-7-(4-fluorophenyl)-$N^4$-methyl-6,7-dihydro-5H-cyclopenta[d]pyrimidine-2,4-diamine

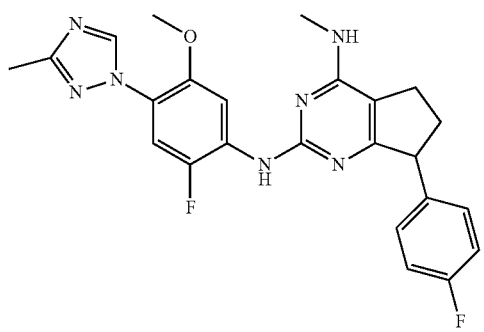 [SMILES: CNc1nc(Nc2cc(OC)c(-n3cnc(C)n3)cc2F)nc2c1CCC2c1ccc(F)cc1]

To a solution of 2-chloro-7-(4-fluorophenyl)-N-methyl-6,7-dihydro-5H-cyclopenta[d]pyrimidin-4-amine (105.0 mg, 0.378 mmol) and 2-fluoro-5-methoxy-4-(3-methyl-1H-1,2,4-triazol-1-yl)aniline (84 mg, 0.378 mmol) in THF (2 mL) was added 60% suspension of sodium hydride in mineral oil (9.07 mg, 0.378 mmol). The reaction mixture was stirred at 80° C. for 40 minutes. The reaction mixture was further stirred at 80° C. for 4 h. The reaction mixture was quenched with an aqueous solution of ammonium chloride and extracted with dichloromethane. The combined organic extracts were dried over anhydrous magnesium sulfate and filtered. The solvent was removed in vacuum and the residue was purified by a reversed phase preparative HPLC system to give $N^2$-(2-fluoro-5-methoxy-4-(3-methyl-1H-1,2,4-triazol-1-yl)phenyl)-7-(4-fluorophenyl)-$N^4$-methyl-6,7-dihydro-5H-cyclopenta[d]pyrimidine-2,4-diamine, 2 TFA (20.2 mg, 0.027 mmol, 7.19% yield) as brown oil. LC-MS (M+H)$^+$ =464.0. $^1$H NMR (500 MHz, methanol-d4) δ ppm 9.06 (1H, s), 7.74 (1H, d, J=10.4 Hz), 7.19-7.28 (3H, m), 7.07 (2H, t, J=8.5 Hz), 4.24 (1H, s), 4.00 (3H, s), 3.76 (3H, s), 2.48 (3H, s), 2.40-2.54 (1H, m), 2.26-2.38 (2H, m), 1.89-2.02 (1H, m).

Example 14

$N^2$-(6-(4-Chloro-1H-imidazol-1-yl)-5-methoxypyridin-3-yl)-7-(4-fluorophenyl)-$N^4$-methyl-6,7-dihydro-5H-cyclopenta[d]pyrimidine-2,4-diamine To a solution of 2-chloro-7-(4-fluorophenyl)-N-methyl-6,7-dihydro-5H-cyclopenta[d]pyrimidin-4-amine (165.3 mg, 0.595 mmol) and 6-(4-chloro-1H-imidazol-1-yl)-5-methoxypyridin-3-amine (134 mg, 0.595 mmol) in THF (3.5 mL) was added 60% suspension of sodium hydride in mineral oil (28.6 mg, 1.190 mmol). The reaction mixture was heated at 80° C. in a capped vial for 6 h. The reaction was carefully quenched with aqueous ammonium chloride solution and the product was extracted with dichloromethane. The combined organic extracts were dried over anhydrous magnesium sulfate and filtered. The solvent was removed in vacuum and the residue was purified by a reversed-phase preparative HPLC method to provide $N^2$-(6-(4-chloro-1H-imidazol-1-yl)-5-methoxypyridin-3-yl)-7-(4-fluorophenyl)-$N^4$-methyl-6,7-dihydro-5H-cyclopenta[d]pyrimidine-2,4-diamine, 2 TFA (26.2 mg, 0.029 mmol, 4.88% yield) as brown oil. LC-MS (M+H)$^+$=466.0. $^1$H NMR (500 MHz, methanol-d4) δ ppm 8.43 (1H, s), 7.96 (1H, s), 7.87 (1H, s), 7.55 (1H, br. s.), 7.19-7.32 (2H, m), 7.07 (2H, t, J=8.7 Hz), 4.20-4.29 (1H, m), 4.06 (3H, s), 3.75 (3H, s), 2.42-2.55 (1H, m), 2.21-2.39 (2H, m), 1.90-2.05 (1H, m).

Example 15

N-(4-(4-Chloro-1H-imidazol-1-yl)-3-methoxyphenyl)-4-(3,3-difluoroazetidin-1-yl)-7-(4-fluorophenyl)-6,7-dihydro-5H-cyclopenta[d]pyrimidin-2-amine

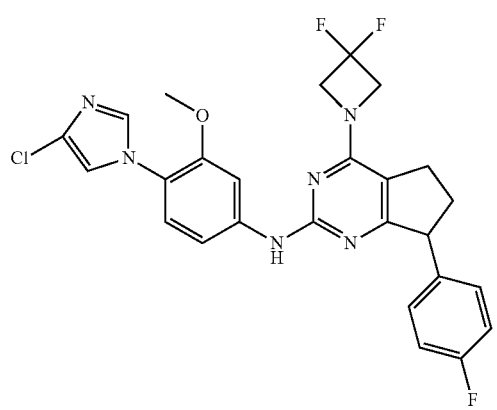 [SMILES: COc1cc(Nc2nc3c(c(N4CC(F)(F)C4)n2)CCC3c2ccc(F)cc2)ccc1-n1cnc(Cl)c1]

A solution of 2-chloro-4-(3,3-difluoroazetidin-1-yl)-7-(4-fluorophenyl)-6,7-dihydro-5H-cyclopenta[d]pyrimidine (42.6 mg, 0.125 mmol) and 4-(4-chloro-1H-imidazol-1-yl)-3-methoxyaniline (28.0 mg, 0.125 mmol) in THF (1 mL) and acetic acid (1.000 mL) was heated at 80° C. overnight. The heating was continued at 120° C. overnight. Upon cooling, the reaction mixture was purified by column chromatography on silica gel to give N-(4-(4-chloro-1H-imidazol-1-yl)-3-methoxyphenyl)-4-(3,3-difluoroazetidin-1-yl)-7-(4-fluorophenyl)-6,7-dihydro-5H-cyclopenta[d]pyrimidin-2-amine, TFA (11.8 mg, 0.018 mmol, 14.54% yield) as brown oil. LC-MS (M+H)$^+$=527.1. $^1$H NMR (500 MHz, CDCl$_3$) δ ppm 11.75 (1H, s), 8.02 (1H, s), 7.40 (1H, dd, J=8.5, 2.1 Hz), 7.32 (1H, d, J=2.1 Hz), 7.16-7.23 (3H, m), 7.12 (1H, s), 7.02 (2H, t, J=8.7 Hz), 4.42 (1H, dd, J=9.5, 4.9 Hz), 4.80 (4H, s), 3.85 (3H, s), 3.11 (1H, s), 2.98 (1H, s), 2.67-2.79 (1H, m), 2.26 (1H, d).

Example 16

4-(3,3-difluoroazetidin-1-yl)-N-(3-fluoro-4-(5-methyl-1H-1,2,4-triazol-1-yl)phenyl)-7-(4-fluorophenyl)-6,7-dihydro-5H-cyclopenta[d]pyrimidin-2-amine

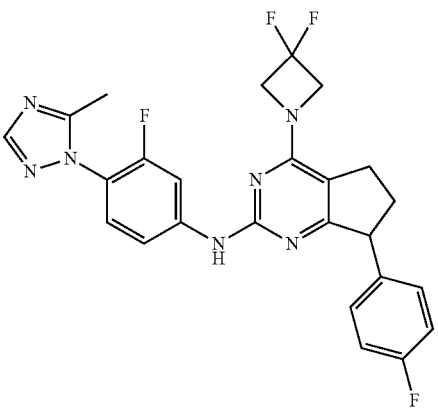

To a solution of 2-chloro-4-(3,3-difluoroazetidin-1-yl)-7-(4-fluorophenyl)-6,7-dihydro-5H-cyclopenta[d]pyrimidine (Preparation IIa) (170 mg, 0.500 mmol) in THF (1498 μL) was added 3-fluoro-4-(3-methyl-1H-1,2,4-triazol-1-yl) aniline (Preparation C) (125 mg, 0.650 mmol) and Acetic Acid (1498 μL). The resulting mixture was heated to 100° C. and stirred overnight. The reaction mixture was then concentrated in vacuo and purified by prep HPLC (C18, 30×150 mm, MeOH/H$_2$O/TFA) to give 4-(3,3-difluoroazetidin-1-yl)-N-(3-fluoro-4-(3-methyl-1H-1,2,4-triazol-1-yl)phenyl)-7-(4-fluorophenyl)-6,7-dihydro-5H-cyclopenta[d]pyrimidin-2-amine, TFA (racemate) (101.49 mg, 33.27% yield) as a beige solid. LC-MS (M+H)$^+$=496.1. $^1$H NMR (500 MHz, MeOD) δ ppm 8.06-8.11 (1H, m), 7.86 (1H, dd, J=12.51, 2.14 Hz), 7.47-7.57 (2H, m), 7.28-7.35 (2H, m), 7.11-7.19 (2H, m), 4.93 (4H, t, J=11.90 Hz), 4.47 (1H, t, J=7.93 Hz), 3.11-3.18

(1H, m), 2.99-3.08 (1H, m), 2.71-2.81 (1H, m, J=13.31, 8.91, 8.91, 4.27 Hz), 2.42 (3H, s), 2.08-2.19 (1H, m, J=13.24, 9.04, 6.71, 6.71 Hz).

Example 16A 4-(3,3-difluoroazetidin-1-yl)-N-(3-fluoro-4-(5-methyl-1H-1,2,4-triazol-1-yl)phenyl)-7-(4-fluorophenyl)-6,7-dihydro-5H-cyclopenta[d]pyrimidin-2-amine

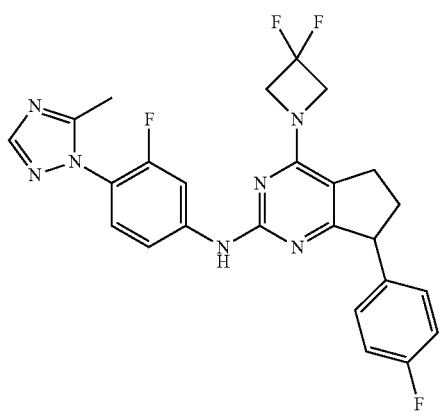

Enantiomer A of Example 16

4-(3,3-difluoroazetidin-1-yl)-N-(3-fluoro-4-(5-methyl-1H-1,2,4-triazol-1-yl)phenyl)-7-(4-fluorophenyl)-6,7-dihydro-5H-cyclopenta[d]pyrimidin-2-amine (Example 16) was separated by multiple injections on chiral SFC (Chiracel OJ-H 30×250 mm, 5 μM, 30% MeOH (0.1% DEA)/CO$_2$ to give 4-(3,3-difluoroazetidin-1-yl)-N-(3-fluoro-4-(5-methyl-1H-1,2,4-triazol-1-yl)phenyl)-7-(4-fluorophenyl)-6,7-dihydro-5H-cyclopenta[d]pyrimidin-2-amine (first to elute, enantiomer A) as an off-white solid. LC-MS (M+H)$^+$=496.1. $^1$H NMR (500 MHz, MeOD) δ ppm 7.87-8.08 (2H, m), 7.35-7.44 (1H, m), 7.31 (1H, t, J=8.70 Hz), 7.24 (2H, dd, J=8.55, 5.49 Hz), 7.04 (2H, t, J=8.70 Hz), 4.64 (4H, t, J=12.05 Hz), 4.19 (1H, t, J=8.24 Hz), 2.98-3.08 (1H, m), 2.86-2.98 (1H, m), 2.55-2.68 (1H, m, J=12.86, 8.60, 8.60, 4.12 Hz), 2.37 (3H, s), 1.97-2.12 (1H, m). The absolute stereochemistry of Example 16A was not determined.

Example 16B 4-(3,3-difluoroazetidin-1-yl)-N-(3-fluoro-4-(5-methyl-1H-1,2,4-triazol-1-yl)phenyl)-7-(4-fluorophenyl)-6,7-dihydro-5H-cyclopenta[d]pyrimidin-2-amine

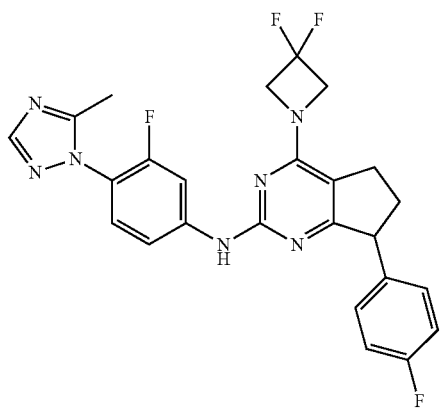 [SMILES: Cc1ncnn1-c1ccc(Nc2nc3c(c(N4CC(F)(F)C4)n2)CCC3c2ccc(F)cc2)cc1F]

Enantiomer B of Example 16

4-(3,3-difluoroazetidin-1-yl)-N-(3-fluoro-4-(5-methyl-1H-1,2,4-triazol-1-yl)phenyl)-7-(4-fluorophenyl)-6,7-dihydro-5H-cyclopenta[d]pyrimidin-2-amine (Example 16) was separated by multiple injections on chiral SFC (Chiracel OJ-H 30×250 mm, 5 μM, 30% MeOH (0.1% DEA)/CO$_2$ to give 4-(3,3-difluoroazetidin-1-yl)-N-(3-fluoro-4-(5-methyl-1H-1,2,4-triazol-1-yl)phenyl)-7-(4-fluorophenyl)-6,7-dihydro-5H-cyclopenta[d]pyrimidin-2-amine (second to elute, enantiomer B) as an off-white solid. LC-MS (M+H)$^+$=496.1. $^1$H NMR (500 MHz, MeOD) δ ppm 7.96-8.09 (2H, m), 7.39 (1H, dd, J=9.00, 1.98 Hz), 7.32 (1H, t, J=8.55 Hz), 7.20-7.28 (2H, m), 6.99-7.11 (2H, m), 4.65 (4H, t, J=12.21 Hz), 4.20 (1H, t, J=8.24 Hz), 2.99-3.09 (1H, m), 2.88-2.99 (1H, m), 2.56-2.71 (1H, m), 2.31-2.46 (3H, m), 1.98-2.15 (1H, m). The absolute stereochemistry of Example 16B was not determined.

Example 17

N-(4-(3-chloro-1H-1,2,4-triazol-1-yl)-3-methoxyphenyl)-4-(3,3-difluoroazetidin-1-yl)-7-(4-fluorophenyl)-6,7-dihydro-5H-cyclopenta[d]pyrimidin-2-amine

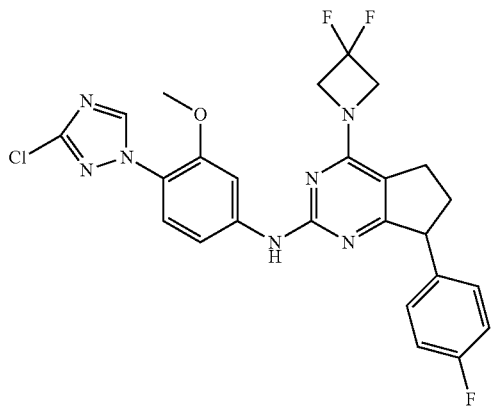

To a solution of 2-chloro-4-(3,3-difluoroazetidin-1-yl)-7-(4-fluorophenyl)-6,7-dihydro-5H-cyclopenta[d]pyrimidine (Preparation Ha) (170 mg, 0.500 mmol) and 4-(3-chloro-1H-1,2,4-triazol-1-yl)-3-methoxyaniline (Preparation F) (146 mg, 0.650 mmol) in THF (1498 µL) was added Acetic Acid (1498 µL). The resulting mixture was heated to 100° C. and stirred overnight. The reaction mixture was then concentrated in vacuo. MeOH was added to the residue which resulted in a suspension. This was filtered to give a solid which was taken up in hot MeOH and filtered. The filtrate was then concentrated in vacuo to give N-(4-(3-chloro-1H-1,2,4-triazol-1-yl)-3-methoxyphenyl)-4-(3,3-difluoroazetidin-1-yl)-7-(4-fluorophenyl)-6,7-dihydro-5H-cyclopenta[d]pyrimidin-2-amine (racemate) (130 mg, 49.22% yield) as a yellow solid. LC-MS (M+H)$^+$=528.1. $^1$H NMR (500 MHz, MeOD) δ ppm 8.81 (1H, s), 7.65 (1H, d, J=8.55 Hz), 7.59 (1H, s), 7.29-7.36 (2H, m), 7.11-7.21 (3H, m), 4.87-4.88 (4H, m), 4.47 (1H, s), 3.91 (3H, s), 3.11-3.19 (1H, m), 2.99-3.08 (1H, m), 2.77 (1H, dddd, J=13.47, 8.96, 4.43, 4.27 Hz), 2.13 (1H, dq, J=8.89, 6.70 Hz).

Example 17A

N-(4-(3-chloro-1H-1,2,4-triazol-1-yl)-3-methoxyphenyl)-4-(3,3-difluoroazetidin-1-yl)-7-(4-fluorophenyl)-6,7-dihydro-5H-cyclopenta[d]pyrimidin-2-amine

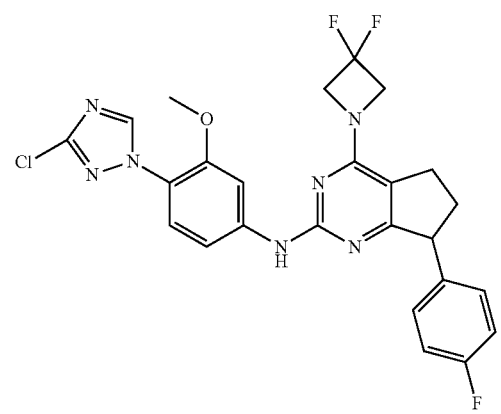

Enantiomer A of Example 17

N-(4-(3-chloro-1H-1,2,4-triazol-1-yl)-3-methoxyphenyl)-4-(3,3-difluoroazetidin-1-yl)-7-(4-fluorophenyl)-6,7-dihydro-5H-cyclopenta[d]pyrimidin-2-amine (Example 17) was separated by multiple injections on chiral SFC (Chiracel AD-H 30×250 mm, 5 µM, 45% MeOH (0.1% DEA)/CO$_2$ to give 4-(3,3-difluoroazetidin-1-yl)-N-(3-fluoro-4-(5-methyl-1H-1,2,4-triazol-1-yl)phenyl)-7-(4-fluorophenyl)-6,7-dihydro-5H-cyclopenta[d]pyrimidin-2-amine (first to elute, enantiomer A) as a yellow film. LC-MS (M+H)$^+$=528.1. $^1$H NMR (500 MHz, DMSO-d6) δ ppm 8.82 (1H, d, J=1.53 Hz), 8.06 (1H, s), 7.35 (1H, d, J=8.85 Hz), 7.21-7.31 (2H, m), 7.07-7.21 (3H, m), 4.70 (4H, t, J=12.36 Hz), 4.20 (1H, t, J=8.24 Hz), 3.63 (3H, br. s.), 3.01 (1H, br. s.), 2.80-2.95 (1H, m), 2.53-

2.63 (1H, m), 1.93 (1H, d, J=8.24 Hz). The absolute stereochemistry of Example 17A was not determined.

Example 17B

N-(4-(3-chloro-1H-1,2,4-triazol-1-yl)-3-methoxyphenyl)-4-(3,3-difluoroazetidin-1-yl)-7-(4-fluorophenyl)-6,7-dihydro-5H-cyclopenta[d]pyrimidin-2-amine

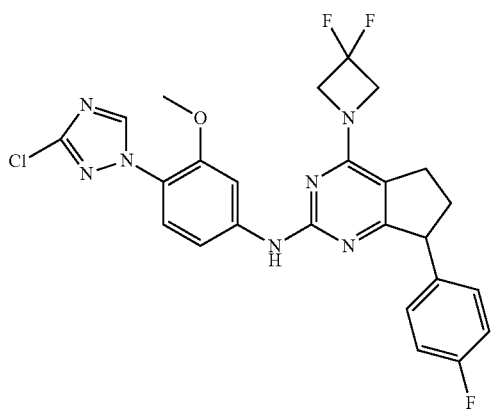 [SMILES: COc1cc(Nc2nc3c(c(N4CC(F)(F)C4)n2)CCC3c2ccc(F)cc2)ccc1-n1cnc(Cl)n1]

Enantiomer B of Example 17

N-(4-(3-chloro-1H-1,2,4-triazol-1-yl)-3-methoxyphenyl)-4-(3,3-difluoroazetidin-1-yl)-7-(4-fluorophenyl)-6,7-dihydro-5H-cyclopenta[d]pyrimidin-2-amine (Example 17) was separated by multiple injections on chiral SFC (Chiracel AD-H 30×250 mm, 5 μM, 45% MeOH (0.1% DEA)/CO$_2$ to give 4-(3,3-difluoroazetidin-1-yl)-N-(3-fluoro-4-(5-methyl-1H-1,2,4-triazol-1-yl)phenyl)-7-(4-fluorophenyl)-6,7-dihydro-5H-cyclopenta[d]pyrimidin-2-amine (second to elute, enantiomer B) as a yellow film. LC-MS (M+H)$^+$=528.1. $^1$H NMR (500 MHz, DMSO-d6) δ ppm 8.76-8.92 (1H, m), 8.06 (1H, br. s.), 7.30-7.45 (1H, m), 7.25 (2H, d, J=5.49 Hz), 7.05-7.19 (3H, m), 4.57-4.80 (4H, m), 4.20 (1H, br. s.), 3.63 (3H, br. s.), 3.00 (1H, br. s.), 2.82-2.94 (1H, m), 2.53-2.61 (1H, m), 1.91 (1H, br. s.). The absolute stereochemistry of Example 17B was not determined.

Example 18

4-((1S,4S)-2-oxa-5-azabicyclo[2.2.1]heptan-5-yl)-N-(4-(4-chloro-1H-imidazol-1-yl)-3-methoxyphenyl)-7-(4-fluorophenyl)-6,7-dihydro-5H-cyclopenta[d]pyrimidin-2-amine

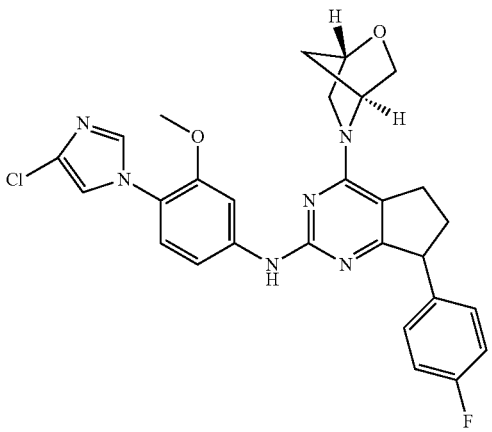

(1S,4S)-5-(2-chloro-7-(4-fluorophenyl)-6,7-dihydro-5H-cyclopenta[d]pyrimidin-4-yl)-2-oxa-5-azabicyclo[2.2.1]heptane (Preparation Hb) (148 mg, 0.428 mmol) and 4-(4-chloro-1H-imidazol-1-yl)-3-methoxyaniline (Preparation A) (124 mg, 0.556 mmol) were combined and purified as per Example 16 to give 4-((1S,4S)-2-oxa-5-azabicyclo[2.2.1]heptan-5-yl)-N-(4-(4-chloro-1H-imidazol-1-yl)-3-methoxyphenyl)-7-(4-fluorophenyl)-6,7-dihydro-5H-cyclopenta[d]pyrimidin-2-amine, TFA (diastereomer mixture) (106 mg, 0.164 mmol, 38.3% yield) as a brown solid. LC-MS (M+H)$^+$ =533.1. $^1$H NMR (500 MHz, DMSO-d6) δ ppm 7.81 (1H, s), 7.67 (1H, br. s.), 7.49 (1H, s), 7.32 (3H, d, J=7.93 Hz), 7.19 (2H, t, J=8.70 Hz), 7.14 (1H, d, J=2.14 Hz), 5.17 (1H, br. s.), 4.74 (1H, s), 4.34 (1H, br. s.), 3.58-3.95 (7H, m), 2.89-3.39 (2H, m), 2.55 (1H, s), 1.97 (3H, br. s.).

Example 18A 4-((1S,4S)-2-oxa-5-azabicyclo[2.2.1]heptan-5-yl)-N-(4-(4-chloro-1H-imidazol-1-yl)-3-methoxyphenyl)-7-(4-fluorophenyl)-6,7-dihydro-5H-cyclopenta[d]pyrimidin-2-amine

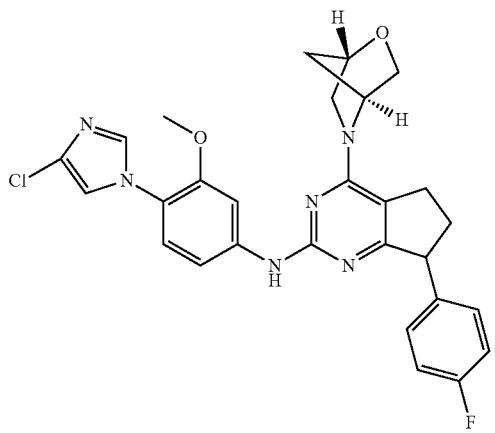 [SMILES: COc1cc(Nc2nc3c(c(N4C[C@@H]5C[C@H]4CO5)n2)CCC3c2ccc(F)cc2)ccc1-n1cnc(Cl)c1]

Enantiomer A of Example 18

4-((1S,4S)-2-oxa-5-azabicyclo[2.2.1]heptan-5-yl)-N-(4-(4-chloro-1H-imidazol-1-yl)-3-methoxyphenyl)-7-(4-fluorophenyl)-6,7-dihydro-5H-cyclopenta[d]pyrimidin-2-amine (Example 18) was separated by multiple chiral SFC injections (OD-H 30×250 mm, 5 µM, 30% MeOH (0.1% DEA)/CO$_2$) to give 4-((1S,4S)-2-oxa-5-azabicyclo[2.2.1]heptan-5-yl)-N-(4-(4-chloro-1H-imidazol-1-yl)-3-methoxyphenyl)-7-(4-fluorophenyl)-6,7-dihydro-5H-cyclopenta[d]pyrimidin-2-amine (first to elute, enantiomer A) as a beige residue. LC-MS (M+H)$^+$=532.9. $^1$H NMR (500 MHz, MeOD) δ ppm 7.82 (1H, br. s.), 7.67 (1H, s), 7.18-7.30 (3H, m), 7.11-7.18 (1H, m), 6.96-7.09 (3H, m), 5.14 (1H, br. s.), 4.72 (1H, br. s.), 4.18 (1H, t, J=8.55 Hz), 3.94-4.01 (1H, m), 3.92 (1H, d, J=6.41 Hz), 3.78-3.86 (1H, m), 3.69-3.78 (1H, m), 3.57 (3H, s), 3.01-3.15 (2H, m), 2.51-2.69 (1H, m), 1.84-2.11 (3H, m). The absolute stereochemistry of Example 18A was not determined.

Example 18B 4-((1S,4S)-2-oxa-5-azabicyclo[2.2.4]heptan-5-yl)-N-(4-(4-chloro-1H-imidazol-1-yl)-3-methoxyphenyl)-7-(4-fluorophenyl)-6,7-dihydro-5H-cyclopenta[d]pyrimidin-2-amine

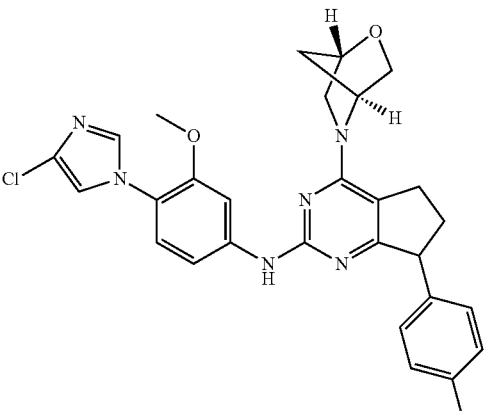

Enantiomer B of Example 18

4-((1S,4S)-2-oxa-5-azabicyclo[2.2.1]heptan-5-yl)-N-(4-(4-chloro-1H-imidazol-1-yl)-3-methoxyphenyl)-7-(4-fluorophenyl)-6,7-dihydro-5H-cyclopenta[d]pyrimidin-2-amine (Example 18) was separated by multiple chiral SFC injections (OD-H 30×250 mm, 5 µM, 30% MeOH (0.1% DEA)/CO$_2$) to give 4-((1S,4S)-2-oxa-5-azabicyclo[2.2.1]heptan-5-yl)-N-(4-(4-chloro-1H-imidazol-1-yl)-3-methoxyphenyl)-7-(4-fluorophenyl)-6,7-dihydro-5H-cyclopenta[d]pyrimidin-2-amine (second to elute, enantiomer B) as a beige residue. LC-MS (M+H)$^+$=532.9. $^1$H NMR (500 MHz, MeOD) δ ppm 7.20-7.31 (3H, m), 7.17 (1H, d, J=8.55 Hz), 7.05 (3H, t, J=8.09 Hz), 5.17 (1H, br. s.), 4.72 (1H, s), 4.14 (1H, t, J=8.09 Hz), 3.94-4.02 (1H, m), 3.89-3.94 (1H, m), 3.70-3.85 (2H, m), 3.50-3.68 (3H, m), 3.20-3.31 (1H, m), 2.96 (1H, ddd, J=14.65, 7.78, 7.48 Hz), 2.48-2.66 (1H, m, J=13.08, 8.72, 8.72, 4.27 Hz), 1.89-2.11 (3H, m). The absolute stereochemistry of Example 18B was not determined.

Example 19

N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine

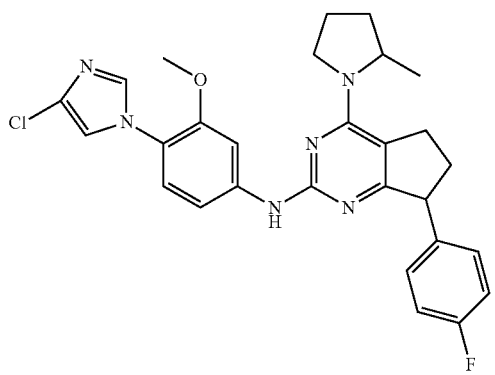

Diastereomer 1
Racemic 2-chloro-7-(4-fluorophenyl)-4-(2-methylpyrrolidin-1-yl)-6,7-dihydro-5H-cyclopenta[d]pyrimidinen (Preparation Hc1) (159 mg, 0.479 mmol) and 4-(4-chloro-1H-imidazol-1-yl)-3-methoxyaniline (Preparation A) (139 mg, 0.623 mmol) were combined and purified as per Example 16 to give N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine, TFA (racemate, diastereomer 1) (84.37 mg, 0.133 mmol, 27.8% yield) as a brown solid. LC-MS (M+H)$^+$=519.1. $^1$H NMR (500 MHz, MeOD) δ ppm 7.80 (1H, s), 7.41 (1H, d, J=8.55 Hz), 7.30-7.37 (4H, m), 7.21-7.32 (1H, m), 7.17 (2H, t, J=8.55 Hz), 4.68 (1H, br. s.), 4.44 (1H, br. s.), 3.94-4.23 (2H, m), 3.88 (3H, s), 3.37 (3H, s), 3.18 (1H, s), 2.72 (1H, br. s.), 2.11 (4H, br. s.), 1.83 (1H, br. s.). The relative stereochemistry of Example 19 was not determined.

Example 19A

N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine

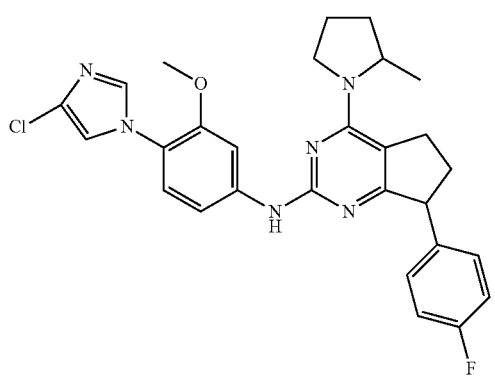

Enantiomer A of Example 19

N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine (Example 19) was separated by multiple chiral SFC injections (OJ-H 30×250 mm, 5 µM, 45% MeOH (0.1% DEA)/CO$_2$) to give N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine (first to elute, enantiomer A, diastereomer 1) as a brown wax. LC-MS (M+H)$^+$=519.1. $^1$H NMR (500 MHz, MeOD) δ ppm 7.76 (1H, s), 7.66 (1H, d, J=1.53 Hz), 7.16-7.27 (3H, m), 7.07-7.16 (2H, m), 7.02 (2H, t, J=8.85 Hz), 4.54 (1H, t, J=5.65 Hz), 4.07 (1H, t, J=8.24 Hz), 3.91 (1H, dt, J=10.45, 4.08 Hz), 3.68-3.79 (1H, m), 3.54-3.68 (3H, m), 3.15-3.28 (1H, m), 2.96-3.13 (1H, m), 2.45-2.58 (1H, m), 2.02-2.18 (2H, m), 1.95-2.02 (1H, m), 1.85-1.95

(1H, m), 1.67-1.81 (1H, m), 1.27 (3H, d, J=6.10 Hz). The absolute stereochemistry of Example 19A was not determined.

Example 19B

N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine

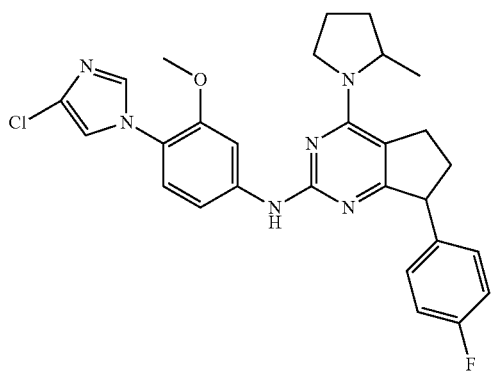

Enantiomer B of Example 19

N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine (Example 19) was separated by multiple chiral SFC injections (OJ-H 30×250 mm, 5 µM, 45% MeOH (0.1% DEA)/CO$_2$) to give N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine (second to elute, enantiomer B, diastereomer 1) as a brown wax. LC-MS (M+H)$^+$=519.1. $^1$H NMR (500 MHz, MeOD) δ ppm 7.76 (1H, d, J=1.53 Hz), 7.65 (1H, d, J=1.22 Hz), 7.15-7.23 (3H, m), 7.06-7.14 (2H, m), 6.96-7.05 (2H, m), 4.48-4.57 (1H, m), 4.05 (1H, t, J=8.39 Hz), 3.85-3.94 (1H, m), 3.66-3.76 (1H, m), 3.60 (3H, s), 3.16-3.26 (1H, m), 2.95-3.08 (1H, m), 2.44-2.55 (1H, m, J=12.78, 8.56, 8.56, 3.97 Hz), 2.01-2.14 (2H, m), 1.94-2.01 (1H, m), 1.85-1.94 (1H, m), 1.68-1.77 (1H, m), 1.26 (3H, d, J=6.10 Hz). The absolute stereochemistry of Example 19B was not determined.

Example 20

N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine Diastereomer 2
Racemic 2-chloro-7-(4-fluorophenyl)-4-(2-methylpyrrolidin-1-yl)-6,7-dihydro-5H-cyclopenta[d]pyrimidinen (Preparation Hc2) (179 mg, 0.539 mmol) and 4-(4-chloro-1H-imidazol-1-yl)-3-methoxyaniline (Preparation A) (157 mg, 0.701 mmol) were combined and purified as per Example 16 to give N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine, TFA (racemate, diastereomer 2) (99.55 mg, 0.157 mmol, 29.2% yield) as a brown solid. LC-MS (M+H)$^+$=519.1. $^1$H NMR (500 MHz, MeOD) δ ppm 7.80 (1H, d, J=1.53 Hz), 7.41-7.60 (1H, m), 7.40 (1H, s), 7.30-7.37 (3H, m), 7.21-7.29 (1H, m), 7.16 (2H, t, J=8.70 Hz), 4.68 (1H, br. s.), 4.45 (1H, d, J=7.93 Hz), 4.17 (1H, br. s.), 4.00 (1H, br. s.), 3.88 (3H, s), 3.34-3.48 (2H, m), 3.17-3.30 (1H, m), 2.73 (1H, br. s.), 2.11 (4H, br. s.), 1.81 (1H, br.

s.), 1.35 (3H, d, J=6.41 Hz). The relative stereochemistry of Example 20 was not determined.

Example 20A

N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine

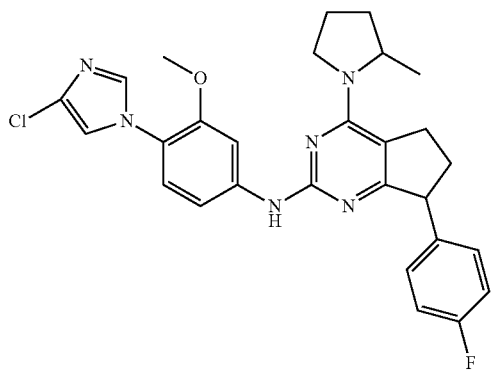

Enantiomer A of Example 20

N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine (Example 20) was separated by multiple chiral SFC injections (OJ-H 30×250 mm, 5 μM, 45% MeOH (0.1% DEA)/CO$_2$) to give N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine (first to elute, enantiomer A, diastereomer 2) as a brown wax. LC-MS (M+H)$^+$=519.1. $^1$H NMR (500 MHz, MeOD) δ ppm 7.75 (1H, d, J=1.83 Hz), 7.65 (1H, d, J=1.53 Hz), 7.14-7.22 (3H, m), 7.05-7.14 (2H, m), 6.96-7.05 (2H, m), 4.55 (1H, td, J=6.41, 2.44 Hz), 4.10 (1H, t, J=8.39 Hz), 3.86-3.95 (1H, m), 3.73 (1H, dt, J=10.15, 7.74 Hz), 3.59 (3H, s), 3.16-3.25 (1H, m), 3.06-3.16 (1H, m), 2.52 (1H, dddd, J=12.70, 8.70, 8.51, 3.97 Hz), 2.02-2.16 (2H, m), 1.82-2.02 (2H, m), 1.65-1.78 (1H, m), 1.27 (3H, d, J=6.10 Hz). The absolute stereochemistry of Example 20A was not determined.

Example 20B

N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine

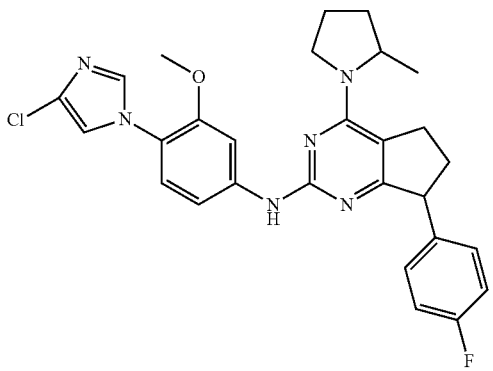

Enantiomer B of Example 20

N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine (Example 20) was separated by multiple chiral SFC injections (OJ-H 30×250 mm, 5 μM, 45% MeOH (0.1% DEA)/CO$_2$) to give N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine (second to elute, enantiomer B, diastereomer 2) as a brown wax. LC-MS (M+H)$^+$=519.1. $^1$H NMR (500 MHz, MeOD) δ ppm 7.75 (1H, s), 7.65 (1H, d, J=1.53 Hz), 7.14-7.21 (3H, m), 7.05-7.14 (2H, m), 6.96-7.04 (2H, m), 4.49-4.58 (1H, m), 4.10 (1H, t, J=8.55 Hz), 3.84-3.93 (1H, m), 3.69-3.78 (1H, m), 3.55-3.61 (3H, m), 3.15-3.24 (1H, m), 3.05-3.15 (1H, m), 2.52 (1H, dddd, J=12.67, 8.62, 8.47, 4.12 Hz), 2.02-2.17 (2H, m), 1.83-2.02 (2H, m), 1.65-1.77 (1H, m), 1.23-1.32 (3H, m). The absolute stereochemistry of Example 20B was not determined.

Example 21

N-(4-(4-chloro-1H-imidazol-1-yl)-3-methoxyphenyl)-4-(2S,6R)-2,6-dimethylmorpholino)-7-(4-fluorophenyl)-6,7-dihydro-5H-cyclopenta[d]pyrimidin-2-amine

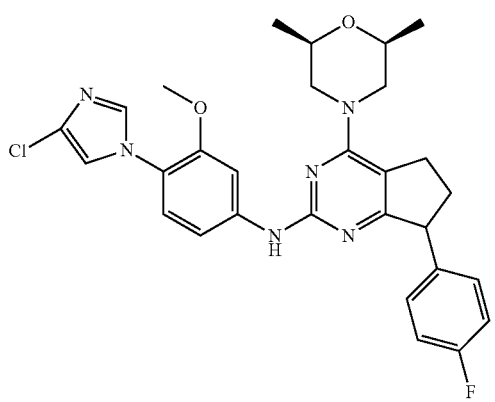

(2S,6R)-4-(2-chloro-7-(4-fluorophenyl)-6,7-dihydro-5H-cyclopenta[d]pyrimidin-4-yl)-2,6-dimethylmorpholine (Preparation Hd) (223 mg, 0.616 mmol) and 4-(4-chloro-1H-imidazol-1-yl)-3-methoxyaniline (Preparation A) (179 mg, 0.801 mmol) were combined and purified as per Example 16 to give N-(4-(4-chloro-1H-imidazol-1-yl)-3-methoxyphenyl)-4-((2S,6R)-2,6-dimethylmorpholino)-7-(4-fluorophenyl)-6,7-dihydro-5H-cyclopenta[d]pyrimidin-2-amine, TFA (144 mg, 0.217 mmol, 35.2% yield) as a brown solid. LC-MS (M+H)$^+$=549.0. $^1$H NMR (500 MHz, MeOD) δ ppm 7.81 (1H, d, J=1.53 Hz), 7.41 (1H, d, J=8.55 Hz), 7.28-7.38 (4H, m), 7.09-7.20 (3H, m), 4.62 (2H, br. s.), 4.45 (1H, t, J=7.93 Hz), 3.83-3.89 (3H, m), 3.69-3.80 (2H, m), 3.25-3.30 (1H, m), 3.13-3.23 (1H, m), 2.94 (2H, br. s.), 2.75 (1H, dddd, J=13.43, 8.93, 8.77, 4.88 Hz), 2.03-2.20 (1H, m), 1.25 (6H, d, J=6.10 Hz).

Example 21A

N-(4-(4-chloro-1H-imidazol-1-yl)-3-methoxyphenyl)-4-(2S,6R)-2,6-dimethylmorpholino)-7-(4-fluorophenyl)-6,7-dihydro-5H-cyclopenta[d]pyrimidin-2-amine

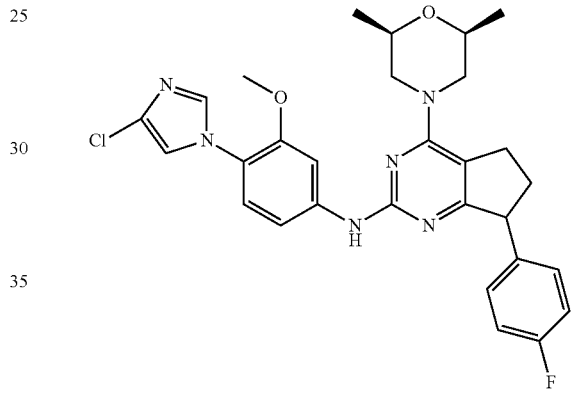

Enantiomer A of Example 21

N-(4-(4-chloro-1H-imidazol-1-yl)-3-methoxyphenyl)-4-((2S,6R)-2,6-dimethylmorpholino)-7-(4-fluorophenyl)-6,7-dihydro-5H-cyclopenta[d]pyrimidin-2-amine (Example 21) was separated by multiple chiral SFC injections (OJ-H 30×250 mm, 5 μM, 35% MeOH (0.1% DEA)/CO$_2$) to give N-(4-(4-chloro-1H-imidazol-1-yl)-3-methoxyphenyl)-4-((2S,6R)-2,6-dimethylmorpholino)-7-(4-fluorophenyl)-6,7-dihydro-5H-cyclopenta[d]pyrimidin-2-amine (first to elute, enantiomer A) as a brown wax. LC-MS (M+H)$^+$=549.0. $^1$H NMR (500 MHz, MeOD) δ ppm 7.81 (1H, d, J=2.14 Hz), 7.63 (1H, d, J=1.53 Hz), 7.11-7.20 (3H, m), 7.08 (1H, d, J=8.55 Hz), 6.96-7.03 (2H, m), 6.92 (1H, dd, J=8.55, 2.44 Hz), 4.27-4.41 (2H, m), 4.08 (1H, t, J=8.70 Hz), 3.58-3.74 (2H, m), 3.49 (3H, s), 2.99-3.08 (1H, m), 2.87-2.99 (1H, m), 2.55-2.72 (2H, m), 2.44-2.55 (1H, m), 1.83-1.96 (1H, m, J=12.70, 8.55, 8.30, 8.30 Hz), 1.17-1.22 (6H, m). The absolute stereochemistry of Example 21A was not determined.

Example 21B

N-(4-(4-chloro-1H-imidazol-1-yl)-3-methoxyphenyl)-4-(2S,6R)-2,6-dimethylmorpholino)-7-(4-fluorophenyl)-6,7-dihydro-5H-cyclopenta[d]pyrimidin-2-amine

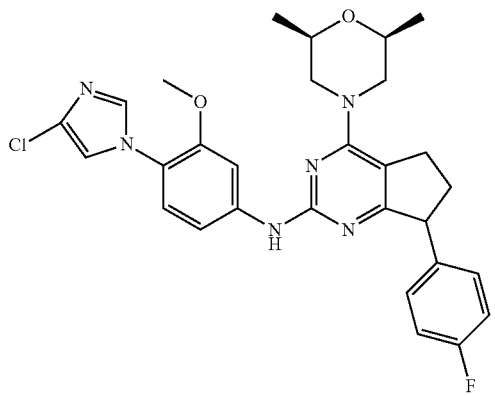 [SMILES: COc1cc(Nc2nc3c(c(N4C[C@@H](C)O[C@@H](C)C4)n2)CCC3c2ccc(F)cc2)ccc1-n1cnc(Cl)c1]

Enantiomer B of Example 21

N-(4-(4-chloro-1H-imidazol-1-yl)-3-methoxyphenyl)-4-((2S,6R)-2,6-dimethylmorpholino)-7-(4-fluorophenyl)-6,7-dihydro-5H-cyclopenta[d]pyrimidin-2-amine (Example 21) was separated by multiple chiral SFC injections (OJ-H 30×250 mm, 5 μM, 35% MeOH (0.1% DEA)/$CO_2$) to give N-(4-(4-chloro-1H-imidazol-1-yl)-3-methoxyphenyl)-4-((2S,6R)-2,6-dimethylmorpholino)-7-(4-fluorophenyl)-6,7-dihydro-5H-cyclopenta[d]pyrimidin-2-amine (second to elute, enantiomer B) as a brown wax. LC-MS (M+H)$^+$=549.0. $^1$H NMR (500 MHz, MeOD) δ ppm 7.81 (1H, d, J=2.14 Hz), 7.63 (1H, d, J=1.53 Hz), 7.11-7.19 (3H, m), 7.04-7.11 (1H, m), 6.95-7.03 (2H, m), 6.92 (1H, dd, J=8.39, 2.29 Hz), 4.27-4.42 (2H, m), 4.08 (1H, t, J=8.70 Hz), 3.59-3.73 (2H, m), 3.49 (3H, s), 2.98-3.08 (1H, m), 2.88-2.98 (1H, m), 2.55-2.70 (2H, m), 2.43-2.55 (1H, m), 1.79-1.97 (1H, m, J=12.70, 8.55, 8.30, 8.30 Hz), 1.17-1.21 (6H, m). The absolute stereochemistry of Example 21B was not determined.

Example 22

1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-4-methylpiperidin-4-ol

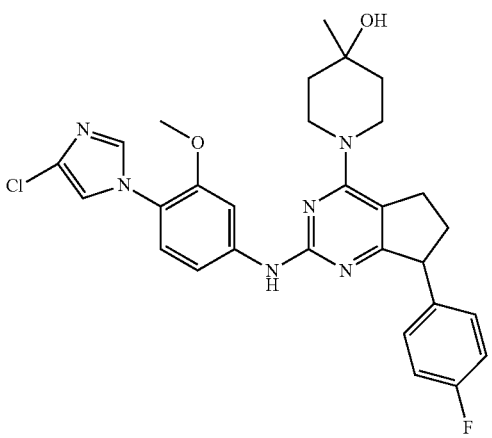

1-(2-chloro-7-(4-fluorophenyl)-6,7-dihydro-5H-cyclopenta[d]pyrimidin-4-yl)-4-methylpiperidin-4-ol (Preparation He) (374 mg, 1.034 mmol) and 4-(4-chloro-1H-imidazol-1-yl)-3-methoxyaniline (Preparation A) (301 mg, 1.344 mmol) were combined and purified as per Example 17 to give 1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-4-methylpiperidin-4-ol (89 mg, 0.162 mmol, 15.68% yield) as a slightly yellow solid. LC-MS (M+H)$^+$ =549.3. $^1$H NMR (500 MHz, DMSO-$d_6$) δ ppm 7.82 (1H, s), 7.64 (1H, br. s.), 7.50 (1H, s), 7.27-7.43 (3H, m), 7.20 (3H, t, J=8.70 Hz), 7.06 (1H, dd, J=8.39, 1.68 Hz), 4.36 (3H, br. s.), 3.73 (3H, br. s.), 2.98-3.26 (3H, m), 2.59 (1H, br. s.), 1.88-2.06 (1H, m), 1.62 (4H, br. s.), 1.25 (2H, br. s.), 1.19 (3H, s).

Example 23

N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine

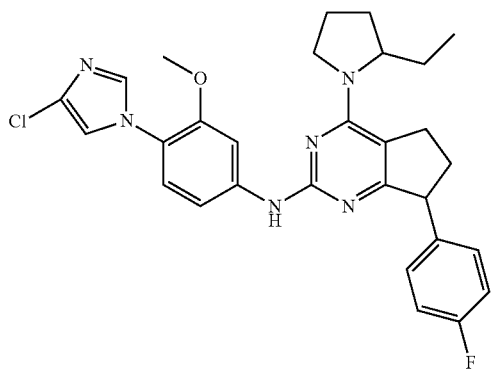

Diastereomer 1
Racemic 2-chloro-4-(2-ethylpyrrolidin-1-yl)-7-(4-fluorophenyl)-6,7-dihydro-5H-cyclopenta[d]pyrimidine (Preparation Hf1) (77 mg, 0.223 mmol) and 4-(4-chloro-1H-imidazol-1-yl)-3-methoxyaniline (Preparation A) (64.7 mg, 0.289 mmol) were combined and purified as per Example 16 to give N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine, TFA (racemic, diastereomer 1) (53.31 mg, 0.082 mmol, 37.0% yield) as a brown solid. LC-MS (M+H)$^+$=533.3. $^1$H NMR (500 MHz, MeOD) δ ppm 7.79 (1H, br. s.), 7.36-7.61 (2H, m), 7.34 (3H, br. s.), 7.17 (3H, br. s.), 4.44 (2H, br. s.), 4.00 (2H, br. s.), 3.88 (3H, br. s.), 3.16-3.27 (1H, m), 2.73 (2H, br. s.), 2.09 (5H, br. s.), 1.32 (2H, br. s.), 0.93 (3H, br. s.). The relative stereochemistry of Example 23 was not determined.

Example 23A

N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine

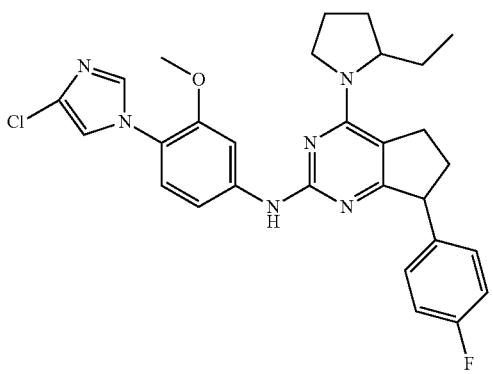

Enantiomer A of Example 23

N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine (Example 23) was separated by multiple chiral SFC injections (OJ-H 30×250 mm, 5 μM, 45% MeOH (0.1% DEA)/CO$_2$) to give N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine (first to elute, enantiomer A) as a brown oil. LC-MS (M+H)$^+$=533.3. $^1$H NMR (500 MHz, MeOD) δ ppm 7.60-7.70 (2H, m), 7.17-7.26 (4H, m), 7.14 (1H, d, J=8.55 Hz), 6.98-7.07 (2H, m), 4.26-4.36 (1H, m), 4.09 (1H, t, J=8.24 Hz), 3.83-3.92 (1H, m), 3.70-3.79 (1H, m), 3.63 (3H, s), 3.15-3.25 (1H, m), 3.04 (1H, ddd, J=14.80, 7.63, 7.48 Hz), 2.48-2.60 (1H, m, J=12.86, 8.60, 8.60, 4.12

Hz), 1.76-2.12 (6H, m), 1.40-1.53 (1H, m), 0.94-1.00 (3H, m). The absolute stereochemistry of Example 23A was not determined.

Example 23B

N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine

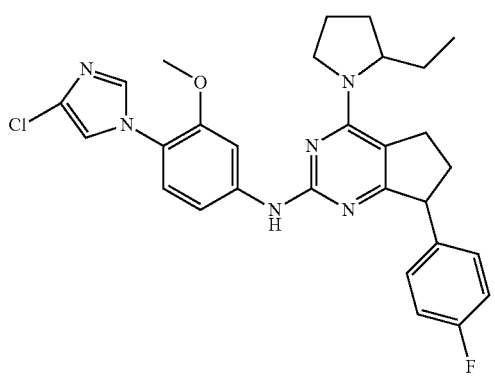

Enantiomer B of Example 23

N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine (Example 23) was separated by multiple chiral SFC injections (OJ-H 30×250 mm, 5 μM, 45% MeOH (0.1% DEA)/CO$_2$) to give N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine (second to elute, enantiomer B) as a brown oil. LC-MS (M+H)$^+$=533.3. $^1$H NMR (500 MHz, MeOD) δ ppm 7.60-7.70 (2H, m), 7.18-7.27 (4H, m), 7.14 (1H, d, J=8.55 Hz), 7.03 (2H, t, J=8.70 Hz), 4.31 (1H, br. s.), 4.04-4.13 (1H, m), 3.81-3.91 (1H, m), 3.70-3.80 (1H, m), 3.63 (3H, s), 3.16-3.26 (1H, m), 3.05 (1H, ddd, J=14.65, 7.78, 7.48 Hz), 2.54 (1H, dddd, J=12.78, 8.70, 8.58, 4.12 Hz), 1.76-2.14 (6H, m), 1.41-1.54 (1H, m), 0.97 (3H, t, J=7.32 Hz). The absolute stereochemistry of Example 23B was not determined.

Example 24

N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine

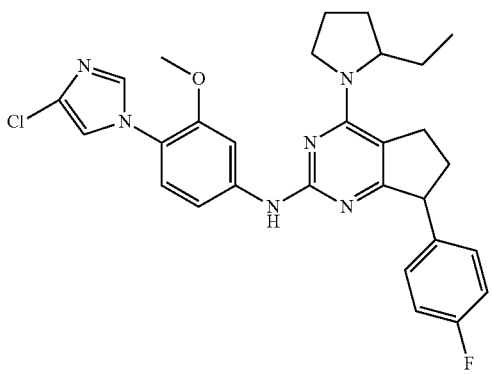

Diastereomer 2
Racemic 2-chloro-4-(2-ethylpyrrolidin-1-yl)-7-(4-fluorophenyl)-6,7-dihydro-5H-cyclopenta[d]pyrimidine (Preparation Hf2) (80 mg, 0.231 mmol) and 4-(4-chloro-1H-imidazol-1-yl)-3-methoxyaniline (Preparation A) (67.3 mg, 0.301 mmol) were combined and purified as per Example 16 to give N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine, TFA (racemic, diastereomer 2) (39.54 mg, 0.061 mmol, 26.4% yield) as a brown solid. LC-MS (M+H)$^+$=533.3. $^1$H NMR (500 MHz, MeOD) δ ppm 7.78 (1H, s), 7.28-7.44 (5H, m), 7.17 (3H, t, J=8.09 Hz), 4.46 (2H, br. s.), 4.00 (2H, br. s.), 3.88 (3H, s), 3.37 (1H, br. s.), 2.73

(2H, br. s.), 2.09 (6H, d, J=4.27 Hz), 1.27-1.73 (1H, m), 0.87 (3H, br. s.). The relative stereochemistry of Example 24 was not determined.

Example 24A

N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine

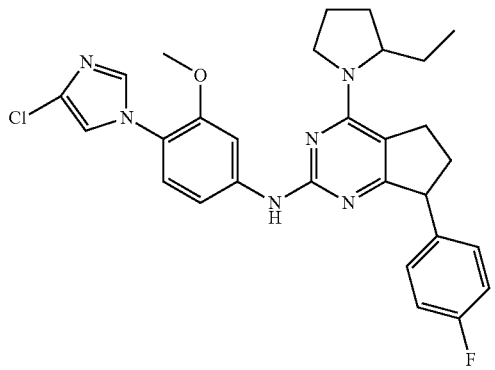

Enantiomer A of Example 24

N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine (Example 24) was separated by multiple chiral SFC injections (OJ-H 30×250 mm, 5 μM, 45% MeOH (0.1% DEA)/CO$_2$) to give N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine (first to elute, enantiomer A) as a brown oil. LC-MS (M+H)$^+$=533.3. $^1$H NMR (500 MHz, MeOD) δ ppm 7.58-7.71 (2H, m), 7.16-7.26 (4H, m), 7.10-7.16 (1H, m), 6.97-7.08 (2H, m), 4.29-4.39 (1H, m), 4.14 (1H, t, J=8.39 Hz), 3.82-3.93 (1H, m), 3.72-3.82 (1H, m), 3.61 (3H, s), 3.17-3.26 (1H, m), 3.12 (1H, ddd, J=14.80, 7.63, 7.48 Hz), 2.56 (1H, dddd, J=12.70, 8.70, 8.51, 3.97 Hz), 1.79-2.09 (6H, m), 1.40-1.56 (1H, m), 0.97 (3H, t, J=7.32 Hz). The absolute stereochemistry of Example 24A was not determined.

Example 24B

N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine Enantiomer B of Example 24

N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine (Example 24) was separated by multiple chiral SFC injections (OJ-H 30×250 mm, 5 μM, 45% MeOH (0.1% DEA)/CO$_2$) to give N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine (second to elute, enantiomer B) as a brown oil. LC-MS (M+H)$^+$=533.3. $^1$H NMR (500 MHz, MeOD) δ ppm 7.59-7.70 (2H, m), 7.16-7.27 (4H, m), 7.11-7.16 (1H, m), 7.03 (2H, t, J=8.70 Hz), 4.29-4.37 (1H, m), 4.09-4.18 (1H, m), 3.83-3.92 (1H, m), 3.73-3.81 (1H, m), 3.61 (3H, s), 3.16-3.27 (1H, m), 3.06-3.16 (1H, m), 2.50-2.61 (1H, m, J=12.74, 8.58, 8.58, 3.97 Hz), 1.80-2.10 (6H, m), 1.42-1.55 (1H, m), 0.97 (3H, t, J=7.48 Hz). The absolute stereochemistry of Example 24B was not determined.

Example 25

4-(4-amino-4-methylpiperidin-1-yl)-N-(4-(4-chloro-1H-imidazol-1-yl)-3-methoxyphenyl)-7-(4-fluorophenyl)-6,7-dihydro-5H-cyclopenta[d]pyrimidin-2-amine

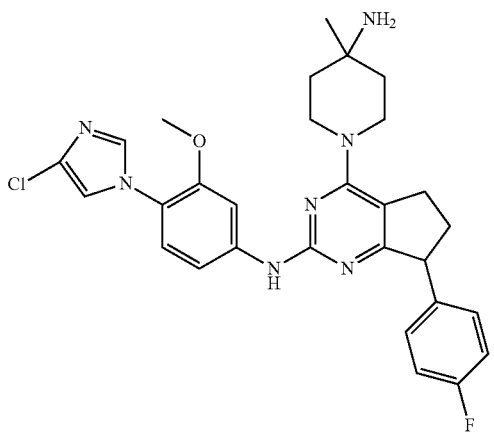 [SMILES: COc1cc(Nc2nc3c(c(N4CCC(C)(O)CC4)n2)CCC3c2ccc(F)cc2)ccc1-n1cnc(Cl)c1]

tert-butyl 1-(2-chloro-7-(4-fluorophenyl)-6,7-dihydro-5H-cyclopenta[d]pyrimidin-4-yl)-4-methylpiperidin-4-yl-carbamate (Preparation Hg) (363 mg, 0.787 mmol) in and 4-(4-chloro-1H-imidazol-1-yl)-3-methoxyaniline (Preparation A) (229 mg, 1.024 mmol) were combined and purified as per Example 16 to give 4-(4-amino-4-methylpiperidin-1-yl)-N-(4-(4-chloro-1H-imidazol-1-yl)-3-methoxyphenyl)-7-(4-fluorophenyl)-6,7-dihydro-5H-cyclopenta[d]pyrimidin-2-amine, TFA (66.5 mg, 0.100 mmol, 12.76% yield) as a slightly yellow solid. LC-MS (M+H)$^+$=548.2. $^1$H NMR (500 MHz, MeOD) δ ppm 7.82 (1H, d, J=2.14 Hz), 7.68 (1H, s), 7.20-7.27 (3H, m), 7.17 (1H, d, J=8.55 Hz), 7.00-7.09 (3H, m), 4.15-4.33 (4H, m), 3.58 (3H, s), 3.44-3.56 (2H, m), 3.02-3.21 (2H, m), 2.61 (1H, dd, J=8.55, 4.27 Hz), 2.01 (1H, dd, J=12.51, 8.24 Hz), 1.81-1.91 (4H, m), 1.38-1.48 (2H, m).

Example 26

N$^2$-(3-fluoro-4-(5-methyl-1H-1,2,4-triazol-1-yl)phenyl)-7-(4-fluorophenyl)-N$^4$-methyl-6,7-dihydro-5H-cyclopenta[d]pyrimidine-2,4-diamine

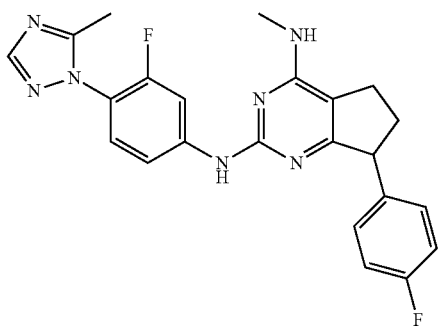

To a solution of 2-chloro-7-(4-fluorophenyl)-N-methyl-6,7-dihydro-5H-cyclopenta[d]pyrimidin-4-amine (Preparation Hh) (144 mg, 0.518 mmol) in Dioxane (2469 μL) was added 3-fluoro-4-(5-methyl-1H-1,2,4-triazol-1-yl)aniline (Preparation C) (100 mg, 0.518 mmol), Tris(dibenzylideneacetone)dipalladium(0) (23.74 mg, 0.026 mmol), 9,9-Dimethyl-4,5-bis(diphenylphosphino)xanthene (30.0 mg, 0.052 mmol), Na2CO3 (82 mg, 0.778 mmol), and water (494 μL). The resulting mixture was heated to 110° C. and stirred overnight. The reaction was then diluted with water (10 mL) and extracted with EtOAc (3×5 mL). The combined organic extracts were washed with brine (10 mL), dried over MgSO$_4$, filtered and concentrated in vacuo. Purification by prep HPLC (C18, 50×250 mm, MeOH/H$_2$O/TFA) gave N$^2$-(3-fluoro-4-(5-methyl-1H-1,2,4-triazol-1-yl)phenyl)-7-(4-fluorophenyl)-N$^4$-methyl-6,7-dihydro-5H-cyclopenta[d]pyrimidine-2,4-diamine, TFA (170 mg, 0.311 mmol, 59.9% yield). LC-MS (M+H)$^+$=434.2. $^1$H NMR (500 MHz, CDCl$_3$) δ ppm 8.06 (1H, s), 7.96 (1H, dd, J=12.51, 2.14 Hz), 7.48-7.59 (2H, m), 7.26-7.33 (2H, m), 7.09-7.18 (2H, m), 4.46-4.54 (1H, m), 3.17 (3H, s), 2.87-2.97 (1H, m), 2.74-2.85 (2H, m), 2.40 (3H, s), 2.09-2.21 (1H, m).

Example 26A

N$^2$-(3-fluoro-4-(5-methyl-1H-1,2,4-triazol-1-yl)phenyl)-7-(4-fluorophenyl)-N$^4$-methyl-6,7-dihydro-5H-cyclopenta[d]pyrimidine-2,4-diamine

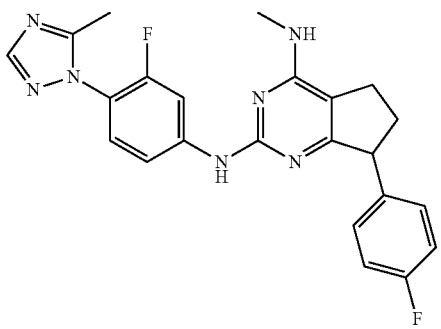 [SMILES: CNc1nc(Nc2ccc(-n3ncnc3C)c(F)c2)nc2c1CCC2c1ccc(F)cc1]

Enantiomer A of Example 26

N$^2$-(3-fluoro-4-(5-methyl-1H-1,2,4-triazol-1-yl)phenyl)-7-(4-fluorophenyl)-N$^4$-methyl-6,7-dihydro-5H-cyclopenta[d]pyrimidine-2,4-diamine (Example 26) was separated by multiple chiral prep HPLC injections (OJ-H 30×250 mm, 10 μM, EtOH/Heptane) to give N$^2$-(3-fluoro-4-(5-methyl-1H-1,2,4-triazol-1-yl)phenyl)-7-(4-fluorophenyl)-N$^4$-methyl-6,7-dihydro-5H-cyclopenta[d]pyrimidine-2,4-diamine, TFA (first to elute, enantiomer A) as a clear, colorless glass. LC-MS (M+H)$^+$=434.2. $^1$H NMR (500 MHz, MeOD) δ ppm 8.03-8.13 (2H, m), 7.41-7.47 (2H, m), 7.23-7.30 (2H, m), 7.04-7.14 (2H, m), 4.33 (1H, t, J=7.93 Hz), 3.12 (3H, s), 2.81-2.92 (1H, m), 2.67-2.81 (2H, m), 2.40 (3H, s). The absolute stereochemistry of Example 26A was not determined.

Example 26B

N²-(3-fluoro-4-(5-methyl-1H-1,2,4-triazol-1-yl)phenyl)-7-(4-fluorophenyl)-N⁴-methyl-6,7-dihydro-5H-cyclopenta[d]pyrimidine-2,4-diamine

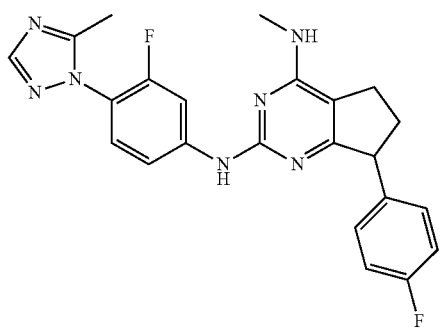

Enantiomer B of Example 26

N²-(3-fluoro-4-(5-methyl-1H-1,2,4-triazol-1-yl)phenyl)-7-(4-fluorophenyl)-N⁴-methyl-6,7-dihydro-5H-cyclopenta[d]pyrimidine-2,4-diamine (Example 26) was separated by multiple chiral prep HPLC injections (OJ-H 30×250 mm, 10 μM, EtOH/Heptane) to give N²-(3-fluoro-4-(5-methyl-1H-1,2,4-triazol-1-yl)phenyl)-7-(4-fluorophenyl)-N⁴-methyl-6,7-dihydro-5H-cyclopenta[d]pyrimidine-2,4-diamine, TFA (second to elute, enantiomer B) as a clear, colorless glass. LC-MS (M+H)⁺=434.2. ¹H NMR (500 MHz, MeOD) δ ppm 8.03-8.10 (2H, m), 7.43-7.48 (2H, m), 7.24-7.30 (2H, m), 7.06-7.14 (2H, m), 4.37 (1H, t, J=7.78 Hz), 3.14 (3H, s), 2.83-2.92 (1H, m), 2.69-2.80 (2H, m), 2.40 (3H, s), 2.05-2.16 (1H, m). The absolute stereochemistry of Example 26B was not determined.

Example 27

1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-3-(trifluoromethyl)pyrrolidin-3-ol Diastereomer 1
Racemic 1-(2-chloro-7-(4-fluorophenyl)-6,7-dihydro-5H-cyclopenta[d]pyrimidin-4-yl)-3-(trifluoromethyl)pyrrolidin-3-ol (Preparation Hi) (245 mg, 0.610 mmol) and 4-(4-chloro-1H-imidazol-1-yl)-3-methoxyaniline (Preparation A) (177 mg, 0.793 mmol) were combined and purified as per Example 16 to give 1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-3-(trifluoromethyl)pyrrolidin-3-ol, TFA (first to elute, diastereomer A) (51.4 mg, 0.073 mmol) as a clear, colorless glass. LC-MS (M+H)⁺=589.1. ¹H NMR (500 MHz, MeOD) δ ppm 7.97 (1H, s), 7.67 (1H, s), 7.17-7.26 (3H, m), 7.14 (1H, d, J=8.55 Hz), 7.04 (2H, t, J=8.70 Hz), 6.91 (1H, d, J=8.55 Hz), 4.14 (2H, t, J=8.85 Hz), 3.93-4.06 (3H, m), 3.58-3.68 (3H, m), 3.21-3.31 (1H, m), 3.09-3.21 (1H, m), 2.51-2.63 (1H, m), 2.28-2.41 (1H, m), 2.16 (1H, dd, J=12.82, 6.41 Hz), 1.95 (1H, dq, J=12.82, 8.55 Hz). The relative stereochemisty of Example 27 was not determined.

Example 27A 1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-3-(trifluoromethyl)pyrrolidin-3-ol

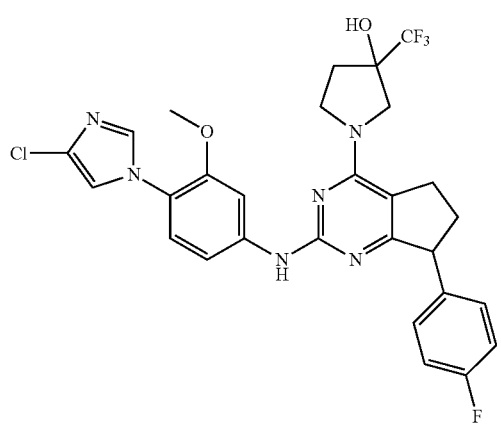

Enantiomer A of Example 27

1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-3-(trifluoromethyl)pyrrolidin-3-ol (Example 12) was separated by multiple chiral SFC injections (OJ-H 30×250 mm, 5 μM, 45% MeOH (0.1% DEA)/$CO_2$) to give 1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-3-(trifluoromethyl)pyrrolidin-3-ol (first to elute, enantiomer A) (11.34 mg, 0.019 mmol) as an opaque glass. LC-MS $(M+H)^+$=589.1. The absolute stereochemistry of Example 27A was not determined.

Example 28

1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-3-(trifluoromethyl)pyrrolidin-3-ol

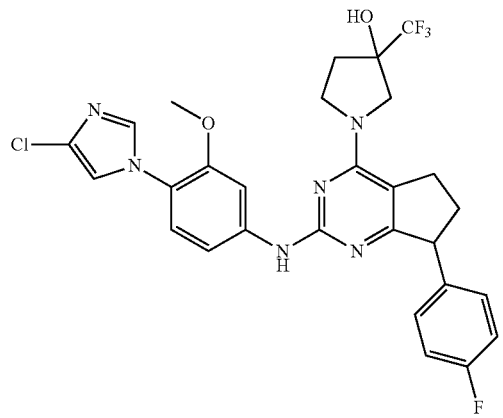

Diastereomer 2
Racemic 1-(2-chloro-7-(4-fluorophenyl)-6,7-dihydro-5H-cyclopenta[d]pyrimidin-4-yl)-3-(trifluoromethyl)pyrrolidin-3-ol (Preparation Hi) (245 mg, 0.610 mmol) and 4-(4-chloro-1H-imidazol-1-yl)-3-methoxyaniline (Preparation A) (177 mg, 0.793 mmol) were combined and purified as per Example 16 to give 1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-3-(trifluoromethyl)pyrrolidin-3-ol, TFA (second to elute, diastereomer 2) (51.1 mg, 0.073 mmol) as a white solid. LC-MS $(M+H)^+$=589.1. $^1$H NMR (500 MHz, MeOD) δ ppm 7.96 (1H, d, J=1.83 Hz), 7.68 (1H, d, J=1.53 Hz), 7.19-7.27 (3H, m), 7.15 (1H, d, J=8.55 Hz), 7.04 (2H, t, J=8.70 Hz), 6.95 (1H, dd, J=8.55, 2.14 Hz), 4.10-4.21 (2H, m), 3.95-4.04 (3H, m), 3.61-3.69 (3H, m), 3.27-3.32 (1H, m), 3.08-3.20 (1H, m), 2.57 (1H, dddd, J=13.16, 8.74, 8.62, 4.58 Hz), 2.37 (1H, dt, J=12.89, 9.88 Hz), 2.18 (1H, dd, J=12.82, 6.41 Hz), 1.93-2.05 (1H, m). The relative stereochemistry of Example 28 was not determined.

Example 28A 1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-3-(trifluoromethyl)pyrrolidin-3-ol

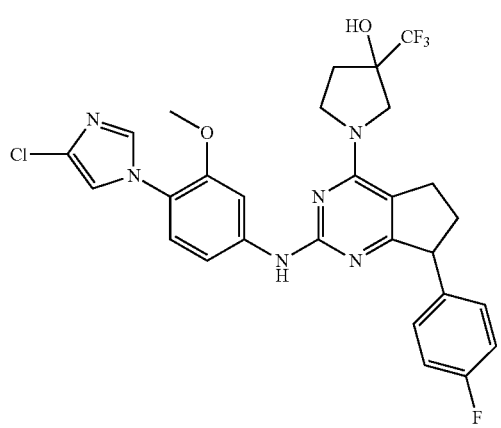

Enantiomer A of Example 28

1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-3-(trifluoromethyl)pyrrolidin-3-ol (Example 28) was separated by multiple chiral SFC injections (OJ-H 30×250 mm, 5 μM, 45% MeOH (0.1% DEA)/CO$_2$) to give 1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-3-(trifluoromethyl)pyrrolidin-3-ol (first to elute, enantiomer A) (17.18 g, 29.2 mmol) as an opaque glass.

LC-MS (M+H)$^+$=589.1. The absolute stereochemistry of Example 28A was not determined.

Example 29

N-(4-(4-chloro-1H-imidazol-1-yl)-3-methoxyphenyl)-4-(3-(dimethylamino)pyrrolidin-1-yl)-7-(4-fluorophenyl)-6,7-dihydro-5H-cyclopenta[d]pyrimidin-2-amine

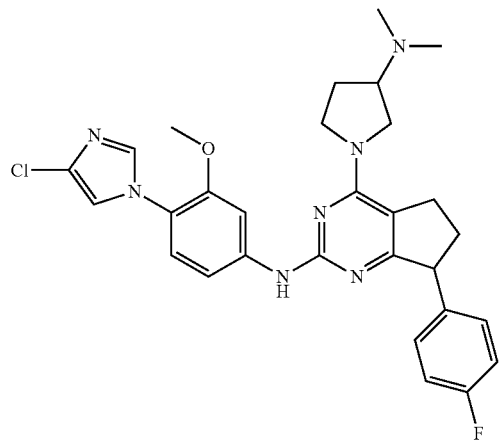

Diastereomer Mixture 1-(2-chloro-7-(4-fluorophenyl)-6,7-dihydro-5H-cyclopenta[d]pyrimidin-4-yl)-N,N-dimethylpyrrolidin-3-amine (Preparation Hj) (109 mg, 0.302 mmol) and 4-(4-chloro-1H-imidazol-1-yl)-3-methoxyaniline (Preparation A) (67.6 mg, 0.302 mmol) were combined and purified as per Example 26 to give N-(4-(4-chloro-1H-imidazol-1-yl)-3-methoxyphenyl)-4-(3-(dimethylamino)pyrrolidin-1-yl)-7-(4-fluorophenyl)-6,7-dihydro-5H-cyclopenta[d]pyrimidin-2-amine, TFA (88 mg, 0.133 mmol, 44.0% yield) as a scrapable tan glass. LC-MS (M+H)$^+$=548.3. $^1$H NMR (500 MHz, MeOD) δ ppm 7.79 (1H, s), 7.38-7.44 (2H, m), 7.29-7.36 (3H, m), 7.24-7.29 (1H, m), 7.11-7.19 (2H, m), 4.39-4.51 (2H, m), 4.28 (1H, br. s.), 4.05-4.17 (2H, m), 4.00 (1H, d, J=2.44 Hz), 3.86 (3H, s), 3.22-3.47 (2H, m), 3.02 (3H, s), 2.76 (1H, br. s.), 2.60 (1H, br. s.), 2.39 (1H, br. s.), 2.13 (1H, br. s.).

Example 29A

N-(4-(4-chloro-1H-imidazol-1-yl)-3-methoxyphenyl)-4-(3-(dimethylamino)pyrrolidin-1-yl)-7-(4-fluorophenyl)-6,7-dihydro-5H-cyclopenta[d]pyrimidin-2-amine

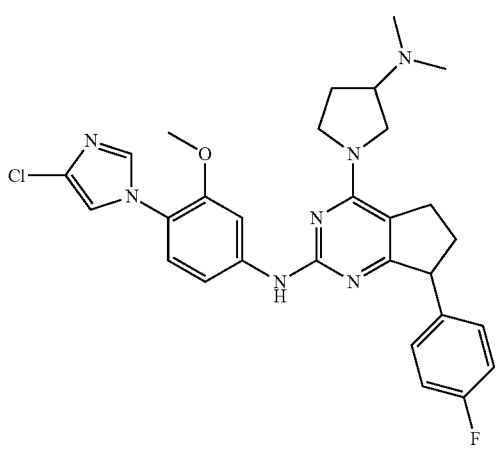

Enantiomer A of Diastereomer A
of Example 29

N-(4-(4-chloro-1H-imidazol-1-yl)-3-methoxyphenyl)-4-(3-(dimethylamino)pyrrolidin-1-yl)-7-(4-fluorophenyl)-6,7-dihydro-5H-cyclopenta[d]pyrimidin-2-amine (Example 29) was separated first by multiple chiral HPLC injections (OJ-H 30×250 mm, 30% EtOH/Heptane) to give N-(4-(4-chloro-1H-imidazol-1-yl)-3-methoxyphenyl)-4-(3-(dimethylamino)pyrrolidin-1-yl)-7-(4-fluorophenyl)-6,7-dihydro-5H-cyclopenta[d]pyrimidin-2-amine (first to elute, diastereomer A) which was then separated by multiple chiral SFC injections (IB 30×250 mm, 5 µM, 35% 50:50 MeOH:MeCN/(0.1% DEA)CO$_2$) to give N-(4-(4-chloro-1H-imidazol-1-yl)-3-methoxyphenyl)-4-(3-(dimethylamino)pyrrolidin-1-yl)-7-(4-fluorophenyl)-6,7-dihydro-5H-cyclopenta[d]pyrimidin-2-amine (first to elute, enantiomer A) as a clear, colorless glass. LC-MS (M+H)$^+$=548.3. $^1$H NMR (500 MHz, MeOD) δ ppm 7.83 (1H, d, J=2.14 Hz), 7.67 (1H, d, J=1.22 Hz), 7.18-7.26 (3H, m), 7.15 (1H, d, J=8.55 Hz), 7.00-7.10 (3H, m), 4.00-4.16 (3H, m), 3.69-3.80 (1H, m), 3.58-3.66 (3H, m), 3.52 (1H, t, J=9.31 Hz), 3.26-3.31 (1H, m), 3.06-3.17 (1H, m), 2.83-2.94 (1H, m), 2.49-2.61 (1H, m, J=13.08, 8.64, 8.64, 4.43 Hz), 2.35 (6H, s), 2.21-2.30 (1H, m), 1.83-

2.03 (2H, m), 1.33-1.41 (1H, m). The absolute stereochemistry of Example 29A was not determined.

Example 29B

N-(4-(4-chloro-1H-imidazol-1-yl)-3-methoxyphenyl)-4-(3-(dimethylamino)pyrrolidin-1-yl)-7-(4-fluorophenyl)-6,7-dihydro-5H-cyclopenta[d]pyrimidin-2-amine

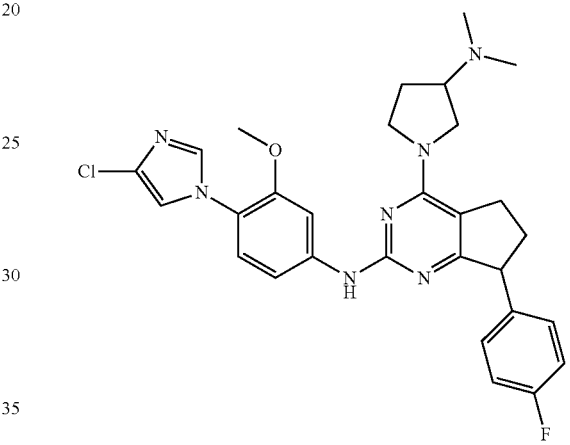

Enantiomer B of Diastereomer A
of Example 29

N-(4-(4-chloro-1H-imidazol-1-yl)-3-methoxyphenyl)-4-(3-(dimethylamino)pyrrolidin-1-yl)-7-(4-fluorophenyl)-6,7-dihydro-5H-cyclopenta[d]pyrimidin-2-amine (Example 29) was separated first by multiple chiral HPLC injections (OJ-H 30×250 mm, 30% EtOH/Heptane) to give N-(4-(4-chloro-1H-imidazol-1-yl)-3-methoxyphenyl)-4-(3-(dimethylamino)pyrrolidin-1-yl)-7-(4-fluorophenyl)-6,7-dihydro-5H-cyclopenta[d]pyrimidin-2-amine (first to elute, diastereomer A) which was then separated by multiple chiral SFC injections (IB 30×250 mm, 5 M, 35% 50:50 MeOH:MeCN/(0.1% DEA)CO$_2$) to give N-(4-(4-chloro-1H-imidazol-1-yl)-3-methoxyphenyl)-4-(3-(dimethylamino)pyrrolidin-1-yl)-7-(4-fluorophenyl)-6,7-dihydro-5H-cyclopenta[d]pyrimidin-2-amine (second to elute, enantiomer B) as a clear, colorless glass. LC-MS (M+H)$^+$=548.3. $^1$H NMR (500 MHz, MeOD) δ ppm 7.85 (1H, d, J=2.14 Hz), 7.67 (1H, d, J=1.53 Hz), 7.17-7.24 (3H, m), 7.12-7.17 (1H, m), 6.99-7.08 (3H, m), 3.99-4.18 (3H, m), 3.68-3.79 (1H, m), 3.58 (3H, s), 3.48-3.56 (1H, m), 3.21-3.30 (1H, m), 3.10-3.21 (1H, m), 2.81-2.94 (1H, m), 2.49-2.62 (1H, m), 2.36 (6H, s), 2.21-2.31 (1H, m), 1.82-1.99 (2H, m). The absolute stereochemistry of Example 29B was not determined.

Example 30

N-(4-(4-chloro-1H-imidazol-1-yl)-3-methoxyphenyl)-7-(4-fluorophenyl)-4-(4-methylpiperazin-1-yl)-6,7-dihydro-5H-cyclopenta[d]pyrimidin-2-amine

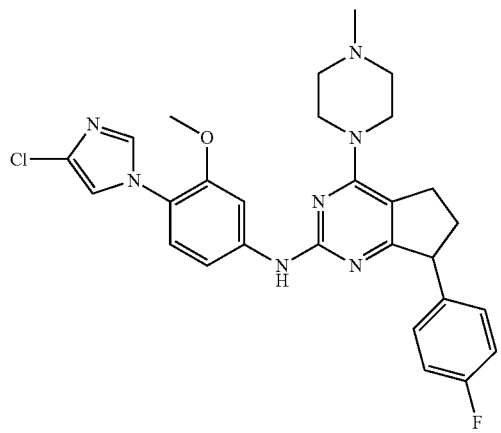

2-chloro-7-(4-fluorophenyl)-4-(4-methylpiperazin-1-yl)-6,7-dihydro-5H-cyclopenta[d]pyrimidine (Preparation Hk) (109 mg, 0.314 mmol) and 4-(4-chloro-1H-imidazol-1-yl)-3-methoxyaniline (Preparation A) (70.3 mg, 0.314 mmol) were combined and purified as per Example 26 to give N-(4-(4-chloro-1H-imidazol-1-yl)-3-methoxyphenyl)-7-(4-fluorophenyl)-4-(4-methylpiperazin-1-yl)-6,7-dihydro-5H-cyclopenta[d]pyrimidin-2-amine, TFA (104 mg, 0.160 mmol, 51.1% yield) as a scrapable tan glass. LC-MS (M+H)$^+$ =534.3. $^1$H NMR (500 MHz, MeOD) δ ppm 7.79 (1H, s), 7.52 (1H, s), 7.26-7.36 (4H, m), 7.08-7.16 (3H, m), 4.41 (1H, t, J=8.09 Hz), 3.73 (3H, s), 3.37-3.63 (7H, m), 3.09-3.28 (3H, m), 2.97-3.03 (3H, m), 2.67-2.79 (1H, m), 2.05-2.20 (1H, m).

Example 30A

N-(4-(4-chloro-1H-imidazol-1-yl)-3-methoxyphenyl)-7-(4-fluorophenyl)-4-(4-methylpiperazin-1-yl)-6,7-dihydro-5H-cyclopenta[d]pyrimidin-2-amine

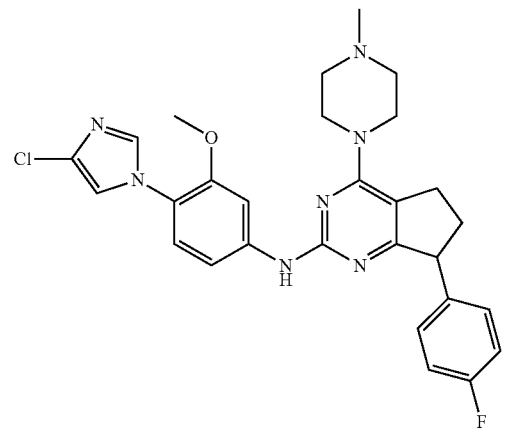 [SMILES: COc1cc(Nc2nc3c(c(N4CCN(C)CC4)n2)CCC3c2ccc(F)cc2)ccc1-n1cnc(Cl)c1]

Enantiomer A of Example 30

N-(4-(4-chloro-1H-imidazol-1-yl)-3-methoxyphenyl)-7-(4-fluorophenyl)-4-(4-methylpiperazin-1-yl)-6,7-dihydro-5H-cyclopenta[d]pyrimidin-2-amine (Example 30) was separated by multiple chiral prep HPLC injections (OJ-H 30×250 mm, 10 μM, 30% EtOH/Heptane) to give N-(4-(4-chloro-1H-imidazol-1-yl)-3-methoxyphenyl)-7-(4-fluorophenyl)-4-(4-methylpiperazin-1-yl)-6,7-dihydro-5H-cyclopenta[d]pyrimidin-2-amine, TFA (first to elute, enantiomer A) (21.6 mg, 0.033 mmol) as a scrapable tan glass. LC-MS (M+H)$^+$=534.3. $^1$H NMR (500 MHz, MeOD) δ ppm 7.77 (1H, br. s.), 7.69 (1H, s), 7.23-7.31 (3H, m), 7.21 (1H, d, J=8.55 Hz), 6.99-7.15 (3H, m), 4.27 (1H, t, J=8.39 Hz), 3.61-3.78 (1H, m), 3.56 (3H, s), 3.38-3.53 (3H, m), 3.23-3.38 (5H, m), 3.03-3.21 (2H, m), 2.98 (3H, s), 2.67 (1H, dt, J=8.47, 4.16 Hz), 1.99-2.13 (1H, m). The absolute stereochemistry of Example 30A was not determined.

Example 30B

N-(4-(4-chloro-1H-imidazol-1-yl)-3-methoxyphenyl)-7-(4-fluorophenyl)-4-(4-methylpiperazin-1-yl)-6,7-dihydro-5H-cyclopenta NJ pyrimidin-2-amine

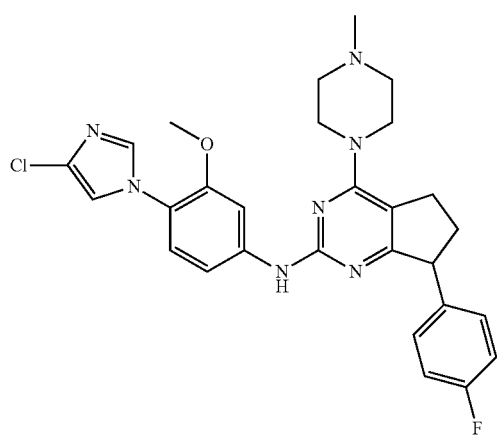

Enantiomer B of Example 30

N-(4-(4-chloro-1H-imidazol-1-yl)-3-methoxyphenyl)-7-(4-fluorophenyl)-4-(4-methylpiperazin-1-yl)-6,7-dihydro-5H-cyclopenta[d]pyrimidin-2-amine (Example 30) was separated by multiple chiral prep HPLC injections (OJ-H 30×250 mm, 10 µM, 30% EtOH/Heptane) to give N-(4-(4-chloro-1H-imidazol-1-yl)-3-methoxyphenyl)-7-(4-fluorophenyl)-4-(4-methylpiperazin-1-yl)-6,7-dihydro-5H-cyclopenta[d]pyrimidin-2-amine, TFA (second to elute, enantiomer B) (21.6 mg, 0.033 mmol) as a scrapable tan glass. LC-MS (M+H)$^+$=534.3. $^1$H NMR (500 MHz, MeOD) δ ppm 7.81 (1H, d, J=2.14 Hz), 7.68 (1H, d, J=1.53 Hz), 7.22-7.29 (3H, m), 7.16-7.21 (1H, m), 7.00-7.11 (3H, m), 4.24 (1H, t, J=8.55 Hz), 3.57-3.70 (1H, m), 3.53 (3H, s), 3.46 (3H, br. s.), 3.27-3.36 (5H, m), 3.02-3.18 (2H, m), 2.98 (3H, s), 2.60-2.72 (1H, m), 2.00-2.10 (1H, m). The absolute stereochemistry of Example 30B was not determined.

Example 31

N-(4-(4-chloro-1H-imidazol-1-yl)-3-methoxyphenyl)-7-(4-fluorophenyl)-4-(piperazin-1-yl)-6,7-dihydro-5H-cyclopenta[d]pyrimidin-2-amine

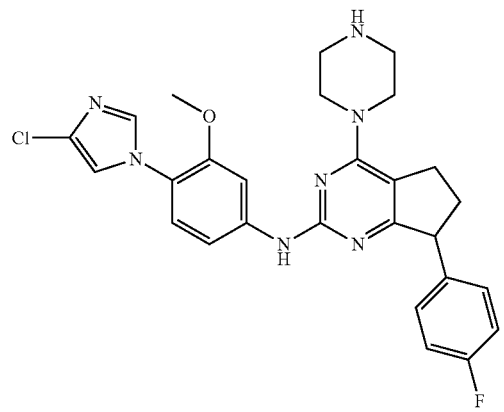 [SMILES: COc1cc(Nc2nc3c(c(N4CCNCC4)n2)CCC3c2ccc(F)cc2)ccc1-n1cnc(Cl)c1]

Intermediate 31-1 tert-butyl 4-(2-(4-(4-chloro-1H-imidazol-1-yl)-3-methoxyphenylamino)-7-(4-fluorophenyl)-6,7-dihydro-5H-cyclopenta[d]pyrimidin-4-yl)piperazine-1-carboxylate

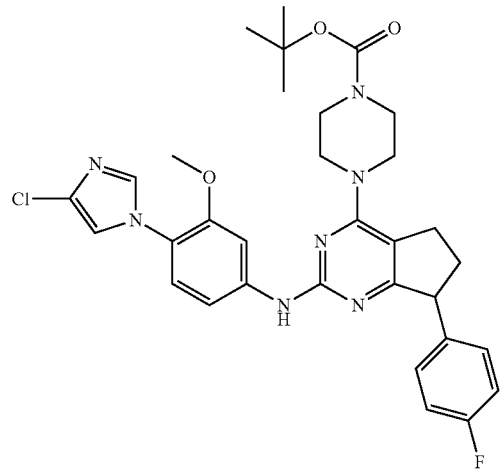 [SMILES: COc1cc(Nc2nc3c(c(N4CCN(C(=O)OC(C)(C)C)CC4)n2)CCC3c2ccc(F)cc2)ccc1-n1cnc(Cl)c1]

tert-butyl 4-(2-chloro-7-(4-fluorophenyl)-6,7-dihydro-5H-cyclopenta[d]pyrimidin-4-yl)piperazine-1-carboxylate (Preparation Hl) (117 mg, 0.270 mmol) and 4-(4-chloro-1H-imidazol-1-yl)-3-methoxyaniline (Preparation A) (60.4 mg, 0.270 mmol) were combined as per Example 26 to give tert-butyl 4-(2-(4-(4-chloro-1H-imidazol-1-yl)-3-methoxyphenylamino)-7-(4-fluorophenyl)-6,7-dihydro-5H-cyclopenta[d]pyrimidin-4-yl)piperazine-1-carboxylate (104 mg, 0.168 mmol, 62.1% yield) crude without purification. LC-MS (M+H)$^+$=620.4.

Example 31

To a solution of tert-butyl 4-(2-(4-(4-chloro-1H-imidazol-1-yl)-3-methoxyphenylamino)-7-(4-fluorophenyl)-6,7-dihydro-5H-cyclopenta[d]pyrimidin-4-yl)piperazine-1-carboxylate (Intermediate 31-1) (167 mg, 0.270 mmol) in DCM (5 mL) was added TFA (500 μL, 6.49 mmol). The reaction mixture was stirred at RT for 1 h. The mixture was then concentrated in vacuo. Purification by prep HPLC (Waters Sunfire C18, 50×250 mm, MeOH/H$_2$O/TFA) gave N-(4-(4-chloro-1H-imidazol-1-yl)-3-methoxyphenyl)-7-(4-fluorophenyl)-4-(piperazin-1-yl)-6,7-dihydro-5H-cyclopenta[d]pyrimidin-2-amine, TFA (39 mg, 0.062 mmol, 22.78% yield) as a brown oil. LC-MS (M+H)$^+$=520.3. $^1$H NMR (500 MHz, MeOD) δ ppm 7.83 (1H, br. s.), 7.28-7.46 (5H, m), 7.08-7.21 (3H, m), 4.41-4.53 (1H, m), 4.18-4.28 (4H, m), 3.80 (3H, s), 3.44 (5H, d, J=4.27 Hz), 3.24-3.31 (1H, m), 3.12-3.23 (1H, m), 2.69-2.82 (1H, m), 2.06-2.22 (1H, m).

Example 32

N-(4-(4-chloro-1H-imidazol-1-yl)-3-methoxyphenyl)-7-(4-fluorophenyl)-4-(3-(methylamino)pyrrolidin-1-yl)-6,7-dihydro-5H-cyclopenta[d]pyrimidin-2-amine

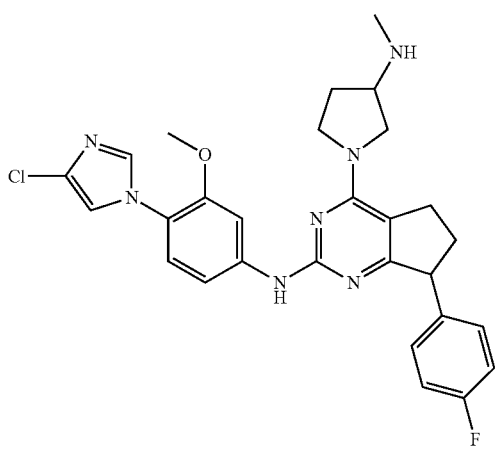 [SMILES: CNC1CCN(c2nc(Nc3ccc(-n4cnc(Cl)c4)c(OC)c3)nc3c2CCC3c2ccc(F)cc2)C1]

Intermediate 32-1 tert-butyl 1-(2-(4-(4-chloro-1H-imidazol-1-yl)-3-methoxyphenylamino)-7-(4-fluorophenyl)-6,7-dihydro-5H-cyclopenta[d]pyrimidin-4-yl)pyrrolidin-3-ylmethyl)carbamate

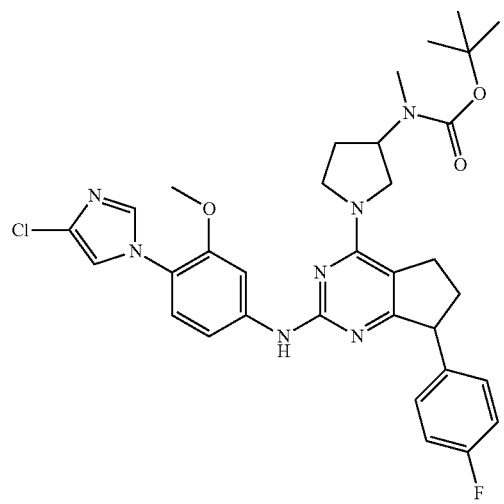 [SMILES: COc1cc(Nc2nc3c(c(N4CCC(N(C)C(=O)OC(C)(C)C)C4)n2)CCC3c2ccc(F)cc2)ccc1-n1cnc(Cl)c1]

tert-butyl 1-(2-chloro-7-(4-fluorophenyl)-6,7-dihydro-5H-cyclopenta[d]pyrimidin-4-yl)pyrrolidin-3-yl(methyl)carbamate (Preparation Hm) (148 mg, 0.331 mmol) and 4-(4-chloro-1H-imidazol-1-yl)-3-methoxyaniline (Preparation A) (74.1 mg, 0.331 mmol) were combined as per Example 26 to give the crude tert-butyl 1-(2-(4-(4-chloro-1H-imidazol-1-yl)-3-methoxyphenylamino)-7-(4-fluorophenyl)-6,7-dihydro-5H-cyclopenta[d]pyrimidin-4-yl)pyrrolidin-3-yl(methyl)carbamate (104 mg, 0.164 mmol, 49.5% yield) which was used without further purification. LC-MS (M+H)$^+$=634.4.

Example 32 tert-butyl 1-(2-(4-(4-chloro-1H-imidazol-1-yl)-3-methoxyphenylamino)-7-(4-fluorophenyl)-6,7-dihydro-5H-cyclopenta[d]pyrimidin-4-yl)pyrrolidin-3-yl(methyl)carbamate (Intermediate 32-1) (210 mg, 0.331 mmol) was deprotected and purified as per Example 31 to give N-(4-(4-chloro-1H-imidazol-1-yl)-3-methoxyphenyl)-7-(4-fluorophenyl)-4-(3-(methylamino)pyrrolidin-1-yl)-6,7-dihydro-5H-cyclopenta[d]pyrimidin-2-amine, TFA (50 mg, 0.077 mmol, 23.31% yield) as a brown oil. LC-MS (M+H)$^+$=534.4. $^1$H NMR (500 MHz, MeOD) δ ppm 7.43 (1H, s), 7.40 (1H, d, J=8.55 Hz), 7.29-7.35 (3H, m), 7.24 (1H, dt, J=8.62, 2.25 Hz), 7.16 (2H, t, J=8.09 Hz), 4.47 (1H, br. s.), 4.23-4.35 (1H, m), 4.12 (3H, br. s.), 4.02 (1H, br. s.), 3.84-3.91 (3H, m), 3.18-3.49 (2H, m), 2.84 (3H, s), 2.68-2.81 (1H, m), 2.56 (1H, br. s.), 2.35 (1H, br. s.), 2.07-2.22 (1H, m).

Example 33

N-(4-(4-chloro-1H-imidazol-1-yl)-3-methoxyphenyl)-7-(4-fluorophenyl)-4-(3-(methylamino)azetidin-1-yl)-6,7-dihydro-5H-cyclopenta[d]pyrimidin-2-amine

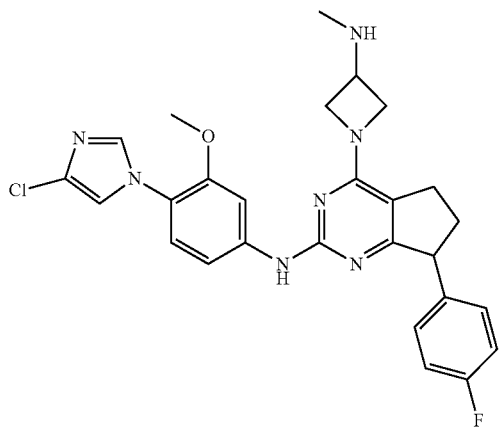 [SMILES: CNC1CN(c2nc(Nc3ccc(-n4cnc(Cl)c4)c(OC)c3)nc3c2CCC3c2ccc(F)cc2)C1]

Intermediate 33-1 tert-butyl 1-(2-(4-(4-chloro-1H-imidazol-1-yl)-3-methoxyphenylamino)-7-(4-fluorophenyl)-6,7-dihydro-5H-cyclopenta[d]pyrimidin-4-yl)azetidin-3-yl(methyl)carbamate

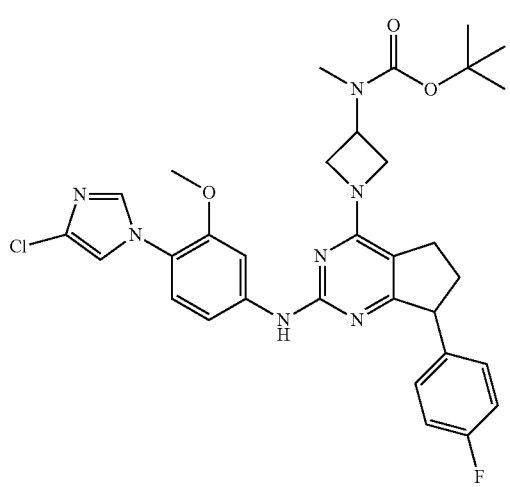 [SMILES: COc1cc(Nc2nc3c(c(N4CC(N(C)C(=O)OC(C)(C)C)C4)n2)CCC3c2ccc(F)cc2)ccc1-n1cnc(Cl)c1]

tert-butyl 1-(2-chloro-7-(4-fluorophenyl)-6,7-dihydro-5H-cyclopenta[d]pyrimidin-4-yl)azetidin-3-yl(methyl)carbamate (Preparation Hn) (147 mg, 0.340 mmol) and 4-(4-chloro-1H-imidazol-1-yl)-3-methoxyaniline (Preparation A) (76 mg, 0.340 mmol) were combined as per Example 26 to give the crude tert-butyl 1-(2-(4-(4-chloro-1H-imidazol-1-yl)-3-methoxyphenylamino)-7-(4-fluorophenyl)-6,7-dihydro-5H-cyclopenta[d]pyrimidin-4-yl)azetidin-3-yl(methyl) carbamate (104 mg, 0.168 mmol, 49.4% yield) which was used without further purification. LC-MS (M+H)$^+$=620.4.

Example 33 tert-butyl 1-(2-(4-(4-chloro-1H-imidazol-1-yl)-3-methoxyphenylamino)-7-(4-fluorophenyl)-6,7-dihydro-5H-cyclopenta[d]pyrimidin-4-yl)azetidin-3-yl(methyl)carbamate (Intermediate 33-1) (211 mg, 0.340 mmol) was deprotected and purified as per Example 31 to give N-(4-(4-chloro-1H-imidazol-1-yl)-3-methoxyphenyl)-7-(4-fluorophenyl)-4-(3-(methylamino)azetidin-1-yl)-6,7-dihydro-5H-cyclopenta[d]pyrimidin-2-amine, TFA (126 mg, 0.199 mmol, 58.5% yield) as a slightly yellow oil. LC-MS (M+H)$^+$=520.4. $^1$H NMR (500 MHz, MeOD) δ ppm 7.80 (1H, s), 7.55 (1H, d, J=2.14 Hz), 7.31-7.40 (2H, m), 7.26-7.31 (2H, m), 7.09-7.20 (3H, m), 4.64 (2H, br. s.), 4.46 (1H, t, J=7.93 Hz), 4.21-4.36 (1H, m), 3.87 (3H, s), 3.37 (2H, s), 3.11-3.21 (1H, m), 3.04 (1H, t, J=14.95 Hz), 2.80-2.84 (3H, m), 2.68-2.80 (1H, m), 2.14 (1H, dddd, J=13.28, 8.85, 6.56, 6.41 Hz).

Example 34

N-(4-(4-chloro-1H-imidazol-1-yl)-3-methoxyphenyl)-4-(3-(dimethylamino)azetidin-1-yl)-7-(4-fluorophenyl)-6,7-dihydro-5H-cyclopenta[d]pyrimidin-2-amine

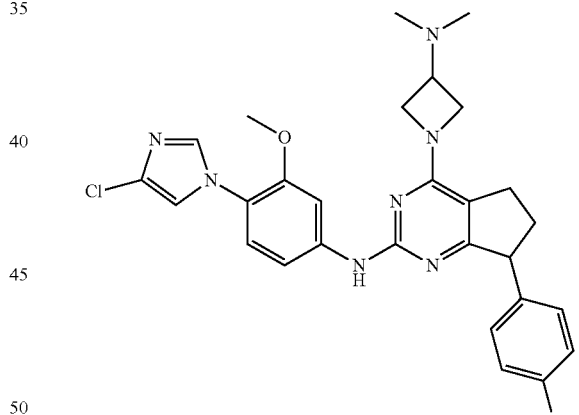

1-(2-chloro-7-(4-fluorophenyl)-6,7-dihydro-5H-cyclopenta[d]pyrimidin-4-yl)-N,N-dimethylazetidin-3-amine (Preparation Ho) (146 mg, 0.421 mmol) and 4-(4-chloro-1H-imidazol-1-yl)-3-methoxyaniline (Preparation A) (94 mg, 0.421 mmol) were combined and purified as per Example 26 to give N-(4-(4-chloro-1H-imidazol-1-yl)-3-methoxyphenyl)-4-(3-(dimethylamino)azetidin-1-yl)-7-(4-fluorophenyl)-6,7-dihydro-5H-cyclopenta[d]pyrimidin-2-amine, TFA (104 mg, 0.160 mmol, 38.1% yield) as a slightly brown gum. LC-MS (M+H)$^+$=534.4. $^1$H NMR (500 MHz, MeOD) δ ppm 7.82 (1H, d, J=1.53 Hz), 7.48 (1H, d, J=2.14 Hz), 7.39 (1H, d, J=8.55 Hz), 7.35 (1H, d, J=1.53 Hz), 7.29-7.33 (2H, m), 7.21 (1H, dd, J=8.55, 2.14 Hz), 7.11-7.18 (2H, m), 4.83 (4H, br. s.), 4.43-4.51 (1H, m), 4.30-4.37 (1H, m), 3.88 (3H, s), 3.12-3.22

(1H, m), 3.04 (1H, d, J=6.10 Hz), 2.99 (6H, s), 2.72-2.84 (1H, m, J=13.47, 8.98, 8.98, 4.58 Hz), 2.14 (1H, dddd, J=13.16, 8.96, 6.56, 6.41 Hz).

Example 35

$N^2$-(3-fluoro-4-(3-methyl-1H-1,2,4-triazol-1-yl)phenyl)-7-(4-fluorophenyl)-$N^4$-methyl-6,7-dihydro-5H-cyclopenta[d]pyrimidine-2,4-diamine

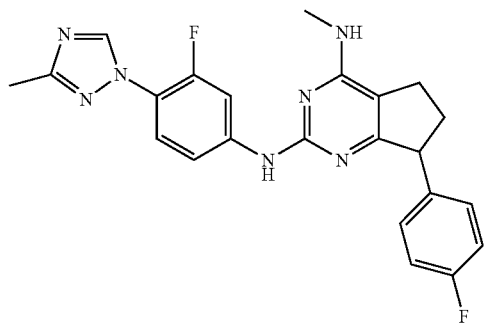 [SMILES: CNc1nc(Nc2ccc(-n3cnc(C)n3)c(F)c2)nc2c1CCC2c1ccc(F)cc1]

2-chloro-7-(4-fluorophenyl)-N-methyl-6,7-dihydro-5H-cyclopenta[d]pyrimidin-4-amine (Preparation Hh) (164 mg, 0.591 mmol) and 3-fluoro-4-(3-methyl-1H-1,2,4-triazol-1-yl)aniline (Preparation B) (113 mg, 0.591 mmol) were combined and purified as per Example 26 to give $N^2$-(3-fluoro-4-(3-methyl-1H-1,2,4-triazol-1-yl)phenyl)-7-(4-fluorophenyl)-$N^4$-methyl-6,7-dihydro-5H-cyclopenta[d]pyrimidine-2,4-diamine, TFA (104 mg, 0.190 mmol, 32.2% yield) as a white solid. LC-MS (M+H)$^+$=434.3. $^1$H NMR (500 MHz, MeOD) δ ppm 8.75 (1H, d, J=2.44 Hz), 7.94 (1H, dd, J=13.28, 2.29 Hz), 7.79 (1H, t, J=8.70 Hz), 7.48 (1H, dt, J=8.85, 1.22 Hz), 7.27-7.35 (2H, m), 7.10-7.19 (2H, m), 4.51 (1H, d, J=2.44 Hz), 3.18 (3H, s), 2.89-2.98 (1H, m), 2.74-2.87 (2H, m), 2.46 (3H, s), 2.09-2.23 (1H, m).

Example 36

N-(4-(4-chloro-1H-imidazol-1-yl)-3-methoxyphenyl)-7-(4-fluorophenyl)-4-((S)-3-fluoropyrrolidin-1-yl)-6,7-dihydro-5H-cyclopenta[d]pyrimidin-2-amine

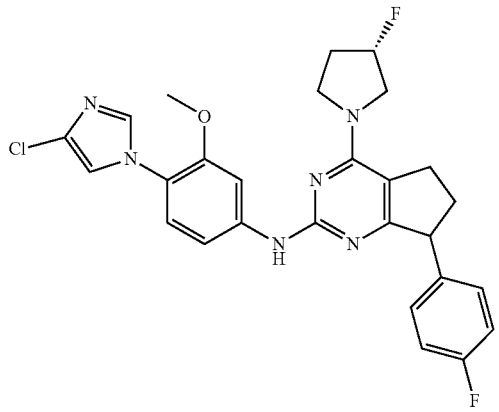 [SMILES: COc1cc(Nc2nc3c(c(N4CC[C@H](F)C4)n2)CCC3c2ccc(F)cc2)ccc1-n1cnc(Cl)c1]

Diasteriomer A

To a solution of 2-chloro-7-(4-fluorophenyl)-4-((S)-3-fluoropyrrolidin-1-yl)-6,7-dihydro-5H-cyclopenta[d]pyrimidine (Preparation Hp1)(30.5 mg, 0.091 mmol) and 4-(4-chloro-1H-imidazol-1-yl)-3-methoxyaniline (Preparation A)(26.4 mg, 0.118 mmol) in THF (272 µL) was added AcOH (272 µL). The solution was heated at 100° C. overnight.

Removed solvent and took residue up in MeOH. Purified by PREP HPLC: (50×250 mm HPLC Sunfire C18 10 µm 0 to 100% A:B over 40 min, 10 min at 100% B (A is 90:10:0.1 water:MeOH:TFA; B is 90:10:0.1 MeOH:water:TFA)). Speedvac'd appropriate fractions to afford N-(4-(4-chloro-1H-imidazol-1-yl)-3-methoxyphenyl)-7-(4-fluorophenyl)-4-((S)-3-fluoropyrrolidin-1-yl)-6,7-dihydro-5H-cyclopenta[d]pyrimidin-2-amine. LC-MS (M+H)$^+$=523.2. $^1$H NMR (500 MHz, CDCl$_3$) δ ppm 7.74 (1H, d, J=2.14 Hz), 7.49 (1H, d, J=1.53 Hz), 7.12-7.19 (2H, m), 7.05 (1H, d, J=8.24 Hz), 6.95-7.01 (4H, m), 6.84 (1H, dd, J=8.55, 2.44 Hz), 5.35 (1H, td, J=52.87, 3.17 Hz), 4.07-4.17 (2H, m), 4.04 (1H, t, J=9.61 Hz), 3.80-3.94 (2H, m), 3.58 (3H, s), 3.25 (1H, ddd, J=14.19, 9.00, 4.58 Hz), 3.05-3.14 (1H, m), 2.55 (1H, dddd, J=13.24, 8.74, 8.55, 4.58 Hz), 2.32-2.43 (1H, m), 2.03-2.19 (1H, m), 1.93-2.02 (1H, m).

Example 37

N-(4-(4-chloro-1H-imidazol-1-yl)-3-methoxyphenyl)-7-(4-fluorophenyl)-4-((S)-3-fluoropyrrolidin-1-yl)-6,7-dihydro-5H-cyclopenta[d]pyrimidin-2-amine

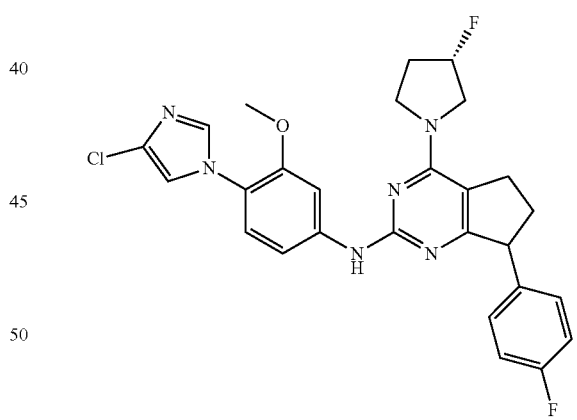

Diastereomer B

The method of Example 36 was used to combine Preparation Hp2 and 4-(4-chloro-1H-imidazol-1-yl)-3-methoxyaniline (Preparation A) to afford N-(4-(4-chloro-1H-imidazol-1-yl)-3-methoxyphenyl)-7-(4-fluorophenyl)-4-((S)-3-fluoropyrrolidin-1-yl)-6,7-dihydro-5H-cyclopenta[d]pyrimidin-2-amine. LC-MS (M+H)$^+$=523.2. $^1$H NMR (500 MHz, CDCl$_3$) δ ppm 7.76 (1H, d, J=1.83 Hz), 7.48 (1H, s), 7.16 (2H, dd, J=8.24, 5.49 Hz), 6.97-7.06 (4H, m), 6.92 (1H, s), 6.80 (1H, dd, J=8.39, 1.98 Hz), 5.27-5.42 (1H, m), 4.00-4.17 (3H, m), 3.80-3.94 (2H, m), 3.53 (3H, s), 3.19-3.26 (1H, m), 3.08-3.17 (1H, m), 2.52-2.61 (1H, m), 2.32-2.43 (1H, m), 2.02-2.18 (1H, m), 1.94 (1H, dq, J=12.97, 8.60 Hz).

Example 38

N-(4-(4-chloro-1H-imidazol-1-yl)-3-methoxyphenyl)-7-(4-fluorophenyl)-4-((R)-3-fluoropyrrolidin-1-yl)-6,7-dihydro-5H-cyclopenta[d]pyrimidin-2-amine

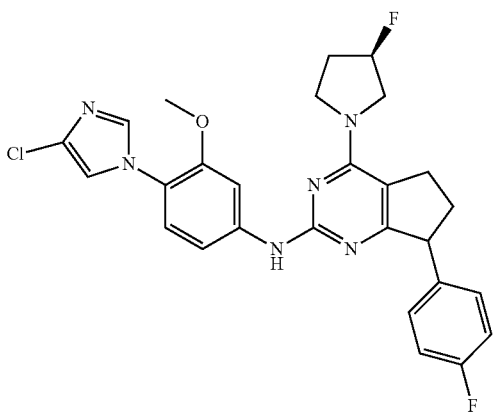 [SMILES: COc1cc(Nc2nc3c(c(N4CC[C@@H](F)C4)n2)CCC3c2ccc(F)cc2)ccc1-n1cnc(Cl)c1]

Diasteriomeric Mixture

The method of Example 36 was used to combine Preparation Hq and 4-(4-chloro-1H-imidazol-1-yl)-3-methoxyaniline (Preparation A) to afford N-(4-(4-chloro-1H-imidazol-1-yl)-3-methoxyphenyl)-7-(4-fluorophenyl)-4-((R)-3-fluoropyrrolidin-1-yl)-6,7-dihydro-5H-cyclopenta[d]pyrimidin-2-amine as a mixture of diasteriomers. LC-MS (M+H)⁺=523.2. ¹H NMR (500 MHz, MeOD) δ ppm 7.87 (1H, s), 7.46-7.57 (1H, m), 7.36-7.43 (2H, m), 7.30-7.36 (2H, m), 7.24-7.30 (1H, m), 7.11-7.18 (2H, m), 5.34-5.57 (1H, m), 4.33-4.52 (2H, m), 4.07-4.26 (2H, m), 3.93-4.01 (1H, m), 3.90 (3H, s), 3.39-3.50 (1H, m), 3.23-3.31 (1H, m), 2.67-2.80 (1H, m), 2.21-2.54 (2H, m), 2.07-2.18 (1H, m).

Examples 38A and 38B

N-(4-(4-chloro-1H-imidazol-1-yl)-3-methoxyphenyl)-7-(4-fluorophenyl)-4-((R)-3-fluoropyrrolidin-1-yl)-6,7-dihydro-5H-cyclopenta[d]pyrimidin-2-amine

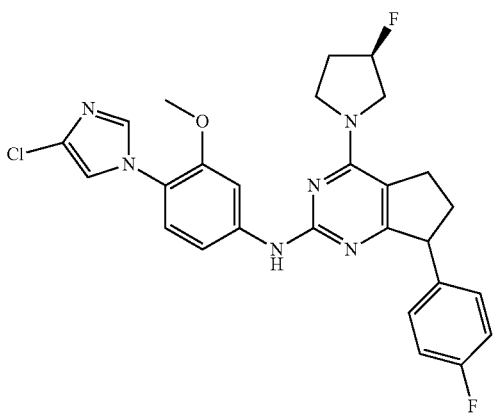 [SMILES: COc1cc(Nc2nc3c(c(N4CC[C@@H](F)C4)n2)CCC3c2ccc(F)cc2)ccc1-n1cnc(Cl)c1]

Individual Diasteriomers

The method of Example 36 was used to combine Preparation Hq and 4-(4-chloro-1H-imidazol-1-yl)-3-methoxyaniline (Preparation A) to afford a mixture of two diasteriomers. After preparative chiral chromatography (25% MeOH, 0.1% DEA; OD-H chiral 30×250 nm column), the two diasteriomers were isolated.

38A: LC-MS (M+H)⁺=523.2. ¹H NMR (500 MHz, MeOD) δ ppm 7.84 (1H, d, J=2.14 Hz), 7.68 (1H, d, J=1.53 Hz), 7.19-7.24 (3H, m), 7.16 (1H, d, J=8.55 Hz), 6.99-7.09 (3H, m), 5.29-5.45 (1H, m), 4.05-4.17 (3H, m), 3.80-3.99 (2H, m), 3.64 (3H, s), 3.13 (1H, dt, J=14.65, 7.32 Hz), 2.51-2.61 (1H, m, J=13.12, 8.70, 8.70, 4.58 Hz), 2.28-2.38 (1H, m), 2.09-2.27 (1H, m), 1.98 (1H, dddd, J=13.20, 8.62, 6.87, 6.71 Hz).

38B: LC-MS (M+H)⁺=523.2. ¹H NMR (500 MHz, MeOD) δ ppm 7.86 (1H, d, J=2.14 Hz), 7.67 (1H, s), 7.18-7.24 (3H, m), 7.15 (1H, d, J=8.55 Hz), 7.00-7.07 (3H, m), 5.29-5.45 (1H, m), 4.03-4.18 (3H, m), 3.80-4.00 (2H, m), 3.60 (3H, s), 3.23-3.31 (1H, m), 3.13-3.21 (1H, m), 2.52-2.61 (1H, m), 2.28-2.39 (1H, m), 2.07-2.26 (1H, m), 1.88-1.99 (1H, m).

Example 39

N-(4-(4-chloro-1H-imidazol-1-yl)-3-methoxyphenyl)-4-(4,4-difluoropiperidin-1-yl)-7-(4-fluorophenyl)-6,7-dihydro-5H-cyclopenta[d]pyrimidin-2-amine

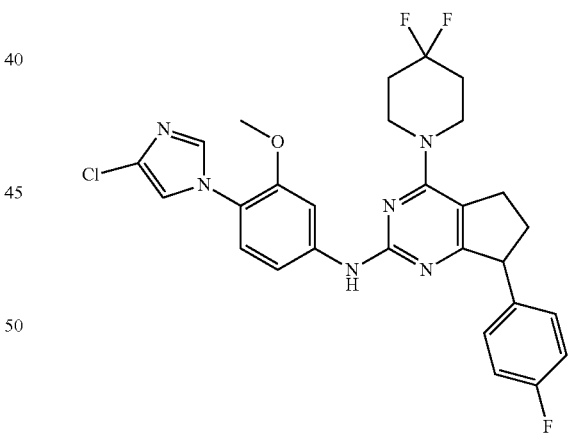

The method of Example 36 was used to combine Preparation Hr and 4-(4-chloro-1H-imidazol-1-yl)-3-methoxyaniline (Preparation A) to afford N-(4-(4-chloro-1H-imidazol-1-yl)-3-methoxyphenyl)-4-(4,4-difluoropiperidin-1-yl)-7-(4-fluorophenyl)-6,7-dihydro-5H-cyclopenta[d]pyrimidin-2-amine (Example 39). LC-MS (M+H)⁺=555.0. ¹H NMR (500 MHz, MeOD) δ ppm 7.68 (1H, d, J=1.83 Hz), 7.55-7.59 (2H, m), 7.18 (2H, dd, J=8.55, 5.49 Hz), 7.07-7.13 (2H, m), 6.95-7.03 (3H, m), 4.16 (1H, t, J=8.39 Hz), 3.90 (4H, t, J=5.34 Hz), 3.57 (3H, s), 2.97-3.13 (2H, m), 2.56-2.66 (1H, m, J=12.78, 8.49, 8.49, 3.81 Hz), 1.95-2.14 (5H, m).

The racemic mixture was separated by chiral chromatography to afford the enantiomers Example 39A and 39B, which had identical spectral data.

Example 40

N-(4-(4-chloro-1H-imidazol-1-yl)-3-methoxyphenyl)-4-(4-fluoro-5,6-dihydropyridin-1(2H)-yl)-7-(4-fluorophenyl)-6,7-dihydro-5H-cyclopenta[d]pyrimidin-2-amine

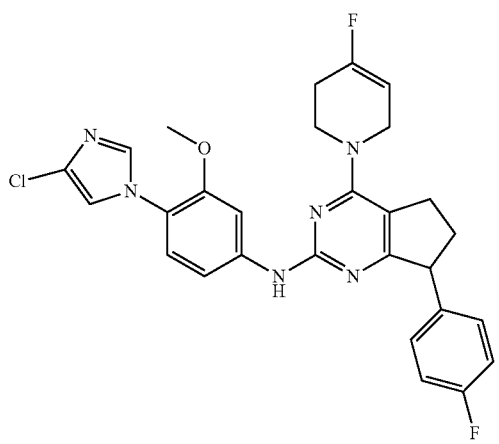 [SMILES: COc1cc(Nc2nc3c(c(N4CC=C(F)CC4)n2)CCC3c2ccc(F)cc2)ccc1-n1cnc(Cl)c1]

The method of Example 36 was used to combine Preparation Hs and 4-(4-chloro-1H-imidazol-1-yl)-3-methoxyaniline (Preparation A) to afford N-(4-(4-chloro-1H-imidazol-1-yl)-3-methoxyphenyl)-4-(4-fluoro-5,6-dihydropyridin-1(2H)-yl)-7-(4-fluorophenyl)-6,7-dihydro-5H-cyclopenta[d]pyrimidin-2-amine (Example 40). LC-MS (M+H)$^+$=535.0. $^1$H NMR (500 MHz, CDCl$_3$) δ ppm 7.72 (1H, d, J=1.83 Hz), 7.49 (1H, d, J=1.53 Hz), 7.13-7.19 (2H, m), 7.05 (1H, d, J=8.55 Hz), 6.97-7.02 (3H, m), 6.95 (1H, s), 6.77 (1H, dd, J=8.55, 2.14 Hz), 5.31 (1H, dt, J=14.80, 2.80 Hz), 4.18-4.33 (2H, m), 4.15 (1H, t, J=8.55 Hz), 3.99-4.06 (1H, m), 3.80-3.88 (1H, m), 3.51 (3H, s), 2.98-3.12 (2H, m), 2.58 (1H, dddd, J=12.63, 8.55, 8.43, 3.66 Hz), 2.37-2.53 (2H, m), 1.99 (1H, dq, J=12.86, 8.33 Hz).

The racemic mixture was separated by chiral chromatography to afford the enantiomers Example 40A and 40B, which had identical spectral data.

Example 41

N-(4-(4-chloro-1H-imidazol-1-yl)-3-methoxyphenyl)-7-(4-fluorophenyl)-4-(3-(trifluoromethyl)pyrrolidin-1-yl)-6,7-dihydro-5H-cyclopenta[d]pyrimidin-2-amine

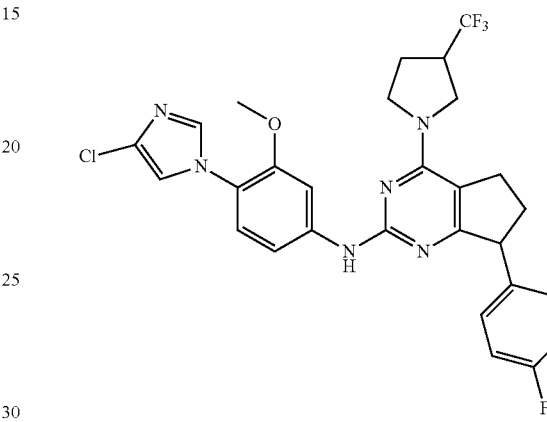

The method of Example 36 was used to combine Preparation Ht and 4-(4-chloro-1H-imidazol-1-yl)-3-methoxyaniline (Preparation A) to afford N-(4-(4-chloro-1H-imidazol-1-yl)-3-methoxyphenyl)-7-(4-fluorophenyl)-4-(3-(trifluoromethyl)pyrrolidin-1-yl)-6,7-dihydro-5H-cyclopenta[d]pyrimidin-2-amine (Example 41).

The mixture of a pair of racemic diasteriomers were separated by chiral chromatography followed by reverse-phase chromatography to afford the individual enantiomers Examples 41A, 41B, 41C, and 41D.

41A: LC-MS (M+H)$^+$=573.1. $^1$H NMR (500 MHz, CDCl$_3$) δ ppm 7.84 (1H, d, J=1.53 Hz), 7.49 (1H, s), 7.15 (2H, dd, J=8.39, 5.34 Hz), 7.04 (1H, d, J=8.24 Hz), 6.95-7.02 (4H, m), 6.72 (1H, dd, J=8.39, 1.98 Hz), 4.11 (1H, t, J=8.39 Hz), 3.94-4.08 (2H, m), 3.78-3.91 (2H, m), 3.56 (3H, s), 3.18-3.27 (1H, m), 2.97-3.14 (2H, m), 2.50-2.62 (1H, m, J=12.86, 8.60, 8.60, 4.12 Hz), 2.17-2.34 (2H, m), 1.91-2.02 (1H, m).

41B: LC-MS (M+H)$^+$=573.1. $^1$H NMR (500 MHz, CDCl$_3$) δ ppm 7.84 (1H, br. s.), 7.48 (1H, d, J=1.53 Hz), 7.11-7.22 (2H, m), 6.95-7.09 (5H, m), 6.69-6.78 (1H, m), 4.12 (1H, t, J=8.55 Hz), 3.95-4.08 (2H, m), 3.77-3.92 (2H, m), 3.55 (3H, s), 3.21 (1H, ddd, J=14.11, 8.93, 3.51 Hz), 2.98-3.16 (2H, m), 2.51-2.65 (1H, m), 2.16-2.35 (2H, m), 1.90-2.04 (1H, m).

41C: LC-MS (M+H)$^+$=573.1. $^1$H NMR (500 MHz, CDCl$_3$) δ ppm 7.84 (1H, br. s.), 7.48 (1H, d, J=1.53 Hz), 7.11-7.22 (2H, m), 6.95-7.09 (5H, m), 6.69-6.78 (1H, m), 4.12 (1H, t, J=8.55 Hz), 3.95-4.08 (2H, m), 3.77-3.92 (2H, m), 3.55 (3H, s), 3.21 (1H, ddd, J=14.11, 8.93, 3.51 Hz), 2.98-3.16 (2H, m), 2.51-2.65 (1H, m), 2.16-2.35 (2H, m), 1.90-2.04 (1H, m).

41D: LC-MS (M+H)$^+$=573.1. $^1$H NMR (500 MHz, CDCl$_3$) δ ppm 7.84 (1H, d, J=1.53 Hz), 7.49 (1H, s), 7.15 (2H, dd, J=8.39, 5.34 Hz), 7.04 (1H, d, J=8.24 Hz), 6.95-7.02 (4H, m), 6.72 (1H, dd, J=8.39, 1.98 Hz), 4.11 (1H, t, J=8.39 Hz), 3.94-4.08 (2H, m), 3.78-3.91 (2H, m), 3.56 (3H, s), 3.18-3.27

(1H, m), 2.97-3.14 (2H, m), 2.50-2.62 (1H, m, J=12.86, 8.60, 8.60, 4.12 Hz), 2.17-2.34 (2H, m), 1.91-2.02 (1H, m).

Example 42

N2-(4-(4-chloro-1H-imidazol-1-yl)-3-methoxyphenyl)-N4-(3-ethoxypropyl)-7-(4-fluorophenyl)-6,7-dihydro-5H-cyclopenta[d]pyrimidine-2,4-diamine

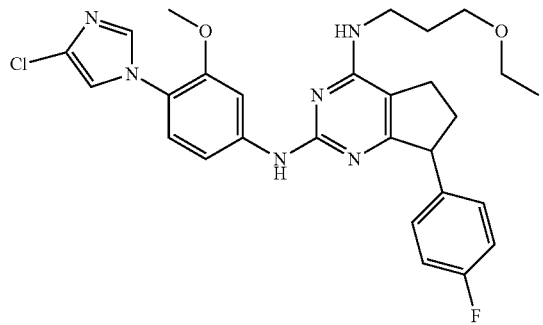 [SMILES: CCOCCCNc1nc(Nc2ccc(-n3cnc(Cl)c3)c(OC)c2)nc2c1CCC2c1ccc(F)cc1]

The method of Example 36 was used to combine Preparation Hu and 4-(4-chloro-1H-imidazol-1-yl)-3-methoxyaniline (Preparation A) to afford N2-(4-(4-chloro-1H-imidazol-1-yl)-3-methoxyphenyl)-N4-(3-ethoxypropyl)-7-(4-fluorophenyl)-6,7-dihydro-5H-cyclopenta[d]pyrimidine-2,4-diamine (Example 42). LC-MS (M+H)$^+$=537.2. $^1$H NMR (500 MHz, CDCl$_3$) δ ppm 7.91 (1H, d, J=2.14 Hz), 7.48 (1H, d, J=1.53 Hz), 7.12-7.19 (2H, m), 7.03 (1H, d, J=8.55 Hz), 6.94-7.01 (4H, m), 6.74 (1H, dd, J=8.55, 2.14 Hz), 5.45 (1H, t, J=4.73 Hz), 4.14-4.21 (1H, m), 3.61-3.71 (4H, m), 3.46-3.57 (5H, m), 2.63 (2H, dd, J=8.85, 6.41 Hz), 1.96-2.05 (1H, m), 1.93 (2H, quin, J=5.72 Hz), 1.25 (3H, t, J=7.02 Hz).

Example 43

3-(2-(4-(4-chloro-1H-imidazol-1-yl)-3-methoxyphenylamino)-7-(4-fluorophenyl)-6,7-dihydro-5H-cyclopenta[d]pyrimidin-4-ylamino)propan-1-ol

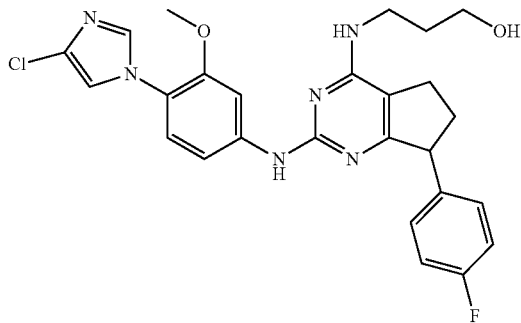 [SMILES: COc1cc(Nc2nc(NCCCO)c3c(n2)C(c2ccc(F)cc2)CC3)ccc1-n1cnc(Cl)c1]

The method of Example 36 was used to combine Preparation Hy and 4-(4-chloro-1H-imidazol-1-yl)-3-methoxyaniline (Preparation A) to afford 3-(2-(4-(4-chloro-1H-imidazol-1-yl)-3-methoxyphenylamino)-7-(4-fluorophenyl)-6,7-dihydro-5H-cyclopenta[d]pyrimidin-4-ylamino)propan-1-ol (Example 43). LC-MS (M+H)$^+$=509.3. $^1$H NMR (500 MHz, MeOD) δ ppm 7.87 (1H, d, J=2.14 Hz), 7.68 (1H, d, J=1.53 Hz), 7.19-7.26 (3H, m), 7.16 (1H, d, J=8.55 Hz), 7.01-7.09 (3H, m), 4.19 (1H, t, J=8.09 Hz), 3.64-3.72 (4H, m), 3.61 (3H, s), 2.77-2.86 (1H, m), 2.60-2.74 (2H, m), 1.96-2.06 (1H, m), 1.90 (2H, qd, J=6.46, 6.26 Hz).

The racemic mixture was separated by chiral chromatography to afford the enantiomers Example 43A and 43B, which had identical spectral data.

Example 44

7-(4-fluorophenyl)-N2-(3-methoxy-4-(3-methyl-1H-1,2,4-triazol-1-yl)phenyl)-N4-methyl-6,7-dihydro-5H-cyclopenta[d]pyrimidine-2,4-diamine

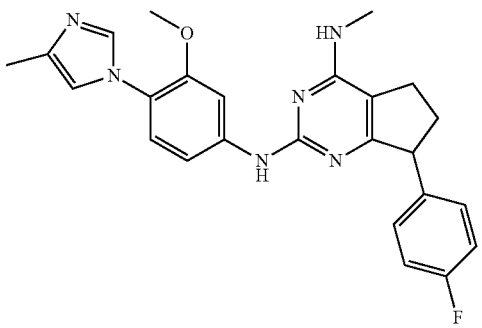 [SMILES: CNc1nc(Nc2ccc(-n3cnc(C)c3)c(OC)c2)nc2c1CCC2c1ccc(F)cc1]

To a solution of 2-chloro-7-(4-fluorophenyl)-N-methyl-6,7-dihydro-5H-cyclopenta[d]pyrimidin-4-amine (Preparation Hh) (141.2 mg, 0.508 mmol) and 3-methoxy-4-(3-methyl-1H-1,2,4-triazol-1-yl)aniline (Preparation D) (208 mg, 1.017 mmol) in N-Methyl-2-pyrrolidinone (4067 µL) was added H$_2$SO$_4$ (43.4 µL, 0.813 mmol). The solution was heated to 100° C. When the reaction was complete, water and NaHCO$_3$ were added. After extraction into CH$_2$Cl$_2$, the organic extracts were dried over MgSO$_4$, filtered, and concentrated in vacuo. Applied the residue to SG and eluted with a EtOAc/Hex gradient, which yielded 7-(4-fluorophenyl)-N2-(3-methoxy-4-(3-methyl-1H-1,2,4-triazol-1-yl)phenyl)-N4-methyl-6,7-dihydro-5H-cyclopenta[d]pyrimidine-2,4-diamine (Example 44).

LC-MS (M+H)$^+$=446.1. $^1$H NMR (500 MHz, CDCl$_3$) δ ppm 9.43 (1H, br. s.), 8.47 (1H, s), 7.77 (1H, br. s.), 7.54 (1H, d, J=8.85 Hz), 7.14-7.20 (2H, m), 6.99 (2H, t, J=8.55 Hz), 4.88 (1H, br. s.), 4.24-4.31 (1H, m), 3.71 (3H, s), 3.15 (3H, d, J=4.90 Hz), 2.73-2.82 (1H, m), 2.63-2.72 (2H, m), 2.46 (3H, s), 2.06-2.16 (1H, m).

The racemic material above was separated by SFC chiral chromatography to obtain the individual enantiomers (Examples 44A and 44B). SFC Method: Chiralpak OJ-H (30× 150 mm), 30% methanol (0.1% diethylamine) in CO$_2$, 100 bar, flow rate 50 mL/min for 12 min, absorbance 268 nm, injection 2.0 mL of 10 mg/mL solution in methanol, t$_R$ (peak A)=4.7 min, t$_R$ (peak B) 9.6 min. The absolute stereochemistry of individual enantiomers (Examples 44A and 44B) was not determined 44A: LC-MS (M+H)$^+$=446.2. LC R$_t$ 13.03 min (Waters Sunfire 4.6×150 mm 10 to 100% B in A over 15 min, 1.5 mL/min. (A is 90:10:0.1 water:MeOH:TFA; B is 90:10:0.1 MeOH:water:TFA)). $^1$H NMR (500 MHz, DMSO-d6) δ ppm 9.22 (1H, s), 8.58 (1H, s), 8.18 (1H, s), 7.30 (1H, d, J=8.85 Hz), 7.22 (2H, t, J=6.26 Hz), 7.08-7.16 (3H, m), 6.93-6.99 (1H, m), 4.17 (1H, t, J=8.09 Hz), 3.63 (3H, s), 2.97 (3H, d, J=4.27 Hz), 2.72-2.81 (1H, m), 2.53-2.66 (2H, m), 2.31 (3H, s), 1.85-1.95 (1H, m). 13C NMR (126 MHz, DMSO-d6) δ ppm 170.7, 160.7 (d, J=241.3 Hz), 159.7, 159.6, 159.2, 151.4, 145.0, 142.9, 140.4 (d, J=2.7 Hz), 129.8 (d, J=7.8 Hz, 2C), 124.6, 117.9, 114.9 (d, J=20.9 Hz, 2C), 109.6, 108.1, 101.5, 55.2, 50.4, 32.7, 27.4, 25.4, 13.5. [α]$_D$ −69.13° (c 2.67, CHCl$_3$).

Example 45

N2-(4-(4-chloro-1H-imidazol-1-yl)-3-methoxyphenyl)-N4-(1-cyclopropyl-2-methoxyethyl)-7-(4-fluorophenyl)-6,7-dihydro-5H-cyclopenta[d]pyrimidine-2,4-diamine

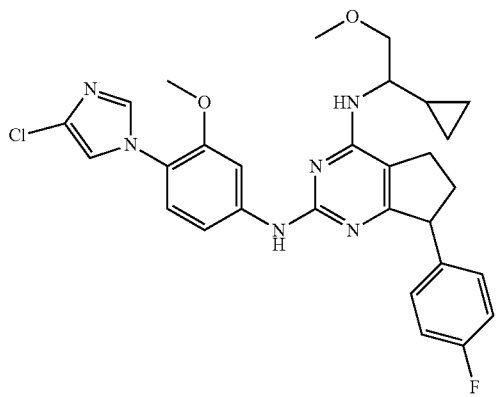 [SMILES: COCC(Nc1nc(Nc2ccc(-n3cnc(Cl)c3)c(OC)c2)nc2c1CCC2c1ccc(F)cc1)C1CC1]

The method of Example 7 was used to combine Preparation Hw and 4-(4-chloro-1H-imidazol-1-yl)-3-methoxyaniline (Preparation A) to afford N2-(4-(4-chloro-1H-imidazol-1-yl)-3-methoxyphenyl)-N4-(1-cyclopropyl-2-methoxyethyl)-7-(4-fluorophenyl)-6,7-dihydro-5H-cyclopenta[d]pyrimidine-2,4-diamine (Example 45). The mixture of a pair of racemic diasteriomers were separated by chiral chromatography followed by reverse-phase chromatography to afford the individual enantiomers Examples 45A, 45B, 45C, and 45D.

45A: LC-MS (M+H)$^+$=549.3. $^1$H NMR (500 MHz, CDCl$_3$) δ ppm 10.75 (1H, br. s.), 7.40 (1H, d, J=8.24 Hz), 7.22-7.29 (3H, m), 7.15-7.21 (3H, m), 6.99-7.08 (2H, m), 5.97 (1H, d, J=8.24 Hz), 4.42-4.50 (1H, m), 3.84 (3H, s), 3.78 (1H, t, J=8.09 Hz), 3.63 (2H, br. s.), 3.43 (3H, s), 2.86-2.97 (1H, m), 2.82 (2H, t, J=8.55 Hz), 2.21-2.32 (1H, m), 1.15-1.27 (1H, m), 0.62-0.70 (1H, m), 0.53-0.62 (1H, m), 0.39 (1H, ddd, J=9.46, 5.19, 4.88 Hz), 0.26-0.33 (1H, m)

45B: LC-MS (M+H)$^+$=549.3. $^1$H NMR (500 MHz, CDCl$_3$) δ ppm 10.58 (1H, br. s.), 7.40 (1H, d, J=8.85 Hz), 7.22-7.29 (3H, m), 7.14-7.20 (3H, m), 7.04 (2H, t, J=8.39 Hz), 6.02 (1H, d, J=8.24 Hz), 4.45 (1H, d, J=3.66 Hz), 3.84 (3H, s), 3.71-3.79 (1H, m), 3.63 (2H, d, J=3.05 Hz), 3.42 (3H, s), 2.91 (1H, d, J=9.46 Hz), 2.79 (2H, dd, J=8.70, 5.34 Hz), 2.21-2.31 (1H, m), 1.19 (1H, dt, J=8.55, 4.27 Hz), 0.62-0.70 (1H, m), 0.54-0.62 (1H, m), 0.39 (1H, dq, J=9.54, 4.86 Hz), 0.24-0.33 (1H, m).

45C: LC-MS (M+H)$^+$=549.3. $^1$H NMR (500 MHz, CDCl$_3$) δ ppm 10.75 (1H, br. s.), 7.40 (1H, d, J=8.24 Hz), 7.22-7.29 (3H, m), 7.15-7.21 (3H, m), 6.99-7.08 (2H, m), 5.97 (1H, d, J=8.24 Hz), 4.42-4.50 (1H, m), 3.84 (3H, s), 3.78 (1H, t, J=8.09 Hz), 3.63 (2H, br. s.), 3.43 (3H, s), 2.86-2.97 (1H, m), 2.82 (2H, t, J=8.55 Hz), 2.21-2.32 (1H, m), 1.15-1.27 (1H, m), 0.62-0.70 (1H, m), 0.53-0.62 (1H, m), 0.39 (1H, ddd, J=9.46, 5.19, 4.88 Hz), 0.26-0.33 (1H, m).

45D: LC-MS (M+H)$^+$=549.3. $^1$H NMR (500 MHz, CDCl$_3$) δ ppm 10.58 (1H, br. s.), 7.40 (1H, d, J=8.85 Hz), 7.22-7.29 (3H, m), 7.14-7.20 (3H, m), 7.04 (2H, t, J=8.39 Hz), 6.02 (1H, d, J=8.24 Hz), 4.45 (1H, d, J=3.66 Hz), 3.84 (3H, s), 3.71-3.79 (1H, m), 3.63 (2H, d, J=3.05 Hz), 3.42 (3H, s), 2.91 (1H, d, J=9.46 Hz), 2.79 (2H, dd, J=8.70, 5.34 Hz), 2.21-2.31 (1H, m), 1.19 (1H, dt, J=8.55, 4.27 Hz), 0.62-0.70 (1H, m), 0.54-0.62 (1H, m), 0.39 (1H, dq, J=9.54, 4.86 Hz), 0.24-0.33 (1H, m).

Example 46

$N^2$-(4-(4-Chloro-1H-imidazol-1-yl)-3-methoxyphenyl)-7-(4-fluorophenyl)-$N^4$,$N^4$-dimethyl-6,7-dihydro-5H-cyclopenta[d]pyrimidine-2,4-diamine

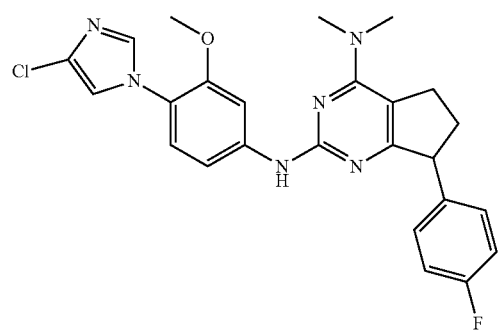

2-Chloro-7-(4-fluorophenyl)-N,N-dimethyl-6,7-dihydro-5H-cyclopenta[d]pyrimidin-4-amine (268 mg, 0.919 mmol) was added to a solution of 4-(4-chloro-1H-imidazol-1-yl)-3-methoxyaniline (205 mg, 0.919 mmol) in THF (1 mL) and acetic acid (1.000 mL). The reaction mixture was stirred overnight at 75° C. The crude reaction mixture was purified by preparative HPLC. The appropriate fractions were evaporated to afford $N^2$-(4-(4-chloro-1H-imidazol-1-yl)-3-methoxyphenyl)-7-(4-fluorophenyl)-$N^4$,$N^4$-dimethyl-6,7-dihydro-5H-cyclopenta[d]pyrimidine-2,4-diamine, TFA salt (60.7 mg, 0.095 mmol, 10.36% yield). LC-MS (M+H)$^+$=479.4. $^1$H NMR (500 MHz, CDCl$_3$) δ ppm 11.64-11.83 (1H, m), 7.62 (1H, d, J=1.5 Hz), 7.39 (2H, d, J=2.1 Hz), 7.22 (1H, d, J=5.2 Hz), 7.15 (1H, d, J=8.5 Hz), 6.96-7.07 (3H, m), 5.29 (1H, s), 4.29-4.38 (1H, m), 3.81 (3H, s), 3.50-3.57 (1H, m), 3.43-3.49 (1H, m), 3.31-3.39 (3H, m), 3.16-3.26 (2H, m), 3.09-3.14 (1H, m), 2.58-2.72 (1H, m), 2.52-2.58 (1H, m), 2.13-2.25 (1H, m).

Examples 46A & 46B (S)—$N^2$-(4-(4-Chloro-1H-imidazol-1-yl)-3-methoxyphenyl)-7-(4-fluorophenyl)-$N^4$,$N^4$-dimethyl-6,7-dihydro-5H-cyclopenta[d]pyrimidine-2,4-diamine
and (R)—$N^2$-(4-(4-Chloro-1H-imidazol-1-yl)-3-methoxyphenyl)-7-(4-fluorophenyl)-$N^4$,$N^4$-dimethyl-6,7-dihydro-5H-cyclopenta[d]pyrimidine-2,4-diamine

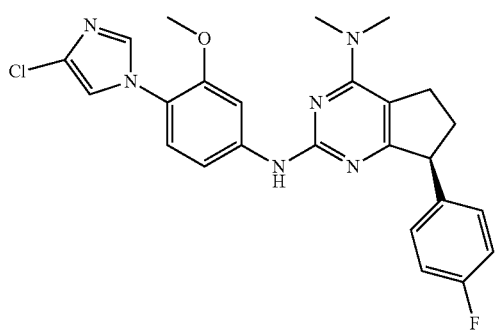

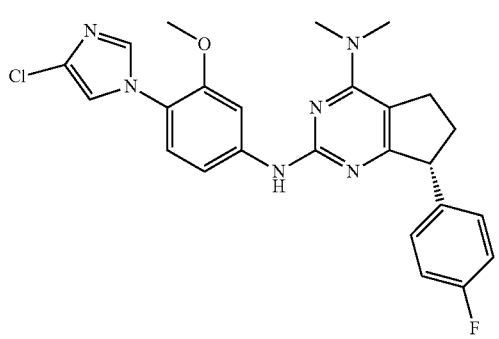 [SMILES: COc1cc(Nc2nc3c(c(N(C)C)n2)CCC3c2ccc(F)cc2)ccc1-n1cnc(Cl)c1]

A racemic mixture of $N^2$-(4-(4-chloro-1H-imidazol-1-yl)-3-methoxyphenyl)-7-(4-fluorophenyl)-$N^4$,$N^4$-dimethyl-6,7-dihydro-5H-cyclopenta[d]pyrimidine-2,4-diamine (Example 46) was purified using chiral SFC to afford peak A (Example 46A) and peak B (Example 46B). SFC Method: Chiralpak OJ-H (4.6×250 mm, 5 μM), 35% methanol (0.1% diethylamine) in $CO_2$, 35° C., flow rate 2.0 mL/min for 14 min, absorbance 268 nm, injection 5 μL of 2 mg/mL solution in methanol (multiple stacked injections), $t_R$ (peak A)=4.3 min, $t_R$ (peak B) 10.8 min. The absolute stereochemistry of individual enantiomers (Examples 46A and 46B) was not determined LC-MS and $^1$H NMR analytical data for the separated enantiomers was identical to the racemate (Example 46).

Example 47

$N^2$-(4-(4-Chloro-1H-imidazol-1-yl)-3-methoxyphenyl)-7-(4-fluorophenyl)-$N^4$-trideuteromethyl-6,7-dihydro-5H-cyclopenta[d]pyrimidine-2,4-diamine

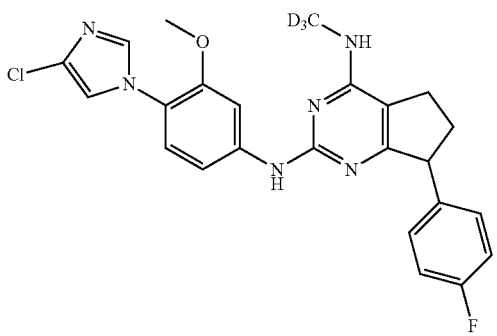 [SMILES: [2H]C([2H])([2H])Nc1nc(Nc2ccc(-n3cnc(Cl)c3)c(OC)c2)nc2c1CCC2c1ccc(F)cc1]

A solution of 2-Chloro-7-(4-fluorophenyl)-N-trideuteromethyl-6,7-dihydro-5H-cyclopenta[d]pyrimidin-4-amine (47.5 mg, 0.169 mmol) and 4-(4-chloro-1H-imidazol-1-yl)-3-methoxyaniline (37.8 mg, 0.169 mmol) in THF (1 mL) and acetic acid (1 mL) was heated at 85° C. overnight. The product was purified by a reverse-phase preparative HPLC method to give $N^2$-(4-(4-chloro-1H-imidazol-1-yl)-3-methoxyphenyl)-7-(4-fluorophenyl)-$N^4$-trideuteromethyl-6,7-dihydro-5H-cyclopenta[d]pyrimidine-2,4-diamine, TFA salt (33.3 mg, 0.057 mmol, 33.8% yield) as brown oil. LC-MS (M+H)$^+$ =467.9. $^1$H NMR (500 MHz, CDCl$_3$) δ ppm 11.21 (1H, s), 8.35-9.96 (1H, m), 8.20 (1H, s), 7.51 (1H, s), 7.43 (1H, d, J=8.5 Hz), 7.25 (1H, s), 7.22 (1H, d, J=8.9 Hz), 7.14-7.20

(2H, m), 7.01 (1H, t, J=8.5 Hz), 5.98 (1H, s), 4.43 (1H, d, J=4.6 Hz), 3.85 (3H, s), 2.88 (1H, d, J=9.5 Hz), 2.69-2.83 (2H, m), 2.20-2.32 (1H, m).

Example 48

N2-(4-(4-chloro-1H-imidazol-1-yl)-3-methoxyphenyl)-7-(4-fluorophenyl)-N4-((R)-1-methoxybutan-2-yl)-6,7-dihydro-5H-cyclopenta[d]pyrimidine-2,4-diamine, 2 TFA

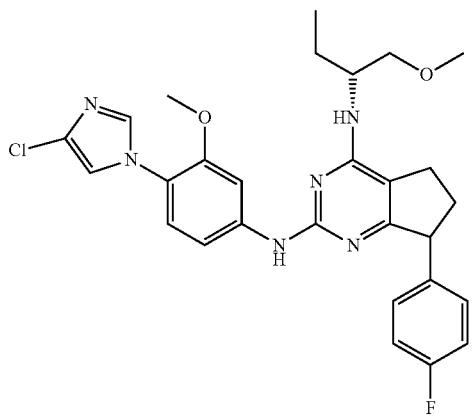

Diasteriomeric Mixture 2-chloro-7-(4-fluorophenyl)-N—((R)-1-methoxybutan-2-yl)-6,7-dihydro-5H-cyclopenta[d]pyrimidin-4-amine (Preparation Hx) was reacted as described in Example 112 with 4-(4-chloro-1H-imidazol-1-yl)-3-methoxyaniline (Preparation A) to give N2-(4-(4-chloro-1H-imidazol-1-yl)-3-methoxyphenyl)-7-(4-fluorophenyl)-N4-((R)-1-methoxybutan-2-yl)-6,7-dihydro-5H-cyclopenta[d]pyrimidine-2,4-diamine, 2 TFA as a mixture of two diasteriomers (Example 48). LC-MS (M+H)$^+$=537.5. $^1$H NMR (500 MHz, CDCl$_3$) δ ppm 11.66 (br. s., 1H) 7.99 (s, 1H) 7.51 (d, J=8.85 Hz, 1H) 7.32 (dd, J=8.85, 1.83 Hz, 1H) 7.18-7.30 (m, 4H) 7.04 (td, J=8.62, 1.68 Hz, 2H) 5.83 (t, J=9.61 Hz, 1H) 4.43-4.51 (m, 1H) 4.28-4.39 (m, 1H) 3.87 (s, 3H) 3.51-3.64 (m, 2H) 3.38-3.49 (m, 3H) 2.87-3.00 (m, 1H) 2.75-2.85 (m, 2H) 2.24-2.35 (m, 1H) 1.69-1.87 (m, 2H) 0.97-1.06 (m, 3H).

The mixture of two diasteriomers was separated by chiral chromatography to afford two diasteriomers Example 48A and 48B as free amines.

Example 48A: LC-MS (M+H)$^+$=537.4. $^1$H NMR (500 MHz, MeOD) δ ppm 7.86 (d, J=2.14 Hz, 1H) 7.66 (d, J=1.53 Hz, 1H) 7.16-7.25 (m, 3H) 7.10-7.16 (m, 1H) 6.99-7.07 (m, 3H) 4.45-4.53 (m, 1H) 4.17 (t, J=8.24 Hz, 1H) 3.61 (s, 3H) 3.56 (dd, J=9.46, 5.80 Hz, 1H) 3.44-3.51 (m, 1H) 3.37 (d, J=7.02 Hz, 3H) 2.76-2.86 (m, 1H) 2.59-2.75 (m, 2H) 1.94-2.04 (m, 1H) 1.73-1.85 (m, 1H) 1.54-1.66 (m, 1H) 0.99 (t, J=7.48 Hz, 3H).

Example 48B: LC-MS (M+H)$^+$=537.4. $^1$H NMR (500 MHz, MeOD) δ ppm 7.86 (d, J=2.14 Hz, 1H) 7.67 (d, J=1.53 Hz, 1H) 7.18-7.26 (m, 3H) 7.11-7.16 (m, 1H) 6.97-7.08 (m, 3H) 4.44-4.53 (m, 1H) 4.17 (t, J=8.09 Hz, 1H) 3.61 (s, 3H) 3.55 (dd, J=9.46, 5.49 Hz, 1H) 3.46 (dd, J=9.61, 5.65 Hz, 1H) 3.35-3.41 (m, 3H) 2.77-2.87 (m, 1H) 2.67-2.76 (m, 1H) 2.64 (ddd, J=12.44, 8.62, 3.66 Hz, 1H) 1.93-2.07 (m, 1H) 1.80 (ddd, J=13.50, 7.71, 5.34 Hz, 1H) 1.56-1.68 (m, 1H) 1.01 (t, J=7.48 Hz, 3H).

Example 49

N2-(4-(4-chloro-1H-imidazol-1-yl)-3-methoxyphenyl)-N4-((R)-1-cyclopropylethyl)-7-(4-fluorophenyl)-6,7-dihydro-5H-cyclopenta[d]pyrimidine-2,4-diamine, 2 TFA

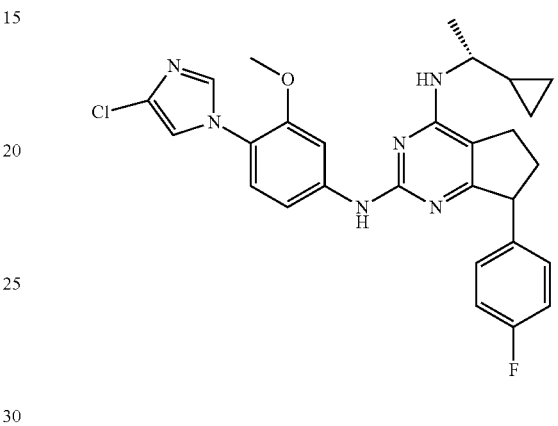

Diasteriomeric Mixture 2-chloro-N—((R)-1-cyclopropylethyl)-7-(4-fluorophenyl)-6,7-dihydro-5H-cyclopenta[d]pyrimidin-4-amine (Preparation Hy) was reacted as described in Example 112 with 4-(4-chloro-1H-imidazol-1-yl)-3-methoxyaniline (Preparation A) to give N2-(4-(4-chloro-1H-imidazol-1-yl)-3-methoxyphenyl)-N4-((R)-1-cyclopropylethyl)-7-(4-fluorophenyl)-6,7-dihydro-5H-cyclopenta[d]pyrimidine-2,4-diamine, 2 TFA as a mixture of two diasteriomers (Example 49). LC-MS (M+H)$^+$=519.5. $^1$H $^1$H NMR (500 MHz, CDCl$_3$) δ ppm 11.81 (s, 1H) 7.85 (s, 1H) 7.38-7.48 (m, 2H) 7.28 (s, 1H) 7.26 (ddd, J=8.77, 5.11, 1.98 Hz, 1H) 7.12 (d, J=1.22 Hz, 1H) 7.04 (td, J=8.62, 1.68 Hz, 2H) 5.65 (t, J=7.02 Hz, 1H) 4.41-4.52 (m, 1H) 3.73-3.88 (m, 4H) 2.88-3.01 (m, 1H) 2.71-2.88 (m, 2H) 2.25-2.39 (m, 1H) 1.40 (dd, J=6.56, 4.12 Hz, 3H) 0.99-1.14 (m, 1H) 0.65-0.75 (m, 1H) 0.53-0.64 (m, 1H) 0.39 (tt, J=9.80, 5.00 Hz, 1H) 0.27-0.35 (m, 1H).

The mixture of two diasteriomers was separated by chiral chromatography to afford two diasteriomers Example 49A and 49B as free amines.

Example 49A: LC-MS (M+H)$^+$=519.3. $^1$H NMR (500 MHz, MeOD) δ ppm 7.87 (d, J=2.14 Hz, 1H) 7.66 (d, J=1.53 Hz, 1H) 7.17-7.28 (m, 3H) 7.08-7.17 (m, 1H) 6.90-7.08 (m, 3H) 4.15 (t, J=8.24 Hz, 1H) 3.78-3.92 (m, 1H) 3.59 (s, 3H) 2.75-2.85 (m, 1H) 2.59-2.74 (m, 2H) 1.33 (d, J=6.71 Hz, 3H) 1.00-1.14 (m, 1H) 0.82-1.00 (m, 1H) 0.39-0.59 (m, 3H) 0.26 (dt, J=9.38, 4.62 Hz, 1H).

Example 49B: LC-MS (M+H)$^+$=519.3. $^1$H NMR (500 MHz, MeOD) δ ppm 7.87 (d, J=2.14 Hz, 1H) 7.66 (d, J=1.53 Hz, 1H) 7.15-7.25 (m, 3H) 7.13 (d, J=8.55 Hz, 1H) 7.02 (t, J=8.85 Hz, 2H) 6.98 (dd, J=8.55, 2.14 Hz, 1H) 4.16 (t, J=8.09 Hz, 1H) 3.82-3.98 (m, 1H) 3.60 (s, 3H) 2.78-2.87 (m, 1H) 2.55-2.75 (m, 2H) 1.91-2.04 (m, 1H) 1.35 (d, J=6.71 Hz, 3H)

0.79-0.98 (m, 1H) 0.55 (td, J=8.70, 4.27 Hz, 1H) 0.45-0.51 (m, 1H) 0.32-0.43 (m, J=9.65, 5.04, 4.86, 4.86 Hz, 1H) 0.16-0.29 (m, 1H).

Example 50

N2-(4-(4-chloro-1H-imidazol-1-yl)-3-methoxyphenyl)-N4-((S)-1-cyclopropylethyl)-7-(4-fluorophenyl)-6,7-dihydro-5H-cyclopenta[d]pyrimidine-2,4-diamine, TFA

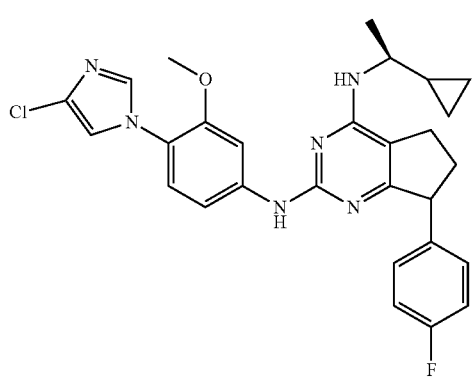 [SMILES: COc1cc(Nc2nc(N[C@@H](C)C3CC3)c3c(n2)C(c2ccc(F)cc2)CC3)ccc1-n1cnc(Cl)c1]

Diasteriomeric Mixture 2-chloro-N—((S)-1-cyclopropylethyl)-7-(4-fluorophenyl)-6,7-dihydro-5H-cyclopenta[d]pyrimidin-4-amine (Preparation Hz) was reacted as described in Example 112 with 4-(4-chloro-1H-imidazol-1-yl)-3-methoxyaniline (Preparation A) to give N2-(4-(4-chloro-1H-imidazol-1-yl)-3-methoxyphenyl)-N4-((S)-1-cyclopropylethyl)-7-(4-fluorophenyl)-6,7-dihydro-5H-cyclopenta[d]pyrimidine-2,4-diamine, TFA as a mixture of two diasteriomers (Example 50). LC-MS (M+H)+=519.5. ¹H NMR (500 MHz, CDCl₃) δ ppm 11.84 (s, 1H) 7.80 (s, 1H) 7.43 (s, 1H) 7.41 (d, J=8.85 Hz, 1H) 7.28 (s, 1H) 7.26 (ddd, J=8.70, 5.19, 1.98 Hz, 1H) 7.19 (d, J=8.55 Hz, 1H) 7.11 (s, 1H) 7.04 (td, J=8.62, 1.68 Hz, 2H) 5.66 (t, J=6.87 Hz, 1H) 4.40-4.52 (m, 1H) 3.72-3.87 (m, 4H) 2.87-3.07 (m, 1H) 2.67-2.86 (m, 2H) 2.26-2.40 (m, 1H) 1.40 (dd, J=6.56, 4.12 Hz, 3H) 1.03-1.15 (m, 1H) 0.56-0.76 (m, 2H) 0.29-0.49 (m, 2H).

The mixture of two diasteriomers was separated by chiral chromatography to afford two diasteriomers Example 50A and 50B as free amines.

Example 50A: LC-MS (M+H)+=519.3. ¹H NMR (500 MHz, MeOD) δ ppm 7.88 (d, J=2.14 Hz, 1H) 7.67 (d, J=1.53 Hz, 1H) 7.17-7.24 (m, 3H) 7.14 (d, J=8.55 Hz, 1H) 6.90-7.08 (m, 3H) 4.18 (t, J=8.09 Hz, 1H) 3.88 (dd, J=8.09, 6.56 Hz, 1H) 3.61 (s, 3H) 2.77-2.89 (m, 1H) 2.58-2.77 (m, 2H) 1.90-2.05 (m, 1H) 1.35 (d, J=6.71 Hz, 3H) 1.07 (dt, J=8.24, 4.88 Hz, 1H) 0.51-0.57 (m, 1H) 0.44-0.51 (m, 1H) 0.40 (dd, J=9.61, 4.73 Hz, 1H) 0.17-0.29 (m, 1H).

Example 50B: LC-MS (M+H)+=519.3. ¹H NMR (500 MHz, MeOD) δ ppm 7.87 (d, J=1.83 Hz, 1H) 7.67 (s, 1H) 7.20-7.27 (m, 3H) 7.14 (d, J=8.55 Hz, 1H) 6.93-7.08 (m, 3H) 4.17 (t, J=8.24 Hz, 1H) 3.75-3.93 (m, 1H) 3.61 (s, 3H) 2.76-2.88 (m, 1H) 2.54-2.73 (m, 2H) 1.89-2.08 (m, 1H) 1.34 (d, J=6.71 Hz, 3H) 0.99-1.12 (m, 1H) 0.54-0.63 (m, 1H) 0.46-0.54 (m, 1H) 0.43 (dd, J=9.61, 4.73 Hz, 1H) 0.18-0.28 (m, 1H).

Example 51

N²-(4-(4-chloro-1H-imidazol-1-yl)-3-methoxyphenyl)-N⁴-methyl-8-phenyl-7,8-dihydro-5H-pyrano[4,3-d]pyrimidine-2,4-diamine

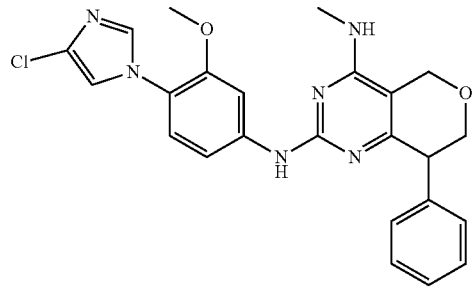 [SMILES: CNc1nc(Nc2ccc(-n3cnc(Cl)c3)c(OC)c2)nc2c1COCC2c1ccccc1]

2-chloro-N-methyl-8-phenyl-7,8-dihydro-5H-pyrano[4,3-d]pyrimidin-4-amine (Preparation Ia) (125 mg, 0.453 mmol) and 4-(4-chloro-1H-imidazol-1-yl)-3-methoxyaniline (Preparation A) (101 mg, 0.453 mmol) were combined and purified as per Example 26 to give N2-(4-(4-chloro-1H-imidazol-1-yl)-3-methoxyphenyl)-N4-methyl-8-phenyl-7,8-dihydro-5H-pyrano[4,3-d]pyrimidine-2,4-diamine, TFA (178 mg, 0.309 mmol, 68.1% yield) as a slightly yellow, scrapable glass. LC-MS (M+H)+=463.2. ¹H NMR (500 MHz, MeOD) δ ppm 7.81 (1H, s), 7.62 (1H, s), 7.32-7.47 (7H, m), 7.14 (1H, dd, J=8.55, 2.14 Hz), 4.54-4.72 (2H, m), 4.19 (1H, dd, J=11.44, 4.73 Hz), 4.10 (1H, t, J=4.43 Hz), 3.94 (1H, dd, J=11.44, 4.73 Hz), 3.86 (3H, s), 3.15-3.19 (3H, m).

Example 51A

N²-(4-(4-chloro-1H-imiazol-1-yl)-3-methoxyphenyl)-N⁴-methyl-8-phenyl-7,8-dihydro-5H-pyrano[4,3-d]pyrimidine-2,4-diamine

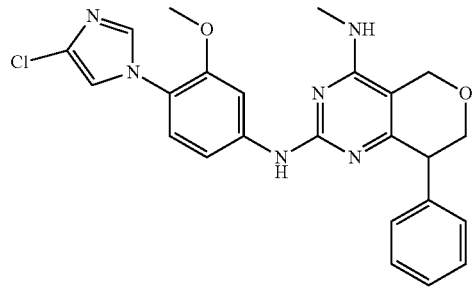

Enantiomer A of Example 51

N²-(4-(4-chloro-1H-imiazol-1-yl)-3-methoxyphenyl)-N⁴-methyl-8-phenyl-7,8-dihydro-5H-pyrano[4,3-d]pyrimidine-2,4-diamine Example 51 was separated by multiple chiral prep HPLC injections (OJ-H 30×250 mm, 10 μM, EtOH/Heptane) to give N²-(4-(4-chloro-1H-imidazol-1-yl)-3-methoxyphenyl)-N⁴-methyl-8-phenyl-7,8-dihydro-5H-pyrano[4,3-d]pyrimidine-2,4-diamine, TFA (first to elute, enantiomer A) (36.5 mg, 0.063 mmol) as a yellow solid. LC-MS (M+H)+=463.2. ¹H NMR (500 MHz, MeOD) δ ppm 7.83 (1H, br. s.), 7.70 (1H, br. s.), 7.35 (2H, t, J=7.32 Hz), 7.24-7.33 (4H, m), 7.21 (1H, d, J=8.55 Hz), 6.97-7.05 (1H, m), 4.52-4.71 (2H, m), 4.16 (1H, dd, J=11.44, 4.73 Hz), 3.98 (1H, br. s.), 3.87-3.96 (1H, m), 3.61 (3H, br. s.), 3.06-3.14 (3H, m). The absolute stereochemistry of Example 51A was not determined.

Example 51B

N²-(4-(4-chloro-1H-imiazol-1-yl)-3-methoxyphenyl)-N⁴-methyl-8-phenyl-7,8-dihydro-5H-pyrano[4,3-d]pyrimidine-2,4-diamine

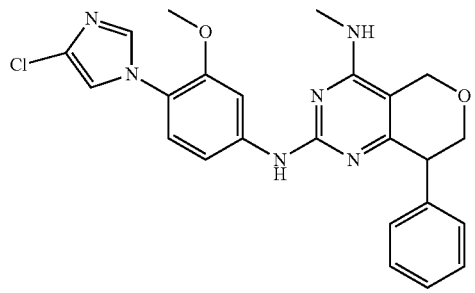

Enantiomer B of Example 51

N²-(4-(4-chloro-1H-imiazol-1-yl)-3-methoxyphenyl)-N⁴-methyl-8-phenyl-7,8-dihydro-5H-pyrano[4,3-d]pyrimidine-2,4-diamine Example 51 was separated by multiple chiral prep HPLC injections (OJ-H 30×250 mm, 10 μM, EtOH/Heptane) to give N²-(4-(4-chloro-1H-imidazol-1-yl)-3-methoxyphenyl)-N⁴-methyl-8-phenyl-7,8-dihydro-5H-pyrano[4,3-d]pyrimidine-2,4-diamine, TFA (second to elute, enantiomer B) (30.9 mg, 0.054 mmol) as a yellow solid. LC-MS (M+H)+=463.2. ¹H NMR (500 MHz, MeOD) δ ppm 7.74 (2H, br. s.), 7.24-7.48 (7H, m), 7.01-7.13 (1H, m), 4.52-4.73 (2H, m), 4.17 (1H, dd, J=11.44, 4.73 Hz), 4.00-4.11 (1H, m), 3.88-4.00 (1H, m), 3.71 (3H, br. s.), 3.12 (3H, s). The absolute stereochemistry of Example 51B was not determined.

Example 52

N²-(4-(4-Chloro-1H-imidazol-1-yl)-3-methoxyphenyl)-N⁴-ethyl-N⁴-methyl-8-phenyl-7,8-dihydro-5H-pyrano[4,3-d]pyrimidine-2,4-diamine

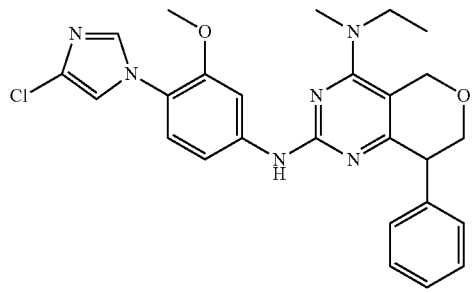 [SMILES: CCN(C)c1nc(Nc2ccc(-n3cnc(Cl)c3)c(OC)c2)nc2c1COCC2c1ccccc1]

To a solution of 2-chloro-N-ethyl-N-methyl-8-phenyl-7,8-dihydro-5H-pyrano[4,3-d]pyrimidin-4-amine (146 mg, 0.481 mmol) and 4-(4-chloro-1H-imidazol-1-yl)-3-methoxyaniline (107 mg, 0.481 mmol) in THF (1.0 mL) and acetic acid (1.0 mL). The reaction mixture was stirred overnight at 75° C. The crude reaction mixture was purified by preparative HPLC. The appropriate fractions were evaporated to afford N²-(4-(4-chloro-1H-imidazol-1-yl)-3-methoxyphenyl)-N⁴-ethyl-N⁴-methyl-8-phenyl-7,8-dihydro-5H-pyrano[4,3-d]pyrimidine-2,4-diamine, TFA salt (59.9 mg, 0.092 mmol, 93% yield). LC-MS (M+H)+=491.4. ¹H NMR (500 MHz, CDCl₃) δ ppm 11.77 (1H, s), 7.67 (1H, d, J=1.5 Hz), 7.39 (1H, dd, J=8.5, 2.1 Hz), 7.26-7.35 (5H, m), 7.16 (1H, s), 7.14 (1H, s), 7.06 (1H, d, J=1.5 Hz), 4.75-4.90 (2H, m), 4.14-4.23 (2H, m), 3.90 (1H, d, J=7.0 Hz), 3.81 (3H, s), 3.62 (2H, s), 3.27 (3H, s), 1.34 (3H, t, J=7.2 Hz).

Examples 52A & 52B (S)—N²-(4-(4-Chloro-1H-imidazol-1-yl)-3-methoxyphenyl)-N⁴-ethyl-N⁴-methyl-8-phenyl-7,8-dihydro-5H-pyrano[4,3-d]pyrimidine-2,4-diamine and (R)—N²-(4-(4-Chloro-1H-imidazol-1-yl)-3-methoxyphenyl)-N⁴-ethyl-N⁴-methyl-8-phenyl-7,8-dihydro-5H-pyrano[4,3-d]pyrimidine-2,4-diamine

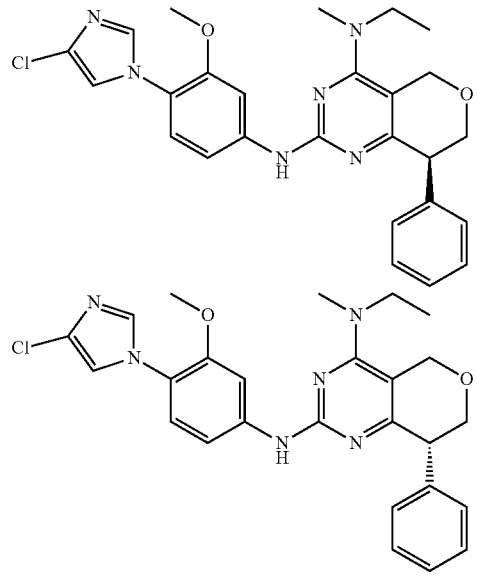

A racemic mixture of N²-(4-(4-chloro-1H-imidazol-1-yl)-3-methoxyphenyl)-8-(4-fluorophenyl)-N⁴,N⁴-dimethyl-5,6,7,8-tetrahydroquinazoline-2,4-diamine (55.0 mg, 0.112 mmol) (Example 52) was purified using chiral SFC to afford peak A (17.2 mg, 0.035 mmol) (Example 52A) and peak B (18.8 mg, 0.038 mmol) (Example 52B). SFC Method: Chiralpak OJ-H (30×250 mm, 5 μM), 35% methanol (0.1% diethylamine) in CO₂, 35° C., flow rate 70 mL/min for 13 min, absorbance 268 nm, injection 5 μL of 27 mg/mL solution in methanol (multiple stacked injections), $t_R$ (peak A)=4.2 min, $t_R$ (peak B) 8.3 min. The absolute stereochemistry of individual enantiomers (Examples 52A and 52B) was not deter-

Example 53

N²-(4-(4-Chloro-1H-imidazol-1-yl)-3-methoxyphenyl)-N⁴,N⁴-dimethyl-8-phenyl-7,8-dihydro-5H-pyrano[4,3-d]pyrimidine-2,4-diamine

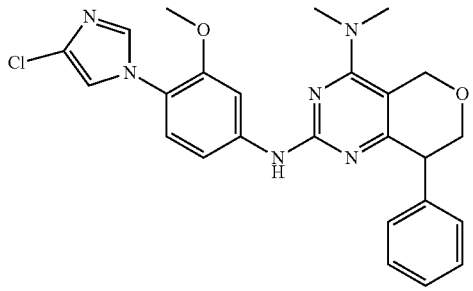 [SMILES: COc1cc(Nc2nc3c(c(N(C)C)n2)COCC3c2ccccc2)ccc1-n1cnc(Cl)c1]

To a solution of 2-chloro-N,N-dimethyl-8-phenyl-7,8-dihydro-5H-pyrano[4,3-d]pyrimidin-4-amine (135 mg, 0.466 mmol) and 4-(4-chloro-1H-imidazol-1-yl)-3-methoxyaniline (104 mg, 0.466 mmol) in THF (1.0 mL) and acetic acid (1.0 mL). The reaction mixture was stirred overnight at 75° C. The crude reaction mixture was purified by preparative HPLC. The appropriate fractions were evaporated to afford N2-(4-(4-chloro-1H-imidazol-1-yl)-3-methoxyphenyl)-N⁴,N⁴-dimethyl-8-phenyl-7,8-dihydro-5H-pyrano[4,3-d]pyrimidine-2,4-diamine, TFA salt (80.1 mg, 0.130 mmol, 96% yield). LC-MS (M+H)⁺=477.3. ¹H NMR (500 MHz, CDCl₃) δ ppm 11.74 (1H, s), 7.74 (1H, d, J=1.5 Hz), 7.36 (1H, s), 7.34-7.26 (6H, m), 7.15 (1H, d, J=8.2 Hz), 7.07 (1H, d, J=1.5 Hz), 4.83 (1H, m), 4.13-4.21 (1H, m), 3.81 (3H, s), 3.47 (3H, s), 3.32 (6H, s).

Examples 53A & 53B (S)—N²-(4-(4-Chloro-1H-imidazol-1-yl)-3-methoxyphenyl)-N⁴,N⁴-dimethyl-8-phenyl-7,8-dihydro-5H-pyrano[4,3-d]pyrimidine-2,4-diamine and (R)—N²-(4-(4-Chloro-1H-imidazol-1-yl)-3-methoxyphenyl)-N⁴,N⁴-dimethyl-8-phenyl-7,8-dihydro-5H-pyrano[4,3-d]pyrimidine-2,4-diamine

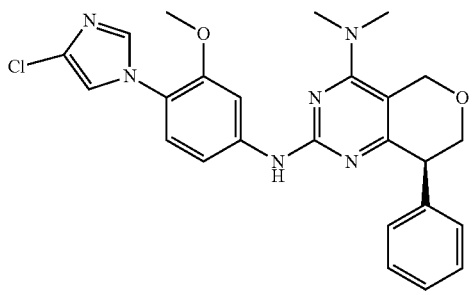

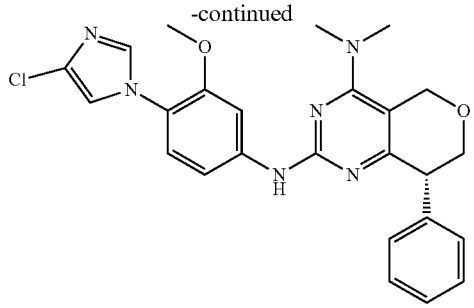

A racemic mixture of N²-(4-(4-Chloro-1H-imidazol-1-yl)-3-methoxyphenyl)-N⁴,N⁴-dimethyl-8-phenyl-7,8-dihydro-5H-pyrano[4,3-d]pyrimidine-2,4-diamine (80.1 mg, 0.130 mmol) (Example 53) was purified using chiral SFC to afford peak A (21.2 mg, 0.044 mmol) (Example 53A) and peak B (24.2 mg, 0.051 mmol) (Example 53B). SFC Method: Chiralpak OJ-H (30×250 mm, 5 μM), 35% methanol (0.1% diethylamine) in CO₂, 35° C., flow rate 70 mL/min for 13 min, absorbance 268 nm, injection 5 μL of 27 mg/mL solution in methanol (multiple stacked injections), $t_R$ (peak A)=4.5 min, $t_R$ (peak B) 9.5 min. The absolute stereochemistry of individual enantiomers (Examples 53A and 53B) was not determined LC-MS and ¹H NMR analytical data for the separated enantiomers was identical to the racemate (Example 53).

Example 54

8-(4-fluorophenyl)-N2-(3-methoxy-4-(3-methyl-1H-1,2,4-triazol-1-yl)phenyl)-N4-methyl-7,8-dihydro-5H-pyrano[4,3-d]pyrimidine-2,4-diamine

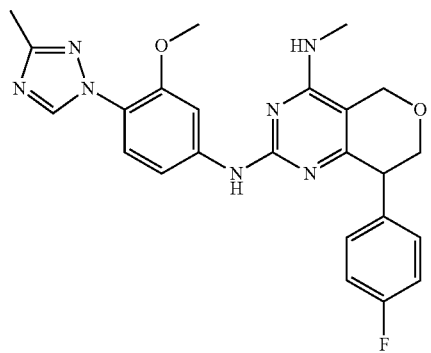 [SMILES: CNc1nc(Nc2ccc(-n3cnc(C)n3)c(OC)c2)nc2c1COCC2c1ccc(F)cc1]

A solution of Preparation D (0.076 g, 0.38 mmol), Preparation Ja (0.11 g, 0.38 mmol), Na₂CO₃ (0.079 g, 0.75 mmol) and xantphos (0.216 g, 0.38 mmol) in dioxane/water (9:1) was purged with argon for 1 h at room temperature. Pd(dba)₃ (0.17 g, 0.18 mmol) was added to the reaction mixture and the resulting solution was purged with argon for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (50 mL×2). The combined organic layer was washed with brine solution (25 mL), dried over anhydrous Na₂SO₄ and evaporated under reduced pressure to get crude compound. The crude compound was purified by prep-HPLC to give 8-(4-fluorophenyl)-N2-(3-methoxy-4-(3-methyl-1H-

1,2,4-triazol-1-yl)phenyl)-N4-methyl-7,8-dihydro-5H-pyrano[4,3-d]pyrimidine-2,4-diamine (0.08 g, 47%) as off-white solid. LC-MS (M+H)+=462.2. ¹H NMR (400 MHz, DMSO-d6): δ ppm 8.70 (1H, s), 7.8 (1H, m), 7.5 (1H, m), 7.34 (2H, m), 7.21 (4H, m), 7.13 (1H, m), 4.60 (1H, d, J=14.0 Hz), 4.46 (1H, d, J=14.0 Hz), 3.83 (2H, m), 3.78 (1H, m), 3.75 (3H, s), 3.01 (3H, d, J=4.0 Hz), 2.32 (3H, s,).

The racemic mixture was separated by chiral chromatography to afford the enantiomers Example 54A and 54B, which had identical spectral data.

Example 55

N4-ethyl-8-(4-fluorophenyl)-N2-(3-methoxy-4-(3-methyl-1H-1,2,4-triazol-1-yl)phenyl)-7,8-dihydro-5H-pyrano[4,3-d]pyrimidine-2,4-diamine

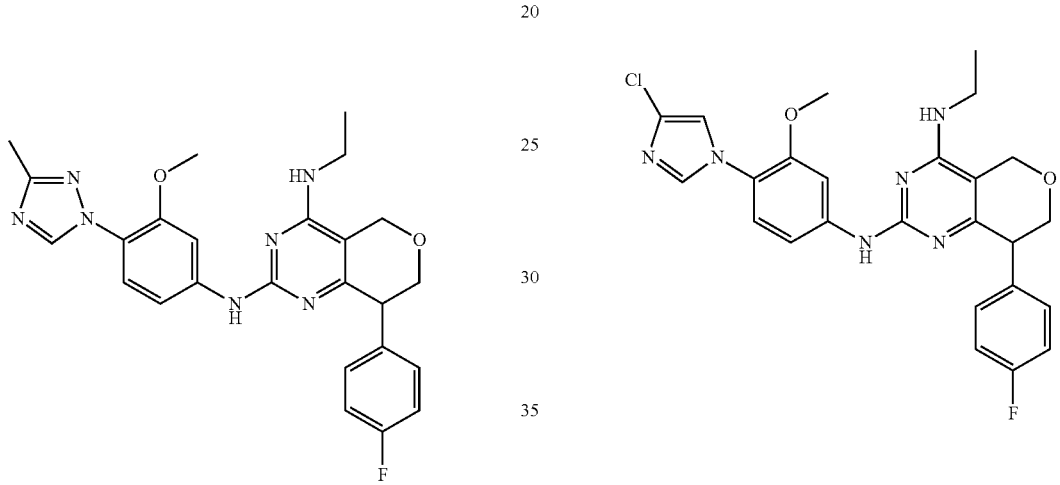

The racemic mixture was separated by chiral chromatography to afford the enantiomers Example 55A and 55B, which had identical spectral data.

Example 56

N2-(4-(4-chloro-1H-imidazol-1-yl)-3-methoxyphenyl)-N4-ethyl-8-(4-fluorophenyl)-7,8-dihydro-5H-pyrano[4,3-d]pyrimidine-2,4-diamine

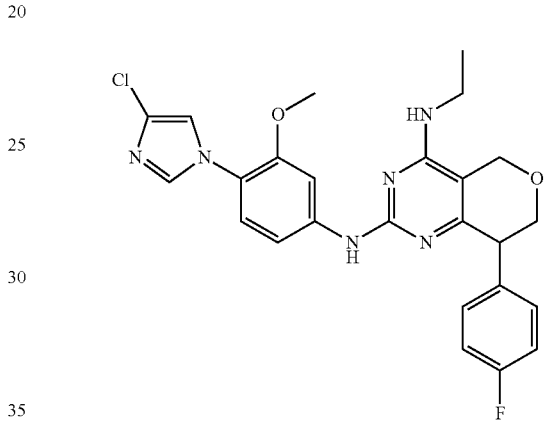

A solution of Preparation D (0.085 g, 0.40 mmol), Preparation Jb (0.16 g, 0.52 mmol), Na₂CO₃ (0.11 g, 1.0 mmol) and xantphos (0.30 g, 0.52 mmol) in dioxane/water (9:1) was purged with argon for 1 h at room temperature. Pd(dba)₃ (0.26 g, 0.26 mmol) was added to the reaction mixture and the resulting solution was purged with argon for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (10 mL×3). The combined organic layer was washed with brine solution (10 mL), dried over anhydrous Na₂SO₄ and evaporated under reduced pressure to get crude compound. The crude compound was purified by prep-HPLC to give N4-ethyl-8-(4-fluorophenyl)-N2-(3-methoxy-4-(3-methyl-1H-1,2,4-triazol-1-yl)phenyl)-7,8-dihydro-5H-pyrano[4,3-d]pyrimidine-2,4-diamine (0.90 g, 40%) as off-white solid. LC-MS (M+H)+=476.2. ¹H NMR (400 MHz, DMSO-d6): δ ppm 8.69 (1H, s), 7.73 (1H, s), 7.48 (1H, s), 7.34 (2H, m), 7.21-7.13 (3H, m), 4.62 (1H, d, J=14.0 Hz), 4.47 (1H, d, J=14.0 Hz), 4.07 (2H, m), 3.92 (2H, m), 3.82 (3H, s), 3.54 (3H, m), 2.33 (3H, s), 1.22 (3H, t, J=7.2.0 Hz).

A solution of Preparation A (0.70 g, 0.32 mmol), Preparation Jb (0.11 g, 0.35 mmol), Na₂CO₃ (0.07 g, 0.71 mmol) and xantphos (0.20 g, 0.35 mmol) in dioxane/water (9:1) was purged with argon for 1 h at room temperature. Pd(dba)₃ (0.18 g, 0.17 mmol) was added to the reaction mixture and the resulting solution was purged for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (50 mL×2). The combined organic layer was washed with brine solution (25 mL), dried over anhydrous Na₂SO₄ and evaporated under reduced pressure to get crude compound. The crude compound was purified by prep-HPLC to give N2-(4-(4-chloro-1H-imidazol-1-yl)-3-methoxyphenyl)-N4-ethyl-8-(4-fluorophenyl)-7,8-dihydro-5H-pyrano[4,3-d]pyrimidine-2,4-diamine (0.70 g, 40%) as off-white solid. LC-MS (M−H)+ =495.2. ¹H NMR (400 MHz, -DMSO-d6): δ ppm 9.91 (1H, sb), 7.83 (1H, m), 7.69 (1H, s), 7.39 (1H, s), 7.22 (4H, m), 7.10 (4H, m), 4.65 (1H, d, J=14.0 Hz), 4.48 (1H, d, J=14.0 Hz), 4.04 (1H, m), 3.83 (3H, s), 3.74 (3H, s), 3.54 (2H, m), 1.22 (3H, t, J=7.2.0 Hz).

313

The racemic mixture was separated by chiral chromatography to afford the enantiomers Example 56A and 56B, which had identical spectral data.

Example 57A

N-(4-(4-chloro-1H-imidazol-1-yl)-3-methoxyphenyl)-8-(4-fluorophenyl)-4-((R)-3-fluoropyrrolidin-1-yl)-7,8-dihydro-5H-pyrano[4,3-d]pyrimidin-2-amine

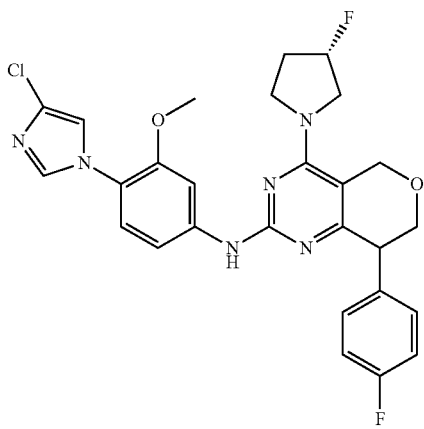 [SMILES: COc1cc(Nc2nc3c(c(N4CC[C@H](F)C4)n2)COCC3c2ccc(F)cc2)ccc1-n1cnc(Cl)c1]

A solution of Preparation A (0.051 g, 0.23 mmol), Preparation Jc1 (0.09 g, 0.25 mmol), Na$_2$CO$_3$ (0.050 g, 0.51 mmol) and xantphos (0.148 g, 0.25 mmol) in dioxane/water (9:1) was purged with argon for 1 h at room temperature. Pd(dba)$_3$ (0.132 g, 0.12 mmol) was added to the reaction mixture and the resulting solution was purged for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (50 mL×2). The combined organic layer was washed with brine solution (25 mL), dried over anhydrous Na$_2$SO$_4$ and evaporated under reduced pressure to get crude compound. The crude compound was purified by column chromatography (60-120 mesh) using 10% methanol in dichloromethane as mobile phase to give N-(4-(4-chloro-1H-imidazol-1-yl)-3-methoxyphenyl)-8-(4-fluorophenyl)-4-((R)-3-fluoropyrrolidin-1-yl)-7,8-dihydro-5H-pyrano[4,3-d]pyrimidin-2-amine (0.030 g, 18%) as an off-white solid.

LC-MS (M+H)$^+$=539.0. $^1$H NMR (400 MHz, DMSO-d6): δ ppm 9.19 (1H, s), 7.89 (1H, s), 7.74 (1H, s), 7.43 (1H, s), 7.27 (2H, m), 7.18-7.11 (4H, m), 5.42 (1H, m), 5.04 (1H, d, J=13.6 Hz), 4.81 (1H, d, J=13.6 Hz), 4.13 (2H, m), 3.91-3.77 (4H, m), 3.66 (1H, m), 3.58 (3H, s), 2.23 (2H, m).

Example 57B

N-(4-(4-chloro-1H-imidazol-1-yl)-3-methoxyphenyl)-8-(4-fluorophenyl)-4-((R)-3-fluoropyrrolidin-1-yl)-7,8-dihydro-5H-pyrano[4,3-d]pyrimidin-2-amine

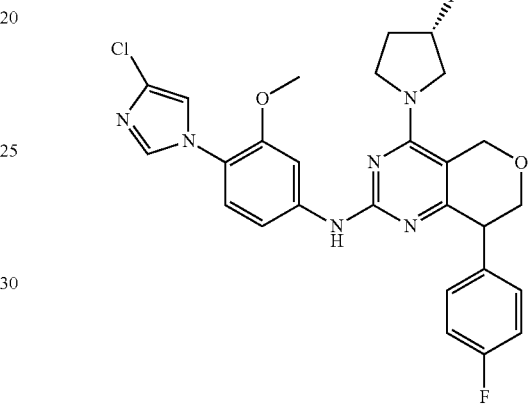

A solution of Preparation A (0.062 g, 0.28 mmol), Preparation Jc2 (0.110 g, 0.31 mmol), Na$_2$CO$_3$ (0.066 g, 0.62 mmol) and xantphos (0.181 g, 0.31 mmol) in dioxane/water (9:1) was purged with argon for 1 h at room temperature. Pd(dba)$_3$ (0.162 g, 0.15 mmol) was added to the reaction mixture and the resulting solution was purged with argon for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (50 mL×2). The combined organic layer was washed with brine solution (50 mL), dried over anhydrous Na$_2$SO$_4$ and evaporated under reduced pressure to get crude compound. The crude compound was purified by column chromatography (60-120 mesh) using 8% methanol in dichloromethane as mobile phase to give N-(4-(4-chloro-1H-imidazol-1-yl)-3-methoxyphenyl)-8-(4-fluorophenyl)-4-((R)-3-fluoropyrrolidin-1-yl)-7,8-dihydro-5H-pyrano[4,3-d]pyrimidin-2-amine (0.031 g, 19%) as an off-white solid.

LC-MS (M+H)$^+$=539.0. $^1$H NMR (400 MHz, DMSO-d6): δ ppm 9.21 (1H, s), 7.87 (1H, s), 7.74 (1H, s), 7.43 (1H, s), 7.24

(2H, m), 7.16-7.09 (4H, m), 5.36 (1H, m), 4.95 (2H, m), 5.05 (1H, m), 3.95-3.80 (2H, m), 3.78-3.70 (4H, m), 3.6 (3H, s), 2.22 (2H, m).

Example 58A

N-(4-(4-chloro-1H-imidazol-1-yl)-3-methoxyphenyl)-8-(4-fluorophenyl)-4-((S)-3-fluoropyrrolidin-1-yl)-7,8-dihydro-5H-pyrano[4,3-d]pyrimidin-2-amine

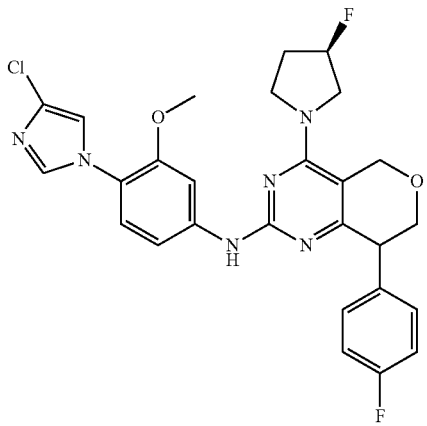 [SMILES: COc1cc(Nc2nc3c(c(N4CC[C@@H](F)C4)n2)COCC3c2ccc(F)cc2)ccc1-n1cnc(Cl)c1]

A solution of Preparation A (0.057 g, 0.28 mmol), Preparation Jd1 (0.10 g, 0.28 mmol), Na$_2$CO$_3$ (0.06 g, 0.56 mmol) and xantphos (0.16 g, 0.28 mmol) in dioxane/water (9:1) was purged with argon for 1 h at room temperature. Pd(dba)$_3$ (0.14 g, 0.14 mmol) was added to the reaction mixture and the resulting solution was purged with argon for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (50 mL×2). The combined organic layer was washed with brine solution (25 mL), dried over anhydrous Na$_2$SO$_4$ and evaporated under reduced pressure to get crude compound. The crude compound was purified by column chromatography (60-120 mesh) using 10% methanol in dichloromethane as mobile phase to give N-(4-(4-chloro-1H-imidazol-1-yl)-3-methoxyphenyl)-8-(4-fluorophenyl)-4-((S)-3-fluoropyrrolidin-1-yl)-7,8-dihydro-5H-pyrano[4,3-d]pyrimidin-2-amine (0.040 g, 27%) as off-white solid. LC-MS (M+H)$^+$=539.0. $^1$H NMR (400 MHz, DMSO-d6): δ ppm 9.45 (1H, sb), 7.79 (1H, s), 7.71 (1H, m), 7.47 (1H, s), 7.34-7.26 (2H, m), 7.21-7.12 (4H, m), 5.41 (1H, m), 5.07 (1H, d, J=14.0 Hz), 4.85 (1H, d, J=14.0 Hz), 4.53-4.38 (2H, m), 4.32-4.30 (4H, m), 3.89-3.64 (4H, m), 2.50-2.58 (2H, m).

Example 58B

N-(4-(4-chloro-1H-imidazol-1-yl)-3-methoxyphenyl)-8-(4-fluorophenyl)-4-((S)-3-fluoropyrrolidin-1-yl)-7,8-dihydro-5H-pyrano[4,3-d]pyrimidin-2-amine

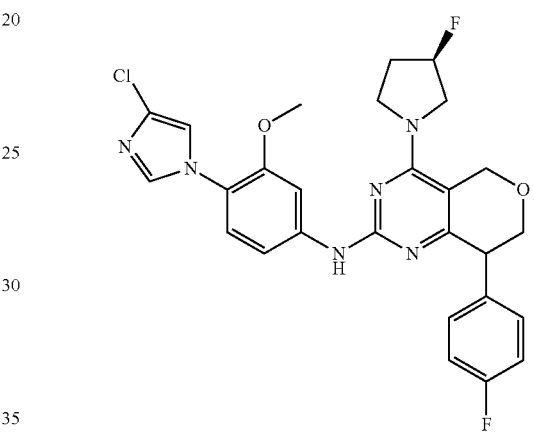

A solution of Preparation A (0.062 g, 0.282 mmol), Preparation Jd2 (0.11 g, 0.310 mmol), Na$_2$CO$_3$ (0.065 g, 0.620 mmol) and xantphos (0.179 g, 0.310 mmol) in dioxane/water (9:1) was purged with argon for 1 h at room temperature. Pd(dba)$_3$ (0.16 g, 0.155 mmol) was added to the reaction mixture and the resulting solution was purged for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (25 mL×3). The combined organic layer was washed with brine solution (25 mL), dried over anhydrous Na$_2$SO$_4$ and evaporated under reduced pressure to get crude compound. The crude compound was purified by column chromatography (60-120 mesh) using 10% methanol in dichloromethane as mobile phase to give N-(4-(4-chloro-1H-imidazol-1-yl)-3-methoxyphenyl)-8-(4-fluorophenyl)-4-((S)-3-fluoropyrrolidin-1-yl)-7,8-dihydro-5H-pyrano[4,3-d]pyrimidin-2-amine (0.040 g, 27%) as off-white solid. LC-MS (M+H)$^+$=539.0. $^1$H NMR (400 MHz, DMSO-d6): δ ppm 9.39 (1H, sb), 7.78 (1H, s), 7.71 (1H, m), 7.46 (1H, s), 7.28-7.13

(6H, m), 5.40 (1H, m), 4.94 (2H, m), 4.04-3.95 (4H, m), 3.83 (3H, m), 3.67 (3H, m), 2.33-2.08 (2H, m).

Example 59

N4-ethyl-N2-(3-fluoro-4-(5-methyl-1H-1,2,4-triazol-1-yl)phenyl)-8-(4-fluorophenyl)-7,8-dihydro-5H-pyrano[4,3-d]pyrimidine-2,4-diamine

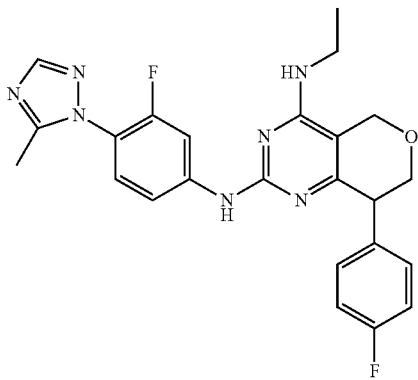 [SMILES: CCNc1nc(Nc2ccc(-n3ncnc3C)c(F)c2)nc2c1COCC2c1ccc(F)cc1]

The method of example 56 was used to combine Preparation C and Preparation Jb to afford N4-ethyl-N2-(3-fluoro-4-(5-methyl-1H-1,2,4-triazol-1-yl)phenyl)-8-(4-fluorophenyl)-7,8-dihydro-5H-pyrano[4,3-d]pyrimidine-2,4-diamine. LC-MS (M+H)⁺=464.3. $^1$H NMR (500 MHz, MeOD) δ ppm 7.99-8.06 (2H, m), 7.24-7.34 (4H, m), 7.04 (2H, t, J=8.70 Hz), 4.65 (1H, d, J=14.30 Hz), 4.56 (1H, d, J=14.30 Hz), 4.16 (1H, dd, J=11.29, 4.58 Hz), 3.94-4.00 (1H, m), 3.92 (1H, t, J=4.88 Hz), 3.57 (2H, q, J=7.12 Hz), 2.37 (3H, s), 1.29 (3H, t, J=7.17 Hz)

The racemic mixture was separated by chiral chromatography to afford the enantiomers Example 59A and 59B, which had identical spectral data.

Example 60

N2-(4-(4-chloro-1H-imidazol-1-yl)-3-methoxyphenyl)-8-(4-fluorophenyl)-N4-methyl-7,8-dihydro-5H-pyrano[4,3-d]pyrimidine-2,4-diamine

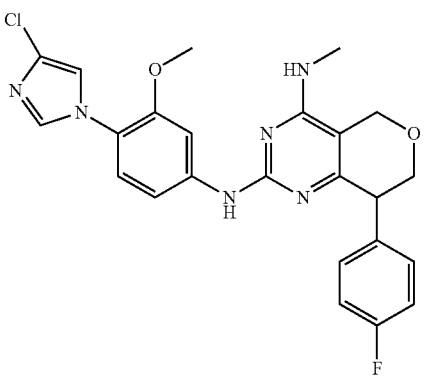 [SMILES: CNc1nc(Nc2ccc(-n3cnc(Cl)c3)c(OC)c2)nc2c1COCC2c1ccc(F)cc1]

A solution of Preparation A (0.15 g, 0.61 mmol), Preparation Ja (0.20 g, 0.61 mmol), Na$_2$CO$_3$ (0.144 g, 1.31 mmol) and xantphos (0.39 g, 0.61 mmol) in dioxane/water (9:1) was purged with argon for 1 h at room temperature. Pd(dba)$_3$ (0.31 g, 0.32 mmol) was added to the reaction mixture and the resulting solution was purged for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (25 mL×2). The combined organic layer was washed with brine solution (25 mL), dried over anhydrous Na$_2$SO$_4$ and evaporated under reduced pressure to get crude compound. The crude compound was purified by column chromatography (Silica gel, 60-120 mesh) using 50% ethyl acetate in pet-ether as mobile phase to give to give N2-(4-(4-chloro-1H-imidazol-1-yl)-3-methoxyphenyl)-8-(4-fluorophenyl)-N4-methyl-7,8-dihydro-5H-pyrano[4,3-d]pyrimidine-2,4-diamine (0.12 g, 37%) as off-white solid. LC-MS (M−H)⁺=479.0. $^1$H NMR (400 MHz, DMSO-d6): δ ppm 12.02 (1H, sb), 9.17 (1H, s), 8.06 (1H, s), 7.73 (1H, s), 7.41 (1H, s), 7.25-7.08 (5H, m), 6.77 (1H, m), 4.57 (1H, d, J=14.4 Hz), 4.44 (1H, d, J=14.4 Hz), 4.02 (1H, m), 3.89 (1H, m), 3.80 (1H, m), 3.3 (3H, s), 2.93 (3H, d, J=4.0 Hz).

The racemic mixture was separated by chiral chromatography to afford the enantiomers Example 60A and 60B, which had identical spectral data.

Example 61

N2-(4-(4-chloro-1H-imidazol-1-yl)-3-methoxyphenyl)-8-(4-fluorophenyl)-N4,N4-dimethyl-7,8-dihydro-5H-pyrano[4,3-d]pyrimidine-2,4-diamine

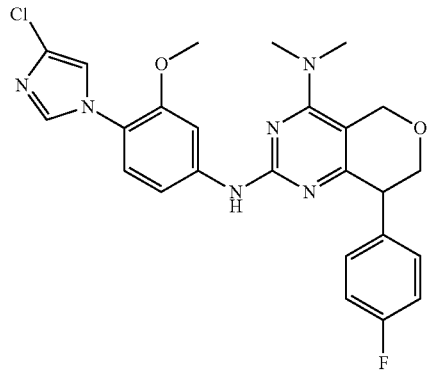 [SMILES: COc1cc(Nc2nc3c(c(N(C)C)n2)COCC3c2ccc(F)cc2)ccc1-n1cnc(Cl)c1]

A solution of Preparation A (0.15 g, 0.70 mmol), Preparation Je (0.24 g, 0.78 mmol), Na$_2$CO$_3$ (0.16 g, 1.56 mmol) and xantphos (0.45 g, 0.78 mmol) in dioxane/water (9:1) was purged with argon for 1 h at room temperature. Pd(dba)$_3$ (0.35 g, 0.39 mmol) was added to the reaction mixture and the resulting solution was purged for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (30 mL×2). The combined organic layer was washed with brine solution (20 mL), dried over anhydrous Na$_2$SO$_4$ and evaporated under reduced pressure to get crude compound. The crude compound was purified by Combiflash (Silica 120 g) using 50% ethyl acetate in pet-ether as mobile phase to give N2-(4-(4-chloro-1H-imidazol-1-yl)-3-methoxyphenyl)-8-(4-fluorophenyl)-N4,N4-dimethyl-7,8-dihydro-5H-pyrano[4,3-d]pyrimidine-2,4-diamine (0.15 g, 47%) as off-white solid. LC-MS (M−H)+=493.0. ¹H NMR (400 MHz, DMSO-d6): δ ppm 9.21 (1H, s), 7.91 (1H, s), 7.73 (1H, s), 7.41 (1H, s), 7.24 (2H, m), 7.14 (4H, m), 4.83 (1H, d, J=13.6 Hz), 4.70 (1H, d, J=13.6 Hz), 4.16 (1H, m), 4.10 (1H, m), 3.72 (1H, m), 3.56 (3H, s), 3.06 (6H, s).

The racemic mixture was separated by chiral chromatography to afford the enantiomers Example 61A and 61B, which had identical spectral data.

Example 62

N2-(4-(4-chloro-1H-imidazol-1-yl)-3-methoxyphenyl)-N4-ethyl-8-(4-fluorophenyl)-N4-methyl-7,8-dihydro-5H-pyrano[4,3-d]pyrimidine-2,4-diamine

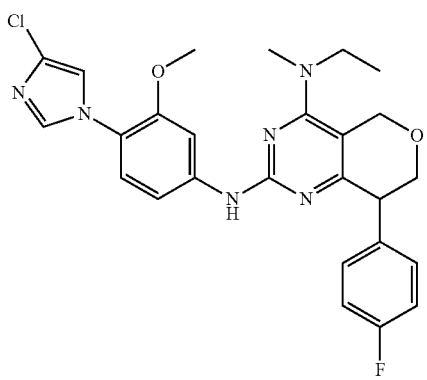 [SMILES: CCN(C)c1nc(Nc2ccc(-n3cnc(Cl)c3)c(OC)c2)nc2c1COCC2c1ccc(F)cc1]

A solution of Preparation A (0.13 g, 0.61 mmol), Preparation Jf (0.20 g, 0.61 mmol), Na₂CO₃ (0.13 g, 1.2 mmol) and xantphos (0.36 g, 0.61 mmol) in dioxane/water (9:1) was purged with argon for 1 h at room temperature. Pd(dba)₃ (0.28 g, 0.31 mmol) was added to the reaction mixture and the resulting solution was purged for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (30 mL×2). The combined organic layer was washed with brine solution (20 mL), dried over anhydrous Na₂SO₄ and evaporated under reduced pressure to get crude compound. The crude compound was purified by Combiflash (Silica 120 g) using 50% ethyl acetate in pet-ether as mobile phase to give N2-(4-(4-chloro-1H-imidazol-1-yl)-3-methoxyphenyl)-N4-ethyl-8-(4-fluorophenyl)-N4-methyl-7,8-dihydro-5H-pyrano[4,3-d]pyrimidine-2,4-diamine (0.097 g, 47%) as off-white solid. LC-MS (M+H)+=509.2. ¹H NMR (400 MHz, DMSO-d6): δ ppm 9.17 (1H, s), 7.83 (1H, s), 7.72 (1H, s), 7.40 (1H, s), 7.24 (2H, m), 7.12 (4H, m), 4.78 (1H, d, J=13.6 Hz), 4.65 (1H, d, J=13.6 Hz), 4.09 (1H, m), 3.73 (1H, m), 3.55 (1H, m), 3.54 (3H, s), 3.38 (2H, m), 3.02 (3H, s), 1.20 (3H, t, J=6.9.0 Hz).

The racemic mixture was separated by chiral chromatography to afford the enantiomers Example 62A and 62B, which had identical spectral data.

Example 63

N-(4-(4-chloro-1H-imidazol-1-yl)-3-methoxyphenyl)-4-(3,3-difluoroazetidin-1-yl)-8-(4-fluorophenyl)-7,8-dihydro-5H-pyrano[4,3-d]pyrimidin-2-amine

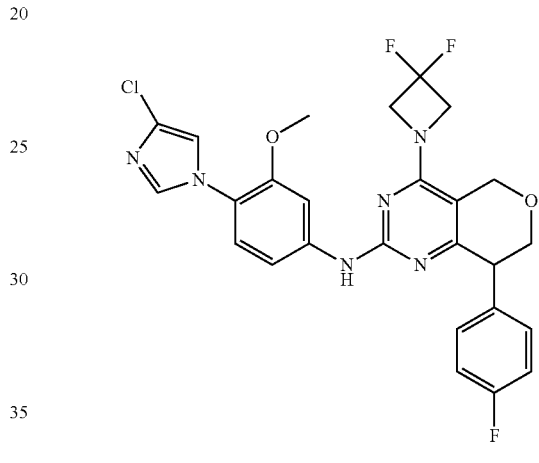

A solution of Preparation A (0.082 g, 0.31 mmol), Preparation Jg (0.13 g, 0.31 mmol), Na₂CO₃ (0.077 g, 0.72 mmol) and xantphos (0.21 g, 0.31 mmol) in dioxane/water (9:1) was purged with argon for 1 h at room temperature. Pd(dba)₃ (0.16 g, 0.12 mmol) was added to the reaction mixture and the resulting solution was purged for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (30 mL×2). The combined organic layer was washed with brine solution (20 mL), dried over anhydrous Na₂SO₄ and evaporated under reduced pressure to get crude compound. The crude compound was purified by Combiflash (Silica 120 g) using 50% ethyl acetate in pet-ether as mobile phase to give N-(4-(4-chloro-1H-imidazol-1-yl)-3-methoxyphenyl)-4-(3,3-difluoroazetidin-1-yl)-8-(4-fluorophenyl)-7,8-dihydro-5H-pyrano[4,3-d]pyrimidin-2-amine (0.070 g, 35%) as off-white solid. LC-MS (M−H)+=541.0. ¹H NMR (400 MHz, DMSO-d6): δ ppm 9.41 (1H, s), 7.88 (1H, s), 7.73 (1H, s), 7.41 (1H, s), 7.25 (2H, m), 7.17-7.08 (4H, m), 4.78-4.63 (6H, m), 4.04 (2H, m), 3.78 (1H, m), 3.50 (3H, s).

The racemic mixture was separated by chiral chromatography to afford the enantiomers Example 63A and 63B, which had identical spectral data.

Example 64

N²-(4-(4-chloro-1H-imidazol-1-yl)-3-methoxyphenyl)-8-(4-chlorophenyl)-N⁴-methyl-7,8-dihydro-5H-pyrano[4,3-d]pyrimidine-2,4-diamine

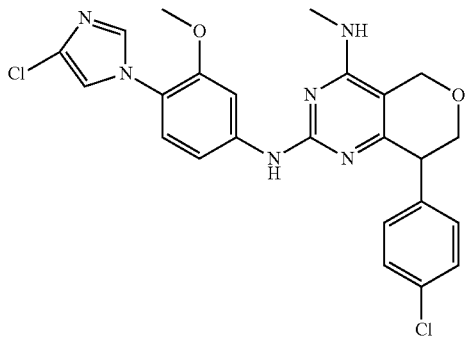

2-chloro-8-(4-chlorophenyl)-N-methyl-7,8-dihydro-5H-pyrano[4,3-d]pyrimidin-4-amine (Preparation Kb) (116 mg, 0.374 mmol) and 4-(4-chloro-1H-imidazol-1-yl)-3-methoxyaniline (Preparation A) (84 mg, 0.374 mmol) were combined and purified as per Example 26 to give N²-(4-(4-chloro-1H-imidazol-1-yl)-3-methoxyphenyl)-8-(4-chlorophenyl)-N⁴-methyl-7,8-dihydro-5H-pyrano[4,3-d]pyrimidine-2,4-diamine, TFA (105 mg, 0.172 mmol, 45.9% yield) as a white solid. LC-MS (M+H)⁺=497.1. ¹H NMR (500 MHz, MeOD) δ ppm 7.86 (1H, br. s.), 7.63 (1H, br. s.), 7.30-7.46 (6H, m), 7.19 (1H, dd, J=8.55, 2.14 Hz), 4.62-4.73 (1H, m), 4.56 (1H, d, J=14.65 Hz), 4.11-4.20 (1H, m), 4.07 (1H, d, J=3.36 Hz), 3.94 (1H, dd, J=11.44, 3.81 Hz), 3.82-3.89 (3H, m), 3.10-3.20 (3H, m).

Example 64A

N²-(4-(4-chloro-1H-imidazol-1-yl)-3-methoxyphenyl)-8-(4-chlorophenyl)-N⁴-methyl-7,8-dihydro-5H-pyrano[4,3-d]pyrimidine-2,4-diamine

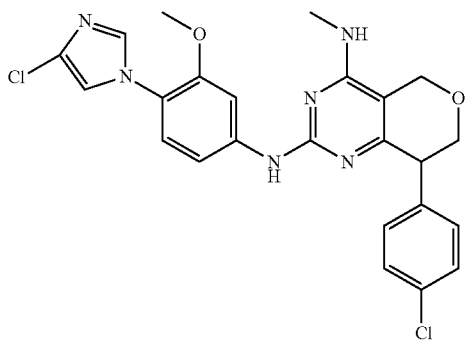

Enantiomer A of Example 64

N²-(4-(4-chloro-1H-imidazol-1-yl)-3-methoxyphenyl)-8-(4-chlorophenyl)-N⁴-methyl-7,8-dihydro-5H-pyrano[4,3-d]pyrimidine-2,4-diamine (Example 64) was separated by multiple chiral HPLC injections (OJ-H 30×250 mm, 10 μM, 35% EtOH/Hexanes) to give N²-(4-(4-chloro-1H-imidazol-1-yl)-3-methoxyphenyl)-8-(4-chlorophenyl)-N⁴-methyl-7,8-dihydro-5H-pyrano[4,3-d]pyrimidine-2,4-diamine, TFA (first to elute, enantiomer A) (35 mg, 0.057 mmol) as an off-white solid. LC-MS (M+H)⁺=497.1. ¹H NMR (500 MHz, MeOD) δ ppm 7.80 (1H, s), 7.71 (1H, s), 7.36 (2H, d, J=8.24 Hz), 7.25-7.30 (3H, m), 7.22 (1H, d, J=8.55 Hz), 7.03 (1H, d, J=8.55 Hz), 4.50-4.68 (2H, m), 4.15 (1H, dd, J=11.29, 4.27 Hz), 3.97 (1H, t, J=4.27 Hz), 3.87-3.94 (1H, m), 3.66 (3H, s), 3.08 (3H, s). The absolute stereochemistry of Example 64A was not determined.

Example 64B

N²-(4-(4-chloro-1H-imidazol-1-yl)-3-methoxyphenyl)-8-(4-chlorophenyl)-N⁴-methyl-7,8-dihydro-5H-pyrano[4,3-d]pyrimidine-2,4-diamine

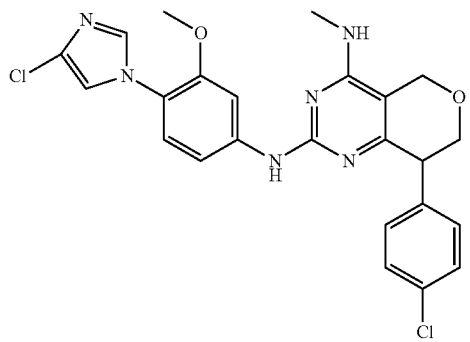 [SMILES: CNc1nc(Nc2ccc(-n3cnc(Cl)c3)c(OC)c2)nc2c1COCC2c1ccc(Cl)cc1]

Enantiomer B of Example 64

N²-(4-(4-chloro-1H-imidazol-1-yl)-3-methoxyphenyl)-8-(4-chlorophenyl)-N⁴-methyl-7,8-dihydro-5H-pyrano[4,3-d]pyrimidine-2,4-diamine (Example 64) was separated by multiple chiral HPLC injections (OJ-H 30×250 mm, 10 μM, 35% EtOH/Hexanes) to give N²-(4-(4-chloro-1H-imidazol-1-yl)-3-methoxyphenyl)-8-(4-chlorophenyl)-N⁴-methyl-7,8-dihydro-5H-pyrano[4,3-d]pyrimidine-2,4-diamine, TFA (second to elute, enantiomer B) (29 mg, 0.047 mmol) as an off-white solid. LC-MS (M+H)⁺=497.1. ¹H NMR (500 MHz, MeOD) δ ppm 7.78 (1H, s), 7.72 (1H, d, J=1.53 Hz), 7.34-7.39 (2H, m), 7.26-7.31 (3H, m), 7.24 (1H, d, J=8.55 Hz), 7.04 (1H, dd, J=8.55, 2.14 Hz), 4.51-4.68 (2H, m), 4.15 (1H, dd, J=11.29, 4.58 Hz), 3.98 (1H, t, J=4.43 Hz), 3.91 (1H, dd, J=11.44, 4.73

Hz), 3.68 (3H, s), 3.09 (3H, s). The absolute stereochemistry of Example 64B was not determined.

Example 65

$N^2$-(4-(4-chloro-1H-imidazol-1-yl)-3-methoxyphenyl)-8-(4-chlorophenyl)-$N^4,N^4$-dimethyl-7,8-dihydro-5H-pyrano[4,3-d]pyrimidine-2,4-diamine

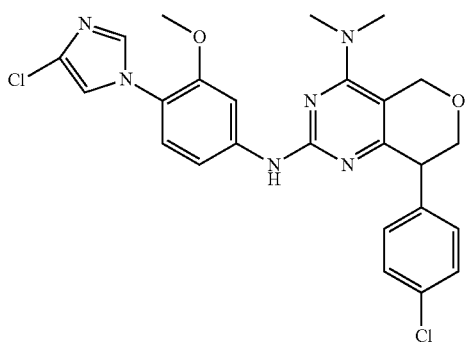

2-chloro-8-(4-chlorophenyl)-N,N-dimethyl-7,8-dihydro-5H-pyrano[4,3-d]pyrimidin-4-amine (Preparation Kc) (125 mg, 0.386 mmol) and 4-(4-chloro-1H-imidazol-1-yl)-3-methoxyaniline (Preparation A) (86 mg, 0.386 mmol) were combined and purified as per Example 26 to give $N^2$-(4-(4-chloro-1H-imidazol-1-yl)-3-methoxyphenyl)-8-(4-chlorophenyl)-$N^4,N^4$-dimethyl-7,8-dihydro-5H-pyrano[4,3-d]pyrimidine-2,4-diamine, TFA (110 mg, 0.176 mmol, 45.6% yield) as a white solid. LC-MS $(M+H)^+$=511.1. $^1$H NMR (500 MHz, MeOD) δ ppm 7.92 (1H, br. s.), 7.31-7.51 (7H, m), 7.16 (1H, dd, J=8.39, 1.98 Hz), 4.91-5.05 (2H, m), 4.12-4.30 (2H, m), 3.76-3.91 (4H, m), 3.34-3.44 (6H, m).

Example 65A $N^2$-(4-(4-chloro-1H-imidazol-1-yl)-3-methoxyphenyl)-8-(4-chlorophenyl)-$N^4,N^4$-dimethyl-7,8-dihydro-5H-pyrano[4,3-d]pyrimidine-2,4-diamine

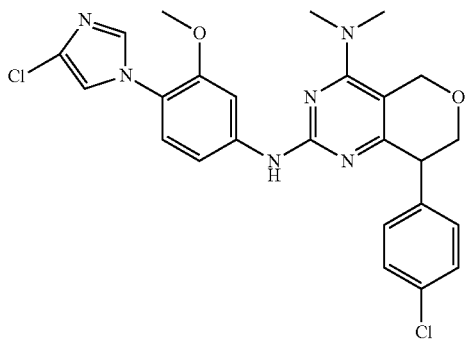

Enantiomer A of Example 65

$N^2$-(4-(4-chloro-1H-imidazol-1-yl)-3-methoxyphenyl)-8-(4-chlorophenyl)-$N^4,N^4$-dimethyl-7,8-dihydro-5H-pyrano[4,3-d]pyrimidine-2,4-diamine (Example 65) was separated by multiple chiral HPLC injections (OJ-H 30×250 mm, 10 μM, 35% EtOH/Hexanes) to give $N^2$-(4-(4-chloro-1H-imidazol-1-yl)-3-methoxyphenyl)-8-(4-chlorophenyl)-$N^4,N^4$-dimethyl-7,8-dihydro-5H-pyrano[4,3-d]pyrimidine-2,4-diamine, TFA (first to elute, enantiomer A) (35 mg, 0.056 mmol) as an off-white solid. LC-MS $(M+H)^+$=511.1. $^1$H NMR (500 MHz, MeOD) δ ppm 7.71 (1H, d, J=1.22 Hz), 7.67 (1H, s), 7.36 (2H, d, J=8.55 Hz), 7.24-7.30 (3H, m), 7.22 (1H, d, J=8.55 Hz), 7.01 (1H, dd, J=8.55, 2.14 Hz), 4.77-4.96 (2H, m), 4.23 (1H, dd, J=11.44, 5.65 Hz), 4.11 (1H, t, J=5.65 Hz), 3.84 (1H, dd, J=11.60, 6.10 Hz), 3.60-3.66 (3H, m), 3.18-3.23 (6H, m). The absolute stereochemistry for Example 65A was not determined.

Example 65B $N^2$-(4-(4-chloro-1H-imidazol-1-yl)-3-methoxyphenyl)-8-(4-chlorophenyl)-$N^4,N^4$-dimethyl-7,8-dihydro-5H-pyrano[4,3-d]pyrimidine-2,4-diamine

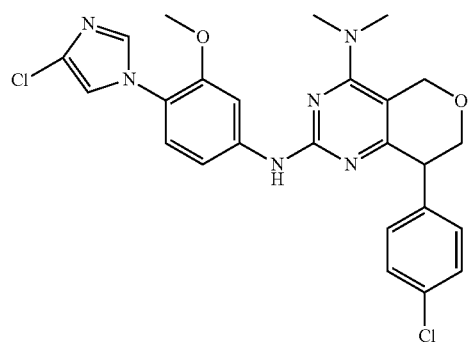 [SMILES: COc1cc(Nc2nc3c(c(N(C)C)n2)COCC3c2ccc(Cl)cc2)ccc1-n1cnc(Cl)c1]

Enantiomer B of Example 65

$N^2$-(4-(4-chloro-1H-imidazol-1-yl)-3-methoxyphenyl)-8-(4-chlorophenyl)-$N^4,N^4$-dimethyl-7,8-dihydro-5H-pyrano[4,3-d]pyrimidine-2,4-diamine (Example 65) was separated by multiple chiral HPLC injections (OJ-H 30×250 mm, 10 μM, 35% EtOH/Hexanes) to give $N^2$-(4-(4-chloro-1H-imidazol-1-yl)-3-methoxyphenyl)-8-(4-chlorophenyl)-$N^4,N^4$-dimethyl-7,8-dihydro-5H-pyrano[4,3-d]pyrimidine-2,4-diamine, TFA (second to elute, enantiomer B) (34 mg, 0.054 mmol) as an off-white solid. LC-MS $(M+H)^+$=511.1. $^1$H NMR (500 MHz, MeOD) δ ppm 7.73 (1H, d, J=1.53 Hz), 7.63 (1H, s), 7.38 (2H, d, J=8.55 Hz), 7.22-7.33 (4H, m), 7.03 (1H, dd, J=8.55, 2.14 Hz), 4.81-4.97 (2H, m), 4.24 (1H, dd, J=11.44, 5.65 Hz), 4.13 (1H, t, J=5.49 Hz), 3.85 (1H, dd, J=11.44, 5.95 Hz), 3.68 (3H, s), 3.24 (6H, s). The absolute stereochemistry for Example 65B was not determined.

Example 66

N-(4-(4-chloro-1H-imidazol-1-yl)-3-methoxyphenyl)-8-(4-chlorophenyl)-4-(3,3-difluoroazetidin-1-yl)-7,8-dihydro-5H-pyrano[4,3-d]pyrimidin-2-amine

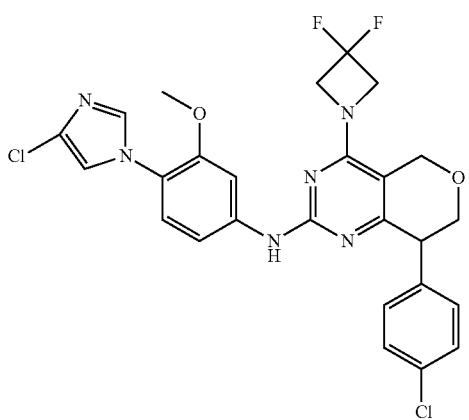

2-chloro-8-(4-chlorophenyl)-4-(3,3-difluoroazetidin-1-yl)-7,8-dihydro-5H-pyrano[4,3-d]pyrimidine (Preparation Ka) (125 mg, 0.336 mmol) and 4-(4-chloro-1H-imidazol-1-yl)-3-methoxyaniline (Preparation A) (75 mg, 0.336 mmol) were combined and purified as per Example 26 to give N-(4-(4-chloro-1H-imidazol-1-yl)-3-methoxyphenyl)-8-(4-chlorophenyl)-4-(3,3-difluoroazetidin-1-yl)-7,8-dihydro-5H-pyrano[4,3-d]pyrimidin-2-amine, TFA (40 mg, 0.059 mmol, 17.69% yield) as a white solid. LC-MS (M+H)⁺=559.1. ¹H NMR (500 MHz, MeOD) δ ppm 7.83 (1H, br. s.), 7.39-7.45 (3H, m), 7.31-7.39 (4H, m), 7.17 (1H, dd, J=8.55, 2.14 Hz), 4.88-4.97 (5H, m), 4.74-4.81 (1H, m), 4.08-4.19 (2H, m), 3.91 (1H, dd, J=11.44, 3.81 Hz), 3.81 (3H, s).

Example 66A

N-(4-(4-chloro-1H-imidazol-1-yl)-3-methoxyphenyl)-8-(4-chlorophenyl)-4-(3,3-difluoroazetidin-1-yl)-7,8-dihydro-5H-pyrano[4,3-d]pyrimidin-2-amine

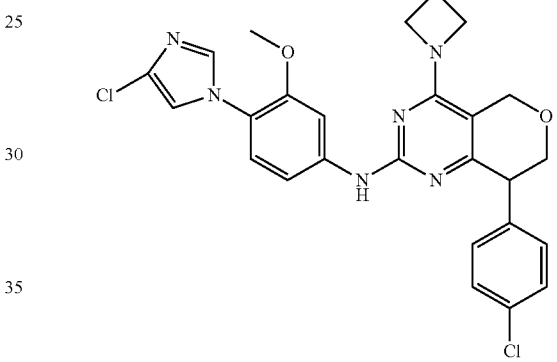

Enantiomer A of Example 66

N-(4-(4-chloro-1H-imidazol-1-yl)-3-methoxyphenyl)-8-(4-chlorophenyl)-4-(3,3-difluoroazetidin-1-yl)-7,8-dihydro-5H-pyrano[4,3-d]pyrimidin-2-amine (Example 66) was separated by multiple chiral SFC injections (OD-H 30×250 mm, 5 μM, 35% MeOH (0.1% DEA)/CO₂) to give N-(4-(4-chloro-1H-imidazol-1-yl)-3-methoxyphenyl)-8-(4-chlorophenyl)-4-(3,3-difluoroazetidin-1-yl)-7,8-dihydro-5H-pyrano[4,3-d]pyrimidin-2-amine (first to elute, enantiomer A) (7.8 mg, 0.014 mmol) as a white solid. LC-MS (M+H)⁺ =559.1. ¹H NMR (500 MHz, MeOD) δ ppm 7.76 (1H, s), 7.66 (1H, s), 7.31 (2H, d, J=8.24 Hz), 7.20-7.27 (3H, m), 7.10-7.16 (1H, m), 6.97 (1H, d, J=8.55 Hz), 4.68-4.83 (2H, m), 4.55-4.66 (4H, m), 4.16 (1H, dd, J=11.44, 5.04 Hz), 4.02 (1H, t, J=4.88 Hz), 3.88 (1H, dd, J=11.29, 5.80 Hz), 3.49 (3H, s). The absolute stereochemistry of Example 66A was not determined.

Example 66B

N-(4-(4-chloro-1H-imidazol-1-yl)-3-methoxyphenyl)-8-(4-chlorophenyl)-4-(3,3-difluoroazetidin-1-yl)-7,8-dihydro-5H-pyrano[4,3-d]pyrimidin-2-amine

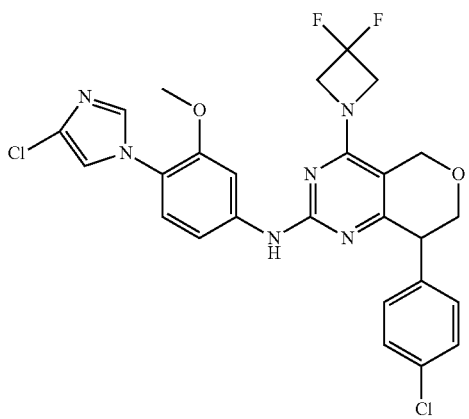 [SMILES: COc1cc(Nc2nc3c(c(N4CC(F)(F)C4)n2)COCC3c2ccc(Cl)cc2)ccc1-n1cnc(Cl)c1]

Enantiomer B of Example 66

N-(4-(4-chloro-1H-imidazol-1-yl)-3-methoxyphenyl)-8-(4-chlorophenyl)-4-(3,3-difluoroazetidin-1-yl)-7,8-dihydro-5H-pyrano[4,3-d]pyrimidin-2-amine (Example 66) was separated by multiple chiral SFC injections (OD-H 30×250 mm, 5 µM, 35% MeOH (0.1% DEA)/CO$_2$) to give N-(4-(4-chloro-1H-imidazol-1-yl)-3-methoxyphenyl)-8-(4-chlorophenyl)-4-(3,3-difluoroazetidin-1-yl)-7,8-dihydro-5H-pyrano[4,3-d]pyrimidin-2-amine (second to elute, enantiomer B) (8.1 mg, 0.014 mmol) as a white solid. LC-MS (M+H)$^+$=559.1. $^1$H NMR (500 MHz, MeOD) δ ppm 7.76 (1H, d, J=2.14 Hz), 7.67 (1H, d, J=1.53 Hz), 7.29-7.34 (2H, m), 7.19-7.27 (3H, m), 7.13 (1H, d, J=8.55 Hz), 6.97 (1H, dd, J=8.55, 2.14 Hz), 4.67-4.84 (2H, m), 4.60 (4H, t, J=12.21 Hz), 4.17 (1H, dd, J=11.44, 5.04 Hz), 4.02 (1H, t, J=5.19 Hz), 3.88 (1H, dd, J=11.29, 5.80 Hz), 3.46-3.51 (3H, m). The absolute stereochemistry of 66B was not determined.

Example 67

8-(4-chlorophenyl)-N$^2$-(3-fluoro-4-(5-methyl-1H-1,2,4-triazol-1-yl)phenyl)-N$^4$,N$^4$-dimethyl-7,8-dihydro-5H-pyrano[4,3-d]pyrimidine-2,4-diamine

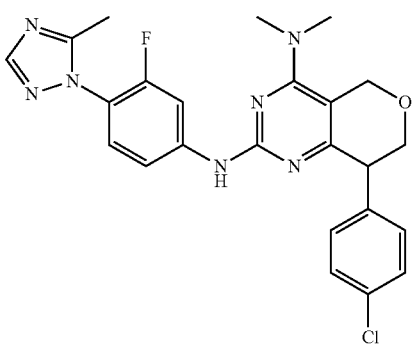

2-chloro-8-(4-chlorophenyl)-N,N-dimethyl-7,8-dihydro-5H-pyrano[4,3-d]pyrimidin-4-amine (Preparation Kc) (128 mg, 0.395 mmol) and 3-fluoro-4-(5-methyl-1H-1,2,4-triazol-1-yl)aniline (Preparation C) (76 mg, 0.395 mmol) were combined and purified as per Example 26 to give 8-(4-chlorophenyl)-N$^2$-(3-fluoro-4-(5-methyl-1H-1,2,4-triazol-1-yl)phenyl)-N$^4$,N$^4$-dimethyl-7,8-dihydro-5H-pyrano[4,3-d]pyrimidine-2,4-diamine, TFA (120 mg, 0.202 mmol, 51.2% yield) as a white solid. LC-MS (M+H)$^+$=480.1. $^1$H NMR (500 MHz, MeOD) δ ppm 8.07 (1H, s), 7.80 (1H, dd, J=12.36, 2.29 Hz), 7.54 (1H, t, J=8.55 Hz), 7.40-7.47 (3H, m), 7.34-7.40 (2H, m), 4.90-5.04 (2H, m), 4.22-4.28 (1H, m), 4.20 (1H, br. s.), 3.87 (1H, dd, J=11.44, 5.34 Hz), 3.39 (6H, s), 2.40 (3H, s).

Example 67A 8-(4-chlorophenyl)-N$^2$-(3-fluoro-4-(5-methyl-1H-1,2,4-triazol-1-yl)phenyl)-N$^4$,N$^4$-dimethyl-7,8-dihydro-5H-pyrano[4,3-d]pyrimidine-2,4-diamine

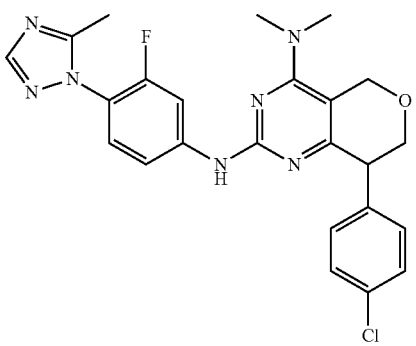 [SMILES: Cc1ncnn1-c1ccc(Nc2nc3c(c(N(C)C)n2)COCC3c2ccc(Cl)cc2)cc1F]

Enantiomer A of Example 67

8-(4-chlorophenyl)-N2-(3-fluoro-4-(5-methyl-1H-1,2,4-triazol-1-yl)phenyl)-N$^4$,N$^4$-dimethyl-7,8-dihydro-5H-pyrano[4,3-d]pyrimidine-2,4-diamine (Example 67) was separated by multiple chiral SFC injections (AD-H 30×250 mm, 5 μM, 40% MeOH (0.1% DEA)/$CO_2$) to give 8-(4-chlorophenyl)-N2-(3-fluoro-4-(5-methyl-1H-1,2,4-triazol-1-yl)phenyl)-$N^4,N^4$-dimethyl-7,8-dihydro-5H-pyrano[4,3-d]pyrimidine-2,4-diamine (first to elute, enantiomer A) (25.8 mg, 0.054 mmol) as an opaque glass. LC-MS (M+H)$^+$=480.1. $^1$H NMR (400 MHz, MeOD) δ ppm 7.99 (1H, s), 7.87-7.95 (1H, m), 7.19-7.33 (6H, m), 4.72-4.83 (2H, m), 4.22 (1H, dd, J=11.33, 5.54 Hz), 4.02 (1H, t, J=5.67 Hz), 3.87-3.95 (1H, m), 3.09 (6H, s), 2.33 (3H, s). The absolute stereochemistry of Example 67A was not determined.

Example 67B 8-(4-chlorophenyl)-$N^2$-(3-fluoro-4-(5-methyl-1H-1,2,4-triazol-1-yl)phenyl)-$N^4,N^4$-dimethyl-7,8-dihydro-5H-pyrano[4,3-d]pyrimidine-2,4-diamine

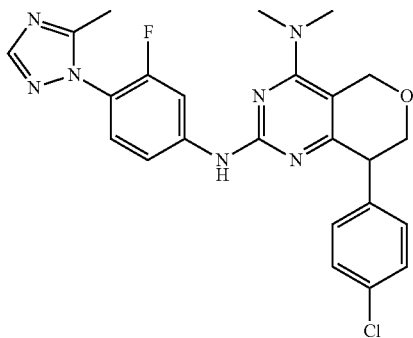

Enantiomer B of Example 67

8-(4-chlorophenyl)-$N^2$-(3-fluoro-4-(5-methyl-1H-1,2,4-triazol-1-yl)phenyl)-$N^4,N^4$-dimethyl-7,8-dihydro-5H-pyrano[4,3-d]pyrimidine-2,4-diamine (Example 67) was separated by multiple chiral SFC injections (AD-H 30×250 mm, 5 μM, 40% MeOH (0.1% DEA)/$CO_2$) to give 8-(4-chlorophenyl)-$N^2$-(3-fluoro-4-(5-methyl-1H-1,2,4-triazol-1-yl)phenyl)-$N^4,N^4$-dimethyl-7,8-dihydro-5H-pyrano[4,3-d]pyrimidine-2,4-diamine (second to elute, enantiomer B) (25.8 mg, 0.054 mmol) as an opaque glass. LC-MS (M+H)$^+$= 480.1. $^1$H NMR (400 MHz, MeOD) δ ppm 7.99 (1H, s), 7.87-7.94 (1H, m), 7.20-7.31 (6H, m), 4.72-4.84 (2H, m), 4.22 (1H, dd, J=11.33, 5.54 Hz), 4.02 (1H, t, J=5.79 Hz), 3.92 (1H, dd, J=11.33, 6.04 Hz), 3.09 (6H, s), 2.33 (3H, s). The absolute stereochemistry of Example 67B was not determined.

Example 68

8-(4-chlorophenyl)-4-(3,3-difluoroazetidin-1-yl)-N-(3-fluoro-4-(5-methyl-1H-1,2,4-triazol-1-yl)phenyl)-7,8-dihydro-5H-pyrano[4,3-d]pyrimidin-2-amine

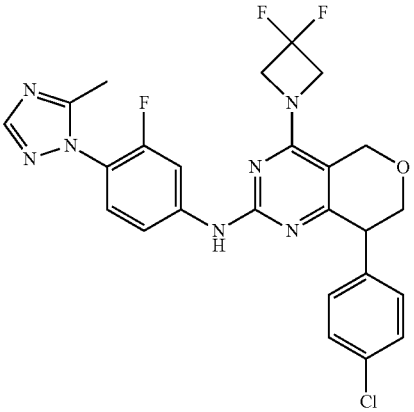 [SMILES: Cc1ncnn1-c1ccc(Nc2nc3c(c(N4CC(F)(F)C4)n2)COCC3c2ccc(Cl)cc2)cc1F]

2-chloro-8-(4-chlorophenyl)-4-(3,3-difluoroazetidin-1-yl)-7,8-dihydro-5H-pyrano[4,3-d]pyrimidine (Preparation Ka) (128 mg, 0.344 mmol) and 3-fluoro-4-(5-methyl-1H-1,2,4-triazol-1-yl)aniline (Preparation C) (66.1 mg, 0.344 mmol) were combined and purified as per Example 26 to give 8-(4-chlorophenyl)-4-(3,3-difluoroazetidin-1-yl)-N-(3-fluoro-4-(5-methyl-1H-1,2,4-triazol-1-yl)phenyl)-7,8-dihydro-5H-pyrano[4,3-d]pyrimidin-2-amine, TFA (120 mg, 0.187 mmol, 54.4% yield) as a white solid. LC-MS (M+1-1)$^+$= 528.1. $^1$H NMR (500 MHz, MeOD) δ ppm 8.01-8.10 (1H, m), 7.75-7.85 (1H, m), 7.25-7.50 (6H, m), 4.70-4.96 (6H, m), 4.13-4.24 (1H, m), 4.02-4.13 (1H, m), 3.96 (1H, dd, J=11.44, 4.73 Hz), 2.32-2.44 (3H, m).

Example 69

8-(4-chlorophenyl)-$N^2$-(3-fluoro-4-(5-methyl-1H-1,2,4-triazol-1-yl)phenyl)-$N^4$-methyl-7,8-dihydro-5H-pyrano[4,3-d]pyrimidine-2,4-diamine

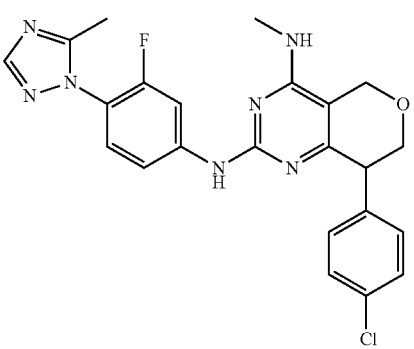

2-chloro-8-(4-chlorophenyl)-N-methyl-7,8-dihydro-5H-pyrano[4,3-d]pyrimidin-4-amine (Preparation Kb) (150 mg, 0.484 mmol) and 3-fluoro-4-(5-methyl-1H-1,2,4-triazol-1-yl)aniline (Preparation C) (93 mg, 0.484 mmol) were combined and purified as per Example 26 to give 8-(4-chlorophenyl)-N2-(3-fluoro-4-(5-methyl-1H-1,2,4-triazol-1-yl)phenyl)-N4-methyl-7,8-dihydro-5H-pyrano[4,3-d]pyrimidine-2,4-diamine, TFA (120 mg, 0.207 mmol, 42.8% yield) as a clear, colorless glass. LC-MS (M+H)$^+$=466.1. $^1$H NMR (500 MHz, MeOD) δ ppm 8.08 (1H, s), 7.89-7.96 (1H, m), 7.57 (1H, t, J=8.55 Hz), 7.47-7.52 (1H, m), 7.42-7.46 (2H, m), 7.34-7.40 (2H, m), 4.53-4.74 (2H, m), 4.18 (1H, dd, J=11.44, 4.43 Hz), 4.07-4.13 (1H, m), 3.95 (1H, dd, J=11.44, 4.12 Hz), 3.17 (3H, s), 2.42 (3H, s).

Example 69A 8-(4-chlorophenyl)-N$^2$-(3-fluoro-4-(5-methyl-1H-1,2,4-triazol-1-yl)phenyl)-N$^4$-methyl-7,8-dihydro-5H-pyrano[4,3-d]pyrimidine-2,4-diamine

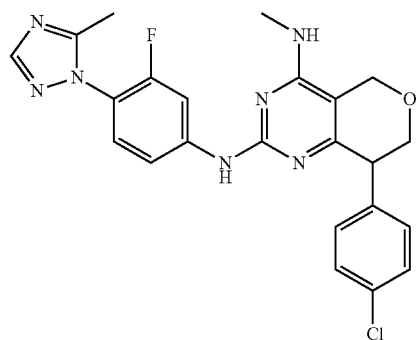

Enantiomer A of Example 69

8-(4-chlorophenyl)-N$^2$-(3-fluoro-4-(5-methyl-1H-1,2,4-triazol-1-yl)phenyl)-N$^4$-methyl-7,8-dihydro-5H-pyrano[4,3-d]pyrimidine-2,4-diamine (Example 69) was separated by multiple chiral SFC injections (AD-H 30×250 mm, 5 μM, 20% MeOH (0.1% DEA)/CO$_2$) to give 8-(4-chlorophenyl)-N$^2$-(3-fluoro-4-(5-methyl-1H-1,2,4-triazol-1-yl)phenyl)-N$^4$-methyl-7,8-dihydro-5H-pyrano[4,3-d]pyrimidine-2,4-diamine (first to elute, enantiomer A) (52.4 mg, 0.112 mmol) as a white solid. LC-MS (M+H)$^+$=466.1. $^1$H NMR (500 MHz, MeOD) δ ppm 7.97-8.13 (2H, m), 7.17-7.41 (6H, m), 4.48-4.72 (2H, m), 4.17 (1H, dd, J=11.29, 4.58 Hz), 3.98 (1H, dd, J=11.44, 5.04 Hz), 3.93 (1H, d, J=4.88 Hz), 2.99-3.08 (3H, m), 2.35-2.42 (3H, m). The absolute stereochemistry of Example 69A was not determined.

Example 69B 8-(4-chlorophenyl)-N$^2$-(3-fluoro-4-(5-methyl-1H-1,2,4-triazol-1-yl)phenyl)-N$^4$-methyl-7,8-dihydro-5H-pyrano[4,3-d]pyrimidine-2,4-diamine

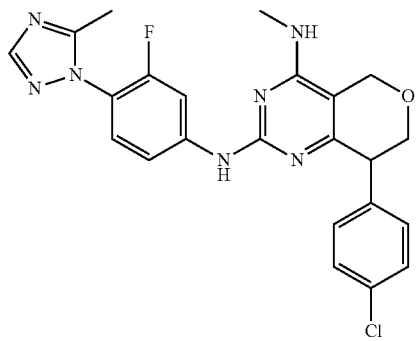 [SMILES: CNc1nc(Nc2ccc(-n3ncnc3C)c(F)c2)nc2c1COCC2c1ccc(Cl)cc1]

Enantiomer B of Example 69

8-(4-chlorophenyl)-N$^2$-(3-fluoro-4-(5-methyl-1H-1,2,4-triazol-1-yl)phenyl)-N$^4$-methyl-7,8-dihydro-5H-pyrano[4,3-d]pyrimidine-2,4-diamine (Example 69) was separated by multiple chiral SFC injections (AD-H 30×250 mm, 5 μM, 20% MeOH (0.1% DEA)/CO$_2$) to give 8-(4-chlorophenyl)-N$^2$-(3-fluoro-4-(5-methyl-1H-1,2,4-triazol-1-yl)phenyl)-N$^4$-methyl-7,8-dihydro-5H-pyrano[4,3-d]pyrimidine-2,4-diamine (second to elute, enantiomer B) (45.9 mg, 0.099 mmol) as a white solid. LC-MS (M+H)$^+$=466.1. $^1$H NMR (500 MHz, MeOD) δ ppm 8.00-8.06 (2H, m), 7.25-7.35 (6H, m), 4.52-4.68 (2H, m), 4.17 (1H, dd, J=11.29, 4.88 Hz), 3.96-4.02 (1H, m), 3.92 (1H, t, J=4.88 Hz), 3.05 (3H, s), 2.38 (3H, s). The absolute stereochemistry of Example 69B was not determined.

Example 70

8-(4-chlorophenyl)-N$^2$-(3-methoxy-4-(4-methyl-1H-imidazol-1-yl)phenyl)-N$^4$-methyl-7,8-dihydro-5H-pyrano[4,3-d]pyrimidine-2,4-diamine

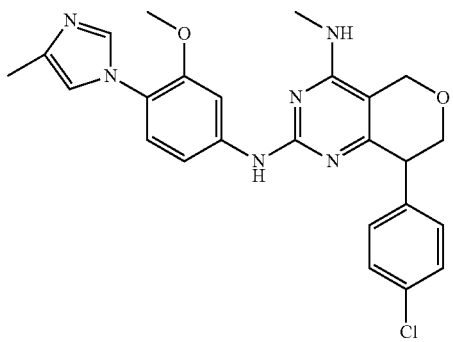

2-chloro-8-(4-chlorophenyl)-N-methyl-7,8-dihydro-5H-pyrano[4,3-d]pyrimidin-4-amine (Preparation Kb) (105.5 mg, 0.340 mmol) and 3-methoxy-4-(4-methyl-1H-imidazol- 1-yl)aniline (Preparation E) (69.1 mg, 0.340 mmol) were combined and purified as per Example 26 to give 8-(4-chlorophenyl)-$N^2$-(3-methoxy-4-(4-methyl-1H-imidazol-1-yl)phenyl)-$N^4$-methyl-7,8-dihydro-5H-pyrano[4,3-d]pyrimidine-2,4-diamine, TFA (120 mg, 0.203 mmol, 59.7% yield) as a clear, colorless glass. LC-MS $(M+H)^+$=477.2. $^1$H NMR (500 MHz, MeOD) δ ppm 9.11 (1H, s), 7.76 (1H, br. s.), 7.51-7.59 (2H, m), 7.34-7.46 (4H, m), 7.26-7.33 (1H, m), 4.52-4.75 (2H, m), 4.17 (1H, dd, J=11.44, 4.43 Hz), 4.08 (1H, br. s.), 3.88-4.04 (4H, m), 3.17 (3H, s), 2.44 (3H, s).

Example 70A 8-(4-chlorophenyl)-$N^2$-(3-methoxy-4-(4-methyl-1H-imidazol-1-yl)phenyl)-$N^4$-methyl-7,8-dihydro-5H-pyrano[4,3-d]pyrimidine-2,4-diamine

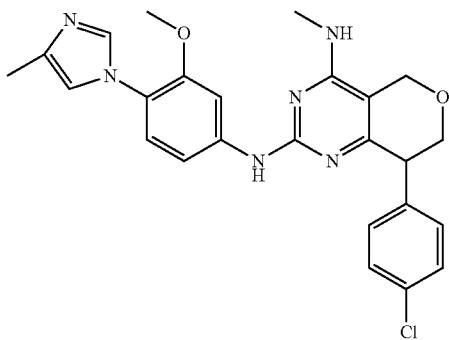

Enantiomer A of Example 70

8-(4-chlorophenyl)-$N^2$-(3-methoxy-4-(4-methyl-1H-imidazol-1-yl)phenyl)-$N^4$-methyl-7,8-dihydro-5H-pyrano[4,3-d]pyrimidine-2,4-diamine (Example 70) was separated by multiple chiral SFC injections (AD-H 30×250 mm, 5 μM, 20% MeOH (0.1% DEA)/CO$_2$) to give 8-(4-chlorophenyl)-$N^2$-(3-methoxy-4-(4-methyl-1H-imidazol-1-yl)phenyl)-$N^4$-methyl-7,8-dihydro-5H-pyrano[4,3-d]pyrimidine-2,4-diamine (first to elute, enantiomer A) as an opaque yellow glass. LC-MS $(M+H)^+$=477.2. $^1$H NMR (500 MHz, MeOD) δ ppm 7.84 (1H, d, J=2.14 Hz), 7.62 (1H, br. s.), 7.30 (2H, d, J=8.55 Hz), 7.19-7.28 (2H, m), 7.06-7.15 (1H, m), 6.94 (2H, dd, J=8.55, 2.14 Hz), 4.48-4.67 (2H, m), 4.06-4.18 (1H, m), 3.84-3.96 (2H, m), 3.54 (3H, s), 3.04 (3H, s), 2.22 (3H, s). The absolute stereochemistry of Example 70A was not determined.

Example 70B 8-(4-chlorophenyl)-$N^2$-(3-methoxy-4-(4-methyl-1H-imidazol-1-yl)phenyl)-$N^4$-methyl-7,8-dihydro-5H-pyrano[4,3-d]pyrimidine-2,4-diamine

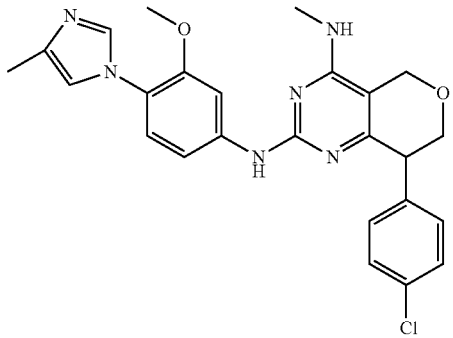 [SMILES: CNc1nc(Nc2ccc(-n3cnc(C)c3)c(OC)c2)nc2c1COCC2c1ccc(Cl)cc1]

Enantiomer B of Example 70

8-(4-chlorophenyl)-$N^2$-(3-methoxy-4-(4-methyl-1H-imidazol-1-yl)phenyl)-$N^4$-methyl-7,8-dihydro-5H-pyrano[4,3-d]pyrimidine-2,4-diamine (Example 70) was separated by multiple chiral SFC injections (AD-H 30×250 mm, 5 μM, 20% MeOH (0.1% DEA)/CO$_2$) to give 8-(4-chlorophenyl)-$N^2$-(3-methoxy-4-(4-methyl-1H-imidazol-1-yl)phenyl)-$N^4$-methyl-7,8-dihydro-5H-pyrano[4,3-d]pyrimidine-2,4-diamine (second to elute, enantiomer B) as an opaque yellow glass. LC-MS $(M+H)^+$=477.2. $^1$H NMR (500 MHz, MeOD) δ ppm 7.85 (1H, d, J=2.14 Hz), 7.60-7.64 (1H, m), 7.27-7.32 (2H, m), 7.19-7.24 (2H, m), 7.06-7.11 (1H, m), 6.90-6.96 (2H, m), 4.48-4.64 (2H, m), 4.06-4.14 (1H, m), 3.84-3.92 (2H, m), 3.51-3.57 (3H, m), 3.01-3.06 (3H, m), 2.19-2.25 (3H, m). The absolute stereochemistry of Example 70B was not determined.

Example 71

8-(4-chlorophenyl)-$N^2$-(3-methoxy-4-(3-methyl-1H-1,2,4-triazol-1-yl)phenyl)-$N^4$-methyl-7,8-dihydro-5H-pyrano[4,3-d]pyrimidine-2,4-diamine

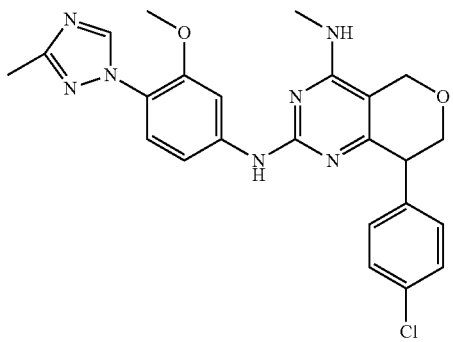 [SMILES: CNc1nc(Nc2ccc(-n3cnc(C)n3)c(OC)c2)nc2c1COCC2c1ccc(Cl)cc1]

2-chloro-8-(4-chlorophenyl)-N-methyl-7,8-dihydro-5H-pyrano[4,3-d]pyrimidin-4-amine (Preparation Kb) (105.5 mg, 0.340 mmol) and 3-methoxy-4-(3-methyl-1H-1,2,4-triazol-1-yl)aniline (Preparation D) (69.5 mg, 0.340 mmol) were combined and purified as per Example 26 to give 8-(4-chlorophenyl)-$N^2$-(3-methoxy-4-(3-methyl-1H-1,2,4-triazol-1-yl)phenyl)-$N^4$-methyl-7,8-dihydro-5H-pyrano[4,3-d]pyrimidine-2,4-diamine, TFA (120 mg, 0.203 mmol, 59.6% yield) as a clear, colorless glass. LC-MS (M+H)$^+$=478.2. $^1$H NMR (500 MHz, MeOD) δ ppm 8.85 (1H, s), 7.67 (1H, d, J=8.55 Hz), 7.64 (1H, s), 7.41-7.48 (2H, m), 7.33-7.40 (2H, m), 7.18 (1H, dd, J=8.55, 2.14 Hz), 4.52-4.73 (2H, m), 4.17 (1H, dd, J=11.44, 4.42 Hz), 4.08 (1H, br. s.), 3.94 (1H, dd, J=11.60, 3.97 Hz), 3.91 (3H, s), 3.17 (3H, s), 2.45 (3H, s).

Example 71A 8-(4-chlorophenyl)-$N^2$-(3-methoxy-4-(3-methyl-1H-1,2,4-triazol-1-yl)phenyl)-$N^4$-methyl-7,8-dihydro-5H-pyrano[4,3-d]pyrimidine-2,4-diamine

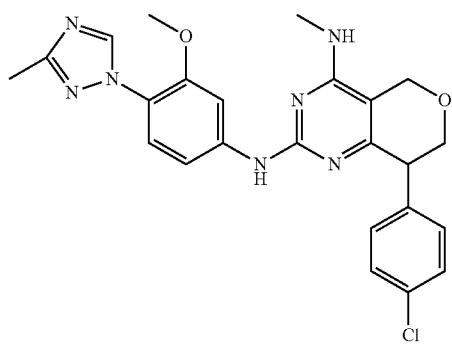

Enantiomer A of Example 71

8-(4-chlorophenyl)-$N^2$-(3-methoxy-4-(3-methyl-1H-1,2,4-triazol-1-yl)phenyl)-$N^4$-methyl-7,8-dihydro-5H-pyrano[4,3-d]pyrimidine-2,4-diamine (Example 71) was separated by multiple chiral SFC injections (OD-H 30×250 mm, 5 μM, 35% MeOH (0.1% DEA)/CO$_2$) to give 8-(4-chlorophenyl)-$N^2$-(3-methoxy-4-(3-methyl-1H-1,2,4-triazol-1-yl)phenyl)-$N^4$-methyl-7,8-dihydro-5H-pyrano[4,3-d]pyrimidine-2,4-diamine (first to elute, enantiomer A) (24 mg, 0.050 mmol) as a scrapable tan glass. LC-MS (M+H)$^+$=478.2. $^1$H NMR (500 MHz, MeOD) δ ppm 8.57 (1H, s), 7.93 (1H, d, J=2.14 Hz), 7.37 (1H, d, J=8.85 Hz), 7.29-7.34 (2H, m), 7.21-7.26 (2H, m), 6.98 (1H, dd, J=8.70, 2.29 Hz), 4.50-4.66 (2H, m), 4.13 (1H, dd, J=10.68, 3.97 Hz), 3.85-3.95 (2H, m), 3.59 (3H, s), 3.05 (3H, s), 2.42 (3H, s). The absolute stereochemistry of Example 71A was not determined.

Example 71B 8-(4-chlorophenyl)-$N^2$-(3-methoxy-4-(3-methyl-1H-1,2,4-triazol-1-yl)phenyl)-$N^4$-methyl-7,8-dihydro-5H-pyrano[4,3-d]pyrimidine-2,4-diamine

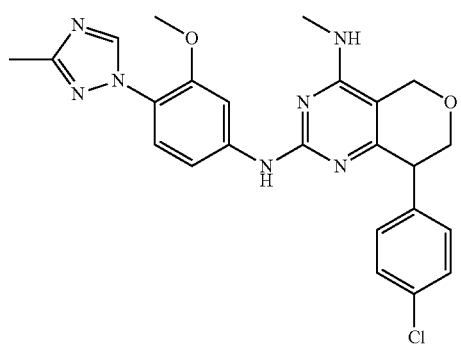

Enantiomer B of Example 71

8-(4-chlorophenyl)-$N^2$-(3-methoxy-4-(3-methyl-1H-1,2,4-triazol-1-yl)phenyl)-$N^4$-methyl-7,8-dihydro-5H-pyrano[4,3-d]pyrimidine-2,4-diamine (Example 71) was separated by multiple chiral SFC injections (OD-H 30×250 mm, 5 μM, 35% MeOH (0.1% DEA)/CO$_2$) to give 8-(4-chlorophenyl)-$N^2$-(3-methoxy-4-(3-methyl-1H-1,2,4-triazol-1-yl)phenyl)-$N^4$-methyl-7,8-dihydro-5H-pyrano[4,3-d]pyrimidine-2,4-diamine (second to elute, enantiomer B) (22 mg, 0.046 mmol) as a scrapable tan glass. LC-MS (M+H)$^+$=478.2. $^1$H NMR (500 MHz, MeOD) δ ppm 8.57 (1H, s), 7.93 (1H, d, J=2.14 Hz), 7.36 (1H, d, J=8.55 Hz), 7.28-7.34 (2H, m), 7.20-7.26 (2H, m), 6.98 (1H, dd, J=8.55, 2.14 Hz), 4.50-4.66 (2H, m), 4.13 (1H, dd, J=10.68, 3.97 Hz), 3.84-3.95 (2H, m), 3.59 (3H, s), 3.04 (3H, s), 2.41 (3H, s). The absolute stereochemistry of Example 71B was not determined.

Example 72

8-(4-bromophenyl)-$N^2$-(4-(4-chloro-1H-imidazol-1-yl)-3-methoxyphenyl)-$N^4$-methyl-7,8-dihydro-5H-pyrano[4,3-d]pyrimidine-2,4-diamine

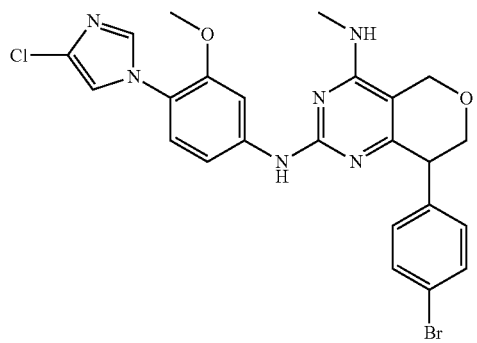 [SMILES: CNc1nc(Nc2ccc(-n3cnc(Cl)c3)c(OC)c2)nc2c1COCC2c1ccc(Br)cc1]

8-(4-bromophenyl)-2-chloro-N-methyl-7,8-dihydro-5H-pyrano[4,3-d]pyrimidin-4-amine (Preparation La) (95 mg, 0.268 mmol) and 4-(4-chloro-1H-imidazol-1-yl)-3-methoxyaniline (Preparation A) (90 mg, 0.402 mmol) were combined and purified as per Example 16 to give 8-(4-bromophenyl)-$N^2$-(4-(4-chloro-1H-imidazol-1-yl)-3-methoxyphenyl)-$N^4$-methyl-7,8-dihydro-5H-pyrano[4,3-d]pyrimidine-2,4-diamine, TFA (38.5 mg, 0.059 mmol, 21.91% yield) as a tan solid. LC-MS (M+H)$^+$=541.1. $^1$H NMR (500 MHz, MeOD) δ ppm 7.83 (1H, br. s.), 7.70 (1H, br. s.), 7.17-7.42 (7H, m), 6.96-7.06 (1H, m), 4.52-4.72 (2H, m), 4.13-4.23 (1H, m), 3.98 (1H, br. s.), 3.87-3.96 (1H, m), 3.62 (3H, d, J=7.02 Hz), 3.06-3.16 (3H, m).

Example 73

8-(4-bromophenyl)-$N^2$-(3-fluoro-4-(5-methyl-1H-1,2,4-triazol-1-yl)phenyl)-$N^4$-methyl-7,8-dihydro-5H-pyrano[4,3-d]pyrimidine-2,4-diamine

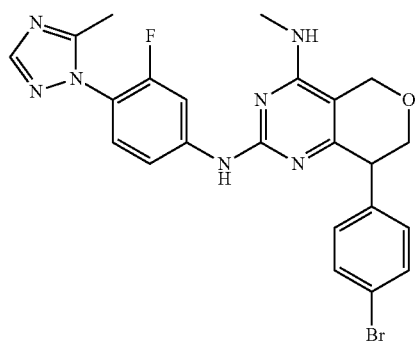

8-(4-bromophenyl)-2-chloro-N-methyl-7,8-dihydro-5H-pyrano[4,3-d]pyrimidin-4-amine (Preparation La) (95 mg, 0.268 mmol) and 3-fluoro-4-(5-methyl-1H-1,2,4-triazol-1-yl)aniline (Preparation C) (77 mg, 0.402 mmol) were combined and purified as per Example 16 to give 8-(4-bromophenyl)-$N^2$-(3-fluoro-4-(5-methyl-1H-1,2,4-triazol-1-yl)phenyl)-$N^4$-methyl-7,8-dihydro-5H-pyrano[4,3-d]pyrimidine-2,4-diamine, TFA (23 mg, 0.037 mmol, 13.75% yield). LC-MS (M+H)$^+$=510.2. $^1$H NMR (500 MHz, MeOD) δ ppm 7.74 (2H, br. s.), 7.25-7.45 (7H, m), 7.00-7.12 (1H, m), 4.53-4.73 (2H, m), 4.17 (1H, dd, J=11.29, 4.88 Hz), 4.00-4.09 (1H, m), 3.89-3.99 (1H, m), 3.71 (3H, br. s.), 3.12 (3H, s).

Examples 74A and 74B

N-(4-(4-chloro-1H-imidazol-1-yl)-3-methoxyphenyl)-7-(4-fluorophenyl)-4-((S)-2-methylpyrrolidin-1-yl)-5,7-dihydrofuro[3,4-d]pyrimidin-2-amine Discrete Diasteriomers To a mixture of (S)-2-chloro-7-(4-fluorophenyl)-4-(2-methylpyrrolidin-1-yl)-5,7-dihydrofuro[3,4-d]pyrimidine (Preparation Me) (192.0 mg, 0.575 mmol), 4-(4-chloro-1H-imidazol-1-yl)-3-methoxyaniline (Preparation A) (154 mg, 0.690 mmol), XANTPHOS (33.3 mg, 0.058 mmol), Pd2(dba)$_3$ (26.3 mg, 0.029 mmol), and Cs$_2$CO$_3$ (562 mg, 1.726 mmol) was added Dioxane (2397 μL). The mixture was flushed with Nitrogen and placed in a capped vial and heated at 100° C. overnight.

Cooled to rt and diluted with EtOAc. Filtered through a Celite® plug and rotovaped. The residue was placed on Silica Gel and eluted with an EtOAc/Hex gradient to obtain (S)—N-(4-(4-chloro-1H-imidazol-1-yl)-3-methoxyphenyl)-7-(4-fluorophenyl)-4-(2-methylpyrrolidin-1-yl)-5,7-dihydrofuro[3,4-d]pyrimidin-2-amine (189 mg, 0.363 mmol, 63.1% yield) as a diasteriomeric mixture. The diasteriomers were separated by chiral SFC chromatography (Chiralcel OJ column, 40% MeOH (0.1% DEA) in CO$_2$) to provide Examples 74A and 74B.

74A: LC-MS (M+H)$^+$=521.2. $^1$H NMR (500 MHz, CDCl$_3$) δ ppm 7.60 (1H, d, J=1.53 Hz), 7.50 (1H, d, J=1.53 Hz), 7.35-7.41 (2H, m), 7.00-7.10 (4H, m), 6.93-6.99 (2H, m), 5.82 (1H, t, J=2.44 Hz), 5.42-5.48 (1H, m), 5.35-5.40

(1H, m), 5.29 (1H, s), 3.72-3.79 (1H, m), 3.68 (3H, s), 3.55-3.63 (1H, m), 1.97-2.14 (3H, m), 1.71-1.76 (1H, m), 1.26 (3H, d, J=6.41 Hz).

Example 75

$N^2$-(4-(4-chloro-1H-imidazol-1-yl)-3-methoxyphenyl)-$N^4$-ethyl-7-(4-fluorophenyl)-5,7-dihydrofuro[3,4-d]pyrimidine-2,4-diamine

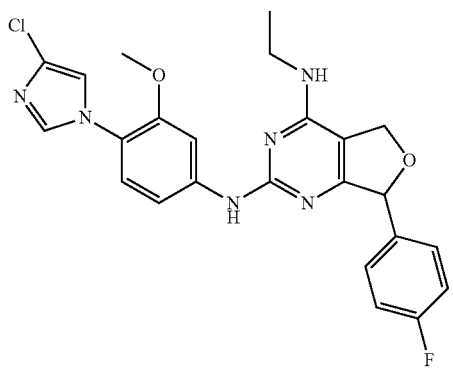 [SMILES: CCNc1nc(Nc2ccc(-n3cnc(Cl)c3)c(OC)c2)nc2c1COC2c1ccc(F)cc1]

To a solution of 2-chloro-N-ethyl-7-(4-fluorophenyl)-5,7-dihydrofuro[3,4-d]pyrimidin-4-amine (Preparation Mb) in Dioxane (619 µL) and Water (124 µL) was added 4-(4-chloro-1H-imidazol-1-yl)-3-methoxyaniline (Preparation A) (29.1 mg, 0.130 mmol), Tris(dibenzylideneacetone)dipalladium(0) (59.5 mg, 0.065 mmol), 9,9-Dimethyl-4,5-bis(diphenylphosphino)xanthene (75 mg, 0.130 mmol), and $Na_2CO_3$ (20.66 mg, 0.195 mmol). The resulting mixture was brought to 110° C. in a sealed tube and stirred overnight The reaction mixture was then diluted with EtOAc (10 mL), washed with water (5 mL), brine (5 mL), dried over $MgSO_4$, filtered and concentrated in vacuo. Purification by flash chromatography (Silica, MeOH/$CHCl_3$) removed the Xanthene ligand as to not have it ppt out on the prep column. Purification of the resulting oil by prep HPLC (C18, 50×250 mm, MeOH/$H_2O$/TFA) gave $N^2$-(4-(4-chloro-1H-imidazol-1-yl)-3-methoxyphenyl)-$N^4$-ethyl-7-(4-fluorophenyl)-5,7-dihydrofuro[3,4-d]pyrimidine-2,4-diamine, TFA (16.94 mg, 0.028 mmol, 21.91% yield) as a clear glass. LC-MS (M+H)$^+$=481.0. $^1$H NMR (500 MHz, $CDCl_3$) δ ppm 7.86 (1H, d, J=1.53 Hz), 7.56 (1H, d, J=2.14 Hz), 7.43-7.49 (2H, m), 7.40 (1H, d, J=8.85 Hz), 7.37 (1H, d, J=1.22 Hz), 7.21 (1H, dd, J=8.55, 2.14 Hz), 7.17 (2H, t, J=8.70 Hz), 6.10 (1H, t, J=3.20 Hz), 5.17 (1H, dd, J=11.44, 3.81 Hz), 5.04 (1H, dd, J=11.60, 2.14 Hz), 3.86 (3H, s), 3.66 (2H, q, J=7.32 Hz), 1.32 (3H, t, J=7.32 Hz).

Example 75A $N^2$-(4-(4-chloro-1H-imidazol-1-yl)-3-methoxyphenyl)-$N^4$-ethyl-7-(4-fluorophenyl)-5,7-dihydrofuro[3,4-d]pyrimidine-2,4-diamine

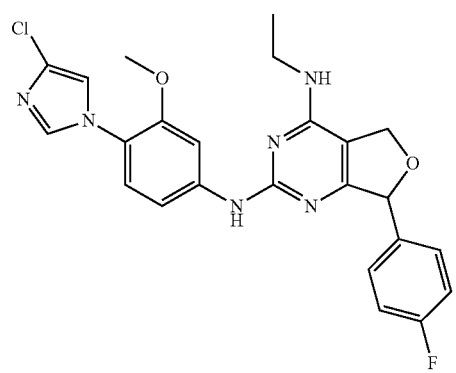

Enantiomer A of Example 75

$N^2$-(4-(4-chloro-1H-imidazol-1-yl)-3-methoxyphenyl)-$N^4$-ethyl-7-(4-fluorophenyl)-5,7-dihydrofuro[3,4-d]pyrimidine-2,4-diamine (Example 75) was separated by multiple chiral SFC injections (OJ-H 30×250 mm, 5 µM, 35% MeOH (0.1% DEA)/$CO_2$) to give $N^2$-(4-(4-chloro-1H-imidazol-1-yl)-3-methoxyphenyl)-$N^4$-ethyl-7-(4-fluorophenyl)-5,7-dihydrofuro[3,4-d]pyrimidine-2,4-diamine (first to elute, enantiomer A) (20.7 mg, 0.043 mmol, 10.71% yield) as an off-white, scrapable foam. LC-MS (M+H)$^+$=481.0. $^1$H NMR (500 MHz, MeOD) δ ppm 7.87 (1H, d, J=2.14 Hz), 7.68 (1H, d, J=1.22 Hz), 7.36-7.42 (2H, m), 7.22 (1H, d, J=1.53 Hz), 7.13-7.17 (1H, m), 7.04-7.11 (3H, m), 5.79 (1H, d, J=2.14 Hz), 5.09-5.15 (1H, m), 4.96-5.03 (1H, m), 3.71 (3H, s), 3.57

(2H, q, J=7.02 Hz), 1.25-1.30 (3H, m). The absolute stereochemistry of Example 75A was not determined.

Example 75B

N²-(4-(4-chloro-1H-imidazol-1-yl)-3-methoxyphenyl)-N⁴-ethyl-7-(4-fluorophenyl)-5,7-dihydrofuro[3,4-d]pyrimidine-2,4-diamine

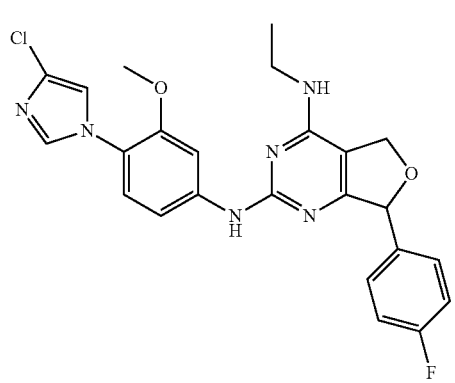

Enantiomer B of Example 75

N²-(4-(4-chloro-1H-imidazol-1-yl)-3-methoxyphenyl)-N⁴-ethyl-7-(4-fluorophenyl)-5,7-dihydrofuro[3,4-d]pyrimidine-2,4-diamine (Example 75) was separated by multiple chiral SFC injections (OJ-H 30×250 mm, 5 µM, 35% MeOH (0.1% DEA)/CO₂) to give N²-(4-(4-chloro-1H-imidazol-1-yl)-3-methoxyphenyl)-N⁴-ethyl-7-(4-fluorophenyl)-5,7-dihydrofuro[3,4-d]pyrimidine-2,4-diamine (second to elute, enantiomer B) (19.6 mg, 0.041 mmol, 10.14% yield) as an off-white, scrapable foam. LC-MS (M+H)⁺=481.0. ¹H NMR (500 MHz, MeOD) δ ppm 7.87 (1H, s), 7.68 (1H, s), 7.40 (2H, td, J=5.80, 2.44 Hz), 7.23 (1H, s), 7.14-7.18 (1H, m), 7.06-7.12 (3H, m), 5.80 (1H, br. s.), 5.13 (1H, dd, J=10.99, 3.05 Hz), 5.00 (1H, d, J=10.99 Hz), 3.72 (3H, s), 3.57 (2H, q, J=7.02 Hz), 1.25-1.31 (3H, m). The absolute stereochemistry of Example 75B was not determined.

Example 76

N-(4-(4-chloro-1H-imidazol-1-yl)-3-methoxyphenyl)-7-(4-fluorophenyl)-4-((S)-3-fluoropyrrolidin-1-yl)-5,7-dihydrofuro[3,4-d]pyrimidin-2-amine

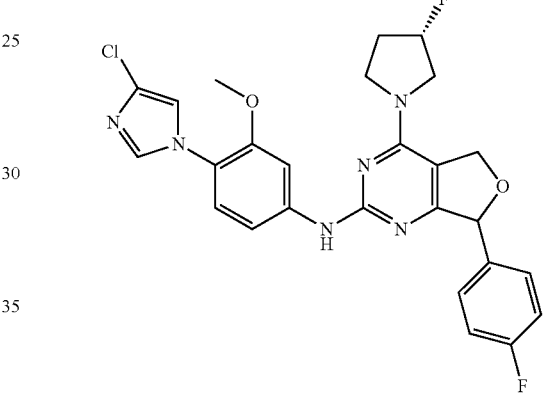

Diastereomer 1
Racemic 2-chloro-7-(4-fluorophenyl)-4-((S)-3-fluoropyrrolidin-1-yl)-5,7-dihydrofuro[3,4-d]pyrimidine (Preparation Mc1) (49 mg, 0.145 mmol) and 4-(4-chloro-1H-imidazol-1-yl)-3-methoxyaniline (Preparation A) (32.4 mg, 0.145 mmol) were combined and purified as per Example 26 to give N-(4-(4-chloro-1H-imidazol-1-yl)-3-methoxyphenyl)-7-(4-fluorophenyl)-4-((S)-3-fluoropyrrolidin-1-yl)-5,7-dihydrofuro[3,4-d]pyrimidin-2-amine, TFA (diastereomer 1, racemate) (24.18 mg, 0.038 mmol, 26.1% yield) as a slightly yellow glass. LC-MS (M+H)⁺=525.1. ¹H NMR (500 MHz, MeOD) δ ppm 7.92 (1H, d, J=1.53 Hz), 7.54 (1H, br. s.), 7.47-7.52 (2H, m), 7.38-7.42 (2H, m), 7.28 (1H, dd, J=8.55, 2.14 Hz), 7.15-7.21 (2H, m), 6.07-6.11 (1H, m), 5.62 (1H, dd, J=10.99, 3.97 Hz), 5.35-5.53 (2H, m), 4.09-4.23 (2H, m), 3.89-4.08

(2H, m), 3.87 (3H, s), 2.44 (1H, br. s.), 2.12-2.38 (1H, m). The relative stereochemistry of Example 76 was not determined.

Example 77

N-(4-(4-chloro-1H-imidazol-1-yl)-3-methoxyphenyl)-7-(4-fluorophenyl)-4-((S)-3-fluoropyrrolidin-1-yl)-5,7-dihydrofuro[3,4-d]pyrimidin-2-amine

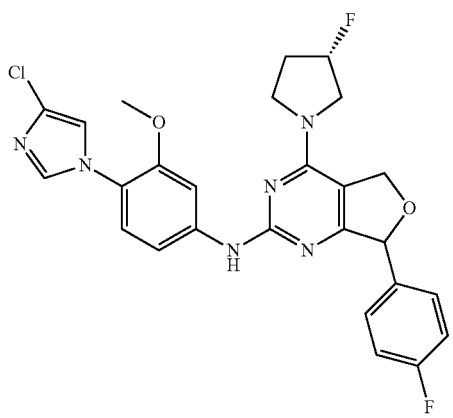

Diastereomer 2
Racemic 2-chloro-7-(4-fluorophenyl)-4-((S)-3-fluoropyrrolidin-1-yl)-5,7-dihydrofuro[3,4-d]pyrimidine (Preparation Mc2) (40 mg, 0.118 mmol) and 4-(4-chloro-1H-imidazol-1-yl)-3-methoxyaniline (Preparation A) (26.5 mg, 0.118 mmol) were combined and purified as per Example 26 to give N-(4-(4-chloro-1H-imidazol-1-yl)-3-methoxyphenyl)-7-(4-fluorophenyl)-4-((S)-3-fluoropyrrolidin-1-yl)-5,7-dihydrofuro[3,4-d]pyrimidin-2-amine, TFA (diastereomer 2, racemate) (25.75 mg, 0.040 mmol, 34.0% yield) as a slightly yellow glass. LC-MS (M+H)$^+$=525.1. $^1$H NMR (500 MHz, MeOD) δ ppm 7.88 (1H, d, J=1.22 Hz), 7.54 (1H, s), 7.46-7.51 (2H, m), 7.36-7.42 (2H, m), 7.16-7.25 (3H, m), 6.08 (1H, t, J=3.20 Hz), 5.52-5.60 (1H, m), 5.36-5.52 (2H, m), 4.02-4.20 (2H, m), 4.00 (2H, s), 3.88-3.99 (1H, m), 3.86 (3H, s), 2.37-2.51 (1H, m), 2.14-2.37 (1H, m). The relative stereochemistry of Example 77 was not determined.

Example 78

N$^4$-ethyl-N$^2$-(3-fluoro-4-(5-methyl-1H-1,2,4-triazol-1-yl)phenyl)-7-(4-fluorophenyl)-5,7-dihydrofuro[3,4-d]pyrimidine-2,4-diamine

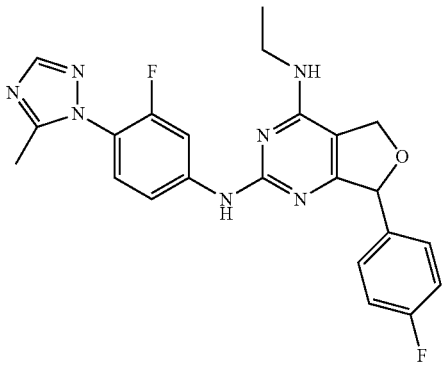 [SMILES: CCNc1nc(Nc2ccc(-n3ncnc3C)c(F)c2)nc2c1COC2c1ccc(F)cc1]

2-chloro-N-ethyl-7-(4-fluorophenyl)-5,7-dihydrofuro[3,4-d]pyrimidin-4-amine (Preparation Mb) and 3-fluoro-4-(5-methyl-1H-1,2,4-triazol-1-yl)aniline (Preparation C) (51.6 mg, 0.268 mmol) were combined and purified as per Example 75 to give N$^4$-ethyl-N$^2$-(3-fluoro-4-(5-methyl-1H-1,2,4-triazol-1-yl)phenyl)-7-(4-fluorophenyl)-5,7-dihydrofuro[3,4-d]pyrimidine-2,4-diamine, TFA (64.1 mg, 0.114 mmol, 42.4% yield) as a white solid. LC-MS (M+H)$^+$=450.0. $^1$H NMR (500 MHz, MeOD) δ ppm 8.08 (1H, s), 7.96-8.02 (1H, m), 7.42-7.53 (4H, m), 7.17 (2H, t, J=8.85 Hz), 6.04 (1H, t, J=3.05 Hz), 5.18 (1H, dd, J=11.44, 3.51 Hz), 5.02-5.08 (1H, m), 3.64 (2H, q, J=7.12 Hz), 2.42 (3H, s), 1.34 (3H, t, J=7.17 Hz).

Example 78A

N$^4$-ethyl-N$^2$-(3-fluoro-4-(5-methyl-1H-1,2,4-triazol-1-yl)phenyl)-7-(4-fluorophenyl)-5,7-dihydrofuro[3,4-d]pyrimidine-2,4-diamine

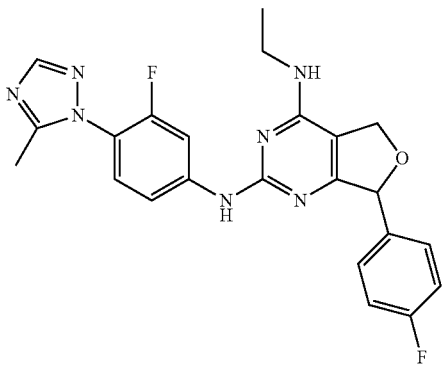

Enantiomer A of Example 78

N$^4$-ethyl-N$^2$-(3-fluoro-4-(5-methyl-1H-1,2,4-triazol-1-yl)phenyl)-7-(4-fluorophenyl)-5,7-dihydrofuro[3,4-d]pyrimidine-2,4-diamine (Example 78) was separated by multiple chiral SFC injections (OJ-H 30×250 mm, 5 μM, 30% MeOH (0.1% DEA)/CO$_2$) to give N$^4$-ethyl-N$^2$-(3-fluoro-4-(5-methyl-1H-1,2,4-triazol-1-yl)phenyl)-7-(4-fluorophenyl)-5,7-dihydrofuro[3,4-d]pyrimidine-2,4-diamine (first to elute, enantiomer A) (25.8 mg, 0.057 mmol, 21.40% yield) as a white solid. LC-MS (M+H)$^+$=450.0. $^1$H NMR (500 MHz, MeOD) δ ppm 8.15 (1H, dd, J=13.89, 2.29 Hz), 8.03 (1H, s), 7.39-7.47 (3H, m), 7.33 (1H, t, J=8.55 Hz), 7.07-7.12 (2H, m), 5.84 (1H, t, J=2.59 Hz), 5.14 (1H, dd, J=11.29, 3.36 Hz), 5.03 (1H, dd, J=11.14, 1.68 Hz), 3.53-3.61 (2H, m), 2.39 (3H, s), 1.27-1.32 (3H, m). The absolute stereochemistry of Example 78A was not determined.

Example 78B

N$^4$-ethyl-N$^2$-(3-fluoro-4-(5-methyl-1H-1,2,4-triazol-1-yl)phenyl)-7-(4-fluorophenyl)-5,7-dihydrofuro[3,4-d]pyrimidine-2,4-diamine Enantiomer B of Example 78

N$^4$-ethyl-N$^2$-(3-fluoro-4-(5-methyl-1H-1,2,4-triazol-1-yl)phenyl)-7-(4-fluorophenyl)-5,7-dihydrofuro[3,4-d]pyrimidine-2,4-diamine (Example 78) was separated by multiple chiral SFC injections (OJ-H 30×250 mm, 5 μM, 30% MeOH (0.1% DEA)/CO$_2$) to give N$^4$-ethyl-N$^2$-(3-fluoro-4-(5-methyl-1H-1,2,4-triazol-1-yl)phenyl)-7-(4-fluorophenyl)-5,7-dihydrofuro[3,4-d]pyrimidine-2,4-diamine (second to elute, enantiomer B) (24.6 mg, 0.055 mmol, 20.40% yield) as a white solid. LC-MS (M+H)$^+$=450.0. $^1$H NMR (500 MHz, CDCl$_3$) δ ppm 7.99-8.06 (1H, m), 7.94 (1H, s), 7.36-7.42 (2H, m), 7.23-7.29 (1H, m), 7.12 (1H, dd, J=8.55, 1.83 Hz), 7.02-7.08 (2H, m), 5.86 (1H, d, J=2.44 Hz), 5.01-5.21 (2H, m), 3.50-3.60 (2H, m), 2.40 (3H, s), 1.27-1.33 (3H, m). The absolute stereochemistry of Example 78B was not determined.

Example 79A

N$^2$-(4-(4-chloro-1H-imidazol-1-yl)-3-methoxyphenyl)-7-(4-fluorophenyl)-N$^4$-methyl-5,7-dihydrofuro[3,4-d]pyrimidine-2,4-diamine

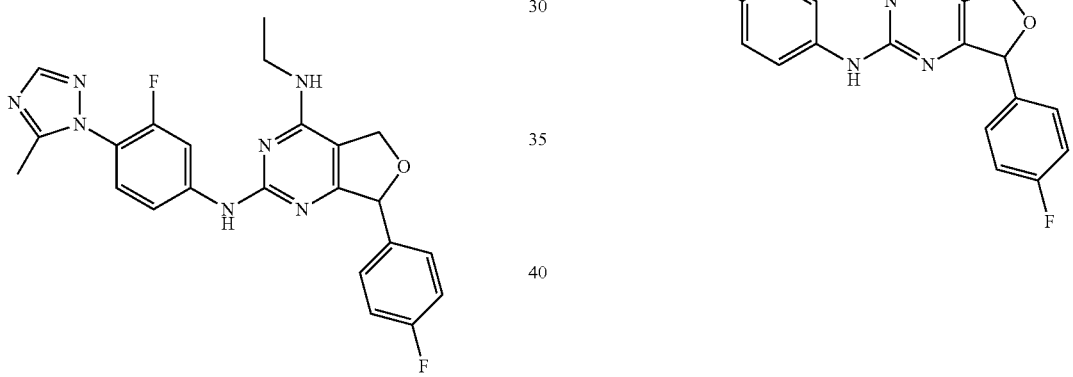

Enantiomer A 2-chloro-7-(4-fluorophenyl)-N-methyl-5,7-dihydrofuro[3,4-d]pyrimidin-4-amine (Preparation Ma) (149 mg, 0.533 mmol) and 4-(4-chloro-1H-imidazol-1-yl)-3-methoxyaniline (Preparation A) (119 mg, 0.533 mmol) were combined and purified as per Example 75 to give the racemate N$^2$-(4-(4-chloro-1H-imidazol-1-yl)-3-methoxyphenyl)-7-(4-fluorophenyl)-N$^4$-methyl-5,7-dihydrofuro[3,4-d]pyrimidine-2,4-diamine which was separated by multiple chiral SFC injections (OJ-H 30×250 mm, 5 μM, 35% MeOH (0.1% DEA)/CO$_2$) to give N$^2$-(4-(4-chloro-1H-imidazol-1-yl)-3-methoxyphenyl)-7-(4-fluorophenyl)-N$^4$-methyl-5,7-dihydrofuro[3,4-d]pyrimidine-2,4-diamine (first to elute, enantiomer A) (18.3 mg, 0.039 mmol, 7.36% yield) as a white scrapable foam. LC-MS (M+H)$^+$=467.0. $^1$H NMR (500 MHz, MeOD) δ ppm 7.89-7.94 (1H, m), 7.65-7.69 (1H, m), 7.36-7.42 (2H, m), 7.20-7.24 (1H, m), 7.13-7.18 (1H, m), 7.03-7.12 (3H, m), 5.79 (1H, br. s.), 5.08-5.16 (1H, m), 4.95-

5.03 (1H, m), 3.68-3.73 (3H, m), 3.02-3.07 (3H, m). The absolute stereochemistry of Example 79A was not determined.

Example 79B

N²-(4-(4-chloro-1H-imidazol-1-yl)-3-methoxyphenyl)-7-(4-fluorophenyl)-N⁴-methyl-5,7-dihydrofuro[3,4-d]pyrimidine-2,4-diamine 2-chloro-7-(4-fluorophenyl)-N-methyl-5,7-dihydrofuro[3,4-d]pyrimidin-4-amine (Preparation Ma) (149 mg, 0.533 mmol) and 4-(4-chloro-1H-imidazol-1-yl)-3-methoxyaniline (Preparation A) (119 mg, 0.533 mmol) were combined and purified as per Example 75 to give the racemate N²-(4-(4-chloro-1H-imidazol-1-yl)-3-methoxyphenyl)-7-(4-fluorophenyl)-N⁴-methyl-5,7-dihydrofuro[3,4-d]pyrimidine-2,4-diamine which was separated by multiple chiral SFC injections (OJ-H 30×250 mm, 5 µM, 35% MeOH (0.1% DEA)/CO₂) to give N²-(4-(4-chloro-1H-imidazol-1-yl)-3-methoxyphenyl)-7-(4-fluorophenyl)-N⁴-methyl-5,7-dihydrofuro[3,4-d]pyrimidine-2,4-diamine (second to elute, enantiomer B) (22.1 mg, 0.047 mmol, 8.89% yield) as a slightly yellow scrapable foam. LC-MS (M+H)⁺=467.0. ¹H NMR (500 MHz, MeOD) δ ppm 7.92 (1H, d, J=2.14 Hz), 7.68 (1H, d, J=1.53 Hz), 7.39 (2H, dd, J=8.70, 5.34 Hz), 7.22 (1H, d, J=1.53 Hz), 7.15 (1H, d, J=8.55 Hz), 7.04-7.11 (3H, m), 5.79 (1H, br. s.), 5.12 (1H, dd, J=10.99, 3.36 Hz), 4.99 (1H, d, J=10.99 Hz), 3.70 (3H, s), 3.05 (3H, s). The absolute stereochemistry of Example 79B was not determined.

Example 80

N-(4-(4-chloro-1H-imidazol-1-yl)-3-methoxyphenyl)-4-(3,3-difluoroazetidin-1-yl)-7-(4-fluorophenyl)-5,7-dihydrofuro[3,4-d]pyrimidin-2-amine

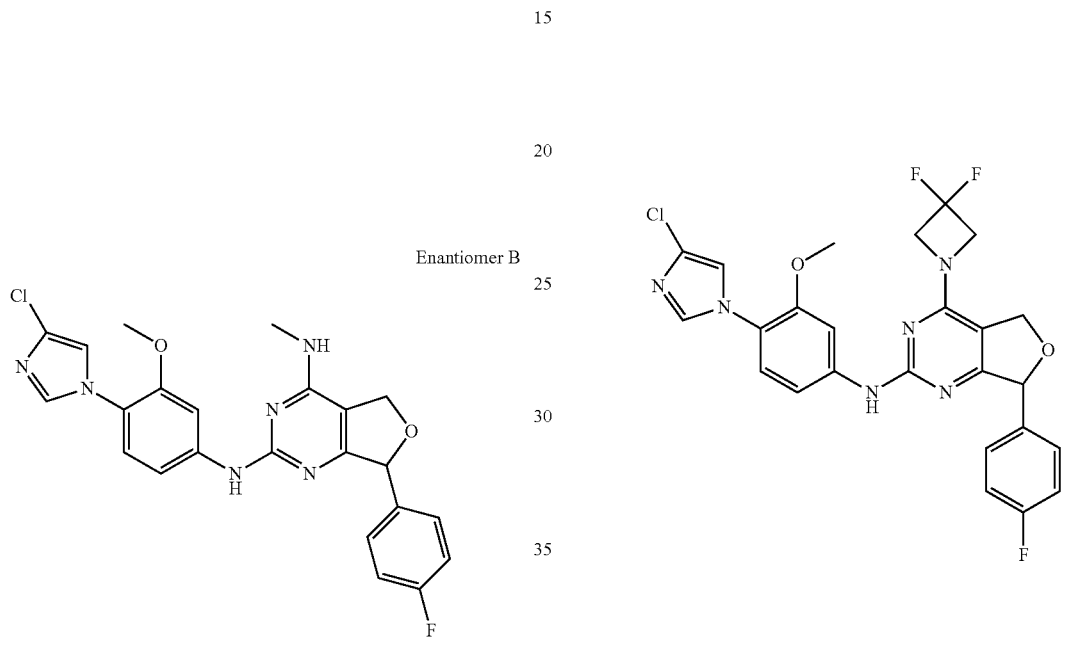

A solution of Preparation A (0.102 g, 0.560 mmol), Preparation Ma (0.160 g, 0.560 mmol), Na₂CO₃ (0.119 g, 0.110 mmol) and xantphos (0.325 g, 0.560 mmol) in dioxane/water (9:1) was purged with argon for 1 h at room temperature. Pd(dba)₃ (0.310 g, 0.21 mmol) was added to the reaction mixture and the resulting solution was purged for another 1 h. The reaction mass was heated at 110° C. for 24 h. The reaction mass was filtered through celite bed and washed with ethyl acetate. The filtrate was evaporated under reduced pressure and the residue was diluted with water. The aqueous solution was extracted with ethyl acetate (75 mL×2). The combined organic layer was washed with brine solution (50 mL), dried over anhydrous Na₂SO₄ and evaporated under reduced pressure to get crude compound. The crude compound was purified by column chromatography (Silica gel, 60-120 mesh) using 21% ethyl acetate in pet-ether as mobile phase to give N-(4-(4-chloro-1H-imidazol-1-yl)-3-methoxyphenyl)-4-(3,3-difluoroazetidin-1-yl)-7-(4-fluorophenyl)-5,7-dihydrofuro[3,4-d]pyrimidin-2-amine (0.90 g, 40%) as off-white solid. LC-MS (M+H)⁺=529.2. ¹H NMR (400 MHz, DMSO-d6): δ ppm 9.6 (1H, s), 7.99 (1H, s), 7.98 (1H, s), 7.76-7.41 (3H, m), 7.23-7.13 (4H, m), 5.87 (1H, s), 5.33 (1H, dd, J=11.1, 3.2 Hz), 5.17 (1H, dd, J=11.1, 3.2), 4.67 (4H, m), 3.72 (3H, s).

The racemic mixture was separated by chiral chromatography to afford the enantiomers Example 80A and 80B, which had identical spectral data.

Example 81

N2-(4-(4-chloro-1H-imidazol-1-yl)-3-methoxyphenyl)-N4-((R)-1-cyclopropylethyl)-7-(4-fluorophenyl)-5,7-dihydrofuro[3,4-d]pyrimidine-2,4-diamine, TFA

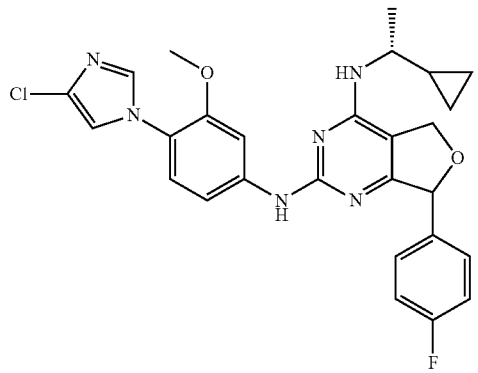 [SMILES: COc1cc(Nc2nc(N[C@H](C)C3CC3)c3c(n2)C(c2ccc(F)cc2)OC3)ccc1-n1cnc(Cl)c1]

Diasteriomeric Mixture 2-chloro-N—((R)-1-cyclopropylethyl)-7-(4-fluorophenyl)-5,7-dihydrofuro[3,4-d]pyrimidin-4-amine (Preparation Mf) was reacted as described in Example 112 with 4-(4-chloro-1H-imidazol-1-yl)-3-methoxyaniline (Preparation A) to give N2-(4-(4-chloro-1H-imidazol-1-yl)-3-methoxyphenyl)-N4-((R)-1-cyclopropylethyl)-7-(4-fluorophenyl)-5,7-dihydrofuro[3,4-d]pyrimidine-2,4-diamine, TFA as a mixture of 2 diasteriomers (Example 81). LC-MS (M+H)$^+$=521.3. $^1$H NMR (500 MHz, MeOD) δ ppm 7.82 (d, J=1.53 Hz, 1H) 7.44-7.51 (m, 3H) 7.38 (d, J=8.55 Hz, 1H) 7.35 (d, J=1.53 Hz, 1H) 7.14-7.22 (m, 3H) 6.08 (br. s., 1H) 5.21 (dd, J=11.60, 3.05 Hz, 1H) 5.07 (dd, J=11.44, 2.59 Hz, 1H) 3.84 (s, 3H) 3.30 (m, 1H) 1.38 (d, J=6.41 Hz, 3H) 1.06-1.13 (m, 1H) 0.59-0.66 (m, 1H) 0.54 (d, J=3.97 Hz, 1H) 0.37 (d, J=4.88 Hz, 1H) 0.28 (d, J=4.88 Hz, 1H).

Example 82

N2-(3-fluoro-4-(5-methyl-1H-1,2,4-triazol-1-yl)phenyl)-7-(4-fluorophenyl)-N4-methyl-5,7-dihydrofuro[3,4-d]pyrimidine-2,4-diamine, TFA

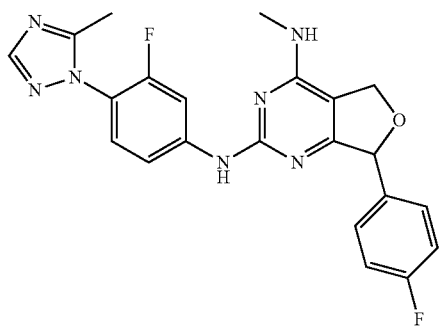 [SMILES: CNc1nc(Nc2ccc(-n3ncnc3C)c(F)c2)nc2c1COC2c1ccc(F)cc1]

2-chloro-7-(4-fluorophenyl)-N-methyl-5,7-dihydrofuro[3,4-d]pyrimidin-4-amine (Preparation Ma) was reacted as described in Example 112 with 3-fluoro-4-(5-methyl-1H-1,2,4-triazol-1-yl)aniline (Preparation C) to give N2-(3-fluoro-4-(5-methyl-1H-1,2,4-triazol-1-yl)phenyl)-7-(4-fluorophenyl)-N4-methyl-5,7-dihydrofuro[3,4-d]pyrimidine-2,4-diamine, TFA (Example 82). LC-MS (M+H)$^+$=436.1. $^1$H NMR (500 MHz, MeOD) δ ppm 8.16 (dd, J=13.89, 2.29 Hz, 1H) 8.03 (s, 1H) 7.38-7.47 (m, 3H) 7.34 (t, J=8.70 Hz, 1H) 7.05-7.14 (m, 2H) 5.85 (d, J=1.83 Hz, 1H) 5.16 (br. s., 1H) 5.04 (br. s., 1H) 3.07 (s, 3H) 2.39 (s, 3H).

The racemic mixture was separated by chiral chromatography to afford the enantiomers Example 82A and 82B as free amines, which had identical spectral data.

Example 83

N-(4-(4-chloro-1H-imidazol-1-yl)-3-methoxyphenyl)-7-(4-fluorophenyl)-4-((R)-3-fluoropyrrolidin-1-yl)-5,7-dihydrofuro[3,4-d]pyrimidin-2-amine, 2 TFA

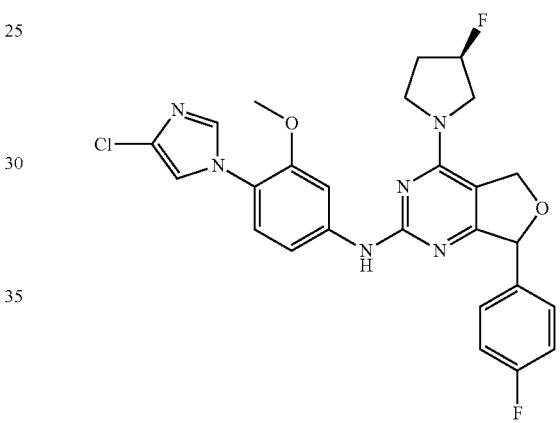

Diasteriomeric Mixture 2-chloro-7-(4-fluorophenyl)-4-((R)-3-fluoropyrrolidin-1-yl)-5,7-dihydrofuro[3,4-d]pyrimidine (Preparation Mg) was reacted as described in Example 112 with 4-(4-chloro-1H-imidazol-1-yl)-3-methoxyaniline (Preparation A) to give N-(4-(4-chloro-1H-imidazol-1-yl)-3-methoxyphenyl)-7-(4-fluorophenyl)-4-((R)-3-fluoropyrrolidin-1-yl)-5,7-dihydrofuro[3,4-d]pyrimidin-2-amine, 2 TFA as a mixture of two diasteriomers (Example 83). LC-MS (M+H)$^+$=525.1. $^1$H NMR (500 MHz, MeOD) δ ppm 7.83 (br. s., 1H) 7.57 (br. s., 1H) 7.43-7.52 (m, 2H) 7.32-7.41 (m, 2H) 7.22-7.29 (m, 1H) 7.10-7.22 (m, 2H) 6.00-6.11 (m, 1H) 5.38-5.50 (m, 3H) 4.10 (br. s., 2H) 3.90 (br. s., 2H) 2.31-2.51 (m, 2H).

The mixture of two diasteriomers was separated by chiral chromatography to afford two diasteriomers Example 83A and 83B as free amines Example 83A: LC-MS (M+H)$^+$=525.2. $^1$H NMR (500 MHz, MeOD) δ ppm 7.80 (d, J=1.83 Hz, 1H) 7.69 (d, J=1.53 Hz, 1H) 7.43 (dd, J=8.70, 5.34 Hz, 2H) 7.23 (d, J=1.22 Hz, 1H) 7.04-7.20 (m, 4H) 5.77 (br. s., 1H) 5.50-5.59 (m, 1H) 5.27-5.39 (m, 2H) 4.00 (d, J=11.90 Hz, 1H) 3.82-3.96 (m, 2H) 3.63-3.82 (m, 4H) 2.26-2.42 (m, 2H).

Example 83B: LC-MS (M+H)$^+$=525.2. $^1$H NMR (500 MHz, MeOD) δ ppm 7.81 (d, J=1.83 Hz, 1H) 7.69 (d, J=1.53 Hz, 1H) 7.39-7.47 (m, 2H) 7.24 (d, J=1.53 Hz, 1H) 7.16-7.21 (m, 1H) 7.05-7.16 (m, 3H) 5.80 (t, J=2.59 Hz, 1H) 5.51 (dd, J=10.38, 3.05 Hz, 1H) 5.36-5.46 (m, 2H) 3.91 (m, 2H) 3.66-3.86 (m, 5H) 2.23-2.42 (m, 2H).

Example 84

N-(4-(4-chloro-1H-imidazol-1-yl)-3-methoxyphenyl)-4-((2S,6R)-2,6-dimethylmorpholino)-7-(4-fluorophenyl)-5,7-dihydrofuro[3,4-d]pyrimidin-2-amine, 2 TFA

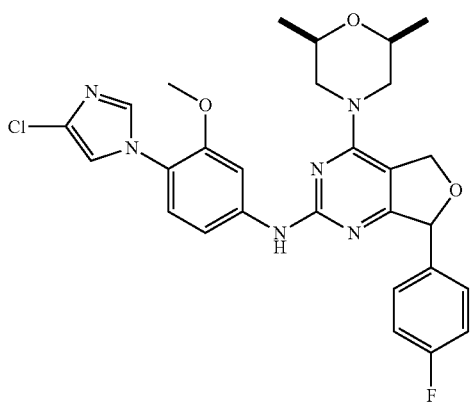 [SMILES: COc1cc(Nc2nc3c(c(N4C[C@@H](C)O[C@@H](C)C4)n2)COC3c2ccc(F)cc2)ccc1-n1cnc(Cl)c1]

2-chloro-4-((2S,6R)-2,6-dimethylmorpholino)-7-(4-fluorophenyl)-5,7-dihydrofuro[3,4-d]pyrimidine (Preparation Mh) was reacted as described in Example 112 with 4-(4-chloro-1H-imidazol-1-yl)-3-methoxyaniline (Preparation A) to give N-(4-(4-chloro-1H-imidazol-1-yl)-3-methoxyphenyl)-4-((2S,6R)-2,6-dimethylmorpholino)-7-(4-fluorophenyl)-5,7-dihydrofuro[3,4-d]pyrimidin-2-amine, 2 TFA (Example 84). LC-MS (M+H)$^+$=551.2. $^1$H NMR (400 MHz, MeOD) δ ppm 7.80 (d, J=1.51 Hz, 1H) 7.55 (d, J=2.27 Hz, 1H) 7.35-7.46 (m, 2H) 7.23-7.33 (m, 2H) 7.01-7.18 (m, 3H) 5.91 (t, J=2.77 Hz, 1H) 5.42 (dd, J=10.45, 3.40 Hz, 1H) 5.28 (dd, J=10.32, 2.27 Hz, 1H) 4.16 (br. s., 2H) 3.60-3.78 (m, 5H) 2.81 (ddd, J=13.41, 10.51, 3.53 Hz, 2H) 1.21 (d, J=6.04 Hz, 6H).

The racemic mixture was separated by chiral chromatography to afford the enantiomers Example 84A and 84B as free amines LC-MS (M+H)$^+$=551.2. $^1$H NMR (500 MHz, MeOD) δ ppm 7.77 (d, J=2.14 Hz, 1H) 7.69 (d, J=1.53 Hz, 1H) 7.35-7.50 (m, 2H) 7.24 (d, J=1.53 Hz, 1H) 7.18 (d, J=8.55 Hz, 1H) 7.10 (t, J=8.70 Hz, 2H) 7.05 (dd, J=8.55, 2.14 Hz, 1H) 5.80 (d, J=2.44 Hz, 1H) 5.42 (dd, J=10.38, 3.05 Hz, 1H) 5.28 (dd, J=10.38, 1.83 Hz, 1H) 4.16 (br. s., 2H) 3.61-3.76 (m, 5H) 2.60-2.80 (m, 2H) 1.23 (d, J=6.41 Hz, 6H).

Example 85

N2-(4-(4-chloro-1H-imidazol-1-yl)-3-methoxyphenyl)-N4-methyl-8-phenyl-6,8-dihydro-5H-pyrano[3,4-d]pyrimidine-2,4-diamine

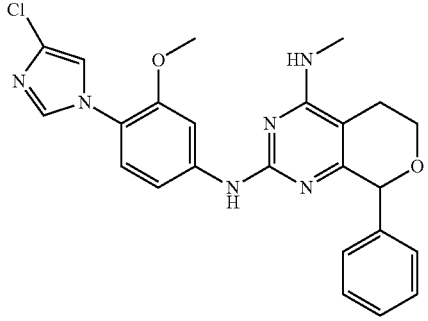 [SMILES: CNc1nc(Nc2ccc(-n3cnc(Cl)c3)c(OC)c2)nc2c1CCOC2c1ccccc1]

A solution of Preparation A (0.168 g, 0.75 mmol), Preparation Na (0.23 g, 0.834 mmol), Na$_2$CO$_3$ (0.176 g, 1.6 mmol) and xantphos (0.482 g, 0.834 mmol) in dioxane/water (9:1) was purged with argon for 1 h at room temperature. Pd(dba)$_3$ (0.38 g, 0.417 mmol) was added to the reaction mixture and the resulting solution was purged for another 1 h. The reaction mass was heated at 110° C. for 24 h. The reaction mass was filtered through celite bed and washed with ethyl acetate. The filtrate was evaporated under reduced pressure and the residue was diluted with water. The aqueous solution was extracted with ethyl acetate (75 mL×2). The combined organic layer was washed with brine solution (50 mL), dried over anhydrous Na$_2$SO$_4$ and evaporated under reduced pressure to get crude compound. The crude compound was purified by prep-HPLC (aqueous 0.1% ammonium acetate in acetonitrile) to give N2-(4-(4-chloro-1H-imidazol-1-yl)-3-methoxyphenyl)-N4-methyl-8-phenyl-6,8-dihydro-5H-pyrano[3,4-d]pyrimidine-2,4-diamine (0.140 g, 36.2%) as off-white solid. LC-MS (M+H)$^+$=463.2. $^1$H NMR (400 MHz, DMSO-d6): δ ppm 9.06 (1H, s), 7.96 (1H, s), 7.72 (1H, s), 7.4 (1H, s), 7.36-7.30 (5H, m), 7.13 (2H, m), 6.94 (1H, m), 5.43

(1H, s), 3.95 (1H, m), 3.81 (1H, s), 3.53 (3H, s), 2.97 (3H, d, J=4.4 Hz), 2.52 (1H, m), 2.45 (1H, m).

Example 86

N2-(3-fluoro-4-(3-methyl-1H-1,2,4-triazol-1-yl)phenyl)-N4-methyl-8-phenyl-6,8-dihydro-5H-pyrano[3,4-d]pyrimidine-2,4-diamine

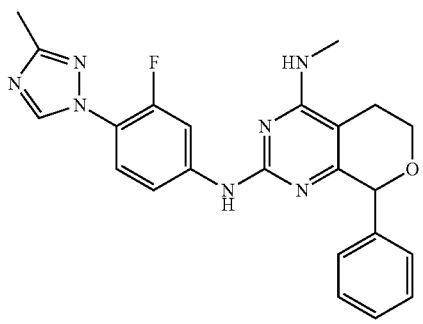 [SMILES: CNc1nc(Nc2ccc(-n3cnc(C)n3)c(F)c2)nc2c1CCOC2c1ccccc1]

A solution of Preparation B (0.119 g, 0.62 mmol), Preparation Na (0.19 g, 0.68 mmol), Na$_2$CO$_3$ (0.146 g, 1.37 mmol) and xantphos (0.399 g, 0.689 mmol) in dioxane/water (9:1) was purged with argon for 1 h at room temperature. Pd(dba)$_3$ (0.315 g, 0.344 mmol) was added to the reaction mixture and the resulting solution was purged for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (75 mL×2). The combined organic layer was washed with brine solution (50 mL), dried over anhydrous Na$_2$SO$_4$ and evaporated under reduced pressure to get crude compound. The crude compound was purified by prep-HPLC (aqueous 0.1% ammonium acetate in acetonitrile) to give N$^2$-(3-fluoro-4-(3-methyl-1H-1,2,4-triazol-1-yl)phenyl)-N4-methyl-8-phenyl-6,8-dihydro-5H-pyrano[3,4-d]pyrimidine-2,4-diamine (0.120 g, 30%) as off-white solid. LC-MS (M+H)$^+$=432.2. $^1$H NMR (400 MHz, DMSO-d6): δ ppm 9.33 (1H, s), 8.68 (1H, s), 8.03 (1H, m), 7.42-7.24 (7H, m), 6.98 (1H, bs), 5.44 (1H, s), 4.06 (1H, m), 3.84 (1H, m), 2.95 (3H, d, J=4.4 Hz), 2.59 (1H, m), 2.44 (1H, m), 2.34 (3H, s).

Example 87

N2-(3-fluoro-4-(5-methyl-1H-1,2,4-triazol-1-yl)phenyl)-N4-methyl-8-phenyl-6,8-dihydro-5H-pyrano[3,4-d]pyrimidine-2,4-diamine

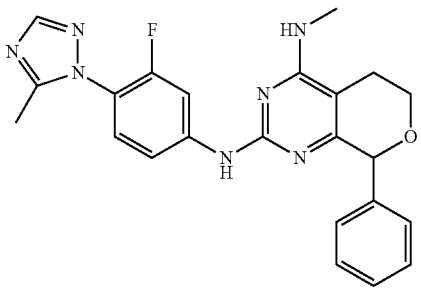 [SMILES: CNc1nc(Nc2ccc(-n3ncnc3C)c(F)c2)nc2c1CCOC2c1ccccc1]

A solution of Preparation C (0.119 g, 0.62 mmol), Preparation Na (0.19 g, 0.68 mmol), Na$_2$CO$_3$ (0.146 g, 1.37 mmol) and xantphos (0.399 g, 0.689 mmol) in dioxane/water (9:1) was purged with argon for 1 h at room temperature. Pd(dba)$_3$ (0.315 g, 0.344 mmol) was added to the reaction mixture and the resulting solution was purged for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (75 mL×2). The combined organic layer was washed with brine solution (50 mL), dried over anhydrous Na$_2$SO$_4$ and evaporated under reduced pressure to get crude compound. The crude compound was purified by prep-HPLC (aqueous 0.1% ammonium acetate in acetonitrile) to give N2-(3-fluoro-4-(5-methyl-1H-1,2,4-triazol-1-yl)phenyl)-N4-methyl-8-phenyl-6,8-dihydro-5H-pyrano[3,4-d]pyrimidine-2,4-diamine (0.130 g, 44%) as off-white solid. LC-MS (M+H)$^+$=432.2. $^1$H NMR (400 MHz, DMSO-d6): δ ppm 9.38 (1H, s), 8.04 (1H, s), 8.01 (1H, s), 7.44 (1H, m), 7.34-7.27 (6H, m), 6.99 (1H, bs), 5.43

(1H, s), 4.06 (1H, m), 3.83 (1H, m), 2.95 (3H, d, J=4.4.0 Hz), 2.51 (1H, m), 2.44 (1H, m), 2.27 (3H, s).

Example 88

N2-(4-(4-chloro-1H-imidazol-1-yl)-3-methoxyphenyl)-N4-ethyl-8-(4-fluorophenyl)-6,8-dihydro-5H-pyrano[3,4-d]pyrimidine-2,4-diamine

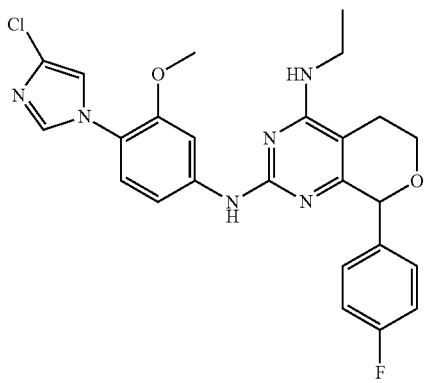 [SMILES: CCNc1nc(Nc2ccc(-n3cnc(Cl)c3)c(OC)c2)nc2c1CCOC2c1ccc(F)cc1]

A solution of Preparation A (0.09 g, 0.38 mmol), Preparation Oa (0.15 g, 0.48 mmol), Na₂CO₃ (0.103 g, 0.97 mmol) and xantphos (0.282 g, 0.41 mmol) in dioxane/water (9:1) was purged with argon for 1 h at room temperature. Pd(dba)₃ (0.270 g, 0.24 mmol) was added to the reaction mixture and the resulting solution was purged for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (75 mL×2). The combined organic layer was washed with brine solution (50 mL), dried over anhydrous Na₂SO₄ and evaporated under reduced pressure to get crude compound. The crude compound was purified by column chromatography (60-120 mesh) using 35% ethyl acetate in pet-ether as mobile phase to give N2-(4-(4-chloro-1H-imidazol-1-yl)-3-methoxyphenyl)-N4-ethyl-8-(4-fluorophenyl)-6,8-dihydro-5H-pyrano[3,4-d]pyrimidine-2,4-diamine (0.90 g, 55%) as off-white solid. LC-MS (M+H)⁺=495.2. ¹H NMR (400 MHz, DMSO-d6): δ ppm 9.06 (1H, s), 7.88 (1H, s), 7.73 (1H, m), 7.42 (1H, m), 7.33-7.44 (2H, m), 7.14-7.15 (4H, m), 6.92 (1H, m), 5.44 (1H, s), 3.96 (1H, m), 3.82 (1H, m), 3.57 (3H, s), 3.50 (2H, m), 2.45 (2H, m), 1.21 (3H, m).

The racemic mixture was separated by chiral chromatography to afford the enantiomers Example 88A and 88B, which had identical spectral data.

Example 89

N2-(4-(4-chloro-1H-imidazol-1-yl)-3-methoxyphenyl)-N4-ethyl-8-(4-fluorophenyl)-N4-methyl-6,8-dihydro-5H-pyrano[3,4-d]pyrimidine-2,4-diamine

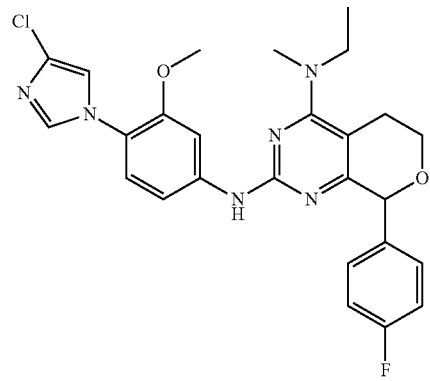 [SMILES: CCN(C)c1nc(Nc2ccc(-n3cnc(Cl)c3)c(OC)c2)nc2c1CCOC2c1ccc(F)cc1]

A solution of Preparation A (0.029 g, 0.10 mmol), Preparation Ob (0.050 g, 0.14 mmol), Na₂CO₃ (0.030 g, 0.28 mmol) and xantphos (0.080 g, 0.14 mmol) in dioxane/water (9:1) was purged with argon for 1 h at room temperature. Pd(dba)₃ (0.078 g, 0.07 mmol) was added to the reaction mixture and the resulting solution was purged for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (75 mL×2). The combined organic layer was washed with brine solution (50 mL), dried over anhydrous Na₂SO₄ and evaporated under reduced pressure to get crude compound. The crude compound was purified by column chromatography (60-120 mesh) using 35% ethyl acetate in pet-ether as mobile phase to give N2-(4-(4-chloro-1H-imidazol-1-yl)-3-methoxyphenyl)-N4-ethyl-8-(4-fluorophenyl)-N4-methyl-6,8-dihydro-5H-pyrano[3,4-d]pyrimidine-2,4-diamine (0.020 g, 30%) as off-white solid. LC-MS (M+H)⁺=509.2. ¹H NMR (400 MHz, DMSO-d6): δ ppm 9.12 (1H, s), 7.75-7.81 (2H, m), 7.38-7.44 (3H, m), 7.15-7.24 (4H, m), 5.51 (1H, s), 4.03 (1H, m), 3.49-3.67 (5H, m), 3.09 (3H, m), 3.01-3.06 (1H, m), 2.51-2.59 (2H, m), 1.22 (3H, t, J=7.2 Hz).

Example 90A

N-(4-(4-chloro-1H-imidazol-1-yl)-3-methoxyphenyl)-8-(4-fluorophenyl)-4-((R)-3-fluoropyrrolidin-1-yl)-6,8-dihydro-5H-pyrano[3,4-d]pyrimidin-2-amine 7.44 (3H, m), 7.15-7.22 (4H, m), 5.50 (1H, s), 5.38 (1H, m), 3.82-4.09 (6H, m), 3.68 (3H, s), 2.98 (2H, m), 2.50-2.43 (2H, m).

Example 90B

N-(4-(4-chloro-1H-imidazol-1-yl)-3-methoxyphenyl)-8-(4-fluorophenyl)-4-((R)-3-fluoropyrrolidin-1-yl)-6,8-dihydro-5H-pyrano[3,4-d]pyrimidin-2-amine

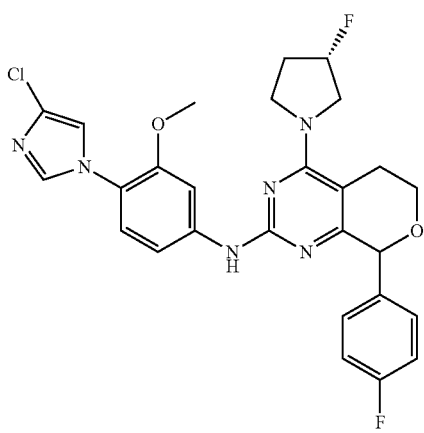

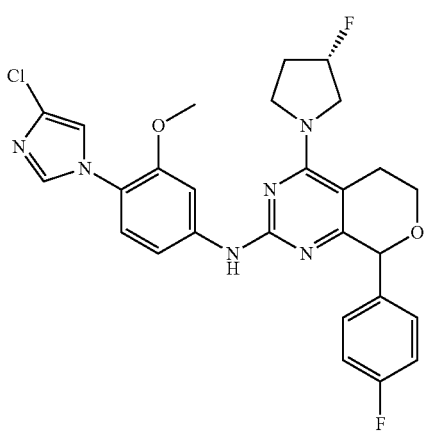

A solution of Preparation A (0.063 g, 0.20 mmol), Preparation Oc1 (0.110 g, 0.3 mmol), Na$_2$CO$_3$ (0.066 g, 0.6 mmol) and xantphos (0.181 g, 0.3 mmol) in dioxane/water (9:1) was purged with argon for 1 h at room temperature. Pd(dba)$_3$ (0172 g, 0.10 mmol) was added to the reaction mixture and the resulting solution was purged for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (75 mL×2). The combined organic layer was washed with brine solution (50 mL), dried over anhydrous Na$_2$SO$_4$ and evaporated under reduced pressure to get crude compound. The crude compound was purified by column chromatography (60-120 mesh) using 35% ethyl acetate in pet-ether as mobile phase to give N-(4-(4-chloro-1H-imidazol-1-yl)-3-methoxyphenyl)-8-(4-fluorophenyl)-4-((R)-3-fluoropyrrolidin-1-yl)-6,8-dihydro-5H-pyrano[3,4-d]pyrimidin-2-amine (0.050 g, 60%) as off-white solid. LC-MS (M+H)$^+$=539.0. $^1$H NMR (400 MHz, DMSO-d6): δ ppm 9.12 (1H, s), 7.75 (2H, m), 7.39-

A solution of Preparation A (0.063 g, 0.20 mmol), Preparation Oc2 (0.110 g, 0.3 mmol), Na$_2$CO$_3$ (0.066 g, 0.6 mmol) and xantphos (0.181 g, 0.3 mmol) in dioxane/water (9:1) was purged with argon for 1 h at room temperature. Pd(dba)$_3$ (0172 g, 0.10 mmol) was added to the reaction mixture and the resulting solution was purged for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (75 mL×2). The combined organic layer was washed with brine solution (50 mL), dried over anhydrous Na$_2$SO$_4$ and evaporated under reduced pressure to get crude compound. The crude compound was purified by column chromatography (60-120 mesh) using 35% ethyl acetate in pet-ether as mobile phase to give N-(4-(4-chloro-1H-imidazol-1-yl)-3-methoxyphenyl)-8-(4-fluorophenyl)-4-((R)-3-fluoropyrrolidin-1-yl)-6,8-dihydro-5H-pyrano[3,4-d]pyrimidin-2-amine (0.070 g, 63%) as off-white solid. LC-MS (M+H)$^+$=539.0. $^1$H NMR (400 MHz, DMSO-d6): δ ppm 9.16 (1H, s), 7.81 (1H, s), 7.74 (1H, s), 7.73 (1H, s), 7.42 (2H, m), 7.17-7.11 (4H, m), 5.54 (1H, s), 5.43 (1H, m), 4.12-3.57 (6H, m), 3.34 (3H, s), 2.97 (2H, m), 2.50-2.43 (2H, m).

Example 91A

N-(4-(4-chloro-1H-imidazol-1-yl)-3-methoxyphenyl)-8-(4-fluorophenyl)-4-((S)-3-fluoropyrrolidin-1-yl)-6,8-dihydro-5H-pyrano[3,4-d]pyrimidin-2-amine

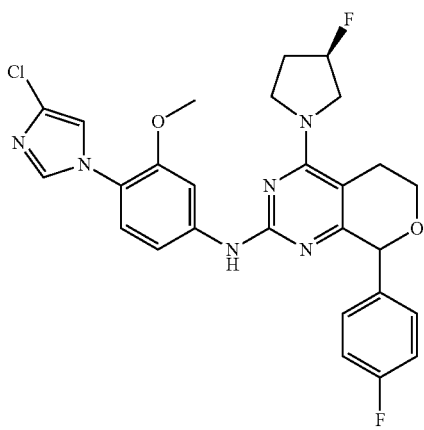

A solution of Preparation A (0.063 g, 0.20 mmol), Preparation Od1 (0.110 g, 0.3 mmol), Na$_2$CO$_3$ (0.066 g, 0.6 mmol) and xantphos (0.181 g, 0.3 mmol) in dioxane/water (9:1) was purged with argon for 1 h at room temperature. Pd(dba)$_3$ (0172 g, 0.10 mmol) was added to the reaction mixture and the resulting solution was purged for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (75 mL×2). The combined organic layer was washed with brine solution (50 mL), dried over anhydrous Na$_2$SO$_4$ and evaporated under reduced pressure to get crude compound. The crude compound was purified by column chromatography (60-120 mesh) using 35% ethyl acetate in pet-ether as mobile phase to N-(4-(4-chloro-1H-imidazol-1-yl)-3-methoxyphenyl)-8-(4-fluorophenyl)-4-((S)-3-fluoropyrrolidin-1-yl)-6,8-dihydro-5H-pyrano[3,4-d]pyrimidin-2-amine (0.040 g, 40%) as off-white solid. LC-MS (M+H)$^+$=539.0. $^1$H NMR (400 MHz, DMSO-d6): δ ppm 9.25 (1H, s), 7.77 (1H, s), 7.77 (1H, s), 7.45 (3H, m), 7.21 (4H, m), 5.53 (1H, s), 5.43 (1H, m), 4.12-3.57 (5H, m), 3.34 (3H, s), 3.33 (1H, m), 3.20 (1H, m), 2.73 (1H, m), 2.31-2.06 (2H, m).

Example 91B

N-(4-(4-chloro-1H-imidazol-1-yl)-3-methoxyphenyl)-4-48)-3-fluoropyrrolidin-1-yl)-6,8-dihydro-5H-pyrano[3,4-d]pyrimidin-2-amine

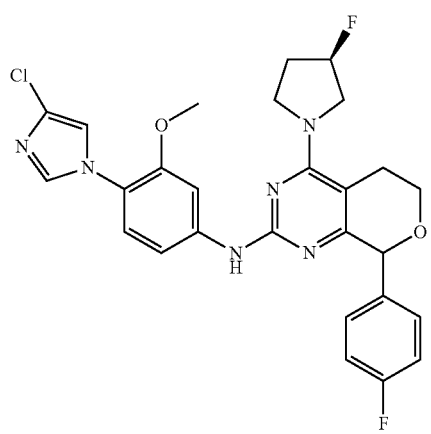

A solution of Preparation A (0.063 g, 0.20 mmol), Preparation Od2 (0.110 g, 0.3 mmol), Na$_2$CO$_3$ (0.066 g, 0.6 mmol) and xantphos (0.181 g, 0.3 mmol) in dioxane/water (9:1) was purged with argon for 1 h at room temperature. Pd(dba)$_3$ (0172 g, 0.10 mmol) was added to the reaction mixture and the resulting solution was purged for another 1 h. The reaction mass was heated at 110° C. for 24 h. The reaction mass was filtered through a bed of diatomaceous earth (Celite®) and washed with ethyl acetate. The filtrate was evaporated under reduced pressure and the residue was diluted with water. The aqueous solution was extracted with ethyl acetate (75 mL×2). The combined organic layer was washed with brine solution (50 mL), dried over anhydrous Na$_2$SO$_4$ and evaporated under reduced pressure to get crude compound. The crude compound was purified by column chromatography (60-120 mesh) using 35% ethyl acetate in pet-ether as mobile phase to give N-(4-(4-chloro-1H-imidazol-1-yl)-3-methoxyphenyl)-8-(4-fluorophenyl)-4-((S)-3-fluoropyrrolidin-1-yl)-6,8-dihydro-5H-pyrano[3,4-d]pyrimidin-2-amine (0.039 g, 39%) as off-white solid. LC-MS (M+H)$^+$=539.0. $^1$H NMR (400 MHz, DMSO-d6): δ ppm 9.15 (1H, s), 7.81 (1H, s), 7.74 (1H, s), 7.43 (1H, s), 7.37 (2H, m), 7.19 (4H, m), 5.54 (1H, s), 5.43 (1H, m), 4.13-3.69 (6H, m), 3.33 (3H, s), 2.96 (2H, m), 2.24-1.91 (2H, m).

Example 92

N²-(4-(4-Chloro-1H-imidazol-1-yl)-3-methoxyphenyl)-7-(4-chlorophenyl)-N⁴,N⁴-dimethyl-6,7-dihydro-5H-cyclopenta[d]pyrimidine-2,4-diamine

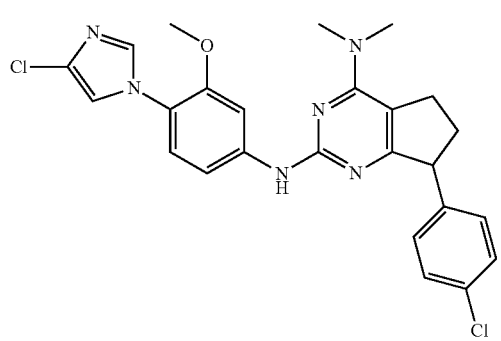 [SMILES: COc1cc(Nc2nc3c(c(N(C)C)n2)CCC3c2ccc(Cl)cc2)ccc1-n1cnc(Cl)c1]

2-Chloro-7-(4-chlorophenyl)-N,N-dimethyl-6,7-dihydro-5H-cyclopenta[d]pyrimidin-4-amine (98 mg, 0.318 mmol) was added to a solution of 4-(4-chloro-1H-imidazol-1-yl)-3-methoxyaniline (71.1 mg, 0.318 mmol) in acetic acid (1.000 mL) and THF (1 mL). The reaction mixture was heated at 75° C. overnight. Partial conversion to the desired product was observed. The reaction was further heated at 120° C. for 6 h. The crude reaction mixture was purified by preparative HPLC. The appropriate fractions were evaporated to afford N²-(4-(4-chloro-1H-imidazol-1-yl)-3-methoxyphenyl)-7-(4-chlorophenyl)-N⁴,N⁴-dimethyl-6,7-dihydro-5H-cyclopenta[d]pyrimidine-2,4-diamine, TFA salt (17.2 mg, 0.028 mmol, 8.70% yield). LC-MS (M+H)⁺=495.1. ¹H NMR (500 MHz, CDCl₃) δ ppm 11.80 (1H, s), 7.61-7.72 (1H, m), 7.34-7.42 (2H, m), 7.27-7.33 (2H, m), 7.21 (2H, d, J=8.5 Hz), 7.16 (1H, d, J=9.2 Hz), 7.06 (1H, d, J=1.5 Hz), 4.30-4.41 (1H, m), 3.82 (6H, s), 3.48 (1H, br. s.), 3.31-3.39 (2H, m), 3.18-3.27 (1H, m), 2.58-2.80 (2H, m), 2.14-2.29 (1H, m).

Example 93

N-(4-(4-Chloro-1H-imidazol-1-yl)-3-methoxyphenyl)-7-(4-chlorophenyl)-4-(3,3-difluoroazetidin-1-yl)-6,7-dihydro-5H-cyclopenta[d]pyrimidin-2-amine

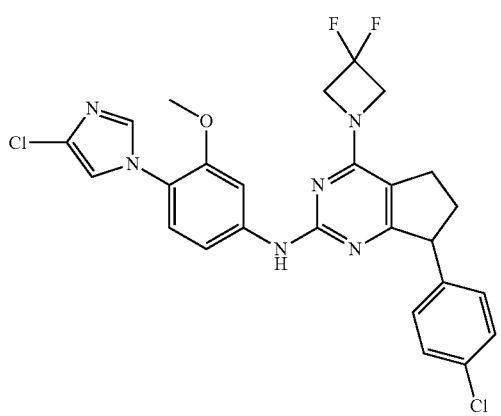 [SMILES: COc1cc(Nc2nc3c(c(N4CC(F)(F)C4)n2)CCC3c2ccc(Cl)cc2)ccc1-n1cnc(Cl)c1]

2-Chloro-7-(4-chlorophenyl)-4-(3,3-difluoroazetidin-1-yl)-6,7-dihydro-5H-cyclopenta[d]pyrimidine (70 mg, 0.197 mmol) was added to a solution of 4-(4-chloro-1H-imidazol-1-yl)-3-methoxyaniline (52.7 mg, 0.236 mmol) in acetic acid (1 mL) and THF (1.000 mL). The reaction mixture was heated at 120° C. in a microwave for 6 h. The crude reaction mixture was purified by preparative HPLC. The appropriate fractions were evaporated to afford N-(4-(4-chloro-1H-imidazol-1-yl)-3-methoxyphenyl)-7-(4-chlorophenyl)-4-(3,3-difluoroazetidin-1-yl)-6,7-dihydro-5H-cyclopenta[d]pyrimidin-2-amine, TFA salt (8.7 mg, 0.013 mmol, 6.46% yield). LC-MS (M+H)⁺=543.1. ¹H NMR (500 MHz, CDCl₃) δ ppm 11.85-11.99 (1H, m), 7.93 (1H, s), 7.38-7.45 (1H, m), 7.31 (2H, d, J=8.2 Hz), 7.19 (3H, t, J=8.2 Hz), 7.10 (1H, d, J=1.5 Hz), 4.37-4.47 (1H, m), 3.85 (3H, s), 3.45-3.51 (1H, m), 3.07-3.18 (2H, m), 2.94-3.04 (2H, m), 2.67-2.81 (2H, m), 2.19-2.37 (2H, m).

Example 94

$N^2$-(4-(4-Chloro-1H-imidazol-1-yl)-3-methoxyphenyl)-7-(4-chlorophenyl)-$N^4$-methyl-6,7-dihydro-5H-cyclopenta[d]pyrimidine-2,4-diamine

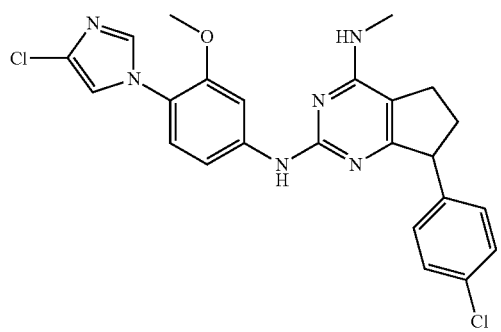 [SMILES: CNc1nc(Nc2ccc(-n3cnc(Cl)c3)c(OC)c2)nc2c1CCC2c1ccc(Cl)cc1]

2-Chloro-7-(4-chlorophenyl)-N-methyl-6,7-dihydro-5H-cyclopenta[d]pyrimidin-4-amine (101 mg, 0.343 mmol) was added to a solution of 4-(4-chloro-1H-imidazol-1-yl)-3-methoxyaniline (77 mg, 0.343 mmol) in acetic acid (2 mL) and THF (2 mL). The reaction mixture was heated at 80° C. overnight. Partial conversion to the desired product was observed. The reaction was further heated at 120° C. for 6 h. The crude reaction mixture was purified by preparative HPLC. The appropriate fractions were evaporated to afford $N^2$-(4-(4-chloro-1H-imidazol-1-yl)-3-methoxyphenyl)-7-(4-chlorophenyl)-$N^4$-methyl-6,7-dihydro-5H-cyclopenta[d]pyrimidine-2,4-diamine, TFA salt (35.5 mg, 0.059 mmol, 17.19% yield). LC-MS (M+H)$^+$=481.3. $^1$H NMR (500 MHz, CDCl$_3$) δ ppm 11.08 (1H, s), 8.33 (1H, s), 7.48 (2H, d, J=2.1 Hz), 7.30 (2H, d, J=8.2 Hz), 7.20 (1H, d, J=1.5 Hz), 7.13 (2H, d, J=8.5 Hz), 5.83-5.93 (1H, m), 4.38-4.48 (1H, m), 3.97 (1H, s), 3.86 (3H, s), 3.22 (3H, d, J=4.9 Hz), 2.85-2.95 (1H, m), 2.77 (2H, dd, J=8.7, 5.3 Hz), 2.20-2.32 (1H, m).

Examples 94A & 94B (S)—$N^2$-(4-(4-Chloro-1H-imidazol-1-yl)-3-methoxyphenyl)-7-(4-chlorophenyl)-$N^4$-methyl-6,7-dihydro-5H-cyclopenta[d]pyrimidine-2,4-diamine and (R)—$N^2$-(4-(4-Chloro-1H-imidazol-1-yl)-3-methoxyphenyl)-7-(4-chlorophenyl)-$N^4$-methyl-6,7-dihydro-5H-cyclopenta[d]pyrimidine-2,4-diamine

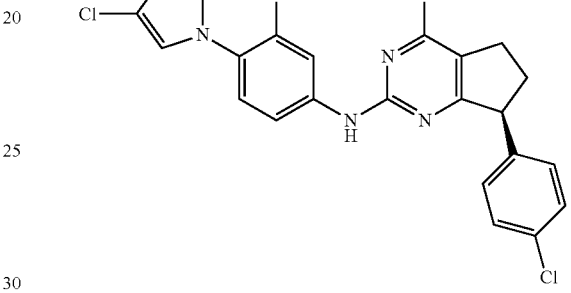

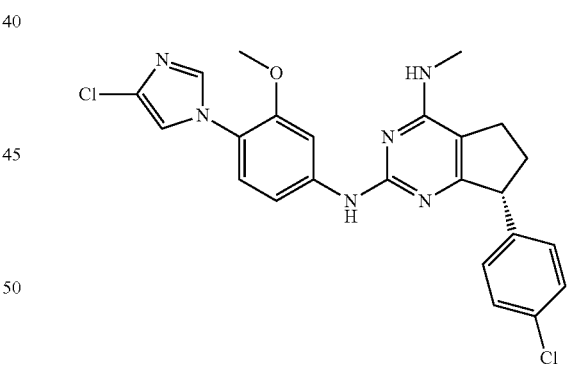

A racemic mixture of $N^2$-(4-(4-chloro-1H-imidazol-1-yl)-3-methoxyphenyl)-7-(4-chlorophenyl)-$N^4$-methyl-6,7-dihydro-5H-cyclopenta[d]pyrimidine-2,4-diamine (37 mg, 0.077 mmol from Example 94) was purified using chiral SFC to afford 10.5 mg of peak A (Example 94A) and 13.6 mg of peak B (Example 94B). SFC Method: Chiralpak OJ-H (4.6×250 mm, 5 μM), 35% methanol (0.1% diethylamine) in CO$_2$, 35° C., flow rate 2.0 mL/min for 20 min, absorbance 268 nm, injection 5 μL of 2 mg/mL solution in 50:50 methanol/chloroform (multiple stacked injections), $t_R$ (peak A)=5.3 min, $t_R$ (peak B) 14.9 min. The absolute stereochemistry of individual enantiomers (Examples 94A and 94B) was not determined LC-MS and ¹H NMR analytical data for the separated enantiomers was identical to the racemate (Example 94).

Example 95

N²-(4-(4-Chloro-1H-imidazol-1-yl)-3-methoxyphenyl)-7-(3,4-difluorophenyl)-N⁴,N⁴-dimethyl-6,7-dihydro-5H-cyclopenta[d]pyrimidine-2,4-diamine 2-Chloro-7-(3,4-difluorophenyl)-N,N-dimethyl-6,7-dihydro-5H-cyclopenta[d]pyrimidin-4-amine (178 mg, 0.575 mmol) was added to a solution of 4-(4-chloro-1H-imidazol-1-yl)-3-methoxyaniline (141 mg, 0.632 mmol) in acetic acid (2 mL) and THF (2.000 mL). The reaction mixture was heated at 80° C. overnight. The crude reaction mixture was purified by preparative HPLC. The appropriate fractions were evaporated to afford N²-(4-(4-chloro-1H-imidazol-1-yl)-3-methoxyphenyl)-7-(3,4-difluorophenyl)-N⁴,N⁴-dimethyl-6,7-dihydro-5H-cyclopenta[d]pyrimidine-2,4-diamine, TFA salt (144.1 mg, 0.233 mmol, 40.6% yield). LC-MS (M+H)⁺ =497.0. ¹H NMR (500 MHz, CDCl₃) δ ppm 11.53-11.67 (1H, m), 8.96 (1H, br s), 7.85-7.96 (1H, m), 7.38 (1H, s), 7.18 (1H, d, J=8.2 Hz), 7.00-7.16 (4H, m), 4.34 (1H, dd, J=9.6, 4.4 Hz), 3.83 (3H, s), 3.30-3.57 (6H, m), 3.25-3.29 (1H, m), 3.19-3.26 (1H, m), 2.61-2.72 (1H, m), 2.14-2.25 (1H, m).

Examples 95A & 95B (S)—N²-(4-(4-Chloro-1H-imidazol-1-yl)-3-methoxyphenyl)-7-(3,4-difluorophenyl)-N⁴,N⁴-dimethyl-6,7-dihydro-5H-cyclopenta[d]pyrimidine-2,4-diamine and (R)—N²-(4-(4-Chloro-1H-imidazol-1-yl)-3-methoxyphenyl)-7-(3,4-difluorophenyl)-N⁴,N⁴-dimethyl-6,7-dihydro-5H-cyclopenta[d]pyrimidine-2,4-diamine

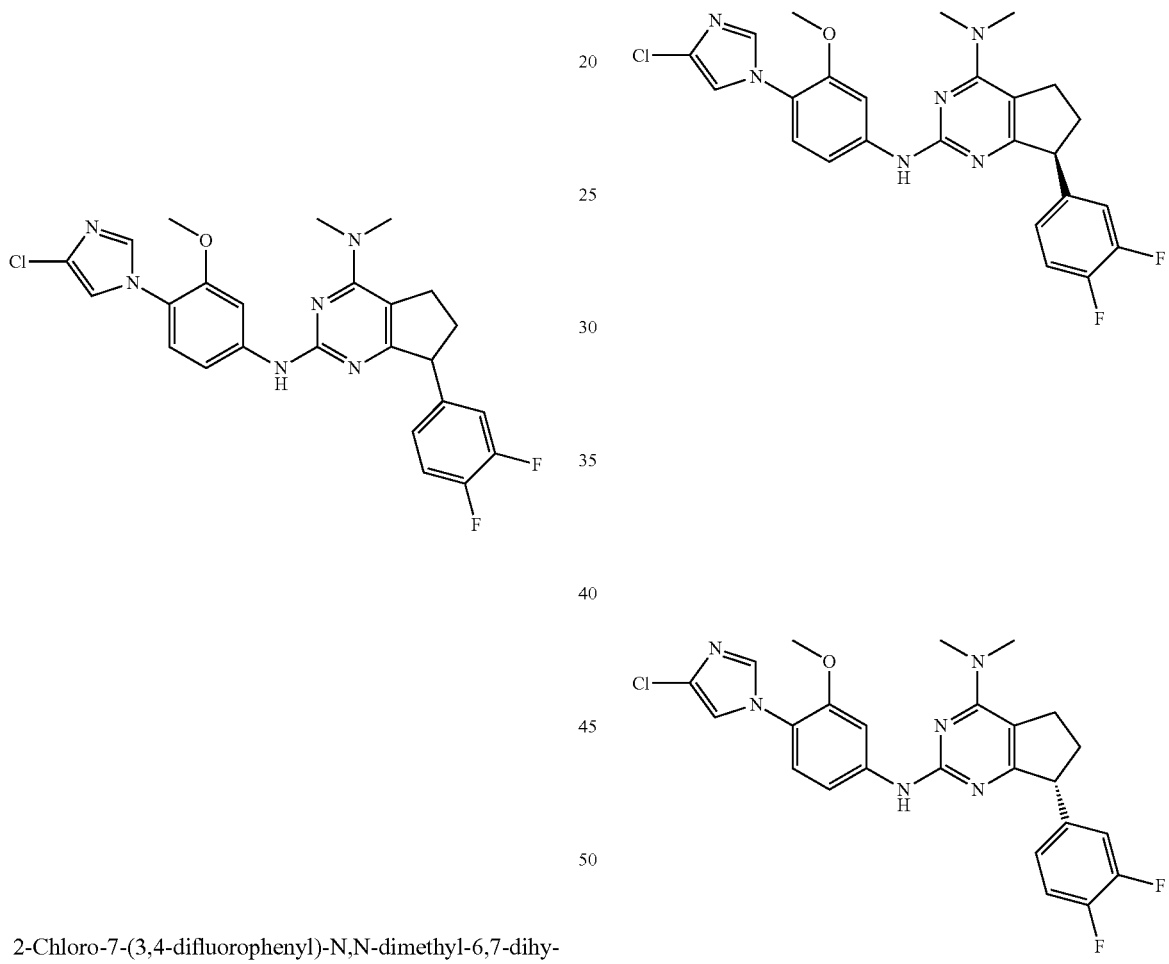

A racemic mixture of N²-(4-(4-chloro-1H-imidazol-1-yl)-3-methoxyphenyl)-7-(3,4-difluorophenyl)-N⁴,N⁴-dimethyl-6,7-dihydro-5H-cyclopenta[d]pyrimidine-2,4-diamine (139 mg, 0.28 mmol from Example 95) was purified using chiral SFC to afford 47.6 mg of peak A (Example 95A) and 47.3 mg of peak B (Example 95B). SFC Method: Chiralpak OJ-H (4.6×250 mm, 5 µM), 35% methanol (0.1% diethylamine) in CO₂, 35° C., flow rate 2.0 mL/min for 8 min, absorbance 268 nm, injection 5 µL of 2 mg/mL solution in methanol (multiple stacked injections), $t_R$ (peak A)=4.6 min, $t_R$ (peak B) 6.3 min. The absolute stereochemistry of individual enantiomers (Examples 95A and 95B) was not determined LC-MS and ¹H NMR analytical data for the separated enantiomers was identical to the racemate (Example 95).

Example 96

N²-(4-(4-Chloro-1H-imidazol-1-yl)-3-methoxyphenyl)-7-(3,4-difluorophenyl)-N⁴-methyl-6,7-dihydro-5H-cyclopenta[d]pyrimidine-2,4-diamine

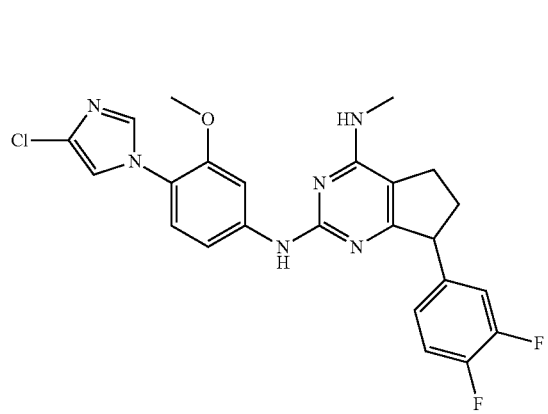 [SMILES: CNc1nc(Nc2ccc(-n3cnc(Cl)c3)c(OC)c2)nc2c1CCC2c1ccc(F)c(F)c1]

2-Chloro-7-(3,4-difluorophenyl)-N-methyl-6,7-dihydro-5H-cyclopenta[d]pyrimidin-4-amine (154 mg, 0.521 mmol) was added to a solution of 4-(4-chloro-1H-imidazol-1-yl)-3-methoxyaniline (175 mg, 0.781 mmol) in acetic acid (2 mL) and THF (2.000 mL). The reaction mixture was heated at 120° C. overnight. The crude reaction mixture was purified by preparative HPLC. The appropriate fractions were evaporated to afford N²-(4-(4-chloro-1H-imidazol-1-yl)-3-methoxyphenyl)-7-(3,4-difluorophenyl)-N⁴-methyl-6,7-dihydro-5H-cyclopenta[d]pyrimidine-2,4-diamine, TFA salt (22.3 mg, 0.034 mmol, 6.46% yield). LC-MS (M+H)⁺=483.2. ¹H NMR (500 MHz, CDCl₃) δ ppm 11.84 (1H, s), 7.83-7.89 (1H, m), 7.55 (1H, s), 7.41-7.46 (1H, m), 7.17-7.21 (1H, m), 7.10 (2H, s), 6.98-7.05 (2H, m), 5.79-5.90 (1H, m), 4.38-4.45 (1H, m), 3.85 (3H, s), 3.20-3.25 (3H, m), 2.90-3.00 (1H, m), 2.70-2.81 (2H, m), 2.20-2.32 (1H, m).

Examples 96A & 96B (S)—N²-(4-(4-Chloro-1H-imidazol-1-yl)-3-methoxyphenyl)-7-(3,4-difluorophenyl)-N⁴-methyl-6,7-dihydro-5H-cyclopenta[d]pyrimidine-2,4-diamine
and (R)—N²-(4-(4-Chloro-1H-imidazol-1-yl)-3-methoxyphenyl)-7-(3,4-difluorophenyl)-N⁴-methyl-6,7-dihydro-5H-cyclopenta[d]pyrimidine-2,4-diamine

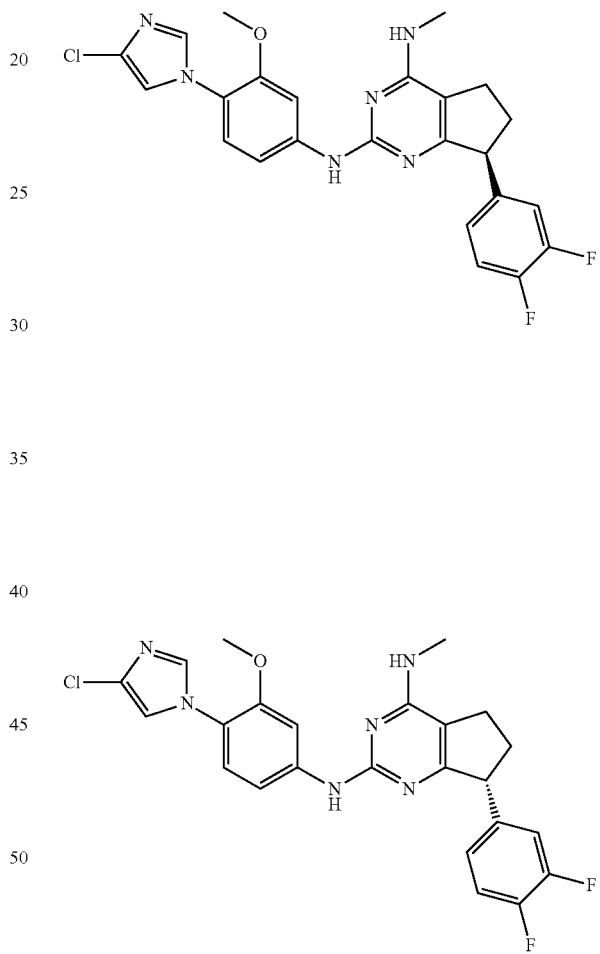

A racemic mixture of N²-(4-(4-chloro-1H-imidazol-1-yl)-3-methoxyphenyl)-7-(3,4-difluorophenyl)-N⁴-methyl-6,7-dihydro-5H-cyclopenta[d]pyrimidine-2,4-diamine (1.4 g, 2.345 mmol from Example 96) was purified using chiral SFC to afford 475 mg of peak A (Example 96A) and 435 mg of peak B (Example 96B). SFC Method: Chiralpak OJ-H (4.6× 250 mm, 5 μM), 25% methanol (0.1% diethylamine) in CO₂, 35° C., flow rate mL/min for 14 min, absorbance 268 nm, injection 5 μL of 2 mg/mL solution in methanol (multiple stacked injections), $t_R$ (peak A)=6.1 min, $t_R$ (peak B) 9.2 min. The absolute stereochemistry of individual enantiomers (Examples 96A and 96B) was not determined LC-MS and ¹H NMR analytical data for the separated enantiomers was identical to the racemate (Example 96).

Example 97

N²-(4-(4-Chloro-1H-imidazol-1-yl)-3-methoxyphenyl)-N⁴-methyl-7-(4-(trifluoromethoxy)phenyl)-6,7-dihydro-5H-cyclopenta[d]pyrimidine-2,4-diamine

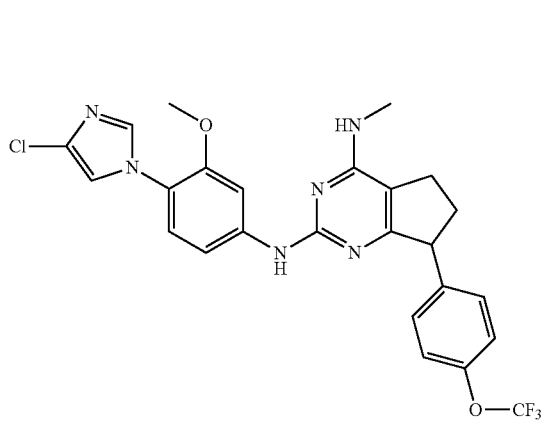 [SMILES: CNc1nc(Nc2ccc(-n3cnc(Cl)c3)c(OC)c2)nc2c1CCC2c1ccc(OC(F)(F)F)cc1]

2-Chloro-N-methyl-7-(4-(trifluoromethoxy)phenyl)-6,7-dihydro-5H-cyclopenta[d]pyrimidin-4-amine (220 mg, 0.640 mmol) was added to a solution of 4-(4-chloro-1H-imidazol-1-yl)-3-methoxyaniline (215 mg, 0.960 mmol) in acetic acid (2 mL) and THF (2.000 mL). The reaction mixture was heated at 80° C. overnight. The crude reaction mixture was purified by preparative HPLC. The appropriate fractions were evaporated to afford N²-(4-(4-chloro-1H-imidazol-1-yl)-3-methoxyphenyl)-N⁴-methyl-7-(4-(trifluoromethoxy)phenyl)-6,7-dihydro-5H-cyclopenta[d]pyrimidine-2,4-diamine (92 mg, 0.172 mmol, 26.8% yield). LC-MS (M+H)⁺ =531.2. ¹H NMR (500 MHz, CDCl₃) δ ppm 7.93 (1H, s), 7.66 (1H, br s), 7.50 (1H, s), 7.10-7.23 (4H, m), 7.02 (2H, d, J=15.3 Hz), 6.83 (1H, d, J=8.2 Hz), 4.70-4.83 (1H, m), 4.13-4.28 (1H, m), 3.12 (3H, d, J=4.9 Hz), 2.74 (1H, br. s.), 2.65 (2H, d, J=8.2 Hz), 1.97-2.08 (1H, m), 1.25 (3H, s).

Examples 97A & 97B (S)—N²-(4-(4-Chloro-1H-imidazol-1-yl)-3-methoxyphenyl)-N⁴-methyl-7-(4-(trifluoromethoxy)phenyl)-6,7-dihydro-5H-cyclopenta[d]pyrimidine-2,4-diamine and (R)—N²-(4-(4-Chloro-1H-imidazol-1-yl)-3-methoxyphenyl)-N⁴-methyl-7-(4-(trifluoromethoxy)phenyl)-6,7-dihydro-5H-cyclopenta[d]pyrimidine-2,4-diamine

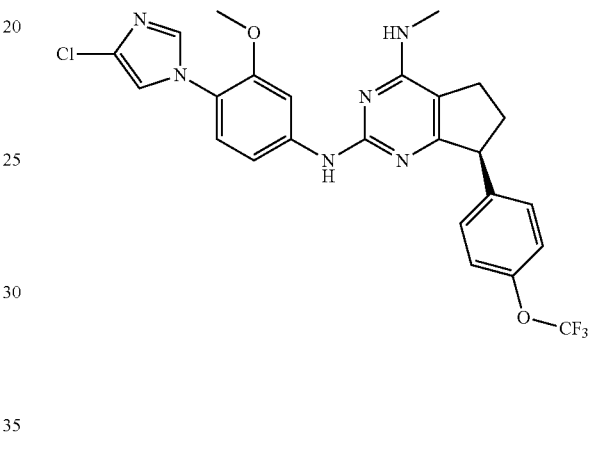

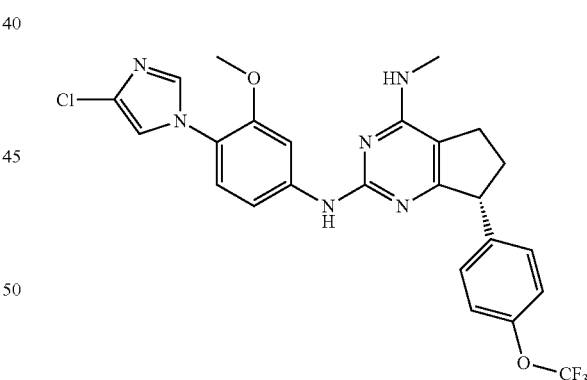

A racemic mixture of N²-(4-(4-chloro-1H-imidazol-1-yl)-3-methoxyphenyl)-N⁴-methyl-7-(4-(trifluoromethoxy)phenyl)-6,7-dihydro-5H-cyclopenta[d]pyrimidine-2,4-diamine (86 mg, 0.162 mmol from Example 97) was purified using chiral SFC to afford 36.6 mg of peak A (Example 97A) and 31.5 mg of peak B (Example 97B). SFC Method: Chiralpak OJ-H (4.6×250 mm, 5 μM), 30% methanol (0.1% diethylamine) in CO₂, 35° C., flow rate 2.0 mL/min for 12 min, absorbance 268 nm, injection 5 μL of 2 mg/mL solution in methanol (multiple stacked injections), t$_R$ (peak A)=3.4 min, t$_R$ (peak B) 7.5 min. The absolute stereochemistry of individual enantiomers (Examples 97A and 97B) was not determined LC-MS and ¹H NMR analytical data for the separated enantiomers was identical to the racemate (Example 97).

Example 98

N²-(4-(4-Chloro-1H-imidazol-1-yl)-3-methoxyphenyl)-N⁴-ethyl-7-(4-(trifluoromethoxy)phenyl)-6,7-dihydro-5H-cyclopenta[d]pyrimidine-2,4-diamine

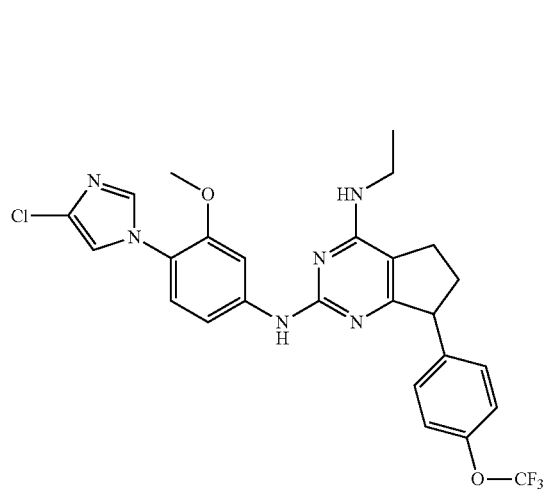 [SMILES: CCNc1nc(Nc2ccc(-n3cnc(Cl)c3)c(OC)c2)nc2c1CCC2c1ccc(OC(F)(F)F)cc1]

2-Chloro-N-ethyl-7-(4-(trifluoromethoxy)phenyl)-6,7-dihydro-5H-cyclopenta[d]pyrimidin-4-amine (190 mg, 0.531 mmol) was added to a solution of 4-(4-chloro-1H-imidazol-1-yl)-3-methoxyaniline (178 mg, 0.797 mmol) in acetic acid (2 mL) and THF (2.000 mL). The reaction mixture was heated at 90° C. overnight. The crude reaction mixture was purified by preparative HPLC. The appropriate fractions were evaporated to afford N²-(4-(4-chloro-1H-imidazol-1-yl)-3-methoxyphenyl)-N⁴-ethyl-7-(4-(trifluoromethoxy)phenyl)-6,7-dihydro-5H-cyclopenta[d]pyrimidine-2,4-diamine, TFA salt (118 mg, 0.174 mmol, 32.7% yield). LC-MS (M+H)⁺=545.0. ¹H NMR (500 MHz, CDCl₃) δ ppm 11.04 (1H, s), 9.01 (1H, br s), 8.29 (1H, s), 7.44 (2H, s), 7.24 (2H, d, J=8.5 Hz), 7.19 (2H, d, J=5.5 Hz), 7.09-7.12 (1H, m), 5.93-5.99 (1H, m), 4.43-4.51 (1H, m), 3.86 (3H, s), 3.62-3.74 (2H, m), 3.46-3.55 (1H, m), 2.85-2.97 (1H, m), 2.71-2.82 (2H, m), 2.26 (1H, m), 1.26-1.41 (3H, m).

Examples 98A & 98B (S)—N²-(4-(4-Chloro-1H-imidazol-1-yl)-3-methoxyphenyl)-N⁴-ethyl-7-(4-(trifluoromethoxy)phenyl)-6,7-dihydro-5H-cyclopenta[d]pyrimidine-2,4-diamine and (R)—N²-(4-(4-Chloro-1H-imidazol-1-yl)-3-methoxyphenyl)-N⁴-ethyl-7-(4-(trifluoromethoxy)phenyl)-6,7-dihydro-5H-cyclopenta[d]pyrimidine-2,4-diamine

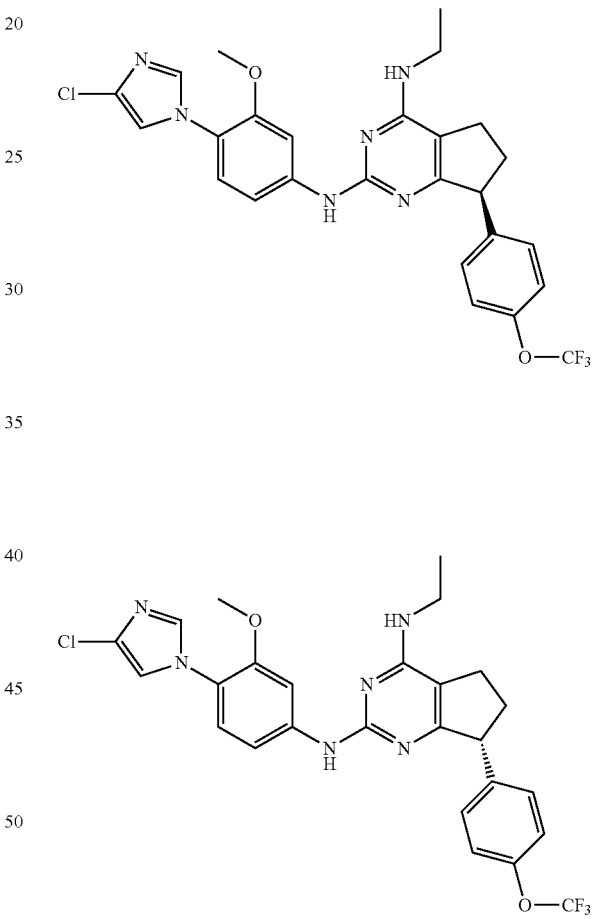

A racemic mixture of N²-(4-(4-chloro-1H-imidazol-1-yl)-3-methoxyphenyl)-N⁴-methyl-7-(4-(trifluoromethoxy)phenyl)-6,7-dihydro-5H-cyclopenta[d]pyrimidine-2,4-diamine (111 mg, 0.204 mmol from Example 98) was purified using chiral SFC to afford 29.5 mg of peak A (Example 98A) and 37.7 mg of peak B (Example 98B). SFC Method: Chiralpak OJ-H (4.6×250 mm, 5 μM), 30% methanol (0.1% diethylamine) in CO₂, 35° C., flow rate 2.0 mL/min for 12 min, absorbance 268 nm, injection 5 μL of 2 mg/mL solution in methanol (multiple stacked injections), $t_R$ (peak A)=3.4 min, $t_R$ (peak B) 8.2 min. The absolute stereochemistry of individual enantiomers (Examples 98A and 98B) was not determined LC-MS and ¹H NMR analytical data for the separated enantiomers was identical to the racemate (Example 98).

Example 99

N-(4-(4-Chloro-1H-imidazol-1-yl)-3-methoxyphenyl)-4-(3,3-difluoroazetidin-1-yl)-7-(4-(trifluoromethoxy)phenyl)-6,7-dihydro-5H-cyclopenta[d]pyrimidin-2-amine

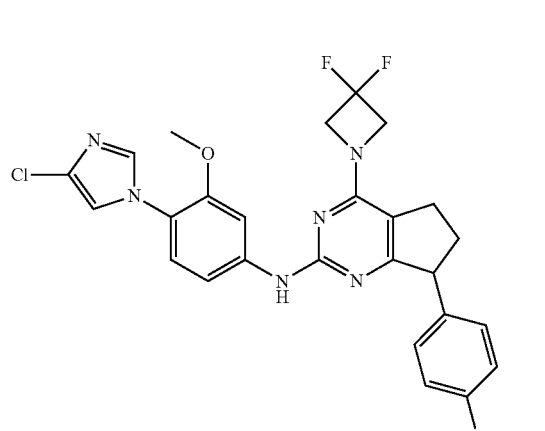

2-Chloro-4-(3,3-difluoroazetidin-1-yl)-7-(4-(trifluoromethoxy)phenyl)-6,7-dihydro-5H-cyclopenta[d]pyrimidine (244 mg, 0.601 mmol) was added to a solution of 4-(4-chloro-1H-imidazol-1-yl)-3-methoxyaniline (202 mg, 0.902 mmol) in acetic acid (2 mL) and THF (2.000 mL). The reaction mixture was heated at 110° C. overnight. The crude reaction mixture was purified by preparative HPLC. The appropriate fractions were evaporated to afford N-(4-(4-chloro-1H-imidazol-1-yl)-3-methoxyphenyl)-4-(3,3-difluoroazetidin-1-yl)-7-(4-(trifluoromethoxy)phenyl)-6,7-dihydro-5H-cyclopenta[d]pyrimidin-2-amine, TFA salt (165.2 mg, 0.229 mmol, 38.1% yield). LC-MS (M+H)⁺=593.3. ¹H NMR (500 MHz, CDCl₃) δ ppm 11.83 (1H, s), 8.00 (1H, s), 7.38-7.43 (1H, m), 7.30-7.33 (1H, m), 7.27-7.28 (1H, m), 7.16-7.22 (3H, m), 7.09-7.12 (1H, m), 4.76 (1H, br s), 4.46 (1H, dd, J=9.5, 4.9 Hz), 3.85 (3H, s), 3.07-3.17 (2H, m), 2.95-3.04 (2H, m), 2.70-2.81 (2H, m), 2.21-2.34 (2H, m).

Examples 99A & 99B (S)—N-(4-(4-Chloro-1H-imidazol-1-yl)-3-methoxyphenyl)-4-(3,3-difluoroazetidin-1-yl)-7-(4-(trifluoromethoxy)phenyl)-6,7-dihydro-5H-cyclopenta[d]pyrimidin-2-amine and (R)—N-(4-(4-Chloro-1H-imidazol-1-yl)-3-methoxyphenyl)-4-(3,3-difluoroazetidin-1-yl)-7-(4-(trifluoromethoxy)phenyl)-6,7-dihydro-5H-cyclopenta[d]pyrimidin-2-amine

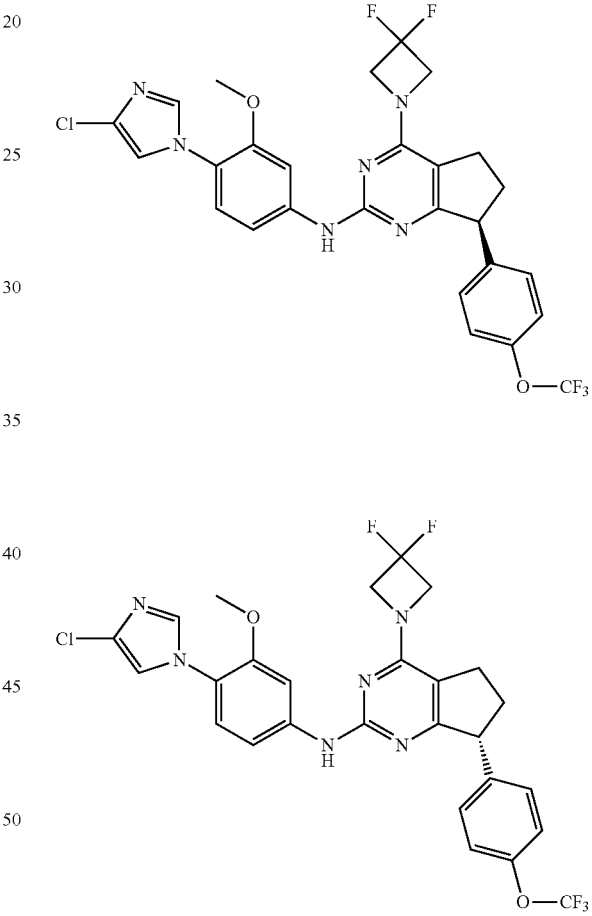

A racemic mixture of N-(4-(4-chloro-1H-imidazol-1-yl)-3-methoxyphenyl)-4-(3,3-difluoroazetidin-1-yl)-7-(4-(trifluoromethoxy)phenyl)-6,7-dihydro-5H-cyclopenta[d]pyrimidin-2-amine (165.2 mg, 0.279 mmol from Example 99) was purified using chiral SFC to afford 16.7 mg of peak A (Example 99A) and 17.0 mg of peak B (Example 99B). SFC Method: Chiralpak OJ-H (4.6×250 mm, 5 μM), 30% methanol (0.1% diethylamine) in CO₂, 35° C., flow rate 2.0 mL/min for 20 min, absorbance 268 nm, injection 5 μL of 2 mg/mL solution in methanol (multiple stacked injections), $t_R$ (peak A)=4.9 min, $t_R$ (peak B) 15.0 min. The absolute stereochemistry of individual enantiomers (Examples 99A and 99B) was

Example 100

N²-(4-(4-Chloro-1H-imidazol-1-yl)-3-methoxyphenyl)-N⁴,N⁴-dimethyl-7-(4-(trifluoromethoxy)phenyl)-6,7-dihydro-5H-cyclopenta[d]pyrimidine-2,4-diamine

Examples 100A & 100B (S)—N²-(4-(4-Chloro-1H-imidazol-1-yl)-3-methoxyphenyl)-N⁴,N⁴-dimethyl-7-(4-(trifluoromethoxy)phenyl)-6,7-dihydro-5H-cyclopenta[d]pyrimidine-2,4-diamine and (R)—N²-(4-(4-Chloro-1H-imidazol-1-yl)-3-methoxyphenyl)-N⁴,N⁴-dimethyl-7-(4-(trifluoromethoxy)phenyl)-6,7-dihydro-5H-cyclopenta[d]pyrimidine-2,4-diamine

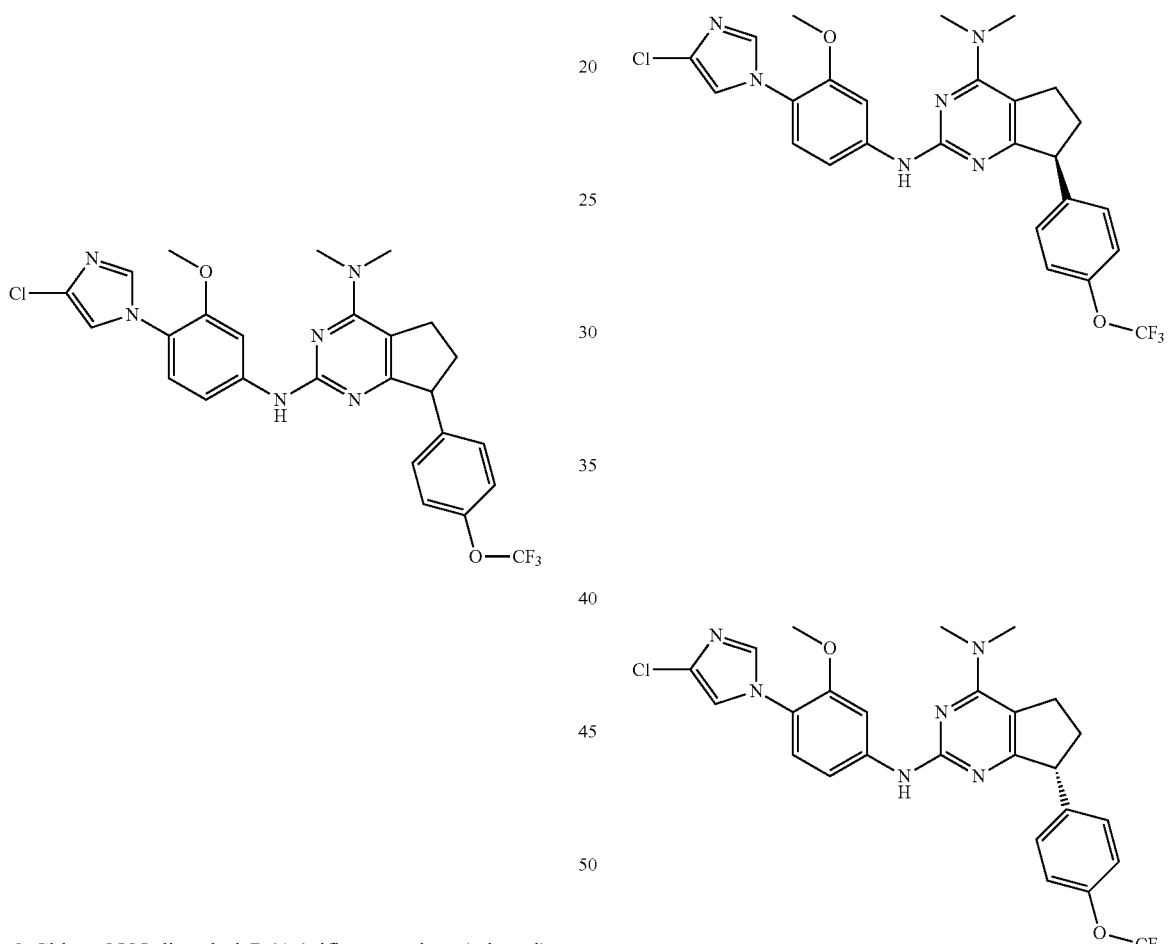

2-Chloro-N,N-dimethyl-7-(4-(trifluoromethoxy)phenyl)-6,7-dihydro-5H-cyclopenta[d]pyrimidin-4-amine (250 mg, 0.699 mmol) was added to a solution of 4-(4-chloro-1H-imidazol-1-yl)-3-methoxyaniline (234 mg, 1.048 mmol) in acetic acid (1 mL) and THF (1 mL). The reaction mixture was heated at 110° C. overnight. The crude reaction mixture was purified by preparative HPLC. The appropriate fractions were evaporated to afford N²-(4-(4-chloro-1H-imidazol-1-yl)-3-methoxyphenyl)-N⁴,N⁴-dimethyl-7-(4-(trifluoromethoxy)phenyl)-6,7-dihydro-5H-cyclopenta[d]pyrimidine-2,4-diamine, TFA salt (235 mg, 0.342 mmol, 49.0% yield). LC-MS $(M+H)^+$=545.3. ¹H NMR (500 MHz, CDCl₃) δ ppm 11.18-11.39 (1H, m), 8.11 (1H, s), 7.40-7.45 (1H, m), 7.30-7.34 (1H, m), 7.28 (1H, s), 7.17-7.23 (3H, m), 7.12-7.15 (1H, m), 4.34-4.44 (1H, m), 3.84 (3H, s), 3.50 (4H, s), 3.33-3.39 (3H, m), 3.18-3.27 (1H, m), 2.57-2.78 (1H, m), 2.10-2.39 (1H, m).

A racemic mixture of N²-(4-(4-chloro-1H-imidazol-1-yl)-3-methoxyphenyl)-N⁴,N⁴-dimethyl-7-(4-(trifluoromethoxy)phenyl)-6,7-dihydro-5H-cyclopenta[d]pyrimidine-2,4-diamine (235 mg, 0.431 mmol from Example 100) was purified using chiral SFC to afford 29.2 mg of peak A (Example 100A) and 29.2 mg of peak B (Example 100B). SFC Method: Chiralpak OJ-H (4.6×250 mm, 5 μM), 30% methanol (0.1% diethylamine) in CO₂, 35° C., flow rate 2.0 mL/min for 11 min, absorbance 268 nm, injection 5 μL of 2 mg/mL solution in methanol (multiple stacked injections), $t_R$ (peak A)=3.7 min, $t_R$ (peak B) 8.4 min. The absolute stereochemistry of individual enantiomers (Examples 100A and 100B) was not determined LC-MS and ¹H NMR analytical data for the separated enantiomers was identical to the racemate (Example 99).

Example 101

4-(Azetidin-1-yl)-N-(4-(4-chloro-1H-imidazol-1-yl)-3-methoxyphenyl)-7-(4-(trifluoromethoxy)phenyl)-6,7-dihydro-5H-cyclopenta[d]pyrimidin-2-amine

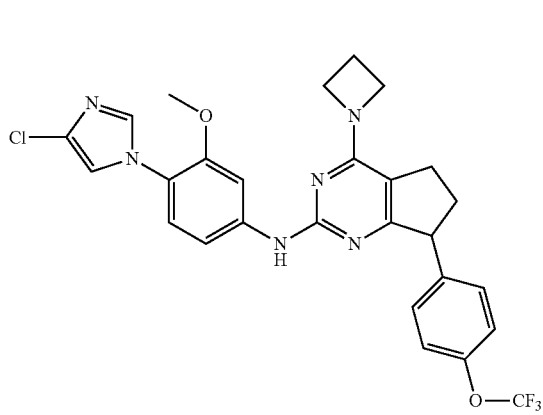 [SMILES: COc1cc(Nc2nc3c(c(N4CCC4)n2)CCC3c2ccc(OC(F)(F)F)cc2)ccc1-n1cnc(Cl)c1]

4-(Azetidin-1-yl)-2-chloro-7-(4-(trifluoromethoxy)phenyl)-6,7-dihydro-5H-cyclopenta[d]pyrimidine (238 mg, 0.644 mmol) was added to a solution of 4-(4-chloro-1H-imidazol-1-yl)-3-methoxyaniline (216 mg, 0.965 mmol) in acetic acid (2 mL) and THF (2 mL). The reaction mixture was heated at 85° C. overnight. The crude reaction mixture was purified by preparative HPLC. The appropriate fractions were evaporated to afford 4-(azetidin-1-yl)-N-(4-(4-chloro-1H-imidazol-1-yl)-3-methoxyphenyl)-7-(4-(trifluoromethoxy)phenyl)-6,7-dihydro-5H-cyclopenta[d]pyrimidin-2-amine, TFA salt (99.3 mg, 0.148 mmol, 22.99% yield). LC-MS (M+H)$^+$=557.2. $^1$H NMR (500 MHz, CDCl$_3$) δ ppm 11.78 (1H, s), 7.51-7.65 (2H, m), 7.33-7.40 (1H, m), 7.26 (2H, d, J=3.1 Hz), 7.17 (3H, s), 7.04 (1H, s), 4.58-4.71 (2H, m), 4.27-4.46 (3H, m), 3.82 (3H, s), 2.91-3.17 (2H, m), 2.61-2.74 (1H, m), 2.50-2.60 (2H, m), 2.14-2.30 (1H, m).

Examples 101A & 101B (S)-4-(Azetidin-1-yl)-N-(4-(4-chloro-1H-imidazol-1-yl)-3-methoxyphenyl)-7-(4-(trifluoromethoxy)phenyl)-6,7-dihydro-5H-cyclopenta[d]pyrimidin-2-amine and (R)-4-(Azetidin-1-yl)-N-(4-(4-chloro-1H-imidazol-1-yl)-3-methoxyphenyl)-7-(4-(trifluoromethoxy)phenyl)-6,7-dihydro-5H-cyclopenta[d]pyrimidin-2-amine

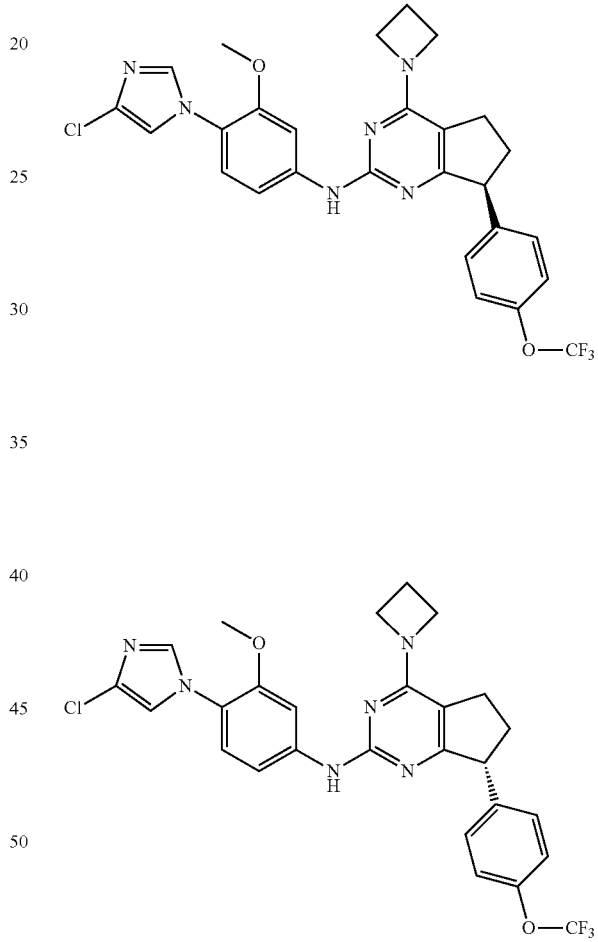

A racemic mixture of 4-(azetidin-1-yl)-N-(4-(4-chloro-1H-imidazol-1-yl)-3-methoxyphenyl)-7-(4-(trifluoromethoxy)phenyl)-6,7-dihydro-5H-cyclopenta[d]pyrimidin-2-amine (92 mg, 0.165 mmol from Example 101) was purified using chiral SFC to afford 37.6 mg of peak A (Example 101A) and 39.1 mg of peak B (Example 101B). SFC Method: Chiralpak OJ-H (4.6×250 mm, 5 μM), 30% methanol (0.1% diethylamine) in CO$_2$, 35° C., flow rate 2.0 mL/min for 18 min, absorbance 268 nm, injection 5 μL of 2 mg/mL solution in methanol (multiple stacked injections), $t_R$ (peak A)=4.7 min, $t_R$ (peak B) 13.6 min. The absolute stereochemistry of individual enantiomers (Examples 101A and 101B)

was not determined LC-MS and ¹H NMR analytical data for the separated enantiomers was identical to the racemate (Example 101).

Example 102

N²-(4-(4-Chloro-1H-imidazol-1-yl)-3-methoxyphenyl)-7-(3,5-difluorophenyl)-N⁴-methyl-6,7-dihydro-5H-cyclopenta[d]pyrimidine-2,4-diamine

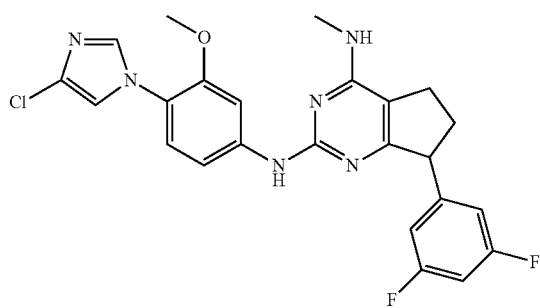 [SMILES: CNc1nc(Nc2ccc(-n3cnc(Cl)c3)c(OC)c2)nc2c1CCC2c1cc(F)cc(F)c1]

2-Chloro-7-(3,5-difluorophenyl)-N-methyl-6,7-dihydro-5H-cyclopenta[d]pyrimidin-4-amine (60 mg, 0.203 mmol) was added to a solution of 4-(4-chloro-1H-imidazol-1-yl)-3-methoxyaniline (68.1 mg, 0.304 mmol) in acetic acid (2 mL) and THF (2.000 mL). The reaction mixture was heated at 80° C. overnight. The crude reaction mixture was purified by preparative HPLC. The appropriate fractions were evaporated to afford N²-(4-(4-chloro-1H-imidazol-1-yl)-3-methoxyphenyl)-7-(3,5-difluorophenyl)-N⁴-methyl-6,7-dihydro-5H-cyclopenta[d]pyrimidine-2,4-diamine, TFA salt (33.6 mg, 0.056 mmol, 27.5% yield). LC-MS (M+H)⁺=483.0. ¹H NMR (500 MHz, MeOD) δ ppm 7.79 (1H, s), 7.70 (1H, s), 7.29-7.45 (2H, m), 7.22 (1H, d, J=8.5 Hz), 6.86-7.03 (3H, m), 4.27-4.60 (1H, m), 3.89 (3H, s), 3.24-3.48 (5H, m), 3.17 (1H, s), 2.88-3.01 (1H, m), 2.67-2.87 (1H, m), 2.03-2.32 (1H, m).

The racemic mixture was separated by chiral chromatography to afford the enantiomers Example 102A and 102B as free amines, which had identical spectral data.

Example 103

N²-(4-(4-chloro-1H-imidazol-1-yl)-3-methoxyphenyl)-N⁴-methyl-7-(3,4,5-trifluorophenyl)-6,7-dihydro-5H-cyclopenta[d]pyrimidine-2,4-diamine

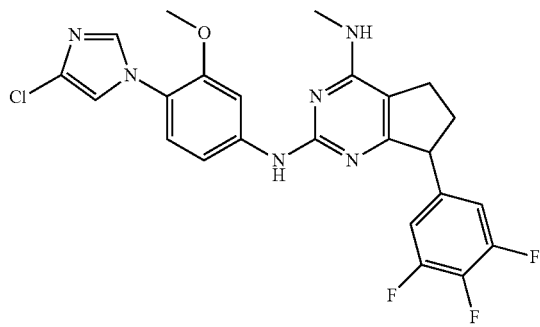 [SMILES: CNc1nc(Nc2ccc(-n3cnc(Cl)c3)c(OC)c2)nc2c1CCC2c1cc(F)c(F)c(F)c1]

2-Chloro-N-methyl-7-(3,4,5-trifluorophenyl)-6,7-dihydro-5H-cyclopenta[d]pyrimidin-4-amine (100 mg, 0.319 mmol) was added to a solution of 4-(4-chloro-1H-imidazol-1-yl)-3-methoxyaniline (107 mg, 0.478 mmol) in acetic acid (2 mL) and THF (2.000 mL). The reaction mixture was heated at 80° C. overnight. The crude reaction mixture was purified by preparative HPLC. The appropriate fractions were evaporated to afford N²-(4-(4-chloro-1H-imidazol-1-yl)-3-methoxyphenyl)-N⁴-methyl-7-(3,4,5-trifluorophenyl)-6,7-dihydro-5H-cyclopenta[d]pyrimidine-2,4-diamine, TFA salt (36.3 mg, 0.057 mmol, 17.78% yield). LC-MS (M+H)⁺=501.0. ¹H NMR (500 MHz, CDCl₃) δ ppm 11.88-11.96 (1H, m), 7.95-8.01 (1H, m), 7.44-7.62 (2H, m), 7.09-7.19 (1H, m), 6.86-6.95 (2H, m), 5.55-5.66 (1H, m), 5.26-5.39 (1H, m), 4.36-4.54 (1H, m), 3.90 (3H, s), 3.22-3.33 (3H, m), 2.72-2.87 (3H, m), 2.18-2.38 (1H, m).

Examples 103A & 103B (S)—N²-(4-(4-chloro-1H-imidazol-1-yl)-3-methoxyphenyl)-N⁴-methyl-7-(3,4,5-trifluorophenyl)-6,7-dihydro-5H-cyclopenta[d]pyrimidine-2,4-diamine and (R)—N²-(4-(4-chloro-1H-imidazol-1-yl)-3-methoxyphenyl)-N⁴-methyl-7-(3,4,5-trifluorophenyl)-6,7-dihydro-5H-cyclopenta[d]pyrimidine-2,4-diamine

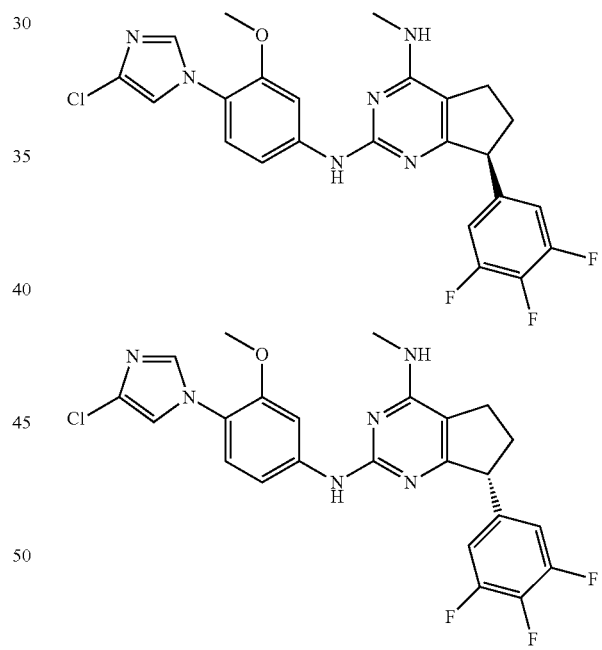

A racemic mixture of N²-(4-(4-chloro-1H-imidazol-1-yl)-3-methoxyphenyl)-N⁴-methyl-7-(3,4,5-trifluorophenyl)-6,7-dihydro-5H-cyclopenta[d]pyrimidine-2,4-diamine (59.8 mg, 0.119 mmol from Example 103) was purified using chiral SFC to afford 19.5 mg of peak A (Example 103A) and 34.8 mg of peak B (Example 103B). SFC Method: Chiralpak OJ-H (4.6×250 mm, 5 µM), 20% methanol (0.1% diethylamine) in CO₂, 35° C., flow rate 2.0 mL/min for 16 min, absorbance 268 nm, injection 5 µL of 2 mg/mL solution in methanol (multiple stacked injections), t_R (peak A)=9.7 min, t_R (peak B) 11.9 min. The absolute stereochemistry of individual enantiomers (Examples 103A and 103B) was not determined LC-MS and

Example 104

N²-(3-fluoro-4-(5-methyl-1H-1,2,4-triazol-1-yl)phenyl)-N⁴-methyl-7-(3,4,5-trifluorophenyl)-6,7-dihydro-5H-cyclopenta[d]pyrimidine-2,4-diamine

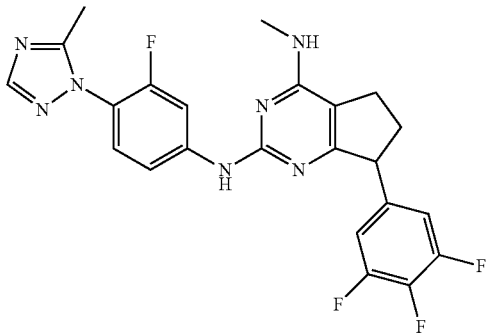 [SMILES: CNc1nc(Nc2ccc(-n3ncnc3C)c(F)c2)nc2c1CCC2c1cc(F)c(F)c(F)c1]

2-Chloro-N-methyl-7-(3,4,5-trifluorophenyl)-6,7-dihydro-5H-cyclopenta[d]pyrimidin-4-amine (65.3 mg, 0.208 mmol) was added to a solution of 3-fluoro-4-(5-methyl-1H-1,2,4-triazol-1-yl)aniline (40 mg, 0.208 mmol) in acetic acid (2 mL) and THF (2.000 mL). The reaction mixture was heated at 80° C. overnight. Partial formation of the desired product was observed. The reaction mixture was heated at 130° C. for 6 h. The crude reaction mixture was purified by preparative HPLC. The appropriate fractions were evaporated to afford N²-(3-fluoro-4-(3-methyl-1H-1,2,4-triazol-1-yl)phenyl)-N⁴-methyl-7-(3,4,5-trifluorophenyl)-6,7-dihydro-5H-cyclopenta[d]pyrimidine-2,4-diamine, TFA salt (5.3 mg, 8.99 μmol, 4.32% yield). LC-MS (M+H)⁺=470.0. ¹H NMR (500 MHz, CDCl₃) δ ppm 12.17 (1H, s), 8.75 (1H, d, J=1.8 Hz), 8.05 (1H, dd, J=13.7, 2.1 Hz), 7.80 (1H, t, J=8.7 Hz), 7.44-7.65 (1H, m), 6.74-6.99 (2H, m), 5.33-5.66 (1H, m), 4.34-4.67 (1H, m), 3.42-3.74 (2H, m), 3.29 (3H, d, J=4.9 Hz), 2.70-2.99 (2H, m), 2.57 (2H, s), 2.14-2.38 (1H, m).

Example 105

N²-(6-(4-Chloro-1H-imidazol-1-yl)-5-methoxypyridin-3-yl)-N⁴-methyl-7-(3,4,5-trifluorophenyl)-6,7-dihydro-5H-cyclopenta[d]pyrimidine-2,4-diamine

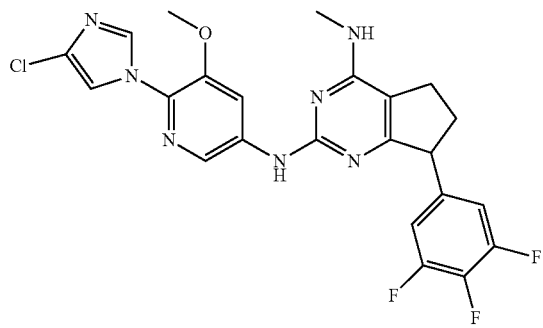 [SMILES: CNc1nc(Nc2cnc(-n3cnc(Cl)c3)c(OC)c2)nc2c1CCC2c1cc(F)c(F)c(F)c1]

2-Chloro-N-methyl-7-(3,4,5-trifluorophenyl)-6,7-dihydro-5H-cyclopenta[d]pyrimidin-4-amine (100 mg, 0.319 mmol) was added to a solution of 6-(4-chloro-1H-imidazol-1-yl)-5-methoxypyridin-3-amine (107 mg, 0.478 mmol) in acetic acid (2 mL) and THF (2.000 mL). The reaction mixture was heated at 80° C. overnight. Partial formation of the desired product was observed. The reaction mixture was heated at 130° C. for 6 h. The crude reaction mixture was purified by preparative HPLC. The appropriate fractions were evaporated to afford N²-(6-(4-chloro-1H-imidazol-1-yl)-5-methoxypyridin-3-yl)-N⁴-methyl-7-(3,4,5-trifluorophenyl)-6,7-dihydro-5H-cyclopenta[d]pyrimidine-2,4-diamine, TFA salt (12.9 mg, 0.021 mmol, 6.50% yield). LC-MS (M+H)⁺= 502.2. ¹H NMR (500 MHz, CDCl₃) δ ppm 12.33 (1H, s), 8.75 (1H, s), 8.56 (1H, s), 7.61-7.89 (2H, m), 6.85-7.00 (2H, m), 5.62-5.79 (1H, m), 4.36-4.49 (1H, m), 4.02 (3H, s), 3.29 (3H, d, J=4.9 Hz), 2.88-2.98 (1H, m), 2.76-2.85 (2H, m), 2.21-2.38 (1H, m).

Example 106

N²-(4-(3-chloro-1H-1,2,4-triazol-1-yl)-3-methoxyphenyl)-N⁴-methyl-7-(3,4,5-trifluorophenyl)-6,7-dihydro-5H-cyclopenta[d]pyrimidine-2,4-diamine

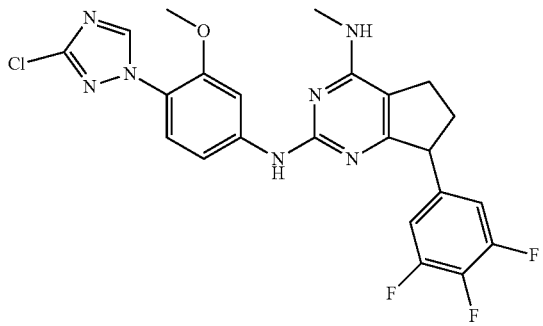 [SMILES: CNc1nc(Nc2ccc(-n3cnc(Cl)n3)c(OC)c2)nc2c1CCC2c1cc(F)c(F)c(F)c1]

2-Chloro-N-methyl-7-(3,4,5-trifluorophenyl)-6,7-dihydro-5H-cyclopenta[d]pyrimidin-4-amine (80 mg, 0.255 mmol) was added to a solution of 4-(3-chloro-1H-1,2,4-triazol-1-yl)-3-methoxyaniline (86 mg, 0.383 mmol) in acetic acid (2 mL) and THF (2.000 mL). The reaction mixture was heated at 80° C. overnight. Partial formation of the desired product was observed. The reaction mixture was heated at 120° C. for 4 h. The crude reaction mixture was purified by preparative HPLC. The appropriate fractions were evaporated to afford N²-(4-(3-chloro-1H-1,2,4-triazol-1-yl)-3-methoxyphenyl)-N⁴-methyl-7-(3,4,5-trifluorophenyl)-6,7-dihydro-5H-cyclopenta[d]pyrimidine-2,4-diamine, TFA salt (15.5 mg, 0.025 mmol, 9.77% yield). LC-MS (M+H)⁺= 502.0. ¹H NMR (500 MHz, CDCl₃) δ ppm 11.88-12.12 (1H, m), 8.63 (1H, s), 7.68-7.81 (1H, m), 7.60 (1H, s), 7.47 (1H, s), 6.92 (1H, t, J=7.2 Hz), 3.94-3.99 (1H, m), 3.52 (8H, s), 3.22-3.29 (1H, m), 2.87-3.01 (1H, m), 2.74-2.85 (1H, m), 2.22-2.38 (1H, m).

Example 107

N-(4-(4-Chloro-1H-imidazol-1-yl)-3-methoxyphenyl)-4-(3,3-difluoropyrrolidin-1-yl)-7-(3,4,5-trifluorophenyl)-6,7-dihydro-5H-cyclopenta[d]pyrimidin-2-amine

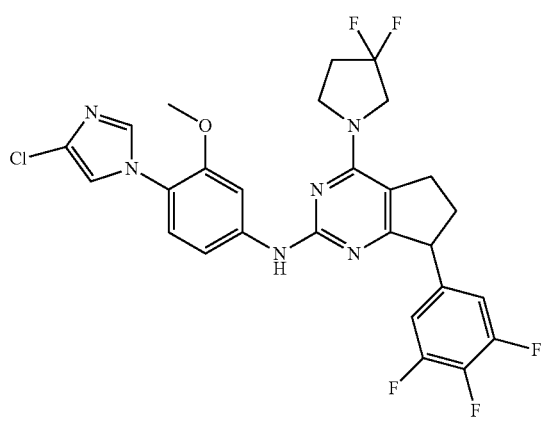 [SMILES: COc1cc(Nc2nc3c(c(N4CCC(F)(F)C4)n2)CCC3c2cc(F)c(F)c(F)c2)ccc1-n1cnc(Cl)c1]

2-Chloro-4-(3,3-difluoropyrrolidin-1-yl)-7-(3,4,5-trifluorophenyl)-6,7-dihydro-5H-cyclopenta[d]pyrimidine (105 mg, 0.269 mmol) was added to a solution of 4-(4-chloro-1H-imidazol-1-yl)-3-methoxyaniline (90 mg, 0.404 mmol) in acetic acid (1 mL) and THF (1.000 mL). The reaction mixture was heated at 80° C. overnight. The crude reaction mixture was purified by preparative HPLC. The appropriate fractions were evaporated to afford N-(4-(4-chloro-1H-imidazol-1-yl)-3-methoxyphenyl)-4-(3,3-difluoropyrrolidin-1-yl)-7-(3,4,5-trifluorophenyl)-6,7-dihydro-5H-cyclopenta[d]pyrimidin-2-amine, TFA salt (54.1 mg, 0.074 mmol, 27.3% yield). LC-MS (M+H)$^+$=577.1. $^1$H NMR (500 MHz, CDCl$_3$) δ ppm 11.70 (1H, s), 8.08-8.24 (1H, m), 7.40-7.57 (1H, m), 7.18 (1H, s), 6.88-7.01 (2H, m), 4.37-4.45 (1H, m), 4.24-4.35 (2H, m), 4.03-4.22 (2H, m), 3.98-4.03 (1H, m), 3.89 (3H, s), 3.50-3.58 (1H, m), 3.15-3.42 (2H, m), 2.48-2.89 (3H, m), 2.18-2.34 (1H, m).

Examples 107A & 107B (S)—N-(4-(4-Chloro-1H-imidazol-1-yl)-3-methoxyphenyl)-4-(3,3-difluoropyrrolidin-1-yl)-7-(3,4,5-trifluorophenyl)-6,7-dihydro-5H-cyclopenta[d]pyrimidin-2-amine and (R)—N-(4-(4-Chloro-1H-imidazol-1-yl)-3-methoxyphenyl)-4-(3,3-difluoropyrrolidin-1-yl)-7-(3,4,5-trifluorophenyl)-6,7-dihydro-5H-cyclopenta[d]pyrimidin-2-amine

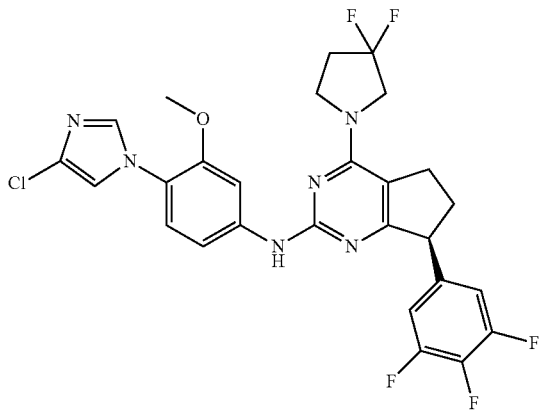

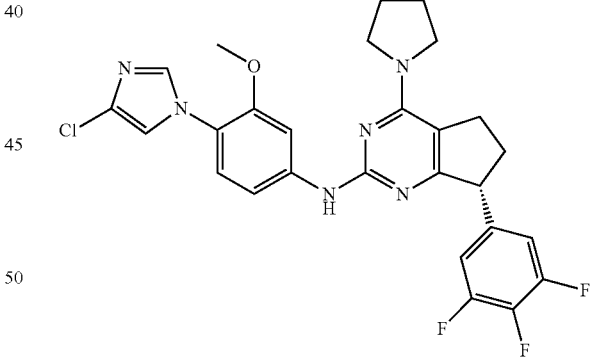

A racemic mixture of N-(4-(4-chloro-1H-imidazol-1-yl)-3-methoxyphenyl)-4-(3,3-difluoropyrrolidin-1-yl)-7-(3,4,5-trifluorophenyl)-6,7-dihydro-5H-cyclopenta[d]pyrimidin-2-amine (48 mg, 0.083 mmol from Example 107) was purified using chiral SFC to afford 19.8 mg of peak A (Example 107A) and 17.2 mg of peak B (Example 107B). SFC Method: Chiralpak OJ-H (4.6×250 mm, 5 µM), 25% methanol (0.1% diethylamine) in CO$_2$, 35° C., flow rate 2.0 mL/min for 30 min, absorbance 268 nm, injection 5 µL of 2 mg/mL solution in methanol (multiple stacked injections), $t_R$ (peak A)=17.4 min, $t_R$ (peak B) 21.2 min. The absolute stereochemistry of individual enantiomers (Examples 107A and 107B) was not determined LC-MS and $^1$H NMR analytical data for the separated enantiomers was identical to the racemate (Example 107).

Example 108

N-(4-(4-Chloro-1H-imidazol-1-yl)-3-methoxyphenyl)-4-(3,3-difluoroazetidin-1-yl)-7-(3,4,5-trifluorophenyl)-6,7-dihydro-5H-cyclopenta[d]pyrimidin-2-amine

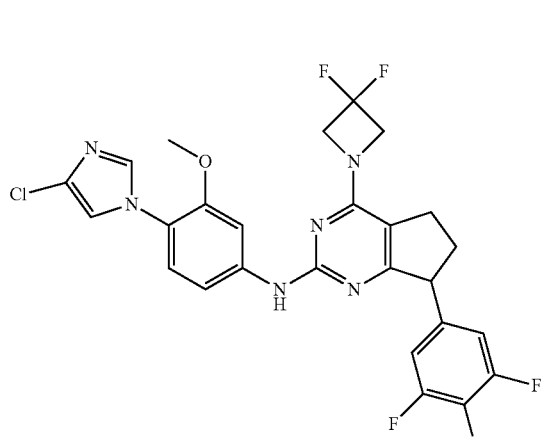

2-Chloro-4-(3,3-difluoroazetidin-1-yl)-7-(3,4,5-trifluorophenyl)-6,7-dihydro-5H-cyclopenta[d]pyrimidine (105 mg, 0.279 mmol) was added to a solution of 4-(4-chloro-1H-imidazol-1-yl)-3-methoxyaniline (94 mg, 0.419 mmol) in acetic acid (1 mL) and THF (1.000 mL). The reaction mixture was heated at 80° C. overnight. The crude reaction mixture was purified by preparative HPLC. The appropriate fractions were evaporated to afford N-(4-(4-chloro-1H-imidazol-1-yl)-3-methoxyphenyl)-4-(3,3-difluoroazetidin-1-yl)-7-(3,4,5-trifluorophenyl)-6,7-dihydro-5H-cyclopenta[d]pyrimidin-2-amine, TFA salt (31.4 mg, 0.044 mmol, 15.60% yield). LC-MS (M+H)$^+$=563.1. $^1$H NMR (500 MHz, CDCl$_3$) δ ppm 11.87 (1H, s), 8.09 (1H, s), 7.45 (1H, dd, J=8.5, 1.5 Hz), 7.36 (1H, s), 7.29 (2H, s), 7.25 (1H, d, J=8.5 Hz), 7.16 (1H, s), 6.91 (2H, t, J=6.9 Hz), 4.40 (1H, dd, J=9.2, 4.9 Hz), 4.00 (1H, s), 3.89 (3H, s), 3.53 (1H, s), 3.08-3.19 (1H, m), 2.97-3.06 (1H, m), 2.72-2.84 (1H, m), 2.26 (1H, td, J=9.2, 4.3 Hz).

Example 109

N$^2$-(4-(4-Chloro-1H-imidazol-1-yl)-3-methoxyphenyl)-7-(2,4-difluorophenyl)-N$^4$-methyl-6,7-dihydro-5H-cyclopenta[d]pyrimidine-2,4-diamine

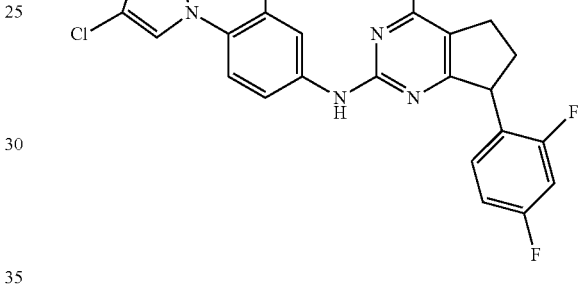

A solution of 2-chloro-7-(2,4-difluorophenyl)-N-methyl-6,7-dihydro-5H-cyclopenta[d]pyrimidin-4-amine (184.6 mg, 0.624 mmol) and 4-(4-chloro-1H-imidazol-1-yl)-3-methoxyaniline (140 mg, 0.624 mmol) in THF (1095 µL) and acetic acid (1095 µL) was heated 80° C. in a capped vial overnight. The solvent was evaporated in vacuum and the residue was partitioned between aqueous sodium bicarbonate solution and dichloromethane. The organic layer was separated and the aqueous layer was extracted with dichloromethane. the combined organic extracts were dried over anhydrous magnesium sulfate and filtered. The solvent was removed in vacuum and the residue was purified by column chromatography on silica gel to give N$^2$-(4-(4-chloro-1H-imidazol-1-yl)-3-methoxyphenyl)-7-(2,4-difluorophenyl)-N$^4$-methyl-6,7-dihydro-5H-cyclopenta[d]pyrimidine-2,4-diamine (179.6 mg, 0.372 mmol, 59.6% yield) as brown solid. LC-MS (M+H)$^+$=483.1. $^1$H NMR (500 MHz, CDCl$_3$) δ ppm 7.97 (1H, d, J=2.1 Hz), 7.49 (1H, d, J=1.5 Hz), 7.01-7.10 (2H, m), 7.00 (1H, d, J=1.5 Hz), 6.73-6.84 (3H, m), 4.44 (1H, s), 3.61 (3H, s), 3.11 (3H, d, J=4.9 Hz), 2.59-2.77 (2H, m), 1.95-2.05 (2H, m).

Examples 109A and 109B (S)—N$^2$-(4-(4-Chloro-1H-imidazol-1-yl)-3-methoxyphenyl)-7-(2,4-difluorophenyl)-N$^4$-methyl-6,7-dihydro-5H-cyclopenta[d]pyrimidine-2,4-diamine and (R)—N$^2$-(4-(4-Chloro-1H-imidazol-1-yl)-3-methoxyphenyl)-7-(2,4-difluorophenyl)-N$^4$-methyl-6,7-dihydro-5H-cyclopenta[d]pyrimidine-2,4-diamine

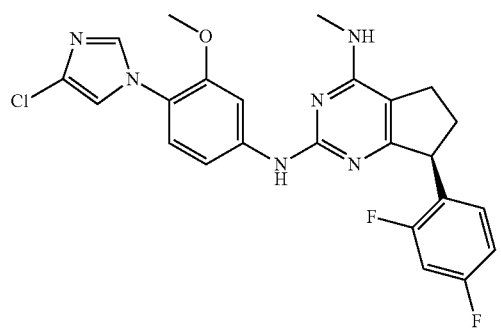

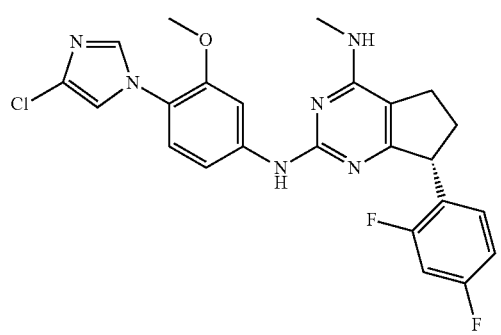

A racemic mixture of N$^2$-(4-(4-chloro-1H-imidazol-1-yl)-3-methoxyphenyl)-N$^4$-trideuteromethyl-7-phenyl-6,7-dihydro-5H-cyclopenta[d]pyrimidine-2,4-diamine (180 mg, 0.206 mmol from Example 109) was purified using chiral supercritical fluid chromatography (SFC) to afford 28.4 mg of peak A (Example 109A) and 27.4 mg of peak B (Example 109B). SFC Method: Chiralpak OJ-H (21×250 mm, 5 μM), 35% methanol (0.1% diethylamine) in CO$_2$, 35° C., flow rate 45 mL/min for 10 min, absorbance 268 nm, injection 0.75 mL of 20 mg/mL solution in methanol (multiple stacked injections), t$_R$ (peak A)=3.6 min, t$_R$ (peak B) 7.2 min. The absolute stereochemistry of individual enantiomers (Examples 109A and 109B) was not determined LC-MS and $^1$H NMR analytical data for the separated enantiomers was identical to the racemate (Example 109).

Example 110

N2-(4-(4-chloro-1H-imidazol-1-yl)-3-methoxyphenyl)-N4-ethyl-7-methyl-7-phenyl-6,7-dihydro-5H-cyclopenta[d]pyrimidine-2,4-diamine

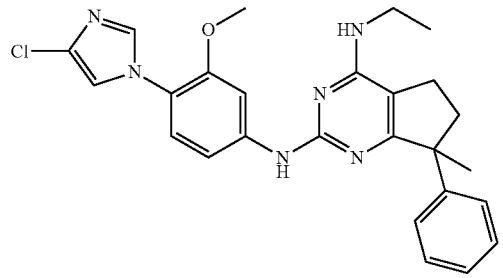 [SMILES: CCNc1nc(Nc2ccc(-n3cnc(Cl)c3)c(OC)c2)nc2c1CCC2(C)c1ccccc1]

The method of Example 74 was used to combine Preparation Va and 4-(4-chloro-1H-imidazol-1-yl)-3-methoxyaniline (Preparation A) to afford N2-(4-(4-chloro-1H-imidazol-1-yl)-3-methoxyphenyl)-N4-ethyl-7-methyl-7-phenyl-6,7-dihydro-5H-cyclopenta[d]pyrimidine-2,4-diamine (Example 110). LC-MS (M+H)$^+$=475.2. $^1$H NMR (500 MHz, METHANOL-d4) δ ppm 8.03 (1H, d, J=2.14 Hz), 7.65 (1H, s), 7.22-7.30 (4H, m), 7.20 (1H, s), 7.10-7.16 (2H, m), 7.02 (1H, dd, J=8.55, 2.14 Hz), 3.66 (3H, s), 3.56 (2H, q, J=7.32 Hz), 2.56-2.69 (2H, m), 2.30-2.38 (1H, m), 2.14-2.22 (1H, m), 1.25 (3H, d, J=7.20 Hz).

The racemic mixture was separated by chiral chromatography to afford the enantiomers Example 110A and 110B, which had identical spectral data.

Example 111

N2-(4-(4-chloro-1H-imidazol-1-yl)-3-methoxyphenyl)-N4-ethyl-7-allyl-7-phenyl-6,7-dihydro-5H-cyclopenta[d]pyrimidine-2,4-diamine

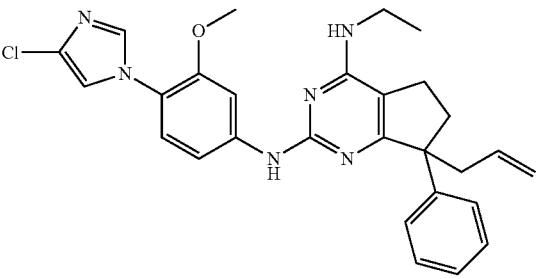 [SMILES: C=CCC1(c2ccccc2)CCc2c(NCC)nc(Nc3ccc(-n4cnc(Cl)c4)c(OC)c3)nc21]

The method of Example 74 was used to combine Preparation Wa and 4-(4-chloro-1H-imidazol-1-yl)-3-methoxyaniline (Preparation A) to afford N2-(4-(4-chloro-1H-imidazol-1-yl)-3-methoxyphenyl)-N4-ethyl-7-allyl-7-phenyl-6,7-dihydro-5H-cyclopenta[d]pyrimidine-2,4-diamine (Example 111). LC-MS (M+H)$^+$=501.2. $^1$H NMR (500 MHz, CDCl$_3$) δ ppm 11.66 (1H, br. s.), 7.45-7.54 (2H, m), 7.32-7.39 (5H, m), 7.25-7.30 (3H, m), 5.57-5.68 (1H, m, J=16.94, 9.92, 7.17, 7.17 Hz), 5.42 (1H, br. s.), 5.22 (1H, d, J=16.17 Hz), 5.12 (1H, d, J=10.07 Hz), 3.85 (3H, s), 3.63-3.70 (2H, m), 3.05-3.12 (2H, m), 2.64-2.80 (2H, m), 2.51-2.63 (2H, m), 1.35 (3H, t, J=7.17 Hz).

Example 112

N2-(4-(4-chloro-1H-imidazol-1-yl)-3-methoxyphenyl)-8-(3,5-difluorophenyl)-N4-ethyl-7,8-dihydro-5H-pyrano[4,3-d]pyrimidine-2,4-diamine, TFA

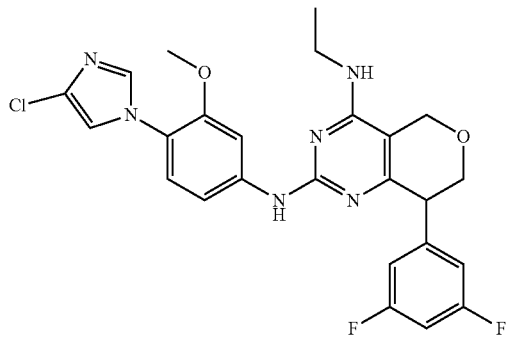 [SMILES: CCNc1nc(Nc2ccc(-n3cnc(Cl)c3)c(OC)c2)nc2c1COCC2c1cc(F)cc(F)c1]

The mixture of 2-chloro-8-(3,5-difluorophenyl)-N-ethyl-7,8-dihydro-5H-pyrano[4,3-d]pyrimidin-4-amine (Preparation Xa) (87 mg, 0.267 mmol), 4-(4-chloro-1H-imidazol-1-yl)-3-methoxyaniline (Preparation A) (71.7 mg, 0.321 mmol), tris(dibenzylideneacetone)dipalladium(0) (12.23 mg, 0.013 mmol), (9,9-dimethyl-9H-xanthene-4,5-diyl)bis(diphenylphosphine) (15.45 mg, 0.027 mmol) and sodium carbonate (42.5 mg, 0.401 mmol) in Dioxane (1272 µL)/Water (254 µL) was heated at 110° C. overnight. The reaction mixture was diluted with water and extracted with EtOAc. The combined organic layers were washed with brine and concentrated in vacuum. The crude product was purified by Prep-HPLC (Solvent A=10% Acetonitrile-90% H2O-0.1% TFA, Solvent B=90% Acetonitrile-10% H2O-0.1% TFA. Column. PHENOMENEX LUNA 21×100 mm, 10uC18, Flow rate: 25 ml/min, 30-100% B, 20 min) to obtain N2-(4-(4-chloro-1H-imidazol-1-yl)-3-methoxyphenyl)-8-(3,5-difluorophenyl)-N4-ethyl-7,8-dihydro-5H-pyrano[4,3-d]pyrimidine-2,4-diamine, TFA (Example 112) (123 mg, 0.177 mmol, 66.1% yield). LC-MS (M+H)+=513.2. 1H NMR (500 MHz, CDCl3) δ ppm 11.71 (s, 1H) 8.04 (s, 1H) 7.49 (d, J=2.14 Hz, 1H) 7.43 (dd, J=8.55, 2.14 Hz, 1H) 7.23 (d, J=8.55 Hz, 1H) 7.17 (d, J=1.53 Hz, 1H) 7.00 (d, J=5.80 Hz, 2H) 6.70-6.84 (m, 1H) 6.09 (t, J=5.19 Hz, 1H) 4.73 (d, J=14.34 Hz, 1H) 4.54 (d, J=14.34 Hz, 1H) 3.95-4.15 (m, 3H) 3.88 (s, 3H) 3.61-3.78 (m, 2H) 1.37 (t, J=7.17 Hz, 3H).

The racemic mixture was separated by chiral chromatography to afford the enantiomers Example 112A and 112B as free amines LC-MS (M+H)+=513.2. 1H NMR (500 MHz, MeOD) δ ppm 7.84 (d, J=2.14 Hz, 1H) 7.67 (d, J=1.53 Hz, 1H) 7.21 (d, J=1.53 Hz, 1H) 7.13 (d, J=8.55 Hz, 1H) 6.98-7.08 (m, 1H) 6.89 (d, J=2.14 Hz, 1H) 6.74-6.85 (m, 1H) 4.65 (d, J=14.34 Hz, 1H) 4.46-4.59 (m, 1H) 4.11 (dd, J=11.44, 4.43 Hz, 1H) 3.96 (dd, J=11.44, 4.12 Hz, 1H) 3.88 (d, J=3.97 Hz, 1H) 3.66 (s, 3H) 3.58 (q, J=7.32 Hz, 2H) 1.27 (t, J=7.17 Hz, 3H).

Example 113

N2-(4-(4-chloro-1H-imidazol-1-yl)-3-methoxyphenyl)-8-(3,4-difluorophenyl)-N4-ethyl-7,8-dihydro-5H-pyrano[4,3-d]pyrimidine-2,4-diamine, TFA

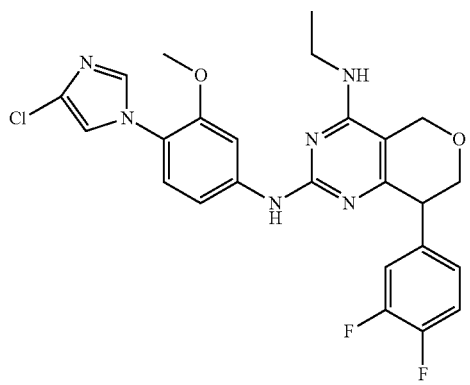 [SMILES: CCNc1nc(Nc2ccc(-n3cnc(Cl)c3)c(OC)c2)nc2c1COCC2c1ccc(F)c(F)c1]

2-chloro-8-(3,4-difluorophenyl)-N-ethyl-7,8-dihydro-5H-pyrano[4,3-d]pyrimidin-4-amine (Preparation Ya) was reacted as described in Example 112 with 4-(4-chloro-1H-imidazol-1-yl)-3-methoxyaniline (Preparation A) to give N2-(4-(4-chloro-1H-imidazol-1-yl)-3-methoxyphenyl)-8-(3,4-difluorophenyl)-N4-ethyl-7,8-dihydro-5H-pyrano[4,3-d]pyrimidine-2,4-diamine, TFA (Example 113). LC-MS (M+H)+=513.5. 1H NMR (500 MHz, MeOD) δ ppm 7.84 (d, J=1.22 Hz, 1H) 7.58 (d, J=2.14 Hz, 1H) 7.32-7.49 (m, 3H) 7.12-7.32 (m, 3H) 4.71 (d, J=14.95 Hz, 1H) 4.55 (d, J=14.65 Hz, 1H) 4.14 (dd, J=11.60, 4.27 Hz, 1H) 4.06 (br. s., 1H) 3.92-4.02 (m, 1H) 3.89 (s, 3H) 3.68-3.70 (m, 2H) 1.32 (t, J=7.17 Hz, 3H).

The racemic mixture was separated by chiral chromatography to afford the enantiomers Example 113A and 113B as free amines LC-MS (M+H)+=513.3. 1H NMR (500 MHz, MeOD) δ ppm 7.83 (d, J=2.14 Hz, 1H) 7.67 (s, 1H) 7.09-7.25 (m, 4H) 6.96-7.09 (m, 2H) 4.59-4.69 (m, 1H) 4.47-4.57 (m, 1H) 4.10 (dd, J=11.29, 4.27 Hz, 1H) 3.92 (dd, J=11.60, 4.27

Hz, 1H) 3.86 (d, J=3.36 Hz, 1H) 3.62-3.68 (m, 3H) 3.57 (q, J=7.32 Hz, 2H) 1.22-1.34 (m, 3H).

Example 114

N-(4-(4-chloro-1H-imidazol-1-yl)-3-methoxyphenyl)-4-(3,3-difluoroazetidin-1-yl)-8-(3,4-difluorophenyl)-7,8-dihydro-5H-pyrano[4,3-d]pyrimidin-2-amine, TFA

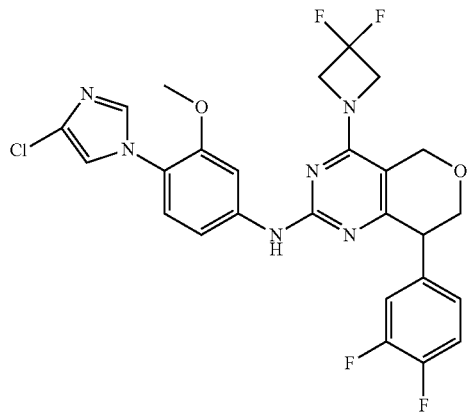 [SMILES: COc1cc(Nc2nc3c(c(N4CC(F)(F)C4)n2)COCC3c2ccc(F)c(F)c2)ccc1-n1cnc(Cl)c1]

2-chloro-4-(3,3-difluoroazetidin-1-yl)-8-(3,4-difluorophenyl)-7,8-dihydro-5H-pyrano[4,3-d]pyrimidine (Preparation Yb) was reacted as described in Example 112 with 4-(4-chloro-1H-imidazol-1-yl)-3-methoxyaniline (Preparation A) to give N-(4-(4-chloro-1H-imidazol-1-yl)-3-methoxyphenyl)-4-(3,3-difluoroazetidin-1-yl)-8-(3,4-difluorophenyl)-7,8-dihydro-5H-pyrano[4,3-d]pyrimidin-2-amine, TFA (Example 114). LC-MS (M+H)+=561.5. $^1$H NMR (500 MHz, CDCl$_3$) δ ppm 12.12 (br. s., 1H) 7.80 (s, 1H) 7.38 (dd, J=8.55, 1.83 Hz, 1H) 7.20-7.31 (m, 4H) 7.09-7.18 (m, 2H) 4.69-4.89 (m, 6H) 4.06 (m, 3H) 3.87 (s, 3H).

The racemic mixture was separated by chiral chromatography to afford the enantiomers Example 114A and 114B as free amines LC-MS (M+H)+=561.3. $^1$H NMR (500 MHz, MeOD) δ ppm 7.74 (s, 1H) 7.66 (s, 1H) 7.10-7.24 (m, 4H) 7.08 (d, J=1.53 Hz, 1H) 7.02 (d, J=8.55 Hz, 1H) 4.76-4.84 (m, 1H) 4.68 (d, J=14.04 Hz, 1H) 4.59 (t, J=12.21 Hz, 4H) 4.14 (dd, J=11.29, 3.66 Hz, 1H) 3.98 (br. s., 1H) 3.86-3.94 (m, 1H) 3.59 (s, 3H).

Example 115

N2-(4-(4-chloro-1H-imidazol-1-yl)-3-methoxyphenyl)-8-(3,4-difluorophenyl)-N4-methyl-7,8-dihydro-5H-pyrano[4,3-d]pyrimidine-2,4-diamine, TFA

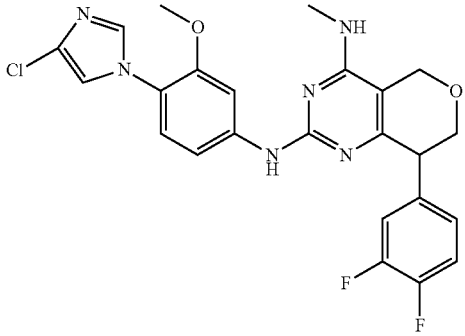 [SMILES: CNc1nc(Nc2ccc(-n3cnc(Cl)c3)c(OC)c2)nc2c1COCC2c1ccc(F)c(F)c1]

2-chloro-8-(3,4-difluorophenyl)-N-methyl-7,8-dihydro-5H-pyrano[4,3-d]pyrimidin-4-amine (Preparation Yc) was reacted as described in Example 112 with 4-(4-chloro-1H-imidazol-1-yl)-3-methoxyaniline (Preparation A) to give N2-(4-(4-chloro-1H-imidazol-1-yl)-3-methoxyphenyl)-8-(3,4-difluorophenyl)-N4-methyl-7,8-dihydro-5H-pyrano[4,3-d]pyrimidine-2,4-diamine, TFA (Example 115). LC-MS (M+H)+=499.5. $^1$H NMR (500 MHz, MeOD) δ ppm 7.86 (d, J=1.53 Hz, 1H) 7.66 (d, J=2.14 Hz, 1H) 7.26-7.41 (m, 4H) 7.17-7.25 (m, 2H) 4.70 (d, J=14.65 Hz, 1H) 4.54 (dd, J=14.95, 1.53 Hz, 1H) 4.15 (dd, J=11.60, 4.27 Hz, 1H) 4.07 (br. s., 1H) 3.96 (dd, J=11.60, 3.36 Hz, 1H) 3.89 (s, 3H) 3.16 (s, 3H).

The racemic mixture was separated by chiral chromatography to afford the enantiomers Example 115A and 115B as free amines LC-MS (M+H)+=499.3. $^1$H NMR (500 MHz, MeOD) δ ppm 7.90 (d, J=2.14 Hz, 1H) 7.67 (d, J=1.53 Hz, 1H) 7.12-7.25 (m, 4H) 7.07 (d, J=2.14 Hz, 1H) 6.98-7.05 (m, 1H) 4.63 (d, J=14.34 Hz, 1H) 4.45-4.57 (m, 1H) 4.11 (dd, J=11.44, 4.43 Hz, 1H) 3.93 (dd, J=11.44, 4.43 Hz, 1H) 3.87 (d, J=3.97 Hz, 1H) 3.61-3.70 (m, 3H) 3.00-3.08 (m, 3H).

Example 116

8-(3,4-difluorophenyl)-N4-ethyl-N2-(3-fluoro-4-(5-methyl-1H-1,2,4-triazol-1-yl)phenyl)-7,8-dihydro-5H-pyrano[4,3-d]pyrimidine-2,4-diamine, TFA

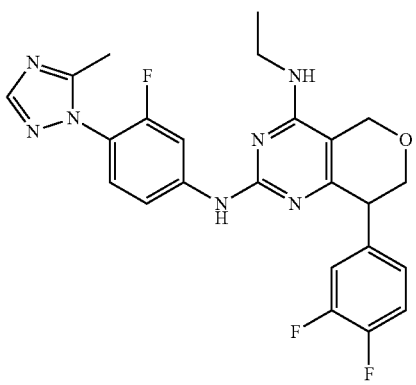 [SMILES: CCNc1nc(Nc2ccc(-n3ncnc3C)c(F)c2)nc2c1COCC2c1ccc(F)c(F)c1]

2-chloro-8-(3,4-difluorophenyl)-N-ethyl-7,8-dihydro-5H-pyrano[4,3-d]pyrimidin-4-amine (Preparation Ya) was reacted as described in Example 112 with 3-fluoro-4-(5-methyl-1H-1,2,4-triazol-1-yl)aniline (Preparation C) to give 8-(3,4-difluorophenyl)-$N^4$-ethyl-N2-(3-fluoro-4-(5-methyl-1H-1,2,4-triazol-1-yl)phenyl)-7,8-dihydro-5H-pyrano[4,3-d]pyrimidine-2,4-diamine, TFA (Example 116).

LC-MS (M+H)$^+$=482.3 $^1$H NMR (500 MHz, MeOD) δ ppm 8.13 (s, 1H) 7.95 (dd, J=12.36, 1.98 Hz, 1H) 7.47-7.62 (m, 2H) 7.30-7.42 (m, 1H) 7.23-7.30 (m, 1H) 7.21 (br. s., 1H) 4.72 (d, J=14.95 Hz, 1H) 4.55 (d, J=14.95 Hz, 1H) 4.14 (dd, J=11.44, 4.12 Hz, 1H) 4.07 (br. s., 1H) 3.91-4.01 (m, 1H) 3.58-3.75 (m, 2H) 2.44 (s, 3H) 1.26-1.43 (m, 3H).

The racemic mixture was separated by chiral chromatography to afford the enantiomers Example 116A and 116B as free amines LC-MS (M+H)$^+$=482.3. $^1$H NMR $^1$H NMR (500 MHz, MeOD) δ ppm 8.05 (d, J=2.14 Hz, 1H) 8.03 (s, 1H) 7.27-7.34 (m, 2H) 7.17-7.25 (m, 2H) 7.12 (d, J=1.83 Hz, 1H) 4.61-4.68 (m, 1H) 4.56 (t, J=14.19 Hz, 1H) 4.15 (dd, J=11.29, 4.58 Hz, 1H) 4.00 (dd, J=11.44, 4.73 Hz, 1H) 3.90 (d, J=4.27 Hz, 1H) 3.58-3.66 (m, 2H) 2.38 (s, 3H) 1.19 (t, J=7.02 Hz, 3H).

Example 117

N2-(4-(4-chloro-1H-imidazol-1-yl)-3-methoxyphenyl)-N4-((R)-1-cyclopropylethyl)-8-(4-(trifluoromethyl)phenyl)-7,8-dihydro-5H-pyrano[4,3-d]pyrimidine-2,4-diamine, TFA

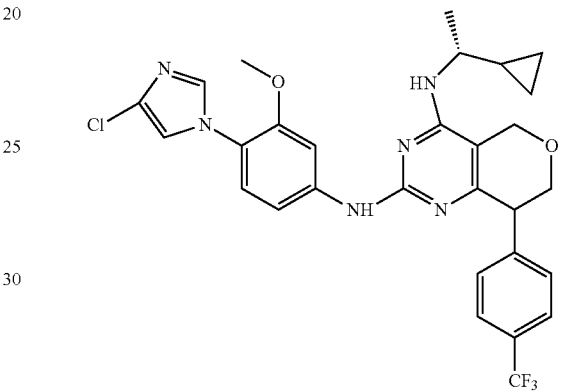

2-chloro-N—((R)-1-cyclopropylethyl)-8-(4-(trifluoromethyl)phenyl)-7,8-dihydro-5H-pyrano[4,3-d]pyrimidin-4-amine (Preparation Zc) was reacted as described in Example 112 with 4-(4-chloro-1H-imidazol-1-yl)-3-methoxyaniline (Preparation A) to give N2-(4-(4-chloro-1H-imidazol-1-yl)-3-methoxyphenyl)-N4-((R)-1-cyclopropylethyl)-8-(4-(trifluoromethyl)phenyl)-7,8-dihydro-5H-pyrano[4,3-d]pyrimidine-2,4-diamine, TFA (Example 117). LC-MS (M+H)$^+$=585.4. $^1$H NMR (500 MHz, CDCl$_3$) δ ppm 11.95 (s, 1H) 7.68 (d, J=1.53 Hz, 1H) 7.52-7.65 (m, 4H) 7.31-7.43 (m, 2H) 7.16-7.22 (m, 1H) 7.10 (d, J=1.53 Hz, 1H) 5.62 (t, J=7.02 Hz, 1H) 4.75 (dd, J=14.34, 4.88 Hz, 1H) 4.58 (dd, J=13.89, 8.39 Hz, 1H) 4.11 (d, J=2.14 Hz, 3H) 3.73-3.91 (m, 4H) 1.40 (dd, J=10.38, 6.71 Hz, 3H) 1.06 (ddd, J=7.78, 3.05, 2.90 Hz, 1H) 0.69 (dt, J=8.62, 4.39 Hz, 1H) 0.51-0.64 (m, 1H) 0.38 (ddd, J=14.50, 9.77, 4.73 Hz, 1H) 0.32 (dd, J=9.61, 4.73 Hz, 1H).

The racemic mixture was separated by chiral chromatography to afford the enantiomers Example 117A and 117B as free amines LC-MS (M+H)$^+$=585.1. $^1$H NMR (500 MHz, MeOD) δ ppm 7.73 (d, J=2.14 Hz, 1H) 7.56-7.68 (m, 3H) 7.44 (d, J=8.24 Hz, 2H) 7.19 (d, J=1.53 Hz, 1H) 7.09 (d, J=8.55 Hz, 1H) 6.94 (dd, J=8.55, 2.14 Hz, 1H) 4.65-4.72 (m, 1H) 4.52-4.62 (m, 1H) 4.16 (dd, J=11.44, 4.73 Hz, 1H) 3.92 (dd, J=11.29, 4.88 Hz, 1H) 3.89 (dd, J=8.24, 6.71 Hz, 1H) 3.49 (s, 3H) 3.06 (q, J=7.32 Hz, 1H) 1.22-1.41 (m, 3H) 1.08

(dt, J=8.24, 4.88 Hz, 1H) 0.51-0.59 (m, 1H) 0.48 (dd, J=8.39, 5.04 Hz, 1H) 0.39 (dd, J=9.77, 4.58 Hz, 1H) 0.19-0.33 (m, 1H).

Example 118

N2-(4-(4-chloro-1H-imidazol-1-yl)-3-methoxyphenyl)-N4-ethyl-8-(4-(trifluoromethyl)phenyl)-7,8-dihydro-5H-pyrano[4,3-d]pyrimidine-2,4-diamine, TFA

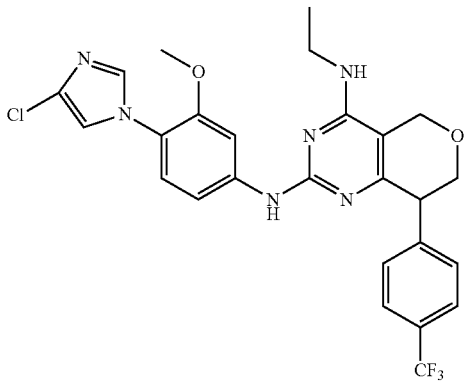 [SMILES: CCNc1nc(Nc2ccc(-n3cnc(Cl)c3)c(OC)c2)nc2c1COCC2c1ccc(C(F)(F)F)cc1]

2-chloro-N-ethyl-8-(4-(trifluoromethyl)phenyl)-7,8-dihydro-5H-pyrano[4,3-d]pyrimidin-4-amine (Preparation Za) was reacted as described in Example 112 with 4-(4-chloro-1H-imidazol-1-yl)-3-methoxyaniline (Preparation A) to give N2-(4-(4-chloro-1H-imidazol-1-yl)-3-methoxyphenyl)-N4-ethyl-8-(4-(trifluoromethyl)phenyl)-7,8-dihydro-5H-pyrano[4,3-d]pyrimidine-2,4-diamine, TFA (Example 118). LC-MS (M+H)$^+$=545.3. $^1$H NMR (500 MHz, CDCl$_3$) δ ppm 11.87 (s, 1H) 7.68 (d, J=1.22 Hz, 1H) 7.59 (m, 4H) 7.49 (d, J=2.14 Hz, 1H) 7.40 (dd, J=8.55, 2.14 Hz, 1H) 7.20 (d, J=8.55 Hz, 1H) 7.11 (d, J=1.53 Hz, 1H) 6.38 (br. s., 1H) 4.76 (d, J=14.34 Hz, 1H) 4.57 (d, J=13.73 Hz, 1H) 4.07-4.16 (m, 3H) 3.86 (s, 3H) 3.59-3.77 (m, 2H) 1.36 (t, J=7.17 Hz, 3H).

The racemic mixture was separated by chiral chromatography to afford the enantiomers Example 118A and 118B as free amines LC-MS (M+H)$^+$=545.1. $^1$H NMR (500 MHz, MeOD) δ ppm 7.79 (d, J=1.83 Hz, 1H) 7.56-7.70 (m, 3H) 7.43 (d, J=7.93 Hz, 2H) 7.19 (d, J=1.53 Hz, 1H) 7.11 (d, J=8.55 Hz, 1H) 6.91-7.03 (m, 1H) 4.60-4.72 (m, 1H) 4.48-4.60 (m, 1H) 4.15 (dd, J=11.14, 4.43 Hz, 1H) 3.99 (t, J=4.27 Hz, 1H) 3.87-3.97 (m, 1H) 3.46-3.66 (m, 5H) 1.28 (t, J=7.17 Hz, 3H).

Example 119

N4-ethyl-N2-(3-fluoro-4-(5-methyl-1H-1,2,4-triazol-1-yl)phenyl)-8-(4-(trifluoromethyl)phenyl)-7,8-dihydro-5H-pyrano[4,3-d]pyrimidine-2,4-diamine, TFA

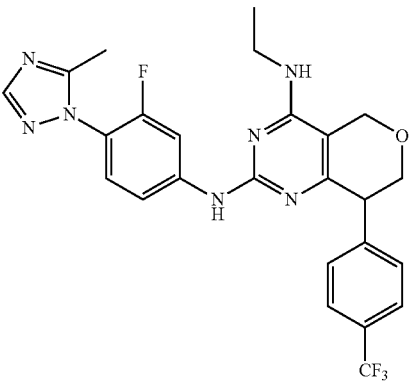 [SMILES: CCNc1nc(Nc2ccc(-n3ncnc3C)c(F)c2)nc2c1COCC2c1ccc(C(F)(F)F)cc1]

2-chloro-N-ethyl-8-(4-(trifluoromethyl)phenyl)-7,8-dihydro-5H-pyrano[4,3-d]pyrimidin-4-amine (Preparation Za) was reacted as described in Example 112 with 3-fluoro-4-(5-methyl-1H-1,2,4-triazol-1-yl)aniline (Preparation C) to give N4-ethyl-N2-(3-fluoro-4-(5-methyl-1H-1,2,4-triazol-1-yl)phenyl)-8-(4-(trifluoromethyl)phenyl)-7,8-dihydro-5H-pyrano[4,3-d]pyrimidine-2,4-diamine, TFA (Example 119). LC-MS (M+H)$^+$=514.3. $^1$H NMR (500 MHz, CDCl$_3$) δ ppm 12.20 (br. s., 1H) 8.01 (s, 1H) 7.93 (dd, J=12.36, 2.29 Hz, 1H) 7.59 (m, 4H) 7.52 (dd, J=8.85, 1.53 Hz, 1H) 7.38 (t, J=8.39 Hz, 1H) 5.97 (br. s., 1H) 4.72 (d, J=14.34 Hz, 1H) 4.54 (d, J=13.73 Hz, 1H) 3.99-4.18 (m, 3H) 3.57-3.75 (m, 2H) 2.43 (s, 3H) 1.37 (t, J=7.17 Hz, 3H).

The racemic mixture was separated by chiral chromatography to afford the enantiomers Example 119A and 119B as free amines LC-MS (M+H)$^+$=514.1. $^1$H NMR (500 MHz, MeOD) δ ppm 8.02 (s, 1H) 8.00 (dd, J=14.04, 2.14 Hz, 1H) 7.62 (m, J=8.24 Hz, 2H) 7.48 (m, J=8.24 Hz, 2H) 7.21-7.34

(m, 2H) 4.62-4.72 (m, 1H) 4.52-4.62 (m, 1H) 4.15-4.27 (m, 1H) 3.94-4.09 (m, 2H) 3.58 (q, J=7.32 Hz, 2H) 2.36 (s, 3H) 1.30 (t, J=7.17 Hz, 3H).

Example 120

N2-(4-(4-chloro-1H-imidazol-1-yl)-3-methoxyphenyl)-N4-methyl-8-(4-(trifluoromethyl)phenyl)-7,8-dihydro-5H-pyrano[4,3-d]pyrimidine-2,4-diamine, TFA

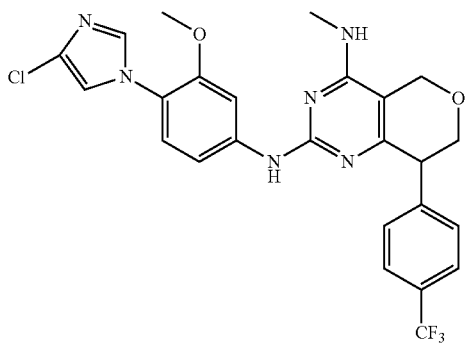 [SMILES: CNc1nc(Nc2ccc(-n3cnc(Cl)c3)c(OC)c2)nc2c1COCC2c1ccc(C(F)(F)F)cc1]

2-chloro-N-methyl-8-(4-(trifluoromethyl)phenyl)-7,8-dihydro-5H-pyrano[4,3-d]pyrimidin-4-amine (Preparation Zb) was reacted as described in Example 112 with 4-(4-chloro-1H-imidazol-1-yl)-3-methoxyaniline (Preparation A) to give N2-(4-(4-chloro-1H-imidazol-1-yl)-3-methoxyphenyl)-N4-methyl-8-(4-(trifluoromethyl)phenyl)-7,8-dihydro-5H-pyrano[4,3-d]pyrimidine-2,4-diamine, TFA (Example 120). LC-MS (M+H)$^+$=531.3. $^1$H NMR (500 MHz, CDCl$_3$) δ ppm 11.80 (s, 1H) 7.87 (d, J=1.53 Hz, 1H) 7.51-7.63 (m, 5H) 7.40 (dd, J=8.85, 2.14 Hz, 1H) 7.28 (s, 1H) 7.20 (d, J=8.55 Hz, 1H) 6.56 (d, J=4.58 Hz, 1H) 4.76 (d, J=14.34 Hz, 1H) 4.57 (d, J=14.04 Hz, 1H) 4.01-4.14 (m, 3H) 3.87 (s, 3H) 3.21 (d, J=4.58 Hz, 3H).

The racemic mixture was separated by chiral chromatography to afford the enantiomers Example 120A and 120B as free amines. LC-MS (M+H)$^+$=531.1. $^1$H NMR (500 MHz, MeOD) δ ppm 7.86 (d, J=2.14 Hz, 1H) 7.65 (d, J=1.53 Hz, 1H) 7.60 (m, J=7.93 Hz, 2H) 7.43 (m, J=7.93 Hz, 2H) 7.19 (d, J=1.53 Hz, 1H) 7.11 (d, J=8.55 Hz, 1H) 6.96 (dd, J=8.55, 2.14 Hz, 1H) 4.59-4.68 (m, 1H) 4.48-4.56 (m, 1H) 4.15 (dd, J=11.29, 4.58 Hz, 1H) 3.98-4.03 (m, 1H) 3.92 (dd, J=11.29, 4.88 Hz, 1H) 3.52 (s, 3H) 3.04 (s, 3H).

Example 121

4-(2-(4-(4-chloro-1H-imidazol-1-yl)-3-methoxyphenylamino)-4-(ethylamino)-7,8-dihydro-5H-pyrano[4,3-d]pyrimidin-8-yl)benzonitrile, TFA

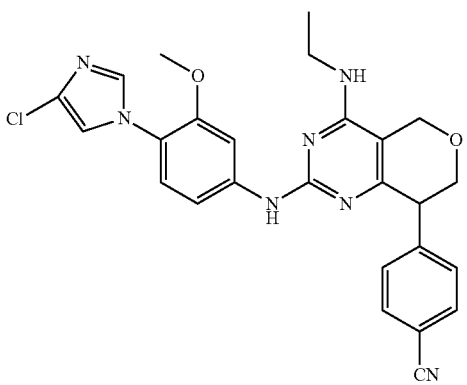 [SMILES: CCNc1nc(Nc2ccc(-n3cnc(Cl)c3)c(OC)c2)nc2c1COCC2c1ccc(C#N)cc1]

4-(2-chloro-4-(ethylamino)-7,8-dihydro-5H-pyrano[4,3-d]pyrimidin-8-yl)benzonitrile (Preparation AAa) was reacted as described in Example 112 with 4-(4-chloro-1H-imidazol-1-yl)-3-methoxyaniline (Preparation A) to give 4-(2-(4-(4-chloro-1H-imidazol-1-yl)-3-methoxyphenylamino)-4-(ethylamino)-7,8-dihydro-5H-pyrano[4,3-d]pyrimidin-8-yl)benzonitrile, TFA (Example 121). LC-MS (M+H)$^+$=502.3. $^1$H NMR (500 MHz, CDCl$_3$) δ ppm 11.80 (s, 1H) 7.93 (s, 1H) 7.61-7.66 (m, 2H) 7.55-7.61 (m, 2H) 7.48 (d, J=1.83 Hz, 1H) 7.41 (dd, J=8.55, 2.14 Hz, 1H) 7.22 (d, J=8.85 Hz, 1H) 7.15 (d, J=1.53 Hz, 1H) 6.22 (t, J=5.34 Hz, 1H) 4.76 (d, J=14.34 Hz, 1H) 4.57 (d, J=14.34 Hz, 1H) 4.09 (s, 3H) 3.87 (s, 3H) 3.66-3.75 (m, 2H) 1.37 (t, J=7.32 Hz, 3H).

The racemic mixture was separated by chiral chromatography to afford the enantiomers Example 121A and 121B as free amines LC-MS (M+H)$^+$=502.1. $^1$H NMR (500 MHz, MeOD) δ ppm 7.80 (d, J=2.14 Hz, 1H) 7.67 (d, J=2.14 Hz, 2H) 7.66 (br. s., 1H) 7.45 (d, J=8.24 Hz, 2H) 7.22 (s, 1H) 7.13 (d, J=8.55 Hz, 1H) 6.98-7.05 (m, 1H) 4.62-4.69 (m, 1H)

4.51-4.57 (m, 1H) 4.15 (dd, J=10.99, 3.97 Hz, 1H) 3.91-4.02 (m, 2H) 3.54-3.64 (m, 5H) 1.28 (t, J=7.17 Hz, 3H).

Example 122

N2-(4-(4-chloro-1H-imidazol-1-yl)-3-methoxyphenyl)-N4-methyl-8-(4-(trifluoromethoxy)phenyl)-7,8-dihydro-5H-pyrano[4,3-d]pyrimidine-2,4-diamine

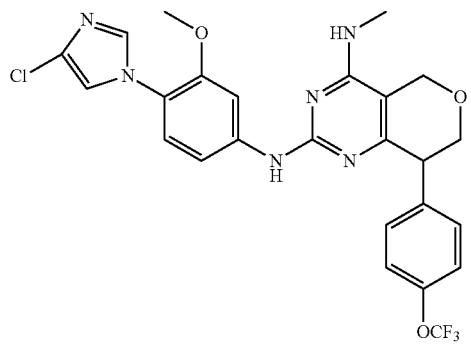 [SMILES: CNc1nc(Nc2ccc(-n3cnc(Cl)c3)c(OC)c2)nc2c1COCC2c1ccc(OC(F)(F)F)cc1]

To a mixture of 2-chloro-N-methyl-8-(4-(trifluoromethoxy)phenyl)-7,8-dihydro-5H-pyrano[4,3-d]pyrimidin-4-amine (69.8 mg, 0.194 mmol), 4-(4-chloro-1H-imidazol-1-yl)-3-methoxyaniline (Preparation A)(52.1 mg, 0.233 mmol), XANTPHOS (11.23 mg, 0.019 mmol), Pd2(dba)3 (8.88 mg, 9.70 μmol), and Cs$_2$CO$_3$ (190 mg, 0.582 mmol) was added Dioxane (808 μL). The mixture was flushed with Nitrogen and placed in a capped vial and heated at 100° C. overnight.

Cooled the reaction to rt and diluted with EtOAc. Filtered through a Celite plug and rotovaped. The residue was placed on Silica gel and eluted with an EtOAc/Hex gradient to obtain N2-(4-(4-chloro-1H-imidazol-1-yl)-3-methoxyphenyl)-N4-methyl-8-(4-(trifluoromethoxy)phenyl)-7,8-dihydro-5H-pyrano[4,3-d]pyrimidine-2,4-diamine LC-MS (M+H)$^+$ =547.2. $^1$H NMR (500 MHz, CDCl$_3$) δ ppm 7.78 (1H, s), 7.48 (1H, s), 7.25-7.29 (2H, m), 7.11-7.20 (2H, m), 6.94-7.09 (3H, m), 6.77 (1H, d, J=8.55 Hz), 4.50-4.67 (2H, m), 4.32 (1H, d, J=4.88 Hz), 4.07-4.19 (1H, m), 3.89-4.01 (2H, m), 3.52 (3H, s), 3.09 (3H, d, J=4.58 Hz).

The racemic mixture was separated by chiral chromatography to afford the enantiomers Example 122A and 122B, which had identical spectral data.

Examples 123A and 123B

N-(4-(4-chloro-1H-imidazol-1-yl)-3-methoxyphenyl)-4-(R)-3-fluoropyrrolidin-1-yl)-8-(4-(trifluoromethoxy)phenyl)-7,8-dihydro-5H-pyrano[4,3-d]pyrimidin-2-amine

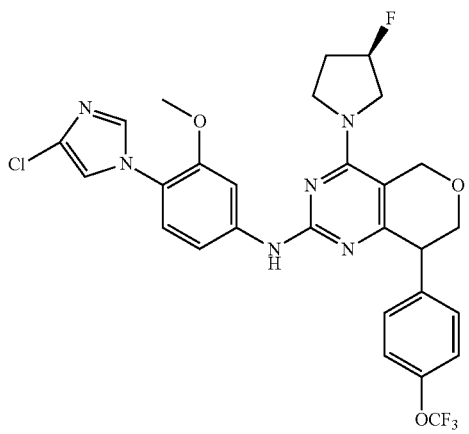 [SMILES: COc1cc(Nc2nc3c(c(N4CC[C@@H](F)C4)n2)COCC3c2ccc(OC(F)(F)F)cc2)ccc1-n1cnc(Cl)c1]

Individual Diasteriomers

To a mixture of 2-chloro-4-((R)-3-fluoropyrrolidin-1-yl)-8-(4-(trifluoromethoxy)phenyl)-7,8-dihydro-5H-pyrano[4,3-d]pyrimidine (57.6 mg, 0.138 mmol), 4-(4-chloro-1H-imidazol-1-yl)-3-methoxyaniline (Preparation A) (37.0 mg, 0.165 mmol), XANTPHOS (7.98 mg, 0.014 mmol), Pd2 (dba)3 (6.31 mg, 6.89 μmol), and Cs2CO3 (135 mg, 0.414 mmol) was added Dioxane (574 μL). The mixture was flushed with Nitrogen and placed in a capped vial and heated at 100° C. overnight. The reaction was cooled to rt and diluted with EtOAc, then filtered through a Celite plug and concentrated. The residue was placed on Silica gel and eluted with an EtOAc/Hex gradient to obtain 2 diasteriomers (Examples 123A and 123B).

123A: LC-MS (M+H)$^+$=605.3. $^1$H NMR (500 MHz, MeOD) δ ppm 7.79 (1H, d, J=1.53 Hz), 7.46-7.53 (3H, m), 7.32-7.41 (4H, m), 7.19 (1H, dd, J=8.55, 2.14 Hz), 5.43 (1H, d, J=52.50 Hz), 5.12-5.18 (1H, m), 4.99 (1H, d, J=14.34 Hz), 3.98-4.33 (6H, m), 3.87 (3H, s), 3.81 (1H, dd, J=10.68, 6.41 Hz), 2.37-2.49 (1H, m), 2.15-2.33 (1H, m).

123B: LC-MS (M+H)$^+$=605.3. $^1$H NMR (500 MHz, CDCl$_3$) ppm 7.56 (1H, d, J=1.83 Hz), 7.48 (1H, d, J=1.53 Hz), 7.22-7.28 (2H, m), 7.14 (2H, d, J=8.24 Hz), 7.04 (1H, d, J=8.55 Hz), 6.99 (1H, d, J=1.22 Hz), 6.82 (1H, dd, J=8.55, 1.83 Hz), 5.33 (1H, d, J=52.80 Hz), 4.90-5.00 (2H, m), 4.16-

4.26 (1H, m), 4.10 (1H, dd, J=11.44, 4.43 Hz), 3.80-4.01 (5H, m), 3.50 (3H, s), 2.32-2.43 (1H, m), 2.00-2.19 (1H, m).

Example 124

N²-(4-(4-Chloro-1H-imidazol-1-yl)-3-methoxyphenyl)-N⁴-ethyl-N⁴-methyl-8-phenyl-5,6,7,8-tetrahydroquinazoline-2,4-diamine

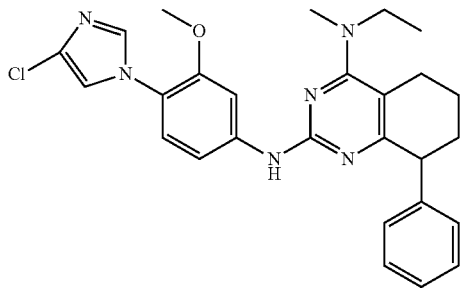

To a solution of 2-chloro-N-ethyl-N-methyl-8-phenyl-5,6,7,8-tetrahydroquinazolin-4-amine (42.9 mg, 0.142 mmol) and 4-(4-chloro-1H-imidazol-1-yl)-3-methoxyaniline (31.8 mg, 0.142 mmol) in THF (2 mL) was added 60% suspension of sodium hydride in mineral oil (6.82 mg, 0.284 mmol). The reaction mixture was heated with stirring in a capped vial at 80° C. for 1.5 h. The reaction mixture was carefully partitioned between an aqueous solution of ammonium chloride and dichloromethane. The organic layer was separated and the aqueous layer was extracted with dichloromethane. The combined organic extracts were dried over anhydrous magnesium sulfate and filtered. The solvent was removed in vacuum and the residue was purified by reverse-phase preparative HPLC to give N²-(4-(4-chloro-1H-imidazol-1-yl)-3-methoxyphenyl)-N⁴-ethyl-N⁴-methyl-8-phenyl-5,6,7,8-tetrahydroquinazoline-2,4-diamine (31.6 mg, 0.048 mmol, 33.5% yield) as brown oil. LC-MS (M+H)⁺=489.2. ¹H NMR (500 MHz, CDCl₃) δ ppm 11.50 (1H, br s), 7.74 (1H, d, J=1.2 Hz), 7.39 (1H, dd, J=8.5, 2.1 Hz), 7.29 (2H, dd, J=4.9, 2.7 Hz), 7.21-7.27 (2H, m), 7.12-7.19 (3H, m), 7.07 (1H, d, J=1.5 Hz), 4.20 (1H, t, J=7.0 Hz), 3.80 (3H, s), 3.68-3.78 (2H, m, J=13.8, 7.0, 7.0, 7.0, 7.0 Hz), 3.31 (3H, s), 2.64-2.82 (2H, m), 2.27 (1H, ddd, J=13.3, 7.5, 5.2 Hz), 1.88-1.99 (1H, m), 1.74-1.85 (1H, m), 1.54-1.67 (1H, m), 1.34 (3H, t, J=7.0 Hz).

Examples 124A and 124B (S)—N²-(4-(4-Chloro-1H-imidazol-1-yl)-3-methoxyphenyl)-N⁴-ethyl-N⁴-methyl-8-phenyl-5,6,7,8-tetrahydroquinazoline-2,4-diamine and (R)—N²-(4-(4-Chloro-1H-imidazol-1-yl)-3-methoxyphenyl)-N⁴-ethyl-N⁴-methyl-8-phenyl-5,6,7,8-tetrahydroquinazoline-2,4-diamine

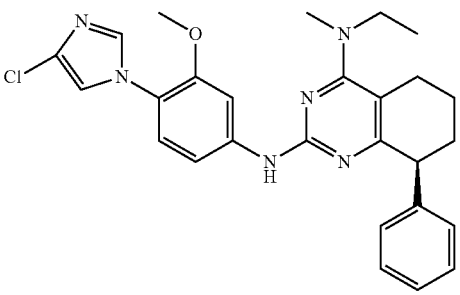

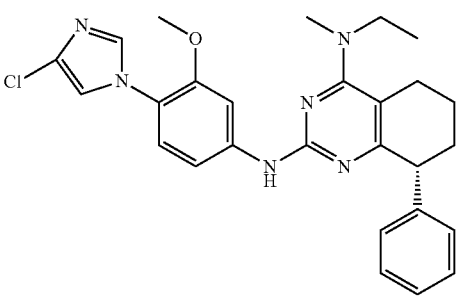 [SMILES: CCN(C)c1nc(Nc2ccc(-n3cnc(Cl)c3)c(OC)c2)nc2c1CCCC2c1ccccc1]

A racemic mixture of N²-(4-(4-Chloro-1H-imidazol-1-yl)-3-methoxyphenyl)-N⁴-ethyl-N⁴-methyl-8-phenyl-5,6,7,8-tetrahydroquinazoline-2,4-diamine (183 mg, 0.206 mmol from Example 124) was purified using chiral supercritical fluid chromatography (SFC) to afford 54.7 mg of peak A (Example 124A) and 53.3 mg of peak B (Example 124B). SFC Method: Chiralpak OJ-H (30×250 mm, 5 μM), 30% methanol (0.1% diethylamine) in CO₂, 35° C., flow rate 70 mL/min for 105 min, absorbance 220 nm, injection 0.75 mL of 26 mg/mL solution in methanol (multiple stacked injections), t$_R$ (peak A)=4.9 min, t$_R$ (peak B) 12.0 min. The absolute stereochemistry of individual enantiomers (Examples

Example 125

N-(4-(4-chloro-1H-imidazol-1-yl)-3-methoxyphenyl)-8-phenyl-5,6,7,8-tetrahydroquinazolin-2-amine

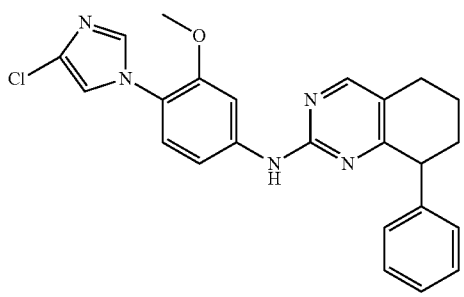 [SMILES: COc1cc(Nc2ncc3c(n2)C(c2ccccc2)CCC3)ccc1-n1cnc(Cl)c1]

To a solution of 2-chloro-8-phenyl-5,6,7,8-tetrahydroquinazoline (33.0 mg, 0.135 mmol) and 4-(4-chloro-1H-imidazol-1-yl)-3-methoxyaniline (33.2 mg, 0.148 mmol) in THF (1.5 mL) in a 2.0-5.0 mL microwave tube was added 0.5 M solution of KHMDS in toluene (0.809 mL, 0.405 mmol). The tube was sealed and the reaction mixture was stirred at 100° C. in a microwave for 2 h. The reaction mixture was diluted with methanol and purified using reverse-phase preparative HPLC method. The solvent was removed in vacuum and the residue was purified by reverse-phase preparative HPLC to give $N^2$-(4-(4-chloro-1H-imidazol-1-yl)-3-methoxyphenyl)-$N^4$-ethyl-$N^4$-methyl-8-phenyl-5,6,7,8-tetrahydroquinazoline-2,4-diamine (31.6 mg, 0.048 mmol, 33.5% yield) as brown oil. LC-MS $(M+H)^+$=432.3. $^1$H NMR (500 MHz, CDCl$_3$) δ ppm 11.68 (1H, s), 8.25 (1H, s), 8.14 (1H, s), 7.32-7.39 (3H, m), 7.26-7.32 (1H, m), 7.05-7.12 (3H, m), 6.96-7.04 (2H, m), 4.20 (1H, t, J=7.2 Hz), 3.41 (3H, s), 2.80-2.94 (2H, m), 2.30-2.40 (1H, m), 1.97-2.12 (2H, m), 1.81-1.93 (1H, m).

Example 126

$N^2$-(4-(4-Chloro-1H-imidazol-1-yl)-3-methoxyphenyl)-$N^4$-ethyl-8-(4-fluorophenyl)-$N^4$-methyl-5,6,7,8-tetrahydroquinazoline-2,4-diamine

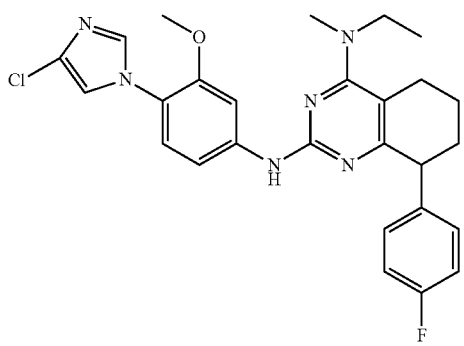 [SMILES: CCN(C)c1nc(Nc2ccc(-n3cnc(Cl)c3)c(OC)c2)nc2c1CCCC2c1ccc(F)cc1]

2-Chloro-N-ethyl-8-(4-fluorophenyl)-N-methyl-5,6,7,8-tetrahydroquinazolin-4-amine (124 mg, 0.388 mmol) was added to a solution of 4-(4-chloro-1H-imidazol-1-yl)-3-methoxyaniline (87 mg, 0.388 mmol) in THF (1 mL) and Acetic Acid (1.000 mL). The reaction mixture was stirred overnight at 75° C. The crude reaction mixture was purified by preparative HPLC. The appropriate fractions were evaporated to afford $N^2$-(4-(4-chloro-1H-imidazol-1-yl)-3-methoxyphenyl)-$N^4$-ethyl-8-(4-fluorophenyl)-$N^4$-methyl-5,6,7,8-tetrahydroquinazoline-2,4-diamine, TFA salt (101.3 mg, 0.153 mmol, 39.5% yield). LC-MS $(M+H)^+$=507.2. $^1$H NMR (500 MHz, CDCl$_3$) δ ppm 10.77-11.01 (1H, m), 7.95-8.15 (1H, m), 7.33-7.44 (1H, m), 7.22-7.24 (1H, m), 7.19 (1H, d, J=8.5 Hz), 7.12-7.16 (2H, m), 6.96-7.03 (2H, m), 4.09-4.21 (1H, m), 3.96 (1H, s), 3.81 (4H, s), 3.67-3.79 (3H, m), 3.32 (3H, s), 2.19-2.33 (1H, m), 1.88-1.99 (1H, m), 1.71-1.81 (1H, m), 1.56-1.69 (1H, m), 1.26-1.38 (3H, m).

Example 127

$N^2$-(4-(4-Chloro-1H-imidazol-1-yl)-3-methoxyphenyl)-8-(4-fluorophenyl)-$N^4$,$N^4$-dimethyl-5,6,7,8-tetrahydroquinazoline-2,4-diamine

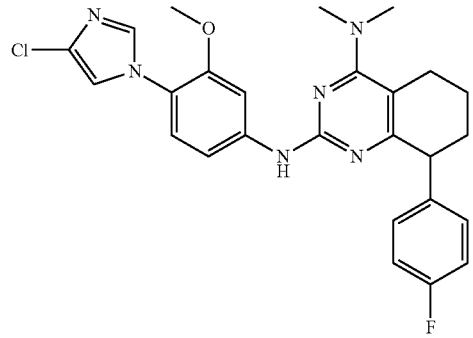

2-Chloro-8-(4-fluorophenyl)-N,N-dimethyl-5,6,7,8-tetrahydroquinazolin-4-amine (118 mg, 0.386 mmol) was added to a solution of 4-(4-chloro-1H-imidazol-1-yl)-3-methoxyaniline (95 mg, 0.424 mmol) in THF (1 mL) and acetic acid (1.000 mL). The reaction mixture was stirred overnight at 75° C. The crude reaction mixture was purified by preparative HPLC. The appropriate fractions were evaporated to afford $N^2$-(4-(4-chloro-1H-imidazol-1-yl)-3-methoxyphenyl)-8-(4-fluorophenyl)-$N^4$,$N^4$-dimethyl-5,6,7,8-tetrahydroquinazoline-2,4-diamine, TFA salt (74.8 mg, 0.123 mmol, 31.9% yield). LC-MS $(M+H)^+$=493.2. $^1$H NMR (500 MHz, CDCl$_3$) δ ppm 11.69 (1H, s), 7.59 (1H, d, J=1.2 Hz), 7.36 (2H, d, J=2.1 Hz), 7.14 (3H, d, J=9.2 Hz), 7.05 (1H, d, J=1.5 Hz), 6.99 (2H, s), 4.17-4.27 (1H, m), 3.81 (3H, s), 3.47

(1H, s), 3.36 (5H, s), 2.65-2.84 (2H, m), 2.21-2.33 (1H, m), 1.87-1.98 (1H, m), 1.69-1.81 (1H, m), 1.53-1.67 (1H, m).

Examples 127A & 127B (S)—$N^2$-(4-(4-Chloro-1H-imidazol-1-yl)-3-methoxyphenyl)-8-(4-fluorophenyl)-$N^4$,$N^4$-dimethyl-5,6,7,8-tetrahydroquinazoline-2,4-diamine and (R)—$N^2$-(4-(4-Chloro-1H-imidazol-1-yl)-3-methoxyphenyl)-8-(4-fluorophenyl)-$N^4$,$N^4$-dimethyl-5,6,7,8-tetrahydroquinazoline-2,4-diamine

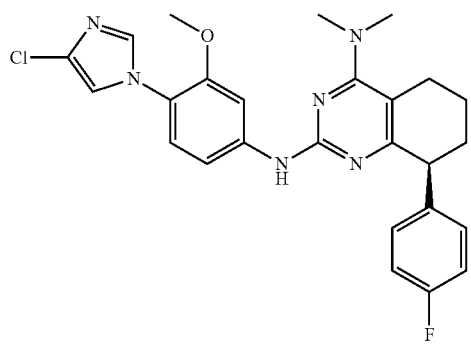

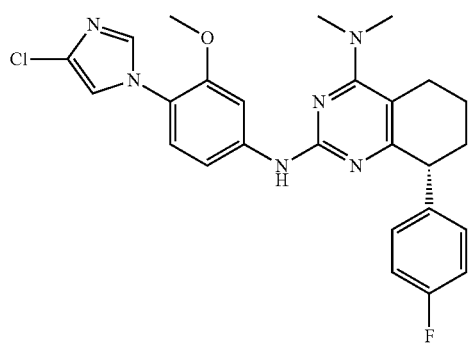 [SMILES: COc1cc(Nc2nc3c(c(N(C)C)n2)CCCC3c2ccc(F)cc2)ccc1-n1cnc(Cl)c1]

A racemic mixture of $N^2$-(4-(4-chloro-1H-imidazol-1-yl)-3-methoxyphenyl)-8-(4-fluorophenyl)-$N^4$,$N^4$-dimethyl-5,6,7,8-tetrahydroquinazoline-2,4-diamine (Example 127) was purified using chiral SFC to afford peak A (Example 127A) and peak B (Example 127B). SFC Method: Chiralpak OJ-H (4.6×250 mm, 5 μM), 30% methanol (0.1% diethylamine) in CO₂, 35° C., flow rate 2.0 mL/min for 13 min, absorbance 268 nm, injection 5 μL of 2 mg/mL solution in methanol (multiple stacked injections), $t_R$ (peak A)=4.3 min, $t_R$ (peak B) 9.6 min. The absolute stereochemistry of individual enantiomers (Examples 7 and 8) was not determined LC-MS and $^1$H NMR analytical data for the separated enantiomers was identical to the racemate (Example 127).

Example 128

N-(4-(4-Chloro-1H-imidazol-1-yl)-3-methoxyphenyl)-8-(4-fluorophenyl)-5,6,7,8-tetrahydroquinazolin-2-amine

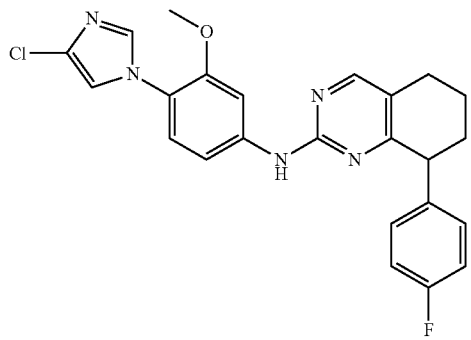 [SMILES: COc1cc(Nc2ncc3c(n2)C(c2ccc(F)cc2)CCC3)ccc1-n1cnc(Cl)c1]

To a solution of 2-chloro-8-(4-fluorophenyl)-5,6,7,8-tetrahydroquinazoline (20 mg, 0.076 mmol) and 4-(4-chloro-1H-imidazol-1-yl)-3-methoxyaniline (18.73 mg, 0.084 mmol) in THF (1.5 mL) in a 2.0-5.0 mL microwave tube, was added a 0.5 M solution of KHMDS (0.167 mL, 0.084 mmol). The tube was sealed and the reaction mixture was stirred at 100° C. in a microwave for 2 h. The reaction mixture was diluted with methanol and purified using preparative HPLC. The appropriate fractions were evaporated to afford N-(4-(4-chloro-1H-imidazol-1-yl)-3-methoxyphenyl)-8-(4-fluorophenyl)-5,6,7,8-tetrahydroquinazolin-2-amine, TFA salt (0.7 mg, 1.229 μmol, 1.614% yield). LC-MS (M+H)⁺=450.2. $^1$H NMR (500 MHz, CDCl₃) δ ppm 8.14-8.26 (1H, m), 7.56-7.62 (1H, m), 7.43-7.48 (1H, m), 7.28-7.31 (1H, m), 7.21 (1H, s), 6.98-7.10 (6H, m), 6.88-6.94 (1H, m), 4.08-4.18 (1H, m), 2.77-2.83 (3H, m), 2.23-2.32 (1H, m), 1.91-2.13 (3H, m), 1.25 (1H, s).

Example 129

N2-(4-(4-chloro-1H-imidazol-1-yl)-3-methoxyphenyl)-N4-methyl-6-(methylsulfonyl)-8-phenyl-5,6,7,8-tetrahydropyrido[4,3-d]pyrimidine-2,4-diamine

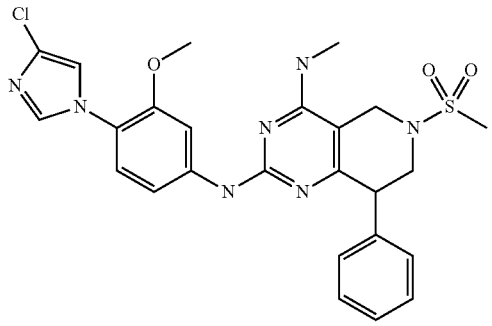 [SMILES: CNc1nc(Nc2ccc(-n3cnc(Cl)c3)c(OC)c2)nc2c1CN(S(C)(=O)=O)CC2c1ccccc1]

To a solution of Preparation AEj (0.2 g, 0.433 mmol) in dichloromethane was added diisopropylethylamine (0.11 g, 0.867 mmol) at −10° C. followed by addition of methane sulfonyl chloride (0.055 g, 0.477 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in acetonitrile) to give N2-(4-(4-chloro-1H-imidazol-1-yl)-3-methoxyphenyl)-N4-methyl-6-(methylsulfonyl)-8-phenyl-5,6,7,8-tetrahydropyrido[4,3-d]pyrimidine-2,4-diamine (0.105 g, 48%) as off-white solid. LC-MS (M+H)$^+$=540.2. $^1$H NMR (400 MHz, DMSO-d6): δ ppm 9.20 (1H, s), 8.03 (1H, s), 7.72 (1H, s), 7.41 (1H, s), 7.31-7.03 (8H, m), 4.21 (1H, m), 4.11 (2H, m), 3.60-3.47 (5H, m), 2.96 (3H, d, J=4.4 Hz), 2.89 (3H, s). The example was separated by chiral chromatography to afford the enantiomers 129A and 129B, which had identical spectral data.

Example 130

N2-(4-(4-chloro-1H-imidazol-1-yl)-3-methoxyphenyl)-6-(cyclopropylsulfonyl)-N4-methyl-8-phenyl-5,6,7,8-tetrahydropyrido[4,3-d]pyrimidine-2,4-diamine

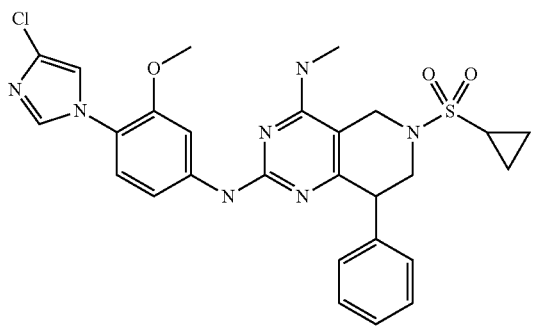 [SMILES: CNc1nc(Nc2ccc(-n3cnc(Cl)c3)c(OC)c2)nc2c1CN(S(=O)(=O)C1CC1)CC2c1ccccc1]

To a solution of Preparation AEj (0.32 g, 0.693 mmol) in dichloromethane was added diisopropylethylamine (0.18 g, 1.38 mmol) at −10° C. followed by addition of cyclopropyl sulfonyl chloride (0.117 g, 0.832 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in acetonitrile) to give N2-(4-(4-chloro-1H-imidazol-1-yl)-3-methoxyphenyl)-6-(cyclopropylsulfonyl)-N4-methyl-8-phenyl-5,6,7,8-tetrahydropyrido[4,3-d]pyrimidine-2,4-diamine (0.11 g, 35%) as white solid. LC-MS (M+H)$^+$=566.0. $^1$H NMR (400 MHz, DMSO-d6): δ ppm 9.18 (1H, s), 8.03 (1H, s), 7.72 (1H, s), 7.40 (1H, s), 7.31-7.04 (8H, m), 4.26 (1H, m), 4.10 (2H, m), 3.68 (1H, m), 3.68-3.65 (4H, m), 2.98 (3H, d, J=4.4 Hz), 2.54 (1H, m), 0.95 (4H, m).

The example was separated by chiral chromatography to afford the enantiomers 130A and 130B, which had identical spectral data.

Example 131

Methyl 2-(4-(4-chloro-1H-imidazol-1-yl)-3-methoxyphenylamino)-4-(ethylamino)-8-phenyl-7,8-dihydropyrido[4,3-d]pyrimidine-6(5H)-carboxylate

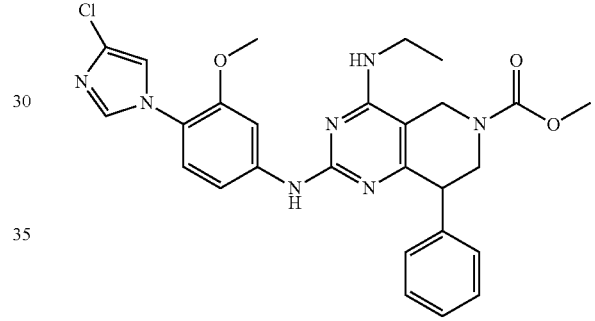

To a solution of Preparation AEk (0.15 g, 0.3 mmol) in dichloromethane was added diisopropylethylamine (0.081 g, 0.6 mmol) at −10° C. followed by addition of methylchloro formate (0.044 g, 0.3 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in acetonitrile) to give methyl 2-(4-(4-chloro-1H-imidazol-1-yl)-3-methoxyphenylamino)-4-(ethylamino)-8-phenyl-7,8-dihydropyrido[4,3-d]pyrimidine-6(5H)-carboxylate (0.12 g, 68%) as white solid. LC-MS (M−H)$^+$=532.2. $^1$H NMR (400 MHz, DMSO-d6): δ ppm 9.16 (1H, s), 7.98 (1H, s), 7.73 (1H, s), 7.42 (1H, s), 7.29-7.26 (2H, m), 7.21-7.12 (5H, m), 7.05 (1H, m), 4.62 (1H, m), 4.23 (1H, m), 3.96-3.87 (3H, m), 3.68-3.51 (8H, m), 1.23 (3H, t, J=8.0 Hz).

The example was separated by chiral chromatography to afford the enantiomers 131A and 131B, which had identical spectral data.

Example 132

(2-(4-(4-chloro-1H-imidazol-1-yl)-3-methoxyphenylamino)-4-(ethylamino)-8-phenyl-7,8-dihydropyrido[4,3-d]pyrimidin-6(5H)-yl)(cyclopropyl)methanone

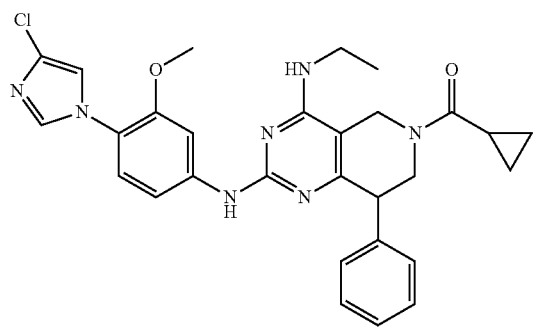 [SMILES: CCNc1nc(Nc2ccc(-n3cnc(Cl)c3)c(OC)c2)nc2c1CN(C(=O)C1CC1)CC2c1ccccc1]

To a solution of Preparation AEk (0.35 g, 0.73 mmol) in dichloromethane was added diisopropylethylamine (0.14 g, 1.1 mmol) at −10° C. followed by addition of cyclopropylcarbonyl chloride (0.085 g, 0.81 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in methanol) to give (2-(4-(4-chloro-1H-imidazol-1-yl)-3-methoxyphenylamino)-4-(ethylamino)-8-phenyl-7,8-dihydropyrido[4,3-d]pyrimidin-6(5H)-yl)(cyclopropyl)methanone (0.12 g, 30%) as white solid. LC-MS (M+H)$^+$=544.2. $^1$H NMR (400 MHz, CDCl$_3$6): δ ppm 7.70 (1H, s), 7.51 (1H, s), 7.31-7.23 (3H, m), 7.12-6.99 (4H, m), 6.93 (1H, bs), 5.05 (1H, m), 4.22 (1H, m), 4.07 (1H, m), 3.99 (1H, m), 3.63 (1H, m), 3.59 (5H, m), 1.33 (3H, t, J=7.2 Hz), 1.25 (1H, m), 0.87 (1H, m), 0.84 (2H, m), 0.63 (1H, m).

The example was separated by chiral chromatography to afford the enantiomers 132A and 132B, which had identical spectral data.

Example 133

1-(2-(4-(4-chloro-1H-imidazol-1-yl)-3-methoxyphenylamino)-4-(ethylamino)-8-phenyl-7,8-dihydropyrido[4,3-d]pyrimidin-6(5H)-yl)-2-methoxyethanone

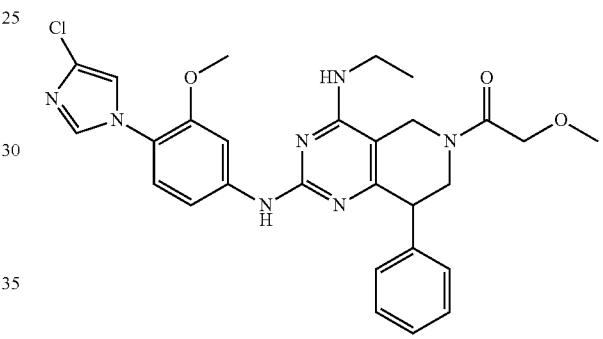

To a solution of Preparation AEk (0.187 g, 0.39 mmol) in dichloromethane was added triethylamine (0.79 g, 0.78 mmol) at −10° C. followed by addition of methoxyacetyl chloride (0.043 g, 0.42 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in acetonitrile) to give 1-(2-(4-(4-chloro-1H-imidazol-1-yl)-3-methoxyphenylamino)-4-(ethylamino)-8-phenyl-7,8-dihydropyrido[4,3-d]pyrimidin-6 (5H)-yl)-2-methoxyethanone (0.10 g, 57%) as off-white solid. LC-MS (M+H)$^+$=548.2. $^1$H NMR (400 MHz, DMSO-d6): δ ppm 9.19 (1H, s), 7.99 (1H, s), 7.73 (1H, 1), 7.42 (1H, s), 7.32-7.09 (8H, m), 4.86 (1H, m), 4.20 (2H, m), 4.09 (2H, m), 4.02-3.50 (5H, m), 3.31 (1H, m), 3.18 (1H, m), 2.99 (3H, s), 1.23 (3H, t, J=7.2 Hz).

The example was separated by chiral chromatography to afford the enantiomers 133A and 133B, which had identical spectral data.

Example 134

N2-(4-(4-chloro-1H-imidazol-1-yl)-3-methoxyphenyl)-N4-ethyl-6-(methylsulfonyl)-8-phenyl-5,6,7,8-tetrahydropyrido[4,3-d]pyrimidine-2,4-diamine

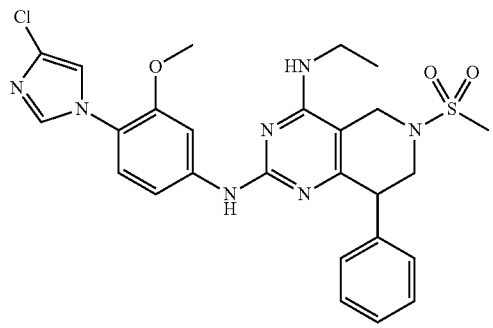 [SMILES: CCNc1nc(Nc2ccc(-n3cnc(Cl)c3)c(OC)c2)nc2c1CN(S(C)(=O)=O)CC2c1ccccc1]

To a solution of Preparation AEk (0.10 g, 0.21 mmol) in dichloromethane was added diisopropylethylamine (0.054 g, 0.42 mmol) at −10° C. followed by addition of methanesulfonyl chloride (0.024 g, 0.21 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in acetonitrile) to give N2-(4-(4-chloro-1H-imidazol-1-yl)-3-methoxyphenyl)-N4-ethyl-6-(methylsulfonyl)-8-phenyl-5,6,7,8-tetrahydropyrido[4,3-d]pyrimidine-2,4-diamine (0.06 g, 54%) as off-white solid. LC-MS (M+H)$^+$=554.0. $^1$H NMR (400 MHz, DMSO-d6): δ ppm 9.17 (1H, s), 7.96 (1H, s), 7.73 (1H, s), 7.42 (1H, s), 7.32-7.20 (5H, m), 7.16-7.10 (2H, m), 6.98 (1H, m), 4.22 (1H, m), 4.11-4.03 (2H, m), 3.62-3.49 (7H, m), 2.91 (3H, s), 1.23 (3H, t, J=7.2 Hz).

The example was separated by chiral chromatography to afford the enantiomers 134A and 134B, which had identical spectral data.

Example 135

1-(2-(4-(4-chloro-1H-imidazol-1-yl)-3-methoxyphenylamino)-4-(ethylamino)-8-phenyl-7,8-dihydropyrido[4,3-d]pyrimidin-6(5H)-yl)-2-(dimethylamino)ethanone

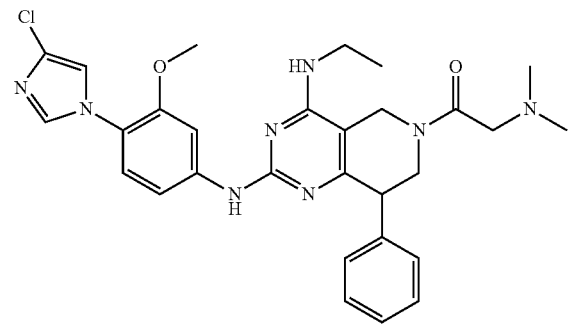 [SMILES: CCNc1nc(Nc2ccc(-n3cnc(Cl)c3)c(OC)c2)nc2c1CN(C(=O)CN(C)C)CC2c1ccccc1]

To a solution of Preparation AEk (0.15 g, 0.31 mmol) in dichloromethane was added triethylamine (0.079 g, 0.78 mmol) at −10° C. followed by addition of N,N-dimethylaminoacetyl chloride.HCl (0.054 g, 0.34 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in acetonitrile) to give 1-(2-(4-(4-chloro-1H-imidazol-1-yl)-3-methoxyphenylamino)-4-(ethylamino)-8-phenyl-7,8-dihydropyrido[4,3-d]pyrimidin-6(5H)-yl)-2-(dimethylamino)ethanone (0.11 g, 72%) as off-white solid. LC-MS (M+H)$^+$=561.2. $^1$H NMR (400 MHz, DMSO-d6): δ ppm 9.16 (1H, s), 7.98 (1H, s), 7.72 (1H, s), 7.40 (1H, s), 7.31-7.11 (7H, m), 7.07 (1H, m), 4.77 (1H, m), 4.06 (2H, m), 3.94 (1H, m), 3.60 (1H, m), 3.52-3.42 (5H, m), 2.72 (1H, m), 2.28 (1H, m), 2.15 (6H, s), 1.20 (3H, m). The example was separated by chiral chromatography to afford the enantiomers 135A and 135B, which had identical spectral data.

Example 136

N2-(4-(4-chloro-1H-imidazol-1-yl)-3-methoxyphenyl)-6-(cyclopropylsulfonyl)-N4-ethyl-8-phenyl-5,6,7,8-tetrahydropyrido[4,3-d]pyrimidine-2,4-diamine

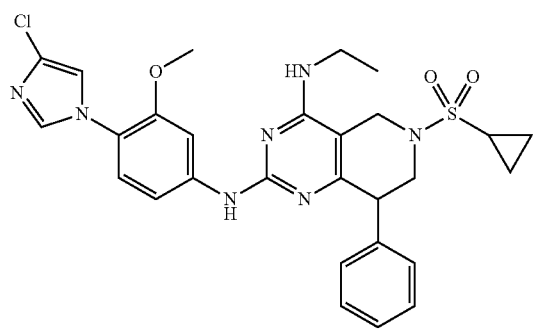 [SMILES: CCNc1nc(Nc2ccc(-n3cnc(Cl)c3)c(OC)c2)nc2c1CN(S(=O)(=O)C1CC1)CC2c1ccccc1]

To a solution of Preparation AEk (0.15 g, 0.31 mmol) in dichloromethane was added diisopropylethylamine (0.77 g, 0.62 mmol) at −10° C. followed by addition of cyclopropanesulfonyl chloride (0.042 g, 0.31 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in methanol) to give N2-(4-(4-chloro-1H-imidazol-1-yl)-3-methoxyphenyl)-6-(cyclopropylsulfonyl)-N4-ethyl-8-phenyl-5,6,7,8-tetrahydropyrido[4,3-d]pyrimidine-2,4-diamine (0.10 g, 55%) as off-white solid. LC-MS (M+H)+=578.2. $^1$H NMR (400 MHz, CDCl$_3$): δ ppm 9.15 (1H, s), 7.95 (1H, s), 7.72 (1H, s), 7.41 (1H, s), 7.29 (2H, m), 7.21 (3H, m), 7.14 (2H, m), 7.01 (1H, bs), 4.26 (1H, m), 4.11 (2H, m), 3.65 (1H, m), 3.56-3.51 (6H, m), 2.5 (1H, m), 1.23 (5H, m), 0.97 (2H, m).

The example was separated by chiral chromatography to afford the enantiomers 136A and 136B, which had identical spectral data.

Example 137

1-(2-(4-(4-chloro-1H-imidazol-1-yl)-3-methoxyphenylamino)-4-(ethylamino)-8-phenyl-7,8-dihydropyrido[4,3-d]pyrimidin-6(5H)-yl)ethanone

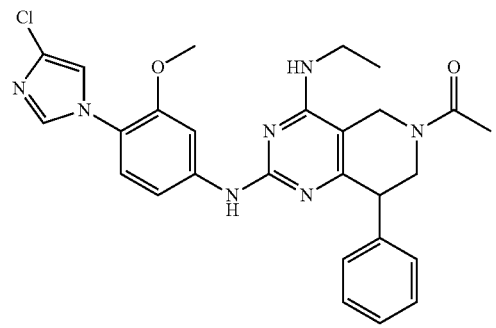 [SMILES: CCNc1nc(Nc2ccc(-n3cnc(Cl)c3)c(OC)c2)nc2c1CN(C(C)=O)CC2c1ccccc1]

To a solution of Preparation AEk (0.15 g, 0.31 mmol) in dichloromethane was added diisopropylethylamine (0.77 g, 0.62 mmol) at −10° C. followed by addition of acetyl chloride (0.027 g, 0.31 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in methanol) to give 1-(2-(4-(4-chloro-1H-imidazol-1-yl)-3-methoxyphenylamino)-4-(ethylamino)-8-phenyl-7,8-dihydropyrido[4,3-d]pyrimidin-6(5H)-yl)ethanone (0.09 g, 57%) as off-white solid. LC-MS (M+H)+= 518.2. $^1$H NMR (400 MHz, DMSO-d6): δ ppm 9.19 (1H, s), 8.00 (1H, s), 7.74 (1H, s), 7.42 (1H, s), 7.28 (3H, m), 7.17-7.07 (5H, m), 4.91 (1H, m), 4.06 (1H, m), 3.93 (1H, m), 3.82 (2H, m), 3.58-3.50 (5H, m), 1.47 (3H, s), 1.23 (3H, m).

The example was separated by chiral chromatography to afford the enantiomers 137A and 137B, which had identical spectral data.

Example 138

N2-(4-(4-chloro-1H-imidazol-1-yl)-3-methoxyphenyl)-N4-ethyl-6-(ethylsulfonyl)-8-phenyl-5,6,7,8-tetrahydropyrido[4,3-d]pyrimidine-2,4-diamine

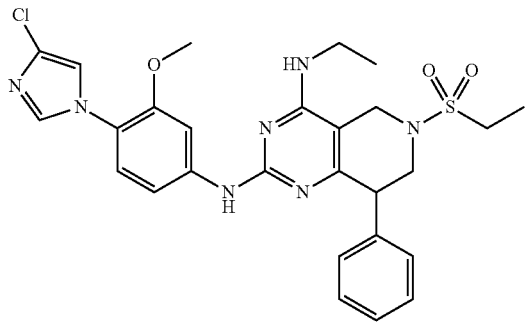 [SMILES: CCNc1nc(Nc2ccc(-n3cnc(Cl)c3)c(OC)c2)nc2c1CN(S(=O)(=O)CC)CC2c1ccccc1]

To a solution of Preparation AEk (0.15 g, 0.31 mmol) in dichloromethane was added diisopropylethylamine (0.77 g, 0.62 mmol) at −10° C. followed by addition of ethanesulfonyl chloride (0.038 g, 0.31 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in methanol) to give N2-(4-(4-chloro-1H-imidazol-1-yl)-3-methoxyphenyl)-N4-ethyl-6-(ethylsulfonyl)-8-phenyl-5,6,7,8-tetrahydropyrido[4,3-d]pyrimidine-2,4-diamine (0.11 g, 62%) as off-white solid. LC-MS (M−H)+ =566.2. $^1$H NMR (400 MHz, DMSO-d6): δ ppm 9.17 (1H, s), 7.96 (1H, s), 7.73 (1H, s), 7.42 (1H, s), 7.31 (2H, m), 7.28 (3H, m), 7.21 (2H, m), 6.97 (1H, m), 4.25 (1H, m), 4.13-4.05 (2H, m), 3.60 (1H, m), 3.58-3.50 (6H, m), 3.05 (2H, m), 1.23 (3H, t, J=8.0 Hz), 1.17 (3H, t, J=7.2 Hz).

The example was separated by chiral chromatography to afford the enantiomers 138A and 138B, which had identical spectral data.

Example 139

N4-ethyl-N2-(3-fluoro-4-(3-methyl-1H-1,2,4-triazol-1-yl)phenyl)-6-(methylsulfonyl)-8-phenyl-5,6,7,8-tetrahydropyrido[4,3-d]pyrimidine-2,4-diamine

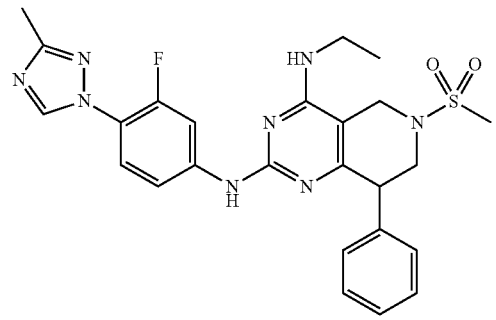 [SMILES: CCNc1nc(Nc2ccc(-n3cnc(C)n3)c(F)c2)nc2c1CN(S(C)(=O)=O)CC2c1ccccc1]

To a solution of Preparation AEm (0.20 g, 0.450 mmol) in dichloromethane was added diisopropylethylamine (0.11 g, 0.90 mmol) at −10° C. followed by addition of methanesulfonyl chloride (0.05 g, 0.450 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in acetonitrile) to give N4-ethyl-N2-(3-fluoro-4-(3-methyl-1H-1,2,4-triazol-1-yl)phenyl)-6-(methylsulfonyl)-8-phenyl-5,6,7,8-tetrahydropyrido[4,3-d]pyrimidine-2,4-diamine (0.048 g, 20%) as off-white solid. LC-MS (M+H)+=523.2. $^1$H NMR (400 MHz, DMSO-d6): δ ppm 9.44 (1H, s), 8.67 (1H, s), 8.00 (1H, m), 7.42 (2H, m), 7.39 (2H, m), 7.32 (3H, m), 7.05 (1H, m), 4.20 (1H, m), 4.08 (2H, m), 3.63 (1H, m), 3.55-3.46 (3H, m), 2.92 (3H, s), 2.33 (3H, s), 1.24 (3H, t, J=7.2 Hz).

The example was separated by chiral chromatography to afford the enantiomers 139A and 139B, which had identical spectral data.

Example 140

N4-ethyl-N2-(3-fluoro-4-(5-methyl-1H-1,2,4-triazol-1-yl)phenyl)-6-(methylsulfonyl)-8-phenyl-5,6,7,8-tetrahydropyrido[4,3-d]pyrimidine-2,4-diamine

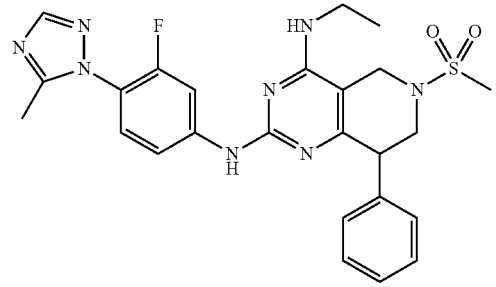 [SMILES: CCNc1nc(Nc2ccc(-n3ncnc3C)c(F)c2)nc2c1CN(S(C)(=O)=O)CC2c1ccccc1]

417

To a solution of Preparation AEo (0.25 g, 0.560 mmol) in dichloromethane was added diisopropylethylamine (0.145 g, 1.120 mmol) at −10° C. followed by addition of methanesulfonyl chloride (0.06 g, 0.560 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in acetonitrile) to give N4-ethyl-N2-(3-fluoro-4-(5-methyl-1H-1,2,4-triazol-1-yl)phenyl)-6-(methylsulfonyl)-8-phenyl-5,6,7,8-tetrahydropyrido[4,3-d]pyrimidine-2,4-diamine (0.05 g, 22%) as off-white solid. LC-MS (M−H)$^+$=521.2. $^1$H NMR (400 MHz, DMSO-d6): δ ppm 9.47 (1H, s), 8.00 (2H, m), 7.44 (1H, m), 7.33-7.22 (6H, m), 7.05 (1H, m), 4.21 (1H, m), 4.11-4.07 (2H, m), 3.63 (1H, m), 3.57-3.50 (3H, m), 2.93 (3H, s), 2.27 (3H, s), 1.24 (3H, t, J=7.2 Hz).

The example was separated by chiral chromatography to afford the enantiomers 140A and 140B, which had identical spectral data.

Example 141

6-(cyclopropylsulfonyl)-N2-(3-fluoro-4-(3-methyl-1H-1,2,4-triazol-1-yl)phenyl)-N4-methyl-8-phenyl-5,6,7,8-tetrahydropyrido[4,3-d]pyrimidine-2,4-diamine

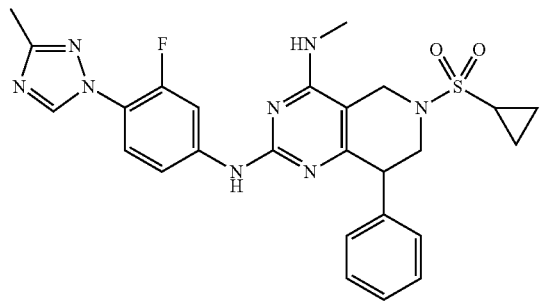 [SMILES: CNc1nc(Nc2ccc(-n3cnc(C)n3)c(F)c2)nc2c1CN(S(=O)(=O)C1CC1)CC2c1ccccc1]

To a solution of Preparation AEl (0.23 g, 0.534 mmol) in dichloromethane was added diisopropylethylamine (0.138 g, 1.060 mmol) at −10° C. followed by addition of cyclopropanesulfonyl chloride (0.089 g, 0.640 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in methanol) to give 6-(cyclopropylsulfonyl)-N2-(3-fluoro-4-(3-methyl-1H-1,2,4-triazol-1-yl)phenyl)-N4-methyl-8-phenyl-5,6,7,8-tetrahydropyrido[4,3-d]pyrimidine-2,4-diamine (0.11 g, 50%) as off-white solid. LC-MS (M+H)$^+$=535.2. $^1$H NMR (400 MHz, DMSO-d$_6$): δ ppm 9.45 (1H, s), 8.68 (1H, s), 8.03 (1H, m), 7.22 (2H, m), 7.32-7.21 (5H, m), 7.11 (1H, m), 4.25 (1H, m), 4.13 (1H, m), 4.08 (1H, m), 3.71 (1H, m), 3.64 (1H, m), 2.96 (3H, d, J=4.0 Hz), 2.58 (1H, m), 2.33 (3H, s), 1.01-0.95 (4H, m).

418

The example was separated by chiral chromatography to afford the enantiomers 141A and 141B, which had identical spectral data.

Example 142

6-(cyclopropylsulfonyl)-N2-(3-fluoro-4-(5-methyl-1H-1,2,4-triazol-1-yl)phenyl)-N4-methyl-8-phenyl-5,6,7,8-tetrahydropyrido[4,3-d]pyrimidine-2,4-diamine

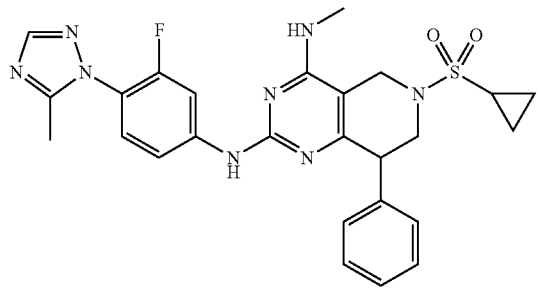 [SMILES: CNc1nc(Nc2ccc(-n3ncnc3C)c(F)c2)nc2c1CN(S(=O)(=O)C1CC1)CC2c1ccccc1]

To a solution of Preparation AEm (0.30 g, 0.690 mmol) in dichloromethane was added diisopropylethylamine (0.180 g, 1.39 mmol) at −10° C. followed by addition of cyclopropanesulfonyl chloride (0.117 g, 0.830 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in methanol) to give 6-(cyclopropylsulfonyl)-N2-(3-fluoro-4-(5-methyl-1H-1,2,4-triazol-1-yl)phenyl)-N4-methyl-8-phenyl-5,6,7,8-tetrahydropyrido[4,3-d]pyrimidine-2,4-diamine (0.14 g, 45%) as off-white solid. LC-MS (M+H)$^+$=535.2. $^1$H NMR (400 MHz, DMSO-d$_6$): δ ppm 9.49 (1H, s), 8.02 (2H, m), 7.46 (1H, m), 7.44-7.33 (3H, m), 7.30-7.21 (3H, m), 7.11 (1H, m), 4.26 (1H, m), 4.15 (1H, m), 4.10 (1H, m), 3.73 (1H, m), 3.59 (1H, m), 3.28 (3H, m), 2.59 (1H, m), 2.27 (3H, s), 1.24-1.0 (4H, m).

Example 143 cyclopropyl(4-(ethylamino)-2-(3-fluoro-4-(3-methyl-1H-1,2,4-triazol-1-yl)phenylamino)-8-phenyl-7,8-dihydropyrido[4,3-d]pyrimidin-6(5H)-yl)methanone

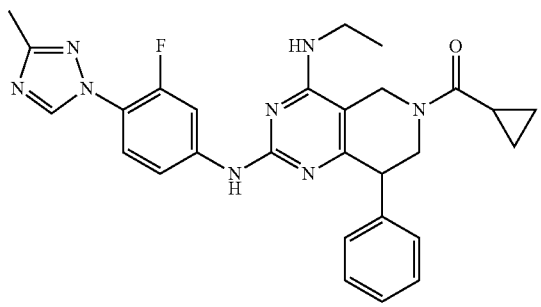 [SMILES: CCNc1nc(Nc2ccc(-n3cnc(C)n3)c(F)c2)nc2c1CN(C(=O)C1CC1)CC2c1ccccc1]

To a solution of Preparation AEm (0.21 g, 0.49 mmol) in dichloromethane was added diisopropylethylamine (0.12 g, 0.70 mmol) at −10° C. followed by addition of cyclopropylcarbonyl chloride (0.056 g, 0.54 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in methanol) to give cyclopropyl(4-(ethylamino)-2-(3-fluoro-4-(3-methyl-1H-1,2,4-triazol-1-yl)phenylamino)-8-phenyl-7,8-dihydropyrido[4,3-d]pyrimidin-6(5H)-yl)methanone (0.090 g, 38%) as white solid. LC-MS (M+H)$^+$=513.4. $^1$H NMR (400 MHz, CDCl$_3$6): δ ppm 8.41 (1H, s), 7.94 (1H, m), 7.63 (1H, m), 7.32 (3H, m), 7.27 (1H, m), 7.10 (2H, m), 4.97 (1H, m), 4.21 (1H, m), 4.10-4.0 (2H, m), 3.91 (1H, m), 3.63 (2H, m), 2.48 (3H, s), 1.35 (3H, t, J=7.2 Hz), 1.22 (1H, m), 0.85 (1H, m), 0.65-0.62 (2H, m), 0.34 (1H, m). The example was separated by chiral chromatography to afford the enantiomers 143A and 143B, which had identical spectral data.

Example 144 cyclopropyl(4-(ethylamino)-2-(3-fluoro-4-(5-methyl-1H-1,2,4-triazol-1-yl)phenylamino)-8-phenyl-7,8-dihydropyrido[4,3-d]pyrimidin-6(5H)-yl)methanone

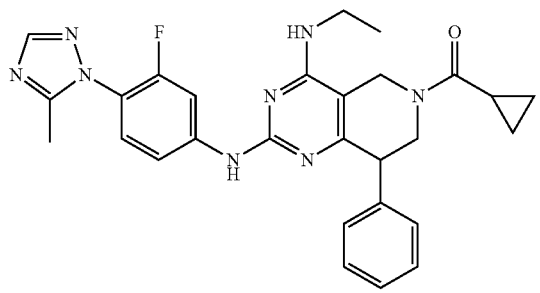 [SMILES: CCNc1nc(Nc2ccc(-n3ncnc3C)c(F)c2)nc2c1CN(C(=O)C1CC1)CC2c1ccccc1]

To a solution of Preparation AEo (0.30 g, 0.67 mmol) in dichloromethane was added diisopropylethylamine (0.17 g, 1.35 mmol) at −10° C. followed by addition of cyclopropylcarbonyl chloride (0.084 g, 0.81 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in methanol) to cyclopropyl(4-(ethylamino)-2-(3-fluoro-4-(5-methyl-1H-1,2,4-triazol-1-yl)phenylamino)-8-phenyl-7,8-dihydropyrido[4,3-d]pyrimidin-6(5H)-yl)methanone (0.14 g, 41%) as white solid. LC-MS (M+H)$^+$=513.4. $^1$H NMR (400 MHz, CDCl$_3$6): δ ppm 7.94 (2H, m), 7.32-7.25 (4H, m), 7.13 (3H, m), 4.96 (1H, m), 4.22 (1H, m), 4.13-4.04 (2H, m), 3.93 (1H, m), 3.63 (2H, m), 2.39 (3H, s), 1.35 (3H, t, J=7.2 Hz), 1.26 (1H, m), 0.87 (1H, m), 0.66 (2H, m), 0.38 (1H, m).

The example was separated by chiral chromatography to afford the enantiomers 144A and 144B, which had identical spectral data.

Example 145

N4-ethyl-N2-(3-fluoro-4-(3-methyl-1H-1,2,4-triazol-1-yl)phenyl)-8-phenyl-6-(2,2,2-trifluoroethyl)-5,6,7,8-tetrahydropyrido[4,3-d]pyrimidine-2,4-diamine

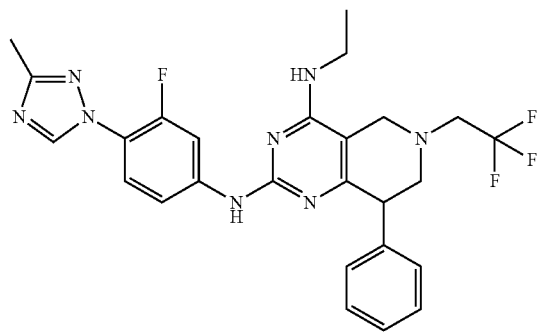 [SMILES: CCNc1nc(Nc2ccc(-n3cnc(C)n3)c(F)c2)nc2c1CN(CC(F)(F)F)CC2c1ccccc1]

To a solution of Preparation AEp (0.20 g, 0.37 mmol) in THF was added borane-DMS (0.061 g, 0.814 mmol, 2M in diethyl ether) at −0° C. The reaction mixture was heated at 55° C. for 18 h. The reaction mixture was quenched with methanol and evaporated the solvent under reduced pressure to get crude compound. The crude compound was purified by prep-HPLC (aqueous 0.1% ammonium acetate in acetonitrile) get crude to give N4-ethyl-N2-(3-fluoro-4-(3-methyl-1H-1,2,4-triazol-1-yl)phenyl)-8-phenyl-6-(2,2,2-trifluoroethyl)-5,6,7,8-tetrahydropyrido[4,3-d]pyrimidine-2,4-diamine (0.025 g, 14%) as yellow solid. LC-MS (M+H)$^+$=527.2. $^1$H NMR (400 MHz, DMSO-d$_6$): δ ppm 9.32 (1H, s), 8.67 (1H, s), 8.03 (1H, m), 7.41-7.38 (2H, m), 7.27-7.18 (5H, m), 6.83 (1H, m), 3.97 (1H, m), 3.73 (1H, m), 3.57 (1H, m), 3.45 (2H, m), 3.37 (2H, m), 3.18 (1H, m), 2.97 (1H, m), 2.33 (3H., s), 1.23 (3H, t, J=7.2 Hz).

Example 146

N4-ethyl-N2-(3-fluoro-4-(5-methyl-1H-1,2,4-triazol-1-yl)phenyl)-8-phenyl-6-(2,2,2-trifluoroethyl)-5,6,7,8-tetrahydropyrido[4,3-d]pyrimidine-2,4-diamine

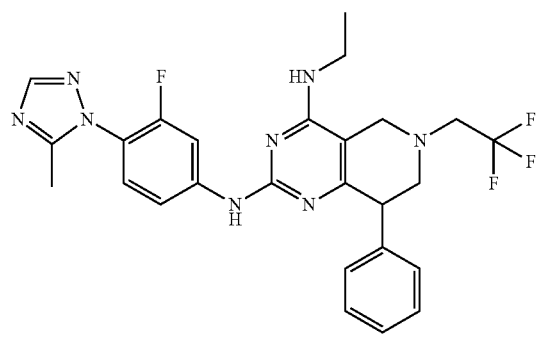 [SMILES: CCNc1nc(Nc2ccc(-n3ncnc3C)c(F)c2)nc2c1CN(CC(F)(F)F)CC2c1ccccc1]

To a solution of Preparation AEq (0.22 g, 0.40 mmol) in THF was added borane-DMS (0.068 g, 0.89 mmol, 2 M in diethyl ether) at −0° C. The reaction mixture was heated at 55° C. for 18 h. The reaction mixture was quenched with methanol and evaporated the solvent under reduced pressure to get crude compound. The crude compound was purified by prep-HPLC (aqueous 0.1% ammonium acetate in acetonitrile) get crude to give N4-ethyl-N2-(3-fluoro-4-(5-methyl-1H-1,2,4-triazol-1-yl)phenyl)-8-phenyl-6-(2,2,2-trifluoroethyl)-5,6,7,8-tetrahydropyrido[4,3-d]pyrimidine-2,4-diamine (0.030 g, 15%) as yellow solid. LC-MS (M+H)$^+$=527.2. $^1$H NMR (400 MHz, DMSO-d6): δ ppm 9.37 (1H, s), 8.04 (1H, s), 8.00 (1H, m), 7.42 (1H, m), 7.30-7.20 (6H, m), 6.84 (1H, m), 3.98 (1H, m), 3.73 (1H, m), 3.69 (1H, m), 3.57-3.48 (4H, m), 3.23 (1H, m), 2.99 (1H, m), 2.26 (3H., s), 1.23 (3H, t, J=7.2 Hz).

Example 147

N2-(4-(4-chloro-1H-imidazol-1-yl)-3-methoxyphenyl)-N4,N4-dimethyl-6-(methylsulfonyl)-8-phenyl-5,6,7,8-tetrahydropyrido[4,3-d]pyrimidine-2,4-diamine

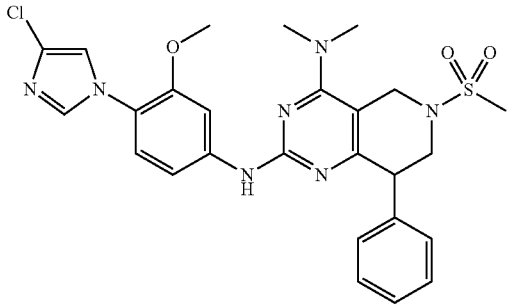 [SMILES: COc1cc(Nc2nc3c(c(N(C)C)n2)CN(S(C)(=O)=O)CC3c2ccccc2)ccc1-n1cnc(Cl)c1]

Using the methods of Preparation AEd, Preparation AEj, and Example 134, Preparation AEc was transformed into N2-(4-(4-chloro-1H-imidazol-1-yl)-3-methoxyphenyl)-N4,N4-dimethyl-6-(methylsulfonyl)-8-phenyl-5,6,7,8-tetrahydropyrido[4,3-d]pyrimidine-2,4-diamine. LC-MS (M−H)$^+$= 552.2. $^1$H NMR (400 MHz, DMSO-d6): δ ppm 9.27 (1H, s), 7.91 (1H, s), 7.73 (1H, m), 7.42 (1H, m), 7.31 (2H, m), 7.25-7.10 (5H, m), 4.46 (1H, m), 4.30-4.24 (2H, m), 3.83 (1H, m), 3.53 (3H, s), 3.28 (1H, m), 3.13 (6H, s), 3.09 (3H, s).

Example 148

N2-(4-(4-chloro-1H-imidazol-1-yl)-3-methoxyphenyl)-N4,6-dimethyl-8-phenyl-5,6,7,8-tetrahydropyrido[4,3-d]pyrimidine-2,4-diamine

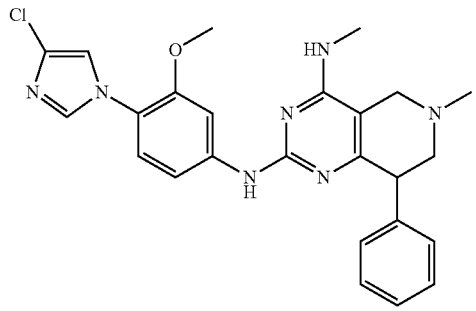 [SMILES: CNc1nc(Nc2ccc(-n3cnc(Cl)c3)c(OC)c2)nc2c1CN(C)CC2c1ccccc1]

A solution of Preparation A (0.26 g, 1.2 mmol), Preparation AFa (0.35 g, 1.2 mmol), Na$_2$CO$_3$ (0.25 g, 2.4 mmol) and xantphos (0.69 g, 1.2 mmol) in dioxane/water (9:1) was purged with argon for 1 h at room temperature. Pd(dba)$_3$ (0.55 g, 0.6 mmol) was added to the reaction mixture and the resulting solution was purged with argon for another 1 h. The reaction mass was heated at 110° C. for 24 h. The reaction mass was filtered through a bed of diamataceous earth (Celite®) and washed with ethyl acetate. The filtrate was evaporated under reduced pressure and the residue was diluted with water. The aqueous solution was extracted with ethyl acetate (25 mL×3). The combined organic layer was washed with brine solution (25 mL), dried over anhydrous Na$_2$SO$_4$ and evaporated under reduced pressure to get crude compound. The crude compound was purified by prep-HPLC (0.5% aqueous ammonium acetate in methanol) give N2-(4-(4-chloro-1H-imidazol-1-yl)-3-methoxyphenyl)-N4,6-dimethyl-8-phenyl-5,6,7,8-tetrahydropyrido[4,3-d]pyrimidine-2,4-diamine (0.10 g, 18%) as off-white solid. LC-MS (M+H)$^+$=476.2. $^1$H NMR (400 MHz, DMSO-d6): δ ppm 9.05 (1H, s), 8.05 (1H, s), 7.71 (1H, s), 7.40 (1H, s), 7.27-7.17 (5H, m), 7.15-7.06 (2H, m), 6.76 (1H, m), 3.94 (1H, m), 3.50 (3H, s), 3.39 (1H, m), 3.18 (1H, m), 2.95 (3H, d, J=4.4 Hz), 2.51 (1H, m), 2.49 (1H, m), 2.12 (3H, s).

The example was separated by chiral chromatography to afford the enantiomers 148A and 148B, which had identical spectral data.

Example 149

N2-(3-fluoro-4-(3-methyl-1H-1,2,4-triazol-1-yl)phenyl)-N4,6-dimethyl-8-phenyl-5,6,7,8-tetrahydropyrido[4,3-d]pyrimidine-2,4-diamine

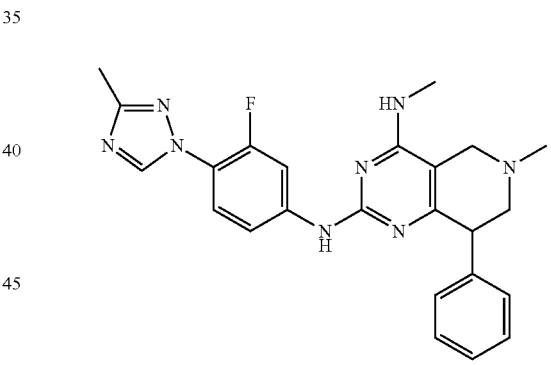

A solution of Preparation B (0.21 g, 1.1 mmol), Preparation AFa (0.35 g, 1.2 mmol), Na$_2$CO$_3$ (0.25 g, 2.4 mmol) and xantphos (0.70 g, 1.1 mmol) in dioxane/water (9:1) was purged with argon for 1 h at room temperature. Pd(dba)$_3$ (0.55 g, 0.6 mmol) was added to the reaction mixture and the resulting solution was purged with argon for another 1 h. The reaction mass was heated at 110° C. for 24 h. The reaction mass was filtered through a bed of diamataceous earth (Celite®) and washed with ethyl acetate. The filtrate was evaporated under reduced pressure and the residue was diluted with water. The aqueous solution was extracted with ethyl acetate (25 mL×3). The combined organic layer was washed with brine solution (25 mL), dried over anhydrous Na$_2$SO$_4$ and evaporated under reduced pressure to get crude compound. The crude compound was purified by prep-HPLC (0.5% aqueous ammonium acetate in methanol) give N$^2$-(3-fluoro-4-(3-methyl-1H-1,2,4-triazol-1-yl)phenyl)-N4,6-dimethyl-8-phenyl-5,6,7,8-tetrahydropyrido[4,3-d]pyrimidine-2,4-diamine (0.2 g, 38%) as off-white solid. LC-MS (M+H)⁺=445.2. ¹H NMR (400 MHz, DMSO-d6): δ ppm 9.33 (1H, s), 8.67 (1H, s), 8.05 (1H, m), 7.41 (2H, m), 7.3-7.20 (5H, m), 6.84 (1H, m), 3.96 (1H, m), 3.42 (1H, m), 3.25 (1H, m), 2.94 (3H, d, J=4.4 Hz), 2.92 (1H, m), 2.71 (1H, m), 2.51 (3H, s), 2.40 (3H, s).

Example 150

N2-(3-fluoro-4-(5-methyl-1H-1,2,4-triazol-1-yl)phenyl)-N4,6-dimethyl-8-phenyl-5,6,7,8-tetrahydropyrido[4,3-d]pyrimidine-2,4-diamine

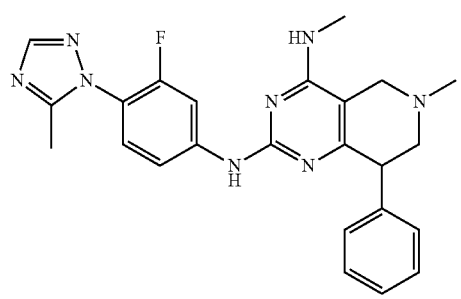 [SMILES: CNc1nc(Nc2ccc(-n3ncnc3C)c(F)c2)nc2c1CN(C)CC2c1ccccc1]

A solution of Preparation C (0.23 g, 1.2 mmol), Preparation AFa (0.35 g, 1.2 mmol), Na₂CO₃ (0.25 g, 2.4 mmol) and xantphos (0.69 g, 1.2 mmol) in dioxane/water (9:1) was purged with argon for 1 h at room temperature. Pd(dba)₃ (0.55 g, 0.6 mmol) was added to the reaction mixture and the resulting solution was purged with argon for another 1 h. The reaction mass was heated at 110° C. for 24 h. The reaction mass was filtered through a bed of diamataceous earth (Celite®) and washed with ethyl acetate. The filtrate was evaporated under reduced pressure and the residue was diluted with water. The aqueous solution was extracted with ethyl acetate (25 mL×3). The combined organic layer was washed with brine solution (25 mL), dried over anhydrous Na₂SO₄ and evaporated under reduced pressure to get crude compound. The crude compound was purified by prep-HPLC (0.5% aqueous ammonium acetate in methanol) give N2-(3-fluoro-4-(5-methyl-1H-1,2,4-triazol-1-yl)phenyl)-N4,6-dimethyl-8-phenyl-5,6,7,8-tetrahydropyrido[4,3-d]pyrimidine-2,4-diamine (0.08 g, 15%) as off-white solid. LC-MS (M+H)⁺=445.2. ¹H NMR (400 MHz, DMSO-d6): δ ppm 9.38 (1H, s), 8.06 (1H, m), 8.00 (1H, s), 7.44 (1H, m), 7.30-7.23 (5H, m), 7.18 (1H, m), 6.84 (1H, m), 3.95 (1H, m), 3.40 (1H, m), 3.22 (1H, m), 2.93 (3H, d, J=4.4 Hz), 2.90 (1H, m), 2.86 (1H, m), 2.36 (3H, s), 2.26 (3H, s).

Example 151

N2-(4-(4-chloro-1H-imidazol-1-yl)-3-methoxyphenyl)-N4-ethyl-6-methyl-8-phenyl-5,6,7,8-tetrahydropyrido[4,3-d]pyrimidine-2,4-diamine

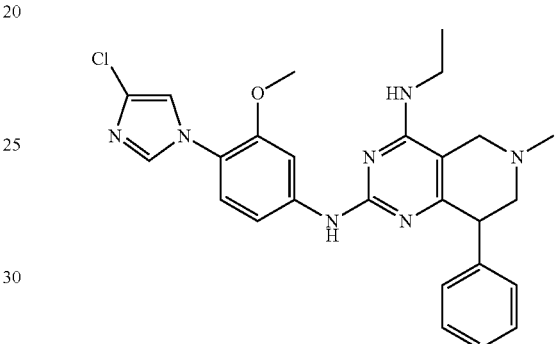

A solution of Preparation A (0.26 g, 1.19 mmol), Preparation AFb (0.4 g, 1.32 mmol), Na₂CO₃ (0.28 g, 2.64 mmol) and xantphos (0.76 g, 1.32 mmol) in dioxane/water (9:1) was purged with argon for 1 h at room temperature. Pd(dba)₃ (0.60 g, 0.66 mmol) was added to the reaction mixture and the resulting solution was purged with argon for another 1 h. The reaction mass was heated at 110° C. for 24 h. The reaction mass was filtered through a bed of diamataceous earth (Celite®) and washed with ethyl acetate. The filtrate was evaporated under reduced pressure and the residue was diluted with water. The aqueous solution was extracted with ethyl acetate (50 mL×2). The combined organic layer was washed with brine solution (50 mL), dried over anhydrous Na₂SO₄ and evaporated under reduced pressure to get crude compound. The crude compound was purified by prep-HPLC (0.5% aqueous ammonium acetate in methanol) to give N2-(4-(4-chloro-1H-imidazol-1-yl)-3-methoxyphenyl)-N4-ethyl-6-methyl-8-phenyl-5,6,7,8-tetrahydropyrido[4,3-d]pyrimidine-2,4-diamine (0.15 g, 24%) as off-white solid. LC-MS (M+H)⁺=490.2. ¹H NMR (400 MHz, DMSO-d6): δ ppm 9.01 (1H, s), 7.97 (1H, s), 7.71 (1H, s), 7.40 (1H, s), 7.39-7.20 (5H, m), 7.18-7.07 (2H, m), 6.70 (1H, m), 3.95 (1H, m), 3.57 (3H, s), 3.56 (2H, m), 3.47 (1H, m), 3.18 (1H, m), 2.85 (1H, m), 2.59 (1H, m), 2.34 (3H, s), 1.22 (3H, t, J=7.2 Hz).

The racemic mixture was separated by chiral chromatography to afford the enantiomers Example 151A and 151B, which had identical spectral data.

Example 152

N4-ethyl-N2-(3-fluoro-4-(3-methyl-1H-1,2,4-triazol-1-yl)phenyl)-6-methyl-8-phenyl-5,6,7,8-tetrahydropyrido[4,3-d]pyrimidine-2,4-diamine

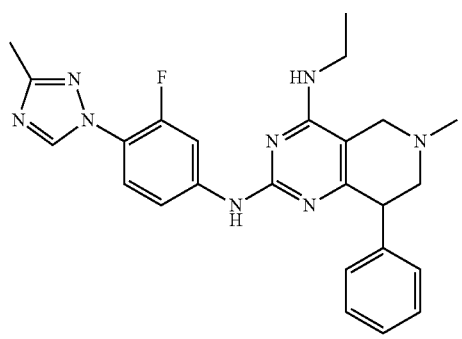

A solution of Preparation B (0.12 g, 0.59 mmol), Preparation AFb (0.20 g, 0.66 mmol), Na$_2$CO$_3$ (0.14 g, 1.32 mmol) and xantphos (0.38 g, 0.66 mmol) in dioxane/water (9:1) was purged with argon for 1 h at room temperature. Pd(dba)$_3$ (0.30 g, 0.33 mmol) was added to the reaction mixture and the resulting solution was purged with argon for another 1 h. The reaction mass was heated at 110° C. for 24 h. The reaction mass was filtered through a bed of diamataceous earth (Celite®) and washed with ethyl acetate. The filtrate was evaporated under reduced pressure and the residue was diluted with water. The aqueous solution was extracted with ethyl acetate (25 mL×3). The combined organic layer was washed with brine solution (25 mL), dried over anhydrous Na$_2$SO$_4$ and evaporated under reduced pressure to get crude compound. The crude compound was purified by prep-HPLC (0.5% aqueous ammonium acetate in methanol) give N4-ethyl-N2-(3-fluoro-4-(3-methyl-1H-1,2,4-triazol-1-yl)phenyl)-6-methyl-8-phenyl-5,6,7,8-tetrahydropyrido[4,3-d]pyrimidine-2,4-diamine (0.03 g, 11%) as off-white solid. LC-MS (M+H)$^+$=459.2. $^1$H NMR (400 MHz, DMSO-d6): δ ppm 9.31 (1H, s), 8.67 (1H, s), 8.04 (1H, m), 7.40 (2H, m), 7.29-7.17 (5H, m), 6.81 (1H, m), 3.95 (1H, m), 3.48 (2H, m), 3.43 (1H, m), 3.21 (1H, m), 2.91 (1H, m), 2.68 (1H, m), 2.38 (3H, s), 2.33 (3H, s), 1.23 (3H, t, J=7.2 Hz).

Example 153

N4-ethyl-N2-(3-fluoro-4-(5-methyl-1H-1,2,4-triazol-1-yl)phenyl)-6-methyl-8-phenyl-5,6,7,8-tetrahydropyrido[4,3-d]pyrimidine-2,4-diamine

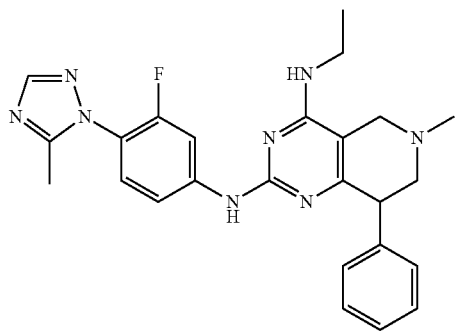 [SMILES: CCNc1nc(Nc2ccc(-n3ncnc3C)c(F)c2)nc2c1CN(C)CC2c1ccccc1]

A solution of Preparation C (0.15 g, 0.82 mmol), Preparation AFb (0.25 g, 0.82 mmol), Na$_2$CO$_3$ (0.17 g, 1.6 mmol) and xantphos (0.42 g, 0.82 mmol) in dioxane/water (9:1) was purged with argon for 1 h at room temperature. Pd(dba)$_3$ (0.37 g, 0.41 mmol) was added to the reaction mixture and the resulting solution was purged with argon for another 1 h. The reaction mass was heated at 110° C. for 24 h. The reaction mass was filtered through a bed of diamataceous earth (Celite®) and washed with ethyl acetate. The filtrate was evaporated under reduced pressure and the residue was diluted with water. The aqueous solution was extracted with ethyl acetate (25 mL×3). The combined organic layer was washed with brine solution (25 mL), dried over anhydrous Na$_2$SO$_4$ and evaporated under reduced pressure to get crude compound. The crude compound was purified by prep-HPLC (0.5% aqueous ammonium acetate in methanol) give N4-ethyl-N2-(3-fluoro-4-(5-methyl-1H-1,2,4-triazol-1-yl)phenyl)-6-methyl-8-phenyl-5,6,7,8-tetrahydropyrido[4,3-d]pyrimidine-2,4-diamine (0.06 g, 17%) as off-white solid. LC-MS (M+H)$^+$=459.2. $^1$H NMR (400 MHz, CDCl$_3$): δ ppm 7.93 (1H, s), 7.84 (1H, m), 7.34-7.27 (5H, m), 7.26-2.20 (2H, m), 7.05 (1H, m), 4.65 (1H, m), 4.11 (1H, m), 3.61-3.54 (2H, m), 3.39 (2H, m), 3.07 (1H, m), 2.81 (1H, m), 2.51 (3H, s), 2.37 (3H, s), 1.34 (3H, t, J=7.2 Hz).

Example 154

N2-(4-(4-chloro-1H-imidazol-1-yl)-3-methoxyphenyl)-8-(4-fluorophenyl)-N4-methyl-6-(methylsulfonyl)-5,6,7,8-tetrahydropyrido[4,3-d]pyrimidine-2,4-diamine

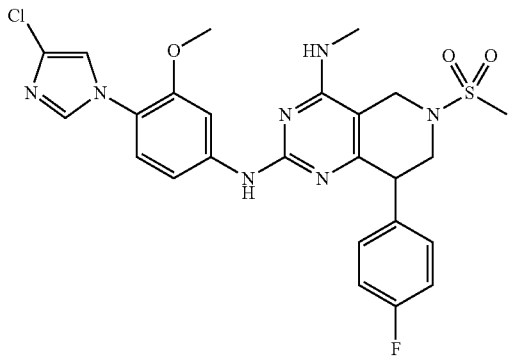 [SMILES: CNc1nc(Nc2ccc(-n3cnc(Cl)c3)c(OC)c2)nc2c1CN(S(C)(=O)=O)CC2c1ccc(F)cc1]

To a solution of Preparation AGk (0.08 g, 0.167 mmol) in dichloromethane was added diisopropylethylamine (0.043 g, 0.33 mmol) followed by methanesulfonyl chloride (0.029 g, 0.167 mmol) at 0° C. The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in acetonitrile) to give N2-(4-(4-chloro-1H-imidazol-1-yl)-3-methoxyphenyl)-8-(4-fluorophenyl)-N4-methyl-6-(methylsulfonyl)-5,6,7,8-tetrahydropyrido[4,3-d]pyrimidine-2,4-diamine (0.02 g, 23%) as off-white solid. LC-MS (M+H)$^+$=558.0. $^1$H NMR (400 MHz, DMSO-d6): δ ppm 9.21 (1H, s), 8.0 (1H, s), 7.73 (1H, s), 7.42 (1H, s), 7.27-7.23 (2H, m), 7.16-7.12 (4H, m), 7.05 (1H, m), 4.20 (1H, m), 4.12 (1H, m), 4.05 (1H, m), 3.56 (3H, s), 3.51-3.47 (2H, m), 2.97 (3H, d, J=4.0 Hz), 2.91 (3H, s).

The example was separated by chiral chromatography to afford the enantiomers 154A and 154B, which had identical spectral data.

Example 155

N2-(4-(4-chloro-1H-imidazol-1-yl)-3-methoxyphenyl)-N4-ethyl-8-(4-fluorophenyl)-6-(methylsulfonyl)-5,6,7,8-tetrahydropyrido[4,3-d]pyrimidine-2,4-diamine

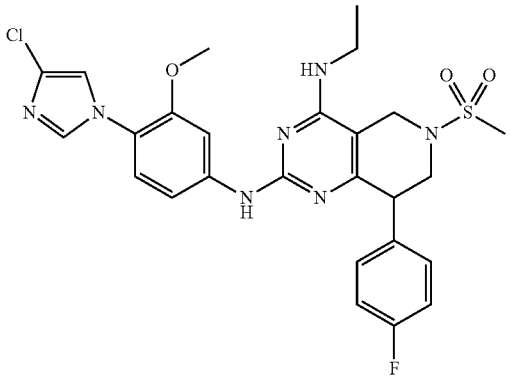 [SMILES: CCNc1nc(Nc2ccc(-n3cnc(Cl)c3)c(OC)c2)nc2c1CN(S(C)(=O)=O)CC2c1ccc(F)cc1]

To a solution of Preparation AGl (0.09 g, 0.018 mmol) in dichloromethane was added triethylamine (0.037 g, 0.36 mmol) followed by methanesulfonyl chloride (0.021 g, 0.182 mmol) at 0° C. The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in acetonitrile) to give N2-(4-(4-chloro-1H-imidazol-1-yl)-3-methoxyphenyl)-N4-ethyl-8-(4-fluorophenyl)-6-(methylsulfonyl)-5,6,7,8-tetrahydropyrido[4,3-d]pyrimidine-2,4-diamine (0.04 g, 39%) as off-white solid. LC-MS (M−H)$^+$=572.0. $^1$H NMR (400 MHz, DMSO-d6): δ ppm 9.18 (1H, s), 7.95 (1H, s), 7.73 (1H, s), 7.42 (1H, s), 7.27-7.23 (2H, m), 7.17-7.12 (4H, m), 6.99 (1H, m), 4.24 (1H, d, J=14.0 Hz), 4.12 (1H, m), 4.04 (1H, d, J=14.0 Hz), 3.56 (3H, s), 3.55-3.47 (4H, m), 2.92 (3H, s), 1.22 (3H, t, J=7.2 Hz).

The example was separated by chiral chromatography to afford the enantiomers 155A and 155B, which had identical spectral data.

Example 156

N4-ethyl-N2-(3-fluoro-4-(3-methyl-1H-1,2,4-triazol-1-yl)phenyl)-8-(4-fluorophenyl)-6-(methylsulfonyl)-5,6,7,8-tetrahydropyrido[4,3-d]pyrimidine-2,4-diamine

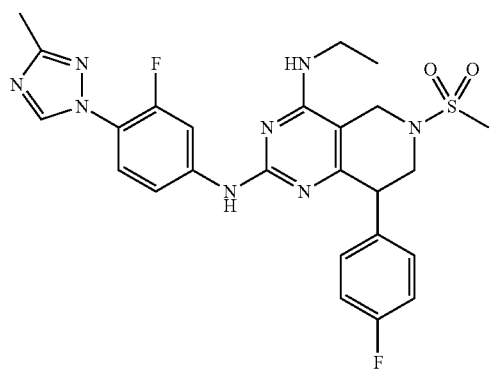 [SMILES: CCNc1nc(Nc2ccc(-n3cnc(C)n3)c(F)c2)nc2c1CN(S(C)(=O)=O)CC2c1ccc(F)cc1]

To a solution of Preparation AGm (0.30 g, 0.649 mmol) in dichloromethane was added diisopropylethylamine (0.168 g, 0.29 mmol) followed by methanesulfonyl chloride (0.07 g, 0.649 mmol) at 0° C. The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in acetonitrile) to give N4-ethyl-N2-(3-fluoro-4-(3-methyl-1H-1,2,4-triazol-1-yl)phenyl)-6-(methylsulfonyl)-8-phenyl-5,6,7,8-tetrahydropyrido[4,3-d]pyrimidine-2,4-diamine (0.250 g, 71%) as off-white solid. LC-MS (M+H)$^+$=541.2. $^1$H NMR (400 MHz, DMSO-d6): δ ppm 9.45 (1H, s), 8.69 (1H, s), 8.01 (1H, m), 7.47-7.40 (2H, m), 7.39-7.26 (2H, m), 7.15-7.07 (3H, m), 4.20 (1H, m), 4.12-4.06 (2H, m), 3.63 (1H, m), 3.54-3.48 (3H, m), 2.94 (3H, s), 2.34 (3H, s), 1.22 (3H, t, J=7.2 Hz).

The example was separated by chiral chromatography to afford the enantiomers 156A and 156B, which had identical spectral data.

Example 157

N4-ethyl-N2-(3-fluoro-4-(5-methyl-1H-1,2,4-triazol-1-yl)phenyl)-6-(methylsulfonyl)-8-(4-fluorophenyl)-5,6,7,8-tetrahydropyrido[4,3-d]pyrimidine-2,4-diamine

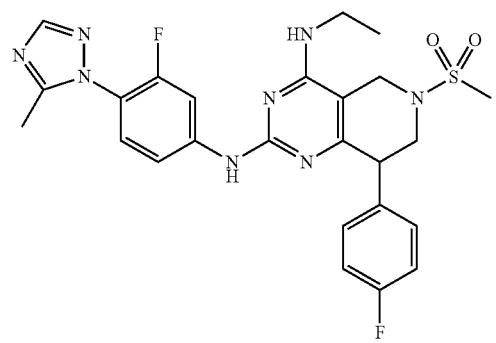 [SMILES: CCNc1nc(Nc2ccc(-n3ncnc3C)c(F)c2)nc2c1CN(S(C)(=O)=O)CC2c1ccc(F)cc1]

To a solution of Preparation AGn (0.25 g, 0.540 mmol) in dichloromethane was added diisopropylethylamine (0.139 g, 1.080 mmol) followed by methanesulfonyl chloride (0.06 g, 0.540 mmol) at 0° C. The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in acetonitrile) to give N4-ethyl-N2-(3-fluoro-4-(5-methyl-1H-1,2,4-triazol-1-yl)phenyl)-6-(methylsulfonyl)-8-(4-fluorophenyl)-5,6,7,8-tetrahydropyrido[4,3-d]pyrimidine-2,4-diamine (0.19 g, 73%) as off-white solid. LC-MS (M−H)$^+$=541.2. $^1$H NMR (400 MHz, DMSO-d6): δ ppm 9.48 (1H, s), 8.01 (1H, m), 7.97 (1H, 1H), 7.43 (1H, m), 7.34-7.27 (3H, m), 7.15-7.11 (2H, m), 7.05 (1H, m), 4.23-4.07 (3H, m), 3.63 (1H, m), 3.55-3.48 (3H, m), 2.94 (3H, s), 2.28 (3H, s), 1.24 (3H, t, J=7.2 Hz).

The example was separated by chiral chromatography to afford the enantiomers 157A and 157B, which had identical spectral data.

Example 158

N2-(4-(4-chloro-1H-imidazol-1-yl)-3-methoxyphenyl)-N4,6-diethyl-8-(4-fluorophenyl)-N4-methyl-5,6,7,8-tetrahydropyrido[4,3-d]pyrimidine-2,4-diamine

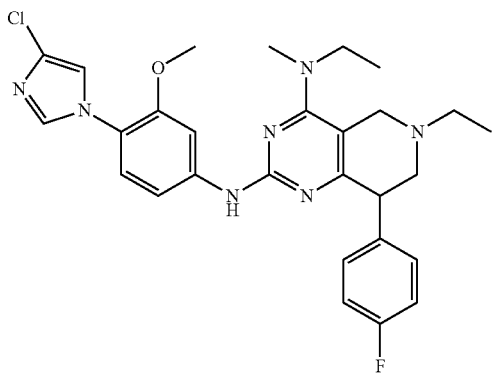 [SMILES: CCN1Cc2c(nc(Nc3ccc(-n4cnc(Cl)c4)c(OC)c3)nc2N(C)CC)C(c2ccc(F)cc2)C1]

To a solution of Preparation AGo (0.010 g, 0.019 mmol) in ethanol was added triethylamine (0.004 g, 0.039 mmol) at 0° C. followed by ethyl iodide (0.030 g, 0.019 mmol). The reaction mixture was heated at 80° C. for 18 h. The solvent was removed under reduced pressure and the residue was diluted with water. The aqueous solution was extracted with ethyl acetate (10 mL×3). The combined organic layer was washed with water, dried over anhydrous $Na_2SO_4$ and evaporated under reduced pressure to get crude compound. The crude compound was purified by prep-HPLC (aqueous 0.1% ammonium acetate in methanol) to give N2-(4-(4-chloro-1H-imidazol-1-yl)-3-methoxyphenyl)-N4,6-diethyl-8-(4-fluorophenyl)-N4-methyl-5,6,7,8-tetrahydropyrido[4,3-d]pyrimidine-2,4-diamine (0.04 g, 40%) as off-white solid. LC-MS $(M+H)^+$=536.2. $^1$H NMR (400 MHz, methanol-d4): δ ppm 7.80 (1H, s), 7.67 (1H, s), 7.26-7.22 (3H, m), 7.13 (1H, m), 7.07-7.00 (2H, m), 6.98 (1H, m), 4.23 (1H, m), 3.75 (1H, m), 3.56-3.48 (6H, m), 3.33 (1H, m), 3.28 (3H, s), 2.69-2.64 (2H, m), 2.53 (1H, m), 1.34 (3H, m), 1.30 (3H, m).

Example 159

N-(4-(4-chloro-1H-imidazol-1-yl)-3-methoxyphenyl)-4-(3,3-difluoroazetidin-1-yl)-8-(4-fluorophenyl)-6-methyl-5,6,7,8-tetrahydropyrido[4,3-d]pyrimidin-2-amine

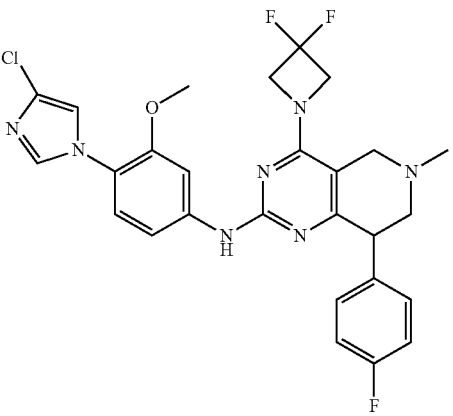 [SMILES: COc1cc(Nc2nc3c(c(N4CC(F)(F)C4)n2)CN(C)CC3c2ccc(F)cc2)ccc1-n1cnc(Cl)c1]

To a solution of Preparation AGp (0.03 g, 0.055 mmol) in acetone was added $K_2CO_3$ (0.011, 0.083 mmol) followed by methyl iodide (0.012 g, 0.083 mmol) at room temperature. The reaction mixture was stirred at room temperature for 2 h. The solvent was removed under reduced pressure and the residue was diluted with water. The aqueous solution was extracted with ethyl acetate (10 mL×3). The combined organic layer was washed with water, dried over anhydrous $Na_2SO_4$ and evaporated under reduced pressure to get crude compound. The crude compound was purified by prep-HPLC (aqueous 0.1% ammonium acetate in methanol) to give N-(4-(4-chloro-1H-imidazol-1-yl)-3-methoxyphenyl)-4-(3,3-difluoroazetidin-1-yl)-8-(4-fluorophenyl)-6-methyl-5,6,7,8-tetrahydropyrido[4,3-d]pyrimidin-2-amine (0.007 g, 24%). LC-MS $(M+H)^+$=556.2. $^1$H NMR (400 MHz, DMSO-d6): δ ppm 10.50 (1H, s), 9.56 (1H, s), 7.75 (1H, s), 7.43 (1H, s), 7.33-7.30 (2H, m), 7.25-7.18 (2H, m), 7.14 (1H, m), 4.09 (1H, m), 4.82-4.76 (2H, m), 4.64 (3H, m), 4.43 (3H, m), 3.88 (1H, m), 3.51 (3H, s), 2.97 (3H, s).

Example 160

N-(4-(4-chloro-1H-imidazol-1-yl)-3-methoxyphenyl)-4-(3,3-difluoroazetidin-1-yl)-8-(4-fluorophenyl)-6-(methylsulfonyl)-5,6,7,8-tetrahydropyrido[4,3-d]pyrimidin-2-amine

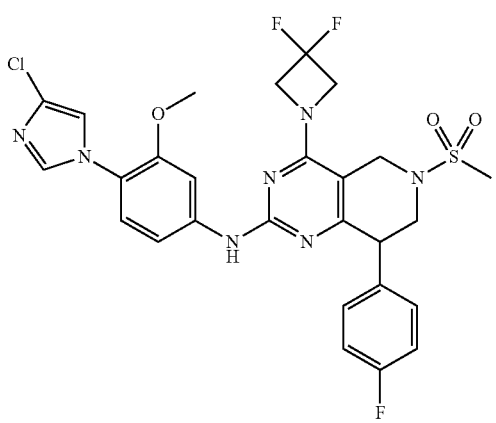 [SMILES: COc1cc(Nc2nc3c(c(N4CC(F)(F)C4)n2)CN(S(C)(=O)=O)CC3c2ccc(F)cc2)ccc1-n1cnc(Cl)c1]

To a solution of Preparation AGp (0.040 g, 0.073 mmol) in acetone was added Cs$_2$CO$_3$ (0.036 g, 0.11 mmol) followed by methanesulfonyl chloride (0.012 g, 0.11 mmol). The reaction mixture was stirred at room temperature for 2 h. The solvent was removed under reduced pressure and the residue was diluted with water. The aqueous solution was extracted with ethyl acetate (10 mL×3). The combined organic layer was washed with water, dried over anhydrous Na$_2$SO$_4$ and evaporated under reduced pressure to get crude compound. The crude compound was purified by prep-HPLC (aqueous 0.1% ammonium acetate in methanol) to give (0.005 g, 12%) as off-white solid. LC-MS (M+H)$^+$=620.0. $^1$H NMR (400 MHz, DMSO-d6): δ ppm 9.47 (1H, s), 7.85 (1H, s), 7.74 (1H, s), 7.43 (1H, s), 7.30-7.26 (2H, m), 7.18-7.09 (4H, m), 4.77-4.70 (4H, m), 4.36 (1H, m), 4.24 (2H, m), 3.66 (1H, m), 3.56 (3H, s), 3.44 (1H, m), 3.0 (3H, s).

The example was separated by chiral chromatography to afford the enantiomers 160A and 160B, which had identical spectral data.

Example 161

N2-(4-(4-chloro-1H-imidazol-1-yl)-3-methoxyphenyl)-N4-ethyl-8-(4-fluorophenyl)-N4-methyl-5,6,7,8-tetrahydropyrido[4,3-d]pyrimidine-2,4-diamine

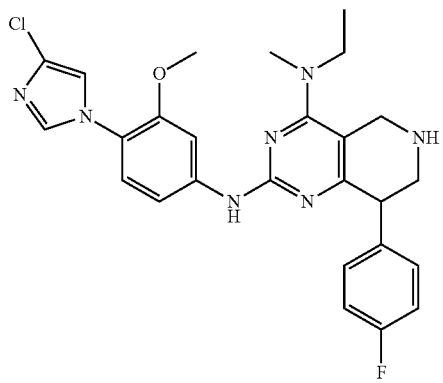 [SMILES: CCN(C)c1nc(Nc2ccc(-n3cnc(Cl)c3)c(OC)c2)nc2c1CNCC2c1ccc(F)cc1]

This compound is identical to Preparation AGo (vide supra).

Example 162

N-(4-(4-chloro-1H-imidazol-1-yl)-3-methoxyphenyl)-4-(3,3-difluoroazetidin-1-yl)-8-(4-fluorophenyl)-5,6,7,8-tetrahydropyrido[4,3-d]pyrimidin-2-amine

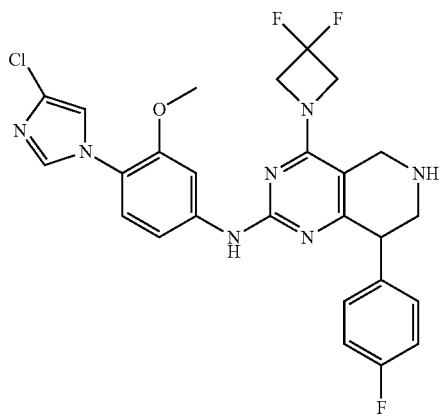 [SMILES: COc1cc(Nc2nc3c(c(N4CC(F)(F)C4)n2)CNCC3c2ccc(F)cc2)ccc1-n1cnc(Cl)c1]

This compound is identical to Preparation AGp (vide supra). The example was separated by chiral chromatography to yield the individual enantiomers 162A and 162B, which each had identical spectral data.

Example 163

N2-(4-(4-chloro-1H-imidazol-1-yl)-3-methoxyphenyl)-8-(4-fluorophenyl)-N4,6-dimethyl-5,6,7,8-tetrahydropyrido[4,3-d]pyrimidine-2,4-diamine

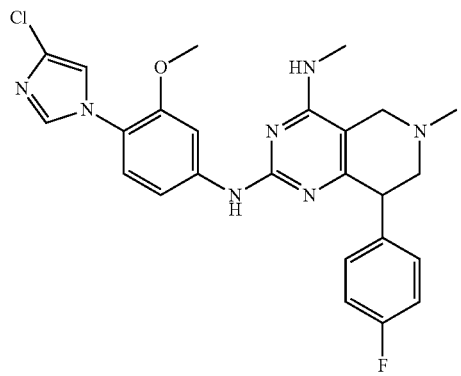 [SMILES: CNc1nc(Nc2ccc(-n3cnc(Cl)c3)c(OC)c2)nc2c1CN(C)CC2c1ccc(F)cc1]

A solution of Preparation A (0.109 g, 0.49 mmol), Preparation AHa (0.15 g, 0.49 mmol), Na$_2$CO$_3$ (0.103 g, 0.98 mmol) and xantphos (0.283 g, 0.49 mmol) in dioxane/water (9:1) was purged with argon for 1 h at room temperature. Pd(dba)$_3$ (0.253 g, 0.24 mmol) was added to the reaction mixture and the resulting solution was purged with argon for another 1 h. The reaction mass was heated at 110° C. for 24 h. The reaction mass was filtered through a bed of diamataceous earth (Celite®) and washed with ethyl acetate. The filtrate was evaporated under reduced pressure and the residue was diluted with water. The aqueous solution was extracted with ethyl acetate (25 mL×3). The combined organic layer was washed with brine solution (25 mL), dried over anhydrous Na$_2$SO$_4$ and evaporated under reduced pressure to get crude compound. The crude compound was purified by prep-HPLC (0.5% aqueous ammonium acetate in methanol) give N2-(4-(4-chloro-1H-imidazol-1-yl)-3-methoxyphenyl)-8-(4-fluorophenyl)-N4,6-dimethyl-5,6,7,8-tetrahydropyrido[4,3-d]pyrimidine-2,4-diamine (0.035 g, 14%) as off-white solid. LC-MS (M+H)$^+$=494.2. $^1$H NMR (400 MHz, DMSO-d6): δ ppm 9.07 (1H, s), 8.32 (1H, s), 8.05 (1H, s), 7.72 (1H, s), 7.26 (2H, m), 7.14-7.05 (4H, m), 6.77 (1H, m), 3.96 (1H, m), 3.94 (3H, s), 3.42 (1H, m), 3.11 (1H, m), 2.92 (3H, d, J=4.4 Hz), 2.82 (1H, m), 2.58 (1H, m), 2.33 (3H, s).

The racemic mixture was separated by chiral chromatography to afford the enantiomers Example 163A and 163B, which had identical spectral data.

Example 164

N2-(4-(4-chloro-1H-imidazol-1-yl)-3-methoxyphenyl)-N4-ethyl-8-(4-fluorophenyl)-6-methyl-5,6,7,8-tetrahydropyrido[4,3-d]pyrimidine-2,4-diamine

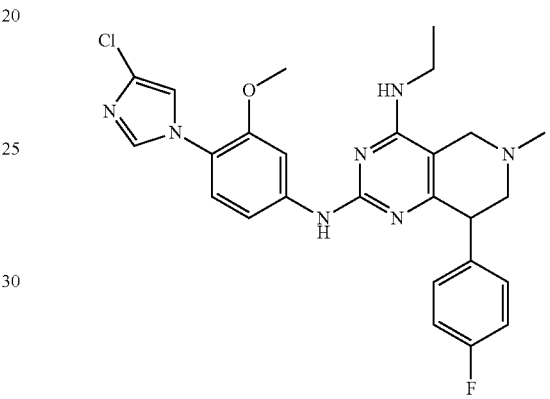

A solution of Preparation A (0.146 g, 0.650 mmol), Preparation AHb (0.210 g, 0.650 mmol), Na$_2$CO$_3$ (0.139 g, 1.30 mmol) and xantphos (0.378 g, 0.650 mmol) in dioxane/water (9:1) was purged with argon for 1 h at room temperature. Pd(dba)$_3$ (0.338 g, 0.327 mmol) was added to the reaction mixture and the resulting solution was purged with argon for another 1 h. The reaction mass was heated at 110° C. for 24 h. The reaction mass was filtered through a bed of diamataceous earth (Celite®) and washed with ethyl acetate. The filtrate was evaporated under reduced pressure and the residue was diluted with water. The aqueous solution was extracted with ethyl acetate (50 mL×2). The combined organic layer was washed with brine solution (50 mL), dried over anhydrous Na$_2$SO$_4$ and evaporated under reduced pressure to get crude compound. The crude compound was purified by prep-HPLC (0.5% aqueous ammonium acetate in methanol) to give N2-(4-(4-chloro-1H-imidazol-1-yl)-3-methoxyphenyl)-N4-ethyl-8-(4-fluorophenyl)-6-methyl-5,6,7,8-tetrahydropyrido[4,3-d]pyrimidine-2,4-diamine (0.022 g, 22%) as off-white solid. LC-MS (M+H)$^+$=508.0. $^1$H NMR (400 MHz, DMSO-d6): δ ppm 9.07 (1H, s), 7.97 (1H, s), 7.73 (1H, s), 7.41 (1H, s), 7.29-7.23 (2H, m), 7.15-7.05 (4H, m), 6.73 (1H, m), 3.96 (1H, m), 3.56 (3H, s), 3.49-3.40 (3H, m), 3.13 (1H, m), 2.83 (1H, m), 2.62 (1H, m) 2.34 (3H, s), 1.21 (3H, t, J=7.2 Hz).

The racemic mixture was separated by chiral chromatography to afford the enantiomers Example 164A and 164B, which had identical spectral data.

Example 165

N2-(4-(4-chloro-1H-imidazol-1-yl)-3-methoxyphenyl)-N4-ethyl-8-(4-fluorophenyl)-N4,6-dimethyl-5,6,7,8-tetrahydropyrido[4,3-d]pyrimidine-2,4-diamine

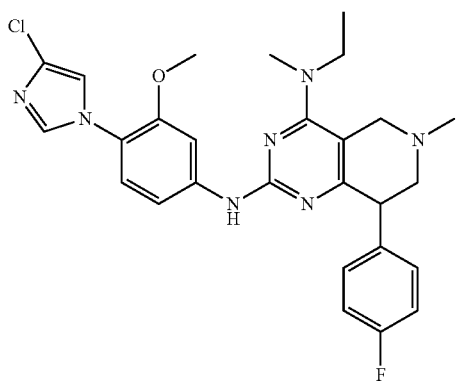 [SMILES: CCN(C)c1nc(Nc2ccc(-n3cnc(Cl)c3)c(OC)c2)nc2c1CN(C)CC2c1ccc(F)cc1]

A solution of Preparation A (0.18 g, 0.80 mmol), Preparation AHc (0.30 g, 0.89 mmol), Na$_2$CO$_3$ (0.190 g, 1.79 mmol) and xantphos (0.519 g, 0.89 mmol) in dioxane/water (9:1) was purged with argon for 1 h at room temperature. Pd(dba)$_3$ (0.465 g, 0.440 mmol) was added to the reaction mixture and the resulting solution was purged with argon for another 1 h. The reaction mass was heated at 110° C. for 24 h. The reaction mass was filtered through a bed of diamataceous earth (Celite®) and washed with ethyl acetate. The filtrate was evaporated under reduced pressure and the residue was diluted with water. The aqueous solution was extracted with ethyl acetate (20 mL×3). The combined organic layer was washed with brine solution (25 mL), dried over anhydrous Na$_2$SO$_4$ and evaporated under reduced pressure to get crude compound. The crude compound was purified by prep-HPLC (0.5% aqueous ammonium acetate in methanol) to give N2-(4-(4-chloro-1H-imidazol-1-yl)-3-methoxyphenyl)-N4-ethyl-8-(4-fluorophenyl)-N4,6-dimethyl-5,6,7,8-tetrahydropyrido[4,3-d]pyrimidine-2,4-diamine (0.13 g, 28%) as off-brown solid. LC-MS (M+H)$^+$=522.0. $^1$H NMR (400 MHz, DMSO-d6): δ ppm 9.13 (1H, s), 7.86 (1H, s), 7.73 (1H, s), 7.42 (1H, s), 7.24 (2H, m), 7.15-7.07 (4H, m), 4.13 (1H, m), 3.55 (3H, s), 3.47-3.41 (4H, m), 3.04 (3H, s), 2.99 (1H, m), 2.48 (1H, m), 2.34 (3H, s), 1.23 (3H, t, J=7.2 Hz).

The racemic mixture was separated by chiral chromatography to afford the enantiomers Example 165A and 165B, which had identical spectral data.

Example 166

N2-(4-(4-chloro-1H-imidazol-1-yl)-3-methoxyphenyl)-N4-ethyl-8-(4-fluorophenyl)-N4-methyl-5,6,7,8-tetrahydropyrido[3,4-d]pyrimidine-2,4-diamine

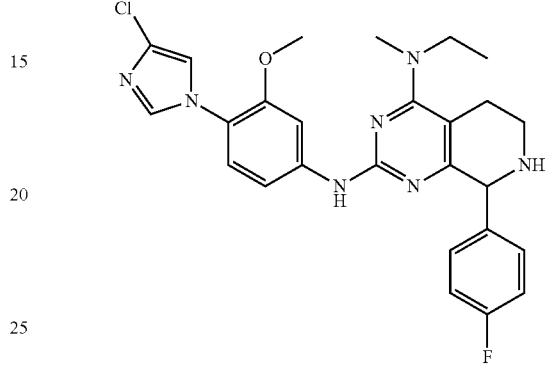

This example is the same compound as Preparation AII (vide supra).

Example 167

N-(4-(4-chloro-1H-imidazol-1-yl)-3-methoxyphenyl)-8-(4-fluorophenyl)-4-((S)-3-fluoropyrrolidin-1-yl)-7-(4-methoxybenzyl)-5,6,7,8-tetrahydropyrido[3,4-d]pyrimidin-2-amine

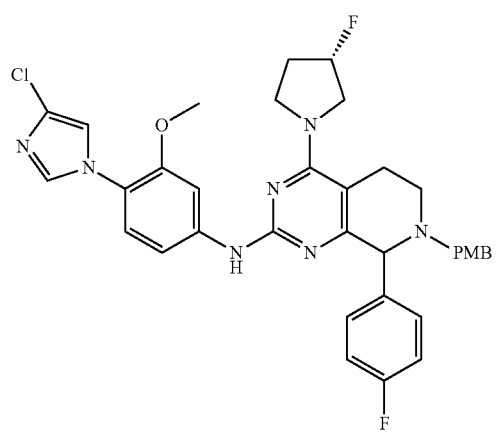

A solution of Preparation A (0.190 g, 0.851 mmol), Preparation AId (0.40 g, 0.851 mmol), Na$_2$CO$_3$ (0.180 g, 1.70 mmol) and xantphos (0.491 g, 0.851 mmol) in dioxane/water (9:1) was purged with argon for 1 h at room temperature. Pd(dba)$_3$ (0.440 g, 0.425 mmol) was added to the reaction mixture and the resulting solution was purged with argon for another 1 h. The reaction mass was heated at 110° C. for 24 h. The reaction mass was filtered through a bed of diamataceous earth (Celite®) and washed with ethyl acetate. The filtrate was evaporated under reduced pressure and the residue was diluted with water. The aqueous solution was extracted with ethyl acetate (25 mL×3). The combined organic layer was washed with brine solution (20 mL), dried over anhydrous Na$_2$SO$_4$ and evaporated under reduced pressure to get crude compound. The crude compound was purified by column chromatography (60-120 mesh) using 50% ethyl acetate in pet-ether as mobile phase to give a mixture of two diasteriomers N-(4-(4-chloro-1H-imidazol-1-yl)-3-methoxyphenyl)-8-(4-fluorophenyl)-4-((S)-3-fluoropyrrolidin-1-yl)-7-(4-methoxybenzyl)-5,6,7,8-tetrahydropyrido[3,4-d]pyrimidin-2-amine (0.40 g, 88%, crude) as off-white solid. LC-MS (M+H)$^+$=658.2. $^1$H NMR (400 MHz, DMSO-d6): δ ppm 8.95 (1H, s), 7.75 (1H, s), 7.74 (1H, s), 7.54 (2H, m), 7.43 (1H, s), 7.29 (1H, m), 7.22-7.14 (5H, m), 6.86 (2H, m), 5.34 (1H, m), 4.38 (1H, s), 4.03 (1H, m), 4.0 (3H, m), 3.72 (6H, s), 3.51 (1H, m), 3.33 (1H, m), 2.95 (2H, m), 2.51 (1H, m), 2.25-2.01 (3H, m).

The diasteriomeric mixture was separated by chiral chromatography to afford two diasteriomers Example 167A and 167B.

Example 168

N2-(4-(4-chloro-1H-imidazol-1-yl)-3-methoxyphenyl)-N4-ethyl-8-(4-fluorophenyl)-7-(methylsulfonyl)-5,6,7,8-tetrahydropyrido[3,4-d]pyrimidine-2,4-diamine

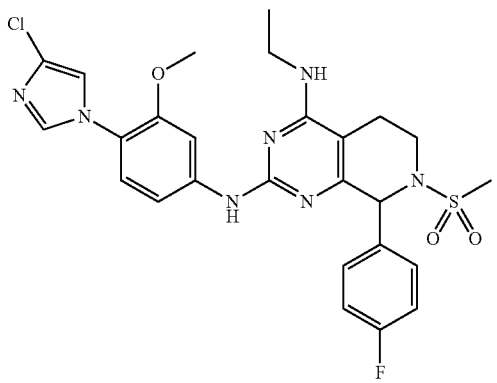 [SMILES: CCNc1nc(Nc2ccc(-n3cnc(Cl)c3)c(OC)c2)nc2c1CCN(S(C)(=O)=O)C2c1ccc(F)cc1]

To a solution of Preparation AIk (0.06 g, 0.121 mmol) in dichloromethane was added diisopropylethylamine (0.041 g, 0.243 mmol) at −10° C. followed by methanesulfonyl chloride (0.013 g, 0.121 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in acetonitrile) to give N2-(4-(4-chloro-1H-imidazol-1-yl)-3-methoxyphenyl)-N4-ethyl-8-(4-fluorophenyl)-7-(methylsulfonyl)-5,6,7,8-tetrahydropyrido[3,4-d]pyrimidine-2,4-diamine (0.020 g, 29%) as off-white solid. LC-MS (M+H)$^+$=572.2. $^1$H NMR (400 MHz, DMSO-d6): δ ppm 9.23 (1H, s), 7.97 (1H, s), 7.74 (1H, s), 7.43 (1H, s), 7.35 (2H, m), 7.23-7.12 (4H, m), 7.0 (1H, m), 5.57 (1H, s), 3.85 (1H, m), 3.79 (3H, s), 3.54 (2H, m), 3.18 (1H, m), 2.88 (3H, s), 2.65 (2H, m), 1.24 (3H, t, J=7.2 Hz).

The racemic mixture was separated by chiral chromatography to afford two enantiomers Example 168A and 168B.

Example 169

N2-(4-(4-chloro-1H-imidazol-1-yl)-3-methoxyphenyl)-N4,7-diethyl-8-(4-fluorophenyl)-5,6,7,8-tetrahydropyrido[3,4-d]pyrimidine-2,4-diamine

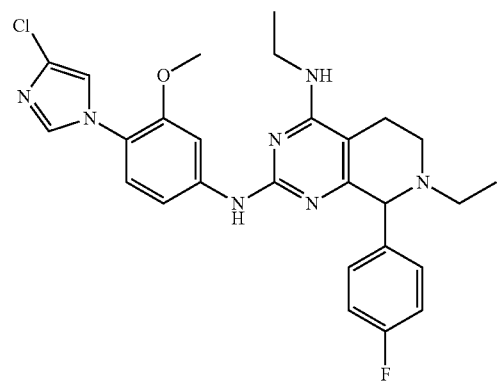 [SMILES: CCNc1nc(Nc2ccc(-n3cnc(Cl)c3)c(OC)c2)nc2c1CCN(CC)C2c1ccc(F)cc1]

To a solution of Preparation AIk (0.20 g, 0.405 mmol) in dichloromethane was added diisopropylethylamine (0.104 g, 0.806 mmol) at −10° C. followed by ethyl iodide (0.31 g, 0.231 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in acetonitrile) to give N2-(4-(4-chloro-1H-imidazol-1-yl)-3-methoxyphenyl)-N4,7-diethyl-8-(4-fluorophenyl)-5,6,7,8-tetrahydropyrido[3,4-d]pyrimidine-2,4-diamine (0.110 g, 62%) as off-white solid. LC-MS (M+H)$^+$=522.2. $^1$H NMR (400 MHz, DMSO-d6): δ ppm 8.90 (1H, s), 7.70 (1H, s), 7.73 (1H, s), 7.42 (1H, s), 7.28 (2H, m), 7.17 (4H, m), 6.78 (1H, m), 4.39 (1H, s), 3.65 (3H, s), 3.48 (2H, m), 3.13 (2H, m), 3.08 (1H, m), 2.51 (1H, m), 2.39 (2H, m), 1.22-1.19 (6H, m).

The racemic mixture was separated by chiral chromatography to afford two enantiomers Example 169A and 169B.

Example 170 methyl 2-(4-(4-chloro-1H-imidazol-1-yl)-3-methoxyphenylamino)-4-(ethylamino)-8-(4-fluorophenyl)-5,6-dihydropyrido[3,4-d]pyrimidine-7(8H)-carboxylate

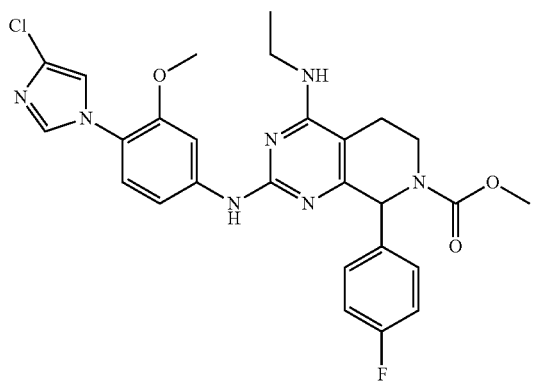 [SMILES: CCNc1nc(Nc2ccc(-n3cnc(Cl)c3)c(OC)c2)nc2c1CCN(C(=O)OC)C2c1ccc(F)cc1]

To a solution of Preparation of AIk (0.10 g, 0.20 mmol) in dichloromethane was added triethylamine (0.019 g, 0.20 mmol) at −10° C. followed by methyl chloroformate (0.18 g, 0.20 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in acetonitrile) to give methyl 2-(4-(4-chloro-1H-imidazol-1-yl)-3-methoxyphenylamino)-4-(ethylamino)-8-(4-fluorophenyl)-5,6-dihydropyrido[3,4-d]pyrimidine-7(8H)-carboxylate (0.080 g, 76%) as off-white solid. LC-MS (M+H)$^+$= 552.2. $^1$H NMR (400 MHz, DMSO-d6): δ ppm 9.22 (1H, s), 7.96 (1H, s), 7.74 (1H, s), 7.48 (1H, s), 7.33 (2H, m), 7.20-7.13 (4H, m), 6.98 (1H, m), 4.06 (1H, s), 3.82 (1H, m), 3.75 (3H, s), 3.68 (3H, s), 3.56 (2H, m), 3.02 (1H, m), 2.33 (2H, m), 1.21 (3H, t, J=7.2 Hz).

The racemic mixture was separated by chiral chromatography to afford two enantiomers Example 170A and 170B.

Example 171

1-(2-(4-(4-chloro-1H-imidazol-1-yl)-3-methoxyphenylamino)-4-(ethylamino)-8-(4-fluorophenyl)-5,6-dihydropyrido[3,4-d]pyrimidin-7(8H)-yl)ethanone

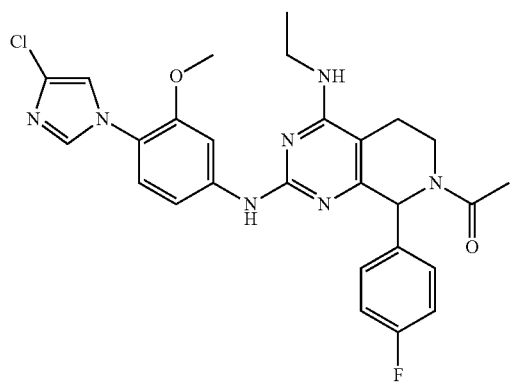 [SMILES: CCNc1nc(Nc2ccc(-n3cnc(Cl)c3)c(OC)c2)nc2c1CCN(C(C)=O)C2c1ccc(F)cc1]

To a solution of Preparation AIk (0.052 g, 0.101 mmol) in dichloromethane was added triethylamine (0.012 g, 0.126 mmol) at −10° C. followed by acetyl chloride (0.007 g, 0.01 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in acetonitrile) to give 1-(2-(4-(4-chloro-1H-imidazol-1-yl)-3-methoxyphenylamino)-4-(ethylamino)-8-(4-fluorophenyl)-5,6-dihydropyrido[3,4-d]pyrimidin-7(8H)-yl)ethanone (0.040 g, 72%) as off-white solid. LC-MS (M+H)$^+$=536.2. $^1$H NMR (400 MHz, DMSO-d6): δ ppm 9.25 (1H, s), 8.0 (1H, s), 7.75 (1H, s), 7.43 (1H, s), 7.32 (2H, m), 7.21-7.14 (4H, m), 6.99 (1H, m), 6.36 (1H, sb), 3.95 (1H, m), 3.90 (2H, m), 3.57 (3H, s), 3.49 (1H, m), 3.20 (1H, m), 2.34 (1H, m), 2.12 (3H, s), 1.22 (3H, t, J=7.2 Hz).

Example 172

N2-(4-(4-chloro-1H-imidazol-1-yl)-3-methoxyphenyl)-N4-ethyl-8-(4-fluorophenyl)-N4-methyl-7-(methylsulfonyl)-5,6,7,8-tetrahydropyrido[3,4-d]pyrimidine-2,4-diamine To a solution of Preparation AB (0.070 g, 0.138 mmol) in dichloromethane was added diisopropylethylamine (0.047 g, 0.276 mmol) at −10° C. followed by methanesulfonyl chloride (0.015 g, 0.138 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in acetonitrile) to give N2-(4-(4-chloro-1H-imidazol-1-yl)-3-methoxyphenyl)-N4-ethyl-8-(4-fluorophenyl)-N4-methyl-7-(methylsulfonyl)-5,6,7,8-tetrahydropyrido[3,4-d]pyrimidine-2,4-diamine (0.030 g, 37%) as off-white solid. LC-MS (M+H)⁺=586.2. ¹H NMR (400 MHz, DMSO-d6): δ ppm 9.26 (1H, s), 7.80 (1H, s), 7.74 (1H, s), 7.43 (1H, s), 7.34 (2H, m), 7.32-7.16 (4H, m), 5.65 (1H, s), 3.55 (1H, m), 3.53 (3H, s), 3.51 (2H, m), 3.18 (1H, m), 3.08 (3H, s), 2.91 (3H, s), 2.67 (1H, m), 1.22 (3H, m).

The racemic mixture was separated by chiral chromatography to afford two enantiomers Example 172A and 172B.

Example 173

N-(4-(4-chloro-1H-imidazol-1-yl)-3-methoxyphenyl)-8-(4-fluorophenyl)-4-(R)-3-fluoropyrrolidin-1-yl)-7-(methylsulfonyl)-5,6,7,8-tetrahydropyrido[3,4-d]pyrimidin-2-amine

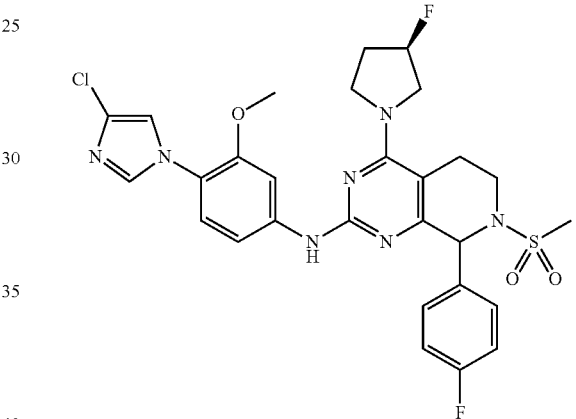

To a solution of Preparation AIm (0.041 g, 0.074 mmol) in dichloromethane was added diisopropylethylamine (0.019 g, 0.148 mmol) at −10° C. followed by addition of methanesulfonyl chloride (0.008 g, 0.074 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in acetonitrile) to N-(4-(4-chloro-1H-imidazol-1-yl)-3-methoxyphenyl)-8-(4-fluorophenyl)-4-((R)-3-fluoropyrrolidin-1-yl)-7-(methylsulfonyl)-5,6,7,8-tetrahydropyrido[3,4-d]pyrimidin-2-amine (0.010 g, 20%) as off-white solid. LC-MS (M+H)⁺=616.0. ¹H NMR (400 MHz, DMSO-d6): δ ppm 9.27 (1H, s), 7.84 (1H, s), 7.75 (1H, s), 7.43 (1H, s), 7.38 (2H, m), 7.22-7.17 (4H, m), 5.50 (1H, s), 4.11 (1H, m), 4.04 (3H, m), 3.82 (1H, m), 3.51 (3H, s), 3.23 (2H, m), 3.05 (2H, m), 2.95 (3H, s), 2.23 (2H, m).

Example 174

N-(4-(4-chloro-1H-imidazol-1-yl)-3-methoxyphenyl)-8-(4-fluorophenyl)-4-(R)-3-fluoropyrrolidin-1-yl)-7-(methylsulfonyl)-5,6,7,8-tetrahydropyrido[3,4-d]pyrimidin-2-amine

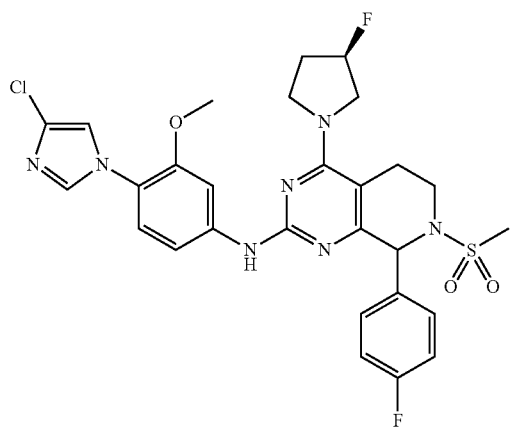 [SMILES: COc1cc(Nc2nc3c(c(N4CC[C@@H](F)C4)n2)CCN(S(C)(=O)=O)C3c2ccc(F)cc2)ccc1-n1cnc(Cl)c1]

To a solution of Preparation AIn (0.041 g, 0.074 mmol) in dichloromethane was added diisopropylethylamine (0.019 g, 0.148 mmol) at −10° C. followed by addition of methanesulfonyl chloride (0.008 g, 0.074 mmol). The reaction mixture was stirred at room temperature for 1 h. The reaction mixture was diluted with dichloromethane, washed with water, evaporated under reduced pressure to get crude compound. The crude compound was purified by prep-HPLC (aqueous 0.1% ammonium acetate in acetonitrile) to N-(4-(4-chloro-1H-imidazol-1-yl)-3-methoxyphenyl)-8-(4-fluorophenyl)-4-((R)-3-fluoropyrrolidin-1-yl)-7-(methylsulfonyl)-5,6,7,8-tetrahydropyrido[3,4-d]pyrimidin-2-amine (0.012 g, 20.6%) as off-white solid. LC-MS (M+H)$^+$=616.0. $^1$H NMR (400 MHz, DMSO-d6): δ ppm 9.25 (1H, s), 7.83 (1H, s), 7.74 (1H, s), 7.42 (1H, s), 7.33 (2H, m), 7.22-7.12 (4H, m), 5.76 (1H, s), 5.57 (1H, m), 4.07 (1H, m), 3.99-3.90 (3H, m), 3.88 (1H, m), 3.54 (3H, s), 3.27 (1H, m), 3.11 (1H, m), 2.93 (3H, s), 2.85 (1H, m), 2.23 (2H, m).

Example 175

N2-(4-(4-chloro-1H-imidazol-1-yl)-3-methoxyphenyl)-N4-ethyl-8-(4-fluorophenyl)-7-methyl-5,6,7,8-tetrahydropyrido[3,4-d]pyrimidine-2,4-diamine

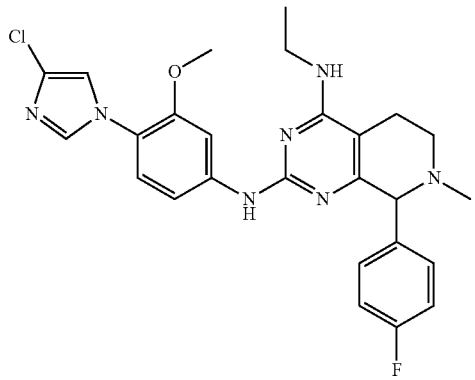 [SMILES: CCNc1nc(Nc2ccc(-n3cnc(Cl)c3)c(OC)c2)nc2c1CCN(C)C2c1ccc(F)cc1]

Preparation AIk was combined with methyl iodide in the manner of Example 169 to give N2-(4-(4-chloro-1H-imidazol-1-yl)-3-methoxyphenyl)-N4-ethyl-8-(4-fluorophenyl)-7-methyl-5,6,7,8-tetrahydropyrido[3,4-d]pyrimidine-2,4-diamine

Example 176

N$^2$-(4-(4-Chloro-1H-imidazol-1-yl)-3-methoxyphenyl)-N$^4$-trideuteromethyl-7-phenyl-6,7-dihydro-5H-cyclopenta[d]pyrimidine-2,4-diamine

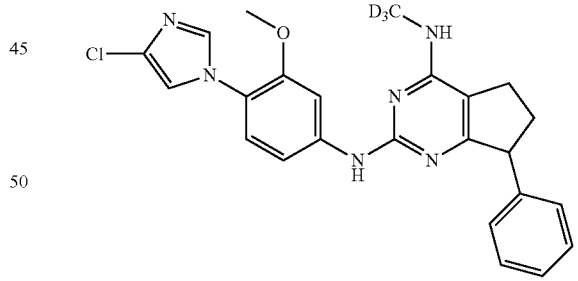

A solution of 2-chloro-N-trideuteromethyl-7-phenyl-6,7-dihydro-5H-cyclopenta[d]pyrimidin-4-amine (121.2 mg, 0.461 mmol) and 4-(4-chloro-1H-imidazol-1-yl)-3-methoxyaniline (103 mg, 0.461 mmol) in THF (1 mL) and acetic acid (1.000 mL) was heated at 80° C. overnight. The reaction mixture was purified by a reverse-phase preparative HPLC method to give N$^2$-(4-(4-chloro-1H-imidazol-1-yl)-3-methoxyphenyl)-N$^4$-trideuteromethyl-7-phenyl-6,7-dihydro-5H-cyclopenta[d]pyrimidine-2,4-diamine, TFA salt (114.3 mg, 43%) as brown solid. LC-MS (M+H)$^+$=450.0. $^1$H NMR (500 MHz, CDCl$_3$) δ ppm 8.86 (1H, s), 7.88 (1H, t, J=8.4 Hz), 7.22-7.31 (4H, m), 7.19 (1H, d, J=8.9 Hz), 7.07 (3H, t, J=8.7

Hz), 4.27 (1H, t, J=8.5 Hz), 3.73 (3H, s), 2.45-2.59 (1H, m), 2.38 (1H, d, J=7.6 Hz), 2.30 (1H, d, J=3.7 Hz), 1.95-2.06 (1H, m).

Examples 176A and 176B (S)—$N^2$-(4-(4-Chloro-1H-imidazol-1-yl)-3-methoxyphenyl)-$N^4$-trideuteromethyl-7-phenyl-6,7-dihydro-5H-cyclopenta[d]pyrimidine-2,4-diamine and (R)—$N^2$-(4-(4-Chloro-1H-imidazol-1-yl)-3-methoxyphenyl)-$N^4$-trideuteromethyl-7-phenyl-6,7-dihydro-5H-cyclopenta[d]pyrimidine-2,4-diamine

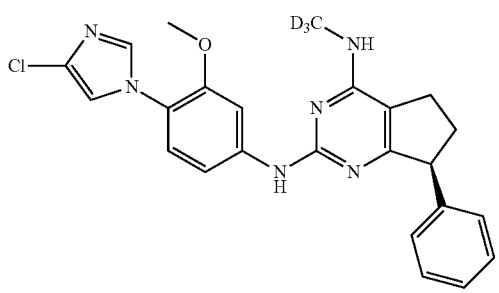 [SMILES: [2H]C([2H])([2H])Nc1nc(Nc2ccc(-n3cnc(Cl)c3)c(OC)c2)nc2c1CCC2c1ccccc1]

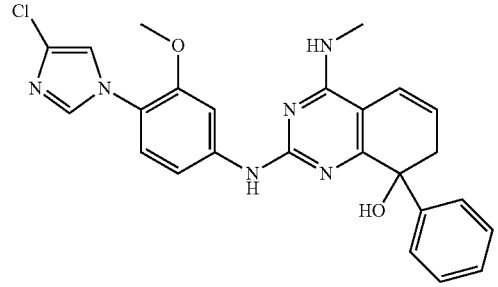 [SMILES: CNc1nc(Nc2ccc(-n3cnc(Cl)c3)c(OC)c2)nc2c1C=CCC2(O)c1ccccc1]

A racemic mixture of $N^2$-(4-(4-chloro-1H-imidazol-1-yl)-3-methoxyphenyl)-$N^4$-trideuteromethyl-7-phenyl-6,7-dihydro-5H-cyclopenta[d]pyrimidine-2,4-diamine (133 mg, 0.206 mmol from Example 176) was purified using chiral supercritical fluid chromatography (SFC) to afford 28.4 mg of peak A (Example 176A) and 27.4 mg of peak B (Example 176B). SFC Method: Chiralpak OJ-H (30×250 mm, 5 µM), 40% methanol (0.1% diethylamine) in $CO_2$, 35° C., flow rate 70 mL/min for 16 min, absorbance 268 nm, injection 1 mL of 22 mg/mL solution in methanol (multiple stacked injections), $t_R$ (peak A)=5.0 min, $t_R$ (peak B) 11.2 min. The absolute stereochemistry of individual enantiomers (Examples 176A and 176B) was not determined LC-MS and $^1$H NMR analytical data for the separated enantiomers was identical to the racemate (Example 176).

Example 177

2-(4-(4-chloro-1H-imidazol-1-yl)-3-methoxyphenylamino)-4-(methylamino)-8-phenyl-7,8-dihydroquinazolin-8-ol A solution of 2-chloro-4-(methylamino)-8-phenyl-7,8-dihydroquinazolin-8-ol (25 mg) and 4-(4-chloro-1H-imidazol-1-yl)-3-methoxyaniline (29 mg) in dioxane (0.2 mL) and acetic acid (0.2 mL) was heated at 85° C. for 4 h. THF was removed in vacuo, and the residue was purified by reverse phase preparative to give the title compound (as its TFA salt) as an oil (18 mg). LC-MS (M+H)$^+$=475.26. $^1$H NMR (TFA salt, 500 MHz, $CD_3OD$) δ ppm 7.2-7.9 (m), 6.56 (1H, m), 6.18 (1H, m), 3.94 (3H, s), 3.20 (3H, s), 3.10 (2H, m).

Example 178

2-(4-(4-chloro-1H-imidazol-1-yl)-3-methoxyphenylamino)-4-(methylamino)-8-phenyl-5,6,7,8-tetrahydroquinazolin-8-ol

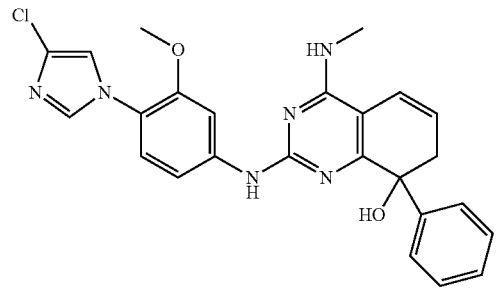 [SMILES: CNc1nc(Nc2ccc(-n3cnc(Cl)c3)c(OC)c2)nc2c1C=CCC2(O)c1ccccc1]

The title compound as its TFA salt form was made in the same fashion as described in Example 177. LC-MS (M+H)$^+$=

477.28. ¹H NMR (TFA salt, 500 MHz, CD₃OD) δ ppm 7.1-8.0 (m), 3.88 (3H, s), 3.18 (3H, s), 1.2-2.5 (6H, m).

Example 179

2-(4-(4-chloro-1H-imidazol-1-yl)-3-methoxyphenylamino)-4-(dimethylamino)-7-phenyl-6,7-dihydro-5H-cyclopenta[d]pyrimidin-7-ol

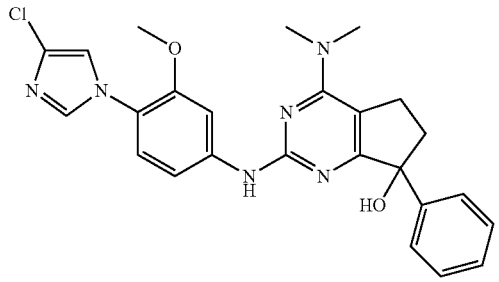 [SMILES: COc1cc(Nc2nc(N(C)C)c3c(n2)C(O)(c2ccccc2)CC3)ccc1-n1cnc(Cl)c1]

The mixture of 4-(4-chloro-1H-imidazol-1-yl)-3-methoxyaniline (37.1 mg, 0.166 mmol), 2-chloro-4-(dimethylamino)-7-phenyl-6,7-dihydro-5H-cyclopenta[d]pyrimidin-7-ol (40 mg, 0.138 mmol), Pd₂(dba)₃ (5.06 mg, 5.52 mmol), xanphos (7.99 mg, 0.014 mmol) and Cs₂CO₃ (135 mg, 0.414 mmol) was heated at 100° C. overnight. The crude product was purified by Prep-HPLC (Column: PHENOMENEX LUNA C18 30×100 mm, Solvent A=10 mM Ammonium Acetate in 95:5 H2O/ACN, Solvent B=10 mM Ammonium Acetate in 5:95 H2O/ACN. Flow rate: 40 ml/min, 35-100% B, 30 min) to give the title compound as its TFA salt (32 mg). LC-MS (M+H)⁺=477.19. ¹H NMR (TFA salt, 500 MHz, CD₃OD) δ ppm 6.8-7.8 (m), 3.64 (3H, s), 3.30 (6H, s), 3.0-3.2 (2H, m), and 2.4 (2H, m).

Example 180

(6S,7S)-2-(4-(4-chloro-1H-imidazol-1-yl)-3-methoxyphenylamino)-4-(dimethylamino)-7-phenyl-6,7-dihydro-5H-cyclopenta[d]pyrimidin-6-ol

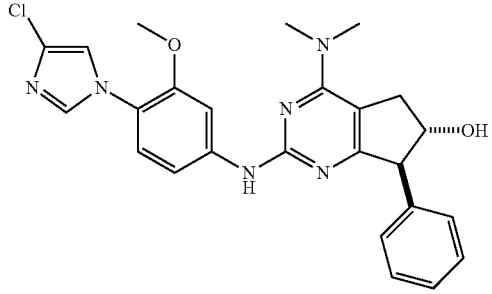 [SMILES: COc1cc(Nc2nc3c(c(N(C)C)n2)C[C@H](O)[C@H]3c2ccccc2)ccc1-n1cnc(Cl)c1]

The reaction was carried out in the same fashion as described in Example 177, but the purification method is different. The crude product was purified by preparative TLC eluting with 50% acetone/hexanes to give the title compound as an oil. LC-MS (M+H)⁺=477.13. ¹H NMR (500 MHz, CDCl₃) δ ppm 6.8-7.9 (m), 4.48 (1H, m), 4.07 (1H, m), 3.58 (1H, m), 3.50 (3H, s), 3.28 (6H, s), 3.12 (1H, m).

Example 181

N-(4-(4-chloro-1H-imidazol-1-yl)-3-methoxyphenyl)-4-(3-chloroazetidin-1-yl)-7-phenyl-6,7-dihydro-5H-cyclopenta[d]pyrimidin-2-amine

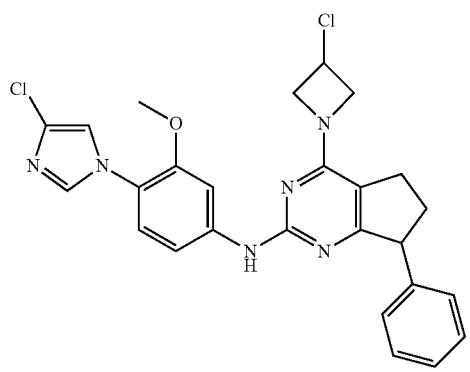

In a manner similar to that described in Example 8, Preparation A and Preparation Gi were reacted to give N-(4-(4-chloro-1H-imidazol-1-yl)-3-methoxyphenyl)-4-(3-chloroazetidin-1-yl)-7-phenyl-6,7-dihydro-5H-cyclopenta[d]pyrimidin-2-amine. LC-MS (M+H)⁺=507.2. ¹H NMR (500 MHz, CHLOROFORM-d) δ ppm 10.71 (d, J=19.84 Hz, 1H) 8.50 (d, J=1.53 Hz, 1H) 7.45 (dd, J=8.85, 1.83 Hz, 1H) 7.24-7.40 (m, 5H) 7.18-7.23 (m, 2H) 5.12 (br. s., 1H) 4.76-4.95 (m, 2H) 4.71 (d, J=10.68 Hz, 1H) 4.35-4.54 (m, 2H) 3.88 (s, 3H) 3.12 (d, J=14.65 Hz, 1H) 3.01 (dd, J=19.99, 6.26 Hz, 1H) 2.68-2.85 (m, 1H) 2.24-2.42 (m, 1H).

The individual enantiomers were separated by chiral SFC chromatography to yield examples 181A and 181B.

Example 182

N-(4-(4-chloro-1H-imidazol-1-yl)-3-methoxyphenyl)-4-(3-fluoroazetidin-1-yl)-7-phenyl-6,7-dihydro-5H-cyclopenta[d]pyrimidin-2-amine

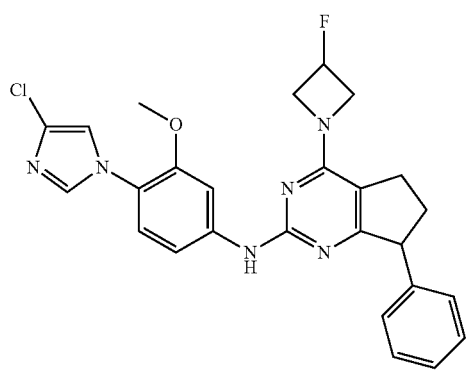 [SMILES: COc1cc(Nc2nc3c(c(N4CC(F)C4)n2)CCC3c2ccccc2)ccc1-n1cnc(Cl)c1]

In a manner similar to that described in Example 8, Preparation A and Preparation Gj were reacted to give N-(4-(4-chloro-1H-imidazol-1-yl)-3-methoxyphenyl)-4-(3-fluoroazetidin-1-yl)-7-phenyl-6,7-dihydro-5H-cyclopenta[d]

pyrimidin-2-amine. LC-MS (M+H)+=491.2. ¹H NMR (500 MHz, CHLOROFORM-d) δ ppm 11.07 (br. s., 1H) 8.30 (br. s., 1H) 7.45 (d, J=8.55 Hz, 2H) 7.38 (br. s., 3H) 7.33 (d, J=4.88 Hz, 2H) 7.13-7.31 (m, 1H) 5.50-5.61 (m, 1H) 4.91 (br. s., 1H) 4.71 (br. s., 2H) 4.43 (br. s., 2H) 3.89 (br. s., 3H) 3.14 (br. s., 1H) 3.03 (d, J=18.92 Hz, 1H) 2.75 (br. s., 1H) 2.20-2.39 (m, 1H).

The individual enantiomers were separated by chiral SFC chromatography to yield examples 182A and 182B.

Example 183

N-(4-(4-chloro-1H-imidazol-1-yl)-3-methoxyphenyl)-4-(3-methoxyazetidin-1-yl)-7-phenyl-6,7-dihydro-5H-cyclopenta[d]pyrimidin-2-amine

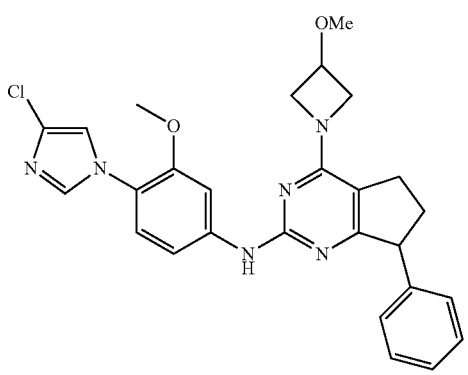 [SMILES: COc1cc(Nc2nc3c(c(N4CC(OC)C4)n2)CCC3c2ccccc2)ccc1-n1cnc(Cl)c1]

In a manner similar to that described in Example 8, Preparation A and Preparation Gk were reacted to give N-(4-(4-chloro-1H-imidazol-1-yl)-3-methoxyphenyl)-4-(3-methoxyazetidin-1-yl)-7-phenyl-6,7-dihydro-5H-cyclopenta[d]pyrimidin-2-amine. LC-MS (M+H)+=503.2. ¹H NMR (500 MHz, CHLOROFORM-d) δ ppm 7.73 (1H, br. s.), 7.49 (1H, s), 7.30-7.35 (2H, m), 7.22 (4H, t, J=8.24 Hz), 7.04-7.07 (1H, m), 7.00 (1H, s), 6.90 (1H, br. s.), 4.45-4.52 (2H, m), 4.33-4.39 (1H, m), 4.16-4.23 (3H, m), 3.57 (3H, s), 2.98-3.07 (1H, m), 2.85-2.96 (1H, m), 2.55-2.67 (1H, m, J=13.28, 8.77, 8.77, 4.58 Hz), 2.06-2.16 (1H, m).

The individual enantiomers were separated by chiral SFC chromatography to yield examples 183A and 183B.

Example 184

N-(4-(4-chloro-1H-imidazol-1-yl)-3-methoxyphenyl)-7-phenyl-4-(5,8-dioxa-2-azaspiro[3.4]octan-2-yl)-6,7-dihydro-5H-cyclopenta[d]pyrimidin-2-amine

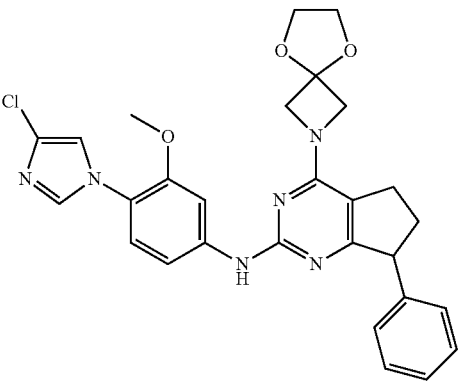 [SMILES: COc1cc(Nc2nc3c(c(N4CC5(C4)OCCO5)n2)CCC3c2ccccc2)ccc1-n1cnc(Cl)c1]

The mixture of 2-(2-chloro-7-phenyl-6,7-dihydro-5H-cyclopenta[d]pyrimidin-4-yl)-5,8-dioxa-2-azaspiro[3.4]octane (Preparation Gl) (23 mg, 0.067 mmol), 4-(4-chloro-1H-imidazol-1-yl)-3-methoxyaniline (Preparation A) (17.95 mg, 0.080 mmol), Tris(dibenzylidineacetone)dipalladium(0) (3.06 mg, 3.34 μmol), (9,9-dimethyl-9H-xanthene-4,5-diyl)bis(diphenylphosphine) (3.87 mg, 6.69 μmol) and sodium carbonate (14.18 mg, 0.134 mmol) in Dioxane (319 μL)/Water (63.7 μL) was heated at 100° C. overnight. The crude product was purified by Prep-HPLC (Solvent A=10% MeOH-90% H2O-0.1% TFA, Solvent B=90% MeOH-10% H2O-0.1% TFA. Column. PHENOMENEX LUNA 30×100 mm, S10, Flow rate: 40 ml/min, 30-100% B, 30 min) to obtain N-(4-(4-chloro-1H-imidazol-1-yl)-3-methoxyphenyl)-7-phenyl-4-(5,8-dioxa-2-azaspiro[3.4]octan-2-yl)-6,7-dihydro-5H-cyclopenta[d]pyrimidin-2-amine, TFA (17 mg, 0.024 mmol, 35.5% yield).

LC-MS (M+H)+=531.1 ¹H NMR (500 MHz, CHLOROFORM-d) δ ppm 11.39 (s, 1H) 8.09 (s, 1H) 7.45 (d, J=8.55 Hz, 1H) 7.35-7.42 (m, 4H) 7.19-7.34 (m, 1H) 7.15 (s, 2H) 4.73 (br. s., 2H) 4.51 (br. s., 2H) 4.42 (dd, J=8.70, 4.12 Hz, 1H) 4.09 (d, J=3.66 Hz, 4H) 3.87 (s, 3H) 3.12 (dd, J=14.34, 7.02 Hz, 1H) 2.90-3.05 (m, 1H) 2.67-2.81 (m, 1H) 2.29 (ddd, J=9.16, 4.43, 4.12 Hz, 1H).

Example 185

1-(2-(4-(4-chloro-1H-imidazol-1-yl)-3-methoxyphenylamino)-7-phenyl-6,7-dihydro-5H-cyclopenta[d]pyrimidin-4-yl)azetidin-3-one

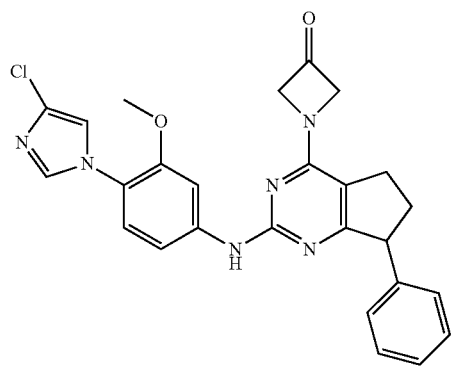 [SMILES: COc1cc(Nc2nc3c(c(N4CC(=O)C4)n2)CCC3c2ccccc2)ccc1-n1cnc(Cl)c1]

The mixture of N-(4-(4-chloro-1H-imidazol-1-yl)-3-methoxyphenyl)-7-phenyl-4-(5,8-dioxa-2-azaspiro[3.4]octan-2-yl)-6,7-dihydro-5H-cyclopenta[d]pyrimidin-2-amine (Example 184) (12 mg, 0.023 mmol) in Acetone (161 μL)/Water (32.3 μL)/HClO4, 70% (32.3 μL) was heated at 50° C. overnight. The crude product was purified by Prep-HPLC to get 1-(2-(4-(4-chloro-1H-imidazol-1-yl)-3-methoxyphenylamino)-7-phenyl-6,7-dihydro-5H-cyclopenta[d]pyrimidin-4-yl)azetidin-3-one (2.5 mg, 4.62 μmol, 20.5% yield). LC-MS (M+H)+=487.2 $^1$H NMR (500 MHz, CHLOROFORM-d) δ ppm 7.57 (s, 1H) 7.42 (t, J=7.63 Hz, 3H) 7.26-7.38 (m, 3H) 7.12-7.26 (m, 2H) 7.00-7.12 (m, 1H) 5.23 (br. s., 4H) 4.43 (br. s., 1H) 3.68-3.79 (m, 3H) 3.10-3.27 (m, 1H) 2.93-3.08 (m, 1H) 2.71-2.84 (m, 1H) 2.37 (br. s., 1H).

Example 186

1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-3-methylazetidine-3-carbonitrile

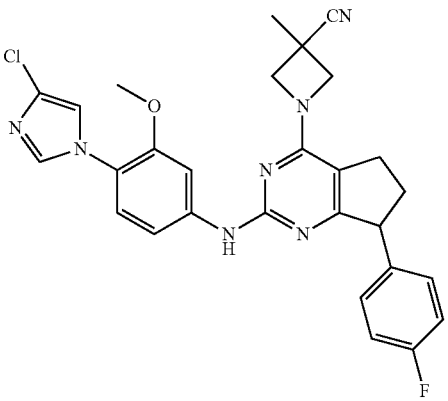 [SMILES: COc1cc(Nc2nc3c(c(N4CC(C)(C#N)C4)n2)CCC3c2ccc(F)cc2)ccc1-n1cnc(Cl)c1]

In a manner similar to that described in Example 184, Preparation Hac and Preparation A were combined to obtain 1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-3-methylazetidine-3-carbonitrile. LC-MS (M+H)+=530.1 $^1$H NMR (500 MHz, CHLOROFORM-d) δ ppm 11.50 (br. s., 1H) 8.18 (br. s., 1H) 7.46 (d, J=7.63 Hz, 1H) 7.12-7.31 (m, 3H) 7.06 (br. s., 3H) 4.99 (br. s., 1H) 4.72 (br. s., 1H) 4.43 (br. s., 2H) 4.28 (br. s., 1H) 3.88 (s, 3H) 3.11 (br. s., 1H) 3.00 (br. s., 1H) 2.76 (br. s., 1H) 2.28 (d, J=5.49 Hz, 1H) 1.87 (s, 3H).

Example 187

N-(4-(4-chloro-1H-imidazol-1-yl)-3-methoxyphenyl)-4-(3-ethoxyazetidin-1-yl)-7-(4-fluorophenyl)-6,7-dihydro-5H-cyclopenta[d]pyrimidin-2-amine

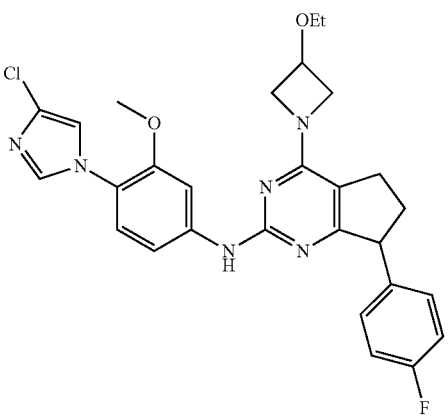 [SMILES: CCOC1CN(c2nc(Nc3ccc(-n4cnc(Cl)c4)c(OC)c3)nc3c2CCC3c2ccc(F)cc2)C1]

In a manner similar to that described in Example 184, Preparation Had and Preparation A were combined to obtain N-(4-(4-chloro-1H-imidazol-1-yl)-3-methoxyphenyl)-4-(3-ethoxyazetidin-1-yl)-7-(4-fluorophenyl)-6,7-dihydro-5H-cyclopenta[d]pyrimidin-2-amine. LC-MS (M+H)+=535.1 $^1$H NMR (500 MHz, CHLOROFORM-d) δ ppm 11.77 (br. s., 1H) 7.74 (d, J=4.58 Hz, 1H) 7.52 (br. s., 1H) 7.34-7.41 (m, 1H) 7.12-7.30 (m, 2H) 7.06-7.12 (m, 1H) 7.03 (br. s., 2H) 4.77 (br. s., 1H) 4.51 (br. s., 2H) 4.49 (d, J=5.49 Hz, 1H) 4.36 (br. s., 1H) 4.24 (br. s., 1H) 3.85 (d, J=4.88 Hz, 3H) 3.55 (dd, J=6.71, 5.49 Hz, 2H) 3.12 (br. s., 1H) 2.99 (br. s., 1H) 2.68 (br. s., 1H) 2.23 (br. s., 1H) 1.21-1.37 (m, 3H).

The individual enantiomers were separated by chiral SFC chromatography to yield examples 187A and 187B.

Example 188

N-(4-(4-chloro-1H-imidazol-1-yl)-3-methoxyphenyl)-7-phenyl-4-(5-oxa-2-azaspiro[3.4]octan-2-yl)-6,7-dihydro-5H-cyclopenta[d]pyrimidin-2-amine

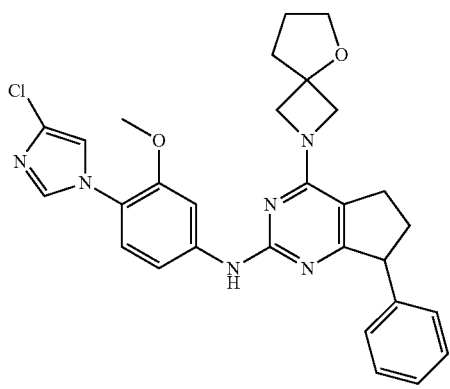 [SMILES: COc1cc(Nc2nc3c(c(N4CC5(CCCO5)C4)n2)CCC3c2ccccc2)ccc1-n1cnc(Cl)c1]

In a manner similar to that described in Example 184, Preparation Gm and Preparation A were combined to obtain N-(4-(4-chloro-1H-imidazol-1-yl)-3-methoxyphenyl)-7-phenyl-4-(5-oxa-2-azaspiro[3.4]octan-2-yl)-6,7-dihydro-5H-cyclopenta[d]pyrimidin-2-amine. LC-MS (M+H)+=529.3 $^1$H NMR (500 MHz, CHLOROFORM-d) δ ppm 10.85 (br. s., 1H) 8.36 (br. s., 1H) 7.49 (br. s., 4H) 7.20-7.39 (m, 4H) 4.56 (d, J=9.16 Hz, 1H) 4.41 (br. s., 3H) 3.92-4.10 (m, 3H) 3.87 (s, 3H) 3.11 (br. s., 1H) 3.00 (d, J=12.51 Hz, 1H) 2.73 (br. s., 1H) 2.26 (t, J=6.87 Hz, 3H) 2.06 (d, J=6.41 Hz, 2H).

Example 189

1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-3-methylazetidin-3-ol

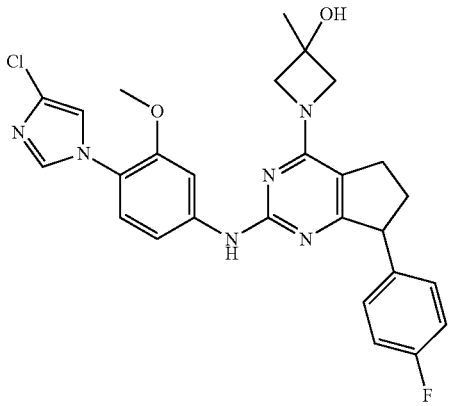 [SMILES: COc1cc(Nc2nc3c(c(N4CC(C)(O)C4)n2)CCC3c2ccc(F)cc2)ccc1-n1cnc(Cl)c1]

In a manner similar to that described in Example 184, Preparation Hae and Preparation A were combined to obtain 1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-3-methylazetidin-3-ol. LC-MS (M+H)+=521.1 $^1$H NMR (400 MHz, MeOD) δ ppm 7.93 (d, J=1.51 Hz, 1H) 7.65 (d, J=2.26 Hz, 1H) 7.26-7.44 (m, 4H) 7.01-7.26 (m, 4H) 4.48-4.68 (m, 2H) 4.44 (dd, J=9.03, 6.78 Hz, 1H) 4.18-4.38 (m, 2H) 3.90 (s, 3H) 3.15 (dd, J=5.27, 3.76 Hz, 1H) 2.96-3.06 (m, 1H) 2.62-2.82 (m, 1H) 2.12 (dddd, J=13.18, 8.85, 6.46, 6.15 Hz, 1H) 1.55-1.66 (m, 3H).

The individual enantiomers were separated by chiral SFC chromatography to yield examples 189A and 189B.

Example 190

N-(4-(4-chloro-1H-imidazol-1-yl)-3-methoxyphenyl)-4-(3-fluoro-3-methylazetidin-1-yl)-7-(4-fluorophenyl)-6,7-dihydro-5H-cyclopenta[d]pyrimidin-2-amine

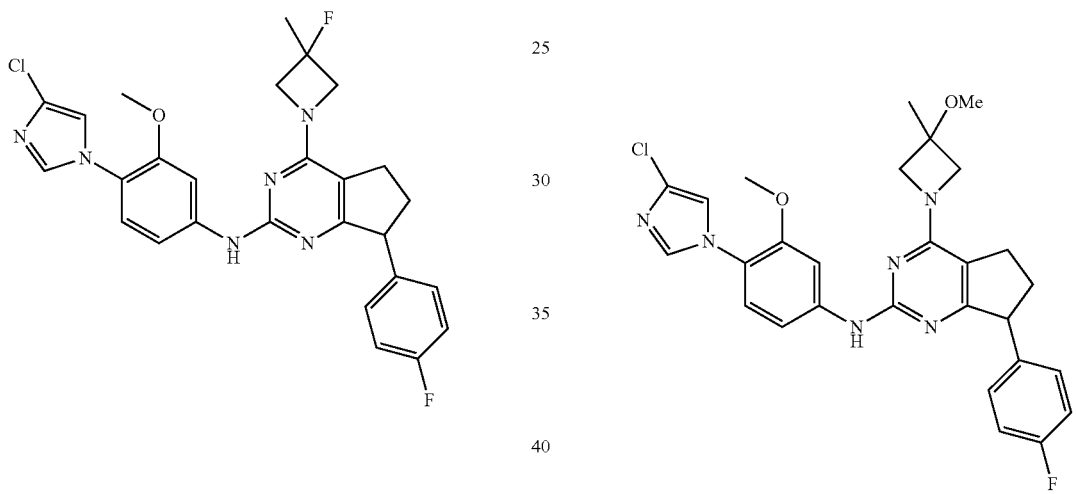

A solution of 1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-3-methylazetidin-3-ol (35 mg, 0.067 mmol) in CH$_2$Cl$_2$ (Volume: 274 µl) was cooled to −78° C. To this mixture was added [Bis(2-methoxyethyl)amino]sulfur trifluoride (13.62 µl, 0.074 mmol) dropwise and the solution was stirred for 30 mins at −78° C. and then warmed to 0° C. and stirred for a further 1 hr. Reaction was quenched with Sat. NaHCO$_3$ solution and brine. The aqueous layer was extracted with CH$_2$Cl$_2$. The organic layer was dried over Na$_2$SO$_4$ and concentrated. The crude product was purified by Prep-HPLC to obtain N-(4-(4-chloro-1H-imidazol-1-yl)-3-methoxyphenyl)-4-(3-fluoro-3-methylazetidin-1-yl)-7-(4-fluorophenyl)-6,7-dihydro-5H-cyclopenta[d]pyrimidin-2-amine, TFA (4.0 mg, 5.65 µmol). LC-MS (M+H)$^+$=523.1 $^1$H NMR (500 MHz, CHLOROFORM-d) δ ppm 11.38 (br. s., 1H) 8.14 (s, 1H) 7.43-7.54 (m, 1H) 7.30-7.38 (m, 1H) 7.20-7.26 (m, 3H) 7.16 (s, 1H) 7.06 (t, J=7.78 Hz, 2H) 4.78 (br. s., 1H) 4.54 (br. s., 2H) 4.42 (br. s., 2H) 3.88 (s, 3H) 3.12 (d, J=7.93 Hz, 1H) 3.00 (br. s., 1H) 2.75 (br. s., 1H) 2.21-2.34 (m, 1H) 1.78-1.82 (br. s, 3H).

Example 191

N-(4-(4-chloro-1H-imidazol-1-yl)-3-methoxyphenyl)-7-(4-fluorophenyl)-4-(3-methoxy-3-methylazetidin-1-yl)-6,7-dihydro-5H-cyclopenta[d]pyrimidin-2-amine In a manner similar to that described in Example 184, Preparation Haf and Preparation A were combined to obtain N-(4-(4-chloro-1H-imidazol-1-yl)-3-methoxyphenyl)-7-(4-fluorophenyl)-4-(3-methoxy-3-methylazetidin-1-yl)-6,7-dihydro-5H-cyclopenta[d]pyrimidin-2-amine. LC-MS (M+H)$^+$=535.1 $^1$H NMR (500 MHz, CHLOROFORM-d) δ ppm 11.75 (d, J=4.27 Hz, 1H) 7.83 (d, J=1.22 Hz, 1H) 7.47 (d, J=1.83 Hz, 1H) 7.44 (d, J=8.55 Hz, 1H) 7.15-7.33 (m, 4H) 7.03 (t, J=7.63 Hz, 2H) 4.53 (d, J=8.85 Hz, 1H) 4.24-4.43 (m, 3H) 4.06-4.19 (m, 1H) 3.86 (s, 3H) 3.34 (s, 3H) 3.13 (ddd, J=12.67, 6.56, 6.41 Hz, 1H) 3.01 (ddd, J=15.95, 4.81, 4.58 Hz, 1H) 2.70 (td, J=9.46, 3.66 Hz, 1H) 2.24 (tt, J=8.96, 4.31 Hz, 1H) 1.63 (s, 3H).

459

The individual enantiomers were separated by chiral SFC chromatography to yield examples 191A and 191B.

Example 192

7-(4-fluorophenyl)-4-(3-methoxy-3-methylazetidin-1-yl)-N-(3-methoxy-4-(3-methyl-1H-1,2,4-triazol-1-yl)phenyl)-6,7-dihydro-5H-cyclopenta[d]pyrimidin-2-amine

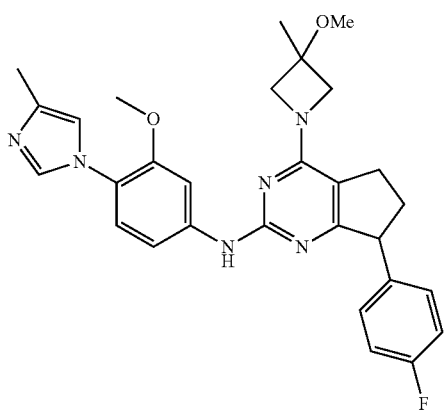 [SMILES: COc1cc(Nc2nc3c(c(N4CC(C)(OC)C4)n2)CCC3c2ccc(F)cc2)ccc1-n1cnc(C)c1]

In a manner similar to that described in Example 184, Preparation Haf and Preparation D were combined to obtain 7-(4-fluorophenyl)-4-(3-methoxy-3-methylazetidin-1-yl)-N-(3-methoxy-4-(3-methyl-1H-1,2,4-triazol-1-yl)phenyl)-6,7-dihydro-5H-cyclopenta[d]pyrimidin-2-amine. LC-MS (M+H)$^+$=516.1 $^1$H NMR (500 MHz, CHLOROFORM-d) δ ppm 11.77 (d, J=3.97 Hz, 1H) 8.88 (s, 1H) 7.69 (d, J=8.55 Hz, 1H) 7.52 (dd, J=8.85, 2.14 Hz, 1H) 7.47 (s, 1H) 7.23 (t, J=5.49 Hz, 2H) 7.03 (t, J=8.39 Hz, 2H) 4.45-4.58 (m, 1H) 4.35 (d, J=4.58 Hz, 2H) 4.27 (d, J=7.63 Hz, 1H) 4.10 (d, J=10.07 Hz, 1H) 3.85-4.04 (m, 3H) 3.33 (s, 3H) 3.05-3.20 (m, 1H) 2.92-3.05 (m, 1H) 2.63-2.79 (m, 1H) 2.45-2.59 (m, 3H) 2.23 (td, J=8.39, 4.27 Hz, 1H) 1.57-1.72 (m, 3H).

The individual enantiomers were separated by chiral SFC chromatography to yield examples 192A and 192B.

Example 193

7-(2,4-difluorophenyl)-N2-(3-methoxy-4-(3-methyl-1H-1,2,4-triazol-1-yl)phenyl)-N4-methyl-6,7-dihydro-5H-cyclopenta[d]pyrimidine-2,4-diamine

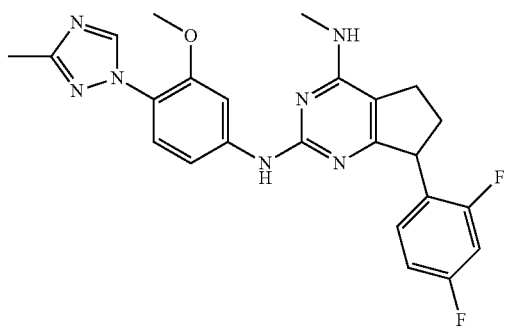 [SMILES: CNc1nc(Nc2ccc(-n3cnc(C)n3)c(OC)c2)nc2c1CCC2c1ccc(F)cc1F]

460

The mixture of 2-chloro-7-(2,4-difluorophenyl)-N-methyl-6,7-dihydro-5H-cyclopenta[d]pyrimidin-4-amine (153 mg, 0.517 mmol), 3-methoxy-4-(3-methyl-1H-1,2,4-triazol-1-yl)aniline (211 mg, 1.035 mmol) and H$_2$SO$_4$ (44.1 μl, 0.828 mmol) in N-Methyl-2-pyrrolidinone (Volume: 2070 μl) was heated at 100° C. overnight. Added Sat.NaHCO$_3$ slowly, and extracted with EtOAc (×3). The combined organic layer was dried over Na$_2$SO$_4$ and concentrated. The crude product was purified by Prep-HPLC (Solvent A=10% MeOH-90% H2O-0.1% TFA, Solvent B=90% MeOH-10% H2O-0.1% TFA. Column. PHENOMENEX LUNA 30×100 mm, S10, Flow rate: 40 ml/min, 30-100% B, 15 min) to get 7-(2,4-difluorophenyl)-N2-(3-methoxy-4-(3-methyl-1H-1,2,4-triazol-1-yl)phenyl)-N4-methyl-6,7-dihydro-5H-cyclopenta[d]pyrimidine-2,4-diamine, TFA (287 mg, 0.447 mmol, 86% yield). LC-MS (M+H)$^+$=464.1. $^1$H NMR (500 MHz, CHLOROFORM-d) δ ppm 11.54 (1H, s), 9.22 (1H, s), 7.75 (1H, d, J=8.85 Hz), 7.65 (1H, s), 7.49 (1H, d, J=8.85 Hz), 7.13-7.21 (1H, m), 6.79-6.91 (2H, m), 6.11 (1H, d, J=4.27 Hz), 4.56-4.63 (1H, m), 3.97 (3H, s), 3.23 (3H, d, J=4.27 Hz), 2.84-2.93 (1H, m), 2.71-2.81 (2H, m), 2.62 (3H, s), 2.19-2.28 (1H, m).

Examples 193A and 193B (S)-7-(2,4-difluorophenyl)-N2-(3-methoxy-4-(3-methyl-1H-1,2,4-triazol-1-yl)phenyl)-N4-methyl-6,7-dihydro-5H-cyclopenta[d]pyrimidine-2,4-diamine and (R)-7-(2,4-difluorophenyl)-N2-(3-methoxy-4-(3-methyl-1H-1,2,4-triazol-1-yl)phenyl)-N4-methyl-6,7-dihydro-5H-cyclopenta[d]pyrimidine-2,4-diamine

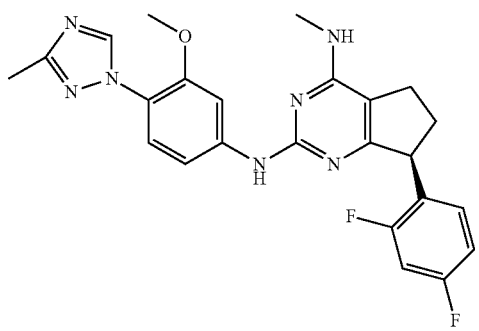

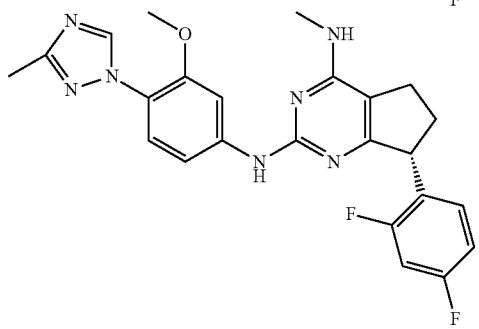

A racemic mixture of 7-(2,4-difluorophenyl)-N2-(3-methoxy-4-(3-methyl-1H-1,2,4-triazol-1-yl)phenyl)-N4-methyl-6,7-dihydro-5H-cyclopenta[d]pyrimidine-2,4-diamine (Example 193) was purified using chiral supercritical fluid chromatography (SFC) to afford peak A (Example 193A) and peak B (Example 193B). SFC Method: Chiralpak OJ-H (30×

150 mm), 30% methanol (0.1% diethylamine) in $CO_2$, 100 bar, flow rate 50 mL/min for 12 min, absorbance 268 nm, injection 2.0 mL of 10 mg/mL solution in methanol, $t_R$ (peak A)=4.7 min, $t_R$ (peak B) 9.6 min. The absolute stereochemistry of individual enantiomers (Examples 193A and 193B) was not determined 193A: LC-MS (M+H)$^+$=446.2. LC $R_t$ 13.03 min (Waters Sunfire 4.6×150 mm 10 to 100% B in A over 15 min, 1.5 mL/min. (A is 90:10:0.1 water:MeOH:TFA; B is 90:10:0.1 MeOH:water:TFA)). $^1$H NMR (500 MHz, CHLOROFORM-d) δ ppm 8.46 (1H, s), 8.04 (1H, s), 7.51 (1H, d, J=8.55 Hz), 7.04-7.13 (2H, m), 6.78-6.87 (3H, m), 4.42-4.50 (1H, m), 3.68 (3H, s), 3.13 (3H, s), 2.62-2.79 (3H, m), 2.49 (3H, s), 1.96-2.08 (1H, m).

Example 194

6-(2,2-difluoroethyl)-N4-ethyl-N2-(3-fluoro-4-(5-methyl-1H-1,2,4-triazol-1-yl)phenyl)-8-phenyl-5,6,7,8-tetrahydropyrido[4,3-d]pyrimidine-2,4-diamine

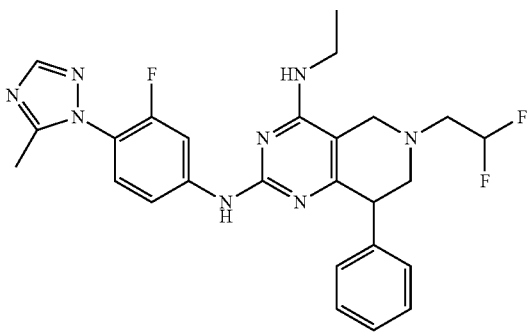 [SMILES: CCNc1nc(Nc2ccc(-n3ncnc3C)c(F)c2)nc2c1CN(CC(F)F)CC2c1ccccc1]

Preparation AEo was reacted with difluoro-2-iodoethane, potassium carbonate, and sodium iodide in DMF at 80° C. to afford 6-(2,2-difluoroethyl)-N4-ethyl-N2-(3-fluoro-4-(5-methyl-1H-1,2,4-triazol-1-yl)phenyl)-8-phenyl-5,6,7,8-tetrahydropyrido[4,3-d]pyrimidine-2,4-diamine (Example 194). LC-MS (M+H)$^+$=509.4.

The individual enantiomers were separated by chiral SFC chromatography to yield examples 194A and 194B.

Example 195

6-(2,2-difluoroethyl)-N4-ethyl-N2-(3-fluoro-4-(3-methyl-1H-1,2,4-triazol-1-yl)phenyl)-8-phenyl-5,6,7,8-tetrahydropyrido[4,3-d]pyrimidine-2,4-diamine

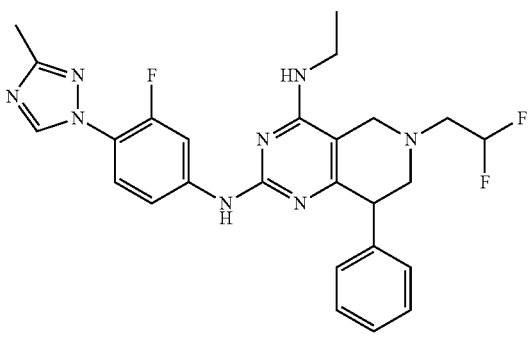 [SMILES: CCNc1nc(Nc2ccc(-n3cnc(C)n3)c(F)c2)nc2c1CN(CC(F)F)CC2c1ccccc1]

Preparation AEm was reacted with difluoro-2-iodoethane, potassium carbonate, and sodium iodide in DMF at 80° C. to afford 6-(2,2-difluoroethyl)-N4-ethyl-N2-(3-fluoro-4-(3-methyl-1H-1,2,4-triazol-1-yl)phenyl)-8-phenyl-5,6,7,8-tetrahydropyrido[4,3-d]pyrimidine-2,4-diamine (Example 195). LC-MS (M+H)$^+$=509.2.

The individual enantiomers were separated by chiral SFC chromatography to yield examples 195A and 195B.

Example 196

N4-ethyl-N2-(3-methoxy-4-(4-chloro-1H-13-imidazol-1-yl)phenyl)-8-phenyl-6-(2,2,2-trifluoroethyl)-5,6,7,8-tetrahydropyrido[4,3-d]pyrimidine-2,4-diamine

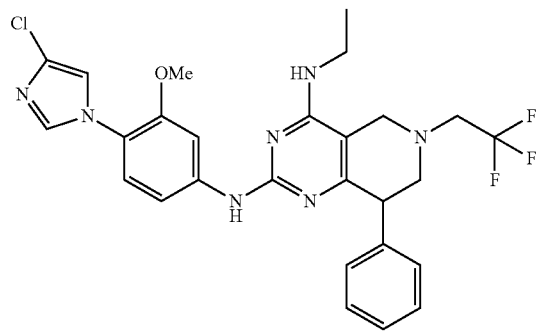 [SMILES: CCNc1nc(Nc2ccc(-n3cnc(Cl)c3)c(OC)c2)nc2c1CN(CC(F)(F)F)CC2c1ccccc1]

In a manner similar to Preparation AEp and Example 146, Preparation AEk was transformed into N4-ethyl-N2-(3-methoxy-4-(4-chloro-1H-13-imidazol-1-yl)phenyl)-8-phenyl-6-(2,2,2-trifluoroethyl)-5,6,7,8-tetrahydropyrido[4,3-d]pyrimidine-2,4-diamine (Example 196). LC-MS (M+H)$^+$=558.2.

The individual enantiomers were separated by chiral SFC chromatography to yield examples 196A and 196B.

Example 197

N4-ethyl-N2-(3-methoxy-4-(4-chloro-1H-13-imidazol-1-yl)phenyl)-8-phenyl-6-(2,2-difluoroethyl)-5,6,7,8-tetrahydropyrido[4,3-d]pyrimidine-2,4-diamine

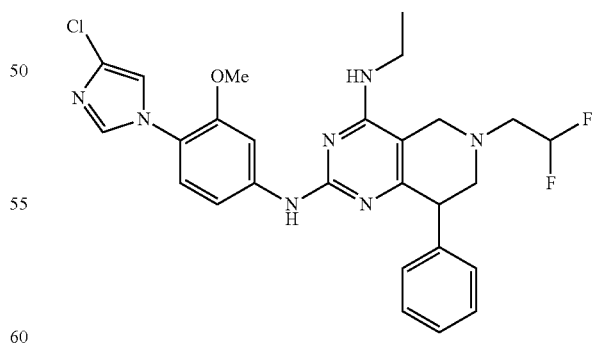

Preparation AEk was reacted with difluoro-2-iodoethane, potassium carbonate, and sodium iodide in DMF at 80° C. to afford N4-ethyl-N2-(3-methoxy-4-(4-chloro-1H-13-imidazol-1-yl)phenyl)-8-phenyl-6-(2,2-difluoroethyl)-5,6,7,8-tetrahydropyrido[4,3-d]pyrimidine-2,4-diamine (Example 197). LC-MS (M+H)$^+$=540.2.

The individual enantiomers were separated by chiral SFC chromatography to yield examples 197A and 197B.

Example 198

8-(4-fluorophenyl)-N2-(3-methoxy-4-(3-methyl-1H-1,2,4-triazol-1-yl)phenyl)-N4,6-dimethyl-5,6,7,8-tetrahydropyrido[4,3-d]pyrimidine-2,4-diamine

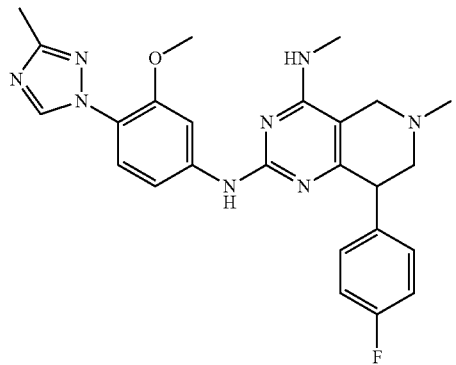 [SMILES: CNc1nc(Nc2ccc(-n3cnc(C)n3)c(OC)c2)nc2c1CN(C)CC2c1ccc(F)cc1]

In a manner similar to that described in Example 8, Preparation D and Preparation AHa were reacted to give 8-(4-fluorophenyl)-N2-(3-methoxy-4-(3-methyl-1H-1,2,4-triazol-1-yl)phenyl)-N4,6-dimethyl-5,6,7,8-tetrahydropyrido[4,3-d]pyrimidine-2,4-diamine. LC-MS (M+H)$^+$=475.2. The racemic mixture was separated by chiral chromatography to afford the enantiomers Example 198A and 198B.

Example 199

8-(4-fluorophenyl)-N2-(3-methoxy-4-(5-methyl-1H-1,2,4-triazol-1-yl)phenyl)-N4,6-dimethyl-5,6,7,8-tetrahydropyrido[4,3-d]pyrimidine-2,4-diamine

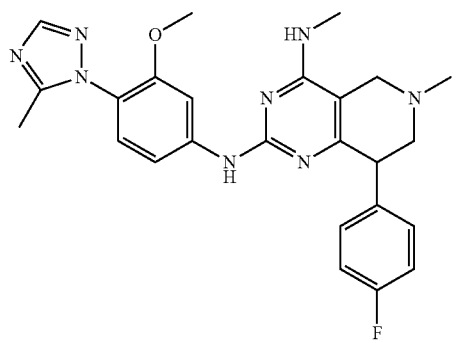 [SMILES: CNc1nc(Nc2ccc(-n3ncnc3C)c(OC)c2)nc2c1CN(C)CC2c1ccc(F)cc1]

In a manner similar to that described in Example 8, Preparation DD and Preparation AHa were reacted to give 8-(4-fluorophenyl)-N2-(3-methoxy-4-(5-methyl-1H-1,2,4-triazol-1-yl)phenyl)-N4,6-dimethyl-5,6,7,8-tetrahydropyrido[4,3-d]pyrimidine-2,4-diamine. LC-MS (M+H)$^+$=475.2.

The racemic mixture was separated by chiral chromatography to afford the enantiomers Example 199A and 199B.

Example 200

(±)-2-(4-(4-chloro-1H-imidazol-1-yl)-3-methoxyphenylamino)-4-(methylamino)-7-phenyl-6,7-dihydro-5H-cyclopenta[d]pyrimidin-5-one

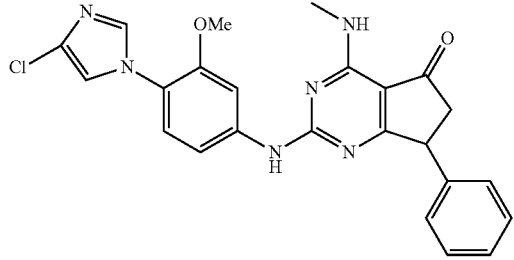 [SMILES: CNc1nc(Nc2ccc(-n3cnc(Cl)c3)c(OC)c2)nc2c1C(=O)CC2c1ccccc1]

A solution of 2-chloro-4-(methylamino)-7-phenyl-6,7-dihydro-5H-cyclopenta[d]pyrimidin-5-one (Preparation AN) (7 mg) and 4-(4-chloro-1H-imidazol-1-yl)-3-methoxyaniline (Preparation A) (7 mg) in THF (0.2 mL) and sulfuric acid (4 mg) was heated at 85° C. for 12 h. THF was removed in vacuo, and the residue was purified by reverse phase preparative to give the title compound (as its TFA salt) as a yellowish oil (9 mg). LC-MS (M+H)$^+$=461.12. $^1$H NMR (500 MHz, CD$_3$OD) δ ppm 7.80 (m), 7.1-7.4 (m), 4.50 (1H, m), 3.25 (1H, m), 2.56 (1H, m), 3.50 (3H, s), and 3.19 (3H, s).

The racemic mixture was separated by chiral chromatography to afford the enantiomers Examples 200A and 200B.

Example 201

(E)-2-(4-(4-chloro-1H-imidazol-1-yl)-3-methoxyphenylamino)-4-(methylamino)-7-phenyl-6,7-dihydro-5H-cyclopenta[d]pyrimidin-5-one O-methyl oxime

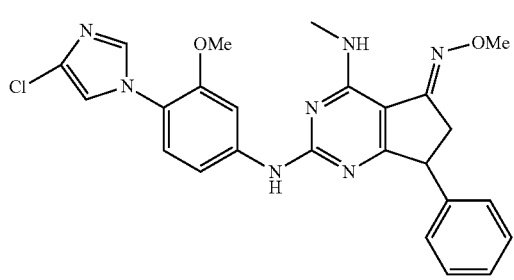 [SMILES: CNc1nc(Nc2ccc(-n3cnc(Cl)c3)c(OC)c2)nc2c1/C(=N/OC)CC2c1ccccc1]

A 0.15M solution of Example 200 in iPrOH was heated with 4 eq methoxyamine hydrochloride at 85° C. for 3 h. Reverse-phase HPLC provided the desired material as a TFA salt. LC-MS (M+H)$^+$=490.2.

The racemic mixture was separated by chiral chromatography to afford the enantiomers Example 201A and 201B.

Example 202

2-(4-(4-chloro-1H-imidazol-1-yl)-3-methoxyphenylamino)-4-(methylamino)-7-phenyl-6,7-dihydro-5H-cyclopenta[d]pyrimidin-5-ol

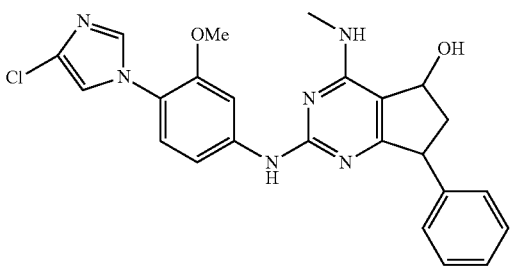 [SMILES: CNc1nc(Nc2ccc(-n3cnc(Cl)c3)c(OC)c2)nc2c1C(O)CC2c1ccccc1]

To a solution of Example 201 in methanol at rt was added NaBH$_4$, and the rxn mixture was stirred at rt for 1 h. The rxn was worked up with EtOAc/H$_2$O to give the desired pdt as a white solid. LC-MS (M+H)$^+$=463.1.

Example 203

N2-(4-(4-chloro-1H-imidazol-1-yl)-3-methoxyphenyl)-N4-methyl-8-phenyl-5,6,7,8-tetrahydroquinazoline-2,4-diamine

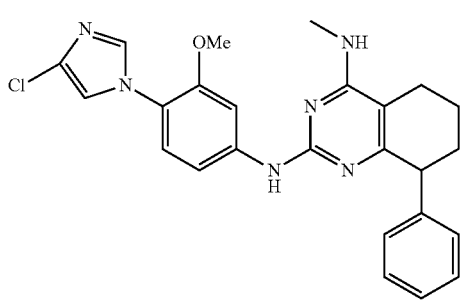 [SMILES: CNc1nc(Nc2ccc(-n3cnc(Cl)c3)c(OC)c2)nc2c1CCCC2c1ccccc1]

LC-MS (M+H)$^+$=466.0. $^1$H NMR (400 MHz, CHLOROFORM-d) δ ppm 7.86 (1H, d, J=2.3 Hz), 7.48 (1H, d, J=1.5 Hz), 7.24-7.32 (4H, m), 7.16-7.23 (1H, m), 7.08-7.14 (2H, m), 7.00 (2H, s), 6.70 (1H, dd, J=8.3, 2.0 Hz), 4.71 (1H, d, J=3.0 Hz), 4.03 (1H, t, J=5.6 Hz), 3.41 (3H, s), 3.12 (3H, d, J=4.8 Hz), 2.30-2.48 (2H, m), 2.09-2.22 (1H, m, J=13.0, 9.7, 6.2, 3.3, 3.1 Hz), 1.74-1.96 (3H, m).

The racemic mixture was separated by chiral chromatography to afford the enantiomers Example 203A and 203B.

Example 204

1-(2-methoxy-4-(4-(methylamino)-7-phenyl-6,7-dihydro-5H-cyclopenta[d]pyrimidin-2-ylamino)phenyl)-1H-imidazole-4-carbonitrile

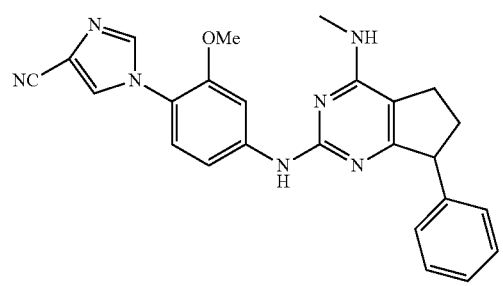 [SMILES: CNc1nc(Nc2ccc(-n3cnc(C#N)c3)c(OC)c2)nc2c1CCC2c1ccccc1]

To a solution of 2-chloro-N-methyl-7-phenyl-6,7-dihydro-5H-cyclopenta[d]pyrimidin-4-amine (Preparation Ga) (150 mg, 0.578 mmol) in Dioxane (Ratio: 1, Volume: 1013 μl) was added 1-(4-amino-2-methoxyphenyl)-1H-imidazole-4-carbonitrile (Preparation AA) (124 mg, 0.578 mmol), and AcOH (Ratio: 1.000, Volume: 1013 μl). The resulting mixture was brought to 100° C. in a sealed vial and stirred overnight. The mixture was brought to pH 8 by the addition of 1 N aqueous sodium Hydroxide. The resulting mixture was extracted with EtOAc (3×1 mL). The combined extracts were dried over MgSO$_4$, filtered and concentrated in vacuo. Purification by prep HPLC (Waters Sunfire C18, 50×250 mm, acetonitrile/H$_2$O/ammonium acetate) gave 1-(2-methoxy-4-(4-(methylamino)-7-phenyl-6,7-dihydro-5H-cyclopenta[d]pyrimidin-2-ylamino)phenyl)-1H-imidazole-4-carbonitrile (57 mg, 0.130 mmol, 22.56% yield). LC-MS (M+H)$^+$=438.2. $^1$H NMR (500 MHz, MeOD) δ ppm 8.02-8.08 (2H, m), 7.90-7.94 (1H, m), 7.31 (2H, t, J=7.63 Hz), 7.16-7.24 (4H, m), 6.99 (1H, dd, J=8.55, 2.14 Hz), 4.18 (1H, t, J=8.09 Hz), 3.56 (3H, s), 3.07 (3H, s), 2.76-2.84 (1H, m), 2.59-2.74 (2H, m), 1.98-2.05

(1H, m). The racemic mixture was separated by chiral chromatography to afford the enantiomers Example 204A and 204B.

Example 205

N-(4-(4-chloro-1H-imidazol-1-yl)-3-methoxyphenyl)-7-phenyl-4-(1,4-dioxa-7-azaspiro[4.4]nonan-7-yl)-6,7-dihydro-5H-cyclopenta[d]pyrimidin-2-amine

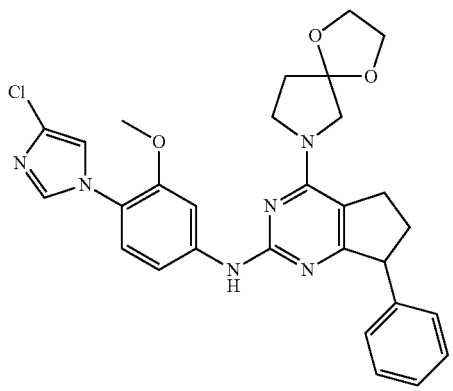 [SMILES: COc1cc(Nc2nc3c(c(N4CCC5(C4)OCCO5)n2)CCC3c2ccccc2)ccc1-n1cnc(Cl)c1]

In a manner similar to that described in Example 184, Preparation Go and Preparation A were combined to obtain N-(4-(4-chloro-1H-imidazol-1-yl)-3-methoxyphenyl)-7-phenyl-4-(1,4-dioxa-7-azaspiro[4.4]nonan-7-yl)-6,7-dihydro-5H-cyclopenta[d]pyrimidin-2-amine. LC-MS (M+H)$^+$ =545.1. 1H NMR (500 MHz, MeOD) δ ppm 7.89 (1H, s), 7.62 (0.5H, br. s.), 7.53 (0.5H, br. s.), 7.37-7.45 (4H, m), 7.32-7.36 (1H, m), 7.30 (2H, d, J=7.63 Hz), 7.23 (0.5H, d, J=7.63 Hz), 7.14 (0.5H, d, J=7.32 Hz), 4.40-4.47 (1H, m), 4.25 (1H, br. s.), 3.96-4.14 (6H, m), 3.88 (4H, br. s.), 3.34-3.46 (1H, m), 3.28 (1H, br. s.), 2.69-2.79 (1H, m), 2.24-2.32 (1H, m), 2.09-2.23 (2H, m).

Example 206

1-(2-(4-(4-chloro-1H-imidazol-1-yl)-3-methoxyphenylamino)-7-phenyl-6,7-dihydro-5H-cyclopenta[d]pyrimidin-4-yl)pyrrolidin-3-one

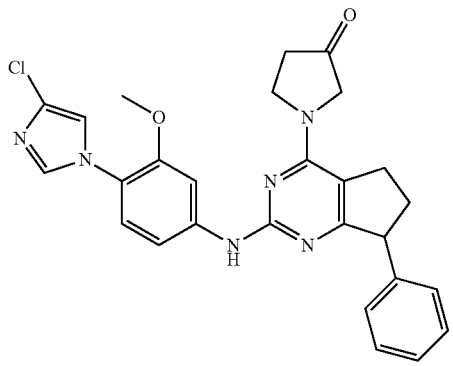 [SMILES: COc1cc(Nc2nc3c(c(N4CCC(=O)C4)n2)CCC3c2ccccc2)ccc1-n1cnc(Cl)c1]

The mixture of N-(4-(4-chloro-1H-imidazol-1-yl)-3-methoxyphenyl)-7-phenyl-4-(1,4-dioxa-7-azaspiro[4.4]nonan-7-yl)-6,7-dihydro-5H-cyclopenta[d]pyrimidin-2-amine (Example 205) (37 mg, 0.068 mmol) and HCl (272 μL, 0.272 mmol) in THF (339 μL) was heated at 60° C. overnight. Concentrated to remove THF and added Acetone (339 μL) and HCl (272 μL, 0.272 mmol) to the mixture. The mixture was heated at 60° C. for 6 h. The crude product was purified by Prep-HPLC (Solvent A=10% MeOH-90% H2O-0.1% TFA, Solvent B=90% MeOH-10% H2O-0.1% TFA. Column. PHENOMENEX LUNA 30×100 mm, S10, Flow rate: 40 ml/min, 35-100% B, 40 min) and then was purified by Prep-HPLC (Column: PHENOMENEX LUNA C18 30×100 mm, Solvent A=10 mM Ammonium Acetate in 95:5 H2O/ACN, Solvent B=10 mM Ammonium Acetate in 5:95 H2O/ACN. Flow rate: 40 ml/min, 30-100% B, 35 min) to get 1-(2-(4-(4-chloro-1H-imidazol-1-yl)-3-methoxyphenylamino)-7-phenyl-6,7-dihydro-5H-cyclopenta[d]pyrimidin-4-yl)pyrrolidin-3-one (2.0 mg, 3.59 μmol, 5.29% yield).

LC-MS (M+H)$^+$=501.3.

Example 207

4-(8-(4-fluorophenyl)-4-(methylamino)-6-(methylsulfonyl)-5,6,7,8-tetrahydropyrido[4,3-d]pyrimidin-2-ylamino)benzonitrile

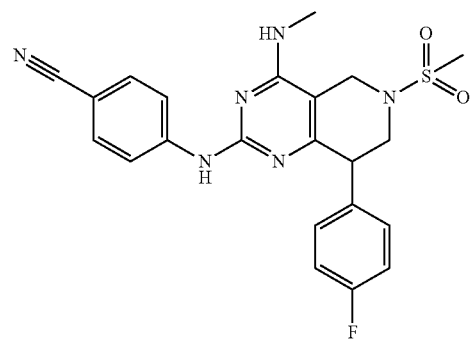 [SMILES: CNc1nc(Nc2ccc(C#N)cc2)nc2c1CN(S(C)(=O)=O)CC2c1ccc(F)cc1]

Utilizing 4-aminobenzonitrile and Preparation AGa successively by the general methods described in Preparation AGj, AGk, and AGp, the title compound was obtained. LC-MS (M+H)$^+$=453.2. $^1$H NMR (400 MHz, DMSO-d) δ ppm 9.25 (s, 1H) 7.85 (d, J=8.80 Hz, 2H) 7.55 (d, J=8.80 Hz, 2H)

7.25-7.29 (m, 2H) 7.10-7.17 (m, 3H) 4.05-4.24 (m, 3H) 3.53-3.63 (m, 2H) 2.95 (d, J=4.4 Hz, 3H) 2.95 (s, 3H).

Example 208

N2-(4-(4-(difluoromethyl)-1H-imidazol-1-yl)-3-methoxyphenyl)-7-(4-fluorophenyl)-N4-methyl-6,7-dihydro-5H-cyclopenta[d]pyrimidine-2,4-diamine

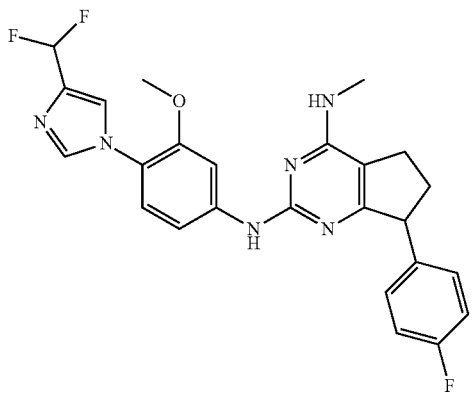 [SMILES: CNc1nc(Nc2ccc(-n3cnc(C(F)F)c3)c(OC)c2)nc2c1CCC2c1ccc(F)cc1]

In a manner similar to that described in Example 8, Preparation EE and Preparation Hh were reacted to give N2-(4-(4-(difluoromethyl)-1H-imidazol-1-yl)-3-methoxyphenyl)-7-(4-fluorophenyl)-N4-methyl-6,7-dihydro-5H-cyclopenta[d]pyrimidine-2,4-diamine. LC-MS (M+H)$^+$=481.1 $^1$H NMR (500 MHz, MeOD) δ ppm 8.19 (s, 1H) 7.75 (br. s., 1H) 7.71 (s, 1H) 7.45 (dd, J=8.55, 3.05 Hz, 1H) 7.31 (ddd, J=8.47, 5.26, 2.75 Hz, 2H) 7.19-7.26 (m, 1H) 7.15 (td, J=8.77, 2.90 Hz, 2H) 6.83 (t, J=55 Hz, 1H) 4.51 (d, J=2.75 Hz, 1H) 3.91 (d, J=3.05 Hz, 3H) 3.18 (d, J=3.05 Hz, 3H) 2.92 (d, J=9.16 Hz, 1H) 2.76-2.85 (m, 2H) 2.10-2.20 (m, 1H).

Example 209

N2-(3-methoxy-4-(1-methyl-1H-pyrazol-4-yl)phenyl)-N4-methyl-7-phenyl-6,7-dihydro-5H-cyclopenta[d]pyrimidine-2,4-diamine

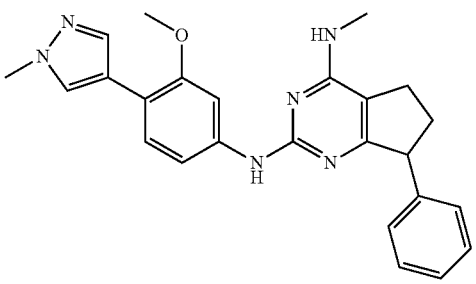 [SMILES: CNc1nc(Nc2ccc(-c3cnn(C)c3)c(OC)c2)nc2c1CCC2c1ccccc1]

In a manner similar to that described in Example 8, Preparation AO and Preparation Ga were reacted to give N2-(3-methoxy-4-(1-methyl-1H-pyrazol-4-yl)phenyl)-N4-methyl-7-phenyl-6,7-dihydro-5H-cyclopenta[d]pyrimidine-2,4-diamine LC-MS (M+H)$^+$=425.4. $^1$H NMR (400 MHz, CHLOROFORM-d) δ ppm 7.84 (1H, d, J=2.01 Hz), 7.81 (1H, s), 7.74 (1H, s), 7.32 (3H, dd, J=13.55, 7.78 Hz), 7.19-7.26 (3H, m), 7.07 (1H, s), 6.78 (1H, dd, J=8.28, 2.01 Hz), 4.60 (1H, q, J=4.52 Hz), 4.16-4.23 (1H, m), 3.91 (3H, s), 3.64 (3H, s), 3.11 (3H, d, J=5.02 Hz), 2.58-2.76 (3H, m), 2.00-2.11 (1H, m).

Example 210

N-(2-(4-(4-chloro-1H-imidazol-1-yl)-3-methoxyphenylamino)-7-phenyl-6,7-dihydro-5H-cyclopenta[d]pyrimidin-4-yl)-N-methylmethanesulfonamide

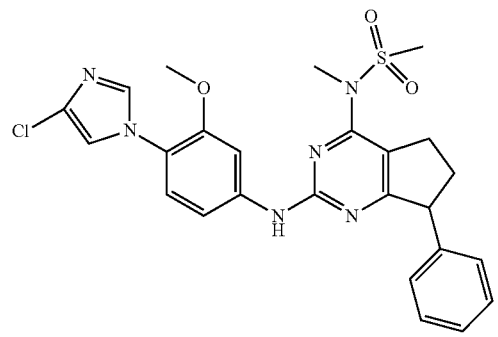 [SMILES: COc1cc(Nc2nc3c(c(N(C)S(C)(=O)=O)n2)CCC3c2ccccc2)ccc1-n1cnc(Cl)c1]

Preparation G was reacted with 0.9 eq MeSO2NHMe, 0.1 eq Pd(OAc)2, 0.15 eq xanphos and Cs2CO3 at 110° C. Preparation A was then added, resulting in the title compound. LC-MS (M+H)$^+$=525.4 $^1$H NMR (400 MHz, DMSO-d) δ ppm 9.79 (s, 1H) 7.75-7.77 (m., 2H) 7.45 (s, 1H) 7.32-7.35 (m, 2H) 7.23-7.27 (m, 4H) 7.16-7.18 (m, 1H) 4.35 (t, J=8.80 Hz, 1H) 3.40 (s, 3H) 3.31 (s, 3H) 2.94-3.06 (m, 2H) 2.57-2.61 (m, 1H) 2.51 (s, 3H) 2.04-2.08 (m, 1H).

Example 211

N-(2-(4-(4-chloro-1H-imidazol-1-yl)-3-methoxyphenylamino)-7-phenyl-6,7-dihydro-5H-cyclopenta[d]pyrimidin-4-yl)-N-methanesulfonamide

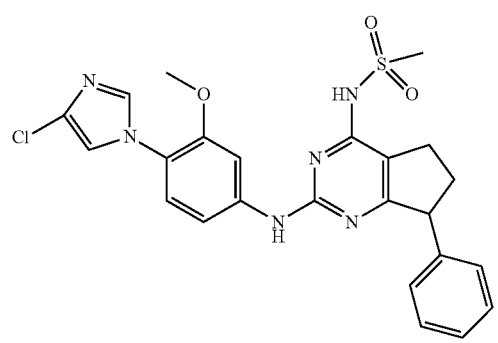 [SMILES: COc1cc(Nc2nc(NS(C)(=O)=O)c3c(n2)C(c2ccccc2)CC3)ccc1-n1cnc(Cl)c1]

The title compound was prepared as for Example 210, substituting MeSO2NH2. LC-MS (M+H)$^+$=511.0 $^1$H NMR (400 MHz, DMSO-d) δ ppm 9.51 (s, 1H) 7.73-7.76 (m., 2H)

7.41 (s, 1H) 7.16-7.31 (m, 8H) 4.21 (t, J=8.40 Hz, 1H) 3.54 (s, 3H) 3.41 (s, 3H) 2.88-2.93 (m, 2H) 2.69-2.73 (m, 1H) 1.91-1.97 (m, 1H).

Example 212

N-(2-(4-(4-chloro-1H-imidazol-1-yl)-3-methoxyphenylamino)-7-phenyl-6,7-dihydro-5H-cyclopenta[d]pyrimidin-4-yl)-N-methylacetamide

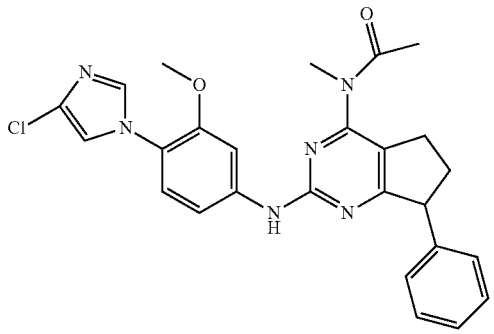 [SMILES: COc1cc(Nc2nc3c(c(N(C)C(C)=O)n2)CCC3c2ccccc2)ccc1-n1cnc(Cl)c1]

Intermediate Ga was reacted with p-methoxybenzylamine in the manner of Preparation Gd. Coupling with Preparation A under the conditions of Example 184, followed by treatment with TFA, led to the C4 NH$_2$ compound. Reaction with AcCl in dichloroethane and DIPEA at ambient temperature for 4 h yielded the named compound. LC-MS (M+H)$^+$=489.2. $^1$H NMR (400 MHz, DMSO-d) δ ppm 9.89 (s, 1H), 7.92 (s, 1H), 7.75 (s, 1H), 7.44 (s, 1H), 7.36-7.12 (m, 7H), 4.38 (t, J=8.6 Hz, 1H), 3.51 (s, 3H), 3.33 (s, 3H), 2.81 (t, J=7.4 Hz, 2H), 2.59-2.55 (m, 1H), 2.17 (s, 3H), 2.03 (dd, J=8.8, 12.4 Hz, 1H).

Example 213

N-(2-(4-(4-chloro-1H-imidazol-1-yl)-3-methoxyphenylamino)-7-phenyl-6,7-dihydro-5H-cyclopenta[d]pyrimidin-4-yl)-N-acetamide

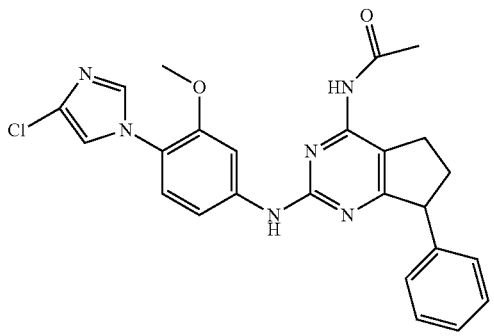 [SMILES: COc1cc(Nc2nc(NC(C)=O)c3c(n2)C(c2ccccc2)CC3)ccc1-n1cnc(Cl)c1]

To a solution of Intermediate Ga was added 1.5 eq AcCl and 2 eq DIPEA and allowed to reflux for 3 days. The product so-obtained was coupled with Preparation A by the method of Example 184 to afford the title compound. LC-MS (M+H)$^+$=475.2 $^1$H NMR (400 MHz, DMSO-d) δ ppm 7.86 (s, 1H) 7.54 (s., 1H) 7.35 (d, J=8.40 1H) 7.23-7.30 (m, 2H) 7.04-7.21 (m, 6H) 6.73-6.76 (m, 1H) 4.26 (t, J=8.00 Hz, 1H) 3.71 (s, 3H) 2.58-2.80 (m, 3H) 2.02 (s, 3H) 1.96-2.00 (m, 1H).

Example 214

N2-(4-(4-chloro-1H-imidazol-1-yl)-3-methoxyphenyl)-N4-(5-isopropyl-2-methylphenyl)-7-phenyl-6,7-dihydro-5H-cyclopenta[d]pyrimidine-2,4-diamine

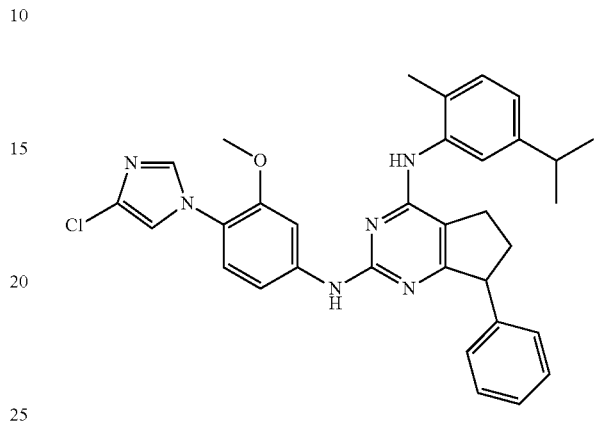

To a solution of 2-chloro-N-methyl-7-phenyl-6,7-dihydro-5H-cyclopenta[d]pyrimidin-4-amine (Preparation Gp) (26.0 mg, 100 µmol) in Dioxane (Ratio: 1, Volume: 175 µl) was added 4-(4-chloro-1H-imidazol-1-yl)-3-methoxyaniline (Preparation A) (22.37 mg, 100 µmol) and AcOH (Ratio: 1.000, Volume: 175 µl). The resulting mixture was brought to 100° C. and stirred overnight. The reaction mixture was brought to pH 10 by the addition of 1 N aqueous NaOH. The resulting mixture was extracted with EtOAc (3×4 mL). The combined organic extracts were washed with brine (4 mL), dried over MgSO$_4$, filtered and concentrated in vacuo. The product was purified by Prep HPLC to yield the title compound. LC-MS (M+H)$^+$=565.2.

Examples 215A and 215B 4-(4-(5-isopropyl-2-methylphenylamino)-7-phenyl-6,7-dihydro-5H-cyclopenta[d]pyrimidin-2-ylamino)benzonitrile

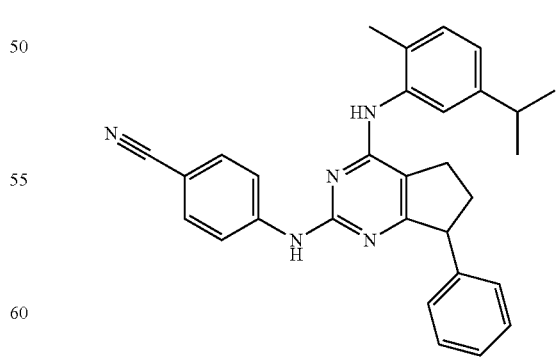

The method of Example 214 was used to combine 4-aminobenzonitrile and Preparation Gp to afford the title compounds as two distinct and separable atropisomers. LC-MS (M+H)$^+$=460.3.

Examples 216-256

The following general methods were used to join the appropriate aniline with Preparation Ga.
Coupling Method A[a]: The method as described in Example 8.
Coupling Method B[a]: The two components were heated at 100° C. in 1:1 HOAc/Dioxane.

Analysis was conducted on one of the following columns[b]:
LC Method A[b]: Phenomenex Luna 3×50 95/5 to 5/95 water/MeOH, 0.1% TFA
LC Method B[b]: Phenomenex Luna 2×50 95/5 to 5/95 water/CH3CN, 0.1% NH4OAc
LC Method C[b]: Phenomenex Luna 2×50 95/5 to 5/95 water/MeOH, 0.1% TFA
LC Method D[b]: Waters 2×50 95/5 to 5/95 water/MeOH, 0.1% NH4OAc
LC Method E[b]: Supelco Ascentis Exp 95/5 to 5/95 water/CH3CN, 0.1% NH4OAc
LC Retention Times[c] are reported along with the gradient run time (rt/grt).

| Example | Compound Name | Coupling Method[a] | LC Method[b] | LC Retention time[c] | (M + H)+ |
|---|---|---|---|---|---|
| 216 | N4-methyl-N2-(2-methylpyridin-4-yl)-7-phenyl-6,7-dihydro-5H-cyclopenta[d]pyrimidine-2,4-diamine | B | A | 1.77/3 | 332.2 |
| 217 | N2-(3-methoxyphenyl)-N4-methyl-7-phenyl-6,7-dihydro-5H-cyclopenta[d]pyrimidine-2,4-diamine | A | D | 3.63/4 | 347.2 |
| 218 | N2-(4-fluorophenyl)-N4-methyl-7-phenyl-6,7-dihydro-5H-cyclopenta[d]pyrimidine-2,4-diamine | A | D | 3.68/4 | 335.2 |
| 219 | N2-(3,5-difluorophenyl)-N4-methyl-7-phenyl-6,7-dihydro-5H-cyclopenta[d]pyrimidine-2,4-diamine | A | D | 3.87/4 | 353.2 |
| 220 | N2-(4-chloro-3-methoxyphenyl)-N4-methyl-7-phenyl-6,7-dihydro-5H-cyclopenta[d]pyrimidine-2,4-diamine | A | D | 3.83/4 | 381.2 |
| 221 | N2-(4-bromo-2-methoxyphenyl)-N4-methyl-7-phenyl-6,7-dihydro-5H-cyclopenta[d]pyrimidine-2,4-diamine | A | D | 4.10/4 | 425.1 |
| 222 | N2-(4-fluoro-3-methoxyphenyl)-N4-methyl-7-phenyl-6,7-dihydro-5H-cyclopenta[d]pyrimidine-2,4-diamine | A | D | 3.63/4 | 365.2 |
| 223 | N4-methyl-7-phenyl-N2-(pyrimidin-5-yl)-6,7-dihydro-5H-cyclopenta[d]pyrimidine-2,4-diamine | A | D | 3.12/4 | 319.2 |
| 224 | N4-methyl-7-phenyl-N2-(pyridin-4-yl)-6,7-dihydro-5H-cyclopenta[d]pyrimidine-2,4-diamine | A | D | 2.85/4 | 318.2 |
| 225 | 4-(4-(methylamino)-7-phenyl-6,7-dihydro-5H-cyclopenta[d]pyrimidin-2-ylamino)benzonitrile | A | D | 3.57/4 | 342.2 |
| 226 | 4-(4-(methylamino)-7-phenyl-6,7-dihydro-5H-cyclopenta[d]pyrimidin-2-ylamino)benzonitrile | A | C | 2.94/4 | 342.1 |
| 227 | 4-(4-(methylamino)-7-phenyl-6,7-dihydro-5H-cyclopenta[d]pyrimidin-2-ylamino)benzonitrile | A | C | 2.92/4 | 342.1 |
| 228 | 2-(4-(methylamino)-7-phenyl-6,7-dihydro-5H-cyclopenta[d]pyrimidin-2-ylamino)benzonitrile | A | E | 2.64/8 | 342.2 |
| 229 | 4-(4-(methylamino)-7-phenyl-6,7-dihydro-5H- | A | E | 5.73/8 | 392.2 |

-continued

| Example | Compound Name | Coupling Method[a] | LC Method[b] | LC Retention time[c] | (M + H)+ |
|---|---|---|---|---|---|
| | cyclopenta[d]pyrimidin-2-ylamino)-1-naphthonitrile | | | | |
| 230 | 5-(4-(methylamino)-7-phenyl-6,7-dihydro-5H-cyclopenta[d]pyrimidin-2-ylamino)picolinonitrile | A | E | 4.54/8 | 343.2 |
| 231 | 2-(4-(4-(methylamino)-7-phenyl-6,7-dihydro-5H-cyclopenta[d]pyrimidin-2-ylamino)phenyl)acetonitrile | A | E | 4.65/8 | 356.2 |
| 232 | 2-(4-(methylamino)-7-phenyl-6,7-dihydro-5H-cyclopenta[d]pyrimidin-2-ylamino)-1H-benzo[d]imidazole-5-carbonitrile | A | E | 4.57/8 | 382.2 |
| 233 | 3-(4-(methylamino)-7-phenyl-6,7-dihydro-5H-cyclopenta[d]pyrimidin-2-ylamino)benzonitrile | B | E | 4.37/8 | 342.1 |
| 234 | N2-(4-tert-butylphenyl)-N4-methyl-7-phenyl-6,7-dihydro-5H-cyclopenta[d]pyrimidine-2,4-diamine | B | E | 5.47/8 | 373.2 |
| 235 | N4-methyl-N2-(4-(methylsulfonyl)phenyl)-7-phenyl-6,7-dihydro-5H-cyclopenta[d]pyrimidine-2,4-diamine | B | E | 3.79/8 | 395.1 |
| 236 | N4-methyl-7-phenyl-N2-(4-(trifluoromethoxy)phenyl)-6,7-dihydro-5H-cyclopenta[d]pyrimidine-2,4-diamine | B | E | 5.13/8 | 400.8 |
| 237 | 4-(4-(methylamino)-7-phenyl-6,7-dihydro-5H-cyclopenta[d]pyrimidin-2-ylamino)phthalonitrile | B | E | 4.47/8 | 367.2 |
| 238 | 4-(4-(methylamino)-7-phenyl-6,7-dihydro-5H-cyclopenta[d]pyrimidin-2-ylamino)-2-(trifluoromethyl)benzonitrile | B | E | 4.90/8 | 410.1 |
| 239 | N4-methyl-7-phenyl-N2-(4-(trifluoromethyl)phenyl)-6,7-dihydro-5H-cyclopenta[d]pyrimidine-2,4-diamine | B | E | 5.13/8 | 385.1 |
| 240 | 5-(4-(methylamino)-7-phenyl-6,7-dihydro-5H-cyclopenta[d]pyrimidin-2-ylamino)-2,3-dihydro-1H-inden-1-one | B | E | 3.89/8 | 371.2 |
| 241 | 2-(4-(methylamino)-7-phenyl-6,7-dihydro-5H-cyclopenta[d]pyrimidin-2-ylamino)-1H-imidazole-4,5-dicarbonitrile | B | E | 4.08/8 | 357.2 |
| 242 | 2-bromo-5-(4-(methylamino)-7-phenyl-6,7-dihydro-5H-cyclopenta[d]pyrimidin-2-ylamino)benzonitrile | B | E | 4.89/8 | 420.1 |
| 243 | N,N-dimethyl-4-(4-(methylamino)-7-phenyl-6,7-dihydro-5H-cyclopenta[d]pyrimidin-2-ylamino)benzamide | B | E | 3.50/8 | 388.2 |
| 244 | 1-(4-(4-(methylamino)-7-phenyl-6,7-dihydro-5H-cyclopenta[d]pyrimidin-2-ylamino)phenyl)cyclopentanecarbonitrile | B | E | 4.91/8 | 410.2 |
| 245 | N4-methyl-7-phenyl-N2-(1,2,3,4-tetrahydroisoquinolin-6-yl)- | B | E | 4.14/8 | 372.2 |

| Example | Compound Name | Coupling Method[a] | LC Method[b] | LC Retention time[c] | (M + H)+ |
|---|---|---|---|---|---|
| | 6,7-dihydro-5H-cyclopenta[d]pyrimidine-2,4-diamine | | | | |
| 246 | 4-(4-(methylamino)-7-phenyl-6,7-dihydro-5H-cyclopenta[d]pyrimidin-2-ylamino)-2-(trifluoromethoxy)benzonitrile | B | E | 5.04/8 | 426.1 |
| 247 | 1-(4-(4-(methylamino)-7-phenyl-6,7-dihydro-5H-cyclopenta[d]pyrimidin-2-ylamino)phenyl)cyclopropanecarbonitrile | B | C | 3.30/4 | 382.3 |
| 248 | 1-(2-methoxy-4-(4-(methylamino)-7-phenyl-6,7-dihydro-5H-cyclopenta[d]pyrimidin-2-ylamino)phenylamino)cyclopropanecarbonitrile | B | C | 3.06/4 | 427.1 |
| 249 | N4-methyl-N2-(2-methyl-1H-indol-5-yl)-7-phenyl-6,7-dihydro-5H-cyclopenta[d]pyrimidine-2,4-diamine | A | B | 1.75/2 | 370.3 |
| 250 | N2-(benzofuran-5-yl)-N4-methyl-7-phenyl-6,7-dihydro-5H-cyclopenta[d]pyrimidine-2,4-diamine | A | B | 1.85/2 | 357.2 |
| 251 | N2-(1H-indol-5-yl)-N4-methyl-7-phenyl-6,7-dihydro-5H-cyclopenta[d]pyrimidine-2,4-diamine | A | B | 1.68/2 | 356.3 |
| 252 | N4-methyl-N2-(2-methylbenzo[d]oxazol-6-yl)-7-phenyl-6,7-dihydro-5H-cyclopenta[d]pyrimidine-2,4-diamine | A | B | 1.73/2 | 372.3 |
| 253 | N2-(1H-benzo[d]imidazol-6-yl)-N4-methyl-7-phenyl-6,7-dihydro-5H-cyclopenta[d]pyrimidine-2,4-diamine | A | B | 1.47/2 | 357.2 |
| 254 | N4-methyl-N2-(1-methyl-1H-indol-5-yl)-7-phenyl-6,7-dihydro-5H-cyclopenta[d]pyrimidine-2,4-diamine | A | B | 1.82/2 | 370.3 |
| 255 | N4-methyl-N2-(2-methylbenzo[d]thiazol-6-yl)-7-phenyl-6,7-dihydro-5H-cyclopenta[d]pyrimidine-2,4-diamine | A | B | 1.78/2 | 388.2 |
| 256 | N2-(4-bromo-3-methoxyphenyl)-N4-methyl-7-phenyl-6,7-dihydro-5H-cyclopenta[d]pyrimidine-2,4-diamine | A | A | 2.63/4 | 425.0/427.0 |

Coupling Method A[a]: The method as described in Example 8.
Coupling Method B[a]: The two components were heated at 100° C. in 1:1 HOAc/Dioxane.
Analysis was conducted on one of the following columns[b]:
LC Method A[b]: Phenomenex Luna 3X50 95/5 to 5/95 water/MeOH, 0.1% TFA
LC Method B[b]: Phenomenex Luna 2X50 95/5 to 5/95 water/CH3CN, 0.1% NH4OAc
LC Method C[b]: Phenomenex Luna 2X50 95/5 to 5/95 water/MeOH, 0.1% TFA
LC Method D[b]: Waters 2X50 95/5 to 5/95 water/MeOH, 0.1% NH4OAc
LC Method E[b]: Supelco Ascentis Exp 95/5 to 5/95 water/CH3CN, 0.1% NH4OAc
LC Retention Times[c] are reported along with the gradient run time (rt/grt).

Example 257

1-(4-(4-(methylamino)-7-phenyl-6,7-dihydro-5H-cyclopenta[d]pyrimidin-2-ylamino)phenyl)ethanone

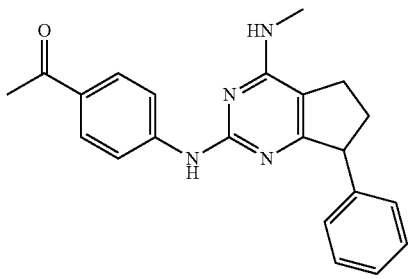 [SMILES: CNc1nc(Nc2ccc(C(C)=O)cc2)nc2c1CCC2c1ccccc1]

A mixture of Example 256 (20 mg, 0.047 mmol), tributyl (1-ethoxyvinyl)stannane (67.9 mg, 0.188 mmol) and Tetrakis (5.43 mg, 4.70 μmol) in toluene (188 μL) was heated at 80° C. for 12 hrs. The crude product was purified by prep HPLC. The resulting product was treated with HCl(0.8 eq.) in acetone (0.285 M) and stirred at RT overnight. The mixture was concentrated and added EtOAc, washed with water, brine, dried over Na2SO4 and concentrated to get 1-(2-methoxy-4-(4-(methylamino)-7-phenyl-6,7-dihydro-5H-cyclopenta[d]pyrimidin-2-ylamino)phenyl)ethanone (4 mg, 10.3 μmol, 22% yield). LC-MS (M+H)$^+$=389.2 $^1$H NMR (500 MHz, MeOD) δ ppm 7.74 (d, J=8.55 Hz, 1H) 7.66 (s, 1H) 7.36-7.49 (m, 3H) 7.19-7.36 (m, 2H) 7.08 (dd, J=8.55, 1.83 Hz, 1H) 4.45 (br. s., 1H) 3.86-3.98 (m, 3H) 3.16-3.24 (m, 3H) 2.93 (br. s., 1H) 2.73-2.86 (m, 2H) 2.53-2.63 (m, 3H) 2.11-2.23 (m, 1H).

Example 258

N2-(4-cyclopropylphenyl)-7-(4-fluorophenyl)-N4-methyl-6,7-dihydro-5H-cyclopenta[d]pyrimidine-2,4-diamine

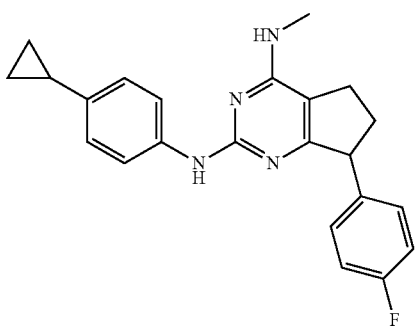 [SMILES: CNc1nc(Nc2ccc(C3CC3)cc2)nc2c1CCC2c1ccc(F)cc1]

To a solution of the fluorinated analog of Example 256 (150 mg, 0.338 mmol) in Toluene (Ratio: 20, Volume: 1611 μl) was added Cyclopropylboronic acid (37.8 mg, 0.440 mmol), PdOAc2 (3.80 mg, 0.017 mmol), Tricyclohexylphosphine (9.49 mg, 0.034 mmol), Potassium orthophosphate (251 mg, 1.184 mmol), and Water (Ratio: 1.000, Volume: 81 μl). The resulting mixture was brought to 110° C. and stirred overnight. The reaction mixture was diluted with EtOAc (5 mL), washed with water (2 mL), brine (2 mL), dried over MgSO4, filtered and concentrated in vacuo. Purification by flash chromatography (Silica, EtOAc/Hexanes) gave N2-(4-cyclopropyl-3-methoxyphenyl)-7-(4-fluorophenyl)-N4-methyl-6,7-dihydro-5H-cyclopenta[d]pyrimidine-2,4-diamine (15 mg, 0.037 mmol, 10.96% yield). LC-MS (M+H)$^+$=405.1 $^1$H NMR (500 MHz, MeOD) δ ppm 7.60 (d, J=1.83 Hz, 1H) 7.19 (dd, J=7.93, 5.80 Hz, 2H) 6.97-7.14 (m, 3H) 6.69-6.78 (m, 1H) 4.05-4.22 (m, 2H) 3.62-3.71 (m, 3H) 2.98-3.11 (m, 3H) 2.72-2.85 (m, 1H) 2.55-2.72 (m, 2H) 1.90-2.05 (m, 2H) 1.26 (t, J=7.17 Hz, 1H) 0.73-0.86 (m, 1H) 0.46-0.61 (m, 1H).

Example 259

N2-(4-ethynylphenyl)-7-(4-fluorophenyl)-N4-methyl-6,7-dihydro-5H-cyclopenta[d]pyrimidine-2,4-diamine

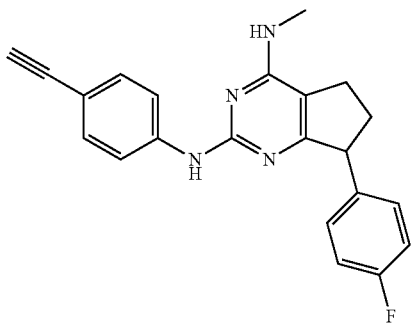 [SMILES: C#Cc1ccc(Nc2nc(NC)c3c(n2)C(c2ccc(F)cc2)CC3)cc1]

The mixture of tributyl(ethynyl)stannane (53.3 mg, 0.169 mmol), the fluorinated analog of Example 256 (50 mg, 0.113 mmol) and Tetrakis (10.0 mg, 0.011 mmol) in toluene (226 μL) was heated at 110° C. for 2 h, and then the solvent was removed in vacuo. The residue was purified by prep HPLC to get N2-(4-ethynyl-3-methoxyphenyl)-7-(4-fluorophenyl)-N4-methyl-6,7-dihydro-5H-cyclopenta[d]pyrimidine-2,4-diamine (1.5 mg, 3.86 μmol). LC-MS (M+H)$^+$=389.2 $^1$H NMR (500 MHz, CHLOROFORM-d) δ ppm 7.86 (s, 1H) 7.31 (d, J=8.55 Hz, 2H) 7.16 (dd, J=7.78, 5.65 Hz, 3H) 7.01 (t, J=8.70 Hz, 2H) 6.71 (br. s., 1H) 4.52 (br. s., 1H) 3.71 (s, 3H) 3.15 (d, J=4.88 Hz, 3H) 2.67 (d, J=9.77 Hz, 3H) 1.95-2.14 (m, 1H).

Example 260

7-(4-fluorophenyl)-N4-methyl-N2-(4-(prop-1-ynyl)phenyl)-6,7-dihydro-5H-cyclopenta[d]pyrimidine-2,4-diamine

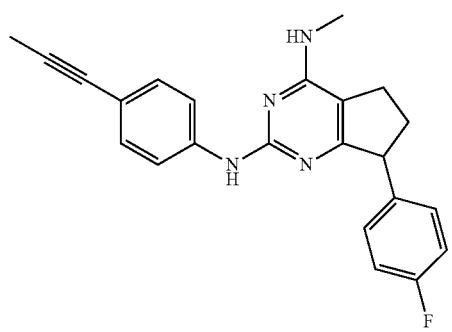 [SMILES: CC#Cc1ccc(Nc2nc(NC)c3c(n2)C(c2ccc(F)cc2)CC3)cc1]

The mixture of tributyl(prop-1-ynyl)stannane (55.7 mg, 0.169 mmol), the fluorinated analog of Example 256 (50 mg, 0.113 mmol) and Tetrakis (10.0 mg, 0.011 mmol) in toluene (226 µL) was heated at 110° C. for 2 h, and then the solvent was removed in vacuo. The residue was purified by prep HPLC to get 7-(4-fluorophenyl)-N2-(3-methoxy-4-(prop-1-ynyl)phenyl)-N4-methyl-6,7-dihydro-5H-cyclopenta[d]pyrimidine-2,4-diamine (2.0 mg, 4.97 µmol). LC-MS (M+H)⁺=403.3 ¹H NMR (400 MHz, CHLOROFORM-d) δ ppm 7.80 (d, J=1.76 Hz, 1H) 7.10-7.23 (m, 3H) 6.93-7.08 (m, 2H) 6.73 (s, 1H) 4.51 (br. s., 1H) 4.05-4.29 (m, 1H) 3.70 (s, 3H) 3.14 (d, J=4.77 Hz, 3H) 2.56-2.79 (m, 3H) 2.09-2.14 (m, 3H) 1.99-2.09 (m, 1H).

Example 261

N2-(3-methoxy-4-(2-methylpyridin-4-yl)phenyl)-N4-methyl-7-phenyl-6,7-dihydro-5H-cyclopenta[d]pyrimidine-2,4-diamine

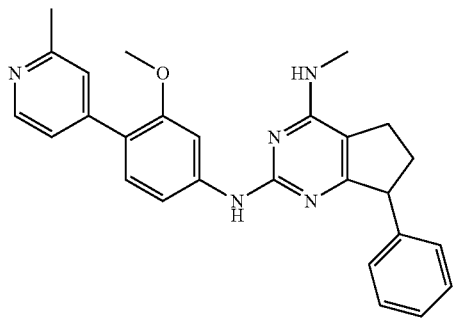 [SMILES: CNc1nc(Nc2ccc(-c3ccnc(C)c3)c(OC)c2)nc2c1CCC2c1ccccc1]

The mixture of 2-methylpyridin-4-ylboronic acid (25.1 mg, 0.183 mmol), Example 256 (26 mg, 0.061 mmol), Tetrakis (14.1 mg, 0.012 mmol) and sodium carbonate (13.0 mg, 0.122 mmol) in toluene (255 µL)/water (50 µL) was heated at 150° C. for 5 h, and then the solvent was removed in vacuo. The residue was purified by prep HPLC to get N2-(3-methoxy-4-(2-methylpyridin-4-yl)phenyl)-N4-methyl-7-phenyl-6,7-dihydro-5H-cyclopenta[d]pyrimidine-2,4-diamine (5.0 mg, 0.011 mmol). LC-MS (M+H)⁺=438.2 ¹H NMR (500 MHz, MeOD) δ ppm 8.60 (br. s., 1H) 8.06-8.19 (m, 2H) 7.75 (d, J=1.83 Hz, 1H) 7.60-7.70 (m, 1H) 7.38-7.49 (m, 2H) 7.22-7.38 (m, 4H) 4.43-4.57 (m, 1H) 3.86-3.99 (m, 3H) 3.17-3.26 (m, 3H) 2.89-3.01 (m, 1H) 2.73-2.89 (m, 5H) 2.19 (dt, J=9.16, 6.87 Hz, 1H).

Example 262

N2-(3-methoxy-4-(pyridin-4-yl)phenyl)-N4-methyl-7-phenyl-6,7-dihydro-5H-cyclopenta[d]pyrimidine-2,4-diamine

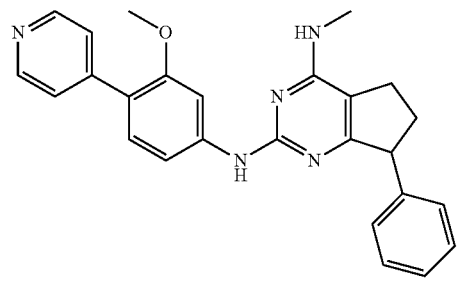 [SMILES: CNc1nc(Nc2ccc(-c3ccncc3)c(OC)c2)nc2c1CCC2c1ccccc1]

The mixture of 4-(tributylstannyl)pyridine (69.2 mg, 0.188 mmol), Example 256 (20 mg, 0.047 mmol) and Tetrakis (5.43 mg, 4.70 µmol) in toluene (196 µL)/water (39 µL) was heated at 100° C. for 12 h, and then the solvent was removed in vacuo. The residue was purified by prep HPLC to get N2-(3-methoxy-4-(pyridin-4-yl)phenyl)-N4-methyl-7-phenyl-6,7-dihydro-5H-cyclopenta[d]pyrimidine-2,4-diamine (4.0 mg, 9.44 µmol). LC-MS (M+H)⁺=424.2 ¹H NMR (500 MHz, MeOD) δ ppm 8.20-8.90 (m, 4H) 7.74 (d, J=1.83 Hz, 1H) 7.62-7.70 (m, 1H) 7.39-7.47 (m, 2H) 7.23-7.37 (m, 4H) 4.43-4.54 (m, 1H) 3.94 (s, 3H) 3.22 (s, 3H) 2.89-3.01 (m, 1H) 2.75-2.87 (m, 2H) 2.12-2.29 (m, 1H).

Example 263

N2-(3-methoxy-4-(pyridin-3-yl)phenyl)-N4-methyl-7-phenyl-6,7-dihydro-5H-cyclopenta[d]pyrimidine-2,4-diamine

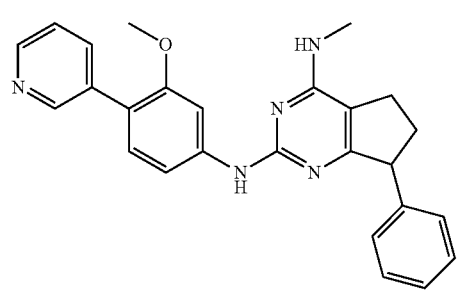 [SMILES: CNc1nc(Nc2ccc(-c3cccnc3)c(OC)c2)nc2c1CCC2c1ccccc1]

The mixture of 3-(tributylstannyl)pyridine (55.4 mg, 0.150 mmol), Example 256 (16 mg, 0.061 mmol) and Tetrakis (4.35 mg, 3.76 µmol) in toluene (188 µL) was heated at 100° C. for 12 h, and then the solvent was removed in vacuo. The residue was purified by prep HPLC to get N2-(3-methoxy-4-(pyridin-3-yl)phenyl)-N4-methyl-7-phenyl-6,7-dihydro-5H-cyclopenta[d]pyrimidine-2,4-diamine (4.0 mg, 9.44 µmol). LC-MS (M+H)⁺=424.2 ¹H NMR (500 MHz, MeOD) δ ppm 8.52 (br. s., 2H) 7.67-7.76 (m, 2H) 7.55-7.64 (m, 1H) 7.43-7.50 (m, 1H) 7.41 (d, J=7.32 Hz, 2H) 7.32-7.37 (m, 1H) 7.17-7.31 (m, 3H) 4.41-4.56 (m, 1H) 3.88 (s, 3H) 3.16-3.28 (m, 3H) 2.88-3.02 (m, 1H) 2.73-2.88 (m, 2H) 2.09-2.26 (m, 1H).

Biological Methods

Cellular Assays for Inhibition of Aβ1-40 and Aβ1-42 Production

H4 cells stably transfected with APP751 containing the Swedish mutation (H4 APP751 SWE clone 8.20, developed at BMS) were maintained in log phase through twice weekly passage at a 1:20 split. For $IC_{50}$ determinations, 30 μl cells ($1.5 \times 10^4$ cells/well) in DMEM media containing 0.0125% BSA (Sigma A8412) were plated directly into 384-well compound plates (Costar 3709) containing 0.1 μl serially diluted compound in DMSO. Following incubation for 19 h in 5% $CO_2$ at 37° C., plates were briefly centrifuged (1000 rpm, 5 min). A 10 μl aliquot from each well was transferred to a second assay plate (Costar 3709) for Aβ40 measurements. Antibody cocktails were freshly prepared by dilution into 40 mM Tris-HCl (pH 7.4) with 0.2% BSA and added to assay plates. For Aβ42 measurements, antibodies specific for the Aβ42 neoepitope (565, developed at BMS; conjugated to the Wallac reagent (Perkin Elmer)) and the N-terminal sequence of Aβ peptide (26D6, developed at SIBIA; conjugated to APC (Perkin Elmer)) were mixed and 20 μl of the mixture was added to each well of the incubated cell plate yielding a final concentration of 0.8 ng/well 565 and 75 ng/well 26D6. For the Aβ40 measurements, antibodies specific for the Aβ40 neoepitope (TSD, developed at BMS; conjugated to the Wallac reagent (Perkin Elmer)) and 26D6 as described above were mixed and 20 μl of the mixture was added to the 10 μl aliquots which had been removed previously from the cell plate yielding a final concentration of 1.6 ng/well TSD and 17.5 ng/well 26D6. Assay plates containing antibodies were sealed with aluminum foil and incubated overnight at 4° C. Signal was determined using a Viewlux counter (Perkin Elmer) and $IC_{50}$ values determined using curve fitting in CurveMaster (Excel Fit based).

The activity of representative compounds of the present disclosure, based on Aβ42 cellular $IC_{50}$ values in H4 APP751 SWE clone 8.20, are illustrated in Table 1 (below).

TABLE 1

| Compound of Example | Activity Rating[a] | Compound of Example | Activity Rating[a] |
|---|---|---|---|
| 1 | +++ | 85 | +++ |
| 2 | +++ | 86 | ++ |
| 3 | ++ | 87 | 60 nM |
| 3A | +++ | 88 | ++ |
| 3B | ++ | 88A | 4.5 nM |
| 4 | +++ | 88B | ++ |
| 4A | +++ | 89 | ++ |
| 4B | ++ | 90A | ++ |
| 5 | +++ | 90B | 270 nM |
| 5A | +++ | 91A | +++ |
| 5B | ++ | 91B | + |
| 6 | ++ | 92 | ++ |
| 6A | +++ | 93 | 20 nM |
| 6B | ++ | 94 | +++ |
| 7A | +++ | 94A | +++ |
| 7B | ++ | 94B | ++ |
| 8 | +++ | 95 | +++ |
| 9 | 8.1 nM | 95A | +++ |
| 10 | +++ | 95B | ++ |
| 11 | +++ | 96 | +++ |
| 11A | 3.8 | 96A | +++ |
| 11B | +++ | 96B | 4.6 nM |
| 12 | +++ | 97 | +++ |

TABLE 1-continued

| Compound of Example | Activity Rating[a] | Compound of Example | Activity Rating[a] |
|---|---|---|---|
| 12A | +++ | 97A | +++ |
| 13 | − | 97B | ++ |
| 14 | − | 98 | ++ |
| 15 | ++ | 98A | +++ |
| 16 | ++ | 98B | ++ |
| 16A | +++ | 99 | 19 nM |
| 16B | + | 99A | ++ |
| 17 | ++ | 99B | 190 nM |
| 17A | 120 nM | 100 | +++ |
| 17B | ++ | 100A | 4.7 nM |
| 18 | ++ | 100B | ++ |
| 18A | 8.8 nM | 101 | ++ |
| 18B | ++ | 101A | +++ |
| 19 | ++ | 101B | ++ |
| 19A | ++ | 102 | +++ |
| 19B | 59 nM | 102A | +++ |
| 20 | +++ | 102B | ++ |
| 20A | +++ | 103 | +++ |
| 20B | ++ | 103A | +++ |
| 21 | ++ | 103B | ++ |
| 21A | ++ | 104 | ++ |
| 21B | + | 105 | 8.8 nM |
| 23 | ++ | 106 | ++ |
| 23A | ++ | 107 | ++ |
| 23B | + | 107A | ++ |
| 24 | ++ | 107B | + |
| 24A | ++ | 108 | 20 nM |
| 24B | 200 nM | 109A | +++ |
| 25 | ++ | 109B | +++ |
| 26 | +++ | 110A | +++ |
| 26A | ++ | 110B | ++ |
| 26B | ++ | 111 | 35 nM |
| 27 | ++ | 112 | +++ |
| 28 | ++ | 112A | +++ |
| 28A | ++ | 112B | ++ |
| 29 | ++ | 113 | 5.7 nM |
| 29A | ++ | 113A | +++ |
| 29B | ++ | 113B | ++ |
| 30 | ++ | 114 | +++ |
| 30A | ++ | 114A | ++ |
| 30B | 230 nM | 114B | + |
| 31 | + | 115 | +++ |
| 32 | ++ | 115A | +++ |
| 33 | 100 nM | 115B | ++ |
| 34 | ++ | 116 | ++ |
| 35 | +++ | 116A | +++ |
| 36 | ++ | 116B | + |
| 37 | +++ | 117 | 45 nM |
| 38 | ++ | 117A | ++ |
| 38A | 12 nM | 117B | + |
| 38B | ++ | 118 | ++ |
| 39 | ++ | 118A | +++ |
| 39B | + | 118B | + |
| 40A | +++ | 119 | ++ |
| 40B | + | 119A | 7.4 nM |
| 41 | ++ | 119B | + |
| 41A | ++ | 120 | ++ |
| 41B | ++ | 120A | +++ |
| 41C | ++ | 120B | + |
| 41D | ++ | 121 | ++ |
| 42 | ++ | 121A | +++ |
| 42A | +++ | 121B | 120 nM |
| 43 | +++ | 122A | +++ |
| 44 | 13 nM | 123A | ++ |
| 44A | +++ | 123B | 370 nM |
| 45A | ++ | 124 | ++ |
| 45B | 2.5 nM | 124A | +++ |
| 45C | ++ | 124B | ++ |
| 45D | +++ | 125 | ++ |
| 46 | +++ | 126 | ++ |
| 46A | +++ | 127 | ++ |
| 46B | ++ | 127A | +++ |
| 47 | +++ | 127B | ++ |
| 48 | 18 nM | 128 | + |
| 48A | +++ | 129 | ++ |
| 48B | 130 nM | 129A | +++ |
| 49 | +++ | 130 | +++ |

TABLE 1-continued

| Compound of Example | Activity Rating[a] |
|---|---|
| 49A | +++ |
| 49B | ++ |
| 50 | +++ |
| 50A | +++ |
| 50B | ++ |
| 51 | 4.5 nM |
| 51A | +++ |
| 51B | +++ |
| 52 | ++ |
| 52A | +++ |
| 52B | ++ |
| 53 | ++ |
| 53A | +++ |
| 53B | ++ |
| 54 | ++ |
| 54A | ++ |
| 54B | +++ |
| 55 | ++ |
| 55B | ++ |
| 56 | ++ |
| 56A | +++ |
| 56B | ++ |
| 57A | 14 nM |
| 57B | + |
| 58A | +++ |
| 58B | 120 nM |
| 59 | ++ |
| 59A | +++ |
| 60 | +++ |
| 60A | 5.6 nM |
| 60B | ++ |
| 61 | ++ |
| 61A | +++ |
| 61B | ++ |
| 62 | ++ |
| 62A | +++ |
| 62B | 86 nM |
| 63 | ++ |
| 63A | ++ |
| 63B | + |
| 64 | ++ |
| 64A | +++ |
| 64B | ++ |
| 65 | ++ |
| 65A | 5.3 nM |
| 65B | 160 nM |
| 66 | ++ |
| 66A | + |
| 66B | +++ |
| 67 | ++ |
| 67A | ++ |
| 67B | 540 nM |
| 68 | ++ |
| 69 | ++ |
| 69A | +++ |
| 69B | + |
| 70 | +++ |
| 70A | +++ |
| 70B | ++ |
| 71 | ++ |
| 71A | +++ |
| 71B | ++ |
| 72 | +++ |
| 73 | 3.8 nM |
| 74A | ++ |
| 75 | ++ |
| 75A | +++ |
| 75B | ++ |
| 76 | ++ |
| 77 | ++ |
| 78 | ++ |
| 78A | 19 nM |
| 78B | ++ |
| 79A | 5.8 nM |
| 79B | ++ |
| 80 | ++ |
| 80A | ++ |
| 81 | ++ |
| 82 | ++ |
| 82A | +++ |
| 82B | ++ |
| 83 | ++ |
| 83A | +++ |
| 83B | ++ |
| 84 | ++ |
| 84A | ++ |
| 84B | 290 nM |
| 130A | +++ |
| 131 | ++ |
| 131A | +++ |
| 132 | ++ |
| 132A | 15 nM |
| 133 | ++ |
| 133A | +++ |
| 134 | +++ |
| 134A | 3.6 nM |
| 135 | ++ |
| 135A | ++ |
| 136 | +++ |
| 136A | +++ |
| 137 | 11 nM |
| 137A | +++ |
| 138 | ++ |
| 138A | +++ |
| 139 | ++ |
| 139A | ++ |
| 140 | ++ |
| 140A | +++ |
| 141 | ++ |
| 141A | +++ |
| 142 | ++ |
| 143 | ++ |
| 143B | 430 nM |
| 144 | ++ |
| 144B | 540 nM |
| 145 | ++ |
| 146 | ++ |
| 147 | ++ |
| 148A | +++ |
| 149 | ++ |
| 150 | ++ |
| 151 | +++ |
| 151A | +++ |
| 152 | ++ |
| 153 | ++ |
| 154 | ++ |
| 154A | +++ |
| 155A | +++ |
| 156 | +++ |
| 156A | 9.8 nM |
| 157 | ++ |
| 157A | ++ |
| 158 | ++ |
| 159 | ++ |
| 160 | ++ |
| 161 | + |
| 162 | ++ |
| 162A | ++ |
| 163A | +++ |
| 164A | ++ |
| 165 | ++ |
| 165A | ++ |
| 165B | 180 nM |
| 166 | + |
| 167A | 26 nM |
| 168A | +++ |
| 169 | ++ |
| 169A | +++ |
| 170 | ++ |
| 170A | +++ |
| 171 | 16 nM |
| 171A | ++ |
| 172A | +++ |
| 172B | + |
| 173 | 490 nM |
| 174 | ++ |
| 175 | ++ |
| 175A | +++ |
| 176 | +++ |
| 176A | +++ |
| 176B | +++ |
| 177 | ++ |
| 178 | +++ |
| 179 | ++ |
| 180 | ++ |
| 181 | ++ |
| 181A | +++ |
| 181B | 50 nM |
| 182 | ++ |
| 182A | +++ |
| 182B | ++ |
| 183 | 11 nM |
| 183A | +++ |
| 183B | ++ |
| 184 | ++ |
| 185 | ++ |
| 186 | ++ |
| 187 | ++ |
| 187A | ++ |
| 187B | ++ |
| 188 | 19 nM |
| 189 | +++ |
| 189A | +++ |
| 189B | ++ |
| 190 | 37 nM |
| 191 | ++ |
| 191A | ++ |
| 191B | 96 nM |
| 192 | 64 nM |
| 192A | 170 nM |
| 192B | 16 nM |
| 193 | ++ |
| 193A | + |
| 194 | ++ |
| 194A | ++ |
| 194B | 175 nM |
| 195 | 17 nM |
| 195A | 26 nM |
| 195B | + |
| 196 | ++ |
| 196A | +++ |
| 196B | 54 nM |
| 197 | 16 nM |
| 197A | 60 nM |
| 197B | +++ |
| 198 | ++ |
| 198A | + |
| 198B | 15 nM |
| 199 | ++ |
| 199A | + |
| 199B | +++ |
| 200 | ++ |
| 200A | ++ |
| 200B | ++ |
| 201 | 5.3 nM |
| 201A | 10 nM |
| 201B | ++ |
| 202 | +++ |
| 203 | 19 nM |
| 203A | +++ |
| 203B | ++ |
| 204 | 19 nM |
| 204A | 19 nM |
| 204B | + |
| 205 | ++ |
| 206 | 15 nM |
| 207 | + |
| 208 | ++ |
| 209 | +++ |
| 210 | 61 nM |
| 211 | +++ |
| 212 | 33 nM |
| 213 | insol |
| 214 | 77 nM |
| 215A | ^ |
| 215B | 173 nM |
| 216 | ^ |
| 217 | ^ |
| 218 | 3700 nM |
| 219 | ^ |
| 220 | 550 nM |
| 221 | ^ |
| 222 | ^ |
| 223 | 11000 nM |
| 224 | ^ |
| 225 | 18 nM |
| 226 | + |
| 193B | ++ |
| 227 | 12 nM |
| 228 | ^ |
| 229 | ^ |
| 230 | 42 nM |
| 231 | + |
| 232 | ^ |
| 233 | ^ |
| 234 | ^ |
| 235 | + |
| 236 | ^ |
| 237 | 29 nM |
| 238 | + |
| 239 | + |
| 240 | Insol |
| 241 | Insol |
| 242 | 67 nM |
| 243 | + |
| 244 | ^ |
| 245 | ^ |
| 246 | 31 nM |
| 247 | + |
| 248 | ^ |
| 249 | ^ |
| 250 | ^ |
| 251 | ^ |
| 252 | ^ |
| 253 | 5900 nM |
| 254 | 1000 nM |
| 255 | ^ |
| 256 | 97 nM |
| 257 | ++ |
| 258 | ^ |
| 259 | 940 nM |
| 260 | 860 nM |
| 261 | +++ |
| 262 | +++ |
| 263 | 32 nM |

[a] Activity based on Aβ42 cellular $IC_{50}$ values in H4 APP751 SWE clone 8.20.
+++ = 1.5 nM-0.0099 μM
++ = 0.010-0.100 μM
+ = 0.100-1.0 μM
^ = >1.0 μM It will be evident to one skilled in the art that the present disclosure is not limited to the foregoing illustrative examples, and that it can be embodied in other specific forms without departing from the essential attributes thereof. It is

What is claimed is:

1. A compound of formula (I)

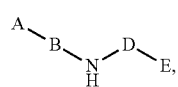

or a pharmaceutically acceptable salt thereof, wherein

A is a five- or six-membered heteroaromatic ring containing from one to three heteroatoms independently selected from nitrogen, oxygen, and sulfur; wherein said heteroaromatic ring is optionally substituted with one or two groups selected from halo, haloC$_{1-6}$alkyl, hydroxy, amino, C$_{1-6}$alkoxy, and C$_{1-6}$alkyl;

B is selected from phenyl and pyridinyl, wherein the phenyl and pyridinyl are optionally substituted with one or two substituents independently selected from C$_{1-6}$alkoxy, C$_{1-6}$alkyl, C$_{1-3}$alkylamino-C$_{1-6}$alkoxy, cyano, C$_{1-3}$dialkylamino-C$_{1-6}$alkoxy, halo, haloC$_{1-6}$alkoxy, haloC$_{1-6}$alkyl, hydroxy, methylamino, and amino;

D is selected from

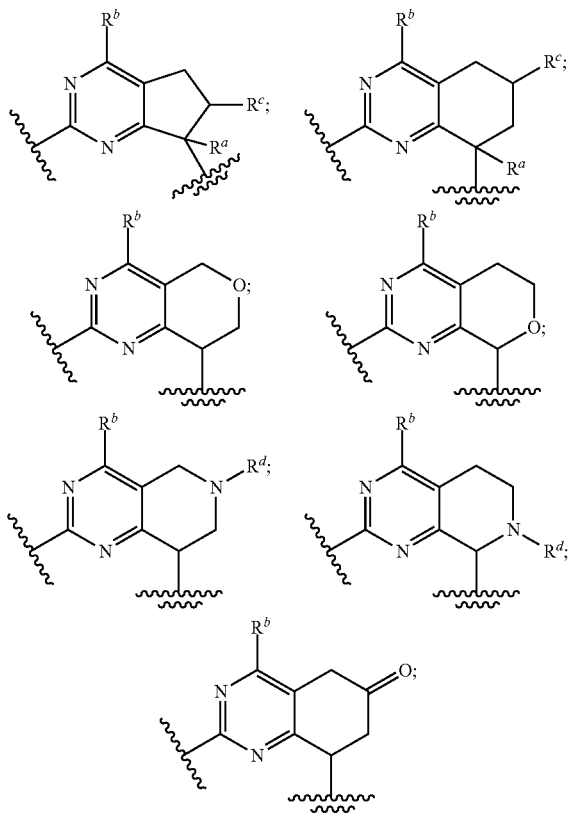

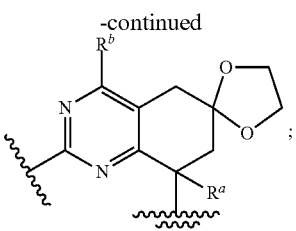

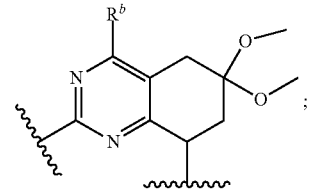

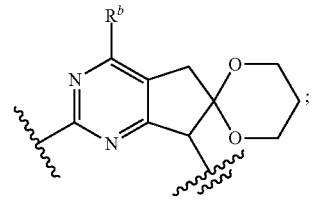

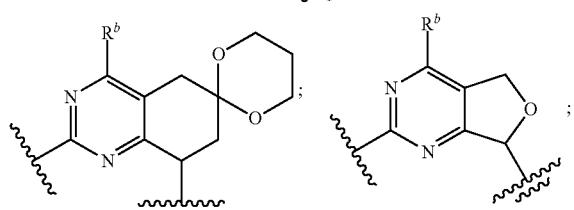

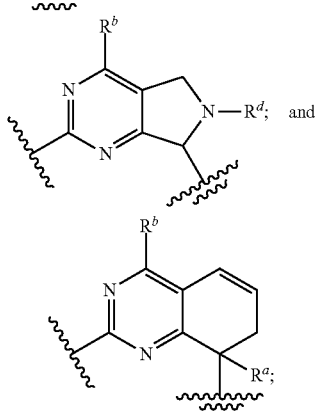

" $\xi$ " denotes the point of attachment to the nitrogen atom of the parent molecule;

" $\sim$ " denotes the point of attachment to the 'E' moiety;

R$^a$ is selected from hydrogen, C$_{1-6}$alkyl, C$_{2-6}$alkenyl, and hydroxy;

R$^b$ is —NR$^x$R$^y$, wherein R$^x$ and R$^y$ are independently selected from hydrogen, C$_{1-4}$alkoxy, C$_{1-4}$alkoxyC$_{1-4}$alkyl, C$_{1-4}$alkoxycarbonyl, C$_{1-6}$alkyl, C$_{3-7}$cycloalkyl, (C$_{3-7}$cycloalkyl)C$_{1-4}$alkyl, hydroxyC$_{1-4}$alkyl, and trideuteromethyl, wherein the alkyl part of the (C$_{3-7}$cycloalkyl)C$_{1-4}$alkyl can be optionally substituted with a C$_{1-4}$alkoxy group; or, R$^x$ and R$^y$, together with the nitrogen atom to which they are attached, form a four- to seven-membered monocyclic or bicyclic ring optionally containing one double bond and optionally containing one additional heteroatom selected from O, NR$^z$, and S; wherein R$^z$ is selected from hydrogen, C$_{1-6}$alkyl, and C$_{1-4}$alkoxycarbonyl; and wherein the ring is optionally substituted with one or two substituents independently selected from $C_{1-6}$alkoxy, $C_{1-6}$alkyl, halo, halo$C_{1-4}$alkyl, hydroxy, —NR$^f$R$^g$, oxo, spirocyclic dioxolanyl; wherein R$^f$ and R$^g$ are independently selected from hydrogen, $C_{1-4}$alkoxycarbonyl, and $C_{1-6}$alkyl;

R$^c$ is selected from hydrogen, $C_{1-4}$alkylsulfonyl, $C_{1-4}$alkylsulfonylamido, amino, $C_{1-6}$alkylamino, $C_{1-6}$dialkylamino, $C_{3-7}$cycloalkylamino, hydroxy, and $C_{1-4}$alkoxy;

R$^d$ is selected from hydrogen, $C_{1-6}$alkyl, $C_{1-4}$alkoxy$C_{1-4}$alkylcarbonyl, $C_{1-6}$alkoxycarbonyl, $C_{1-6}$alkylcarbonyl, $C_{1-6}$alkylsulfonyl, $C_{3-7}$cycloalkylsulfonyl, $C_{3-7}$cycloalkylcarbonyl, $C_{1-6}$dialkylamino$C_{1-4}$alkylcarbonyl, and halo$C_{1-4}$alkyl, wherein the alkyl part of the alkoxycarbonyl, the alkylcarbonyl, and the alkylsulfonyl are optionally substituted with one substituent selected from $C_{1-4}$dialkylamino, and $C_{1-4}$alkoxy; and E is selected from $C_{4-6}$cycloalkyl, ($C_{4-7}$cycloalkyl)$C_{1-4}$alkyl, benzyl, phenyl, and a five- to six-membered heteroaromatic ring containing one or two nitrogen atoms, wherein the phenyl, the phenyl part of the benzyl, and the heteroaromatic ring are each optionally substituted with one, two, or three substituents independently selected from $C_{1-6}$alkyl, $C_{1-6}$alkoxy, cyano, halo, halo$C_{1-6}$alkoxy, and halo$C_{1-6}$alkyl.

2. A compound of claim 1, or a pharmaceutically acceptable salt thereof, wherein A is a five-membered heteroaromatic ring containing from one to three nitrogen atoms; wherein said heteroaromatic ring is optionally substituted with one group selected from halo and $C_{1-6}$alkyl.

3. A compound of claim 2, or a pharmaceutically acceptable salt thereof, wherein B is selected from phenyl and pyridinyl, wherein the phenyl and pyridinyl are optionally substituted with one or two substituents independently selected from $C_{1-6}$alkoxy and halo.

4. A compound of claim 1, or a pharmaceutically acceptable salt thereof, wherein D is selected from

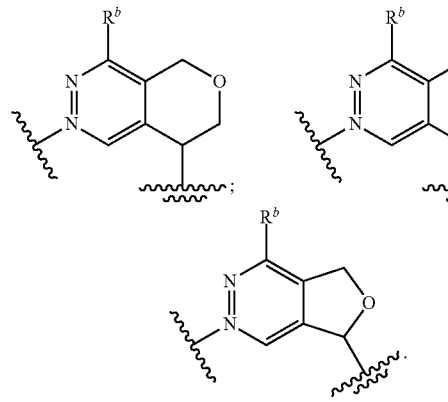

5. A compound of claim 4, or a pharmaceutically acceptable salt thereof, wherein R$^b$ is —NR$^x$R$^y$, wherein R$^x$ and R$^y$ are independently selected from hydrogen, $C_{1-4}$alkoxy$C_{1-4}$alkyl, $C_{1-6}$alkyl, $C_{3-7}$cycloalkyl, hydroxy$C_{1-4}$alkyl, and trideuteromethyl, wherein the alkyl part of the ($C_{3-7}$cycloalkyl)$C_{1-4}$alkyl can be optionally substituted with a $C_{1-4}$alkoxy group.

6. A compound of claim 4, or a pharmaceutically acceptable salt thereof, wherein R$^b$ is —NR$^x$R$^y$, wherein R$^x$ and R$^y$, together with the nitrogen atom to which they are attached, form a four- to seven-membered monocyclic or bicyclic ring optionally containing one additional heteroatom selected from O and NR$^z$; wherein R$^z$ is selected from $C_{1-6}$alkyl, and $C_{1-4}$alkoxycarbonyl; and wherein the ring is optionally substituted with one or two substituents independently selected from $C_{1-6}$alkoxy, $C_{1-6}$alkyl, halo, halo$C_{1-4}$alkyl, hydroxy, —NR$^f$R$^g$, oxo, and spirocycle dioxolanyl; wherein R$^f$ and R$^g$ are independently selected from hydrogen, $C_{1-4}$alkoxycarbonyl, and $C_{1-6}$alkyl.

7. A compound of formula (I)

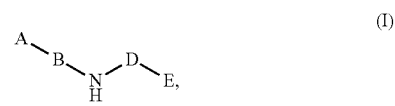

or a pharmaceutically acceptable salt thereof, wherein

A is a five-membered heteroaromatic ring containing from one to three nitrogen atoms; wherein said heteroaromatic ring is optionally substituted with one group selected from halo and $C_{1-6}$alkyl;

B is selected from phenyl and pyridinyl, wherein the phenyl and pyridinyl are optionally substituted with one or two substituents independently selected from $C_{1-6}$alkoxy and halo;

D is selected from

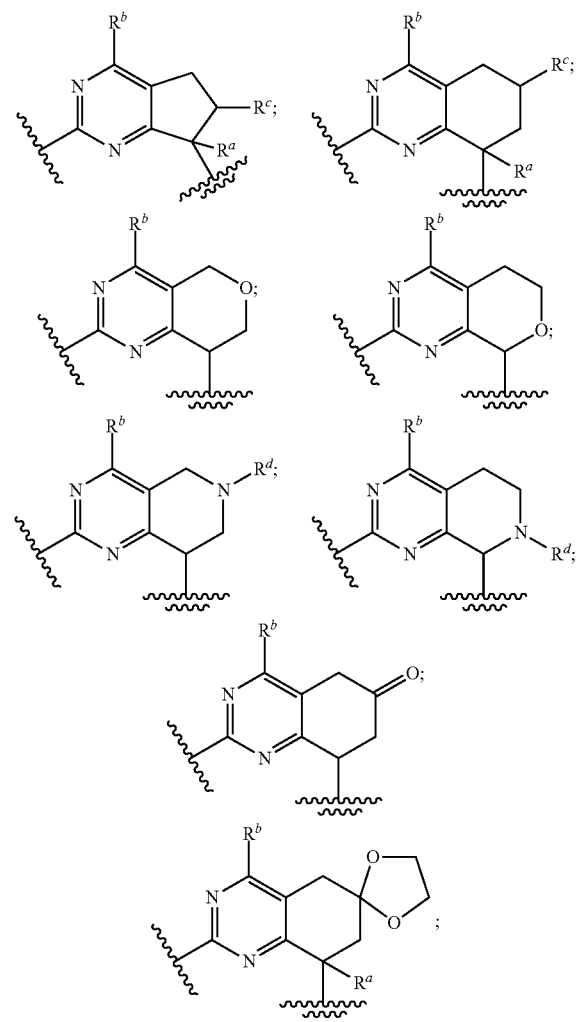

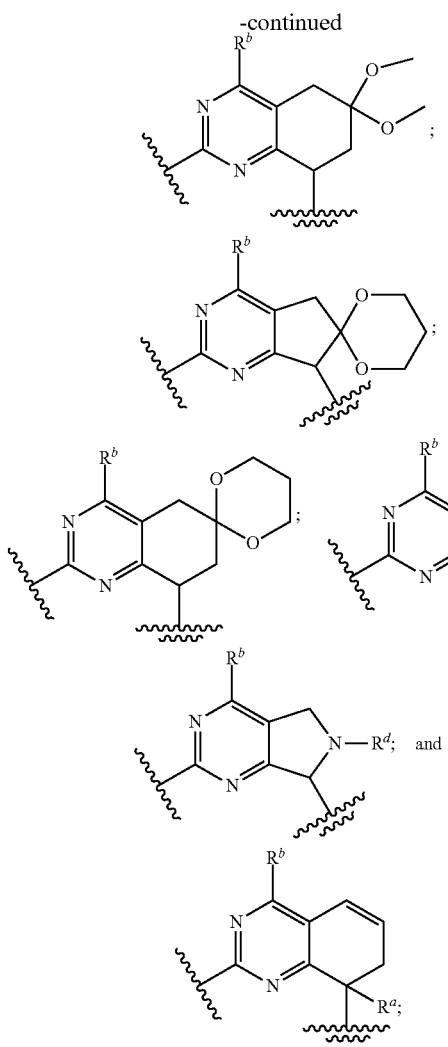

"⌇" denotes the point of attachment to the nitrogen atom of the parent molecule;

"⌇⌇" denotes the point of attachment to the 'E' moiety;

$R^a$ is selected from hydrogen, $C_{1-6}$alkyl, $C_{2-6}$alkenyl, and hydroxy;

$R^b$ is —$NR^xR^y$, wherein $R^x$ and $R^y$ are independently selected from hydrogen, $C_{1-4}$alkoxy, $C_{1-4}$alkoxy$C_{1-4}$alkyl, $C_{1-4}$alkoxycarbonyl, $C_{1-6}$alkyl, $C_{3-7}$cycloalkyl, $(C_{3-7}$cycloalkyl$)C_{1-4}$alkyl, hydroxy$C_{1-4}$alkyl, and trideuteromethyl, wherein the alkyl part of the $(C_{3-7}$cycloalkyl$)C_{1-4}$alkyl can be optionally substituted with a $C_{1-4}$alkoxy group; or, $R^x$ and $R^y$, together with the nitrogen atom to which they are attached, form a four- to seven-membered monocyclic or bicyclic ring optionally containing one double bond and optionally containing one additional heteroatom selected from O, $NR^z$, and S; wherein $R^z$ is selected from hydrogen, $C_{1-6}$alkyl, and $C_{1-4}$alkoxycarbonyl; and wherein the ring is optionally substituted with one or two substituents independently selected from $C_{1-6}$alkoxy, $C_{1-6}$alkyl, halo, halo$C_{1-4}$alkyl, hydroxy, —$NR^fR^g$, oxo, spirocyclic dioxolanyl; wherein $R^f$ and $R^g$ are independently selected from hydrogen, $C_{1-4}$alkoxycarbonyl, and $C_{1-6}$alkyl;

$R^c$ is selected from hydrogen, $C_{1-4}$alkylsulfonyl, $C_{1-4}$alkylsulfonylamido, amino, $C_{1-4}$alkylamino, $C_{1-6}$dialkylamino, $C_{3-7}$cycloalkylamino, hydroxy, and $C_{1-4}$alkoxy;

$R^d$ is selected from hydrogen, $C_{1-6}$alkyl, $C_{1-4}$alkoxy$C_{1-4}$alkylcarbonyl, $C_{1-6}$alkoxycarbonyl, $C_{1-6}$alkylcarbonyl, $C_{1-6}$alkylsulfonyl, $C_{3-7}$cycloalkylsulfonyl, $C_{3-7}$cycloalkylcarbonyl, $C_{1-6}$dialkylamino$C_{1-4}$alkylcarbonyl, and halo$C_{1-4}$alkyl, wherein the alkyl part of the alkoxycarbonyl, the alkylcarbonyl, and the alkylsulfonyl are optionally substituted with one substituent selected from $C_{1-4}$dialkylamino, and $C_{1-4}$alkoxy; and E is phenyl, wherein the phenyl is optionally substituted with one, two, or three substituents independently selected from $C_{1-6}$alkyl, $C_{1-6}$alkoxy, cyano, halo, halo $C_{1-6}$alkoxy, and halo$C_{1-6}$alkyl.

8. A compound of claim 7, or a pharmaceutically acceptable salt thereof, wherein D is selected from

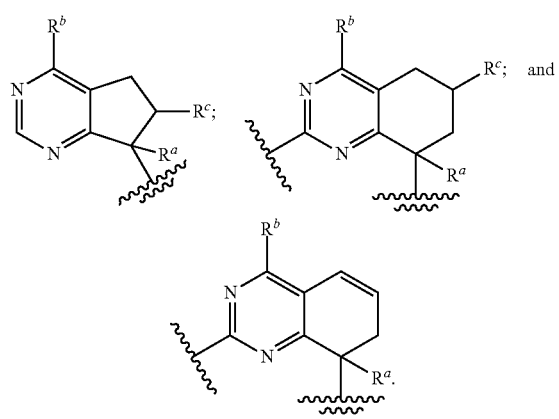

9. A compound of claim 8, or a pharmaceutically acceptable salt thereof, wherein $R^b$ is —$NR^xR^y$, wherein $R^x$ and $R^y$ are independently selected from hydrogen, $C_{1-4}$alkoxy$C_{1-4}$alkyl, $C_{1-6}$alkyl, $C_{3-7}$cycloalkyl, hydroxy$C_{1-4}$alkyl, and trideuteromethyl, wherein the alkyl part of the $(C_{3-7}$cycloalkyl$)C_{1-4}$alkyl can be optionally substituted with a $C_{1-4}$alkoxy group.

10. A compound of claim 8, or a pharmaceutically acceptable salt thereof, wherein $R^b$ is —$NR^xR^y$, wherein $R^x$ and $R^y$, together with the nitrogen atom to which they are attached, form a four- to seven-membered monocyclic or bicyclic ring optionally containing one additional heteroatom selected from O and $NR^z$; wherein $R^z$ is selected from $C_{1-6}$alkyl, and $C_{1-4}$alkoxycarbonyl; and wherein the ring is optionally substituted with one or two substituents independently selected from $C_{1-6}$alkoxy, $C_{1-6}$alkyl, halo, halo$C_{1-4}$alkyl, hydroxy, —$NR^fR^g$, oxo, and spirocycle dioxolanyl; wherein $R^f$ and $R^g$ are independently selected from hydrogen, $C_{1-4}$alkoxycarbonyl, and $C_{1-6}$alkyl.

11. A compound of claim 1, or a pharmaceutically acceptable salt thereof, wherein D is selected from

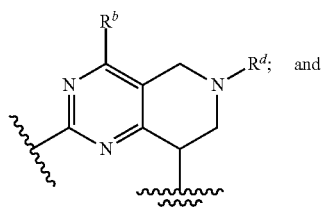

-continued

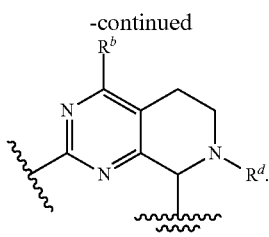

12. A compound of claim 11, or a pharmaceutically acceptable salt thereof, wherein $R^b$ is —$NR^xR^y$, wherein $R^x$ and $R^y$ are independently selected from hydrogen, $C_{1-4}$alkoxy$C_{1-4}$alkyl, $C_{1-6}$alkyl, $C_{3-7}$cycloalkyl, hydroxy$C_{1-4}$alkyl, and trideuteromethyl, wherein the alkyl part of the ($C_{3-7}$cycloalkyl)$C_{1-4}$alkyl can be optionally substituted with a $C_{1-4}$alkoxy group.

13. A compound of claim 11, or a pharmaceutically acceptable salt thereof, wherein $R^b$ is —$NR^xR^y$, wherein $R^x$ and $R^y$, together with the nitrogen atom to which they are attached, form a four- to seven-membered monocyclic or bicyclic ring optionally containing one additional heteroatom selected from O and $NR^z$; wherein $R^z$ is selected from $C_{1-6}$alkyl, and $C_{1-4}$alkoxycarbonyl; and wherein the ring is optionally substituted with one or two substituents independently selected from $C_{1-6}$alkoxy, $C_{1-6}$alkyl, halo, halo$C_{1-4}$alkyl, hydroxy, —$NR^fR^g$, oxo, and spirocycle dioxolanyl; wherein $R^f$ and $R^g$ are independently selected from hydrogen, $C_{1-4}$alkoxycarbonyl, and $C_{1-6}$alkyl.

14. A compound selected from
N2-(3-methoxy-4-(3-methyl-1H-1,2,4-triazol-1-yl)phenyl)-N4-methyl-7-phenyl-6,7-dihydro-5H-cyclopenta[d]pyrimidine-2,4-diamine;
N2-(3-fluoro-4-(3-methyl-1H-1,2,4-triazol-1-yl)phenyl)-N4-methyl-7-phenyl-6,7-dihydro-5H-cyclopenta[d]pyrimidine-2,4-diamine;
N2-(3-fluoro-4-(5-methyl-1H-1,2,4-triazol-1-yl)phenyl)-N4-methyl-7-phenyl-6,7-dihydro-5H-cyclopenta[d]pyrimidine-2,4-diamine;
$N^2$-(3-fluoro-4-(5-methyl-1H-1,2,4-triazol-1-yl)phenyl)-$N^4$-methyl-7-phenyl-6,7-dihydro-5H-cyclopenta[d]pyrimidine-2,4-diamine;
$N^2$-(3-fluoro-4-(5-methyl-1H-1,2,4-triazol-1-yl)phenyl)-$N^4$-methyl-7-phenyl-6,7-dihydro-5H-cyclopenta[d]pyrimidine-2,4-diamine;
$N^2$-(4-(4-chloro-1H-imidazol-1-yl)-3-methoxyphenyl)-$N^4$,$N^4$-dimethyl-7-phenyl-6,7-dihydro-5H-cyclopenta[d]pyrimidine-2,4-diamine;
(S)—$N^2$-(4-(4-chloro-1H-imidazol-1-yl)-3-methoxyphenyl)-$N^4$,$N^4$-dimethyl-7-phenyl-6,7-dihydro-5H-cyclopenta[d]pyrimidine-2,4-diamine;
(R)—$N^2$-(4-(4-chloro-1H-imidazol-1-yl)-3-methoxyphenyl)-$N^4$,$N^4$-dimethyl-7-phenyl-6,7-dihydro-5H-cyclopenta[d]pyrimidine-2,4-diamine;
$N^2$-(4-(4-chloro-1H-imidazol-1-yl)-3-methoxyphenyl)-$N^4$-ethyl-$N^4$-methyl-7-phenyl-6,7-dihydro-5H-cyclopenta[d]pyrimidine-2,4-diamine;
(S)—$N^2$-(4-(4-chloro-1H-imidazol-1-yl)-3-methoxyphenyl)-$N^4$-ethyl-$N^4$-methyl-7-phenyl-6,7-dihydro-5H-cyclopenta[d]pyrimidine-2,4-diamine;
(R)—$N^2$-(4-(4-chloro-1H-imidazol-1-yl)-3-methoxyphenyl)-$N^4$-ethyl-$N^4$-methyl-7-phenyl-6,7-dihydro-5H-cyclopenta[d]pyrimidine-2,4-diamine;
4-(Azetidin-1-yl)-N-(4-(4-chloro-1H-imidazol-1-yl)-3-methoxyphenyl)-7-phenyl-6,7-dihydro-5H-cyclopenta[d]pyrimidin-2-amine;
(S)-4-(Azetidin-1-yl)-N-(4-(4-chloro-1H-imidazol-1-yl)-3-methoxyphenyl)-7-phenyl-6,7-dihydro-5H-cyclopenta[d]pyrimidin-2-amine;
(R)-4-(Azetidin-1-yl)-N-(4-(4-chloro-1H-imidazol-1-yl)-3-methoxyphenyl)-7-phenyl-6,7-dihydro-5H-cyclopenta[d]pyrimidin-2-amine;
$N^2$-(4-(4-chloro-1H-imidazol-1-yl)-3-methoxyphenyl)-$N^4$-methyl-7-phenyl-6,7-dihydro-5H-cyclopenta[d]pyrimidine-2,4-diamine;
(S)—$N^2$-(4-(4-chloro-1H-imidazol-1-yl)-3-methoxyphenyl)-$N^4$-methyl-7-phenyl-6,7-dihydro-5H-cyclopenta[d]pyrimidine-2,4-diamine;
(R)—$N^2$-(4-(4-chloro-1H-imidazol-1-yl)-3-methoxyphenyl)-$N^4$-methyl-7-phenyl-6,7-dihydro-5H-cyclopenta[d]pyrimidine-2,4-diamine;
N2-(4-(4-chloro-1H-imidazol-1-yl)-3-methoxyphenyl)-N4-cyclopropyl-7-phenyl-6,7-dihydro-5H-cyclopenta[d]pyrimidine-2,4-diamine;
N2-(4-(4-chloro-1H-imidazol-1-yl)-3-methoxyphenyl)-N4-cyclobutyl-7-phenyl-6,7-dihydro-5H-cyclopenta[d]pyrimidine-2,4-diamine;
N2-(4-(4-chloro-1H-imidazol-1-yl)-3-methoxyphenyl)-N4-isopropyl-7-phenyl-6,7-dihydro-5H-cyclopenta[d]pyrimidine-2,4-diamine;
$N^2$-(4-(4-chloro-1H-imidazol-1-yl)-3-methoxyphenyl)-7-(4-fluorophenyl)-$N^4$-methyl-6,7-dihydro-5H-cyclopenta[d]pyrimidine-2,4-diamine;
(S)—$N^2$-(4-(4-chloro-1H-imidazol-1-yl)-3-methoxyphenyl)-7-(4-fluorophenyl)-$N^4$-methyl-6,7-dihydro-5H-cyclopenta[d]pyrimidine-2,4-diamine;
(R)—$N^2$-(4-(4-chloro-1H-imidazol-1-yl)-3-methoxyphenyl)-7-(4-fluorophenyl)-$N^4$-methyl-6,7-dihydro-5H-cyclopenta[d]pyrimidine-2,4-diamine;
$N^2$-(3-Fluoro-4-(5-methyl-1H-1,2,4-triazol-1-yl)phenyl)-7-(4-fluorophenyl)-$N^4$-methyl-6,7-dihydro-5H-cyclopenta[d]pyrimidine-2,4-diamine;
$N^2$-(2-Fluoro-5-methoxy-4-(3-methyl-1H-1,2,4-triazol-1-yl)phenyl)-7-(4-fluorophenyl)-$N^4$-methyl-6,7-dihydro-5H-cyclopenta[d]pyrimidine-2,4-diamine;
$N^2$-(6-(4-chloro-1H-imidazol-1-yl)-5-methoxypyridin-3yl)-7-(4-fluorophenyl)-$N^4$-methyl-6,7-dihydro-5H-cyclopenta[d]pyrimidine-2,4-diamine;
N-(4-(4-chloro-1H-imidazol-1-yl)-3-methoxyphenyl)-4-(3,3-difluoroazetidin-1-yl)-7-(4-fluorophenyl)-6,7-dihydro-5H-cyclopenta[d]pyrimidin-2-amine;
4-(3,3-difluoroazetidin-1-yl)-N-(3-fluoro-4-(5-methyl-1H-1,2,4-triazol-1-yl)phenyl)-7-(4-fluorophenyl)-6,7-dihydro-5H-cyclopenta[d]pyrimidin-2-amine;
4-(3,3-difluoroazetidin-1-yl)-N-(3-fluoro-4-(5-methyl-1H-1,2,4-triazol-1-yl)phenyl)-7-(4-fluorophenyl)-6,7-dihydro-5H-cyclopenta[d]pyrimidin-2-amine;
4-(3,3-difluoroazetidin-1-yl)-N-(3-fluoro-4-(5-methyl-1H-1,2,4-triazol-1-yl)phenyl)-7-(4-fluorophenyl)-6,7-dihydro-5H-cyclopenta[d]pyrimidin-2-amine;
N-(4-(3-chloro-1H-1,2,4-triazol-1-yl)-3-methoxyphenyl)-4-(3,3-difluoroazetidin-1-yl)-7-(4-fluorophenyl)-6,7-dihydro-5H-cyclopenta[d]pyrimidin-2-amine;
N-(4-(3-chloro-1H-1,2,4-triazol-1-yl)-3-methoxyphenyl)-4-(3,3-difluoroazetidin-1-yl)-7-(4-fluorophenyl)-6,7-dihydro-5H-cyclopenta[d]pyrimidin-2-amine;
N-(4-(3-chloro-1H-1,2,4-triazol-1-yl)-3-methoxyphenyl)-4-(3,3-difluoroazetidin-1-yl)-7-(4-fluorophenyl)-6,7-dihydro-5H-cyclopenta[d]pyrimidin-2-amine;
4-((1S,4S)-2-oxa-5-azabicyclo[2.2.1]heptan-5-yl)-N-(4-(4-chloro-1H-imidazol-1-yl)-3-methoxyphenyl)-7-(4-fluorophenyl)-6,7-dihydro-5H-cyclopenta[d]pyrimidin-2-amine;

4-((1S,4S)-2-oxa-5-azabicyclo[2.2.1]heptan-5-yl)-N-(4-(4-chloro-1H-imidazol-1-yl)-3-methoxyphenyl)-7-(4-fluorophenyl)-6,7-dihydro-5H-cyclopenta[d]pyrimidin-2-amine;

4-((1S,4S)-2-oxa-5-azabicyclo[2.2.1]heptan-5-yl)-N-(4-(4-chloro-1H-imidazol-1-yl)-3-methoxyphenyl)-7-(4-fluorophenyl)-6,7-dihydro-5H-cyclopenta[d]pyrimidin-2-amine;

N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine;

N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine;

N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine;

N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine;

N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine;

N-(4-(4-chloro-1H-imidazol-1-yl)-3-methoxyphenyl)-7-(4-fluorophenyl)-4-(2-methylpyrrolidin-1-yl)-6,7-dihydro-5H-cyclopenta[d]pyrimidin-2-amine;

N-(4-(4-chloro-1H-imidazol-1-yl)-3-methoxyphenyl)-4-((2S,6R)-2,6-dimethylmorpholino)-7-(4-fluorophenyl)-6,7-dihydro-5H-cyclopenta[d]pyrimidin-2-amine;

N-(4-(4-chloro-1H-imidazol-1-yl)-3-methoxyphenyl)-4-((2S,6R)-2,6-dimethylmorpholino)-7-(4-fluorophenyl)-6,7-dihydro-5H-cyclopenta[d]pyrimidin-2-amine;

N-(4-(4-chloro-1H-imidazol-1-yl)-3-methoxyphenyl)-4-((2S,6R)-2,6-dimethylmorpholino)-7-(4-fluorophenyl)-6,7-dihydro-5H-cyclopenta[d]pyrimidin-2-amine;

1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-4-methylpiperidin-4-ol;

N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine;

N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine;

N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine;

N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine;

N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine;

N-(4-(4-chloro-1H-imidazol-1-yl)-3-methoxyphenyl)-4-(2-ethylpyrrolidin-1-yl)-7-(4-fluorophenyl)-6,7-dihydro-5H-cyclopenta[d]pyrimidin-2-amine;

4-(4-amino-4-methylpiperidin-1-yl)-N-(4-(4-chloro-1H-imidazol-1-yl)-3-methoxyphenyl)-7-(4-fluorophenyl)-6,7-dihydro-5H-cyclopenta[d]pyrimidin-2-amine;

$N^2$-(3-fluoro-4-(5-methyl-1H-1,2,4-triazol-1-yl)phenyl)-7-(4-fluorophenyl)-$N^4$-methyl-6,7-dihydro-5H-cyclopenta[d]pyrimidine-2,4-diamine;

$N^2$-(3-fluoro-4-(5-methyl-1H-1,2,4-triazol-1-yl)phenyl)-7-(4-fluorophenyl)-$N^4$-methyl-6,7-dihydro-5H-cyclopenta[d]pyrimidine-2,4-diamine;

$N^2$-(3-fluoro-4-(5-methyl-1H-1,2,4-triazol-1-yl)phenyl)-7-(4-fluorophenyl)-$N^4$-methyl-6,7-dihydro-5H-cyclopenta[d]pyrimidine-2,4-diamine;

1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-3-(trifluoromethyl)pyrrolidin-3-ol;

1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-3-(trifluoromethyl)pyrrolidin-3-ol;

1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-3-(trifluoromethyl)pyrrolidin-3-ol;

1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-3-(trifluoromethyl)pyrrolidin-3-ol;

N-(4-(4-chloro-1H-imidazol-1-yl)-3-methoxyphenyl)-4-(3-(dimethylamino)pyrrolidin-1-yl)-7-(4-fluorophenyl)-6,7-dihydro-5H-cyclopenta[d]pyrimidin-2-amine;

N-(4-(4-chloro-1H-imidazol-1-yl)-3-methoxyphenyl)-4-(3-(dimethylamino)pyrrolidin-1-yl)-7-(4-fluorophenyl)-6,7-dihydro-5H-cyclopenta[d]pyrimidin-2-amine;

N-(4-(4-chloro-1H-imidazol-1-yl)-3-methoxyphenyl)-4-(3-(dimethylamino)pyrrolidin-1-yl)-7-(4-fluorophenyl)-6,7-dihydro-5H-cyclopenta[d]pyrimidin-2-amine;

N-(4-(4-chloro-1H-imidazol-1-yl)-3-methoxyphenyl)-7-(4-fluorophenyl)-4-(4-methylpiperazin-1-yl)-6,7-dihydro-5H-cyclopenta[d]pyrimidin-2-amine;

N-(4-(4-chloro-1H-imidazol-1-yl)-3-methoxyphenyl)-7-(4-fluorophenyl)-4-(4-methylpiperazin-1-yl)-6,7-dihydro-5H-cyclopenta[d]pyrimidin-2-amine;

N-(4-(4-chloro-1H-imidazol-1-yl)-3-methoxyphenyl)-7-(4-fluorophenyl)-4-(4-methylpiperazin-1-yl)-6,7-dihydro-5H-cyclopenta[d]pyrimidin-2-amine;

N-(4-(4-chloro-1H-imidazol-1-yl)-3-methoxyphenyl)-7-(4-fluorophenyl)-4-(piperazin-1-yl)-6,7-dihydro-5H-cyclopenta[d]pyrimidin-2-amine;

N-(4-(4-chloro-1H-imidazol-1-yl)-3-methoxyphenyl)-7-(4-fluorophenyl)-4-(3-(methylamino)pyrrolidin-1-yl)-6,7-dihydro-5H-cyclopenta[d]pyrimidin-2-amine;

N-(4-(4-chloro-1H-imidazol-1-yl)-3-methoxyphenyl)-7-(4-fluorophenyl)-4-(3-(methylamino)azetidin-1-yl)-6,7-dihydro-5H-cyclopenta[d]pyrimidin-2-amine;

N-(4-(4-chloro-1H-imidazol-1-yl)-3-methoxyphenyl)-4-(3-(dimethylamino)azetidin-1-yl)-7-(4-fluorophenyl)-6,7-dihydro-5H-cyclopenta[d]pyrimidin-2-amine;

$N^2$-(3-fluoro-4-(3-methyl-1H-1,2,4-triazol-1-yl)phenyl)-7-(4-fluorophenyl)-$N^4$-methyl-6,7-dihydro-5H-cyclopenta[d]pyrimidine-2,4-diamine;

N-(4-(4-chloro-1H-imidazol-1-yl)-3-methoxyphenyl)-7-(4-fluorophenyl)-4-((S)-3-fluoropyrrolidin-1-yl)-6,7-dihydro-5H-cyclopenta[d]pyrimidin-2-amine;

N-(4-(4-chloro-1H-imidazol-1-yl)-3-methoxyphenyl)-7-(4-fluorophenyl)-4-((S)-3-fluoropyrrolidin-1-yl)-6,7-dihydro-5H-cyclopenta[d]pyrimidin-2-amine;

N-(4-(4-chloro-1H-imidazol-1-yl)-3-methoxyphenyl)-7-(4-fluorophenyl)-4-((R)-3-fluoropyrrolidin-1-yl)-6,7-dihydro-5H-cyclopenta[d]pyrimidin-2-amine;

N-(4-(4-chloro-1H-imidazol-1-yl)-3-methoxyphenyl)-7-(4-fluorophenyl)-4-((R)-3-fluoropyrrolidin-1-yl)-6,7-dihydro-5H-cyclopenta[d]pyrimidin-2-amine);

N-(4-(4-chloro-1H-imidazol-1-yl)-3-methoxyphenyl)-4-(4,4-difluoropiperidin-1-yl)-7-(4-fluorophenyl)-6,7-dihydro-5H-cyclopenta[d]pyrimidin-2-amine;

N-(4-(4-chloro-1H-imidazol-1-yl)-3-methoxyphenyl)-4-(4-fluoro-5,6-dihydropyridin-1(2H)-yl)-7-(4-fluorophenyl)-6,7-dihydro-5H-cyclopenta[d]pyrimidin-2-amine;

N-(4-(4-chloro-1H-imidazol-1-yl)-3-methoxyphenyl)-7-(4-fluorophenyl)-4-(3-(trifluoromethyl)pyrrolidin-1-yl)-6,7-dihydro-5H-cyclopenta[d]pyrimidin-2-amine;

N2-(4-(4-chloro-1H-imidazol-1-yl)-3-methoxyphenyl)-N4-(3-ethoxypropyl)-7-(4-fluorophenyl)-6,7-dihydro-5H-cyclopenta[d]pyrimidine-2,4-diamine;

3-(2-(4-(4-chloro-1H-imidazol-1-yl)-3-methoxyphenylamino)-7-(4-fluorophenyl)-6,7-dihydro-5H-cyclopenta[d]pyrimidin-4-ylamino)propan-1-ol;

7-(4-fluorophenyl)-N2-(3-methoxy-4-(3-methyl-1H-1,2,4-triazol-1-yl)phenyl)-N4-methyl-6,7-dihydro-5H-cyclopenta[d]pyrimidine-2,4-diamine;

N2-(4-(4-chloro-1H-imidazol-1-yl)-3-methoxyphenyl)-N4-(1-cyclopropyl-2-methoxyethyl)-7-(4-fluorophenyl)-6,7-dihydro-5H-cyclopenta[d]pyrimidine-2,4-diamine;

$N^2$-(4-(4-chloro-1H-imidazol-1-yl)-3-methoxyphenyl)-7-(4-fluorophenyl)-$N^4$,$N^4$-dimethyl-6,7-dihydro-5H-cyclopenta[d]pyrimidine-2,4-diamine;

(S)—$N^2$-(4-(4-chloro-1H-imidazol-1-yl)-3-methoxyphenyl)-7-(4-fluorophenyl)-$N^4$,$N^4$-dimethyl-6,7-dihydro-5H-cyclopenta[d]pyrimidine-2,4-diamine;

(R)—$N^2$-(4-(4-chloro-1H-imidazol-1-yl)-3-methoxyphenyl)-7-(4-fluorophenyl)-$N^4$,$N^4$-dimethyl-6,7-dihydro-5H-cyclopenta[d]pyrimidine-2,4-diamine;

$N^2$-(4-(4-chloro-1H-imidazol-1-yl)-3-methoxyphenyl)-7-(4-fluorophenyl)-$N^4$-trideuteromethyl-6,7-dihydro-5H-cyclopenta[d]pyrimidine-2,4-diamine;

N2-(4-(4-chloro-1H-imidazol-1-yl)-3-methoxyphenyl)-7-(4-fluorophenyl)-N4-((R)-1-methoxybutan-2-yl)-6,7-dihydro-5H-cyclopenta[d]pyrimidine-2,4-diamine;

N2-(4-(4-chloro-1H-imidazol-1-yl)-3-methoxyphenyl)-N4-((R)-1-cyclopropylethyl)-7-(4-fluorophenyl)-6,7-dihydro-5H-cyclopenta[d]pyrimidine-2,4-diamine;

N2-(4-(4-chloro-1H-imidazol-1-yl)-3-methoxyphenyl)-N4-((S)-1-cyclopropylethyl)-7-(4-fluorophenyl)-6,7-dihydro-5H-cyclopenta[d]pyrimidine-2,4-diamine;

$N^2$-(4-(4-chloro-1H-imidazol-1-yl)-3-methoxyphenyl)-$N^4$-methyl-8-phenyl-7,8-dihydro-5H-pyrano[4,3-d]pyrimidine-2,4-diamine;

$N^2$-(4-(4-chloro-1H-imiazol-1-yl)-3-methoxyphenyl)-$N^4$-methyl-8-phenyl-7,8-dihydro-5H-pyrano[4,3-d]pyrimidine-2,4-diamine;

$N^2$-(4-(4-chloro-1H-imiazol-1-yl)-3-methoxyphenyl)-$N^4$-methyl-8-phenyl-7,8-dihydro-5H-pyrano[4,3-d]pyrimidine-2,4-diamine;

$N^2$-(4-(4-chloro-1H-imidazol-1-yl)-3-methoxyphenyl)-$N^4$-ethyl-$N^4$-methyl-8-phenyl-7,8-dihydro-5H-pyrano[4,3-d]pyrimidine-2,4-diamine;

(S)—$N^2$-(4-(4-chloro-1H-imidazol-1-yl)-3-methoxyphenyl)-$N^4$-ethyl-$N^4$-methyl-8-phenyl-7,8-dihydro-5H-pyrano[4,3-d]pyrimidine-2,4-diamine;

(R)—$N^2$-(4-(4-chloro-1H-imidazol-1-yl)-3-methoxyphenyl)-$N^4$-ethyl-$N^4$-methyl-8-phenyl-7,8-dihydro-5H-pyrano[4,3-d]pyrimidine-2,4-diamine;

$N^2$-(4-(4-chloro-1H-imidazol-1-yl)-3-methoxyphenyl)-$N^4$,$N^4$-dimethyl-8-phenyl-7,8-dihydro-5H-pyrano[4,3-d]pyrimidine-2,4-diamine;

(S)—$N^2$-(4-(4-chloro-1H-imidazol-1-yl)-3-methoxyphenyl)-$N^4$,$N^4$-dimethyl-8-phenyl-7,8-dihydro-5H-pyrano[4,3-d]pyrimidine-2,4-diamine;

(R)—$N^2$-(4-(4-chloro-1H-imidazol-1-yl)-3-methoxyphenyl)-$N^4$,$N^4$-dimethyl-8-phenyl-7,8-dihydro-5H-pyrano[4,3-d]pyrimidine-2,4-diamine;

8-(4-fluorophenyl)-N2-(3-methoxy-4-(3-methyl-1H-1,2,4-triazol-1-yl)phenyl)-N4-methyl-7,8-dihydro-5H-pyrano[4,3-d]pyrimidine-2,4-diamine;

N4-ethyl-8-(4-fluorophenyl)-N2-(3-methoxy-4-(3-methyl-1H-1,2,4-triazol-1-yl)phenyl)-7,8-dihydro-5H-pyrano[4,3-d]pyrimidine-2,4-diamine;

N2-(4-(4-chloro-1H-imidazol-1-yl)-3-methoxyphenyl)-N4-ethyl-8-(4-fluorophenyl)-7,8-dihydro-5H-pyrano[4,3-d]pyrimidine-2,4-diamine;

N-(4-(4-chloro-1H-imidazol-1-yl)-3-methoxyphenyl)-8-(4-fluorophenyl)-4-((R)-3-fluoropyrrolidin-1-yl)-7,8-dihydro-5H-pyrano[4,3-d]pyrimidin-2-amine;

N-(4-(4-chloro-1H-imidazol-1-yl)-3-methoxyphenyl)-8-(4-fluorophenyl)-4-((R)-3-fluoropyrrolidin-1-yl)-7,8-dihydro-5H-pyrano[4,3-d]pyrimidin-2-amine;

N-(4-(4-chloro-1H-imidazol-1-yl)-3-methoxyphenyl)-8-(4-fluorophenyl)-4-((S)-3-fluoropyrrolidin-1-yl)-7,8-dihydro-5H-pyrano[4,3-d]pyrimidin-2-amine;

N-(4-(4-chloro-1H-imidazol-1-yl)-3-methoxyphenyl)-8-(4-fluorophenyl)-4-((S)-3-fluoropyrrolidin-1-yl)-7,8-dihydro-5H-pyrano[4,3-d]pyrimidin-2-amine;

N4-ethyl-N2-(3-fluoro-4-(5-methyl-1H-1,2,4-triazol-1-yl)phenyl)-8-(4-fluorophenyl)-7,8-dihydro-5H-pyrano[4,3-d]pyrimidine-2,4-diamine;

N2-(4-(4-chloro-1H-imidazol-1-yl)-3-methoxyphenyl)-8-(4-fluorophenyl)-N4-methyl-7,8-dihydro-5H-pyrano[4,3-d]pyrimidine-2,4-diamine;

N2-(4-(4-chloro-1H-imidazol-1-yl)-3-methoxyphenyl)-8-(4-fluorophenyl)-N4,N4-dimethyl-7,8-dihydro-5H-pyrano[4,3-d]pyrimidine-2,4-diamine;

N2-(4-(4-chloro-1H-imidazol-1-yl)-3-methoxyphenyl)-N4-ethyl-8-(4-fluorophenyl)-N4-methyl-7,8-dihydro-5H-pyrano[4,3-d]pyrimidine-2,4-diamine;

N-(4-(4-chloro-1H-imidazol-1-yl)-3-methoxyphenyl)-4-(3,3-difluoroazetidin-1-yl)-8-(4-fluorophenyl)-7,8-dihydro-5H-pyrano[4,3-d]pyrimidin-2-amine;

$N^2$-(4-(4-chloro-1H-imidazol-1-yl)-3-methoxyphenyl)-8-(4-chlorophenyl)-$N^4$-methyl-7,8-dihydro-5H-pyrano[4,3-d]pyrimidine-2,4-diamine;

$N^2$-(4-(4-chloro-1H-imidazol-1-yl)-3-methoxyphenyl)-8-(4-chlorophenyl)-$N^4$-methyl-7,8-dihydro-5H-pyrano[4,3-d]pyrimidine-2,4-diamine;

$N^2$-(4-(4-chloro-1H-imidazol-1-yl)-3-methoxyphenyl)-8-(4-chlorophenyl)-$N^4$-methyl-7,8-dihydro-5H-pyrano[4,3-d]pyrimidine-2,4-diamine;

$N^2$-(4-(4-chloro-1H-imidazol-1-yl)-3-methoxyphenyl)-8-(4-chlorophenyl)-$N^4$,$N^4$-dimethyl-7,8-dihydro-5H-pyrano[4,3-d]pyrimidine-2,4-diamine;

$N^2$-(4-(4-chloro-1H-imidazol-1-yl)-3-methoxyphenyl)-8-(4-chlorophenyl)-$N^4$,$N^4$-dimethyl-7,8-dihydro-5H-pyrano[4,3-d]pyrimidine-2,4-diamine;

$N^2$-(4-(4-chloro-1H-imidazol-1-yl)-3-methoxyphenyl)-8-(4-chlorophenyl)-$N^4$,$N^4$-dimethyl-7,8-dihydro-5H-pyrano[4,3-d]pyrimidine-2,4-diamine;

N-(4-(4-chloro-1H-imidazol-1-yl)-3-methoxyphenyl)-8-(4-chlorophenyl)-4-(3,3-difluoroazetidin-1-yl)-7,8-dihydro-5H-pyrano[4,3-d]pyrimidin-2-amine;

N-(4-(4-chloro-1H-imidazol-1-yl)-3-methoxyphenyl)-8-(4-chlorophenyl)-4-(3,3-difluoroazetidin-1-yl)-7,8-dihydro-5H-pyrano[4,3-d]pyrimidin-2-amine;

N-(4-(4-chloro-1H-imidazol-1-yl)-3-methoxyphenyl)-8-(4-chlorophenyl)-4-(3,3-difluoroazetidin-1-yl)-7,8-dihydro-5H-pyrano[4,3-d]pyrimidin-2-amine;

8-(4-chlorophenyl)-$N^2$-(3-fluoro-4-(5-methyl-1H-1,2,4-triazol-1-yl)phenyl)-$N^4$,$N^4$-dimethyl-7,8-dihydro-5H-pyrano[4,3-d]pyrimidine-2,4-diamine;

8-(4-chlorophenyl)-$N^2$-(3-fluoro-4-(5-methyl-1H-1,2,4-triazol-1-yl)phenyl)-$N^4$,$N^4$-dimethyl-7,8-dihydro-5H-pyrano[4,3-d]pyrimidine-2,4-diamine;

8-(4-chlorophenyl)-$N^2$-(3-fluoro-4-(5-methyl-1H-1,2,4-triazol-1-yl)phenyl)-$N^4$,$N^4$-dimethyl-7,8-dihydro-5H-pyrano[4,3-d]pyrimidine-2,4-diamine;

8-(4-chlorophenyl)-4-(3,3-difluoroazetidin-1-yl)-N-(3-fluoro-4-(5-methyl-1H-1,2,4-triazol-1-yl)phenyl)-7,8-dihydro-5H-pyrano[4,3-d]pyrimidin-2-amine;

8-(4-chlorophenyl)-$N^2$-(3-fluoro-4-(5-methyl-1H-1,2,4-triazol-1-yl)phenyl)-$N^4$-methyl-7,8-dihydro-5H-pyrano[4,3-d]pyrimidine-2,4-diamine;

8-(4-chlorophenyl)-$N^2$-(3-fluoro-4-(5-methyl-1H-1,2,4-triazol-1-yl)phenyl)-$N^4$-methyl-7,8-dihydro-5H-pyrano[4,3-d]pyrimidine-2,4-diamine;

8-(4-chlorophenyl)-$N^2$-(3-fluoro-4-(5-methyl-1H-1,2,4-triazol-1-yl)phenyl)-$N^4$-methyl-7,8-dihydro-5H-pyrano[4,3-d]pyrimidine-2,4-diamine;

8-(4-chlorophenyl)-$N^2$-(3-methoxy-4-(4-methyl-1H-imidazol-1-yl)phenyl)-$N^4$-methyl-7,8-dihydro-5H-pyrano[4,3-d]pyrimidine-2,4-diamine;

8-(4-chlorophenyl)-$N^2$-(3-methoxy-4-(4-methyl-1H-imidazol-1-yl)phenyl)-$N^4$-methyl-7,8-dihydro-5H-pyrano[4,3-d]pyrimidine-2,4-diamine;

8-(4-chlorophenyl)-$N^2$-(3-methoxy-4-(4-methyl-1H-imidazol-1-yl)phenyl)-$N^4$-methyl-7,8-dihydro-5H-pyrano[4,3-d]pyrimidine-2,4-diamine;

8-(4-chlorophenyl)-$N^2$-(3-methoxy-4-(3-methyl-1H-1,2,4-triazol-1-yl)phenyl)-$N^4$-methyl-7,8-dihydro-5H-pyrano[4,3-d]pyrimidine-2,4-diamine;

8-(4-chlorophenyl)-$N^2$-(3-methoxy-4-(3-methyl-1H-1,2,4-triazol-1-yl)phenyl)-$N^4$-methyl-7,8-dihydro-5H-pyrano[4,3-d]pyrimidine-2,4-diamine;

8-(4-chlorophenyl)-$N^2$-(3-methoxy-4-(3-methyl-1H-1,2,4-triazol-1-yl)phenyl)-$N^4$-methyl-7,8-dihydro-5H-pyrano[4,3-d]pyrimidine-2,4-diamine;

8-(4-bromophenyl)-$N^2$-(4-(4-chloro-1H-imidazol-1-yl)-3-methoxyphenyl)-$N^4$-methyl-7,8-dihydro-5H-pyrano[4,3-d]pyrimidine-2,4-diamine;

8-(4-bromophenyl)-$N^2$-(3-fluoro-4-(5-methyl-1H-1,2,4-triazol-1-yl)phenyl)-$N^4$-methyl-7,8-dihydro-5H-pyrano[4,3-d]pyrimidine-2,4-diamine;

N-(4-(4-chloro-1H-imidazol-1-yl)-3-methoxyphenyl)-7-(4-fluorophenyl)-4-((S)-2-methylpyrrolidin-1-yl)-5,7-dihydrofuro[3,4-d]pyrimidin-2-amine;

$N^2$-(4-(4-chloro-1H-imidazol-1-yl)-3-methoxyphenyl)-$N^4$-ethyl-7-(4-fluorophenyl)-5,7-dihydrofuro[3,4-d]pyrimidine-2,4-diamine;

$N^2$-(4-(4-chloro-1H-imidazol-1-yl)-3-methoxyphenyl)-$N^4$-ethyl-7-(4-fluorophenyl)-5,7-dihydrofuro[3,4-d]pyrimidine-2,4-diamine;

$N^2$-(4-(4-chloro-1H-imidazol-1-yl)-3-methoxyphenyl)-$N^4$-ethyl-7-(4-fluorophenyl)-5,7-dihydrofuro[3,4-d]pyrimidine-2,4-diamine;

N-(4-(4-chloro-1H-imidazol-1-yl)-3-methoxyphenyl)-7-(4-fluorophenyl)-4-((S)-3-fluoropyrrolidin-1-yl)-5,7-dihydrofuro[3,4-d]pyrimidin-2-amine;

N-(4-(4-chloro-1H-imidazol-1-yl)-3-methoxyphenyl)-7-(4-fluorophenyl)-4-((S)-3-fluoropyrrolidin-1-yl)-5,7-dihydrofuro[3,4-d]pyrimidin-2-amine;

$N^4$-ethyl-$N^2$-(3-fluoro-4-(5-methyl-1H-1,2,4-triazol-1-yl)phenyl)-7-(4-fluorophenyl)-5,7-dihydrofuro[3,4-d]pyrimidine-2,4-diamine;

$N^4$-ethyl-$N^2$-(3-fluoro-4-(5-methyl-1H-1,2,4-triazol-1-yl)phenyl)-7-(4-fluorophenyl)-5,7-dihydrofuro[3,4-d]pyrimidine-2,4-diamine;

$N^4$-ethyl-$N^2$-(3-fluoro-4-(5-methyl-1H-1,2,4-triazol-1-yl)phenyl)-7-(4-fluorophenyl)-5,7-dihydrofuro[3,4-d]pyrimidine-2,4-diamine;

$N^2$-(4-(4-chloro-1H-imidazol-1-yl)-3-methoxyphenyl)-7-(4-fluorophenyl)-$N^4$-methyl-5,7-dihydrofuro[3,4-d]pyrimidine-2,4-diamine;

$N^2$-(4-(4-chloro-1H-imidazol-1-yl)-3-methoxyphenyl)-7-(4-fluorophenyl)-$N^4$-methyl-5,7-dihydrofuro[3,4-d]pyrimidine-2,4-diamine;

N-(4-(4-chloro-1H-imidazol-1-yl)-3-methoxyphenyl)-4-(3,3-difluoroazetidin-1-yl)-7-(4-fluorophenyl)-5,7-dihydrofuro[3,4-d]pyrimidin-2-amine;

N2-(4-(4-chloro-1H-imidazol-1-yl)-3-methoxyphenyl)-N4-((R)-1-cyclopropylethyl)-7-(4-fluorophenyl)-5,7-dihydrofuro[3,4-d]pyrimidine-2,4-diamine;

N2-(3-fluoro-4-(5-methyl-1H-1,2,4-triazol-1-yl)phenyl)-7-(4-fluorophenyl)-N4-methyl-5,7-dihydrofuro[3,4-d]pyrimidine-2,4-diamine;

N-(4-(4-chloro-1H-imidazol-1-yl)-3-methoxyphenyl)-7-(4-fluorophenyl)-4-((R)-3-fluoropyrrolidin-1-yl)-5,7-dihydrofuro[3,4-d]pyrimidin-2-amine;

N-(4-(4-chloro-1H-imidazol-1-yl)-3-methoxyphenyl)-4-((2S,6R)-2,6-dimethylmorpholino)-7-(4-fluorophenyl)-5,7-dihydrofuro[3,4-d]pyrimidin-2-amine;

N2-(4-(4-chloro-1H-imidazol-1-yl)-3-methoxyphenyl)-N4-methyl-8-phenyl-6,8-dihydro-5H-pyrano[3,4-d]pyrimidine-2,4-diamine;

N2-(3-fluoro-4-(3-methyl-1H-1,2,4-triazol-1-yl)phenyl)-N4-methyl-8-phenyl-6,8-dihydro-5H-pyrano[3,4-d]pyrimidine-2,4-diamine;

N2-(3-fluoro-4-(5-methyl-1H-1,2,4-triazol-1-yl)phenyl)-N4-methyl-8-phenyl-6,8-dihydro-5H-pyrano[3,4-d]pyrimidine-2,4-diamine;

N2-(4-(4-chloro-1H-imidazol-1-yl)-3-methoxyphenyl)-N4-ethyl-8-(4-fluorophenyl)-6,8-dihydro-5H-pyrano[3,4-d]pyrimidine-2,4-diamine;

N2-(4-(4-chloro-1H-imidazol-1-yl)-3-methoxyphenyl)-N4-ethyl-8-(4-fluorophenyl)-N4-methyl-6,8-dihydro-5H-pyrano[3,4-d]pyrimidine-2,4-diamine;

N-(4-(4-chloro-1H-imidazol-1-yl)-3-methoxyphenyl)-8-(4-fluorophenyl)-4-((R)-3-fluoropyrrolidin-1-yl)-6,8-dihydro-5H-pyrano[3,4-d]pyrimidin-2-amine;

N-(4-(4-chloro-1H-imidazol-1-yl)-3-methoxyphenyl)-8-(4-fluorophenyl)-4-((R)-3-fluoropyrrolidin-1-yl)-6,8-dihydro-5H-pyrano[3,4-d]pyrimidin-2-amine;

N-(4-(4-chloro-1H-imidazol-1-yl)-3-methoxyphenyl)-8-(4-fluorophenyl)-4-((S)-3-fluoropyrrolidin-1-yl)-6,8-dihydro-5H-pyrano[3,4-d]pyrimidin-2-amine;

N-(4-(4-chloro-1H-imidazol-1-yl)-3-methoxyphenyl)-8-(4-fluorophenyl)-4-((S)-3-fluoropyrrolidin-1-yl)-6,8-dihydro-5H-pyrano[3,4-d]pyrimidin-2-amine;

$N^2$-(4-(4-chloro-1H-imidazol-1-yl)-3-methoxyphenyl)-7-(4-chlorophenyl)-$N^4$,$N^4$-dimethyl-6,7-dihydro-5H-cyclopenta[d]pyrimidine-2,4-diamine;

N-(4-(4-chloro-1H-imidazol-1-yl)-3-methoxyphenyl)-7-(4-chlorophenyl)-4-(3,3-difluoroazetidin-1-yl)-6,7-dihydro-5H-cyclopenta[d]pyrimidin-2-amine;

$N^2$-(4-(4-chloro-1H-imidazol-1-yl)-3-methoxyphenyl)-7-(4-chlorophenyl)-$N^4$-methyl-6,7-dihydro-5H-cyclopenta[d]pyrimidine-2,4-diamine;

(S)—$N^2$-(4-(4-chloro-1H-imidazol-1-yl)-3-methoxyphenyl)-7-(4-chlorophenyl)-$N^4$-methyl-6,7-dihydro-5H-cyclopenta[d]pyrimidine-2,4-diamine;

(R)—N²-(4-(4-chloro-1H-imidazol-1-yl)-3-methoxyphenyl)-7-(4-chlorophenyl)-N⁴-methyl-6,7-dihydro-5H-cyclopenta[d]pyrimidine-2,4-diamine;

N²-(4-(4-chloro-1H-imidazol-1-yl)-3-methoxyphenyl)-7-(3,4-difluorophenyl)-N⁴,N⁴-dimethyl-6,7-dihydro-5H-cyclopenta[d]pyrimidine-2,4-diamine;

(S)—N²-(4-(4-chloro-1H-imidazol-1-yl)-3-methoxyphenyl)-7-(3,4-difluorophenyl)-N⁴,N⁴-dimethyl-6,7-dihydro-5H-cyclopenta[d]pyrimidine-2,4-diamine;

(R)—N²-(4-(4-chloro-1H-imidazol-1-yl)-3-methoxyphenyl)-7-(3,4-difluorophenyl)-N⁴,N⁴-dimethyl-6,7-dihydro-5H-cyclopenta[d]pyrimidine-2,4-diamine;

N²-(4-(4-chloro-1H-imidazol-1-yl)-3-methoxyphenyl)-7-(3,4-difluorophenyl)-N⁴-methyl-6,7-dihydro-5H-cyclopenta[d]pyrimidine-2,4-diamine;

(S)—N²-(4-(4-chloro-1H-imidazol-1-yl)-3-methoxyphenyl)-7-(3,4-difluorophenyl)-N⁴-methyl-6,7-dihydro-5H-cyclopenta[d]pyrimidine-2,4-diamine;

(R)—N²-(4-(4-chloro-1H-imidazol-1-yl)-3-methoxyphenyl)-7-(3,4-difluorophenyl)-N⁴-methyl-6,7-dihydro-5H-cyclopenta[d]pyrimidine-2,4-diamine;

N²-(4-(4-chloro-1H-imidazol-1-yl)-3-methoxyphenyl)-N⁴-methyl-7-(4-(trifluoromethoxy)phenyl)-6,7-dihydro-5H-cyclopenta[d]pyrimidine-2,4-diamine;

(S)—N²-(4-(4-chloro-1H-imidazol-1-yl)-3-methoxyphenyl)-N⁴-methyl-7-(4-(trifluoromethoxy)phenyl)-6,7-dihydro-5H-cyclopenta[d]pyrimidine-2,4-diamine;

(R)—N²-(4-(4-chloro-1H-imidazol-1-yl)-3-methoxyphenyl)-N⁴-methyl-7-(4-(trifluoromethoxy)phenyl)-6,7-dihydro-5H-cyclopenta[d]pyrimidine-2,4-diamine;

N²-(4-(4-chloro-1H-imidazol-1-yl)-3-methoxyphenyl)-N⁴-ethyl-7-(4-(trifluoromethoxy)phenyl)-6,7-dihydro-5H-cyclopenta[d]pyrimidine-2,4-diamine;

(S)—N²-(4-(4-chloro-1H-imidazol-1-yl)-3-methoxyphenyl)-N⁴-ethyl-7-(4-(trifluoromethoxy)phenyl)-6,7-dihydro-5H-cyclopenta[d]pyrimidine-2,4-diamine;

(R)—N²-(4-(4-chloro-1H-imidazol-1-yl)-3-methoxyphenyl)-N⁴-ethyl-7-(4-(trifluoromethoxy)phenyl)-6,7-dihydro-5H-cyclopenta[d]pyrimidine-2,4-diamine;

N-(4-(4-chloro-1H-imidazol-1-yl)-3-methoxyphenyl)-4-(3,3-difluoroazetidin-1-yl)-7-(4-(trifluoromethoxy)phenyl)-6,7-dihydro-5H-cyclopenta[d]pyrimidin-2-amine;

(S)—N-(4-(4-chloro-1H-imidazol-1-yl)-3-methoxyphenyl)-4-(3,3-difluoroazetidin-1-yl)-7-(4-(trifluoromethoxy)phenyl)-6,7-dihydro-5H-cyclopenta[d]pyrimidin-2-amine;

(R)—N-(4-(4-chloro-1H-imidazol-1-yl)-3-methoxyphenyl)-4-(3,3-difluoroazetidin-1-yl)-7-(4-(trifluoromethoxy)phenyl)-6,7-dihydro-5H-cyclopenta[d]pyrimidin-2-amine;

N²-(4-(4-chloro-1H-imidazol-1-yl)-3-methoxyphenyl)-N⁴,N⁴-dimethyl-7-(4-(trifluoromethoxy)phenyl)-6,7-dihydro-5H-cyclopenta[d]pyrimidine-2,4-diamine;

(S)—N²-(4-(4-chloro-1H-imidazol-1-yl)-3-methoxyphenyl)-N⁴,N⁴-dimethyl-7-(4-(trifluoromethoxy)phenyl)-6,7-dihydro-5H-cyclopenta[d]pyrimidine-2,4-diamine;

(R)—N²-(4-(4-chloro-1H-imidazol-1-yl)-3-methoxyphenyl)-N⁴,N⁴-dimethyl-7-(4-(trifluoromethoxy)phenyl)-6,7-dihydro-5H-cyclopenta[d]pyrimidine-2,4-diamine;

4-(Azetidin-1-yl)-N-(4-(4-chloro-1H-imidazol-1-yl)-3-methoxyphenyl)-7-(4-(trifluoromethoxy)phenyl)-6,7-dihydro-5H-cyclopenta[d]pyrimidin-2-amine;

(S)-4-(Azetidin-1-yl)-N-(4-(4-chloro-1H-imidazol-1-yl)-3-methoxyphenyl)-7-(4-(trifluoromethoxy)phenyl)-6,7-dihydro-5H-cyclopenta[d]pyrimidin-2-amine;

(R)-4-(Azetidin-1-yl)-N-(4-(4-chloro-1H-imidazol-1-yl)-3-methoxyphenyl)-7-(4-(trifluoromethoxy)phenyl)-6,7-dihydro-5H-cyclopenta[d]pyrimidin-2-amine;

N²-(4-(4-chloro-1H-imidazol-1-yl)-3-methoxyphenyl)-7-(3,5-difluorophenyl)-N⁴-methyl-6,7-dihydro-5H-cyclopenta[d]pyrimidine-2,4-diamine;

N²-(4-(4-chloro-1H-imidazol-1-yl)-3-methoxyphenyl)-N⁴-methyl-7-(3,4,5-trifluorophenyl)-6,7-dihydro-5H-cyclopenta[d]pyrimidine-2,4-diamine;

(S)—N²-(4-(4-chloro-1H-imidazol-1-yl)-3-methoxyphenyl)-N⁴-methyl-7-(3,4,5-trifluorophenyl)-6,7-dihydro-5H-cyclopenta[d]pyrimidine-2,4-diamine;

(R)—N²-(4-(4-chloro-1H-imidazol-1-yl)-3-methoxyphenyl)-N⁴-methyl-7-(3,4,5-trifluorophenyl)-6,7-dihydro-5H-cyclopenta[d]pyrimidine-2,4-diamine;

N²-(3-fluoro-4-(5-methyl-1H-1,2,4-triazol-1-yl)phenyl)-N⁴-methyl-7-(3,4,5-trifluorophenyl)-6,7-dihydro-5H-cyclopenta[d]pyrimidine-2,4-diamine;

N2-(6-(4-chloro-1H-imidazol-1-yl)-5-methoxypyridin-3-yl)-N4-methyl-7-(3,4,5-trifluorophenyl)-6,7-dihydro-5H-cyclopenta[d]pyrimidine-2,4-diamine;

N²-(4-(3-chloro-1H-1,2,4-triazol-1-yl)-3-methoxyphenyl)-N⁴-methyl-7-(3,4,5-trifluorophenyl)-6,7-dihydro-5H-cyclopenta[d]pyrimidine-2,4-diamine;

N-(4-(4-chloro-1H-imidazol-1-yl)-3-methoxyphenyl)-4-(3,3-difluoropyrrolidin-1-yl)-7-(3,4,5-trifluorophenyl)-6,7-dihydro-5H-cyclopenta[d]pyrimidin-2-amine;

(S)—N-(4-(4-chloro-1H-imidazol-1-yl)-3-methoxyphenyl)-4-(3,3-difluoropyrrolidin-1-yl)-7-(3,4,5-trifluorophenyl)-6,7-dihydro-5H-cyclopenta[d]pyrimidin-2-amine;

(R)—N-(4-(4-chloro-1H-imidazol-1-yl)-3-methoxyphenyl)-4-(3,3-difluoropyrrolidin-1-yl)-7-(3,4,5-trifluorophenyl)-6,7-dihydro-5H-cyclopenta[d]pyrimidin-2-amine;

N-(4-(4-chloro-1H-imidazol-1-yl)-3-methoxyphenyl)-4-(3,3-difluoroazetidin-1-yl)-7-(3,4,5-trifluorophenyl)-6,7-dihydro-5H-cyclopenta[d]pyrimidin-2-amine;

N²-(4-(4-chloro-1H-imidazol-1-yl)-3-methoxyphenyl)-7-(2,4-difluorophenyl)-N⁴-methyl-6,7-dihydro-5H-cyclopenta[d]pyrimidine-2,4-diamine;

(S)—N²-(4-(4-chloro-1H-imidazol-1-yl)-3-methoxyphenyl)-7-(2,4-difluorophenyl)-N⁴-methyl-6,7-dihydro-5H-cyclopenta[d]pyrimidine-2,4-diamine;

(R)—N²-(4-(4-chloro-1H-imidazol-1-yl)-3-methoxyphenyl)-7-(2,4-difluorophenyl)-N⁴-methyl-6,7-dihydro-5H-cyclopenta[d]pyrimidine-2,4-diamine;

N2-(4-(4-chloro-1H-imidazol-1-yl)-3-methoxyphenyl)-N4-ethyl-7-methyl-7-phenyl-6,7-dihydro-5H-cyclopenta[d]pyrimidine-2,4-diamine;

N2-(4-(4-chloro-1H-imidazol-1-yl)-3-methoxyphenyl)-N4-ethyl-7-allyl-7-phenyl-6,7-dihydro-5H-cyclopenta[d]pyrimidine-2,4-diamine;

N2-(4-(4-chloro-1H-imidazol-1-yl)-3-methoxyphenyl)-8-(3,5-difluorophenyl)-N4-ethyl-7,8-dihydro-5H-pyrano[4,3-d]pyrimidine-2,4-diamine;

N2-(4-(4-chloro-1H-imidazol-1-yl)-3-methoxyphenyl)-8-(3,4-difluorophenyl)-N4-ethyl-7,8-dihydro-5H-pyrano[4,3-d]pyrimidine-2,4-diamine;

N-(4-(4-chloro-1H-imidazol-1-yl)-3-methoxyphenyl)-4-(3,3-difluoroazetidin-1-yl)-8-(3,4-difluorophenyl)-7,8-dihydro-5H-pyrano[4,3-d]pyrimidin-2-amine;

N2-(4-(4-chloro-1H-imidazol-1-yl)-3-methoxyphenyl)-N4-methyl-7,8-dihydro-5H-pyrano[4,3-d]pyrimidine-2,4-diamine;

8-(3,4-difluorophenyl)-N4-ethyl-N2-(3-fluoro-4-(5-methyl-1H-1,2,4-triazol-1-yl)phenyl)-7,8-dihydro-5H-pyrano[4,3-d]pyrimidine-2,4-diamine;

N2-(4-(4-chloro-1H-imidazol-1-yl)-3-methoxyphenyl)-N4-((R)-1-cyclopropylethyl)-8-(4-(trifluoromethyl)phenyl)-7,8-dihydro-5H-pyrano[4,3-d]pyrimidine-2,4-diamine;

N2-(4-(4-chloro-1H-imidazol-1-yl)-3-methoxyphenyl)-N4-ethyl-8-(4-(trifluoromethyl)phenyl)-7,8-dihydro-5H-pyrano[4,3-d]pyrimidine-2,4-diamine;

N4-ethyl-N2-(3-fluoro-4-(5-methyl-1H-1,2,4-triazol-1-yl)phenyl)-8-(4-(trifluoromethyl)phenyl)-7,8-dihydro-5H-pyrano[4,3-d]pyrimidine-2,4-diamine;

N2-(4-(4-chloro-1H-imidazol-1-yl)-3-methoxyphenyl)-N4-methyl-8-(4-(trifluoromethyl)phenyl)-7,8-dihydro-5H-pyrano[4,3-d]pyrimidine-2,4-diamine;

4-(2-(4-(4-chloro-1H-imidazol-1-yl)-3-methoxyphenylamino)-4-(ethylamino)-7,8-dihydro-5H-pyrano[4,3-d]pyrimidin-8-yl)benzonitrile;

N2-(4-(4-chloro-1H-imidazol-1-yl)-3-methoxyphenyl)-N4-methyl-8-(4-(trifluoromethoxy)phenyl)-7,8-dihydro-5H-pyrano[4,3-d]pyrimidine-2,4-diamine;

N-(4-(4-chloro-1H-imidazol-1-yl)-3-methoxyphenyl)-4-((R)-3-fluoropyrrolidin-1-yl)-8-(4-(trifluoromethoxy)phenyl)-7,8-dihydro-5H-pyrano[4,3-d]pyrimidin-2-amine;

$N^2$-(4-(4-chloro-1H-imidazol-1-yl)-3-methoxyphenyl)-$N^4$-ethyl-$N^4$-methyl-8-phenyl-5,6,7,8-tetrahydroquinazoline-2,4-diamine;

(S)—$N^2$-(4-(4-chloro-1H-imidazol-1-yl)-3-methoxyphenyl)-$N^4$-ethyl-$N^4$-methyl-8-phenyl-5,6,7,8-tetrahydroquinazoline-2,4-diamine;

(R)—$N^2$-(4-(4-chloro-1H-imidazol-1-yl)-3-methoxyphenyl)-$N^4$-ethyl-$N^4$-methyl-8-phenyl-5,6,7,8-tetrahydroquinazoline-2,4-diamine;

N-(4-(4-chloro-1H-imidazol-1-yl)-3-methoxyphenyl)-8-phenyl-5,6,7,8-tetrahydroquinazolin-2-amine;

$N^2$-(4-(4-chloro-1H-imidazol-1-yl)-3-methoxyphenyl)-$N^4$-ethyl-8-(4-fluorophenyl)-$N^4$-methyl-5,6,7,8-tetrahydroquinazoline-2,4-diamine;

$N^2$-(4-(4-chloro-1H-imidazol-1-yl)-3-methoxyphenyl)-8-(4-fluorophenyl)-$N^4$,$N^4$-dimethyl-5,6,7,8-tetrahydroquinazoline-2,4-diamine;

(S)—$N^2$-(4-(4-chloro-1H-imidazol-1-yl)-3-methoxyphenyl)-8-(4-fluorophenyl)-$N^4$,$N^4$-dimethyl-5,6,7,8-tetrahydroquinazoline-2,4-diamine;

(R)—$N^2$-(4-(4-chloro-1H-imidazol-1-yl)-3-methoxyphenyl)-8-(4-fluorophenyl)-$N^4$,$N^4$-dimethyl-5,6,7,8-tetrahydroquinazoline-2,4-diamine;

N-(4-(4-chloro-1H-imidazol-1-yl)-3-methoxyphenyl)-8-(4-fluorophenyl)-5,6,7,8-tetrahydroquinazolin-2-amine;

N2-(4-(4-chloro-1H-imidazol-1-yl)-3-methoxyphenyl)-N4-methyl-6-(methylsulfonyl)-8-phenyl-5,6,7,8-tetrahydropyrido[4,3-d]pyrimidine-2,4-diamine;

N2-(4-(4-chloro-1H-imidazol-1-yl)-3-methoxyphenyl)-6-(cyclopropylsulfonyl)-N4-methyl-8-phenyl-5,6,7,8-tetrahydropyrido[4,3-d]pyrimidine-2,4-diamine;

Methyl 2-(4-(4-chloro-1H-imidazol-1-yl)-3-methoxyphenylamino)-4-(ethylamino)-8-phenyl-7,8-dihydropyrido[4,3-d]pyrimidine-6(5H)-carboxylate;

(2-(4-(4-chloro-1H-imidazol-1-yl)-3-methoxyphenylamino)-4-(ethylamino)-8-phenyl-7,8-dihydropyrido[4,3-d]pyrimidin-6(5H)-yl)(cyclopropyl)methanone;

1-(2-(4-(4-chloro-1H-imidazol-1-yl)-3-methoxyphenylamino)-4-(ethylamino)-8-phenyl-7,8-dihydropyrido[4,3-d]pyrimidin-6(5H)-yl)-2-methoxyethanone;

N2-(4-(4-chloro-1H-imidazol-1-yl)-3-methoxyphenyl)-N4-ethyl-6-(methylsulfonyl)-8-phenyl-5,6,7,8-tetrahydropyrido[4,3-d]pyrimidine-2,4-diamine;

1-(2-(4-(4-chloro-1H-imidazol-1-yl)-3-methoxyphenylamino)-4-(ethylamino)-8-phenyl-7,8-dihydropyrido[4,3-d]pyrimidin-6(5H)-yl)-2-(dimethylamino)ethanone;

N2-(4-(4-chloro-1H-imidazol-1-yl)-3-methoxyphenyl)-6-(cyclopropylsulfonyl)-N4-ethyl-8-phenyl-5,6,7,8-tetrahydropyrido[4,3-d]pyrimidine-2,4-diamine;

1-(2-(4-(4-chloro-1H-imidazol-1-yl)-3-methoxyphenylamino)-4-(ethylamino)-8-phenyl-7,8-dihydropyrido[4,3-d]pyrimidin-6(5H)-ylethanone;

N2-(4-(4-chloro-1H-imidazol-1-yl)-3-methoxyphenyl)-N4-ethyl-6-(ethylsulfonyl)-8-phenyl-5,6,7,8-tetrahydropyrido[4,3-d]pyrimidine-2,4-diamine;

N4-ethyl-N2-(3-fluoro-4-(3-methyl-1H-1,2,4-triazol-1-yl)phenyl)-6-(methylsulfonyl)-8-phenyl-5,6,7,8-tetrahydropyrido[4,3-d]pyrimidine-2,4-diamine;

N4-ethyl-N2-(3-fluoro-4-(5-methyl-1H-1,2,4-triazol-1-yl)phenyl)-6-(methylsulfonyl)-8-phenyl-5,6,7,8-tetrahydropyrido[4,3-d]pyrimidine-2,4-diamine;

6-(cyclopropylsulfonyl)-N2-(3-fluoro-4-(3-methyl-1H-1,2,4-triazol-1-yl)phenyl)-N4-methyl-8-phenyl-5,6,7,8-tetrahydropyrido[4,3-d]pyrimidine-2,4-diamine;

6-(cyclopropylsulfonyl)-N2-(3-fluoro-4-(5-methyl-1H-1,2,4-triazol-1-yl)phenyl)-N4-methyl-8-phenyl-5,6,7,8-tetrahydropyrido[4,3-d]pyrimidine-2,4-diamine;

cyclopropyl(4-(ethylamino)-2-(3-fluoro-4-(3-methyl-1H-1,2,4-triazol-1-yl)phenylamino)-8-phenyl-7,8-dihydropyrido[4,3-d]pyrimidin-6(5H)-yl)methanone;

cyclopropyl(4-(ethylamino)-2-(3-fluoro-4-(5-methyl-1H-1,2,4-triazol-1-yl)phenylamino)-8-phenyl-7,8-dihydropyrido[4,3-d]pyrimidin-6(5H)-yl)methanone;

N4-ethyl-N2-(3-fluoro-4-(3-methyl-1H-1,2,4-triazol-1-yl)phenyl)-8-phenyl-6-(2,2,2-trifluoroethyl)-5,6,7,8-tetrahydropyrido[4,3-d]pyrimidine-2,4-diamine;

N4-ethyl-N2-(3-fluoro-4-(5-methyl-1H-1,2,4-triazol-1-yl)phenyl)-8-phenyl-6-(2,2,2-trifluoroethyl)-5,6,7,8-tetrahydropyrido[4,3-d]pyrimidine-2,4-diamine;

N2-(4-(4-chloro-1H-imidazol-1-yl)-3-methoxyphenyl)-N4,N4-dimethyl-6-(methylsulfonyl)-8-phenyl-5,6,7,8-tetrahydropyrido[4,3-d]pyrimidine-2,4-diamine;

N2-(4-(4-chloro-1H-imidazol-1-yl)-3-methoxyphenyl)-N4,6-dimethyl-8-phenyl-5,6,7,8-tetrahydropyrido[4,3-d]pyrimidine-2,4-diamine;

N2-(3-fluoro-4-(3-methyl-1H-1,2,4-triazol-1-yl)phenyl)-N4,6-dimethyl-8-phenyl-5,6,7,8-tetrahydropyrido[4,3-d]pyrimidine-2,4-diamine;

N2-(3-fluoro-4-(5-methyl-1H-1,2,4-triazol-1-yl)phenyl)-N4,6-dimethyl-8-phenyl-5,6,7,8-tetrahydropyrido[4,3-d]pyrimidine-2,4-diamine;

N2-(4-(4-chloro-1H-imidazol-1-yl)-3-methoxyphenyl)-N4-ethyl-6-methyl-8-phenyl-5,6,7,8-tetrahydropyrido[4,3-d]pyrimidine-2,4-diamine;

N4-ethyl-N2-(3-fluoro-4-(3-methyl-1H-1,2,4-triazol-1-yl)phenyl)-6-methyl-8-phenyl-5,6,7,8-tetrahydropyrido[4,3-d]pyrimidine-2,4-diamine;

N4-ethyl-N2-(3-fluoro-4-(5-methyl-1H-1,2,4-triazol-1-yl)phenyl)-6-methyl-8-phenyl-5,6,7,8-tetrahydropyrido[4,3-d]pyrimidine-2,4-diamine;

N2-(4-(4-chloro-1H-imidazol-1-yl)-3-methoxyphenyl)-8-(4-fluorophenyl)-N4-methyl-6-(methylsulfonyl)-5,6,7,8-tetrahydropyrido[4,3-d]pyrimidine-2,4-diamine;

N2-(4-(4-chloro-1H-imidazol-1-yl)-3-methoxyphenyl)-N4-ethyl-8-(4-fluorophenyl)-6-(methylsulfonyl)-5,6,7,8-tetrahydropyrido[4,3-d]pyrimidine-2,4-diamine;

N4-ethyl-N2-(3-fluoro-4-(3-methyl-1H-1,2,4-triazol-1-yl)phenyl)-8-(4-fluorophenyl)-6-(methylsulfonyl)-5,6,7,8-tetrahydropyrido[4,3-d]pyrimidine-2,4-diamine;

N4-ethyl-N2-(3-fluoro-4-(5-methyl-1H-1,2,4-triazol-1-yl)phenyl)-6-(methylsulfonyl)-8-(4-fluorophenyl)-5,6,7,8-tetrahydropyrido[4,3-d]pyrimidine-2,4-diamine;

N2-(4-(4-chloro-1H-imidazol-1-yl)-3-methoxyphenyl)-N4,6-diethyl-8-(4-fluorophenyl)-N4-methyl-5,6,7,8-tetrahydropyrido[4,3-d]pyrimidine-2,4-diamine;

N-(4-(4-chloro-1H-imidazol-1-yl)-3-methoxyphenyl)-4-(3,3-difluoroazetidin-1-yl)-8-(4-fluorophenyl)-6-methyl-5,6,7,8-tetrahydropyrido[4,3-d]pyrimidin-2-amine;

N-(4-(4-chloro-1H-imidazol-1-yl)-3-methoxyphenyl)-4-(3,3-difluoroazetidin-1-yl)-8-(4-fluorophenyl)-6-(methylsulfonyl)-5,6,7,8-tetrahydropyrido[4,3-d]pyrimidin-2-amine;

N2-(4-(4-chloro-1H-imidazol-1-yl)-3-methoxyphenyl)-N4-ethyl-8-(4-fluorophenyl)-N4-methyl-5,6,7,8-tetrahydropyrido[4,3-d]pyrimidine-2,4-diamine;

N-(4-(4-chloro-1H-imidazol-1-yl)-3-methoxyphenyl)-4-(3,3-difluoroazetidin-1-yl)-8-(4-fluorophenyl)-5,6,7,8-tetrahydropyrido[4,3-d]pyrimidin-2-amine;

N2-(4-(4-chloro-1H-imidazol-1-yl)-3-methoxyphenyl)-8-(4-fluorophenyl)-N4,6-dimethyl-5,6,7,8-tetrahydropyrido[4,3-d]pyrimidine-2,4-diamine;

N2-(4-(4-chloro-1H-imidazol-1-yl)-3-methoxyphenyl)-N4-ethyl-8-(4-fluorophenyl)-6-methyl-5,6,7,8-tetrahydropyrido[4,3-d]pyrimidine-2,4-diamine;

N2-(4-(4-chloro-1H-imidazol-1-yl)-3-methoxyphenyl)-N4-ethyl-8-(4-fluorophenyl)-N4,6-dimethyl-5,6,7,8-tetrahydropyrido[4,3-d]pyrimidine-2,4-diamine;

N2-(4-(4-chloro-1H-imidazol-1-yl)-3-methoxyphenyl)-N4-ethyl-8-(4-fluorophenyl)-N4-methyl-5,6,7,8-tetrahydropyrido[3,4-d]pyrimidine-2,4-diamine;

N-(4-(4-chloro-1H-imidazol-1-yl)-3-methoxyphenyl)-8-(4-fluorophenyl)-4-((S)-3-fluoropyrrolidin-1-yl)-7-(4-methoxybenzyl)-5,6,7,8-tetrahydropyrido[3,4-d]pyrimidin-2-amine;

N2-(4-(4-chloro-1H-imidazol-1-yl)-3-methoxyphenyl)-N4-ethyl-8-(4-fluorophenyl)-7-(methylsulfonyl)-5,6,7,8-tetrahydropyrido[3,4-d]pyrimidine-2,4-diamine;

N2-(4-(4-chloro-1H-imidazol-1-yl)-3-methoxyphenyl)-N4,7-diethyl-8-(4-fluorophenyl)-5,6,7,8-tetrahydropyrido[3,4-d]pyrimidine-2,4-diamine;

methyl 2-(4-(4-chloro-1H-imidazol-1-yl)-3-methoxyphenylamino)-4-(ethylamino)-8-(4-fluorophenyl)-5,6-dihydropyrido[3,4-d]pyrimidine-7(8H)-carboxylate;

1-(2-(4-(4-chloro-1H-imidazol-1-yl)-3-methoxyphenylamino)-4-(ethylamino)-8-(4-fluorophenyl)-5,6-dihydropyrido[3,4-d]pyrimidin-7(8H)-yl)ethanone;

N2-(4-(4-chloro-1H-imidazol-1-yl)-3-methoxyphenyl)-N4-ethyl-8-(4-fluorophenyl)-N4-methyl-7-(methylsulfonyl)-5,6,7,8-tetrahydropyrido[3,4-d]pyrimidine-2,4-diamine;

N-(4-(4-chloro-1H-imidazol-1-yl)-3-methoxyphenyl)-8-(4-fluorophenyl)-4-((R)-3-fluoropyrrolidin-1-yl)-7-(methylsulfonyl)-5,6,7,8-tetrahydropyrido[3,4-d]pyrimidin-2-amine;

N-(4-(4-chloro-1H-imidazol-1-yl)-3-methoxyphenyl)-8-(4-fluorophenyl)-4-((R)-3-fluoropyrrolidin-1-yl)-7-(methylsulfonyl)-5,6,7,8-tetrahydropyrido[3,4-d]pyrimidin-2-amine;

N2-(4-(4-chloro-1H-imidazol-1-yl)-3-methoxyphenyl)-N4-ethyl-8-(4-fluorophenyl)-7-methyl-5,6,7,8-tetrahydropyrido[3,4-d]pyrimidine-2,4-diamine;

$N^2$-(4-(4-chloro-1H-imidazol-1-yl)-3-methoxyphenyl)-$N^4$-trideuteromethyl-7-phenyl-6,7-dihydro-5H-cyclopenta[d]pyrimidine-2,4-diamine;

(S)—$N^2$-(4-(4-chloro-1H-imidazol-1-yl)-3-methoxyphenyl)-$N^4$-trideuteromethyl-7-phenyl-6,7-dihydro-5H-cyclopenta[d]pyrimidine-2,4-diamine;

(R)—$N^2$-(4-(4-chloro-1H-imidazol-1-yl)-3-methoxyphenyl)-$N^4$-trideuteromethyl-7-phenyl-6,7-dihydro-5H-cyclopenta[d]pyrimidine-2,4-diamine;

2-(4-(4-chloro-1H-imidazol-1-yl)-3-methoxyphenylamino)-4-(methylamino)-8-phenyl-7,8-dihydroquinazolin-8-ol;

2-(4-(4-chloro-1H-imidazol-1-yl)-3-methoxyphenylamino)-4-(methylamino)-8-phenyl-5,6,7,8-tetrahydroquinazolin-8-ol;

2-(4-(4-chloro-1H-imidazol-1-yl)-3-methoxyphenylamino)-4-(dimethylamino)-7-phenyl-6,7-dihydro-5H-cyclopenta[d]pyrimidin-7-ol;  7S)-2-(4-(4-chloro-1H-imidazol-1-yl)-3-methoxyphenylamino)-4-(dimethylamino)-7-phenyl-6,7-dihydro-5H-cyclopenta[d]pyrimidin-6-ol;

N-(4-(4-chloro-1H-imidazol-1-yl)-3-methoxyphenyl)-4-(3-chloroazetidin-1-yl)-7-phenyl-6,7-dihydro-5H-cyclopenta[d]pyrimidin-2-amine;

N-(4-(4-chloro-1H-imidazol-1-yl)-3-methoxyphenyl)-4-(3-fluoroazetidin-1-yl)-7-phenyl-6,7-dihydro-5H-cyclopenta[d]pyrimidin-2-amine;

N-(4-(4-chloro-1H-imidazol-1-yl)-3-methoxyphenyl)-4-(3-methoxyazetidin-1-yl)-7-phenyl-6,7-dihydro-5H-cyclopenta[d]pyrimidin-2-amine;

N-(4-(4-chloro-1H-imidazol-1-yl)-3-methoxyphenyl)-7-phenyl-4-(5,8-dioxa-2-azaspiro[3.4]octan-2-yl)-6,7-dihydro-5H-cyclopenta[d]pyrimidin-2-amine;

1-(2-(4-(4-chloro-1H-imidazol-1-yl)-3-methoxyphenylamino)-7-phenyl-6,7-dihydro-5H-cyclopenta[d]pyrimidin-4-yl)azetidin-3-one;

1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-3-methylazetidine-3-carbonitrile;

N-(4-(4-chloro-1H-imidazol-1-yl)-3-methoxyphenyl)-4-(3-ethoxyazetidin-1-yl)-7-(4-fluorophenyl)-6,7-dihydro-5H-cyclopenta[d]pyrimidin-2-amine;

N-(4-(4-chloro-1H-imidazol-1-yl)-3-methoxyphenyl)-7-phenyl-4-(5-oxa-2-azaspiro[3.4]octan-2-yl)-6,7-dihydro-5H-cyclopenta[d]pyrimidin-2-amine;

1-(2-(4-(4-chloro-1H-imidazol-1-yl)-3-methoxyphenylamino)-7-(4-fluorophenyl)-6,7-dihydro-5H-cyclopenta[d]pyrimidin-4-yl)-3-methylazetidin-3-ol;

N-(4-(4-chloro-1H-imidazol-1-yl)-3-methoxyphenyl)-4-(3-fluoro-3-methylazetidin-1-yl)-7-(4-fluorophenyl)-6,7-dihydro-5H-cyclopenta[d]pyrimidin-2-amine;

N-(4-(4-chloro-1H-imidazol-1-yl)-3-methoxyphenyl)-7-(4-fluorophenyl)-4-(3-methoxy-3-methylazetidin-1-yl)-6,7-dihydro-5H-cyclopenta[d]pyrimidin-2-amine;

7-(4-fluorophenyl)-4-(3-methoxy-3-methylazetidin-1-yl)-N-(3-methoxy-4-(3-methyl-1H-1,2,4-triazol-1-yl)phenyl)-6,7-dihydro-5H-cyclopenta[d]pyrimidin-2-amine;

7-(2,4-difluorophenyl)-N2-(3-methoxy-4-(3-methyl-1H-1,2,4-triazol-1-yl)phenyl)-N4-methyl-6,7-dihydro-5H-cyclopenta[d]pyrimidine-2,4-diamine;

(S)-7-(2,4-difluorophenyl)-N2-(3-methoxy-4-(3-methyl-1H-1,2,4-triazol-1-yl)phenyl)-N4-methyl-6,7-dihydro-5H-cyclopenta[d]pyrimidine-2,4-diamine;

(R)-7-(2,4-difluorophenyl)-N2-(3-methoxy-4-(3-methyl-1H-1,2,4-triazol-1-yl)phenyl)-N4-methyl-6,7-dihydro-5H-cyclopenta[d]pyrimidine-2,4-diamine;

6-(2,2-difluoroethyl)-N4-ethyl-N2-(3-fluoro-4-(5-methyl-1H-1,2,4-triazol-1-yl)phenyl)-8-phenyl-5,6,7,8-tetrahydropyrido[4,3-d]pyrimidine-2,4-diamine;

6-(2,2-difluoroethyl)-N4-ethyl-N2-(3-fluoro-4-(3-methyl-1H-1,2,4-triazol-1-yl)phenyl)-8-phenyl-5,6,7,8-tetrahydropyrido[4,3-d]pyrimidine-2,4-diamine;

N4-ethyl-N2-(3-methoxy-4-(4-chloro-1H-13-imidazol-1-yl)phenyl)-8-phenyl-6-(2,2,2-trifluoroethyl)-5,6,7,8-tetrahydropyrido[4,3-d]pyrimidine-2,4-diamine;

N4-ethyl-N2-(3-methoxy-4-(4-chloro-1H-13-imidazol-1-yl)phenyl)-8-phenyl-6-(2,2-difluoroethyl)-5,6,7,8-tetrahydropyrido[4,3-d]pyrimidine-2,4-diamine;

8-(4-fluorophenyl)-N2-(3-methoxy-4-(3-methyl-1H-1,2,4-triazol-1-yl)phenyl)-N4,6-dimethyl-5,6,7,8-tetrahydropyrido[4,3-d]pyrimidine-2,4-diamine;

8-(4-fluorophenyl)-N2-(3-methoxy-4-(5-methyl-1H-1,2,4-triazol-1-yl)phenyl)-N4,6-dimethyl-5,6,7,8-tetrahydropyrido[4,3-d]pyrimidine-2,4-diamine;

(±)-2-(4-(4-chloro-1H-imidazol-1-yl)-3-methoxyphenylamino)-4-(methylamino)-7-phenyl-6,7-dihydro-5H-cyclopenta[d]pyrimidin-5-one;

(E)-2-(4-(4-chloro-1H-imidazol-1-yl)-3-methoxyphenylamino)-4-(methylamino)-7-phenyl-6,7-dihydro-5H-cyclopenta[d]pyrimidin-5-one O-methyl oxime; 2-(4-(4-chloro-1H-imidazol-1-yl)-3-methoxyphenylamino)-4-(methylamino)-7-phenyl-6,7-dihydro-5H-cyclopenta[d]pyrimidin-5-ol;

N2-(4-(4-chloro-1H-imidazol-1-yl)-3-methoxyphenyl)-N4-methyl-8-phenyl-5,6,7,8-tetrahydroquinazoline-2,4-diamine;

1-(2-methoxy-4-(4-(methylamino)-7-phenyl-6,7-dihydro-5H-cyclopenta[d]pyrimidin-2-ylamino)phenyl)-1H-imidazole-4-carbonitrile;

N-(4-(4-chloro-1H-imidazol-1-yl)-3-methoxyphenyl)-7-phenyl-4-(1,4-dioxa-7-azaspiro[4.4]nonan-7-yl)-6,7-dihydro-5H-cyclopenta[d]pyrimidin-2-amine;

1-(2-(4-(4-chloro-1H-imidazol-1-yl)-3-methoxyphenylamino)-7-phenyl-6,7-dihydro-5H-cyclopenta[d]pyrimidin-4-yl)pyrrolidin-3-one;

4-(8-(4-fluorophenyl)-4-(methylamino)-6-(methylsulfonyl)-5,6,7,8-tetrahydropyrido[4,3-d]pyrimidin-2-ylamino)benzonitrile;

N2-(4-(4-(difluoromethyl)-1H-imidazol-1-yl)-3-methoxyphenyl)-7-(4-fluorophenyl)-N4-methyl-6,7-dihydro-5H-cyclopenta[d]pyrimidine-2,4-diamine;

N2-(3-methoxy-4-(1-methyl-1H-pyrazol-4-yl)phenyl)-N4-methyl-7-phenyl-6,7-dihydro-5H-cyclopenta[d]pyrimidine-2,4-diamine;

N-(2-(4-(4-chloro-1H-imidazol-1-yl)-3-methoxyphenylamino)-7-phenyl-6,7-dihydro-5H-cyclopenta[d]pyrimidin-4-yl)-N-methylmethanesulfonamide;

N-(2-(4-(4-chloro-1H-imidazol-1-yl)-3-methoxyphenylamino)-7-phenyl-6,7-dihydro-5H-cyclopenta[d]pyrimidin-4-yl)-N-methanesulfonamide;

N-(2-(4-(4-chloro-1H-imidazol-1-yl)-3-methoxyphenylamino)-7-phenyl-6,7-dihydro-5H-cyclopenta[d]pyrimidin-4-yl)-N-methylacetamide;

N-(2-(4-(4-chloro-1H-imidazol-1-yl)-3-methoxyphenylamino)-7-phenyl-6,7-dihydro-5H-cyclopenta[d]pyrimidin-4-yl)-N-acetamide;

N2-(4-(4-chloro-1H-imidazol-1-yl)-3-methoxyphenyl)-N4-(5-isopropyl-2-methylphenyl)-7-phenyl-6,7-dihydro-5H-cyclopenta[d]pyrimidine-2,4-diamine;

4-(4-(5-isopropyl-2-methylphenylamino)-7-phenyl-6,7-dihydro-5H-cyclopenta[d]pyrimidin-2-ylamino)benzonitrile;

N4-methyl-N2-(2-methylpyridin-4-yl)-7-phenyl-6,7-dihydro-5H-cyclopenta[d]pyrimidine-2,4-diamine;

N2-(3-methoxyphenyl)-N4-methyl-7-phenyl-6,7-dihydro-5H-cyclopenta[d]pyrimidine-2,4-diamine;

N2-(4-fluorophenyl)-N4-methyl-7-phenyl-6,7-dihydro-5H-cyclopenta[d]pyrimidine-2,4-diamine;

N2-(3,5-difluorophenyl)-N4-methyl-7-phenyl-6,7-dihydro-5H-cyclopenta[d]pyrimidine-2,4-diamine;

N2-(4-chloro-3-methoxyphenyl)-N4-methyl-7-phenyl-6,7-dihydro-5H-cyclopenta[d]pyrimidine-2,4-diamine;

N2-(4-bromo-2-methoxyphenyl)-N4-methyl-7-phenyl-6,7-dihydro-5H-cyclopenta[d]pyrimidine-2,4-diamine;

N2-(4-fluoro-3-methoxyphenyl)-N4-methyl-7-phenyl-6,7-dihydro-5H-cyclopenta[d]pyrimidine-2,4-diamine;

N4-methyl-7-phenyl-N2-(pyrimidin-5-yl)-6,7-dihydro-5H-cyclopenta[d]pyrimidine-2,4-diamine;

N4-methyl-7-phenyl-N2-(pyridin-4-yl)-6,7-dihydro-5H-cyclopenta[d]pyrimidine-2,4-diamine;

4-(4-(methylamino)-7-phenyl-6,7-dihydro-5H-cyclopenta[d]pyrimidin-2-ylamino)benzonitrile;

4-(4-(methylamino)-7-phenyl-6,7-dihydro-5H-cyclopenta[d]pyrimidin-2-ylamino)benzonitrile;

4-(4-(methylamino)-7-phenyl-6,7-dihydro-5H-cyclopenta[d]pyrimidin-2-ylamino)benzonitrile;

2-(4-(methylamino)-7-phenyl-6,7-dihydro-5H-cyclopenta[d]pyrimidin-2-ylamino)benzonitrile;

4-(4-(methylamino)-7-phenyl-6,7-dihydro-5H-cyclopenta[d]pyrimidin-2-ylamino)-1-naphthonitrile;

5-(4-(methylamino)-7-phenyl-6,7-dihydro-5H-cyclopenta[d]pyrimidin-2-ylamino)picolinonitrile;

2-(4-(4-(methylamino)-7-phenyl-6,7-dihydro-5H-cyclopenta[d]pyrimidin-2-ylamino)phenyl)acetonitrile;

2-(4-(methylamino)-7-phenyl-6,7-dihydro-5H-cyclopenta[d]pyrimidin-2-ylamino)-1H-benzo[d]imidazole-5-carbonitrile;

3-(4-(methylamino)-7-phenyl-6,7-dihydro-5H-cyclopenta[d]pyrimidin-2-ylamino)benzonitrile;

N2-(4-tert-butylphenyl)-N4-methyl-7-phenyl-6,7-dihydro-5H-cyclopenta[d]pyrimidine-2,4-diamine;

N4-methyl-N2-(4-(methylsulfonyl)phenyl)-7-phenyl-6,7-dihydro-5H-cyclopenta[d]pyrimidine-2,4-diamine;

N4-methyl-7-phenyl-N2-(4-(trifluoromethoxy)phenyl)-6,7-dihydro-5H-cyclopenta[d]pyrimidine-2,4-diamine;

4-(4-(methylamino)-7-phenyl-6,7-dihydro-5H-cyclopenta[d]pyrimidin-2-ylamino)phthalonitrile;

4-(4-(methylamino)-7-phenyl-6,7-dihydro-5H-cyclopenta[d]pyrimidin-2-ylamino)-2-(trifluoromethyl)benzonitrile;

N4-methyl-7-phenyl-N2-(4-(trifluoromethyl)phenyl)-6,7-dihydro-5H-cyclopenta[d]pyrimidine-2,4-diamine;

5-(4-(methylamino)-7-phenyl-6,7-dihydro-5H-cyclopenta[d]pyrimidin-2-ylamino)-2,3-dihydro-1H-inden-1-one;

2-(4-(methylamino)-7-phenyl-6,7-dihydro-5H-cyclopenta[d]pyrimidin-2-ylamino)-1H-imidazole-4,5-dicarbonitrile;

2-bromo-5-(4-(methylamino)-7-phenyl-6,7-dihydro-5H-cyclopenta[d]pyrimidin-2-ylamino)benzonitrile;

N,N-dimethyl-4-(4-(methylamino)-7-phenyl-6,7-dihydro-5H-cyclopenta[d]pyrimidin-2-ylamino)benzamide;

1-(4-(4-(methylamino)-7-phenyl-6,7-dihydro-5H-cyclopenta[d]pyrimidin-2-ylamino)phenyl)cyclopentanecarbonitrile;

N4-methyl-7-phenyl-N2-(1,2,3,4-tetrahydroisoquinolin-6-yl)-6,7-dihydro-5H-cyclopenta[d]pyrimidine-2,4-diamine;

4-(4-(methylamino)-7-phenyl-6,7-dihydro-5H-cyclopenta[d]pyrimidin-2-ylamino)-2-(trifluoromethoxy)benzonitrile;

1-(4-(4-(methylamino)-7-phenyl-6,7-dihydro-5H-cyclopenta[d]pyrimidin-2-ylamino)phenyl)cyclopropanecarbonitrile;

1-(2-methoxy-4-(4-(methylamino)-7-phenyl-6,7-dihydro-5H-cyclopenta[d]pyrimidin-2-ylamino)phenylamino)cyclopropanecarbonitrile;

N4-methyl-N2-(2-methyl-1H-indol-5-yl)-7-phenyl-6,7-dihydro-5H-cyclopenta[d]pyrimidine-2,4-diamine;

N2-(benzofuran-5-yl)-N4-methyl-7-phenyl-6,7-dihydro-5H-cyclopenta[d]pyrimidine-2,4-diamine;

N2-(1H-indol-5-yl)-N4-methyl-7-phenyl-6,7-dihydro-5H-cyclopenta[d]pyrimidine-2,4-diamine;

N4-methyl-N2-(2-methylbenzo[d]oxazol-6-yl)-7-phenyl-6,7-dihydro-5H-cyclopenta[d]pyrimidine-2,4-diamine;

N2-(1H-benzo[d]imidazol-6-yl)-N4-methyl-7-phenyl-6,7-dihydro-5H-cyclopenta[d]pyrimidine-2,4-diamine;

N4-methyl-N2-(1-methyl-1H-indol-5-yl)-7-phenyl-6,7-dihydro-5H-cyclopenta[d]pyrimidine-2,4-diamine;

N4-methyl-N2-(2-methylbenzo[d]thiazol-6-yl)-7-phenyl-6,7-dihydro-5H-cyclopenta[d]pyrimidine-2,4-diamine;

N2-(4-bromo-3-methoxyphenyl)-N4-methyl-7-phenyl-6,7-dihydro-5H-cyclopenta[d]pyrimidine-2,4-diamine;

1-(4-(4-(methylamino)-7-phenyl-6,7-dihydro-5H-cyclopenta[d]pyrimidin-2-ylamino)phenyl)ethanone;

N2-(4-cyclopropylphenyl)-7-(4-fluorophenyl)-N4-methyl-6,7-dihydro-5H-cyclopenta[d]pyrimidine-2,4-diamine;

N2-(4-ethynylphenyl)-7-(4-fluorophenyl)-N4-methyl-6,7-dihydro-5H-cyclopenta[d]pyrimidine-2,4-diamine;

7-(4-fluorophenyl)-N4-methyl-N2-(4-(prop-1-ynyl)phenyl)-6,7-dihydro-5H-cyclopenta[d]pyrimidine-2,4-diamine;

N2-(3-methoxy-4-(2-methylpyridin-4-yl)phenyl)-N4-methyl-7-phenyl-6,7-dihydro-5H-cyclopenta[d]pyrimidine-2,4-diamine;

N2-(3-methoxy-4-(pyridin-4-yl)phenyl)-N4-methyl-7-phenyl-6,7-dihydro-5H-cyclopenta[d]pyrimidine-2,4-diamine, and N2-(3-methoxy-4-(pyridin-3-yl)phenyl)-N4-methyl-7-phenyl-6,7-dihydro-5H-cyclopenta[d]pyrimidine-2,4-diamine; or a pharmaceutically acceptable salt thereof.

15. A pharmaceutical composition for treating disorders responsive to reduction of β-amyloid peptide production comprising a therapeutically effective amount of a compound of claim 1, or a pharmaceutically acceptable salt thereof, in association with a pharmaceutically acceptable carrier or diluent.

* * * * *